United States Patent
Kobayashi et al.

(10) Patent No.: US 9,580,444 B2
(45) Date of Patent: Feb. 28, 2017

(54) POLYCYCLIC PYRAZOLINONE DERIVATIVE AND HERBICIDE COMPRISING SAME AS EFFECTIVE COMPONENT THEREOF

(71) Applicants: SAGAMI CHEMICAL RESEARCH INSTITUTE, Ayase-shi, Kanagawa (JP); KAKEN PHARMACEUTICAL CO., LTD., Tokyo (JP)

(72) Inventors: Osamu Kobayashi, Ayase (JP); Naoko Niikura, Ayase (JP); Tomoko Inoue, Ayase (JP); Satoshi Mizuta, Ayase (JP); Reiko Takatsuna, Ayase (JP); Kenji Hirai, Ayase (JP); Kentaro Shirouzu, Tokyo (JP); Miyoo Obata, Fujieda (JP)

(73) Assignees: Sagami Chemical Research Institute, Kanagawa (JP); Kaken Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 14/775,312

(22) PCT Filed: Mar. 14, 2014

(86) PCT No.: PCT/JP2014/056910
§ 371 (c)(1),
(2) Date: Sep. 11, 2015

(87) PCT Pub. No.: WO2014/142307
PCT Pub. Date: Sep. 18, 2014

(65) Prior Publication Data
US 2016/0024110 A1   Jan. 28, 2016

(30) Foreign Application Priority Data

Mar. 15, 2013  (JP) ................................ 2013-053102

(51) Int. Cl.
| | | |
|---|---|---|
| *C07D 498/04* | (2006.01) | |
| *C07D 487/04* | (2006.01) | |
| *A01N 43/90* | (2006.01) | |
| *A01N 47/06* | (2006.01) | |

(52) U.S. Cl.
CPC .......... *C07D 498/04* (2013.01); *A01N 43/90* (2013.01); *A01N 47/06* (2013.01); *C07D 487/04* (2013.01)

(58) Field of Classification Search
CPC .... C07D 498/04; C07D 487/04; A01N 47/06; A01N 43/90
See application file for complete search history.

(56) References Cited

U.S. PATENT DOCUMENTS

| | | |
|---|---|---|
| 4,619,687 A | 10/1986 | Haga et al. |
| 4,640,707 A | 2/1987 | Nagano et al. |
| 4,792,605 A | 12/1988 | Nagano et al. |
| 4,880,925 A | 11/1989 | Nagano et al. |
| 5,108,483 A | 4/1992 | Kunisch et al. |
| 5,332,720 A * | 7/1994 | Kruger .................. A01N 43/56 504/281 |
| 5,358,924 A | 10/1994 | Kruger et al. |
| 5,474,974 A | 12/1995 | Kruger et al. |
| 5,661,110 A | 8/1997 | Kruger et al. |
| 5,739,389 A | 4/1998 | Kruger et al. |
| 5,780,394 A | 7/1998 | Kruger et al. |
| 6,221,810 B1 | 4/2001 | Kruger et al. |
| 6,294,567 B1 | 9/2001 | Hashizume et al. |
| 6,410,480 B1 | 6/2002 | Muhlebach et al. |

FOREIGN PATENT DOCUMENTS

| | | | |
|---|---|---|---|
| CH | WO 2012175666 A1 * | 12/2012 | ........... C07D 255/02 |
| JP | 61-76486 A | 4/1986 | |
| JP | 61-152683 A | 7/1986 | |
| JP | 3-153685 A | 7/1991 | |
| JP | 5-117240 A | 5/1993 | |
| JP | 2000-226374 A | 8/2000 | |
| JP | 2002-506870 A | 3/2002 | |
| WO | 96/21652 A1 | 7/1996 | |
| WO | 2012/175666 A1 | 12/2012 | |

OTHER PUBLICATIONS

Aboul-Ella et al. "Synthesis of some pyrazolone derivatives of expected antipyretic activity" J. Chem. U.A.R. 1968, 11, 289-92.*
International Search Report mailed Apr. 28, 2014, which issued during the prosecution of Applicant's PCT/JP2014/056910.
File registry on STN, RN 22944-59-8, Entered STN: Nov. 16, 1984.

* cited by examiner

*Primary Examiner* — Joseph Kosack
*Assistant Examiner* — Amanda L Aguirre
(74) *Attorney, Agent, or Firm* — Sughrue Mion, PLLC

(57) ABSTRACT

Provided are a polycyclic pyrazolinone derivative indicated by general formula (1) (in the formula, $R^1$, $X^1$, $X^2$, $X^3$, and Y indicate the definitions provided in the Specification) and a herbicide comprising same as effective component thereof.

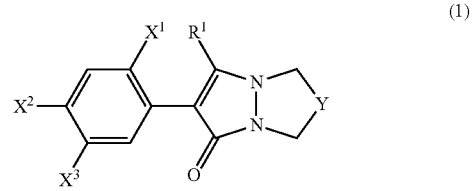

(1)

12 Claims, No Drawings

POLYCYCLIC PYRAZOLINONE DERIVATIVE AND HERBICIDE COMPRISING SAME AS EFFECTIVE COMPONENT THEREOF

CROSS REFERENCE TO RELATED APPLICATIONS

This application is a National Stage of International Application No. PCT/JP2014/056910, filed Mar. 14, 2014 (claiming priority based on Japanese Patent Application No. 2013-053102, filed Mar. 15, 2013), the contents of which are incorporated herein by reference in their entirety.

TECHNICAL FIELD

The present invention relates to bicyclic pyrazolinone derivatives and a herbicide containing the same as an effective component.

BACKGROUND ART

So far, wide research and development for controlling harmful weeds, which hinder the growth of crops have been performed, and a great number of compounds having an weed-controlling effect, which are useful as an effective component of a herbicide have been found. However, it cannot be said that these compounds are sufficiently satisfactory in performance desirable as a herbicide such as an weed-controlling effect, sustainability of the effect, or selectivity between a crop and a weed, and since the presence of weeds exhibiting resistance to some of these existing herbicides has been already confirmed, novel herbicides have been strongly demanded.

In the related art, as a herbicide having to bicyclic pyrazolinone as a basic skeleton, an acetyl-CoA carboxylase (ACCase) inhibition type herbicidal active compound such as pinoxaden is known (refer to PTLs 1 to 3). It has been suggested that it is critical for the expression of ACCase inhibitory activity that, in such a ACCase inhibition type herbicide, the hydroxyl group on a bicyclic pyrazolinone ring which is a basic skeleton thereof is a substituent essential for the expression of activity, and that the electron donating group represented by a methyl group or an ethyl group, as a substituent on the benzene ring, is substituted at an ortho-position or a para-position.

CITATION LIST

Patent Literature

[PTL 1] JP-T-2002-506870
[PTL 2] JP-A-5-117240
[PTL 3] Pamphlet of International Publication No. 1996-021652

SUMMARY OF INVENTION

Technical Problem

An object of the present invention is to provide a compound useful as an effective component of a herbicide, which has performance desirable as a herbicide such as an excellent weed-controlling effect and sustainability of the effect or selectivity between a crop and a weed.

Solution to Problem

The present inventors, as a result of intensive studies to solve the above problems, found that among bicyclic pyrazolinone compounds which have not been known so far, a bicyclic pyrazolinone compound has an excellent profile desirable as an effective component of a herbicide in addition to an excellent weed-controlling effect, and completed the present invention.

That is, the present invention relates to:
(i) a bicyclic pyrazolinone derivative represented by General Formula (1):

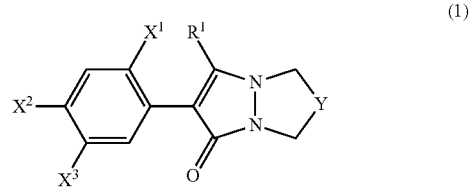

[in which,
$R^1$ represents a halogen atom, a $C_1$-$C_4$ alkyl group, or a $C_1$-$C_4$ haloalkyl group;
$X^1$ represents a hydrogen atom or a halogen atom;
$X^2$ represents a halogen atom, a cyano group, a thiocyano group, a trifluoromethyl group, a hydroxyl group, a methoxy group, a nitro group, or an amino group;
$X^3$ represents a hydrogen atom; a halogen atom; a hydroxyl group; a cyano group; a thiocyano group; a $C_1$-$C_6$ alkyl group which may be substituted with one or more substituents selected from the group consisting of a halogen atom, a ($C_1$-$C_4$ alkyl)oxycarbonyl group, and a cyano group; a $C_2$-$C_6$ alkenyl group which may be substituted with one or more substituents selected from the group consisting of a halogen atom, a ($C_1$-$C_4$ alkyl)oxycarbonyl group, and a cyano group; a $C_1$-$C_{12}$ alkyloxy group which may be substituted with one or more substituents selected from the group consisting of a $C_1$-$C_6$ alkyloxy group, a ($C_1$-$C_4$ alkyl)oxycarbonyl group, and a cyano group; a $C_1$-$C_{12}$ haloalkyloxy group; a $C_3$-$C_8$ cycloalkyloxy group; a glycidyloxy group; a $C_2$-$C_6$ alkenyloxy group which may be substituted with one or more substituents selected from the group consisting of a halogen atom and a ($C_1$-$C_4$ alkyl)oxycarbonyl group; an alkenyloxy group represented by General Formula (1-1a):

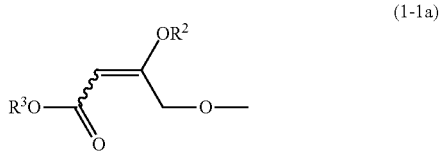

(in which, $R^2$ represents a $C_1$-$C_6$ alkyl group, and $R^3$ represents a $C_1$-$C_6$ alkyl group or a $C_2$-$C_6$ alkenyl group); a $C_5$-$C_8$ cycloalkenyloxy group; a $C_2$-$C_6$ alkynyloxy group which may be substituted with a halogen atom; a $C_7$-$C_8$ aralkyloxy group which may be substituted with one or more substituents selected from the group consisting of a halogen atom and a trifluoromethyl group; a ($C_1$-$C_4$ alkyl)oxycarbonyloxy group; a ($C_2$-$C_6$ alkenyl)oxycarbonyloxy group; a phenyloxycarbonyloxy group which may be substituted with a halogen atom; a $C_1$-$C_4$ alkyl sulfonyloxy group; a $C_1$-$C_4$ haloalkyl sulfonyloxy group; a phenyl sulfonyloxy group which may be substituted with one or more substituents selected from the group consisting of a halogen atom and a $C_1$-$C_4$ alkyl group; a nitro group; an amino group which may be substituted with one or more substituents selected from the group consisting of a $C_1$-$C_4$ alkyl group, a $C_2$-$C_6$ alkenyl group, a $C_2$-$C_6$ alkynyl group, a $C_2$-$C_8$ acyl group which may be substituted with a halogen atom, a $C_1$-$C_4$ alkyl sulfonyl group which may be substituted with a halogen atom, a $C_3$-$C_8$ cycloalkyl sulfonyl group, a $C_2$-$C_6$ alkenyl sulfonyl group, a $C_7$-$C_8$ aralkyl sulfonyl group, a (phenyl which may be substituted with one or more substituents selected from the group consisting of a halogen atom, a $C_1$-$C_4$ alkyl group, a trifluoromethyl group, and phenyloxy group) sulfonyl amino group, and a di($C_1$-$C_4$ alkyl)amino sulfonyl group; a $C_4$-$C_7$ cyclic polymethylene imino group; a carboxyl group; a ($C_1$-$C_4$ alkyl)oxycarbonyl group; a ($C_2$-$C_6$ alkenyl)oxycarbonyl group; a phenyloxycarbonyl group which may be substituted with a halogen atom; a phenyloxy group which may be substituted, represented by General Formula (1-2a):

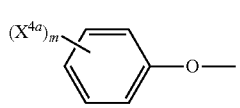

(1-2a)

(in which, $X^{4a}$ represents a hydrogen atom; a halogen atom; a $C_1$-$C_6$ alkyl group which may be substituted with one or more substituents selected from the group consisting of a ($C_1$-$C_4$ alkyl)oxycarbonyl group and a cyano group; a $C_1$-$C_6$ haloalkyl group; a $C_1$-$C_6$ alkyloxy group which may be substituted with one or more substituents selected from the group consisting of a ($C_1$-$C_4$ alkyl)oxycarbonyl group and a cyano group; a $C_1$-$C_6$ haloalkyloxy group; a $C_2$-$C_6$ alkenyloxy group which may be substituted with one or more substituents selected from the group consisting of a halogen atom and a phenyl group which may be substituted with a halogen atom; a $C_2$-$C_6$ alkynyloxy group which may be substituted with a halogen atom; a phenyl group which may be substituted with one or more substituents selected from the group consisting of a halogen atom and a trifluoromethyl group; a ($C_1$-$C_4$ alkyl)oxycarbonyl group; a cyano group; a nitro group; an amino group; or an alkenyloxy group represented by General Formula (1-1a), and m represents an integer of 1 to 3, and when $X^{4a}$ is an alkenyloxy group represented by General Formula (1-1a), m is 1); a pyridyloxy group which may be substituted with one or more substituents selected from the group consisting of a halogen atom, a $C_1$-$C_4$ alkyl group, a $C_1$-$C_4$ haloalkyl group, a $C_1$-$C_4$ alkyloxy group, a $C_1$-$C_4$ alkyloxy carbonyl methyloxy group, a cyano group, and a nitro group; a pyridylmethyloxy group which may be substituted with one or more substituents selected from the group consisting of a halogen atom, a $C_1$-$C_4$ alkyl group, a $C_1$-$C_4$ haloalkyl group, a cyano group, and a nitro group; or an isoxazolin-5-yl methyloxy group represented by General Formula (1-3):

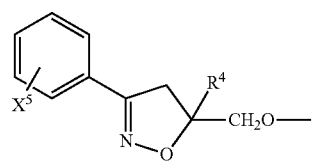

(1-3)

(in which, $X^5$ represents a hydrogen atom, a halogen atom, a $C_1$-$C_6$ alkyl group, a $C_1$-$C_6$ haloalkyl group, a $C_1$-$C_6$ alkyloxy group, or a $C_1$-$C_6$ haloalkyloxy group, and $R^4$ represents a $C_1$-$C_4$ alkyl group); and Y represents a methylene group, a fluoromethylene group, a dimethylene group, a trimethylene group, a tetramethylene group, an oxamethylene group, or an oxadimethylene group];

(ii) the bicyclic pyrazolinone derivative according to (i), in which, in General Formula (1), each of $X^4$ and $X^2$ is independently the same as or different from each other, and is a halogen atom, $R^1$ is a halogen atom or a trifluoromethyl group, and Y is a methylene group, a dimethylene group, a trimethylene group, or an oxadimethylene group;

(iii) the bicyclic pyrazolinone derivative according to (i) or (ii), in which, in General Formula (1), $X^1$ is a fluorine atom or a chlorine atom, $X^2$ is a chlorine atom, $R^1$ is a chlorine atom or a trifluoromethyl group, and Y is a dimethylene group;

(iv) the bicyclic pyrazolinone derivative according to any one of (i) to (iii), in which, in General Formula (1), $X^3$ represents a $C_1$-$C_{12}$ alkyloxy group which may be substituted with one or more substituents selected from the group consisting of a $C_1$-$C_6$ alkyloxy group, a ($C_1$-$C_4$ alkyl)oxycarbonyl group, and a cyano group; a $C_3$-$C_8$ cycloalkyloxy group; a $C_2$-$C_6$ alkenyloxy group which may be substituted with a halogen atom; an alkenyloxy group represented by General Formula (1-1a):

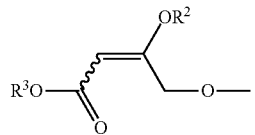

(1-1a)

(in which, $R^2$ represents a $C_1$-$C_6$ alkyl group, and $R^3$ represents a $C_1$-$C_6$ alkyl group or a $C_2$-$C_6$ alkenyl group); a $C_2$-$C_6$ alkynyloxy group which may be substituted with a halogen atom; a $C_7$-$C_8$ aralkyloxy group which may be substituted with one or more substituents selected from the group consisting of a halogen atom and a trifluoromethyl group; a ($C_1$-$C_4$ alkyl)oxycarbonyl group; a cyano group; a phenyloxy group, which may be substituted, represented by General Formula (1-2a):

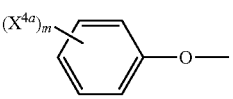

(1-2a)

(in which, $X^{4a}$ represents a hydrogen atom; a halogen atom; a $C_1$-$C_6$ alkyl group which may be substituted with one or more substituents selected from the group consisting of a ($C_1$-$C_4$ alkyl)oxycarbonyl group and a cyano group; a $C_1$-$C_6$ haloalkyl group; a $C_1$-$C_6$ alkyloxy group which may be substituted with one or more substituents selected from the group consisting of a ($C_1$-$C_4$ alkyl)oxycarbonyl group and a cyano group; a $C_1$-$C_6$ haloalkyloxy group; a $C_2$-$C_6$ alkenyloxy group which may be substituted with one or more substituents selected from the group consisting of a halogen atom and a phenyl group which may be substituted with a halogen atom; a $C_2$-$C_6$ alkynyloxy group which may be substituted with a halogen atom; a phenyl group which may be substituted with one or more substituents selected from the group consisting of a halogen atom and a trifluoromethyl group; a ($C_1$-$C_4$ alkyl)oxycarbonyl group; a cyano group; a nitro group; or an alkenyloxy group represented by General Formula (1-1a), and m represents an integer of 1 to 3, and when $X^{4a}$ is an alkenyloxy group represented by General Formula (1-1a), m is 1); a pyridyloxy group which may be substituted with one or more substituents selected from the group consisting of a halogen atom, a $C_1$-$C_4$ alkyl group, a $C_1$-$C_4$ haloalkyl group, a $C_1$-$C_4$ alkyloxy group, a $C_1$-$C_4$ alkyloxy carbonyl methyloxy group, a cyano group, and a nitro group; or an isoxazolin-5-yl methyloxy group represented by General Formula (1-3):

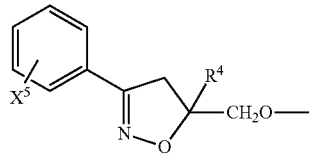

(1-3)

(in which, $X^5$ represents a hydrogen atom, a halogen atom, a $C_1$-$C_6$ alkyl group, a $C_1$-$C_6$ haloalkyl group, a $C_1$-$C_6$ alkyloxy group, or a $C_1$-$C_6$ haloalkyloxy group, and $R^4$ represents a $C_1$-$C_4$ alkyl group);

(v) the bicyclic pyrazolinone derivative according to any one of (i) to (iv), in which, in General Formula (1), $X^3$ is a $C_2$-$C_6$ alkenyloxy group or a $C_2$-$C_6$ alkynyloxy group;

(vi) the bicyclic pyrazolinone derivative according to (i), in which the compound represented by General Formula (1) is one compound selected from the group consisting of
4-(5-allyloxy-4-chloro-2-fluorophenyl)-5-chloro-1,2-tetramethylene-4-pyrazolin-3-one,
5-chloro-4-[4-chloro-2-fluoro-5-(propargyloxy)phenyl]-1,2-tetramethylene-4-pyrazolin-3-one,
5-chloro-4-[5-(2-butynyloxy)-4-chloro-2-fluorophenyl]-1,2-tetramethylene-4-pyrazolin-3-one,
5-chloro-4-[4-chloro-2-fluoro-5-(propargyloxy)phenyl]-1,2-pentamethylene-4-pyrazolin-3-one,
5-chloro-4-[4-chloro-2-fluoro-5-(2-methoxyphenoxy)phenyl]-1,2-tetramethylene-4-pyrazolin-3-one,
5-chloro-4-[2,4-dichloro-5-(propargyloxy)phenyl]-1,2-oxadiethylene-4-pyrazolin-3-one,
5-chloro-4-[2,4-dichloro-5-(propargyloxy)phenyl]-1,2-tetramethylene-4-pyrazolin-3-one, and
methyl (E)-4-[2-chloro-5-(5-chloro-3-oxo-1,2-oxadiethylene-4-pyrazolin-4-yl)-4-fluorophenyloxy]-3-methoxy-2-butenoate;

(vii) a herbicide, including the bicyclic pyrazolinone derivative according to any one of (i) to (vi) as an effective component;

(viii) the herbicide according to (vii), which is for upland field weed control or for paddy field weed control;

(ix) the herbicide according (viii), which is for upland field weed control, in which a crop in the upland field is any one of wheat, soybean, or corn;

(x) the herbicide according to any one of (vii) to (ix), which is a foliage and/or soil treatment agent;

(xi) use of the bicyclic pyrazolinone derivative according to any one of (i) to (vi) for controlling weeds; and (xii) a method for controlling weeds, including applying an effective amount of the bicyclic pyrazolinone derivative according to any one of (i) to (vi).

Advantageous Effects of Invention

A novel bicyclic pyrazolinone derivative of the present invention exhibits an excellent weed-controlling effect, and has an excellent profile desirable as a herbicide such as sustainability of the effect or selectivity between a crop and a weed. Therefore, the bicyclic pyrazolinone derivative of the present invention is useful as an effective component of a herbicide.

DESCRIPTION OF EMBODIMENTS

Hereinafter, the present invention will be described in more detail.

First, $R^1$, $R^{1a}$, $R^{1b}$, $R^2$, $R^3$, $R^4$, $R^5$, $X^1$, $X^2$, $X^{2a}$, $X^{2b}$, $X^3$, $X^{3a}$, $X^{3c}$, $X^{3d}$, $X^{3e}$, $X^{3f}$, $X^{3g}$, $X^{3h}$, $X^{4a}$, $X^{4b}$, $X^{4c}$, $X^{4d}$, $X^{4e}$, $X^5$, $X^6$, and Y used in General Formula (1) and other general formulas described below will be described.

Examples of the halogen atom represented by $R^1$ and $R^{1a}$ can include a fluorine atom, a chlorine atom, and a bromine atom. From the viewpoint of high herbicidal activity, a chlorine atom and a fluorine atom is preferable, and among these, a chlorine atom is more preferable.

The $C_1$-$C_4$ alkyl group represented by $R^1$, $R^{1a}$, and $R^{1b}$ may be any one of a linear group or a branched group, and examples thereof can include a methyl group, an ethyl group, a propyl group, an isopropyl group, a butyl group, an isobutyl group, a sec-butyl group, and a tert-butyl group. From the viewpoint of high herbicidal activity, a methyl group and an ethyl group is preferable.

The $C_1$-$C_4$ haloalkyl group represented by $R^1$, $R^{1a}$, and $R^{1b}$ may be any one of a linear group or a branched group, and examples thereof can include a fluoromethyl group, a difluoromethyl group, a trifluoromethyl group, a 2,2,2-trifluoroethyl group, a perfluoroethyl group, a 3-fluoropropyl group, a dichloromethyl group, and a trichloromethyl group. From the viewpoint of high herbicidal activity, a trifluoromethyl group is preferable.

The $C_1$-$C_6$ alkyl group represented by $R^2$ and $R^3$ may be any one of a linear group or a branched group, and examples thereof can include a methyl group, an ethyl group, a propyl group, an isopropyl group, a butyl group, an isobutyl group, a sec-butyl group, a tert-butyl group, a pentyl group, and a hexyl group. From the viewpoint of high herbicidal activity, a $C_1$-$C_4$ alkyl group is preferable.

Examples of the $C_2$-$C_6$ alkenyl group represented by $R^3$ can include a vinyl group, an allyl group, a crotyl group, a methallyl group, a 1-buten-3-yl group, a prenyl group, a 3-butenyl group, and a 2-hexenyl group. From the viewpoint of high herbicidal activity, an allyl group, a crotyl group, or a metally group is preferable.

The $C_1$-$C_4$ alkyl group represented by $R^4$ may be any one of a linear group or a branched group, and examples thereof can include a methyl group, an ethyl group, a propyl group, an isopropyl group, a butyl group, an isobutyl group, a sec-butyl group, and a tert-butyl group. From the viewpoint of high herbicidal activity, a methyl group is preferable.

The $C_1$-$C_4$ alkyl group represented by $R^5$ may be any one of a linear group or a branched group, and examples thereof can include a methyl group, an ethyl group, a propyl group, an isopropyl group, a butyl group, and an isobutyl group. From the viewpoint of favorable production efficiency, an ethyl group is preferable.

Examples of the halogen atom represented by $X^1$ include a fluorine atom, a chlorine atom, a bromine atom, and an iodine atom. From the viewpoint of high herbicidal activity, a fluorine atom and a chlorine atom are preferable.

Examples of the halogen atom represented by $X^2$, $X^{2a}$, and $X^{2b}$ can include a fluorine atom, a chlorine atom, a bromine atom, and an iodine atom. From the viewpoint of high herbicidal activity, a chlorine atom or a fluorine atom is preferable. Examples of the halogen atom represented by $X^3$, $X^{3a}$, $X^{3d}$, and $X^{3g}$ can include a fluorine atom, a chlorine atom, a bromine atom, and an iodine atom.

The $C_1$-$C_6$ alkyl group represented by $X^3$ and $X^{3g}$ may be any one of a linear group or a branched group, and examples thereof can include a methyl group, an ethyl group, a propyl group, an isopropyl group, a butyl group, an isobutyl group, a sec-butyl group, a tert-butyl group, a pentyl group, and a hexyl group. The alkyl group may be substituted with one or more substituents selected from the group consisting of halogen atoms such as a chlorine atom and a fluorine atom; ($C_1$-$C_4$ alkyl)oxycarbonyl groups such as a methoxycarbonyl group, an ethoxycarbonyl group, an isopropyloxycarbonyl group, an isobutyloxycarbonyl group, and a tert-butyloxycarbonyl group; and cyano groups. From the viewpoint of high herbicidal activity, a 2-chloro-2-(methoxycarbonyl)ethyl group or a 2-chloro-2-(ethoxycarbonyl)ethyl group is preferable.

The $C_2$-$C_6$ alkenyl group represented by $X^3$ and $X^{3g}$ may be any one of a linear group or a branched group, and examples thereof can include a vinyl group, an allyl group, a crotyl group, a methallyl group, a 1-buten-3-yl group, a prenyl group, a 3-butenyl group, and a 2-hexenyl group. The alkenyl group may be substituted with one or more substituents selected from the group consisting of halogen atoms such as a chlorine atom and a fluorine atom; ($C_1$-$C_4$ alkyl) oxycarbonyl groups such as a methoxycarbonyl group, an ethoxycarbonyl group, an isopropyloxycarbonyl group, an isobutyloxycarbonyl group, and a tert-butyloxycarbonyl group; and cyano groups.

The $C_1$-$C_{12}$ alkyloxy group represented by $X^3$ may be any one of a linear group or a branched group, and examples thereof can include a methoxy group, an ethoxy group, a propyloxy group, an isopropyloxy group, a butyloxy group, an isobutyloxy group, a sec-butyloxy group, a tert-butyloxy group, a pentyloxy group, a hexyloxy group, a heptyloxy group, an octyloxy group, a decyloxy group, a undecyloxy group, and a dodecyloxy group. The alkyloxy group may be substituted with one or more substituents selected from the group consisting of $C_1$-$C_6$ alkyloxy groups such as a methoxy group, an ethoxy group, a propyloxy group, an isopropyloxy group, a butyloxy group, an isobutyloxy group, a sec-butyloxy group, a tert-butyloxy group, a pentyloxy group, and a hexyloxy group; ($C_1$-$C_4$ alkyl)oxycarbonyl groups such as a methoxycarbonyl group, an ethoxycarbonyl group, an isopropyloxycarbonyl group, an isobutyloxycarbonyl group, and a tert-butyloxycarbonyl group; and cyano groups. From the viewpoint of high herbicidal activity, a $C_1$-$C_6$ alkyloxy group such as a methoxy group, an ethoxy group, a propyloxy group, an isopropyloxy group, or an isobutyloxy group is preferable.

The $C_1$-$C_{12}$ alkyl group represented by $X^{3c}$ may be any one of a linear group or a branched group, and examples thereof can include a methyl group, an ethyl group, a propyl group, an isopropyl group, a butyl group, an isobutyl group, a sec-butyl group, a tert-butyl group, a pentyl group, a hexyl group, a heptyl group, an octyl group, a decyl group, a undecyl group, and a dodecyl group. The alkyl group may be substituted with one or more substituents selected from the group consisting of $C_1$-$C_6$ alkyloxy groups such as a methoxy group, an ethoxy group, a propyloxy group, an isopropyloxy group, a butyloxy group, an isobutyloxy group, a sec-butyloxy group, a tert-butyloxy group, a pentyloxy group, and a hexyloxy group; ($C_1$-$C_4$ alkyl)oxycarbonyl groups such as a methoxycarbonyl group, an ethoxycarbonyl group, an isopropyloxycarbonyl group, an isobutyloxycarbonyl group, and a tert-butyloxycarbonyl group; and cyano groups. From the viewpoint of high herbicidal activity, a $C_1$-$C_6$ alkyl group such as a methyl group, an ethyl group, a propyl group, an isopropyl group, or an isobutyl group is preferable.

The $C_1$-$C_{12}$ alkyloxy group represented by $X^{3a}$ and $X^{3d}$ may be any one of a linear group or a branched group, and examples thereof can include a methoxy group, an ethoxy group, a propyloxy group, an isopropyloxy group, a butyloxy group, an isobutyloxy group, a sec-butyloxy group, a tert-butyloxy group, a pentyloxy group, a hexyloxy group, a heptyloxy group, an octyloxy group, a decyloxy group, a undecyloxy group, and a dodecyloxy group. From the viewpoint of high herbicidal activity, a $C_1$-$C_6$ alkyloxy group such as a methoxy group, an ethoxy group, a propyloxy group, an isopropyloxy group, or an isobutyloxy group is preferable.

The $C_1$-$C_{12}$ haloalkyloxy group represented by $X^3$ may be any one of a linear group or a branched group, and examples thereof can include a fluoromethyloxy group, a difluoromethyloxy group, a trifluoromethyloxy group, a 2,2,2-trifluoroethyloxy group, a perfluoroethyloxy group, a 3-fluoropropyloxy group, a dichloromethyloxy group, and a trichloromethyloxy group. From the viewpoint of high herbicidal activity, a difluoromethyloxy group is preferable.

The $C_1$-$C_{12}$ haloalkyl group represented by $X^{3c}$ may be any one of a linear group or a branched group, and examples thereof can include a fluoromethyl group, a difluoromethyl group, a trifluoromethyl group, a 2,2,2-trifluoroethyl group, a perfluoroethyl group, a 3-fluoropropyl group, a dichloromethyl group, and a trichloromethyl group. From the viewpoint of high herbicidal activity, a difluoromethyl group is preferable.

Examples of the $C_3$-$C_8$ cycloalkyloxy group represented by $X^3$, $X^{3a}$, and $X^{3d}$ can include a cyclopropyloxy group, a cyclopropylmethyloxy group, a cyclobutyloxy group, a cyclobutylmethyloxy group, a cyclopentyloxy group, a cyclopentylmethyloxy group, a cyclohexyloxy group, a cyclohexylmethyloxy group, a cycloheptyloxy group, and a cyclooctyloxy group. From the viewpoint of high herbicidal activity, a cyclopentyloxy group or a cyclohexyloxy group is preferable.

Examples of the $C_3$-$C_8$ cycloalkyl group represented by $X^{3c}$ can include a cyclopropyl group, a cyclopropylmethyl group, a cyclobutyl group, a cyclobutylmethyl group, a cyclopentyl group, a cyclopentylmethyl group, a cyclohexyl group, a cyclohexylmethyl group, a cycloheptyl group, and a cyclooctyl group. From the viewpoint of high herbicidal activity, a cyclopentyl group or a cyclohexyl group is preferable.

The $C_2$-$C_6$ alkenyloxy group represented by $X^3$ may be any one of a linear group or a branched group, and examples thereof can include a vinyloxy group, an allyloxy group, a crotyloxy group, a methallyloxy group, a 1-buten-3-yloxy group, a prenyloxy group, a 3-butenyloxy group, and a 2-hexenyloxy group. The alkenyloxy group may be substituted with a halogen atom such as a chlorine atom or a fluorine atom, or a ($C_1$-$C_4$ alkyl)oxycarbonyl group such as a methoxycarbonyl group, an ethoxycarbonyl group, an isopropyloxycarbonyl group, an isobutyloxycarbonyl group, or a tert-butyloxycarbonyl group, and examples thereof can include a 2-chloroallyloxy group and a 3-(ethoxycarbonyl)allyloxy group. From the viewpoint of high herbicidal activity, an allyloxy group, a crotyloxy group, a methallyloxy group, or a 1-buten-3-yloxy group is preferable.

The $C_2$-$C_6$ alkenyloxy group represented by $X^{3a}$ and $X^{3d}$ may be any one of a linear group or a branched group, and examples thereof can include a vinyloxy group, an allyloxy group, a crotyloxy group, a methallyloxy group, a 1-buten-3-yloxy group, a prenyloxy group, a 3-butenyloxy group, and a 2-hexenyloxy group. From the viewpoint of high herbicidal activity, an allyloxy group, a crotyloxy group, a methallyloxy group, or a 1-buten-3-yloxy group is preferable.

The $C_2$-$C_6$ alkenyl group represented by $X^{3c}$ may be any one of a linear group or a branched group, and examples thereof can include a vinyl group, an allyl group, a crotyl group, a methallyl group, a 1-buten-3-yl group, a prenyl group, a 3-butenyl group, and a 2-hexenyl group. The alkenyl group may be substituted with a halogen atom such as a chlorine atom or a fluorine atom; a ($C_1$-$C_4$ alkyl) oxycarbonyl group such as a methoxycarbonyl group, an ethoxycarbonyl group, an isopropyloxycarbonyl group, an isobutyloxycarbonyl group, or a tert-butyloxycarbonyl group; or a cyano group, and examples thereof can include a 2-chloroallyloxy group and a 3-(ethoxycarbonyl)allyloxy group. From the viewpoint of high herbicidal activity, an allyl group, a crotyl group, a methallyl group, or a 1-buten-3-yl group is preferable.

Examples of the $C_5$-$C_8$ cycloalkenyloxy group represented by $X^3$, $X^{3a}$, and $X^{3d}$ can include a cyclopenten-3-yloxy group, a cyclohexen-3-yloxy group, a cyclohepten-3-yloxy group, and a cycloocten-3-yloxy group.

Examples of the $C_5$-$C_8$ cycloalkenyl group represented by $X^{3c}$ can include a cyclopenten-3-yl group, a cyclohexen-3-yl group, a cyclohepten-3-yl group, and a cycloocten-3-yl group.

Examples of the $C_2$-$C_6$ alkynyloxy group represented by $X^3$ can include an ethynyloxy group, a propargyloxy group, a 1-butyn-3-yloxy group, a 2-butynyloxy group, a 3-butynyloxy group, and a 2-pentynyloxy group. The alkynyloxy group may be substituted with a halogen atom such as a chlorine atom or a fluorine atom. From the viewpoint of high herbicidal activity, a propargyloxy group or a 1-butyn-3-yloxy group is preferable.

Examples of the $C_2$-$C_6$ alkynyl group represented by $X^{3c}$ can include an ethynyl group, a propargyl group, a 1-butyn-3-yl group, a 2-butynyl group, a 3-butynyl group, and a 2-pentynyl group. The alkynyl group may be substituted with a halogen atom such as a chlorine atom or a fluorine atom. From the viewpoint of high herbicidal activity, a propargyl group or a 1-butyn-3-yl group is preferable.

Examples of the $C_7$-$C_8$ aralkyloxy group represented by $X^3$ can include a benzyloxy group, an α-phenethyloxy group, and a β-phenethyloxy group. The aralkyloxy group may be substituted with a halogen atom such as a chlorine atom or a fluorine atom, or a trifluoromethyl group, and examples thereof include a 2-fluorobenzyloxy group, a 3-fluorobenzyloxy group, a 4-fluorobenzyloxy group, a 2-chlorobenzyloxy group, a 3-chlorobenzyloxy group, a 4-chlorobenzyloxy group, a 2,4-difluorobenzyloxy group, a 2,6-difluorobenzyloxy group, a 2,4,6-trifluorobenzyloxy group, a 2,3,4,5,6-pentafluorobenzyloxy group, a 2,4-dichlorobenzyloxy group, a 3,5-dichlorobenzyloxy group, a 2-(trifluoromethyl)benzyloxy group, a 3-(trifluoromethyl) benzyloxy group, and 4-(trifluoromethyl)benzyloxy group.

Examples of the $C_7$-$C_8$ aralkyl group represented by $X^{3c}$ can include a benzyl group, an α-phenethyl group, and a β-phenethyl group. The aralkyl group may be substituted with a halogen atom such as a chlorine atom or a fluorine atom, or a trifluoromethyl group, and examples thereof can include a 2-fluorobenzyl group, a 3-fluorobenzyl group, a 4-fluorobenzyl group, a 2-chlorobenzyl group, a 3-chlorobenzyl group, a 4-chlorobenzyl group, a 2,4-difluorobenzyl group, a 2,6-difluorobenzyl group, a 2,4,6-trifluorobenzyl group, a 2,3,4,5,6-pentafluorobenzyl group, a 2,4-dichlorobenzyl group, a 3,5-dichlorobenzyl group, a 2-(trifluoromethyl)benzyl group, a 3-(trifluoromethyl)benzyl group, and a 4-(trifluoromethyl)benzyl group.

Examples of the ($C_1$-$C_4$ alkyl)oxycarbonyloxy group represented by $X^3$ can include a methoxycarbonyloxy group, an ethoxycarbonyloxy group, a propyloxycarbonyloxy group, an isopropyloxycarbonyloxy group, an isobutyloxycarbonyloxy group, and a tert-butyloxycarbonyloxy group.

Examples of the ($C_1$-$C_4$ alkyl)oxycarbonyl group represented by $X^{3c}$ can include a methoxycarbonyl group, an ethoxycarbonyl group, a propyloxycarbonyl group, an isopropyloxycarbonyl group, an isobutyloxycarbonyl group, and a tert-butyloxycarbonyl group.

Examples of the ($C_2$-$C_6$ alkenyl)oxycarbonyloxy group represented by $X^3$ can include an allyloxycarbonyloxy group, a crotyloxycarbonyloxy group, and a methallyloxycarbonyloxy group.

Examples of the ($C_2$-$C_6$ alkenyl)oxycarbonyl group represented by $X^{3c}$ can include an allyloxycarbonyl group, a crotyloxycarbonyl group, and a methallyloxycarbonyl group.

Examples of the phenyloxycarbonyloxy group, which may be substituted with a halogen atom, represented by $X^3$ can include a phenyloxycarbonyloxy group, a 2-fluorophenyloxycarbonyloxy group, a 4-fluorophenyloxycarbonyloxy group, a 2-chlorophenyloxycarbonyloxy group, and a 4-chlorophenyloxycarbonyloxy group.

Examples of the phenyloxycarbonyl group, which may be substituted with a halogen atom, represented by $X^{3c}$ can include a phenyloxycarbonyl group, a 2-fluorophenyloxycarbonyl group, a 4-fluorophenyloxycarbonyl group, a 2-chlorophenyloxycarbonyl group, and a 4-chlorophenyloxycarbonyl group.

Examples of the $C_1$-$C_4$ alkyl sulfonyloxy group represented by $X^3$ can include a methyl sulfonyloxy group, an ethyl sulfonyloxy group, a propyl sulfonyloxy group, an isopropyl sulfonyloxy group, a butyl sulfonyloxy group, and an isobutyl sulfonyloxy group.

Examples of the $C_1$-$C_4$ alkyl sulfonyl group represented by $X^{3c}$ can include a methyl sulfonyl group, an ethyl sulfonyl group, a propyl sulfonyl group, an isopropyl sulfonyl group, a butyl sulfonyl group, and an isobutyl sulfonyl group.

Examples of the $C_1$-$C_4$ haloalkyl sulfonyloxy group represented by $X^3$ can include a chloromethyl sulfonyloxy group, a 2-chloroethyl sulfonyloxy group, a trifluoromethyl sulfonyloxy group, and a 2,2,2-trifluoroethyl sulfonyloxy group.

Examples of the $C_1$-$C_4$ haloalkyl sulfonyl group represented by $X^{3c}$ can include a chloromethyl sulfonyl group, a 2-chloroethyl sulfonyl group, a trifluoromethyl sulfonyl group, and a 2,2,2-trifluoroethyl sulfonyl group.

Examples of the phenyl sulfonyloxy group, which may be substituted with one or more substituents selected from the group consisting of a halogen atom and a $C_1$-$C_4$ alkyl group, represented by $X^3$ can include a phenyl sulfonyloxy group, a 4-methylphenyl sulfonyloxy group, a 4-fluorophenyl sulfonyloxy group, and a 4-chlorophenyl sulfonyloxy group.

The pyridyloxy group of pyridyloxy group, which may be substituted, represented by $X^3$ may be any regioisomer of a 2-pyridyloxy group, a 3-pyridyloxy group, and a 4-pyridyloxy group.

The pyridyl group of pyridyl group, which may be substituted, represented by $X^{3c}$ may be any regioisomer of a 2-pyridyl group, a 3-pyridyl group, and a 4-pyridyl group.

Moreover, the pyridine ring of the pyridyloxy group and the pyridyl group may be substituted with one or more substituents selected from the group consisting of a halogen atom, a $C_1$-$C_4$ alkyl group, a $C_1$-$C_4$ haloalkyl group, a $C_1$-$C_4$ alkyloxy group, a $C_1$-$C_4$ alkyloxy carbonyl methyloxy group, a cyano group, and a nitro group, and examples of the halogen atom can include a fluorine atom, a chlorine atom, a bromine atom, and an iodine atom, examples of the $C_1$-$C_4$ alkyl group can include a methyl group, an ethyl group, an isopropyl group, a butyl group, an isobutyl group, a sec-butyl group, and a tert-butyl group, examples of the $C_1$-$C_4$ haloalkyl group can include a difluoromethyl group, a chlorodifluoromethyl group, and a trifluoromethyl group, examples of the $C_1$-$C_4$ alkyloxy group can include a methoxy group, an ethoxy group, an isopropyloxy group, a butyloxy group, an isobutyloxy group, a sec-butyloxy group, and a tert-butyloxy group, and examples of the $C_1$-$C_4$ alkyloxy carbonyl methyloxy group can include a methoxycarbonyl methyloxy group, an ethoxycarbonyl methyloxy group, an isopropyloxycarbonyl methyloxy group, and a tert-butyloxycarbonyl methyloxy group. Among substituents on these pyridine rings, from the viewpoint of a favorable yield when introducing the pyridyl group, an electron withdrawing group such as a halogen atom, a trifluoromethyl group, a cyano group, or a nitro group is preferable.

The pyridyl methyloxy group of pyridyl methyloxy group, which may be substituted, represented by $X^3$ may be any regioisomer of a 2-pyridyl methyloxy group, a 3-pyridyl methyloxy group, and a 4-pyridyl methyloxy group. The pyridyl methyl group of pyridyl methyl group, which may be substituted, represented by $X^{3c}$ may be any regioisomer of a 2-pyridyl methyl group, a 3-pyridyl methyl group, and a 4-pyridyl methyl group.

Moreover, the pyridine ring of the pyridyl methyloxy group and the pyridyl methyl group may be substituted with one or more substituents selected from the group consisting of a halogen atom, a $C_1$-$C_4$ alkyl group, a $C_1$-$C_4$ haloalkyl group, a cyano group, and a nitro group, and examples of the halogen atom can include a fluorine atom, a chlorine atom, a bromine atom, and an iodine atom, examples of the $C_1$-$C_4$ alkyl group can include a methyl group, an ethyl group, an isopropyl group, a butyl group, an isobutyl group, a sec-butyl group, and a tert-butyl group, and examples of the $C_1$-$C_4$ haloalkyl group can include a difluoromethyl group, a chlorodifluoromethyl group, and a trifluoromethyl group.

Examples of the phenyl sulfonyl group, which may be substituted with one or more substituents selected from the group consisting of a halogen atom and a $C_1$-$C_4$ alkyl group, represented by $X^{3c}$ can include a phenyl sulfonyl group, a 4-methylphenyl sulfonyl group, a 4-fluorophenyl sulfonyl group, and a 4-chlorophenyl sulfonyl group.

For amino groups which may be substituted with one or more substituents selected from the group consisting of a $C_1$-$C_4$ alkyl group, a $C_2$-$C_6$ alkenyl group, a $C_2$-$C_6$ alkynyl group, a $C_2$-$C_8$ acyl group, a $C_1$-$C_4$ alkyl sulfonyl group which may be substituted with a halogen atom, a $C_3$-$C_8$ cycloalkyl sulfonyl group, a $C_2$-$C_6$ alkenyl sulfonyl group, a $C_7$-$C_8$ aralkyl sulfonyl group, a (phenyl which may be substituted with one or more substituents selected from the group consisting of a halogen atom, a $C_1$-$C_4$ alkyl group, a trifluoromethyl group, and phenyloxy group) sulfonyl group, and a di($C_1$-$C_4$ alkyl)amino sulfonyl group, represented by $X^3$, each substituted amino group will be described below.

Examples of the $C_1$-$C_4$ alkyl amino group represented by $X^3$ can include a methyl amino group, an ethyl amino group, a propyl amino group, an isopropyl amino group, a butyl amino group, a sec-butyl amino group, and a tert-butyl amino group.

Examples of the $C_2$-$C_6$ alkenyl amino group represented by $X^3$ can include a vinyl amino group, an allyl amino group, a crotyl amino group, a methallyl amino group, a (1-buten-3-yl)amino group, a prenyl amino group, a 3-butenyl amino group, and 2-hexenyl amino group.

Examples of the $C_2$-$C_6$ alkynyl amino group represented by $X^3$ can include an ethynyl amino group, a propargyl amino group, a (1-butyn-3-yl)amino group, a 2-butynyl amino group, a 3-butynyl amino group, and a 2-pentynyl amino group.

Examples of the $C_2$-$C_8$ acyl amino group represented by $X^3$ can include an acetyl amino group, a propionyl amino group, a butyryl amino group, an isobutyryl amino group, a valeryl amino group, an isovaleryl amino group, and a pivaloyl amino group.

Examples of the $C_1$-$C_4$ alkyl sulfonyl amino group, which may be substituted with a halogen atom, represented by $X^3$ can include a methyl sulfonyl amino group, an ethyl sulfonyl amino group, a trifluoromethyl sulfonyl amino group, and a chloromethyl sulfonyl amino group.

Examples of the $C_3$-$C_8$ cycloalkyl sulfonyl amino group represented by $X^3$ can include a cyclopropyl sulfonyl amino group, a cyclopentyl sulfonyl amino group, a cyclohexyl sulfonyl amino group, and a cyclooctyl sulfonyl amino group.

Examples of the $C_2$-$C_6$ alkenyl sulfonyl amino group represented by $X^3$ can include a vinyl sulfonyl amino group, an allyl sulfonyl amino group, a crotyl sulfonyl amino group, and a methallyl sulfonyl amino group.

Examples of the $C_7$-$C_8$ aralkyl sulfonyl amino group represented by $X^3$ can include a benzyl sulfonyl amino group, an α-phenethyl sulfonyl amino group, and a β-phenethyl sulfonyl amino group.

Examples of the (phenyl which may be substituted with one or more substituents selected from the group consisting of a halogen atom, a $C_1$-$C_4$ alkyl group, a trifluoromethyl group, and a phenyloxy group) sulfonyl amino group represented by $X^3$ can include a phenyl sulfonyl amino group, a 2-fluorophenyl sulfonyl amino group, a 4-fluorophenyl sulfonyl amino group, a 2-chlorophenyl sulfonyl amino group, a 4-chlorophenyl sulfonyl amino group, a 4-methylphenyl sulfonyl amino group, a 4-(trifluoromethyl)phenyl sulfonyl amino group, a 4-(phenyloxy)phenyl sulfonyl amino group, and a 3-(phenyloxy)phenyl sulfonyl amino group.

Examples of the di($C_1$-$C_4$ alkyl) amino sulfonyl amino group represented by $X^3$ can include a dimethyl amino sulfonyl amino group, a diethyl amino sulfonyl amino group, a diisopropyl amino sulfonyl amino group, and a dibutyl amino sulfonyl amino group.

Examples of the $C_4$-$C_7$ cyclic polymethylene imino group represented by $X^3$ can include a pyrrolidino group, a piperidino group, an azepan-1-yl group, and an azocan-1-yl group.

The $C_1$-$C_4$ alkyl group represented by $X^{3f}$ may be any one of a linear group or a branched group, and examples thereof can include a methyl group, an ethyl group, a propyl group, an isopropyl group, a butyl group, a sec-butyl group, and a tert-butyl group.

Examples of the $C_2$-$C_6$ alkenyl group represented by $X^{3f}$ can include a vinyl group, an allyl group, a crotyl group, a methallyl group, a 1-buten-3-yl group, a prenyl group, a 3-butenyl group, and a 2-hexenyl group.

Examples of the $C_2$-$C_6$ alkynyl group represented by $X^{3f}$ can include an ethynyl group, a propargyl group, a 1-butyn-3-yl group, a 2-butynyl group, a 3-butynyl group, and a 2-pentynyl group.

Examples of the $C_2$-$C_8$ acyl group, which may be substituted with a halogen atom, represented by $X^{3f}$ can include a acetyl group, a propionyl group, a butyryl group, an isobutyryl group, a valeryl group, an isovaleryl group, a pivaloyl group, a chloroacetyl group, a trifluoroacetyl group, a chlorodifluoroacetyl group, and a bromodifluoroacetyl group.

Examples of the $C_1$-$C_4$ alkyl sulfonyl group, which may be substituted with a halogen atom, represented by $X^{3f}$ can include a methyl sulfonyl group, a difluoromethyl sulfonyl group, a chloromethyl sulfonyl group, a trifluoromethyl sulfonyl group, an ethyl sulfonyl group, a (2-fluoroethyl) sulfonyl group, a (2-chloroethyl) sulfonyl group, and a (2-bromoethyl) sulfonyl group.

Examples of the $C_3$-$C_8$ cycloalkyl sulfonyl group represented by $X^{3f}$ can include a cyclopropyl sulfonyl group, a cyclopentyl sulfonyl group, a cyclohexyl sulfonyl group, and a cyclooctyl sulfonyl group.

Examples of the $C_2$-$C_6$ alkenyl sulfonyl group represented by $X^{3f}$ can include a vinyl sulfonyl group, an allyl sulfonyl group, a crotyl sulfonyl group, and a methallyl sulfonyl group.

Examples of the $C_7$-$C_8$ aralkyl sulfonyl group represented by $X^{3f}$ can include a benzyl sulfonyl group, an α-phenethyl sulfonyl group, and a β-phenethyl sulfonyl group.

Examples of the (phenyl which may be substituted with one or more substituents selected from the group consisting of a halogen atom, a $C_1$-$C_4$ alkyl group, a trifluoromethyl group, and a phenyloxy group) sulfonyl group represented by $X^{3f}$ can include a phenyl sulfonyl group, a 2-fluorophenyl sulfonyl group, a 4-fluorophenyl sulfonyl group, a 2-chlorophenyl sulfonyl group, a 4-chlorophenyl sulfonyl group, a 4-methylphenyl sulfonyl group, a 4-(trifluoromethyl)phenyl sulfonyl group, a 3-(phenyloxy)phenyl sulfonyl group, and a 4-(phenyloxy)phenyl sulfonyl group.

Examples of the di($C_1$-$C_4$ alkyl) amino sulfonyl group represented by $X^{3f}$ can include a dimethyl amino sulfonyl group, a diethyl amino sulfonyl group, a diisopropyl amino sulfonyl group, and a dibutyl amino sulfonyl group.

Examples of the $C_4$-$C_7$ cyclic polymethylene imino group formed by joining two $X^{3f}$s on the nitrogen atom together with the nitrogen atom can include a pyrrolidino group, a piperidino group, an azepan-1-yl group, and an azocan-1-yl group.

Examples of the ($C_1$-$C_4$ alkyl)oxycarbonyl group represented by $X^3$, $X^{3a}$, and $X^{3d}$ can include a methoxycarbonyl group, an ethoxycarbonyl group, propyloxycarbonyl group, an isopropyloxycarbonyl group, a butyloxycarbonyl group, an isobutyloxycarbonyl group, a sec-butyloxycarbonyl group, and a tert-butyloxycarbonyl group.

Examples of the ($C_2$-$C_6$ alkenyl)oxycarbonyl group represented by $X^3$, $X^{3a}$, and $X^{3d}$ can include a vinyloxycarbonyl group, an allyloxycarbonyl group, a crotyloxycarbonyl group, a methallyloxycarbonyl group, a prenyloxycarbonyl group, and a (1-buten-3-yl)oxycarbonyl group.

Examples of the phenyloxycarbonyl group, which may be substituted with a halogen atom, represented by $X^3$, $X^{3a}$, and $X^{3d}$ can include a phenyloxycarbonyl group, a 2-fluorophenyloxycarbonyl group, a 4-fluorophenyloxycarbonyl group, a 2,4-difluorophenyloxycarbonyl group, a 2-chlorophenyloxycarbonyl group, and a 4-chlorophenyloxycarbonyl group. The $C_1$-$C_4$ alkyl group represented by $X^{3h}$ can include a methyl group, an ethyl group, an isopropyl group, a butyl group, an isobutyl group, a sec-butyl group, and a tert-butyl group.

Examples of the $C_3$-$C_6$ alkenyl group represented by $X^{3h}$ can include an allyl group, a crotyl group, a methallyl group, a 1-buten-3-yl group, a prenyl group, and a 3-butenyl group.

Examples of the $C_3$-$C_6$ alkynyl group represented by $X^{3h}$ can include a propargyl group, a 1-butyn-3-yl group, a 2-butynyl group, and a 3-butynyl group.

Examples of the $C_7$-$C_8$ aralkyl group, which may be substituted, represented by $X^{3h}$ can include a benzyl group, an α-phenethyl group, and a β-phenethyl group. The aralkyl group may be substituted with a halogen atom such as a chlorine atom or a fluorine atom, or a trifluoromethyl group, and examples thereof include a 2-fluorobenzyl group, a 3-fluorobenzyl group, a 4-fluorobenzyl group, a 2-chlorobenzyl group, a 3-chlorobenzyl group, a 4-chlorobenzyl group, a 2,4-difluorobenzyl group, a 2,6-difluorobenzyl group, a 2,4,6-trifluorobenzyl group, a 2,3,4,5,6-pentafluorobenzyl group, a 2,4-dichlorobenzyl group, a 3,5-dichlorobenzyl group, a 2-(trifluoromethyl)benzyl group, a 3-(trifluoromethyl)benzyl group, and a 4-(trifluoromethyl)benzyl group.

The phenyl group, which may be substituted, represented by $X^{3h}$, may be substituted with one or more substituents selected from the group consisting of a halogen atom, a $C_1$-$C_4$ alkyl group, a $C_1$-$C_4$ haloalkyl group, a $C_1$-$C_4$ alkyloxy group, a $C_1$-$C_4$ haloalkyloxy group, a ($C_1$-$C_4$ alkyl) oxycarbonyl group, a cyano group, and a nitro group, and examples of the halogen atom can include a fluorine atom, a chlorine atom, a bromine atom, and an iodine atom, examples of the $C_1$-$C_4$ alkyl group can include a methyl group, an ethyl group, an isopropyl group, a butyl group, an isobutyl group, a sec-butyl group, and a tert-butyl group, examples of the $C_1$-$C_4$ haloalkyl group can include a difluoromethyl group, a chlorodifluoromethyl group, and a trifluoromethyl group, examples of the $C_1$-$C_4$ alkyloxy group can include a methoxy group, an ethoxy group, an isopropyloxy group, a butyloxy group, an isobutyloxy group, a sec-butyloxy group, and a tert-butyloxy group, examples of the $C_1$-$C_4$ haloalkyloxy group can include a trifluoromethyloxy group, and examples of the ($C_1$-$C_4$ alkyl) oxycarbonyl methyloxy group can include a methoxycarbonyl methyloxy group, an ethoxycarbonyl methyloxy group, an isopropyloxycarbonyl methyloxy group, and a tert-butyloxycarbonyl methyloxy group.

Examples of the halogen atom represented by $X^{4a}$, $X^{4b}$, $X^{4c}$, and $X^{4d}$ can include a fluorine atom, a chlorine atom, a bromine atom, and an iodine atom.

The $C_1$-$C_6$ alkyl group represented by $X^{4a}$ may be any one of a linear group or a branched group, and examples thereof can include a methyl group, an ethyl group, a propyl group, an isopropyl group, a butyl group, an isobutyl group, a sec-butyl group, a tert-butyl group, a pentyl group, and a hexyl group. The alkyl group may be substituted with one or more substituents selected from the group consisting of a ($C_1$-$C_4$ alkyl)oxycarbonyl group and a cyano group.

The $C_1$-$C_6$ alkyl group represented by $X^{4b}$ and $X^{4d}$ may be any one of a linear group or a branched group, and examples thereof can include a methyl group, an ethyl group, a propyl group, an isopropyl group, a butyl group, an isobutyl group, a sec-butyl group, a tert-butyl group, a pentyl group, and a hexyl group.

The $C_1$-$C_6$ haloalkyl group represented by $X^{4a}$, $X^{4b}$, $X^{4c}$, and $X^{4d}$ may be any one of a linear group or a branched group, and examples thereof can include a fluoromethyl group, a difluoromethyl group, a trifluoromethyl group, a 2,2,2-trifluoroethyl group, a perfluoroethyl group, a 3-fluoropropyl group, a trichloromethyl group, a dichloromethyl group, and a 2-chloroethyl group.

The $C_1$-$C_6$ alkyloxy group represented by $X^{4a}$ may be any one of a linear group or a branched group, and examples thereof can include a methoxy group, an ethoxy group, a propyloxy group, an isopropyloxy group, a butyloxy group, an isobutyloxy group, a sec-butyloxy group, a tert-butyloxy group, a pentyloxy group, and a hexyloxy group. The alkyloxy group may be substituted with a ($C_1$-$C_4$ alkyl) oxycarbonyl group such as a methoxycarbonyl group, an ethoxycarbonyl group, an isopropyloxycarbonyl group, an isobutyloxycarbonyl group, or a tert-butyloxycarbonyl group, or a cyano group, and examples thereof can include a methoxycarbonyl methyloxy group, an ethoxycarbonyl methyloxy group, a 1-(methoxycarbonyl)ethyloxy group, a 1-(ethoxycarbonyl)ethyloxy group, a 1-(methoxycarbonyl) propyloxy group, a 1-(ethoxycarbonyl)propyloxy group, a 1-(methoxycarbonyl)-2-methylpropyloxy group, a 1-(ethoxycarbonyl)-2-methylpropyloxy group, a 2-(methoxycarbonyl)ethyloxy group, a 2-(ethoxycarbonyl) ethyloxy group, a 3-(methoxycarbonyl)propyloxy group, a 3-(ethoxycarbonyl)propyloxy group, a 1-(ethoxycarbonyl) hexyloxy group, a cyanomethyloxy group, a 1-cyanoethyloxy group, 2-cyanoethyloxy group, and a 3-cyanopropyloxy group.

The $C_1$-$C_6$ alkyloxy group represented by $X^{4b}$ may be any one of a linear group or a branched group, and examples thereof can include a methoxy group, an ethoxy group, a propyloxy group, an isopropyloxy group, a butyloxy group, an isobutyloxy group, a sec-butyloxy group, a tert-butyloxy group, a pentyloxy group, and a hexyloxy group.

The $C_1$-$C_6$ alkyl group represented by $X^{4e}$ may be any one of a linear group or a branched group, and examples thereof can include a methyl group, an ethyl group, a propyl group, an isopropyl group, a butyl group, an isobutyl group, a sec-butyl group, a tert-butyl group, a pentyl group, and a hexyl group. The alkyl group may be substituted with a ($C_1$-$C_4$ alkyl)oxycarbonyl group such as a methoxycarbonyl group, an ethoxycarbonyl group, an isopropyloxycarbonyl group, an isobutyloxycarbonyl group, or a tert-butyloxycarbonyl group, or a cyano group, and examples thereof can include a methoxycarbonyl methyl group, an ethoxycarbonyl methyl group, a 1-(methoxycarbonyl)ethyl group, a 1-(ethoxycarbonyl)ethyl group, a 1-(methoxycarbonyl)propyl group, a 1-(ethoxycarbonyl)propyl group, a 1-(methoxycarbonyl)-2-methylpropyl group, a 1-(ethoxycarbonyl)-2-methylpropyl group, a 2-(methoxycarbonyl)ethyl group, a 2-(ethoxycarbonyl)ethyl group, a 3-(methoxycarbonyl)propyl group, a 3-(ethoxycarbonyl)propyl group, a 1-(ethoxycarbonyl)hexyl group, a cyanomethyl group, a 1-cyanoethyl group, 2-cyanoethyl group, and a 3-cyanopropyl group.

The $C_1$-$C_6$ haloalkyloxy group represented by $X^{4a}$, $X^{4b}$, and $X^{4c}$ may be any one of a linear group or a branched group, and examples thereof can include a fluoromethyloxy group, a difluoromethyloxy group, a trifluoromethyloxy group, a 2,2,2-trifluoroethyloxy group, a perfluoroethyloxy group, a 3-fluoropropyloxy group, a dichloromethyloxy group, and a trichloromethyloxy group.

The $C_1$-$C_6$ haloalkyl group represented by $X^{4e}$ may be any one of a linear group or a branched group, and examples thereof can include a fluoromethyl group, a difluoromethyl group, a trifluoromethyl group, a 2,2,2-trifluoroethyl group, a perfluoroethyl group, a 3-fluoropropyl group, a dichloromethyl group, and a trichloromethyl group.

The $C_2$-$C_6$ alkenyloxy group represented by $X^{4a}$ may be any one of a linear group or a branched group, and examples thereof can include a vinyloxy group, an allyloxy group, a crotyloxy group, a methallyloxy group, a 1-buten-3-yloxy group, a prenyloxy group, a 3-butenyloxy group, and a 2-hexenyloxy group. The alkenyloxy group may be substituted with one or more substituents selected from the group consisting of halogen atoms such as a chlorine atom and a fluorine atom; and phenyl groups which may be substituted with a halogen atom, such as a phenyl group, a 2-fluorophenyl group, a 4-fluorophenyl group, a 2-chlorophenyl group, and a 4-chlorophenyl group. From the viewpoint of high herbicidal activity, an allyloxy group, a crotyloxy group, a methallyloxy group, or a 1-buten-3-yloxy group is preferable.

The $C_2$-$C_6$ alkenyloxy group represented by $X^{4b}$ may be any one of a linear group or a branched group, and examples thereof can include a vinyloxy group, an allyloxy group, a crotyloxy group, a methallyloxy group, a 1-buten-3-yloxy group, a prenyloxy group, a 3-butenyloxy group, and a 2-hexenyloxy group.

The $C_2$-$C_6$ alkenyl group represented by $X^{4e}$ may be any one of a linear group or a branched group, and examples thereof can include a vinyl group, an allyl group, a crotyl group, a methallyl group, a 1-buten-3-yl group, a prenyl group, a 3-butenyl group, and a 2-hexenyl group. The alkenyl group may be substituted with one or more substituents selected from the group consisting of halogen atoms such as a chlorine atom and a fluorine atom; and phenyl groups which may be substituted with a halogen atom, such as a phenyl group, a 2-fluorophenyl group, a 4-fluorophenyl group, a 2-chlorophenyl group, and a 4-chlorophenyl group. From the viewpoint of high herbicidal activity, an allyl group, a crotyl group, a methallyl group, or a 1-buten-3-yl group is preferable.

Examples of the $C_2$-$C_6$ alkynyloxy group represented by $X^{4a}$ can include an ethynyloxy group, a propargyloxy group, and a 1-butyn-3-yloxy group. The alkynyl group may be substituted with a halogen atom such as a chlorine atom or a fluorine atom. From the viewpoint of high herbicidal activity, a propargyloxy group or a 1-butyn-3-yloxy group is preferable.

Examples of the $C_2$-$C_6$ alkynyl group represented by $X^{4e}$ can include an ethynyl group, a propargyl group, and a 1-butyn-3-yl group. The alkynyl group may be substituted with a halogen atom such as a chlorine atom or a fluorine atom. From the viewpoint of high herbicidal activity, a propargyl group or a 1-butyn-3-yl group is preferable.

Examples of the phenyl group, which may be substituted with one or more substituents selected from the group consisting of a halogen atom and a trifluoromethyl group, represented by $X^{4a}$ and $X^{4d}$ can include a 2-fluorophenyl group, a 3-fluorophenyl group, a 4-fluorophenyl group, a 2-chlorophenyl group, a 3-chlorophenyl group, a 4-chlorophenyl group, a 2,4-difluorophenyl group, a 2,4-dichlorophenyl group, a 2,4,6-trifluorophenyl group, a 2,4,6-trichlorophenyl group, a 2,6-difluoro-4-(trifluoromethyl)phenyl group, a 2,6-dichloro-4-(trifluoromethyl)phenyl group, a 2-chloro-6-fluoro-4-(trifluoromethyl)phenyl group, a 2-(trifluoromethyl)phenyl group, a 3-(trifluoromethyl)phenyl group, a 4-(trifluoromethyl)phenyl group, a 2,4-bis(trifluoromethyl)phenyl group, a 2-chloro-3,5-bis(trifluoromethyl) phenyl group, and a 2-bromo-3,5-bis(trifluoromethyl)phenyl group.

Examples of the ($C_1$-$C_4$ alkyl)oxycarbonyl group represented by $X^{4a}$ and $X^{4c}$ can include a methoxycarbonyl group, an ethoxycarbonyl group, a propyloxycarbonyl group, an isopropyloxycarbonyl group, an isobutyloxycarbonyl group, and a tert-butyloxycarbonyl group.

Examples of the halogen atom represented by $X^5$ can include a fluorine atom, a chlorine atom, a bromine atom, and an iodine atom.

The $C_1$-$C_6$ alkyl group represented by $X^5$ may be any one of a linear group or a branched group, and examples thereof can include a methyl group, an ethyl group, a propyl group, an isopropyl group, a butyl group, an isobutyl group, a sec-butyl group, a tert-butyl group, a pentyl group, and a hexyl group.

The $C_1$-$C_6$ haloalkyl group represented by $X^5$ may be any one of a linear group or a branched group, and examples thereof can include a fluoromethyl group, a difluoromethyl group, a trifluoromethyl group, a 2,2,2-trifluoroethyl group, a perfluoroethyl group, a 3-fluoropropyl group, a trichloromethyl group, and a dichloromethyl group.

The $C_1$-$C_6$ alkyloxy group represented by $X^5$ may be any one of a linear group or a branched group, and examples thereof can include a methoxy group, an ethoxy group, a propyloxy group, an isopropyloxy group, a butyloxy group, an isobutyloxy group, a sec-butyloxy group, a tert-butyloxy group, a pentyloxy group, and a hexyloxy group.

The $C_1$-$C_6$ haloalkyloxy group represented by $X^5$ may be any one of a linear group or a branched group, and examples thereof can include a fluoromethyloxy group, a difluoromethyloxy group, a trifluoromethyloxy group, a 2,2,2-trifluoroethyloxy group, a perfluoroethyloxy group, a 3-fluoropropyloxy group, a trichloromethyloxy group, and a dichloromethyloxy group.

Examples of the halogen atom represented by $X^6$ can include a fluorine atom, a chlorine atom, a bromine atom, and an iodine atom.

Examples of the counter ion represented by $X^7$ can include $Cl^-$, $F^-$, $Br^-$, $HSO_4^-$, $NO_3^-$, $ClO_4^-$, and $BF_4^-$. From the viewpoint of a favorable yield, $Cl^-$ or $BF_4^-$ is preferable.

Y represents a methylene group (—$CH_2$—), a fluoromethylene group (—CHF— or —$CF_2$—), a dimethylene group (—$CH_2CH_2$—), a trimethylene group (—$CH_2CH_2CH_2$—), a tetramethylene group (—$CH_2CH_2CH_2CH_2$—), an oxamethylene group (—$OCH_2$— or —$CH_2O$—), or an oxadimethylene group (—$OCH_2CH_2$—, —$CH_2OCH_2$—, or —$CH_2CH_2O$—). From the viewpoint of high herbicidal activity, Y is preferably a methylene group, a dimethylene group, a trimethylene group, or an oxadimethylene group, and more preferably a dimethylene group.

$R^1$, $X^1$, $X^2$, $X^3$ and Y in the compound of the present invention will be further described below.

When $R^1$ represents a halogen atom, a $C_1$-$C_4$ alkyl group, or a $C_1$-$C_4$ haloalkyl group as described above, $R^1$ is preferably a halogen atom or a trifluoromethyl group, and more preferably a chlorine atom or a trifluoromethyl group.

Each of $X^1$ and $X^2$ preferably independently may be the same as or different from each other, and represents a halogen atom, and $X^1$ more preferably represents a fluorine atom or a chlorine atom, and $X^2$ more preferably represents a chlorine atom.

$X^3$ represents a $C_1$-$C_{12}$ alkyloxy group which may be substituted with one or more substituents selected from the group consisting of a $C_1$-$C_6$ alkyloxy group, a ($C_1$-$C_4$ alkyl)oxycarbonyl group, and a cyano group; a $C_3$-$C_8$ cycloalkyloxy group; a $C_2$-$C_6$ alkenyloxy group which may be substituted with a halogen atom; an alkenyloxy group represented by General Formula (1-1a); a $C_2$-$C_6$ alkynyloxy group which may be substituted with a halogen atom; a $C_7$-$C_8$ aralkyloxy group which may be substituted with one or more substituents selected from the group consisting of a halogen atom and a trifluoromethyl group; a ($C_1$-$C_4$ alkyl) oxycarbonyl group; a cyano group; a phenyloxy group which may be substituted, represented by General Formula (1-2a); or an isoxazolin-5-yl methyloxy group represented by General Formula (1-3). A hydrogen atom or a fluorine atom is more preferable. $X^3$ is more preferably a $C_2$-$C_6$ alkenyloxy group or a $C_2$-$C_6$ alkynyloxy group.

Y is preferably a methylene group, a dimethylene group, a trimethylene group, or oxadimethylene group, and more preferably a dimethylene group.

The compound of the present invention having two or more types of preferable atoms or groups in $R^1$, $X^1$, $X^2$, $X^3$, and Y is preferable. For example, the following compounds are preferable.

A compound, in which (ii) in General Formula (1), each of $X^1$ and $X^2$ is independently the same as or different from each other, and is a halogen atom, $R^1$ is a halogen atom or a trifluoromethyl group, and Y is a methylene group, a dimethylene group, a trimethylene group, or an oxadimethylene group, and (iv) in General Formula (1), $X^3$ is a $C_1$-$C_{12}$ alkyloxy group which may be substituted with one or more substituents selected from the group consisting of a $C_1$-$C_6$ alkyloxy group, a ($C_1$-$C_4$ alkyl)oxycarbonyl group, and a cyano group; a $C_3$-$C_8$ cycloalkyloxy group; a $C_2$-$C_6$ alkenyloxy group which may be substituted with a halogen atom; an alkenyloxy group represented by General Formula (1-1a); a $C_2$-$C_6$ alkynyloxy group which may be substituted with a halogen atom; a $C_7$-$C_8$ aralkyloxy group which may be substituted with one or more substituents selected from the group consisting of a halogen atom and a trifluoromethyl group; a ($C_1$-$C_4$ alkyl)oxycarbonyl group; a cyano group; phenyloxy group which may be substituted, represented by General Formula (1-2a); or an isoxazolin-5-yl methyloxy group represented by General Formula (1-3). In the compound, a compound in which (v) $X^3$ is a $C_2$-$C_6$ alkenyloxy group or a $C_2$-$C_6$ alkynyloxy group is more preferable.

A compound, in which (iii) in General Formula (1), $X^1$ is a fluorine atom or a chlorine atom, $X^2$ is a chlorine atom, $R^1$ is a chlorine atom or a trifluoromethyl group, and Y is a dimethylene group, and (iv) in General Formula (1), $X^3$ is a $C_1$-$C_{12}$ alkyloxy group which may be substituted with one or more substituents selected from the group consisting of a $C_1$-$C_6$ alkyloxy group, a ($C_1$-$C_4$ alkyl)oxycarbonyl group, and a cyano group; a $C_3$-$C_8$ cycloalkyloxy group; a $C_2$-$C_6$ alkenyloxy group which may be substituted with a halogen atom; an alkenyloxy group represented by General Formula (1-1a); a $C_2$-$C_6$ alkynyloxy group which may be substituted with a halogen atom; a $C_7$-$C_8$ aralkyloxy group which may be substituted with one or more substituents selected from the group consisting of a halogen atom and a trifluoromethyl group; a ($C_1$-$C_4$ alkyl)oxycarbonyl group; a cyano group; a phenyloxy group which may be substituted, represented by General Formula (1-2a); or an isoxazolin-5-yl methyloxy group represented by General Formula (1-3). In the compound, a compound in which (v) $X^3$ is a $C_2$-$C_6$ alkenyloxy group or a $C_2$-$C_6$ alkynyloxy group is more preferable.

Next, representative preparation methods of the bicyclic pyrazolinone derivative of the present invention (hereinafter, also referred to as "the compound of the present invention") will be described; however, the present invention is not limited the preparation methods.

The bicyclic pyrazolinone derivative represented by the following general formula (1a) which is a part of the compound of the present invention can be prepared, for example, by the following Preparation Method-1.

Preparation Method-1

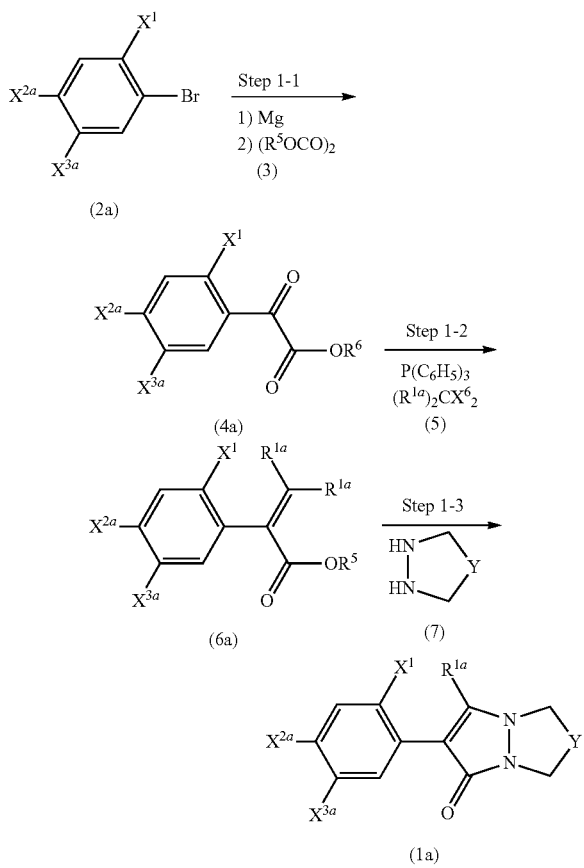

In the formula, $X^1$ and Y each have the same definition as described above. $X^{2a}$ represents a halogen atom, a cyano group, a thiocyano group, or a trifluoromethyl group. $R^{1a}$ represents a halogen atom, and two $R^{1a}$s may be the same as or different from each other. $R^5$ represents a $C_1$-$C_4$ alkyl group. $X^{3a}$ represents a hydrogen atom, a halogen atom, a $C_1$-$C_{12}$ alkyloxy group, a $C_3$-$C_8$ cycloalkyloxy group, a $C_2$-$C_6$ alkenyloxy group, a $C_5$-$C_8$ cycloalkenyloxy group, a nitro group, a ($C_1$-$C_4$ alkyl)oxycarbonyl group, a ($C_2$-$C_6$ alkenyl)oxycarbonyl group, a phenyloxycarbonyl group which may be substituted with a halogen atom, a cyano group, or a phenyloxy group which may be substituted, represented by General Formula (1-2b):

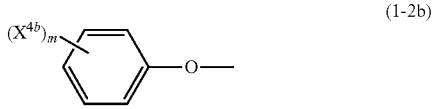

(in the formula, m has the same definition as described above; and $X^{4b}$ represents a hydrogen atom, a halogen atom, a $C_1$-$C_6$ alkyl group, a $C_1$-$C_6$ haloalkyl group, a $C_1$-$C_6$ alkyloxy group, a $C_1$-$C_6$ haloalkyloxy group, or a $C_2$-$C_6$ alkenyloxy group). $X^6$ represents a halogen atom.

Preparation Method 1 includes Step 1-1 of preparing a 2-substituted phenyl-2-oxoacetic acid ester (4a) by reacting the Grignard reagent prepared from a substituted phenyl bromide (2a) with oxalic acid diester (3); Step 1-2 of performing dihalomethylenation by treating the α-position carbonyl group of the 2-substituted phenyl-2-oxoacetic acid ester (4a) with the Wittig reagent prepared from triphenylphosphine and the compound represented by General Formula (5); and Step 1-3 of preparing a bicyclic pyrazolinone derivative (1a) which is a part of the compound of the present invention, by reacting a 2-substituted phenyl acrylic acid ester (6a) with cyclic hydrazine (7) or a chemically acceptable salt thereof, optionally in the presence of a base. Hereinafter, each step in Preparation Method-1 will be described in detail.

Step 1-1 is a step of preparing the 2-substituted phenyl-2-oxoacetic acid ester (4a) by reacting the Grignard reagent prepared from the substituted phenyl bromide (2a) with oxalic acid diester (3).

The Grignard reagent prepared from the substituted phenyl bromide (2a) can be prepared according to a general preparation method of a Grignard reagent, and, for example, the Grignard reagent can be easily prepared by adding an organic solvent to magnesium metal, by adding the substituted phenyl bromide (2a) thereto, and by stirring the resultant product. As the organic solvent, an ether-based solvent such as tetrahydrofuran (hereinafter, abbreviated to as THF), dimethoxyethane (hereinafter, abbreviated to as DME), or diethyl ether can be used, and THF is preferable from the viewpoint of a favorable yield. The reaction temperature is not particularly limited, and the reaction sufficiently proceeds at room temperature; however, if necessary, heating may be performed. In addition, by adding a catalytic amount of iodine, the reaction can be promoted.

The Grignard reagent prepared from the substituted phenyl bromide (2a) can also be prepared according to a Grignard exchange reaction (for example, refer to P. Knochel, A. Krasovskiy and I. Sapountzis, Hand book of Functionalized Organometallics, WILEY-VCH Verlag GmbH & Co. KGaA, Weinheim, p. 09-172) known to those skilled in the art, and for example, the Grignard reagent can be easily prepared by adding a solution of isopropyl magnesium chloride in THF to a solution (for example, THF solution) of a substituted phenyl bromide (2a) at a low temperature, and by reacting the resultant product while slowly raising the temperature to room temperature. As the organic solvent, in addition to THF, an ether-based solvent such as DME or diethyl ether can be used, and THF is preferable from the viewpoint of a favorable yield.

It is known to those skilled in the art that the Grignard reagent can also be prepared using substituted phenyl iodide instead of using a substituted phenyl bromide (2a), and in this case, commercially available substituted phenyl iodide or substituted phenyl iodide which can be easily prepared from commercially available raw materials may be used.

The Grignard reagent prepared from the substituted phenyl bromide (2a), in a solution state without isolation, can be reacted with oxalic acid diester (3). That is, for example, the 2-substituted phenyl-2-oxoacetic acid ester (4a) which is a target substance can be prepared by adding the Grignard reagent prepared from the substituted phenyl bromide (2a) to a solution (for example, THF solution) of diethyl oxalate at a low temperature, and by reacting the resultant product while slowly raising the temperature to room temperature. In addition, the 2-substituted phenyl-2-oxoacetic acid ester (4a) which is a target substance can also be prepared by adding a solution (for example, THF solution) of diethyl oxalate (3) to a solution of the Grignard reagent prepared from the substituted phenyl bromide (2a) at a low temperature, and by reacting the resultant product while slowly raising the temperature to room temperature. As the organic solvent, an ether-based solvent such as THF, DME, or diethyl ether can be used, and THF is preferable from the viewpoint of a favorable yield. Although the reaction temperature is not particularly limited, in order to suppress a vigorous reaction, it is preferable from the viewpoint of a favorable yield that the reaction is performed at a low temperature of about −78° C. to −40° C. in the initial stage of reaction, and the reaction is performed while slowly raising the temperature to room temperature.

A part of commercially unavailable compounds among the substituted phenyl bromides (2a) used in Step 1-1 can be easily prepared by making a commercially available corresponding compound have desired substituents on the benzene ring by a general chemical method known to those skilled in the art. As a specific example, for example, a substituted phenyl bromide (5-bromo-2-chloro-4-fluoroanisole) in which $X^1$ is a fluorine atom, $X^{2a}$ is a chlorine atom, and $X^{3a}$ is a methoxy group can be prepared by the following methods.

Example (1) of a preparation method of 5-bromo-2-chloro-4-fluoroanisole

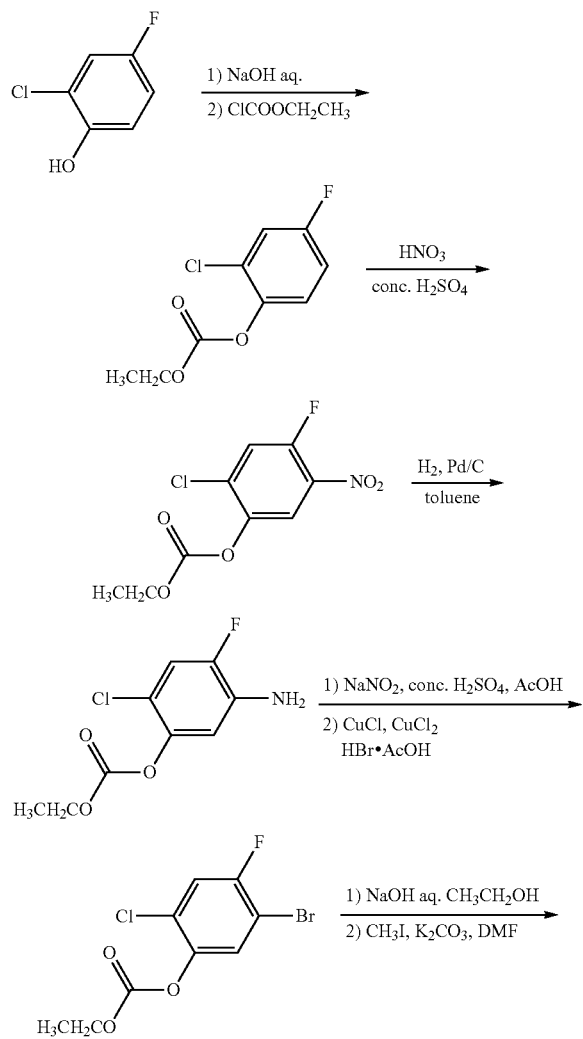

Example (2) of a preparation method of 5-bromo-chloro-4-fluoroanisole

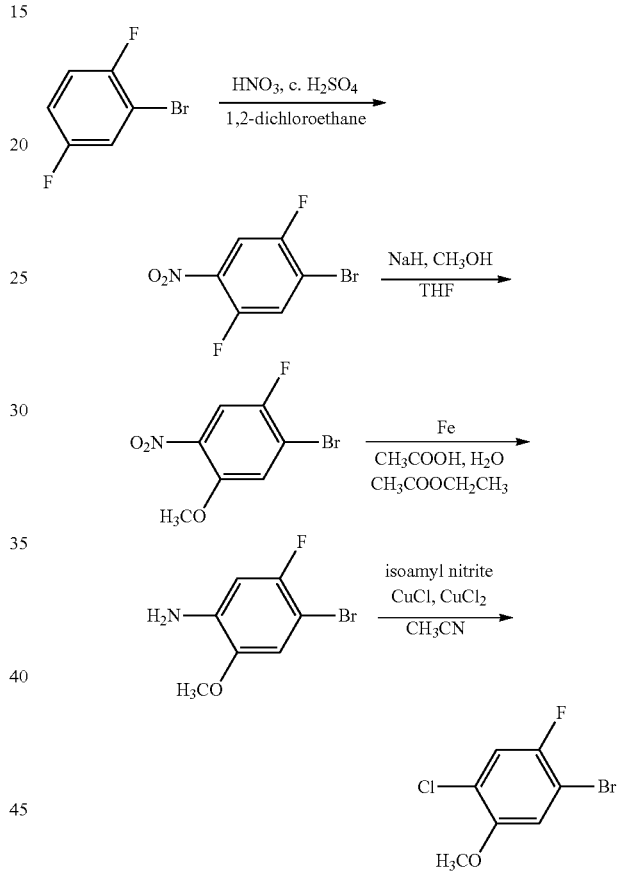

Step 1-2 is a step of preparing the 2-substituted phenyl acrylic acid ester (6a) by performing dihalomethylenation by treating the α-position carbonyl group of the 2-substituted phenyl-2-oxoacetic acid ester (4a) with the Wittig reagent prepared from triphenylphosphine and the compound represented by General Formula (5).

The 2-substituted phenyl acrylic acid ester (6a) in which $R^{1a}$ is a chlorine atom can be easily prepared by reacting dichloromethylene triphenyl phosphorane (phosphorus ylide) of a Wittig reagent prepared from triphenylphosphine and carbon tetrachloride ($R^{1a}$=$X^6$=Cl) with the 2-substituted phenyl-2-oxo acetic acid ester (4a).

Dichloromethylene triphenyl phosphorane can be easily prepared by reacting triphenylphosphine with carbon tetrachloride, for example, at a temperature of about 0° C. to room temperature in an organic solvent such as dichloromethane. The reaction of dichloromethylene triphenyl phosphorane with the 2-substituted phenyl-2-oxoacetic acid ester (4a) can be performed under heat conditions of about room temperature to 100° C. The reaction can be performed in an organic solvent, and any solvent can be used as long as it does not adversely affect the reaction, and a halogen-based solvent such as dichloromethane or chloroform is preferable from the viewpoint of a favorable yield. After the reaction is completed, the 2-substituted phenyl acrylic acid ester (6a) can be obtained by a general post-treatment, and can be purified by silica gel column chromatography or distillation.

Although the tertiary phosphine used in the preparation of phosphorus ylide is not limited to triphenylphosphine, triphenylphosphine is preferable from the viewpoint of ease of availability and a favorable yield.

The 2-substituted phenyl acrylic acid ester (6a) in which $R^{1a}$ is a fluorine atom can be easily prepared by reacting difluoromethylene triphenyl phosphorane which is a Wittig reagent with the 2-substituted phenyl-2-oxoacetic acid ester (4a).

As the difluoromethylenation reaction of α-ketoesters using difluoromethylene triphenyl phosphorane, a method (U.S. Pat. No. 4,001,301, Pamphlet of International Publication No. 2001-095721, or JP-A-2004-503475) using difluoromethyl triphenyl phosphorane prepared from sodium chlorodifluoroacetate and triphenylphosphine is disclosed. In addition, a method (JP-A-2008-195678 or JP-A-2008-195679) in which dibromodifluoromethane is reacted with triphenylphosphine in an N,N-dimethylacetamide solution to form a phosphonium salt, and powdered zinc is added thereto to prepare difluoromethylene triphenyl phosphorane, and the obtained difluoromethylene triphenyl phosphorane is used in the difluoromethylenation reaction of α-ketoesters is disclosed. In Step 1-2, the 2-substituted phenyl acrylic acid ester (6a) in which $R^{1a}$ is a fluorine atom, which is a target substance can be easily prepared by performing a reaction according to the method described in these patent literature.

In addition, in the Step 1-2, the 2-substituted phenyl acrylic acid ester (6a) in which one of two $R^{1a}$s is a chlorine atom, and the other is a fluorine atom can be prepared by preparing chlorofluoromethylene triphenyl phosphorane using trichlorofluoromethane instead of dibromodifluoromethane, as the compound represented by General Formula (5), and by reacting this with the 2-substituted phenyl-2-oxoacetic acid ester (4a).

Step 1-3 is a step of preparing the bicyclic pyrazolinone derivative (1a) which is a part of the compound of the present invention, by reacting the 2-substituted phenyl acrylic acid ester (6a) with the cyclic hydrazine (7) or a chemically acceptable salt thereof, optionally in the presence of a base.

Specific examples of the cyclic hydrazine (7) can include pyrazolidine, 4-fluoropyrazolidine, hexahydropyridazine, 1,2-diazacycloheptane, 1,3,4-oxadiazolidine, 1,4,5-oxadiazepane, 4-methyl-1,2,4-triazolidine, and 5-methyl-1,2,5-triazepane. Although these cyclic hydrazines can be used in the reaction in a free form, these cyclic hydrazines can also be used in a form of chemically acceptable salt such as hydrochloride or sulfate thereof. A part of commercially unavailable compounds among these cyclic hydrazines (7) can be easily prepared by a general chemical method known to those skilled in the art. For example, hexahydropyridazine can be prepared by a known method (JP-A-8-109170 or JP-A-10-29981).

The reaction of Step 1-3 can be performed in a solvent. As the solvent, any solvent can be used as long as it does not adversely affect the reaction, and examples thereof can include ether-based solvents such as 1,4-dioxane, THF, DME, diethyl ether, diisopropyl ether, and cyclopentyl methyl ether, aromatic hydrocarbon-based solvents such as benzene, toluene, and chlorobenzene, hydrocarbon-based solvents such as hexane and octane, ketone-based solvents such as acetone, methyl ethyl ketone, diethyl ketone, and cyclohexanone, ester-based solvents such as ethyl acetate and ethyl propionate, nitrile-based solvents such as acetonitrile and propionitrile, amide-based solvents such as N,N-dimethyl formamide (hereinafter, abbreviated to as DMF) and N,N-dimethyl acetamide, sulfoxide-based solvents such as dimethyl sulfoxide (hereinafter, abbreviated to as DMSO), water, and mixed solvents thereof. Preferably, ether-based solvents such as 1,4-dioxane and THF can be exemplified.

The reaction temperature is not particularly limited, and the reaction can be performed at a temperature suitably selected within the range of room temperature to a reflux temperature of the solvent used.

When performing the reaction, the reaction can also be promoted by adding a base. Examples of the base can include organic bases such as triethylamine, tributylamine, and pyridine, inorganic bases such as sodium carbonate, potassium carbonate, cesium carbonate, sodium hydroxide, and potassium hydroxide, and alkali metal alkoxides such as sodium methoxide, sodium ethoxide, and potassium tert-butoxide. Preferably, organic bases such as triethylamine can be exemplified. In the case of using a salt of the cyclic hydrazine (7), it is preferable from the viewpoint of a short reaction time and a favorable yield that the reaction is performed by adding a greater amount of base than the amount corresponding to acid forming the salt.

In Steps 1-1, 1-2, and 1-3, after the reaction is completed, the target substance is isolated from the reaction system including the target substance by a method generally used in the related art, and if necessary, the target substance can be purified by recrystallization, distillation, column chromatography, or the like. In addition, without purifying the obtained target product, the obtained target product can be used in the subsequent step as a starting material, in some case.

The bicyclic pyrazolinone derivative represented by the following general formula (1c, 1d), which is a part of the compound of the present invention, can be prepared, for example, by the following Preparation Method-2.

Preparation Method-2

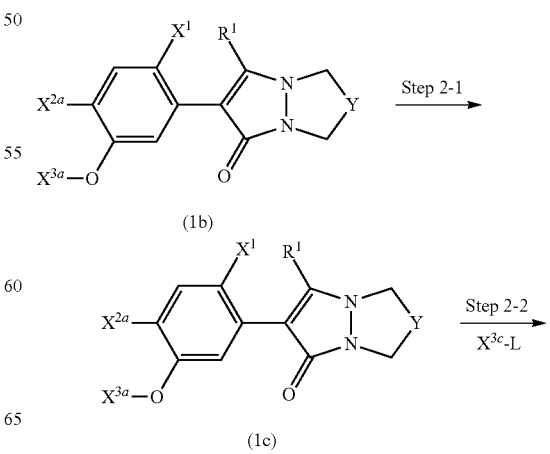

-continued

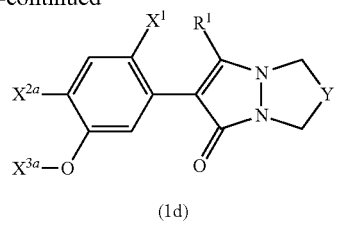

(1d)

In the formula, $R^1$, $X^1$, $X^{2a}$, and Y each have the same definition as described above. $X^{3b}$ represents a methyl group or a tert-butyl group. $X^{3c}$ represents a $C_1$-$C_{12}$ alkyl group which may be substituted with one or more substituents selected from the group consisting of a $C_1$-$C_6$ alkyloxy group, a ($C_1$-$C_4$ alkyl)oxycarbonyl group, and a cyano group; a $C_1$-$C_{12}$ haloalkyl group; a $C_3$-$C_8$ cycloalkyl group; a glycidyl group; a $C_2$-$C_6$ alkenyl group which may be substituted with one or more substituents selected from the group consisting of a halogen atom and a ($C_1$-$C_4$ alkyl) oxycarbonyl group; an alkenyl group represented by General Formula (1-1b):

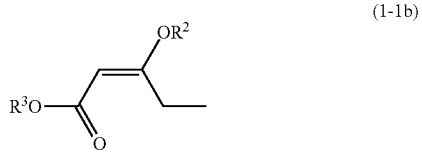

(1-1b)

(in the formula, $R^2$ and $R^3$ each have the same definition as described above); a $C_5$-$C_8$ cycloalkenyl group; a $C_2$-$C_6$ alkynyl group which may be substituted with a halogen atom; a $C_7$-$C_8$ aralkyl group which may be substituted with a halogen atom or a trifluoromethyl group; a ($C_1$-$C_4$ alkyl) oxycarbonyl group; a ($C_2$-$C_6$ alkenyl)oxycarbonyl group; a phenyloxycarbonyl group which may be substituted with a halogen atom; a $C_1$-$C_4$ alkyl sulfonyl group; a $C_1$-$C_4$ haloalkyl sulfonyl group; a phenyl sulfonyl group which may be substituted with one or more substituents selected from the group consisting of a halogen atom and a $C_1$-$C_4$ alkyl group; a phenyl group which may be substituted, represented by General Formula (1-2c):

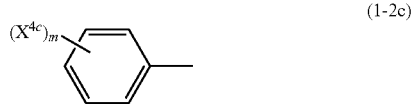

(1-2c)

(in the formula, m has the same definition as described above; and $X^{4c}$ represents a halogen atom, a $C_1$-$C_6$ haloalkyl group, a $C_1$-$C_6$ haloalkyloxy group, a ($C_1$-$C_4$ alkyl)oxycarbonyl group, a cyano group, a nitro group, or an amino group); a pyridyl group which may be substituted with one or more substituents selected from the group consisting of a halogen atom, a $C_1$-$C_4$ alkyl group, a $C_1$-$C_4$ haloalkyl group, a $C_1$-$C_4$ alkyloxy group, a $C_1$-$C_4$ alkyloxycarbonyl methyloxy group, a cyano group, and a nitro group; or a pyridyl methyl group which may be substituted with one or more substituents selected from the group consisting of a halogen atom, a $C_1$-$C_4$ alkyl group, a $C_1$-$C_4$ haloalkyl group, a cyano group, and a nitro group. L represents a leaving group.

Preparation Method-2 includes Step 2-1 of preparing a bicyclic pyrazolinone derivative (1c) having a hydroxyl group on a benzene ring by removing the protecting group of the hydroxyl group on the benzene ring of a bicyclic pyrazolinone derivative (1b); and Step 2-2 of preparing a bicyclic pyrazolinone derivative (1d) which is a part of the compound of the present invention by reacting the bicyclic pyrazolinone derivative (1c) with the compound represented by General Formula (8a) in the presence of a base. Hereinafter, each step in Preparation Method-2 will be described in detail.

Step 2-1 is a step of preparing the bicyclic pyrazolinone derivative (1c) having a hydroxyl group on a benzene ring by removing the protecting group (substituent $X^{3b}$ is a methyl group or a tert-butyl group) of the hydroxyl group on the benzene ring of the bicyclic pyrazolinone derivative (1b).

In a case where $X^{3b}$ is a methyl group, the bicyclic pyrazolinone derivative (1c) which is a target substance can be prepared by a known method (for example, P. G. M. Wuts and T. W. Greene, Protective Groups in Organic Synthesis, A John Wiley & Sons, Inc., p. 25-30, p. 370-382) effective for cleavage of the methyl ether bond. Among these, deprotection using boron tribromide is preferable from the viewpoint of a favorable yield or selectivity.

The deprotection reaction using boron tribromide can be performed in an organic solvent such as dichloromethane or ethyl acetate. From the viewpoint of a favorable yield, a method using dichloromethane is preferable. The reaction can be performed at a temperature suitably selected within the range of −80° C. to 60° C. Although the used amount of boron tribromide is not particularly limited, usually, about 1 mole to 5 moles thereof may be used with respect to 1 mole of the bicyclic pyrazolinone derivatives (1b).

In a case where $X^{3b}$ is a tert-butyl group, the bicyclic pyrazolinone derivative (1c) which is a target substance can be prepared by a known method (for example, P. G. M. Wuts and T. W. Greene, Greene's Protective Groups in Organic Synthesis, A John Wiley & Sons, Inc., p. 82-84, p. 396) effective for cleavage of the tert-butyl ether bond. Usually, deprotection using acid such as hydrochloric acid, hydrobromic acid, or trifluoroacetic acid is preferable from the viewpoints of simplicity of a reaction, or a favorable yield or selectivity.

The bicyclic pyrazolinone derivatives (1b) which is a starting material in Step 2-1 is a bicyclic pyrazolinone derivative in which the substituent $X^{3a}$ on the benzene ring of the bicyclic pyrazolinone derivative (1a) described in Preparation Method-1 is a methoxy group ($X^{3b}$=methyl group) or a tert-butyloxy group ($X^{3b}$=tert-butyl group), and can be prepared by the method described in Preparation Method-1.

Step 2-2 is a step of preparing the bicyclic pyrazolinone derivative (1d) which is a part of the compound of the present invention by reacting the bicyclic pyrazolinone derivatives (1c) with the compound represented by General Formula (8a) in the presence of a base.

Step 2-2 is performed in the presence of a base. Examples of the base can include organic bases such as triethylamine, tributylamine, and pyridine, inorganic bases such as sodium hydride, sodium amide, sodium carbonate, potassium carbonate, cesium carbonate, sodium hydroxide, and potassium hydroxide, alkali metal alkoxides such as sodium methoxide, sodium ethoxide, and potassium tert-butoxide, lithium bases such as methyl lithium and butyl lithium.

The reaction of Step 2-2 can be performed in an organic solvent. As the organic solvent, any organic solvent can be used as long as it does not adversely affect the reaction, and examples thereof can include ether-based solvents such as 1,4-dioxane, THF, DME, diethyl ether, diisopropyl ether, and cyclopentyl methyl ether, aromatic hydrocarbon-based solvents such as benzene, toluene, and chlorobenzene, hydrocarbon-based solvents such as hexane and octane, ketone-based solvents such as acetone, methyl ethyl ketone, diethyl ketone, and cyclohexanone, ester-based solvents such as ethyl acetate and ethyl propionate, nitrile-based solvents such as acetonitrile and propionitrile, amide-based solvents such as DMF and N,N-dimethyl acetamide, sulfoxide-based solvents such as DMSO, and mixed solvents thereof.

The reaction temperature is not particularly limited, and the reaction may be performed at a temperature suitably selected within the range of −78° C. to a reflux temperature of the solvent used.

In the compound ($X^{3c}$-L) represented by General Formula (8a), examples of the leaving group represented by L can include a fluorine atom, a chlorine atom, a bromine atom, an iodine atom, and substituted sulfonyloxy groups such as a methyl sulfonyloxy group, a trifluoromethyl sulfonyloxy group, a phenyl sulfonyloxy group, and a 4-methyl phenyl sulfonyloxy group.

A part of commercially unavailable compounds among the compounds represented by General Formula (8a) can be easily prepared by a general chemical method known to those skilled in the art. For example, 3-alkoxy-4-chlorocrotonic acid ester in which $X^{3c}$ is an alkenyl group represented by General Formula (1-1b), and the leaving group L is a chlorine atom can be prepared by the following method. In the 3-alkoxy-4-chlorocrotonic acid ester prepared by this method, a compound in which the stereochemistry of the double bond thereof is an E-form is the main product, but, the present invention may have any form of an E-form, a Z-form, or a mixture thereof.

Example of a preparation method of 3-alkoxy-4-chlorocrotonic acid ester

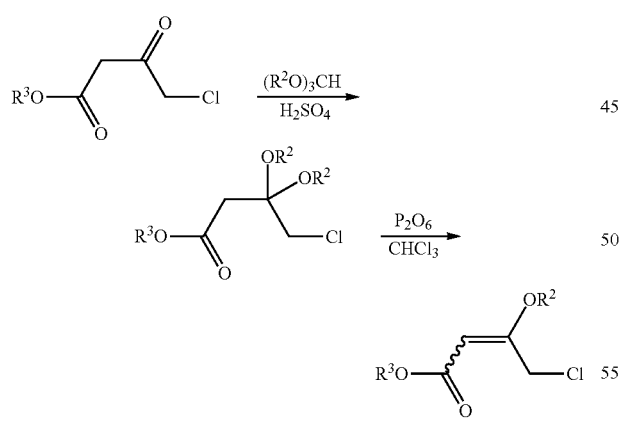

In the formula, $R^2$ and $R^3$ each have the same definition as described above.

A part of commercially unavailable compounds among the halobenzenes in which $X^{3c}$ is a phenyl group which may be substituted, represented by General Formula (1-2c) and the leaving group L is a halogen atom can be easily prepared by a general chemical method known to those skilled in the art. In the case of using the halobenzene as a reaction reagent in Step 2-2, the substituent $X^{4c}$ on the benzene ring is preferably an electron withdrawing group such as a halogen atom such as a fluorine atom or a chlorine atom, a fluorine-substituted alkyl group such as a trifluoromethyl group, a fluorine-substituted alkyloxy group such as a trifluoromethyloxy group, an alkyloxycarbonyl group such as a methoxycarbonyl group, a cyano group, or a nitro group from the viewpoint of a favorable yield.

In Steps 2-1 and 2-2, after the reaction is completed, the target substance is isolated from the reaction system including the target substance by a method generally used in the related art, and if necessary, the target substance can be purified by recrystallization, distillation, column chromatography, or the like. In addition, without purifying the obtained target product, the obtained target product can be used in the subsequent step as a starting material, in some case.

In addition, the bicyclic pyrazolinone derivative represented by the following general formulas (1e, 1f, 1g), which is a part of the compound of the present invention, can be prepared, for example, by the following Preparation Method-3.

Preparation Method-3

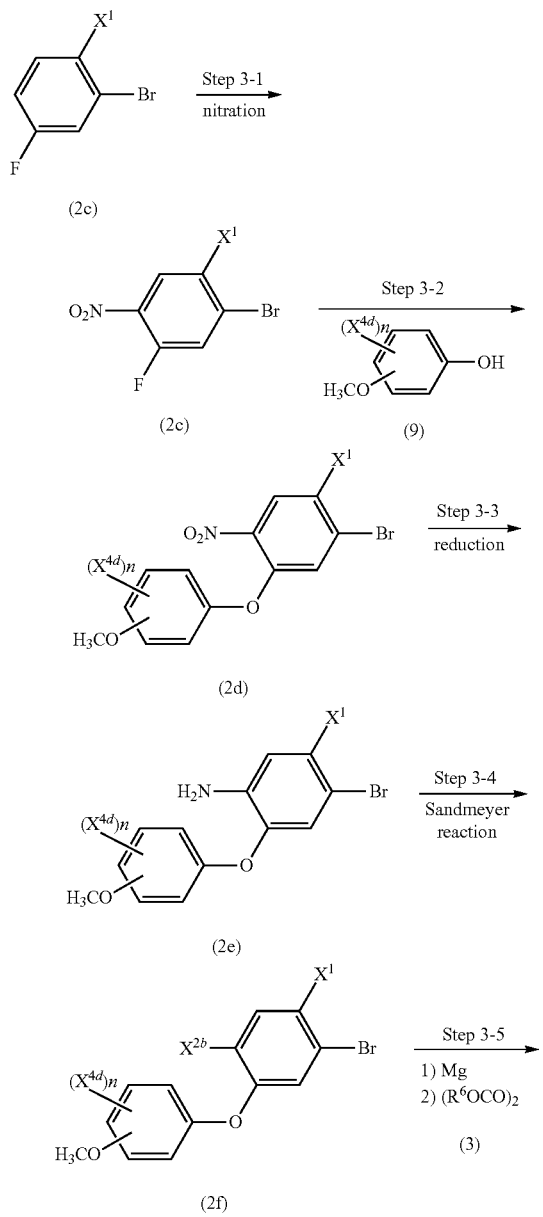

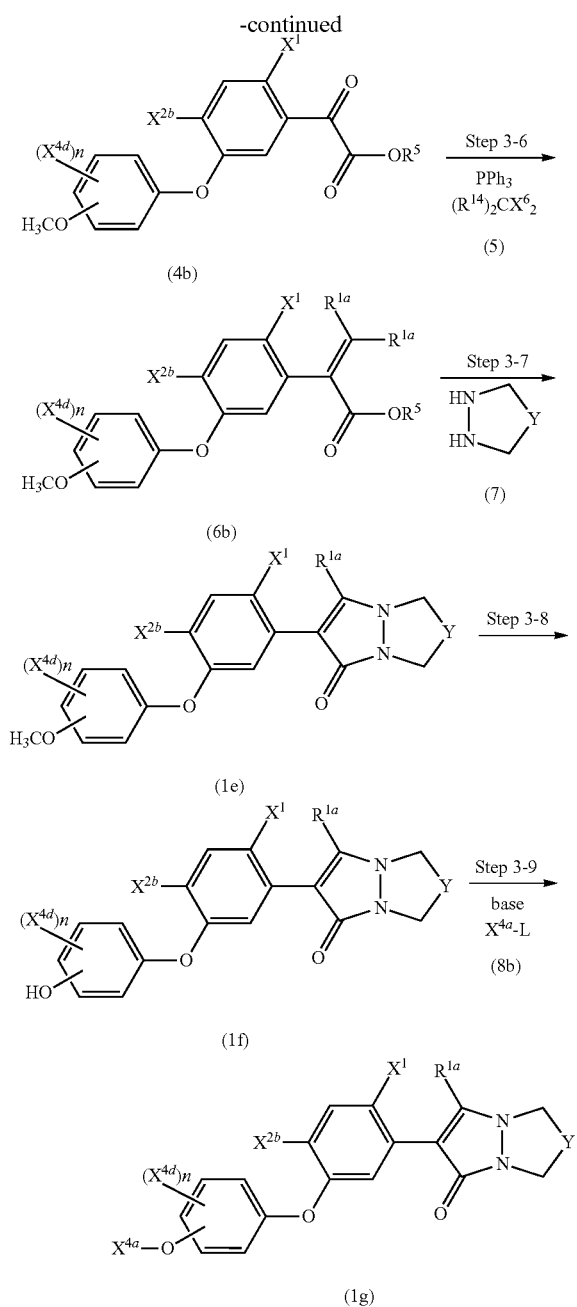

Preparation Method-3 includes Step 3-1 of preparing 3-fluoro-4-nitrophenyl bromide (2c) by nitrating 3-fluorophenyl bromide (2b); Step 3-2 of preparing 3-substituted phenoxy-4-nitrophenyl bromide (2d) by substituting the 3-position fluorine atom with a phenoxy group by reacting the 3-fluoro-4-nitrophenyl bromide (2c) with phenol (9) in the presence of a base; Step 3-3 of preparing 3-substituted phenoxy-4-aminophenyl bromide (2e) by converting into an amino group by reducing the nitro group of the 3-substituted phenoxy-4-nitrophenyl bromide (2d); Step 3-4 of preparing substituted phenyl bromide (2f) by azidating the amino group of the 3-substituted phenoxy-4-aminophenyl bromide (2e) and by converting into a halogen atom, a cyano group, or a thiocyano group by a so-called Sandmeyer reaction; Step 3-5 of preparing 2-substituted phenyl-2-oxoacetic acid ester (4b) by reacting the Grignard reagent prepared from the substituted phenyl bromide (2f) with oxalic acid diester (3); Step 3-6 of preparing 2-substituted phenyl acrylic acid ester (6b) by performing dihalomethylenation by treating the α-position carbonyl group of the 2-substituted phenyl-2-oxoacetic acid ester (4b) with the Wittig reagent prepared from triphenylphosphine and the compound represented by General Formula (5); Step 3-7 of preparing a bicyclic pyrazolinone derivative (1e) which is a part of the compound of the present invention by reacting the 2-substituted phenyl acrylic acid ester (6b) with the cyclic hydrazine (7) or a chemically acceptable salt thereof, optionally in the presence of a base; Step 3-8 of preparing a bicyclic pyrazolinone derivative (1f) which is a part of the compound of the present invention by converting the methoxy group on the benzene ring of the bicyclic pyrazolinone derivative (1e) into a hydroxyl group; and Step 3-9 of preparing a bicyclic pyrazolinone derivative (1g) which is a part of the compound of the present invention by reacting the bicyclic pyrazolinone derivative (1f) with the compound represented by General Formula (8b) in the presence of a base. Hereinafter, each step in Preparation Method-3 will be described in detail.

Step 3-1 is a step of preparing the 3-fluoro-4-nitrophenyl bromides (2c) by nitrating 3-fluorophenyl bromide (2b).

As the nitration in Step 3-1, for example, a method for nitrating using a mixed acid prepared from concentrated nitric acid and concentrated sulfuric acid in concentrated sulfuric acid or a method for nitrating using fuming nitric acid without a solvent or in a solvent such as dichloromethane can be used. The reaction conditions are not particularly limited, and the 3-fluoro-4-nitrophenyl bromide (2c) which is a target substance can be prepared with a favorable yield and regioselectivity by performing a reaction according to a general method for nitrating a benzene ring. Step 3-2 is a step of preparing the 3-substituted phenoxy-4-nitrophenyl bromide (2d) by substituting the 3-position fluorine atom with a phenoxy group by reacting the 3-fluoro-4-nitrophenyl bromides (2c) with phenol (9) in the presence of a base.

The reaction of Step 3-2 is performed in the presence of a base. Examples of the base can include organic bases such as triethylamine, tributylamine, and pyridine, inorganic bases such as sodium hydride, sodium amide, sodium carbonate, potassium carbonate, cesium carbonate, sodium hydroxide, and potassium hydroxide, alkali metal alkoxides such as sodium methoxide, sodium ethoxide, and potassium tert-butoxide, and lithium bases such as methyl lithium and butyl lithium. From the viewpoint of a favorable yield, sodium hydride or potassium tert-butoxide is preferable.

The reaction of Step 3-2 can be performed in an organic solvent. As the organic solvent, any organic solvent can be used as long as it does not adversely affect the reaction, and In the formula, $R^{1a}$, $R^5$, $X^1$, $X^6$, and Y each have the same definition as described above. $X^{2b}$ represents a halogen atom, a cyano group, or a thiocyano group. $X^{4d}$ represents a hydrogen atom; a halogen atom; a $C_1$-$C_6$ alkyl group; a $C_1$-$C_6$ haloalkyl group; or a phenyl group which may be substituted with one or more substituents selected from the group consisting of a halogen atom and a trifluoromethyl group. n is 1 or 2. $X^{4e}$ represents a $C_1$-$C_6$ alkyl group which may be substituted with one or more substituents selected from the group consisting of a ($C_1$-$C_4$ alkyl)oxycarbonyl group and a cyano group; a $C_1$-$C_6$ haloalkyl group; a $C_2$-$C_6$ alkenyl group which may be substituted with one or more substituents selected from the group consisting of a halogen atom and a phenyl group which may be substituted with a halogen atom; a $C_2$-$C_6$ alkynyl group which may be substituted with a halogen atom; or an alkenyl group represented by General Formula (1-1b).

examples thereof can include ether-based solvents such as 1,4-dioxane, THF, DME, diethyl ether, diisopropyl ether, and cyclopentyl methyl ether, aromatic hydrocarbon-based solvents such as benzene, toluene, and chlorobenzene, hydrocarbon-based solvents such as hexane and octane, ketone-based solvents such as acetone, methyl ethyl ketone, diethyl ketone, and cyclohexanone, ester-based solvents such as ethyl acetate and ethyl propionate, nitrile-based solvents such as acetonitrile and propionitrile, amide-based solvents such as DMF and N,N-dimethyl acetamide, sulfoxide-based solvents such as DMSO, and mixed solvents thereof.

The reaction of Step 3-2 can be performed at a temperature suitably selected within the range of −30° C. to 100° C. From the viewpoint that a side reaction or an excessive reaction can be suppressed, the reaction of Step 3-2 is preferably performed at a temperature of about 0° C. to 60° C.

Examples of the phenol (9) can include phenols in which a methoxy group is substituted; phenols in which a halogen atom such as a fluorine atom or a chlorine atom, and a methoxy group are substituted; phenols in which an alkyl group such as a methyl group, an ethyl group, an isopropyl group, a tert-butyl group, a hexyl group, or a cyclohexyl group, and a methoxy group are substituted; phenols in which a haloalkyl group such as a trifluoromethyl group, a perfluoroethyl group, a hexafluoroisopropyl group, a perfluoroisopropyl group, or a perfluorohexyl group, and a methoxy group are substituted; phenols in which one or more substituents selected from the group consisting of a halogen atom, a $C_1$-$C_6$ alkyl group, and a $C_1$-$C_6$ haloalkyl group, and a methoxy group are substituted; and phenols in which a phenyl group which may substituted with one or more substituents selected from the group consisting of a halogen atom such a fluorine atom or a chlorine atom and a trifluoromethyl group, and a methoxy group are substituted. A part of commercially unavailable compounds among these phenols (9) can be easily prepared by a general chemical method known to those skilled in the art. The substitution position of the methoxy group in the phenols (9) is preferably the ortho position of the hydroxyl group from the viewpoint of high herbicidal activity of the bicyclic pyrazolinone derivative (1g) prepared by a conversion step after the present step.

Step 3-3 is a step of preparing the 3-substituted phenoxy-4-aminophenyl bromide (2e) by reducing the nitro group of the 3-substituted phenoxy-4-nitrophenyl bromide (2d).

In the reduction, catalytic reduction using hydrogen gas or hydrazine, or metal reduction using a metal such as iron, tin, or zinc, or a metal compound thereof can be used.

In the catalytic reduction, a metal catalyst such as palladium, platinum, nickel, ruthenium, rhodium, or osmium is used. Examples of the palladium catalyst can include palladium black and palladium on carbon, examples of the platinum catalyst can include platinum on carbon and platinum(IV) oxide hydrate, examples of the nickel catalyst can include is Raney nickel, and examples of the metal catalyst of ruthenium, rhodium, or osmium can include ruthenium on carbon, rhodium on carbon, and osmium on carbon. The used amount of the metal catalyst may usually be 0.0001 mol % to 10 mol %, and preferably about 0.1 mol % to 1.0 mol % with respect to the 3-substituted phenoxy-4-nitrophenyl bromide (2d).

In the case of using hydrogen gas as a reductant, the pressure of the hydrogen gas is not particularly limited, and may be applied if necessary, and in this case, a reaction may be performed at a pressure suitably selected within the range of usually 0.1 MPa to 1 MPa, and preferably 0.1 MPa to 0.5 MPa. In the case of using hydrazine as a reductant, a target substance can be obtained with a high yield by using 1 mole to 25 moles of hydrazine with respect to 1 mole of the 3-substituted phenoxy-4-nitrophenyl bromide (2d).

The reduction reaction may be performed at a reaction temperature suitably selected within the range of usually 20° C. to 100° C., and preferably 40° C. to 80° C.

In the reaction of the catalytic reduction, a suitable reaction solvent is used if necessary. Examples of the reaction solvent include water and organic solvents including alcohol-based solvents such as methanol, ethanol, propyl alcohol, isopropyl alcohol, butyl alcohol, isobutyl alcohol, sec-butyl alcohol, and tert-butyl alcohol, halogen-based solvents such as dichloromethane, 1,2-dichloroethane, chloroform, and carbon tetrachloride, ether-based solvents such as diethyl ether, DME, diethoxyethane, and THF, hydrocarbon-based solvents such as hexane, heptane, and cyclohexane, aromatic hydrocarbon-based solvents such as benzene, toluene, and xylene, and ester-based solvents such as ethyl acetate and butyl acetate, and methanol, ethyl acetate, THF, or toluene is preferable. These reaction solvents may be used alone or in suitable combination of two or more types thereof.

In the metal reduction using a metal such as iron, tin, or zinc, or a metal compound thereof, a target substance can be obtained with a high yield by suitably selecting reaction conditions suitable for each metal and performing the reaction. For example, iron-acetic acid, iron-hydrochloric acid, tin-hydrochloric acid, zinc-hydrochloric acid, or the like may be used. In the reaction, a suitable reaction solvent is used if necessary.

Step 3-4 is a step of preparing the substituted phenyl bromide (2f) by diazotizing the amino group of the 3-substituted phenoxy-4-aminophenyl bromide (2e) and by converting into a halogen atom, a cyano group, or a thiocyano group by a so-called Sandmeyer reaction.

As the diazotizing agent, nitrosyl chloride, nitrosyl sulfuric acid, nitric monoxide, or nitrite such as sodium nitrite or potassium nitrite can be used, and sodium nitrite is preferable. The used amount of the diazotizing agent is 1 mole to 3 moles, and preferably 1.1 moles to 1.5 moles with respect to 1 mole of the 3-substituted phenoxy-4-aminophenyl bromide (2e). In the diazotization reaction, an amino group is changed to an ammonium salt using, for example, acid such as hydrochloric acid, hydrobromic acid, sulfuric acid, acetic acid, perchloric acid, tetrafluoroboric acid, or hexafluorophosphoric acid, and the salt may be reacted with the diazotizing agent. Although, usually, the reaction can be performed in an aqueous solution, the reaction may be performed in a mixed solvent with acetone or ethyl methyl ketone. The reaction is performed at a temperature suitably selected within the range of 0° C. to 80° C., and preferably 0° C. to 40° C. As the ammonium salt of the 3-substituted phenoxy-4-aminophenyl bromide (2e), the ammonium salt prepared in advance may be used, or an ammonium salt may be prepared in the reaction system by adding the above-described acid to the 3-substituted phenoxy-4-aminophenyl bromide (2e).

As other diazotizing agents, nitrite ester such as methyl nitrite, ethyl nitrite, propyl nitrite, isobutyl nitrite, tert-butyl nitrite, or isoamyl nitrite may be used. The used amount of the diazotizing agent is 1 mole to 3 moles, and preferably 1.1 moles to 1.5 moles with respect to 1 mole of the 3-substituted phenoxy-4-aminophenyl bromide (2e). When the reaction can be performed in an organic solvent, the organic solvent to be used is not particularly limited, but from the viewpoint of a favorable yield or suppression of by-products, a hydrocarbon solvent such as hexane or heptane, an aromatic halogen-based solvent such as chlorobenzene or dichlorobenzene, or an ether-based solvent such as THF or DME is preferable. Among these, a hydrocarbon-based solvent such as hexane or heptane, or an aromatic halogen-based solvent such as chlorobenzene or dichlorobenzene is more preferable. The used amount of the organic solvent is not particularly limited. The reaction is performed at a temperature suitably selected within the range of 0° C. to 80° C., and preferably 0° C. to 40° C.

Examples of the counter anion of a diazonium salt can include $HSO_4^-$, $Cl^-$, $NO_3^-$, $ClO_4^-$, $BF_4^-$, and $PF_6^-$. In the case of suitably selecting the counter anion, it is possible to isolate a diazonium salt as a solid, but it is possible to be subjected to the next Sandmeyer reaction without isolation.

Next, it is possible to respectively convert into a halogen atom excluding fluorine, a cyano group, or a thiocyano group by reacting the diazonium salt of the 3-substituted phenoxy-4-aminophenyl bromide (2e) prepared with copper (I) halide excluding fluorine, copper(I) cyanide, or copper(I) thiocyanate.

The reaction of Step 3-4 can be performed in a solvent used in a diazotization reaction. The reaction is performed at a temperature suitably selected within the range of room temperature to 100° C., and preferably 40° C. to 80° C.

In addition, it is possible to convert the amino group into a fluorine atom by thermally decomposing tetrafluoroborate of the diazonium salt prepared from the 3-substituted phenoxy-4-aminophenyl bromide (2e). The tetrafluoroborate of the diazonium salt can be prepared by sequentially allowing nitrous acid and tetrafluoroboric acid (or a salt thereof) to act on the 3-substituted phenoxy-4-aminophenyl bromide (2e). The tetrafluoroborate of the diazonium salt can also be prepared by treating sodium nitrite and the diazonium salt prepared from acid with tetrafluoroboric acid or a sodium salt thereof, or boron trifluoride.

The thermal decomposition can be performed at a temperature suitably selected within the range of room temperature to 100° C., and preferably 40° C. to 80° C.

Furthermore, the diazonium salt of the 3-substituted phenoxy-4-aminophenyl bromide (2e) can be converted into an iodine atom by treating with potassium iodide, and converted into a hydroxyl group by treating with water, respectively.

Step 3-5 is a step of preparing 2-substituted phenyl-2-oxoacetic acid ester (4b) by reacting the Grignard reagent prepared from substituted phenyl bromide (2f) with oxalic acid diester (3).

The present step is the same reaction as Step 1-1 of Preparation Method-1 described above, and the details thereof are as described in Step 1-1. However, the substituted phenyl bromide (2a) in the description of Step 1-1 shall be replaced with the substituted phenyl bromide (2f), and the 2-substituted phenyl 2-oxoacetic acid ester (4a) in the description of Step 1-1 shall be replaced with the 2-substituted phenyl 2-oxoacetic acid ester (4b).

Step 3-6 is a step of preparing the 2-substituted phenyl acrylic acid ester (6b) by performing dihalomethylenation by treating the α-position carbonyl group of the 2-substituted phenyl-2-oxoacetic acid ester (4b) with the Wittig reagent prepared from triphenylphosphine and the compound represented by General Formula (5).

The present step is the same reaction as Step 1-2 of Preparation Method-1 described above, and the details thereof are as described in Step 1-2. However, the 2-substituted phenyl 2-oxoacetic acid ester (4a) in the description of Step 1-2 shall be replaced with the 2-substituted phenyl 2-oxoacetic acid ester (4b), and the 2-substituted phenyl acrylic acid ester (6a) in the description of Step 1-2 shall be replaced with the 2-substituted phenyl acrylic acid ester (6b).

Step 3-7 is a step of preparing the bicyclic pyrazolinone derivative (1e) which is a part of the compound of the present invention, by reacting the 2-substituted phenyl acrylic acid ester (6b) with the cyclic hydrazine (7) or a chemically acceptable salt thereof, optionally in the presence of a base.

The present step is the same reaction as Step 1-3 of Preparation Method-1 described above, and the details thereof are as described in Step 1-3. However, the 2-substituted phenyl acrylic acid ester (6a) in the description of Step 1-3 shall be replaced with the 2-substituted phenyl acrylic acid ester (6b), and the bicyclic pyrazolinone derivative (1a) in the description of Step 1-3 shall be replaced with the bicyclic pyrazolinone derivative (1e).

Step 3-8 is a step of preparing the bicyclic pyrazolinone derivative (1f) which is a part of the compound of the present invention by converting into a hydroxyl group by cleaving the methyl ether bond on the benzene ring of the bicyclic pyrazolinone derivative (1e).

In Step 3-8, the bicyclic pyrazolinone derivative (1f) which is a target substance can be prepared by a known method (for example, P. G. M. Wuts and T. W. Greene, Greene's Protective Groups in Organic Synthesis, Fourth Edition, Wiley-Interscience, p. 25-30) effective for cleavage of the methyl ether bond. Among these, deprotection using boron tribromide is preferable from the viewpoint of a favorable yield or selectivity.

The deprotection reaction using boron tribromide can be performed in an organic solvent such as dichloromethane or ethyl acetate. From the viewpoint of a favorable yield, a method using dichloromethane is preferable. The reaction can be performed at a temperature suitably selected within the range of −80° C. to 60° C. Although the used amount of boron tribromide is not particularly limited, usually, about 1 mole to 5 moles thereof may be used with respect to 1 mole of the bicyclic pyrazolinone derivative (1e).

Step 3-9 is a step of preparing the bicyclic pyrazolinone derivative (1g) which is a part of the compound of the present invention by reacting the bicyclic pyrazolinone derivatives (1f) with the compound represented by General Formula (8b) in the presence of a base.

The present step is the same reaction as Step 2-2 of Preparation Method-2 described above, and the details thereof are as described in Step 2-2. However, the bicyclic pyrazolinone derivative (1c) in the description of Step 2-2 shall be replaced with the bicyclic pyrazolinone derivative (1f), General Formula (8a) in the description of Step 2-2 shall be replaced with General Formula (8b), and the bicyclic pyrazolinone derivatives (1d) in the description of Step 2-2 shall be replaced with the bicyclic pyrazolinone derivative (1g).

In Steps 3-1, 3-2, 3-3, 3-4, 3-5, 3-6, 3-7, 3-8, and 3-9, after the reaction is completed, the target substance is isolated from the reaction system including the target substance by a method generally used in the related art, and if necessary, the target substance can be purified by recrystallization, distillation, column chromatography, or the like. In addition, without purifying the obtained target product, the obtained target product can be used in the subsequent step as a starting material, in some case.

In addition, the bicyclic pyrazolinone derivative represented by the following general formula (1i), which is a part of the compound of the present invention, can be prepared, for example, by the following Preparation Method-4.

Preparation Method-4

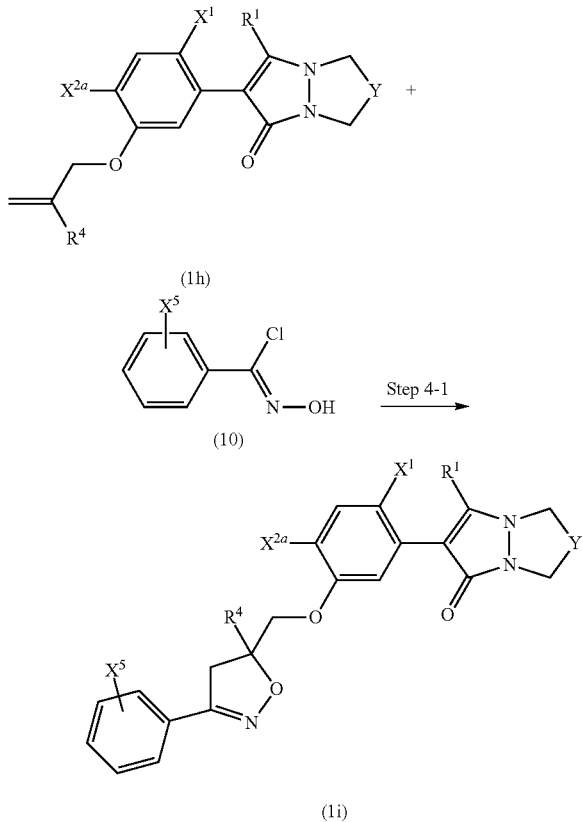

In the formula, $R^1$, $R^4$, $X^1$, $X^{2a}$, $X^5$, and Y each have the same definition as described above.

Preparation Method-4 includes Step 4-1 of preparing the bicyclic pyrazolinone derivative (1i) which is a part of the compound of the present invention by reacting the bicyclic pyrazolinone derivative (1h) having an alkenyloxy group on the benzene ring with benzohydroxamic acid chloride represented by General Formula (10) in the presence of a base. Hereinafter, Step 4-1 will be described in detail.

The reaction of Step 4-1 is performed in the presence of a base. Examples of the base can include organic bases such as triethylamine, tributylamine, and pyridine, inorganic bases such as sodium hydride, sodium amide, sodium carbonate, potassium carbonate, cesium carbonate, sodium hydroxide, and potassium hydroxide, alkali metal alkoxides such as sodium methoxide, sodium ethoxide, and potassium tert-butoxide, and lithium bases such as methyl lithium and butyl lithium. From the viewpoint of easy handling and a favorable yield, an organic base such as triethylamine is preferable. The base may usually be used in an equivalent with respect to benzohydroxamic acid chloride (10).

The reaction of Step 4-1 can be performed in an organic solvent. As the organic solvent, any organic solvent can be used as long as it does not adversely affect the reaction, and examples thereof can include halogen-based solvents such as dichloromethane, ether-based solvents such as 1,4-dioxane, THF, DME, diethyl ether, diisopropyl ether, and cyclopentyl methyl ether, aromatic hydrocarbon-based solvents such as benzene, toluene, and chlorobenzene, hydrocarbon-based solvents such as hexane and octane, nitrile-based solvents such as acetonitrile and propionitrile, amide-based solvents such as DMF and N,N-dimethyl acetamide, sulfoxide-based solvents such as DMSO, and mixed solvents thereof.

The reaction temperature is not particularly limited, and the reaction may be performed at a temperature suitably selected within the range of 0° C. to 60° C.

The bicyclic pyrazolinone derivative (1h) which is a starting material of the reaction can be prepared by the method in shown in Preparation Method-1 or Preparation Method-2.

In addition, the benzohydroxamic acid chloride (10) can be prepared by treating corresponding substituted benzaldehyde with hydroxylamine or hydrochloride to obtain substituted benzaldoxime and treating the substituted benzaldoxime with N-succinchlorimide. The used amount of the benzohydroxamic acid chloride (10) may be about 1 mole to 3 moles with respect to 1 mole of the bicyclic pyrazolinone derivative (1h).

In Step 4-1, after the reaction is completed, the target substance is isolated from the reaction system including the target substance by a method generally used in the related art, and if necessary, the target substance can be purified by recrystallization, distillation, column chromatography, or the like. In addition, without purifying the obtained target product, the obtained target product can be used in the subsequent step as a starting material, in some case.

In addition, the bicyclic pyrazolinone derivative represented by the following general formula (1j), which is a part of the compound of the present invention can be prepared, for example, by the following Preparation Method-5.

Preparation Method-5

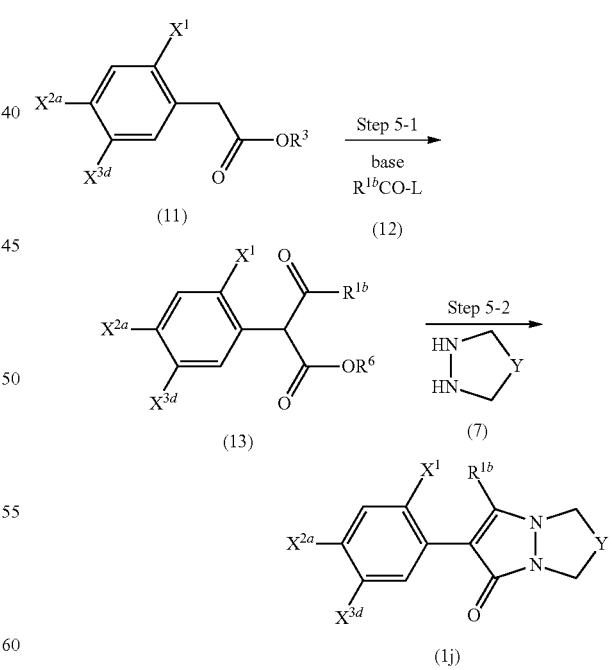

In the formula, $R^5$, $X^1$, $X^{2a}$, and Y each have the same definition as described above. $R^{1b}$ represents a $C_1$-$C_4$ alkyl group or a $C_1$-$C_4$ haloalkyl group. $X^{3d}$ represents a hydrogen atom; a halogen atom; a $C_1$-$C_{12}$ alkyloxy group; a $C_3$-$C_8$ cycloalkyloxy group; a $C_2$-$C_6$ alkenyloxy group; a $C_5$-

$C_8$ cycloalkenyloxy group; a nitro group; a ($C_1$-$C_4$ alkyl) oxycarbonyl group; a ($C_2$-$C_6$ alkenyl)oxycarbonyl group; a phenyloxycarbonyl group which may be substituted with a halogen atom; or a cyano group. L represents a leaving group.

Preparation Method-5 includes Step 5-1 of preparing β-ketocarboxylic acid ester (13) by acylating the benzyl position by reacting the substituted phenyl acetic acid ester (11) with an acylating agent (12) in the presence of a base; and Step 5-2 of preparing the bicyclic pyrazolinone ring (1j) of the present invention by reacting the β-ketocarboxylic acid ester (13) with the cyclic hydrazine (7). Hereinafter, each step in Preparation Method-5 will be described in detail.

Step 5-1 is a step of preparing the β-ketocarboxylic acid ester (13) by acylating the benzyl position by reacting the substituted phenyl acetic acid ester (11) with the acylating agent (12) in the presence of a base.

The reaction is performed in the presence of a base. As the base, a base which have the strength can withdraw the hydrogen atom at the benzyl position of the substituted phenyl acetic acid ester (11) can be used, examples thereof can include inorganic bases such as sodium hydride and sodium amide, alkali metal alkoxides such as sodium methoxide, sodium ethoxide, and potassium tert-butoxide, and lithium bases such as methyl lithium, butyl lithium, and lithium diisopropyl amide. The base may usually be used in an equivalent or greater with respect to the substituted phenyl acetic acid ester (11).

The reaction of Step 5-1 can be performed in an organic solvent. As the organic solvent, any organic solvent can be used as long as it does not adversely affect the reaction, and examples thereof can include ether-based solvents such as 1,4-dioxane, THF, DME, diethyl ether, diisopropyl ether, and cyclopentyl methyl ether, hydrocarbon-based solvents such as hexane and octane, amide-based solvents such as DMF and N,N-dimethyl acetamide, sulfoxide-based solvents such as DMSO, and mixed solvents thereof. An ether-base solvent such as THF is preferable.

The reaction of Step 5-1 is performed at a temperature suitably selected within the range of −78° C. to 100° C. The reaction of substituted phenyl acetic acid esters (11) with a base is preferably performed at a low temperature.

The substituted phenyl acetic acid esters (11) which are starting materials can be easily prepared by a known chemical method.

Examples of the acylating agent ($R^{1b}$CO-L) represented by General Formula (12) can include carboxylic acid halides such as acetyl chloride, acetyl bromide, propionyl chloride, butyryl chloride, isobutyryl chloride, valeryl chloride, isovaleryl chloride, and pivaloyl chloride, and halocarboxylic acid halides such as fluoroacetyl chloride, difluoroacetyl chloride, trifluoroacetyl chloride, trichloroacetyl chloride, 3,3,3-trifluoropropionyl chloride, and 4-fluorobutyryl chloride. From the viewpoint of high activity, acetyl chloride, acetyl bromide, or trifluoroacetyl chloride is preferable. A part of commercially unavailable compounds among these acylating agents can be easily prepared by a general chemical method known to those skilled in the art. Examples of the leaving group L in the acylating agent (12) can include an acyloxy group and an alkoxy group in addition to halogen atoms such as chlorine atom and a bromine atom. That is, for example, in a case where L is an acyloxy group, a mixed acid anhydride such as acetic anhydride or trifluoroacetic anhydride can be used as the acylating agent (12), and in a case where L is an alkoxy group, ester such as methyl acetate, ethyl acetate, or ethyl trifluoroacetate can be used as the acylating agent (12). The leaving group L is preferably a chlorine atom which is easily prepared.

Step 5-2 is a step of preparing the bicyclic pyrazolinone ring (1j) of the present invention, by reacting β-ketocarboxylic acid ester (13) with cyclic hydrazine (7) or a chemically acceptable salt thereof, optionally in the presence of a base.

Specific examples of the cyclic hydrazine (7) can include pyrazolidine, 4-fluoropyrazolidine, hexahydropyridazine, 1,2-diazacycloheptane, 1,3,4-oxadiazolidine, 1,4,5-oxadiazepane, 4-methyl-1,2,4-triazolidine, and 5-methyl-1,2,5-triazepane. Although these cyclic hydrazines can be used in the reaction in a free form, these cyclic hydrazines can also be used in a form of chemically acceptable salt such as hydrochloride or sulfate thereof. A part of commercially unavailable compounds among these cyclic hydrazines (7) can be easily prepared by a general chemical method known to those skilled in the art. For example, hexahydropyridazine can be prepared by a known method (JP-A-8-109170 or JP-A-10-29981).

The reaction of Step 5-2 can be performed in a solvent. As the solvent, any solvent can be used as long as it does not adversely affect the reaction, and examples thereof can include ether-based solvents such as 1,4-dioxane, THF, DME, diethyl ether, diisopropyl ether, and cyclopentyl methyl ether, aromatic hydrocarbon-based solvents such as benzene, toluene, and chlorobenzene, hydrocarbon-based solvents such as hexane and octane, ketone-based solvents such as acetone, methyl ethyl ketone, diethyl ketone, and cyclohexanone, ester-based solvents such as ethyl acetate and ethyl propionate, nitrile-based solvents such as acetonitrile and propionitrile, amide-based solvents such as DMF and N,N-dimethyl acetamide, sulfoxide-based solvents such as DMSO, water, and mixed solvents thereof. An ether-based solvent such as 1,4-dioxane, THF, or DME is preferable.

The reaction temperature is not particularly limited, and the reaction can be performed at a temperature suitably selected within the range of room temperature to a reflux temperature of the solvent used.

When performing the reaction of Step 5-2, the reaction can also be promoted by adding a base. Examples of the base can include organic bases such as triethylamine, tributylamine, and pyridine, inorganic bases such as sodium carbonate, potassium carbonate, cesium carbonate, sodium hydroxide, and potassium hydroxide, and alkali metal alkoxides such as sodium methoxide, sodium ethoxide, and potassium tert-butoxide. In the case of using a salt of cyclic hydrazine (7), it is preferable from the viewpoint of a short reaction time and a favorable yield that the reaction is performed by adding a greater amount of base than the amount corresponding to acid forming the salt.

In this reaction, an amide intermediate (13-1) is produced as a by-product in some cases. The amide intermediate (13-1) can be converted into the bicyclic pyrazolinone ring (1j) which is a target substance by heating to be cyclized in the presence of a catalytic amount of acid (for example, p-toluene sulfonic acid). The amide intermediate (13-1) is not necessary to be isolated, and may be continuously reacted by adding acid in the latter stage of the reaction of the β-ketocarboxylic acid ester (13) with the cyclic hydrazine (7)

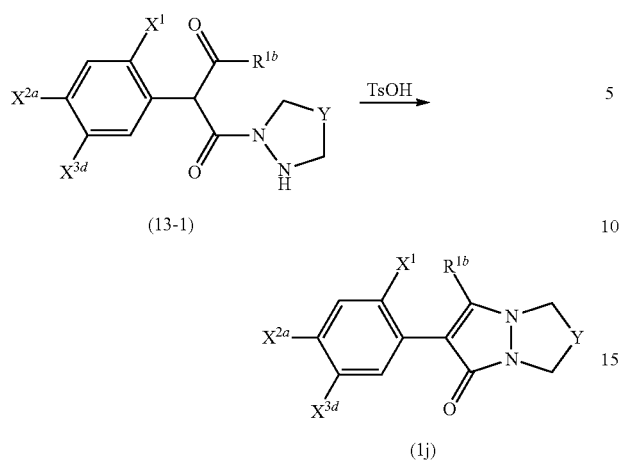

(13-1)

(1j)

In the formula, $R^{1b}$, $X^1$, $X^{2a}$, $X^{3d}$, and Y each have the same definition as described above.

In Steps 5-1 and 5-2, after the reaction is completed, the target substance is isolated from the reaction system including the target substance by a method generally used in the related art, and if necessary, the target substance can be purified by recrystallization, distillation, column chromatography, or the like. In addition, without purifying the obtained target product, the obtained target product can be used in the subsequent step as a starting material, in some case.

The bicyclic pyrazolinone derivative, which is a part of the compound of the present invention, is represented by the following general formula (1l, 1m, 1n, or 1o), and has a nitro group or an amino group which may be substituted on the benzene ring can be prepared, for example, by the following Preparation Method-6.

Preparation Method-6

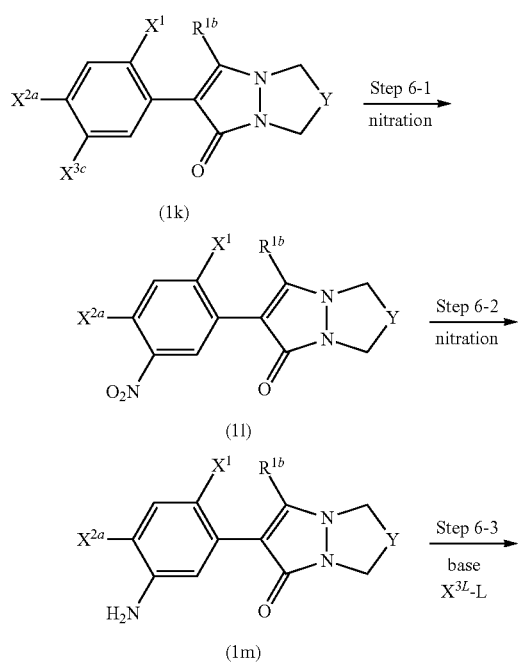

(1k)

(1l)

(1m)

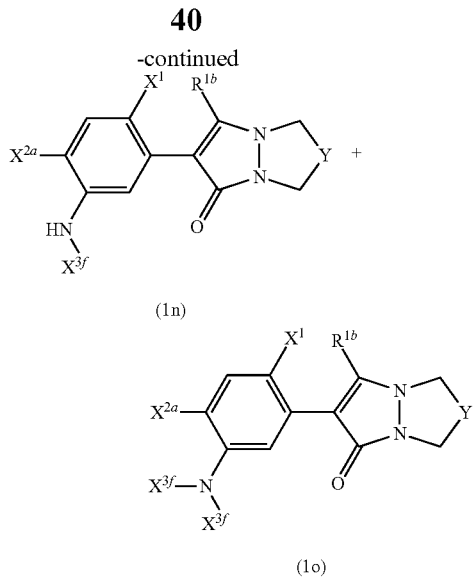

(1n)

(1o)

In the formula, $R^1$, $X^1$, $X^{2a}$, and Y each have the same definition as described above. $X^{3e}$ represents a hydrogen atom. $X^{3f}$ represents a $C_1$-$C_4$ alkyl group; a $C_2$-$C_6$ alkenyl group; a $C_2$-$C_6$ alkynyl group; a $C_2$-$C_8$ acyl group which may be substituted with a halogen atom; a $C_1$-$C_4$ alkyl sulfonyl group which may be substituted with a halogen atom; a $C_3$-$C_8$ cycloalkyl sulfonyl group; a $C_2$-$C_6$ alkenyl sulfonyl group; a $C_7$-$C_8$ aralkyl sulfonyl group; a phenyl sulfonyl group which may be substituted with one or more substituents selected from the group consisting of a halogen atom, a $C_1$-$C_4$ alkyl group, a trifluoromethyl group, and a phenyloxy group; and a di($C_1$-$C_4$ alkyl) amino sulfonyl group. Two $X^{3f}$s may be the same as or different from each other, and may form a $C_4$-$C_7$ cyclic polymethylene imino group by joining together with the nitrogen atom to which the two $X^{3f}$s are bonded. L represents a leaving group.

Preparation Method-6 includes Step 6-1 of preparing a bicyclic pyrazolinone derivative (1l) by nitrating a bicyclic pyrazolinone derivative (1k); Step 6-2 of preparing a bicyclic pyrazolinone derivative (1m) having an amino group on the benzene ring by reducing the nitro group of the bicyclic pyrazolinone derivative (1l), and Step 6-3 of preparing a bicyclic pyrazolinone derivative (1n and/or 1o) which is a part of the compound of the present invention having a substituted amino group on the benzene ring by reacting the bicyclic pyrazolinone derivative (1m) with a compound represented by General Formula (14) in the presence of a base. Hereinafter, each step in Preparation Method-6 will be described in detail.

Step 6-1 is a step of preparing the bicyclic pyrazolinone derivative (1l) by nitrating the bicyclic pyrazolinone derivative (1k).

As the nitration in Step 6-1, for example, a method for nitrating using a mixed acid prepared from concentrated nitric acid and concentrated sulfuric acid in concentrated sulfuric acid or a method for nitrating using fuming nitric acid without a solvent or in a solvent such as dichloromethane can be used. The reaction conditions are not particularly limited, and the bicyclic pyrazolinone derivative (1l) which is a target substance can be prepared with a favorable yield and regioselectivity by performing a reaction according to a general method for nitrating a benzene ring.

Step 6-2 is a step of preparing the bicyclic pyrazolinone derivative (1m) having an amino group on the benzene ring by reducing the nitro group of the bicyclic pyrazolinone derivative (1l).

Step 6-2 is the same reaction as Step 3-3 of Preparation Method-3 described above, and the details thereof are as described in Step 3-3. However, the 3-substituted phenoxy-4-nitrophenyl bromide (2d) in the description of Step 3-3 shall be replaced with the bicyclic pyrazolinone derivative (1l), and the 3-substituted phenoxy-4-aminophenyl bromide (2e) in the description of Step 3-3 shall be replaced with the bicyclic pyrazolinone derivative (1m).

Step 6-3 is a step of preparing the bicyclic pyrazolinone derivative (1n and/or 1o) which is a part of the compound of the present invention having a substituted amino group on the benzene ring by reacting the bicyclic pyrazolinone derivative (1m) with the compound represented by General Formula (14) in the presence of a base.

The reaction of Step 6-3 is performed in the presence of a base. Examples of the base can include inorganic bases such as sodium hydride, sodium amide, sodium carbonate, potassium carbonate, and cesium carbonate, alkali metal alkoxides such as sodium methoxide, sodium ethoxide, and potassium tert-butoxide, and lithium bases such as methyl lithium, butyl lithium, and lithium diisopropyl amide. From the viewpoint of easy handling and a favorable yield, an inorganic base such as sodium hydride, sodium amide, sodium carbonate, potassium carbonate, or cesium carbonate is preferable. The base may usually be used in an equivalent or greater with respect to the bicyclic pyrazolinone derivatives (1m).

The reaction of Step 6-3 can be performed in an organic solvent. As the organic solvent, any organic solvent can be used as long as it does not adversely affect the reaction, and examples thereof can include ether-based solvents such as 1,4-dioxane, THF, DME, diethyl ether, diisopropyl ether, and cyclopentyl methyl ether, hydrocarbon-based solvents such as hexane and octane, halogen-based solvents such as dichloromethane and 1,2-dichloroethane, amide-based solvents such as DMF and N,N-dimethyl acetamide, sulfoxide-based solvents such as DMSO, and mixed solvents thereof. The reaction solvent is suitably selected and used depending on the base to be used. An ether-based solvent such as THF or a halogen-based solvent such as dichloromethane is preferable.

The reaction of Step 6-3 may be performed at a temperature suitably selected within the range of 0° C. to a reflux temperature of the solvent.

In the compound ($X^{3'}$-L) represented by General Formula (14), examples of the leaving group represented by L can include a fluorine atom, a chlorine atom, a bromine atom, an iodine atom, and substituted sulfonyloxy groups such as a methyl sulfonyloxy group, a trifluoromethyl sulfonyloxy group, a phenyl sulfonyloxy group, and a 4-methyl phenyl sulfonyloxy group.

Specific examples of the compound (14) include alkyl halides or sulfonic acid esters such as methyl iodide, ethyl bromide, ethyl iodide, isopropyl bromide, isopropyl iodide, and isopropyl trifluoromethane sulfonate; alkenyl halides or sulfonic acid esters such as allyl chloride, allyl bromide, crotyl chloride, crotyl bromide, methallyl chloride, methallyl bromide, 3-butenyl trifluoromethane sulfonate, and prenyl bromide; and alkynyl halides or sulfonic acid esters such as propargyl bromide, propargyl trifluoromethane sulfonate, and 1-butyne-3-yl trifluoromethane sulfonate.

Examples of the compound (14) can include acyl halides or acid anhydrides such as acetyl chloride, acetyl bromide, acetic anhydride, propionyl chloride, butyryl chloride, isobutyryl chloride, valeryl chloride, isovaleryl chloride, and pivaloyl chloride.

Furthermore, examples of the compound (14) can include $C_1$-$C_4$ alkyl sulfonyl halides which may be substituted with a halogen atom, such as methyl sulfonyl chloride, methyl sulfonyl bromide, difluoromethyl sulfonyl chloride, trifluoromethyl sulfonyl chloride, ethyl sulfonyl chloride, (2-fluoroethyl)sulfonyl fluoride, (2-fluoroethyl)sulfonyl chloride, (2-fluoroethyl)sulfonyl bromide, (2-chloroethyl)sulfonyl fluoride, (2-chloroethyl)sulfonyl chloride, (2-chloroethyl) sulfonyl bromide, (2-bromoethyl)sulfonyl fluoride, (2-bromoethyl)sulfonyl chloride, and (2-bromoethyl) sulfonyl bromide; $C_3$-$C_8$ cycloalkyl sulfonyl halides such as cyclopropyl sulfonyl chloride, cyclopentyl sulfonyl chloride, cyclohexyl sulfonyl chloride, and cyclohexyl sulfonyl bromide; $C_2$-$C_6$ alkenyl sulfonyl chlorides such as vinyl sulfonyl chloride, allyl sulfonyl chloride, crotyl sulfonyl chloride, and methallyl sulfonyl chloride; ($C_7$-$C_8$ aralkyl)sulfonyl chlorides such as benzyl sulfonyl chloride, α-phenethyl sulfonyl chloride, and β-phenethyl sulfonyl chloride; phenyl sulfonyl halides which may be substituted, such as phenyl sulfonyl chloride, phenyl sulfonyl bromide, 2-fluorophenyl sulfonyl chloride, 4-fluorophenyl sulfonyl chloride, 2-chlorophenyl sulfonyl chloride, 4-chlorophenyl sulfonyl chloride, 4-chlorophenyl sulfonyl bromide, 4-methylphenyl sulfonyl chloride, 4-(trifluoromethyl)phenyl sulfonyl chloride, and 4-(phenyloxy)phenyl sulfonyl chloride; and di($C_1$-$C_4$ alkyl) amino sulfonyl chlorides such as dimethyl amino sulfonyl chloride, diethyl amino sulfonyl chloride, diisopropyl amino sulfonyl chloride, and dibutyl amino sulfonyl chloride.

In addition, in a case where a $C_4$-$C_7$ cyclic polymethylene imino group is formed by the two $X^{3'}$s joining together with the nitrogen atom to which the two $X^{3'}$s are bonded, α,ω-dihaloalkane such as 1,4-dibromobutane or 1,5-dibromopentane may be used as the compound (14). In this case, the base may be used in 2 equivalents or greater with respect to the bicyclic pyrazolinone derivative (1m).

A part of commercially unavailable compounds among the compounds represented by General Formula (14) can be easily prepared by a general chemical method known to those skilled in the art. From the viewpoint of ease of industrial availability, methyl iodide, ethyl bromide, allyl chloride, allyl bromide, propargyl bromide, acetyl chloride, acetyl bromide, acetic anhydride, pivaloyl chloride, methyl sulfonyl chloride, trifluoromethyl sulfonyl chloride, 2-chloroethane sulfonyl fluoride, (2-chloroethyl)sulfonyl chloride, (2-chloroethyl)sulfonyl bromide, phenyl sulfonyl chloride, 4-chlorophenyl sulfonyl chloride, 4-methylphenyl sulfonyl chloride, or the like is preferable.

In Steps 6-1, 6-2, and 6-3, after the reaction is completed, the target substance is isolated from the reaction system including the target substance by a method generally used in the related art, and if necessary, the target substance can be purified by recrystallization, distillation, column chromatography, or the like. In addition, without purifying the obtained target product, the obtained target product can be used in the subsequent step as a starting material, in some cases.

In addition, the bicyclic pyrazolinone derivative represented by the following general formula (1q), which is a part of the compound of the present invention, can be prepared, for example, by the following Preparation Method-7.

Preparation Method-7

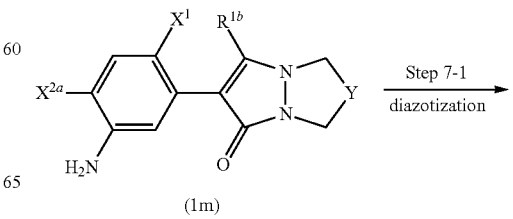

(1m)

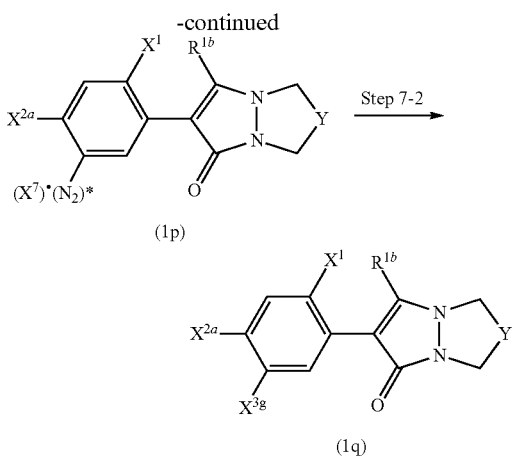

In the formula, $R^1$, $X^1$, $X^{2a}$, and Y each have the same definition as described above. $X^7$ represents a counter ion of a diazonium salt. $X^{3g}$ represents a hydrogen atom; a halogen atom; a hydroxyl group; a cyano group; a thiocyano group; a $C_1$-$C_6$ alkyl group which may be substituted with one or more substituents selected from the group consisting of a halogen atom, a ($C_1$-$C_4$ alkyl)oxycarbonyl group, and a cyano group; or a $C_2$-$C_6$ alkenyl group which may be substituted with one or more substituents selected from the group consisting of a halogen atom, a ($C_1$-$C_4$ alkyl)oxycarbonyl group, and a cyano group.

Preparation Method-7 includes Step 7-1 of preparing the diazonium salt (1p) from the bicyclic pyrazolinone derivative (1m) having an amino group on the benzene ring; and Step 7-2 of preparing a bicyclic pyrazolinone derivative (1q) which is a part of the compound of the present invention having a hydroxyl group, a halogen atom, a cyano group, a thiocyano group, a substituted alkyl group, or a substituted alkenyl group on the benzene ring by subjecting the diazonium salt (1p) to the Sandmeyer reaction. Hereinafter, each step in Preparation Method-7 will be described in detail.

Step 7-1 is a step of preparing the diazonium salt (1p) from the bicyclic pyrazolinone derivative (1m) having an amino group on the benzene ring.

As the diazotizing agent, nitrosyl chloride, nitrosyl sulfuric acid, nitric monoxide, or nitrite such as sodium nitrite or potassium nitrite can be used, and sodium nitrite is preferable. The used amount of the diazotizing agent is 1 mole to 3 moles, and preferably 1.1 moles to 1.5 moles with respect to 1 mole of the bicyclic pyrazolinone derivative (1m). In the diazotization reaction, an amino group is changed to an ammonium salt using, for example, protonic acid such as hydrochloric acid, hydrobromic acid, sulfuric acid, or acetic acid, and the salt may be reacted with the diazotizing agent. Although, usually, the reaction can be performed in an aqueous solution, the reaction may be performed in a mixed solvent with acetone, ethyl methyl ketone, or acetonitrile. The reaction is performed at a temperature suitably selected within the range of 0° C. to 80° C., and preferably 0° C. to 40° C. As the ammonium salt of the bicyclic pyrazolinone derivative (1m), the ammonium salt prepared in advance may be used, or an ammonium salt may be prepared in the reaction system by adding acid to the bicyclic pyrazolinone derivative (1m).

As other diazotizing agents, nitrite ester such as methyl nitrite, ethyl nitrite, propyl nitrite, isobutyl nitrite, tert-butyl nitrite, or isoamyl nitrite may be used. The used amount of the diazotizing agent is 1 mole to 3 moles, and preferably 1.1 moles to 1.5 moles with respect to 1 mole of the bicyclic pyrazolinone derivative (1m). When the reaction can be performed in an organic solvent, the organic solvent to be used is not particularly limited, but from the viewpoint of a favorable yield or suppression of by-products, a hydrocarbon solvent such as hexane or heptane, an aromatic halogen-based solvent such as chlorobenzene or dichlorobenzene, an ether-based solvent such as THF or DME, or a nitrile-based solvent such as acetonitrile or propionitrile is preferable. Among these, a hydrocarbon-based solvent, an aromatic halogen-based solvent, or a nitrile-based solvent is more preferable. The used amount of the organic solvent is not particularly limited. The reaction is performed at a temperature suitably selected within the range of 0° C. to 80° C., and preferably 0° C. to 40° C.

Examples of the counter anion of a diazonium salt can include $HSO_4^-$, $Cl^-$, $NO_3^-$, $ClO_4^-$, $BF_4^-$, and $PF_6^-$. In the case of suitably selecting the counter anion, it is possible to isolate the diazonium salt (1p) as a solid, but it is possible to be subjected to the reaction of the next step without isolation.

Step 7-2 is a step of preparing the bicyclic pyrazolinone derivative (1q) which is a part of the compound of the present invention having a hydroxyl group, a halogen atom, a substituted alkyl group, or a substituted alkenyl group on the benzene ring by a reaction of the diazonium salt (1p) according to a commonly used method such as the Sandmeyer reaction. More specifically, Step 7-2 includes a reaction of preparing the bicyclic pyrazolinone derivative (1q) in which a halogen atom, a hydroxyl group, a cyano group, or a thiocyano group is introduced on the benzene ring by subjecting the diazonium salt (1p) to a so-called Sandmeyer reaction, and a reaction of preparing the bicyclic pyrazolinone derivative (1q) in which a substituted alkyl group is introduced on the benzene ring by a so-called Meerwein arylation reaction which adds the diazonium salt (1p) to an alkene having an electron withdrawing substituent using a copper(I) chloride catalyst.

First, the Sandmeyer reaction of the diazonium salt (1p) will be described. It is possible to respectively convert the diazonium salt (1p) into a halogen atom excluding fluorine, a cyano group, or a thiocyano group by reacting the diazonium salt (1p) with copper(I) halide excluding fluorine, copper(I) cyanide, or copper(I) thiocyanate.

The reaction of Step 7-2 can be performed in a solvent used in a diazotization reaction. The reaction is performed at a temperature suitably selected within the range of room temperature to 100° C., and preferably 40° C. to 80° C.

It is possible to convert the amino group into a fluorine atom by thermally decomposing tetrafluoroborate of the diazonium salt (1p). The tetrafluoroborate of the diazonium salt can be prepared by sequentially allowing nitrite and tetrafluoroboric acid (or a salt thereof) to act on the bicyclic pyrazolinone derivative (1m). The tetrafluoroborate of the diazonium salt can also be prepared by treating sodium nitrite and the diazonium salt prepared from an acid with tetrafluoroboric acid or a sodium salt thereof, or boron trifluoride.

The thermal decomposition can be performed at a temperature suitably selected within the range of room temperature to 100° C., and preferably 40° C. to 80° C.

The diazonium salt (1p) can be converted into an iodine atom by treating with potassium iodide, and converted into a hydroxyl group by treating with water, respectively.

Next, the Meerwein arylation reaction of the diazonium salt (1p) will be described. As shown in the following reaction scheme in which methyl acrylate is exemplified, this reaction is a reaction of giving a bicyclic pyrazolinone derivative (1q-1) of the present invention having a substituted alkyl group on the benzene ring by addition of a phenyl radical to a double bond with denitrification by reacting the diazonium salt (1p) with an alkene having an electron withdrawing group such as acrylic acid such as acrylic acid or α-(trifluoromethyl)acrylic acid or $C_1$-$C_6$ alkyl ester thereof; crotonic acid or $C_1$-$C_6$ alkyl ester thereof; methacrylic acid or $C_1$-$C_6$ alkyl ester thereof; or a cyano substituted alkene such as acrylonitrile in the presence of a catalytic amount of a copper halide such as cuprous chloride, cupric chloride, cuprous bromide, or cupric bromide.

Reaction Example of the Diazonium Salt with Methyl Acrylate

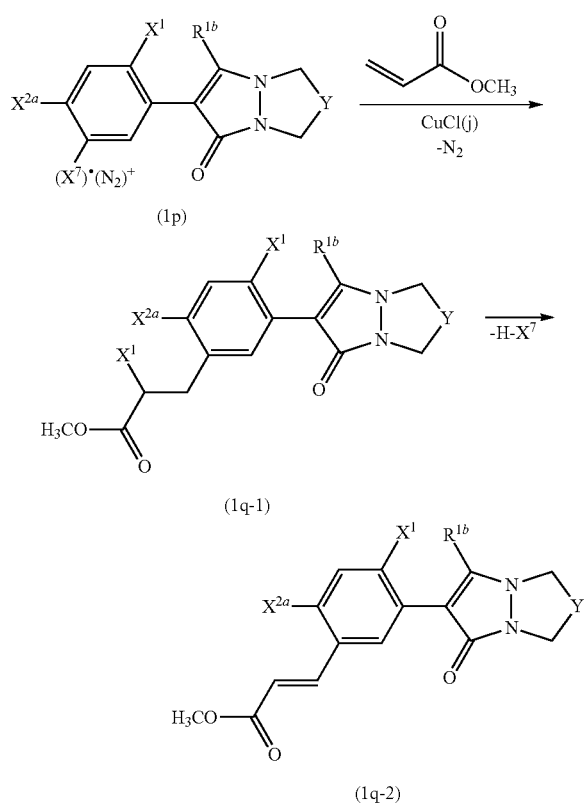

In the formula, $X^1$, $X^{2a}$, $X^7$, $R^1$ and Y each have the same definition as described above.

The Meerwein arylation reaction of the diazonium salt (1p) can be performed at a temperature suitably selected within the range of 0° C. to 60° C., and is preferably performed at a low temperature of about 0° C. to room temperature. This reaction can be performed in a solvent. As the solvent, in the case of applying the diazonium salt (1p) without isolation to the reaction of Step 7-2, the reaction can also be performed in the solvent used in preparation of the diazonium salt (1p), and in the case of using the isolated diazonium salt (1p), the solvent is not particularly limited as long as it does not adversely affect the reaction. In the diazonium salt (1p), usually, $Cl^-$ or $Br^-$ can be used as $X^7$ of a counter anion, and $BF_4^-$ also is preferable from the viewpoint of stability of the diazonium salt. In the case of using the tetrafluoroborate of the diazonium salt (1p), the bicyclic pyrazolinone derivative (1q-1) which is a target substance can be obtained by performing the reaction in the presence of a protonic acid such as hydrochloric acid or hydrobromic acid.

The reaction is usually performed in the presence of a catalytic amount of copper(I) halide. Usually, the catalyst may be used in about 0.001 moles to 0.5 moles with respect to 1 mole of the diazonium salt (1p). In addition, in the case of using α-(trifluoromethyl)acrylic acid as an alkene having an electron withdrawing group, copper(II) halide such as cupric chloride or cupric bromide can also be used according to a known method (for example, JP-A-61-204150).

A bicyclic pyrazolinone derivative (1q-2) having a substituted alkenyl group can be prepared by de-H—$X^7$ reacting the bicyclic pyrazolinone derivative (1q-1) of the present invention obtained in the above manner in the presence of a base such as triethylamine.

In Steps 7-1 and 7-2, after the reaction is completed, the target substance is isolated from the reaction system including the target substance by a method generally used in the related art, and if necessary, the target substance can be purified by recrystallization, distillation, column chromatography, or the like. In addition, without purifying the obtained target product, the obtained target product can be used in the subsequent step as a starting material, in some case.

The bicyclic pyrazolinone derivative which is represented by the following general formula (1s, 1t, 1u, 1v, or 1w) which is a part of the compound of the present invention and in which the 5-position on the benzene ring is a nitro group or an amino group which may be substituted, and the 4-position is a hydroxyl group or an alkoxy group can be prepared, for example, by the following Preparation Method-8.

Preparation Method-8

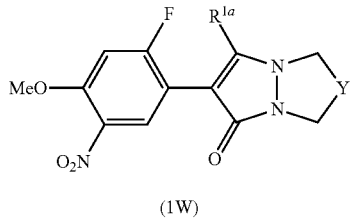

(1W)

Step 8-5 methoxyaltion

Step 8-6

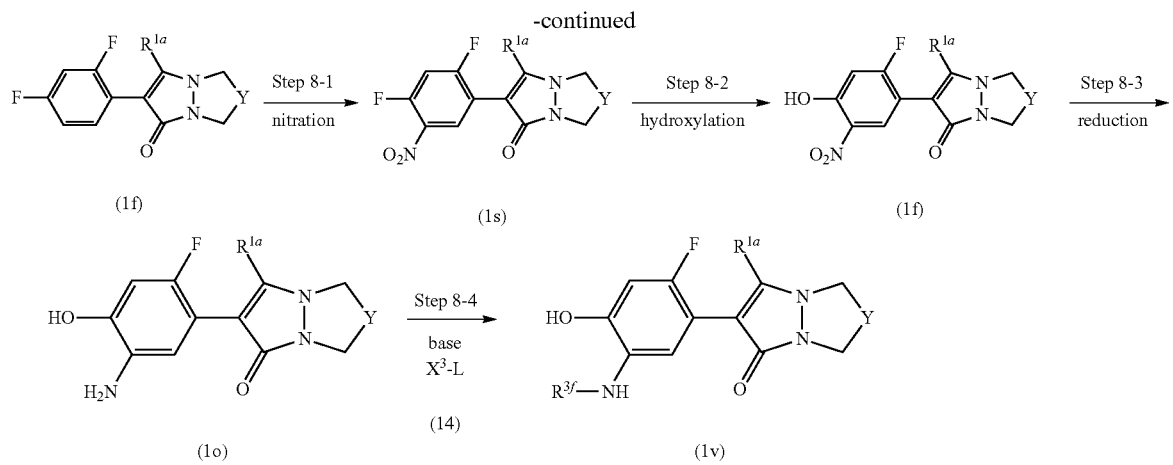

In the formula, $R^{1a}$, $R^{3f}$, and Y each have the same definition as described above. L represents a leaving group.

Preparation Method-8 includes Step 8-1 of preparing a bicyclic pyrazolinone derivative (1s) having a nitro group at the 5-position on the benzene ring from a bicyclic pyrazolinone derivative (1r) having a fluorine atom at the 2-position and the 4-position on the benzene ring; Step 8-2 of preparing a bicyclic pyrazolinone derivative (1t) having a hydroxyl group at the 4-position on the benzene ring; Step 8-3 of preparing a bicyclic pyrazolinone derivative (1u) having an amino group at the 5-position on the benzene ring; Step 8-4 of preparing a bicyclic pyrazolinone derivative (1v) having a substituent on the amino group at the 5-position on the benzene ring; Step 8-5 of preparing a bicyclic pyrazolinone derivative (1w) having a methoxy group at the 4-position on the benzene ring by nucleophilic substitution of the fluorine atom of the 4-position on the benzene ring of the bicyclic pyrazolinone derivative (1s) with methanol; and Step 8-6 of preparing the bicyclic pyrazolinone derivative (1t) having a hydroxyl group at the 4-position on the benzene ring by acid decomposition of the methoxy group of the bicyclic pyrazolinone derivative (1w). Hereinafter, each step in Preparation Method-8 will be described in detail.

Step 8-1 is a step of preparing the bicyclic pyrazolinone derivative (1s) by nitrating the bicyclic pyrazolinone derivative (1r).

As the nitration in Step 8-1, for example, a method for nitrating using a mixed acid prepared from concentrated nitric acid and concentrated sulfuric acid in concentrated sulfuric acid or a method for nitrating using fuming nitric acid without a solvent or in a solvent such as dichloromethane can be used. The reaction conditions are not particularly limited, and the bicyclic pyrazolinone derivative (1s) which is a target substance can be prepared with a favorable yield and regioselectivity by performing a reaction according to a general method for nitrating a benzene ring.

Step 8-2 is a step of converting the fluorine atom at the 4-position on the benzene ring of the bicyclic pyrazolinone derivative (is) into a hydroxyl group.

The reaction of Step 8-2 is performed in an aqueous solution of alkali metal hydroxide. Examples of the alkali metal hydroxide include sodium hydroxide and potassium hydroxide. Although the concentration of the aqueous solution of alkali metal hydroxide is not particularly limited, the reaction may be performed at a concentration suitably selected within the range of 12% by weight to 48% by weight.

The reaction of Step 8-2 can be performed in an organic solvent. As the organic solvent, any organic solvent can be used as long as it does not adversely affect the reaction, and examples thereof can include ether-based solvents such as 1,4-dioxane and THF, amide-based solvents such as DMF and N,N-dimethyl acetamide, sulfoxide-based solvents such as DMSO, and mixed solvents thereof. Since the reaction of Step 8-2 can be performed in an aqueous solution, a solvent which is homogeneously miscible with water is preferable, and a solvent such as DMF or DMSO is preferable.

The reaction temperature is not particularly limited, and since the reaction sufficiently proceeds at room temperature, the bicyclic pyrazolinone derivative (1t) which is a target substance can be obtained with a high yield.

Step 8-3 is a step of reducing the nitro group at the 5-position on the benzene ring of the bicyclic pyrazolinone derivative (1t).

Step 8-3 is the same reaction as Step 3-3 of Preparation Method-3 described above, and the details thereof are as described in Step 3-3. However, the 3-substituted phenoxy-4-nitrophenyl bromide (2d) in the description of Step 3-3 shall be replaced with the bicyclic pyrazolinone derivative (1t), and the 3-substituted phenoxy-4-aminophenyl bromide (2e) in the description of Step 3-3 shall be replaced with the bicyclic pyrazolinone derivative (1u).

Step 8-4 is a step of preparing the bicyclic pyrazolinone derivative (1v) having a substituted amino group on the benzene ring by reacting the bicyclic pyrazolinone derivative (1u) with the compound represented by General Formula (14) in the presence of a base.

Step 8-4 is the same reaction as Step 6-3 of Preparation Method-6 described above, and the details thereof are as described in Step 6-3. However, the bicyclic pyrazolinone derivative (1m) in the description of Step 6-3 shall be replaced with the bicyclic pyrazolinone derivative (1u), and the bicyclic pyrazolinone derivatives (1n and/or 1o) in the description of Step 6-3 shall be replaced with the bicyclic pyrazolinone derivative (1v).

Step 8-5 is a step of preparing the bicyclic pyrazolinone derivative (1w) having a methoxy group at the 4-position on the benzene ring by reacting the bicyclic pyrazolinone derivative (1s) with methanol in the presence of a base.

The reaction of Step 8-5 is performed in the presence of a base. Examples of the base can include inorganic bases such as sodium hydride and sodium amide, alkali metal alkoxides such as sodium methoxide and potassium tert-butoxide, lithium bases such as methyl lithium, butyl lithium, and lithium diisopropyl amide. From the viewpoint of easy handling and a favorable yield, an inorganic base such as sodium hydride or sodium amide is preferable. The base may usually be used in an equivalent or greater with respect to the bicyclic pyrazolinone derivative (1s).

The reaction temperature is not particularly limited, and since the reaction sufficiently proceeds at room temperature, the bicyclic pyrazolinone derivative (1w) which is a target substance can be obtained with a high yield.

The reaction of Step 8-5 can be performed in an organic solvent. As the organic solvent, any organic solvent can be used as long as it does not adversely affect the reaction, and examples thereof can include ether-based solvents such as 1,4-dioxane and THF, amide-based solvents such as DMF and N,N-dimethyl acetamide, sulfoxide-based solvents such as DMSO, and mixed solvents thereof.

Step 8-6 is a step of converting the methoxy group at the 4-position on the benzene ring of the bicyclic pyrazolinone derivative (1w) into a hydroxyl group.

Step 8-6 is the same reaction as Step 3-8 of Preparation Method-3 described above, and the details thereof are as described in Step 3-8. However, the bicyclic pyrazolinone derivative (1e) in the description of Step 3-8 shall be replaced with the bicyclic pyrazolinone derivative (1w), and the bicyclic pyrazolinone derivative (1f) in the description of Step 3-8 shall be replaced with the bicyclic pyrazolinone derivative (1t).

In Steps 8-1 to 8-6, after the reaction is completed, the target substance is isolated from the reaction system including the target substance by a method generally used in the related art, and if necessary, the target substance can be purified by recrystallization, distillation, column chromatography, or the like. In addition, without purifying the obtained target substance, the obtained target substance can be used in the subsequent step as a starting material, in some case.

The bicyclic pyrazolinone derivative which is represented by the following general formula (1y, 1z, or 1aa) which is a part of the compound of the present invention and in which the 4-position on the benzene ring is a nitro group or an amino group, and the 5-position is a fluorine atom, a substituted oxy group, or a substituted amino group can be prepared, for example, by the following Preparation Method-9.

Preparation Method-9

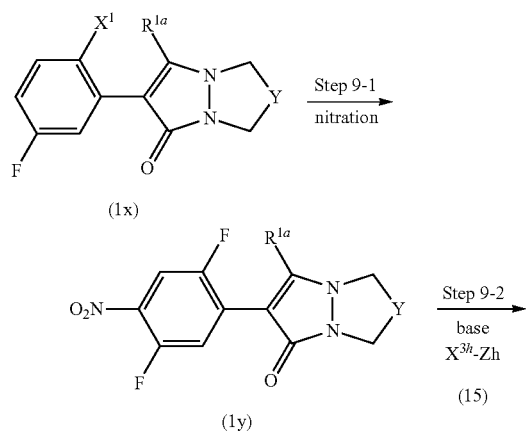

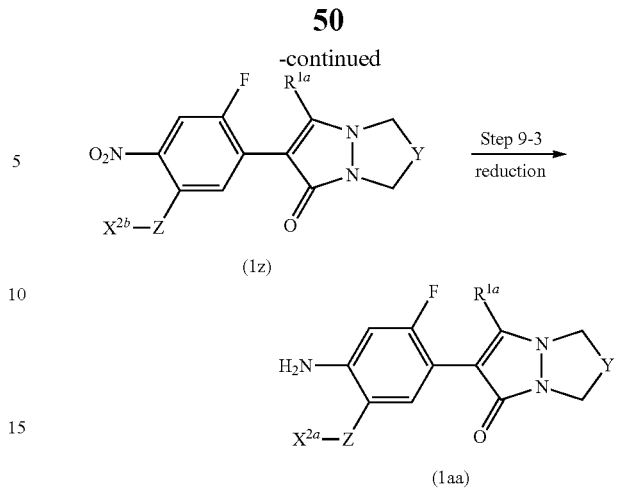

In the formula, $R^{1a}$ and Y each have the same definition as described above. $X^{3h}$ represents a $C_1$-$C_4$ alkyl group; a $C_3$-$C_6$ alkenyl group; a $C_3$-$C_6$ alkynyl group; a $C_7$-$C_8$ aralkyl group which may be substituted with a halogen atom or a trifluoromethyl group; or a phenyl group which may be substituted with one or more substituents selected from the group consisting of a halogen atom, a $C_1$-$C_4$ alkyl group, a $C_1$-$C_4$ haloalkyl group, a $C_1$-$C_4$ alkyloxy group, a $C_1$-$C_4$ haloalkyloxy group, a ($C_1$-$C_4$ alkyl)oxycarbonyl group, a cyano group, and a nitro group. Z represents O (oxygen atom) or NH.

Preparation Method-9 includes Step 9-1 of preparing a bicyclic pyrazolinone derivative (1y) having a nitro group at the 4-position on the benzene ring from a bicyclic pyrazolinone derivative (1x) having a fluorine atom at the 2-position and the 5-position on the benzene ring; Step 9-2 of preparing a bicyclic pyrazolinone derivative (1z) having a substituted oxy group or a substituted amino group at the 5-position on the benzene ring by substituting the fluorine atom at the 5-position on the benzene ring by an oxygen or nitrogen nucleophilic agent; and Step 9-3 of preparing a bicyclic pyrazolinone derivative (1aa) having an amino group at the 4-position on the benzene ring. Hereinafter, each step in Preparation Method-9 will be described in detail.

Step 9-1 is a step of preparing the bicyclic pyrazolinone derivative (1y) by nitrating the bicyclic pyrazolinone derivative (1x).

As the nitration in Step 9-1, for example, a method for nitrating using a mixed acid prepared from concentrated nitric acid and concentrated sulfuric acid in concentrated sulfuric acid or a method for nitrating using fuming nitric acid without a solvent or in a solvent such as dichloromethane can be used. The reaction conditions are not particularly limited, and the bicyclic pyrazolinone derivative (1y) which is a target substance can be prepared with a favorable yield and regioselectivity by performing a reaction according to a general method for nitrating a benzene ring.

The bicyclic pyrazolinone derivative (1x) which is a raw material in Step 9-1 can be prepared according to the method described in Steps 1-1, 1-2, and 1-3 of Preparation Method-1 using 2,5-difluoro-1-bromobenzene as a raw material.

Step 9-2 is a step of preparing the bicyclic pyrazolinone derivative (1z) by nucleophilic substitution of the fluorine atom at the 5-position on the benzene ring of the bicyclic pyrazolinone derivative (1y) with an alcohol or an amine represented by General Formula (15) in the presence of a base.

When performing the reaction of Step 9-2, the reaction can be promoted by adding a base. Examples of the base can include organic bases such as triethylamine, diisopropylethylamine, tributylamine, and pyridine, inorganic bases such as sodium hydride, sodium amide, sodium carbonate, potassium carbonate, and cesium carbonate, alkali metal alkoxides such as sodium methoxide, sodium ethoxide, and potassium tert-butoxide, lithium bases such as methyl lithium and butyl lithium.

In addition, in a case where Z is O (oxygen atom), that is, in the case of nucleophilic substitution with an alcohol, an alkali metal salt of an corresponding alcohol such as sodium methoxide, sodium ethoxide, or potassium tert-butoxide can be used as a reaction reagent.

In a case where Z is O (oxygen atom), it is possible to obtain a target substance with a high yield by using an equal amount or more with respect to the raw material, as the used amount of the base. Since amines used as a raw material act as a base in a case where Z is NH, the reaction proceeds sufficiently even without adding a base, and it is possible to obtain a target substance with a high yield.

The reaction of Step 9-2 can be performed in a solvent. As the solvent, any solvent can be used as long as it does not adversely affect the reaction, and examples thereof can include ether-based solvents such as 1,4-dioxane, THF, DME, diethyl ether, diisopropyl ether, and cyclopentyl methyl ether, aromatic hydrocarbon-based solvents such as benzene, toluene, and chlorobenzene, hydrocarbon-based solvents such as hexane and octane, nitrile-based solvents such as acetonitrile and propionitrile, amide-based solvents such as DMF and N,N-dimethyl acetamide, sulfoxide-based solvents such as DMSO, and mixed solvents thereof. Preferably, ether-based solvents such as 1,4-dioxane and THF can be exemplified.

The reaction of Step 9-2 can be performed at a temperature suitably selected from 0° C. to 100° C.

Step 9-3 is a step of reducing the nitro group at the 4-position on the benzene ring of the bicyclic pyrazolinone derivative (1z).

Step 9-3 is the same reaction as Step 3-3 of Preparation Method-3 described above, and the details thereof are as described in Step 3-3. However, the 3-substituted phenoxy-4-nitrophenyl bromide (2d) in the description of Step 3-3 shall be replaced with the bicyclic pyrazolinone derivative (1z), and the 3-substituted phenoxy-4-aminophenyl bromide (2e) in the description of Step 3-3 shall be replaced with the bicyclic pyrazolinone derivative (1aa).

In Steps 9-1 to 9-3, after the reaction is completed, the target substance is isolated from the reaction system including the target substance by a method generally used in the related art, and if necessary, the target substance can be purified by recrystallization, distillation, column chromatography, or the like. In addition, without purifying the obtained target substance, the obtained target substance can be used in the subsequent step as a starting material, in some case.

Next, the herbicide of the present invention containing the bicyclic pyrazolinone derivative of the present invention as an effective component and the method for use thereof will be described.

The bicyclic pyrazolinone derivative of the present invention has an excellent weed-controlling effect, and can be used as an effective component of a herbicide. In addition, the bicyclic pyrazolinone derivative of the present invention has an excellent profile such as a favorable residual effect or selectivity between a crop and a weed.

The bicyclic pyrazolinone derivative of the present invention is useful for controlling annual, biennial, and perennial weeds which are generated in a paddy field, an upland field, an arboricultural land, or a wetland. More specifically, the bicyclic pyrazolinone derivative of the present invention can control upland field weeds such as crabgrass, green foxtail, common barnyard grass, shortawn foxtail, wild oat, green *amaranthus*, purslane, redroot pigweed, velvetleaf, common lambsquarters, creeping smartweed, tall morning glory, pitted morning glory, purple deadnettle, henbit deadnettle, cocklebur, ragweed, cleavers, chickweed, shepherd's purse, Japanese mugwort, and persian speedwell, or paddy field weeds such as barnyard grass, smallflower umbrella plant, needle spikerush, rock bulrush, tidalmarsh flatsedge, *Eleocharis kuroguwai, monochoria*, common false pimpernel, indian toothcup, *monochoria korsakowii, Ammannia multiflora*, waterwort, dwarf arrowhead, arrowhead, false pimpernel, *eclipta prostrata*, and marsh-dayflower.

In addition, the bicyclic pyrazolinone derivative of the present invention has a favorable selectivity with respect to cultivated crops such as corn, wheat, and soybean, and has an excellent profile as a herbicide, and has an excellent profile as a herbicide which can be applied to the various cultivated crops (for example, corn, wheat, barley, rice, soybean, rapeseed, sugar beet, and cotton).

The bicyclic pyrazolinone derivative of the present invention exhibits an excellent herbicidal effect with respect to weeds before and after budding, and thus, when used as a herbicide, by treating a planting planned site of a crop with the bicyclic pyrazolinone derivative of the present invention in advance or by treating with the bicyclic pyrazolinone derivative of the present invention in the generation period to the growing season of the weed after planting the crop, it is possible to more effectively exhibit a distinctive physiological activity of the bicyclic pyrazolinone derivative of the present invention. However, use of the herbicide of the present invention is not limited to use in such aspects, and, for example, the herbicide of the present invention can also be used for exterminating weeds of an upland field, a paddy field, a paddy field after reaping, a fallow field, a levee, a farm road, a waterway, a pasture developed land, a cemetery, a park, a road, a playground, a vacant lot in the vicinity of a building, a reclaimed land, a side of railroad, or a forest. In this case, although economically it is most advantageous and effective to treat a weed until the generation period of the weed, the period is not necessarily limited thereto, and it is also possible to control weeds in the growing season.

When the bicyclic pyrazolinone derivative of the present invention is used as a herbicide, the bicyclic pyrazolinone derivative may be used after being formed into a shape convenient in use according to a commonly used method in the agrochemical formulation. In general, the bicyclic pyrazolinone derivative of the present invention is formulated in a dosage form suitable for the intended purpose by being formulated with a suitable liquid carrier or solid carrier in a suitable ratio, and dissolved, dispersed, suspended, mixed, impregnated, or adsorbed.

Examples of the formulation form of the herbicide of the present invention can include a wettable powder, a water dispersible granule, a water soluble powder, an emulsifiable concentrate, a liquid formulation, an oil solution, a spray, a dust formulation, a low drift (less drifting) dust, granules, a microgranule, a microgranule F, a fine granule F, a flowable, a dry flowable, a jumbo agent, a tablets, and a paste.

These formulations can be prepared by, as necessary, further adding an auxiliary agent such as an emulsifier, a dispersant, a spreading agent, a penetrating agent, a wetting agent, a binding agent, a thickening agent, a preservative, an antioxidant, or a colorant thereto in a suitable ratio according to a known method.

Examples of the liquid carrier used when formulating can include water; alcohol such as methanol, ethanol, propyl alcohol, isopropyl alcohol, and ethylene glycol; ketones such as acetone, methyl ethyl ketone, methyl isobutyl ketone, diisobutyl ketone, and cyclohexanone; ethers such as dioxane, THF, dipropyl ether, ethylene glycol monomethyl ether, diethylene glycol monomethyl ether, and propylene glycol monomethyl ether; aliphatic hydrocarbons such as hexane, octane, cyclohexane, kerosene, fuel oil, and machine oil; aromatic hydrocarbons such as benzene, toluene, xylene, solvent naphtha, and methylnaphthalene; halogenated hydrocarbons such as dichloromethane, chloroform, and carbon tetrachloride; acid amides such as DMF, dimethylacetamide, and N-methyl pyrrolidone, and esters such as ethyl acetate, butyl acetate, diisopropyl phthalate, dibutyl phthalate, and fatty acid glycerin ester; nitriles such as acetonitrile and propionitrile; sulfoxides such as dimethyl sulfoxide. These liquid carriers can also be used alone or in combination of two or more types thereof in a suitable ratio.

Examples of the solid carrier used when formulating include mineral powders such as clays including kaolin, bentonite, acid clay, and clay, talcs including a talcum powder and a pagodite powder, and silicas including diatomaceous earth, white carbon, and a mica powder; vegetable powders such as soy flour, CMC, a tobacco powder, wheat flour (grain flour), and wood flour; inorganic salts such as calcium carbonate, sodium bicarbonate, potassium chloride, ammonium sulfate, and potassium sulfate; sugars such as lactose and glucose; and other solid carriers such as alumina and activated carbon. These solid carriers can also be used alone or in combination of two or more types thereof in a suitable ratio.

The liquid carrier or the solid carrier used when formulating is usually used in a ratio of 1% by weight to 99% by weight, and preferably in a ratio of about 10% by weight to 99% by weight, with respect to the entirety of formulation.

When formulating, an auxiliary agent such as an emulsifier, a dispersant, a spreading agent, a penetrating agent, or a wetting agent is used depending on the purpose. The auxiliary agent may be used in combination of one or more types, or may not be used at all, depending on the usage. Usually, a surfactant is used for the purpose of emulsification or dispersion of an effective component to a carrier, solubilization, and/or wetting of the effective component.

Examples of the surfactant include nonionic surfactants such as polyoxyethylene alkyl ether, polyoxyethylene alkylaryl ether, a polyoxyethylene alkyl polyoxypropylene block copolymer, polyethylene glycol fatty acid ester, polyoxyethylene polyhydric alcohol fatty acid ester, sucrose fatty acid ester, and sorbitan fatty acid ester; anionic surfactants such as an alkyl sulfuric acid ester salt, alkyl aryl sulfonate, dialkyl sulfosuccinate, polyoxyalkylene allyl phenyl ether sulfonate, polyoxyethylene alkyl phenyl ether sulfonate, a polyoxyethylene alkyl aryl ether phosphoric acid ester salt, lignin sulfonate, a naphthalene sulfonate formaldehyde polycondensate; cationic surfactants such as ammonium type surfactants such as alkyl trimethyl ammonium chloride ($C_{12-18}$), methyl-polyoxyethylene-alkyl ammonium chloride ($C_{12-18}$), alkyl-N-methyl pyridinium bromide ($C_{12-18}$), mono or dialkyl ($C_{12-18}$) methylated ammonium chloride, and alkyl ($C_{12-18}$) pentamethyl propylene diamine dichloride, and benzalkonium type surfactants such as alkyl dimethyl benzalkonium chloride ($C_{12-18}$) and benzethonium chloride (octyl phenoxy ethoxy ethyl dimethyl benzyl ammonium chloride); and amphoteric surfactants such as dialkyl ($C_{8-12}$) diaminoethyl betaine, alkyl ($C_{12-18}$) dimethylbenzyl betaine, dialkyl ($C_{8-12}$) diaminoethyl glycine, and alkyl ($C_{12-18}$) dimethylbenzyl glycine. One or more types of these surfactants can be used depending on the usage. In addition, the surfactant is usually used in a ratio of 0.1% by weight to 50% by weight, and preferably in a ratio of about 0.1% by weight to 25% by weight, with respect to the entirety of formulation.

Examples of the binder and the thickener include dextrin, a sodium salt of carboxymethyl cellulose, a polycarboxylic acid-based polymer compound, polyvinyl pyrrolidone, polyvinyl alcohol, sodium lignin sulfonate, calcium lignin sulfonate, sodium polyacrylate, gum arabic, sodium alginate, mannitol, sorbitol, a bentonite type mineral matter, polyacrylic acid and derivatives thereof, white carbon, and natural saccharide derivatives (for example, xanthan gum and guar gum).

Since the content ratio of the bicyclic pyrazolinone derivative of the present invention in the herbicide of the present invention may be suitably adjusted depending on the intended purpose, the content ratio is not particularly limited; however, the content ratio is usually about 0.01% by weight to 90% by weight, and, for example, the ratio is usually about 1% by weight to 90% by weight in an emulsifiable concentrate, a wettable powder, a water dispersible granule, a liquid formulation, a water soluble powder, a flowable, or the like, the ratio is usually 0.01% by weight to 10% by weight in an oil solution, a dust formulation, a low drift dust, or the like, and the ratio is usually 0.05% by weight to 10% by weight in a microgranule, a microgranule F, a fine granule F, a granule, or the like. An emulsifiable concentrate, a wettable powder, a water dispersible granule, a liquid formulation, a water soluble powder, a flowable, or the like is used after being suitably diluted with water, and, usually, is used after being diluted to about 100 times to 100,000 times.

Next, the method for using the herbicide of the present invention will be described. The herbicide of the present invention can be applied by an application method of known agricultural chemicals such as spray onto soil, spray on water surface, foliage application, or aerial application.

Although the used amount (that is, effective amount) in the case of using the herbicide of the present invention as a herbicide for an upland field or a paddy field may be suitably set in consideration of an application area, an application period, an application method, a target weed species, and a cultivated crop, in general, the used amount is about 1 g to 5,000 g, and preferably about 10 g to 1,000 g per hectare of an upland field or a paddy field as the compound of the present invention.

The herbicide of the present invention when used for control upland field weeds is used usually as a preemergence soil-mixing treatment agent, a preemergence soil treatment agent, or a postemergence foliage treatment agent. The herbicide of the present invention when used for controlling paddy field weeds is used usually as a submerged soil treatment agent or a foliage and soil treatment agent.

In addition, the herbicide of the present invention can also be used in mixture or in combination with one or more types of other herbicides, insecticides, acaricides, nematicides, fungicides, and plant-growth regulators, as necessary. The herbicide of the present invention may be formulated with other effective components of the one or more types of herbicides, insecticides, acaricides, nematicides, fungicides, and plant-growth regulators, and may be used in mixture with these other effective components.

Examples of other effective components of herbicides which can be used by being applied and/or formulated with the compound of the present invention include (1) phenoxy fatty acid-based herbicide compound [2,4-PA, MCP, MCPB, phenolthiol, mecoprop, fluroxypyr, triclopyr, clomeprop, naproanilide, and the like], (2) benzoic acid-based herbicide compound [2,3,6-TBA, dicamba, clopyralid, picloram, aminopyralide, quinclorac, quinmerac, and the like], (3) urea-based herbicide compound [diuron, linuron, chlortoluron, isoproturon, fluometuron, isouron, tebuthiuron, methabenzthiazuron, cumyluron, dymron, methyl dymron, and the like], (4) triazine-based herbicide compound [atrazine, ametryn, cyanazine, simazine, propazine, simetryn, dimethametryn, prometryn, metribuzin, triaziflam, and the like], (5) bipyridinium-based herbicide compound [paraquat, diquat, and the like], (6) hydroxybenzonitrile-based herbicide compound [bromoxynil, ioxynil, and the like], (7) dinitroaniline-based herbicide compound [pendimethalin, prodiamine, trifluralin, and the like], (8) organic phosphorus-based herbicide compound [amiprophos-methyl, butamifos, bensulide, piperophos, anilofos, glyphosate, glufosinate, glufosinate-P, bialaphos, and the like], (9) carbamate-based herbicide compound [diallate, triallate, EPIC, butylate, benthiocarb, esprocarb, molinate, dimepiperate, swep, chlorpropham, phenmedipham, phenisopham, pyributicarb, asulam, and the like],

(10) acid amide-based herbicide compound [propanil, propyzamide, bromobutide, etobenzanide, and the like],

(11) chloroacetanilide-based herbicide compound [acetochlor, alachlor, butachlor, dimethenamid, propachlor, metazachlor, metolachlor, pretilachlor, thenylchlor, pethoxamid, and the like],

(12) diphenyl ether-based herbicide compound [acifluorfen, bifenox, oxyfluorfen, lactofen, fomesafen, chlomethoxynil, aclonifen, and the like],

(13) cyclic imide-based herbicide compound [oxadiazon, cinidon-ethyl, carfentrazone-ethyl, sulfentrazone, flumiclorac-pentyl, flumioxazin, pyraflufen-ethyl, oxadiargyl, pentoxazone, fluthiacet-methyl, butafenacil, benzfendizone, bencarbazone, saflufenacil, and the like],

(14) pyrazole-based herbicide compound [benzofenap, pyrazolate, pyrazoxyfen, topramezone, pyrasulfotole, and the like],

(15) triketone-based herbicide compound [isoxaflutole, benzobicyclon, sulcotrione, mesotrione, tembotrione, tefuryltrione, and the like],

(16) aryloxy phenoxy propionic acid-based herbicide compound [clodinafop-propargyl, cyhalofop-butyl, dichlofop-methyl, fenoxaprop-ethyl, fulazifop-butyl, haloxyfop-methyl, quizalofop-ethyl, metamifop, and the like],

(17) trione oxime-based herbicide compound [alloxydim, sethoxydim, butroxydim, clethodim, cloproxydim, cycloxydim, tepraloxydim, tralkoxydim, profoxydim, and the like],

(18) sulfonylurea-based herbicide compound [chlorsulfuron, sulfometuron-methyl, metsulfuron-methyl, chlorimuron-ethyl, tribenuron-methyl, triasulfuron, bensulfuron-methyl, thifensulfuron-methyl, pyrazosulfuron-ethyl, primisulfuron-methyl, nicosulfuron, amidosulfuron, cinosulfuron, imazosulfuron, rimsulfuron, halosulfuron-methyl, prosulfuron, ethametsulfuron-methyl, triflusulfuron-methyl, flazasulfuron, cyclosulfamuron, flupyrsulfuron, sulfosulfuron, azimsulfuron, ethoxysulfuron, oxasulfuron, iodosulfuron-methyl sodium, foramsulfuron, mesosulfuron-methyl, trifloxysulfuron, tritosulfuron, orthosulfamuron, flucetosulfuron, propyrisulfuron, and the like],

(19) imidazolinone-based herbicide compound [imazamethabenz-methyl, imazamethapyr, imazamox, imazapyr, imazaquin, imazethapyr, and the like],

(20) sulfonamide-based herbicide compound [flumetsulam, metosulam, diclosulam, florasulam, cloransulam-methyl, penoxsulam, pyroxsulam, and the like],

(21) pyrimizinyloxy benzoic acid-based herbicide compound [pyrithiobac sodium, bispyribac sodium, pyriminobac-methyl, pyribenzoxim, pyriftalid, pyrimisulfan, and the like], and

(22) other herbicidal compounds [bentazone, bromacil, terbacil, chlorthiamid, isoxaben, dinoseb, amitrole, cinmethylin, tridiphane, dalapon, diflufenzopyr sodium, dithiopyr, thiazopyr, flucarbazone sodium, propoxycarbazone sodium, mefenacet, flufenacet, fentrazamide, cafenstrole, indanofan, oxaziclomefone, benfuresate, ACN, pyridate, chloridazon, norflurazon, flurtamone, diflufenican, picolinafen, beflubutamid, clomazone, amicarbazone, pinoxaden, pyraclonil, pyroxasulfone, thiencarbazone-methyl, aminocyclopyrachlor, ipfencarbazone, and the like], examples of the effective component of a plant growth regulator include hymexazol, paclobutrazol, uniconazole-P, inabenfide, prohexadione calcium, aviglycine, 1-naphthylacetamide, abscisic acid, indolebutyric acid, ethychlozate, ethephon, cloxyfonac, chlormequat, dichlorprop, gibberellin, prohydrojasmon, benzylaminopurine, forchlorfenuron, maleic hydrazide acid, calcium peroxide, mepiquat chloride, and 4-CPA, examples of the effective component of the fungicide include (1) polyhaloalkylthio-based fungicidal compounds [captan, folpet, and the like], (2) organic phosphorus-based fungicidal compounds [IBP, EDDP, tolclofos-methyl, and the like], (3) benzimidazole-based fungicidal compounds [benomyl, carbendazim, thiophanate-methyl, thiabendazole, and the like], (4) carboxyamide-based fungicidal compounds [carboxin, mepronil, flutolanil, thifluzamide, furametpyr, boscalid, penthiopyrad, and the like], (5) dicarboximide-based fungicidal compounds [procymidone, iprodione, vinclozolin, and the like], (6) acyl alanine-based fungicidal compounds [metalaxyl and the like], (7) azole-based fungicidal compounds [triadimefon, triadimenol, propiconazole, tebuconazole, cyproconazole, epoxiconazole, prothioconazole, ipconazole, triflumizole, prochloraz, penconazole, flusilazole, diniconazole, bromuconazole, difenoconazole, metconazole, tetraconazole, myclobutanil, fenbuconazole, hexaconazole, fluquinconazole, triticonazole, bitertanol, imazalil, flutriafol, and the like], (8) morpholine-based fungicidal compounds [dodemorph, tridemorph, fenpropimorph, and the like], (9) strobilurin-based fungicidal compounds [azoxystrobin, kresoxim-methyl, metominostrobin, trifloxystrobin, picoxystrobin, pyraclostrobin, fluoxastrobin, dimoxystrobin, and the like],

(10) antibiotic-based fungicidal compounds [validamycin A, blasticidin S, kasugamycin, polyoxins and the like],

(11) dithiocarbamate-based fungicidal compounds [mancozeb, maneb, thiuram, and the like], and

(12) other fungicidal compounds [fthalide, probenazole, isoprothiolane, tricyclazole, pyroquilon, ferimzone, acibenzolar-S-methyl, carpropamid, diclocymet, fenoxanil, tiadinil, diclomezine, tecloftalam, pencycuron, oxolinic acid, TPN, triforine, fenpropidin, spiroxamine, fluazinam, iminoctadine, fenpiclonil, fludioxonil, quinoxyfen, fenhexamid, silthiofam, proquinazid, cyflufenamid, copper calcium hydroxide sulfate, dichlofluanid, cyprodinil, pyrimethanil, mepanipyrim, diethofencarb, pyribencarb, famoxadone, fenamidone, zoxamide, ethaboxam, amisulbrom, iprovaricarb, benthiavalicarb, cyazofamid, mandipropamid, metrafenone, fluopyram, bixafen, and the like], examples of the effective component of the insecticide include (1) organic phosphorus-based insecticidal compounds [fenthion, fenitrothion, pirimiphos-methyl, diazinon, quinalphos, isoxathion, pyridaphenthion, chlorpyrifos, chlorpyrifos-methyl, vamidothion, malathion, phenthoate, dimethoate, disulfoton, monocrotophos, tetrachlorvinphos, chlorfenvinphos, propaphos, acephate, trichlorfon, EPN, pyraclofos, butathiofos, chlorethoxyfos, cyanophos, dichlofenthion, dichlorvos, dimethylvinphos, ethion, ethoprophos, etrimfos, formothion, isofenphos, mesulfenfos, methidathion, naled, oxydeprofos, parathion, phosalone, phosmet, profenofos, prothiofos, salithion, sulprofos, tebupirimfos, temephos, terbufos, thiometon, folate, and the like], (2) carbamate-based insecticidal compounds [carbaryl, metolcarb, isoprocarb, BPMC, propoxur, XMC, carbofuran, carbosulfan, benfuracarb, furathiocarb, methomyl, thiodicarb, alanycarb, bendiocarb, chloethocarb, ethiofencarb, fenobucarb, oxamyl, pirimicarb, xylylcarb, aldicarb, and the like], (3) synthetic pyrethroid-based insecticidal compounds [tefluthrin, bifenthrin, cycloprothrin, ethofenprox, acrinathrin, allethrin, benfluthrin, beta-cyfluthrin, cyfluthrin, cyhalothrin, cypermethrin, deltamethrin, esfenvalerate, fenpropathrin, fenvalerate, flucythrinate, flufenprox, flumethrin, fluvalinate, halfenprox, imiprothrin, permethrin, prallethrin, pyrethrin, resmethrin, sigma-cypermethrin, silafluofen, tralomethrin, transfluthrin, tetramethrin, phenothrin, cyphenothrin, alpha-cypermethrin, zeta-cypermethrin, lambda cyhalothrin, gamma-cyhalothrin, furamethrin, tau-fluvalinate, metofluthrin, profluthrin, dimefluthrin, protrifenbute, and the like], (4) nereistoxin-based insecticidal compounds [cartap, bensultap, thiocyclam, and the like], (5) neonicotinoid-based insecticidal compounds [imidacloprid, nitenpyram, acetamiprid, thiamethoxam, thiacloprid, dinotefuran, clothianidin, and the like], (6) benzoylphenyl urea-based insecticidal compounds [chlorfluazuron, fluazuron, flufenoxuron, hexaflumuron, lufenuron, novaluron, bistrifluron, diflubenzuron, flucycloxuron, noviflumuron, teflubenzuron, triflumuron, and the like], (7) macrolide-based insecticidal compounds [emamectin, abamectin, milbemectin, lepimectin, spinosad, spinetoram, and the like], and (8) other insecticidal compounds [buprofezin, tebufenozide, chromafenozide, halofenozide, methoxyfenozide, fipronil, ethiprole, acetoprole, vaniliprole, pyriprole, pyrafluprole, pymetrozine, pyrifluquinazon, diafenthiuron, indoxacarb, metaflumizone, tolfenpyrad, flufenerim, pyridalyl, flonicamid, spiromesifen, spirotetramat, flubendiamide, chlorantraniliprole, pyriproxyfen, cyromazine, metoxadiazone, triazamate, chlordane, nicotine sulfate, tralopyril, Bt toxin-based insecticide, and the like], examples of the effective component of the acaricide include hexythiazox, pyridaben, fenpyroximate, tebufenpyrad, chlorfenapyr, etoxazole, pyrimidifen, acequinocyl, bifenazate, spirodiclofen, fenazaquin, bromopropylate, formetanate, amitraz, benzoximate, quinomethionate, chlorobenzilate, chlorfenson, clofentezine, cyflumetofen, dicofol, fenbutatin oxide, fenothiocarb, fluacrypyrim, propargite, polynactins, tetradifon, amidoflumet, and cyenopyrafen, and examples of the effective component of the nematicide include fosthiazate, cadusafos, benclothiaz, metam-ammonium, metam-sodium, DCIP, levamisole hydrochloride, methyl isothiocyanate, morantel tartrate, and imicyafos.

The above compounds represented by the general name are compounds described in known literature (for example, refer to "The Pesticide Manual, 16th Edition, 2012)", and "SHIBUYA INDEX-2012-16th Edition, Narumi Shibuya et al., May 2012").

Among these, from the viewpoint of expansion of a herbicidal spectrum or a synergistic effect on weeds hard to control, ALS inhibition type herbicides such as amidosulfuron, azimsulfuron, bensulfuron-methyl, chlorimuron, cyclosulfamuron, ethoxysulfuron, flazasulfuron, flucetosulfuron, flupyrsulfuron, foramsulfuron, halosulfuron-methyl, imazosulfuron, mesosulfuron, nicosulfuron, orthosulfamuron, oxasulfuron, pyrimisulfuron, pyrazosulfuron-ethyl, rimsulfuron, sulfometuron, sulfosulfuron, trifloxysulfuron, chlorsulfuron, cinosulfuron, ethamesulfuron, iodosulfuron, met sulfur on, prosulfuron, thifensulfuron, triasulfuron, tribenuron, triflusulfuron, tritosulfuron, bispyribac, pyriminobac-methyl, a pyrithiobac-sodium salt, pyriftalid, pyrimisulfan, penoxsulam, and propyrisulfuron;

photosynthesis inhibition type herbicides such as isonoruron, isouron, methabenzthiazuron, monisouron, noruron, anisuron, buturon, chlorbromuron, chloreturon, chlorotoluron, chloroxuron, daimuron, cumyluron, difenoxuron, dimefuron, diuron, fenuron, flumeturon, fluothiuron, isoproturon, linuron, methiuron, methyl dymron, metobenzuron, metobromuron, metoxuron, monolinuron, monuron, neburon, atrazine, dimethametryn, methoprotryne, prometryn, and simetryn;

fatty acid biosynthesis inhibition type herbicides such as chlorazifop, clodinafop, clofop, cyhalofop-butyl, diclofop, fenoxaprop, fenoxaprop-P, fenthiaprop, fluazifop, fluazifop-P, haloxyfop, haloxyfop-P, isoxapyrifop, metamifop, propaquizafop, quizalofop, quizalofop-P, alloxydim, butoxydim, clethodim, cloproxydim, cycloxydim, profoxydim, sethoxydim, tepraloxydim, and tralkoxydim;

PDS inhibition type herbicides such as beflubutamid, picolinafen, and diflufenican;

HPPD inhibition type herbicides such as benzofenap, pyrasulfotole, pyrazolate, pyrazoxyfen, mesotrione, sulcotrione, tefuryltrione, tembotrione, benzobicyclon, isoxachlotole, and isoxaflutole;

PPO inhibition type herbicides such as pentoxazone, azafenidin, flumiclorac, flumioxazin, flumipropyn, pyraflufen-ethyl, oxadiargyl, and oxadiazon; and herbicides of other mechanism of action such as indanofan, oxaziclomefone, butachlor, pretilachlor, thenylchlor, naproanilide, clomeprop, fentrazamide, ipfencarbazone, mefenacet, bromobutide, anilofos, esprocarb, pyributicarb, thiobencarb, benfuresate, molinate, quinoclamine, MCPA ethyl, MCPA thioethyl, an MCPA sodium salt, MCPB, cafenstrole, pyraclonil, and fenoxasulfone are preferable.

In the case of being used as a herbicide for paddy field, azimsulfuron, bensulfuron-methyl, cyclosulfamuron, flucetosulfuron, orthosulfamuron, ethoxysulfuron, halosulfuron-methyl, a bispyribac sodium salt, pyriminobac-methyl, pyriftalid, penoxsulam, pyrimisulfan, pyrazosulfuron-ethyl, imazosulfuron, daimuron, cumyluron, simetryn, cyhalofop-butyl, metamifop, benzofenap, pyrazolate, pyrazoxyfen, benzobicyclon, tefuryltrione, pentoxazone, oxadiazon, indanofan, oxaziclomefone, butachlor, pretilachlor, thenylchlor, napropanilide, clomeprop, fentrazamide, mefenacet, bromobutide, cafenstrole, anilofos, esprocarb, pyributicarb, thiobencarb, benfuresate, molinate, quinoclamine, MCPA thioethyl, MCPB, pyraclonil, propyrisulfuron, or fenoxasulfone is particularly preferable.

A phytotoxicity reducing agent (for example, furilazole, dichlormid, benoxacor, allidochlor, isoxadifen-ethyl, fenchlorazole-ethyl, mefenpyr-diethyl, cloquintocet-mexyl, fenclorim, cyprosulfamide, cyometrinil, oxabetrinil, fluxofenim, flurazole, 2-dichloromethyl-2-methyl-1,3-dioxolane, or 1,8-naphthalic anhydride), coloring matter, a fertilizer (for example, urea), or the like may be suitably mixed into a herbicide containing the compound of the present invention as an effective component.

The herbicide containing the compound of the present invention as an effective component can be used as a herbicide for agricultural land or non-agricultural land such as a upland field, a paddy field, a lawn, or an orchard. For example, the herbicide containing the compound of the present invention as an effective component is useful as a herbicide on agricultural land where the following "crops" are cultivated.

Agricultural crops: corn, rice, wheat, barley, rye, oat, sorghum, cotton, soybean, peanut, buckwheat, sugar beet, rapeseed, sunflower, sugar cane, tobacco, and the like, Vegetables: vegetables from the family Solanaceae (eggplant, tomato, green pepper, red pepper, potato, and the like), vegetables from the family Cucurbitaceae (cucumber, squash, zucchini, watermelon, melon, and the like), vegetables from the family Cruciferae (radish, turnip, horseradish, kohlrabi, chinese cabbage, cabbage, mustard, broccoli, cauliflower, and the like), vegetables from the family Compositae (burdock, edible *chrysanthemum*, artichoke, lettuce, and the like), vegetables from the family Liliaceae (green onion, onion, garlic, asparagus, and the like), vegetables from the family Apiaceae (carrot, parsley, celery, parsnip, and the like), vegetables from the family Chenopodiaceae (spinach, chard, and the like), vegetables from the family Lamiaceae (perilla, mint, basil, and the like), strawberry, sweet potato, Japanese yam, taro, and the like, Fruit trees: pomaceous fruits (apple, European pear, japanese pear, Chinese quince, quince, and the like), stone fruits (peach, plum, nectarine, Japanese apricot, cherry, apricot, prune, and the like), citrus (Citrus unshiu, orange, lemon, lime, grapefruit, and the like), nuts (chestnut, walnut, hazelnut, almond, pistachio, cashew nut, macadamia nut, and the like), berries (blueberry, cranberry, blackberry, raspberry, and the like), grape, persimmon, olive, loquat, banana, coffee, date palm, coconut, oil palm, and the like, Trees other than fruit trees: tea, mulberry, flowering plant, roadside trees (ash, birch, dogwood, *eucalyptus, Ginkgo biloba*, lilac, maple, *Quercus*, poplar, *Cercis chinensis, Liquidambar formosana*, plane tree, *zelkova*, Japanese arborvitae, fir tree, hemlock, juniper, *Pinus*, Spruce tree, and *Taxus cuspidata*), and the like.

Others: flowers and ornamental plants (rose, carnation, *chrysanthemum*, Russell prairie gentian, *gypsophila*, *gerbera*, marigold, *salvia, petunia, verbena*, tulip, aster, gentian, lily, pansy, cyclamen, orchid, lily of the valley, lavender, stock, ornamental cabbage, *primula*, poinsettia, *gladiolus*, cattleya, daisy, cymbidium, *begonia*, and the like), foliage plants, and the like.

The above "crops" also include crops such as rapeseed, wheat, sunflower, rice, corn, and soybean to which resistance to HPPD inhibitors such as isoxaflutole, ALS inhibitors such as imazethapyr and thifensulfuron-methyl, EPSP synthetase inhibitors such as glyphosate, glutamine synthetase inhibitors such as glufosinate, acetyl-CoA carboxylase inhibitors such as sethoxydim, PPO inhibitors such as flumioxazin, and herbicides such as bromoxynil, dicamba, and 2,4-D is imparted by a classical breeding method or gene recombination technologies.

Examples of the "crops" to which resistance is imparted by a classical breeding method can include crops such as rapeseed, wheat, sunflower, rice, and corn having resistance to imidazolinone-based ALS inhibition type herbicides; soybean having resistance to sulfonylurea-based ALS inhibition type herbicides; and SR corn as an example of a crop to which resistance to acetyl-CoA carboxylase inhibitors is imparted.

Examples of the "crops" to which resistance is imparted by gene recombination technologies can include crops such as corn, soybean, cotton, rapeseed, and sugar beet varieties having resistance to glyphosate; corn, soybean, cotton, and rapeseed varieties having resistance to glufosinate; and cotton having resistance to bromoxynil.

The above "crops" also include, for example, crops which can synthesize selective toxins or the like known as genus *Bacillus*, crops which have an ability to generate antipathogenic substances having a selective action, and crops to which useful traits such as an oil component modification or an amino acid content enhancing trait are imparted, using gene recombination technologies.

For the above-described classical herbicide trait, a herbicide resistance gene, an insecticidal pest resistant gene, an antipathogenic substance generating gene, and useful traits such as an oil component modification or an amino acid content enhancing trait, stacked GM plants in which a plurality of these are combined are also included in the above "crops".

When using the compound of the present invention in a crop which has a herbicide resistance, it is possible to control overall weeds by a systematic treatment and/or a mixing treatment of a herbicide (for example, glyphosate or a salt thereof, glufosinate or a salt thereof, dicamba or a salt thereof, imazethapyr or a salt thereof, and isoxaflutole) to which the crop has a resistance and the compound of the present invention.

EXAMPLES

The present invention is described below in further detail based on Examples, Reference Examples, Preparation Examples, and Test Examples, but the present invention is not limited thereto.

Reference Example-1

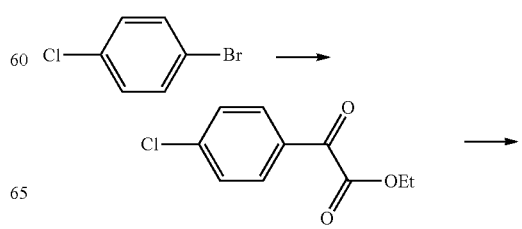

-continued

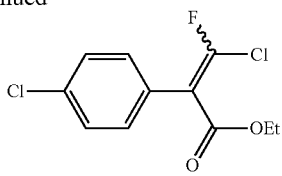

A solution of 1-bromo-4-chlorobenzene (15.0 g, 38.4 mmol) in THF was added dropwise to a suspension of magnesium (2.1 g, 86.2 mmol) in THF at 40° C. (oil bath temperature) in the presence of a catalytic amount of iodine in an argon gas atmosphere, whereby a Grignard reagent was prepared. The Grignard reagent was added dropwise to a solution of diethyl oxalate (17.7 g, 94.2 mmol) in THF at −45° C., and the temperature was slowly raised to room temperature, followed by stirring for 18 hours. After the reaction was completed, the reaction solution was poured into ice, then, acidified with concentrated hydrochloric acid, and the resultant product was extracted with ether (100 mL×2). The organic layer was dried over anhydrous magnesium sulfate, and concentrated under reduced pressure, whereby a yellow oily crude product (14.8 g) was obtained. This was purified by silica gel column chromatography (hexane:ethyl acetate=5:1), whereby ethyl 2-(4-chlorophenyl)-2-oxoacetate (4.68 g, yield: 22%) was obtained as a yellow oily material. $^1$H-NMR (400 MHz, CDCl$_3$): δ1.43 (t, J=7.2 Hz, 3H), 4.45 (q, J=7.2 Hz, 2H), 7.49 (d, J=8.7 Hz, 2H), 7.99 (d, J=8.7 Hz, 2H).

Triphenylphosphine (5.18 g, 19.8 mmol) and N,N-dimethyl acetamide (30 mL) were put into an autoclave made of stainless steel, then, ethyl 2-(4-chlorophenyl)-2-oxoacetate (3.0 g, 14.1 mmol) and zinc (1.86 g, 28.2 mmol) were added thereto, and trichlorofluoromethane (7.75 g, 56.4 mmol) was further added thereto, followed by stirring at 70° C. for 42 hours. After the reaction was completed, the reaction mixture was filtered using Celite, then, water (200 mL) was added to the filtrate, and the resultant product was extracted with ethyl acetate (50 mL×3). The organic layer was dried over anhydrous magnesium sulfate, and concentrated under reduced pressure, whereby a crude product (10.1 g) was obtained as a dark brown semi-solid. This was purified by silica gel column chromatography (hexane:ethyl acetate=5:1), whereby ethyl 3-chloro-2-(4-chlorophenyl)-3-fluoroacrylate (723 mg, yield: 16%) was obtained as an orange oily material. $^1$H-NMR (400 MHz, CDCl$_3$): δ1.27 (t, J=6.6 Hz, 3H), 4.25 (q, J=6.6 Hz, 2H), 7.24-7.27 (m, 2H), 7.34-7.39 (m, 2H). $^{19}$F-NMR (376 MHz, CDCl$_3$): δ−58.4 (s, 1F).

Reference Example-2

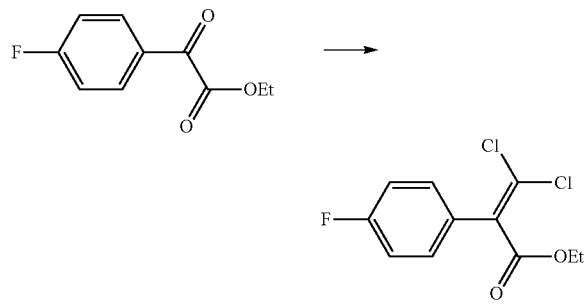

Carbon tetrachloride (3.06 g, 19.9 mmol) and ethyl 2-(4-fluorophenyl)-2-oxoacetate (1.95 g, 9.94 mmol) were added to a solution of triphenylphosphine (7.82 g, 29.8 mmol) in dichloromethane under ice-cooling, followed by stirring at room temperature for 3 hours. After the reaction was completed, water (50 mL) was added to the reaction solution, and the resultant product was extracted with chloroform (20 mL×2). The organic layer was dried over anhydrous magnesium sulfate, and concentrated under reduced pressure. Ether was added to the residue, then, the precipitated solid was filtered using a glass filter, and the resultant product was washed with ether. The filtrate and the reaction solution were combined, and the resultant product was concentrated under reduced pressure, whereby a crude product (4.57 g) was obtained as a pale yellow solid. This was purified by silica gel column chromatography (hexane:ethyl acetate=10:1), whereby ethyl 3,3-dichloro-2-(4-fluorophenyl)acrylate (1.65 g, yield: 39%) was obtained as a colorless oily material. $^1$H-NMR (400 MHz, CDCl$_3$): δ1.30 (t, J=7.1 Hz, 3H), 4.27 (q, J=7.1 Hz, 2H), 7.08 (dd, J=8.8 and 8.8 Hz, 2H), 7.37 (t, J=6.0 and 8.8 Hz, 2H). $^{19}$F-NMR (376 MHz, CDCl$_3$): δ−111 (s, 1F).

Reference Example-3

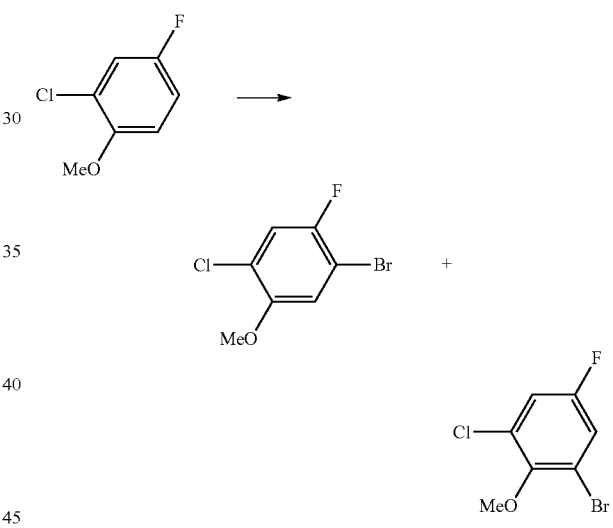

Bromine (19 mL, 31 mmol) was added to a solution of 2-chloro-4-fluoroanisole (38 g, 24 mmol) in concentrated sulfuric acid (100 mL) under ice-cooling, followed by stirring for 1.5 hours. The reaction solution was added little by little to ice water, and the resultant product was extracted with ether (300 mL×3). After the organic layer was washed with a 5% sodium thiosulfate aqueous solution (300 mL), the organic layer was dried over anhydrous magnesium sulfate, filtered, and concentrated under reduced pressure, and the obtained crude product was purified by silica gel chromatography (hexane:ethyl acetate=1:0 to 10:1), whereby 5-bromo-2-chloro-4-fluoroanisole (8.0 g, yield: 14%) was obtained as a white solid, and 2-bromo-6-chloro-4-fluoroanisole (16.7 g, yield: 24%) was obtained as a white solid. 5-Bromo-2-chloro-4-fluoroanisole: $^1$H-NMR (400 MHz, CDCl$_3$): δ3.88 (s, 3H), 7.07 (d, J=6.0 Hz, 1H), 7.19 (d, J=7.8 Hz, 1H). $^{19}$F-NMR (376 MHz, CDCl$_3$): δ−116.1 (s, 1F). 2-Bromo-6-chloro-4-fluoroanisole: $^1$H-NMR (400 MHz, CDCl$_3$): δ3.86 (s, 3H), 7.11 (dd, J=3.0 and 7.9 Hz, 1H), 7.22 (dd, J=3.0 and 7.6 Hz, 1H). $^{19}$F-NMR (376 MHz, CDCl$_3$): δ−115.4 (s, 1F).

Reference Example-4

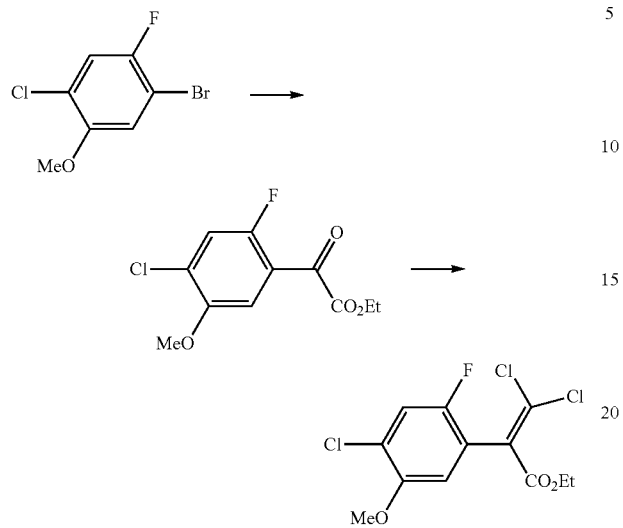

THF (30 mL) was added to metal magnesium (926 mg, 36.7 mmol), and 5-bromo-2-chloro-4-fluoroanisole (8.0 g, 33.4 mmol) was slowly added thereto, whereby a Grignard reagent was prepared. The previously prepared Grignard reagent was added dropwise to the separately prepared solution of diethyl oxalate (5.4 g, 36.7 mmol) in THF (30 mL) at −40° C. The resultant product was stirred for 18 hours while slowly returning the reaction temperature to room temperature. A saturated ammonium chloride aqueous solution and water (200 mL) were added to the reaction solution, and the resultant product was extracted with ethyl acetate (200 mL×2). The organic layer was dried over magnesium sulfate, filtered, and concentrated under reduced pressure, and the resultant product was purified by silica gel column chromatography (hexane:ethyl acetate=10:1), whereby ethyl 2-(4-chloro-2-fluoro-5-methoxyphenyl)-2-oxoacetate (4.27 g, yield: 49%) was obtained as a colorless liquid. $^1$H-NMR (400 MHz, CDCl$_3$): δ1.40 (t, J=7.2 Hz, 3H), 3.95 (s, 3H), 4.43 (q, J=7.2 Hz, 2H), 7.25 (d, J=9.9 Hz, 1H), 7.42 (d, J=5.9 Hz, 1H). $^{19}$F-NMR (376 MHz, CDCl$_3$): δ−119.7 (s, 1F).

Carbon tetrachloride (5.1 g, 32.8 mmol) was added to a solution of triphenylphosphine (8.6 g, 32.8 mmol) in dichloromethane (60 mL) at 0° C., followed by stirring for 15 minutes. To the solution, ethyl 2-(4-chloro-2-fluoro-5-methoxyphenyl)-2-oxoacetate (4.27 g, 16.4 mmol) was added, followed by stirring at room temperature for 24 hours. The solvent was removed from the reaction mixture under reduced pressure, then, a mixed solvent of chloroform and ether was added to the residue, and the solid was separated by filtration. The filtrate was concentrated under reduced pressure, and the obtained crude product was purified by silica gel column chromatography (hexane:ethyl acetate=10:1), whereby ethyl 3,3-dichloro-2-(4-chloro-2-fluoro-5-methoxyphenyl)acrylate (4.4 g, yield: 82%) was obtained as a colorless liquid. $^1$H-NMR (400 MHz, CDCl$_3$): δ1.27 (t, J=7.2 Hz, 3H), 3.89 (s, 3H), 4.26 (q, J=7.2 Hz, 2H), 6.85 (d, J=6.2 Hz, 1H), 7.18 (d, J=8.7 Hz, 1H). $^{19}$F-NMR (376 MHz, CDCl$_3$): δ−121.6 (s, 1F).

Reference Example-5

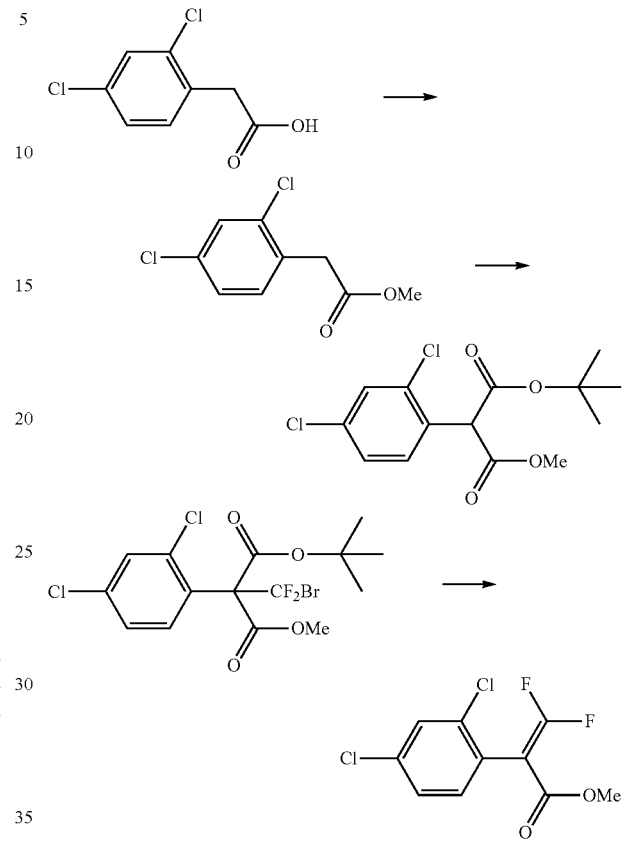

After 2-(2,4-Dichlorophenyl) acetic acid (9.86 g, 48.1 mmol) was dissolved in DMF (50 mL), potassium carbonate (6.65 g, 48.1 mmol) was added thereto, and methyl iodide (21.6 g, 144 mmol) was added thereto, followed by stirring at room temperature for 21 hours. After the reaction was completed, 2N hydrochloric acid (100 mL) was added to the reaction solution, and the resultant product was extracted with ethyl acetate (50 mL×1, 30 mL×2). The organic layer was washed with a saturated saline solution (10 mL), dried over anhydrous magnesium sulfate, and concentrated under reduced pressure, whereby a brown oily crude product (15.1 g) was obtained. This was purified by silica gel column chromatography (hexane:ethyl acetate=5:1), whereby methyl 2-(2,4-dichlorophenyl) acetate (10.7 g, yield: quantitative) was obtained as a colorless oily material. $^1$H-NMR (400 MHz, CDCl$_3$): δ3.72 (s, 3H), 3.75 (s, 2H), 7.22 (d, J=1.2 Hz, 2H), 7.41 (t, J=1.2 Hz, 1H).

Methyl 2-(2,4-dichlorophenyl) acetate (10.6 g, 48.4 mmol) was dissolved in THF (100 mL), and sodium hydride (55% w/w, 2.53 g, 58.1 mmol) was added little by little thereto under ice-cooling, followed by stirring for 10 minutes. tert-Butyl dicarbonate (11.1 g, 50.8 mmol) was added to the reaction solution at the same temperature, and the temperature was slowly raised to room temperature, followed by stirring for 23 hours. Thereafter, tetrabutyl ammonium chloride (4.03 g, 14.5 mmol) was added to the reaction solution, followed by stirring for 20 hours. Sodium hydride (55% w/w, 2.53 g, 58.1 mmol) was added little by little to the reaction solution under ice-cooling, followed by refluxing for 23 hours. After the reaction was completed, the reaction solution was added little by little to saturated ammonium chloride aqueous solution (150 mL) under ice-cooling, and the resultant product was extracted with ethyl acetate (100 mL×2, 50 mL×1). The organic layer was dried over anhydrous magnesium sulfate, and concentrated under reduced pressure, whereby a brown oily crude product (13.4 g) was obtained. This was purified by silica gel column chromatography (hexane:ethyl acetate=10:1), whereby tert-butyl 2-(2,4-dichlorophenyl) malonate (5.41 g, yield: 35%) was obtained as a yellow oily material. $^1$H-NMR (400 MHz, CDCl$_3$): δ1.46 (s, 9H), 3.67 (s, 3H), 5.09 (s, 1H), 7.27-7.44 (m, 3H).

tert-Butyl 2-(2,4-dichlorophenyl) malonate (5.41 g, 16.9 mmol) was dissolved in THF (70 mL), and sodium hydride (55% w/w, 1.48 g, 33.9 mmol) was added little by little thereto under ice-cooling. After the temperature of the reaction solution was returned to room temperature, dibromodifluoromethane (10.7 g, 50.9 mmol) was added thereto, followed by stirring for 94 hours. After the reaction was completed, the reaction solution was added little by little to saturated ammonium chloride aqueous solution (250 mL) under ice-cooling, and the resultant product was extracted with ethyl acetate (50 mL×2). The organic layer was dried over anhydrous magnesium sulfate, and concentrated under reduced pressure, whereby a brown oily crude product (5.99 g) was obtained. This was purified by silica gel column chromatography (hexane:ethyl acetate=10:1), whereby tert-butyl 2-(bromodifluoromethyl)-2-(2,4-dichlorophenyl) malonate (4.08 g, yield: 54%) was obtained as an yellow oily material. This was distilled under reduced pressure, whereby methyl 2-(2,4-dichlorophenyl)-3,3-difluoroacrylate (931 mg, yield: 38%) was obtained as a colorless oily material. $^1$H-NMR (400 MHz, CDCl$_3$): δ3.77 (s, 3H), 7.21-7.49 (m, 3H). $^{19}$F-NMR (376 MHz, CDCl$_3$): δ−67.0 (d, J=22 Hz, 1F), −67.3 (d, J=22 Hz, 1F).

Reference Example-6

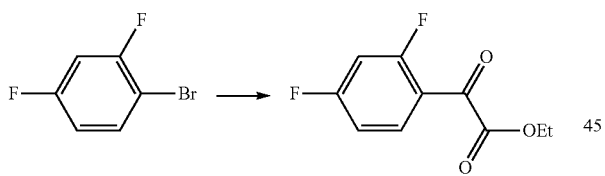

THF (50 mL) and a small amount of iodine were added to magnesium (1.32 g, 54.6 mmol) in an argon atmosphere, followed by heating. To this, a solution of 1-bromo-2,4-difluoro benzene (5.9 mL, 52 mmol) in THF was added dropwise, whereby a Grignard reagent was prepared. A solution of diethyl oxalate (7.38 mL, 54.6 mmol) in THF was cooled to −78° C., and the previously prepared Grignard reagent was added dropwise thereto. After the dropping was completed, the resultant product was stirred for 18 hours while slowly heating to room temperature. After the reaction was completed, a saturated ammonium chloride aqueous solution was added thereto, then, the resultant product was extracted with ethyl acetate (100 mL×3), and the organic layer was washed with a saturated saline solution, and dried over anhydrous magnesium sulfate. After the desiccant was separated by filtration, the filtrate was concentrated under reduced pressure, and the solvent was distilled off, whereby a crude product was obtained. This was purified by silica gel column chromatography (hexane:ethyl acetate=50:3), whereby ethyl 2-(2,4-difluorophenyl)-2-oxoacetate (6.06 g, yield: 53%) was obtained as a yellow oily material. $^1$H-NMR (400 MHz, CDCl$_3$): δ1.40 (t, J=7.2 Hz, 3H), 4.43 (q, J=7.2 Hz, 3H), 6.91 (ddd, J=2.3, 8.6 and 10.8 Hz, 1H), 7.0 (dddd, J=0.9, 2.3, 8.6 and 10.8 Hz, 1H), 7.99 (ddd, J=6.5, 8.2 and 8.7 Hz, 1H). $^{19}$F-NMR (376 MHz, CDCl$_3$): δ−106 (d, J=13.5 Hz, 1F), −97.2 (d, J=13.5 Hz, 1F).

Reference Example-7

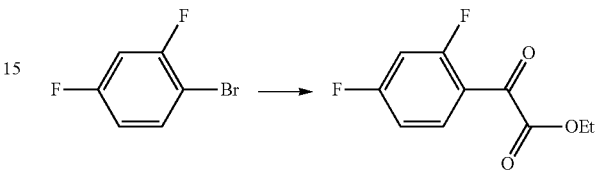

A solution of 1-bromo-2,4-difluorobenzene (489 g, 2.48 mol) in THF (0.7 L) was added dropwise to a solution of magnesium (61.8 g, 2.53 mol) and iodine (50 mg) in THF (1.0 L) over 2.5 hours while maintaining the temperature of the reaction solution at 40° C. or lower, in an argon gas atmosphere, whereby a solution of 2,4-difluorophenyl magnesium bromide in THF was prepared. The solution was added dropwise to a solution of diethyl oxalate (363 g, 2.43 mol) in THF (0.25 mL) over 2.5 hours while maintaining the temperature of the reaction solution at −40° C. or lower, followed by stirring for 1 hour under ice-cooling. After the reaction was completed, saturated ammonium chloride aqueous solution (0.5 L) and water (1.5 L) were added to the reaction solution, and the resultant product was extracted with ethyl acetate (0.2 L×3). The combined organic layer was washed with a saturated saline solution (0.5 L), and the organic layer was dried over anhydrous magnesium sulfate (50 g). The solvent was distilled off from this under reduced pressure, and the resultant product was distilled under reduced pressure, whereby ethyl 2-(2,4-difluorophenyl)-2-oxoacetate (389 g, yield: 73%) was obtained as a pale yellow solid.

Reference Example-8

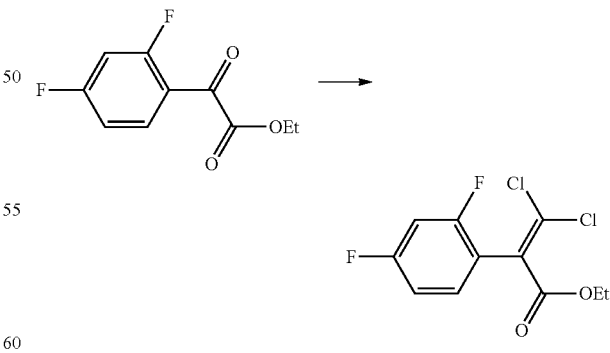

Carbon tetrachloride (8.98 mL, 93 mmol) and ethyl 2-(2,4-difluorophenyl)-2-oxoacetate (6.64 g, 31 mmol) were added to a solution of triphenylphosphine (24.4 g, 93 mmol) in dichloromethane (60 mL) under ice-cooling in an argon atmosphere, followed by stirring at room temperature for 24 hours. After the reaction was completed, the solvent was distilled off under reduced pressure, and a mixed solvent of chloroform (10 mL) and hexane (100 mL) was added to the residue, followed by stirring. The insoluble matters were removed by filtration, and the organic layer was concentrated under reduced pressure, whereby a crude product was obtained. This crude product was purified by silica gel column chromatography (hexane:chloroform=4:1), whereby ethyl 3,3-dichloro-2-(2,4-difluorophenyl)acrylate (7.15 g, yield: 82%) was obtained as a yellow oily material. $^1$H-NMR (400 MHz, CDCl$_3$): δ1.26 (t, J=7.1 Hz, 3H), 4.25 (q, J=7.1 Hz, 2H), 6.87 (ddd, J=2.1, 8.8 and 10.4 Hz, 1H), 6.92 (dddd, J=1.0 Hz, 2.1, 6.7 and 9.6 Hz, 1H), 7.31 (ddd, J=6.7, 8.4 and 8.4 Hz, 1H). $^{19}$F-NMR (376 MHz, CDCl$_3$): δ−108 (d, J=7.5 Hz, 1F), −107 (d, J=7.5 Hz, 1F).

Reference Example-9

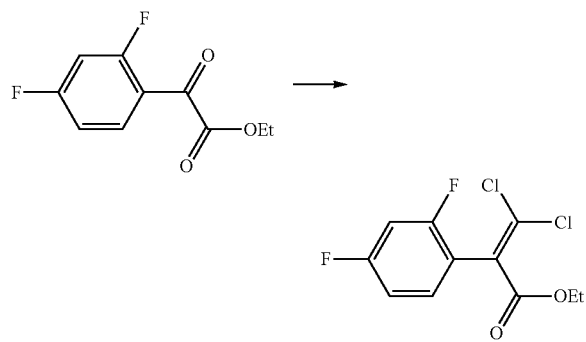

Carbon tetrachloride (557 g, 3.60 mol) was added to a solution of triphenylphosphine (973 g, 3.60 mol) in dichloromethane (720 mL) under ice-cooling, followed by stirring for 5 minutes, and a solution of ethyl 2-(2,4-difluorophenyl)-2-oxoacetate (386 g, 1.80 mol) in dichloromethane (0.18 L) was added dropwise thereto, followed by stirring at 30° C. or lower for 20 hours. After the reaction was completed, the solvent was distilled off under reduced pressure. Next, the residue was dissolved in hexane (1.5 L), then, the insoluble matters were removed by filtration, and an operation of concentrating the filtrate under reduced pressure was repeated two times. The obtained oily material was distilled under reduced pressure, whereby ethyl 3,3-dichloro-2-(2,4-difluorophenyl)acrylate (455 g, yield: 90%) was obtained as a pale yellow oily material.

Reference Example-10

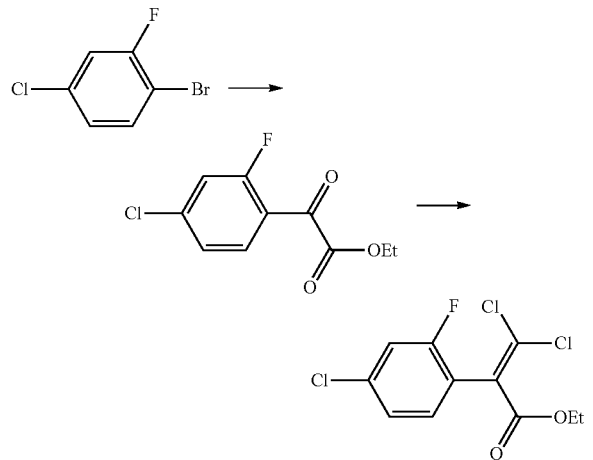

A solution of 1-bromo-4-chloro-2-fluoro benzene (10.0 g, 47.8 mmol) in THF was added dropwise to a suspension of magnesium (1.28 g, 52.5 mmol) in THF (50 mL) at 40° C. (oil bath temperature) in the presence of a catalytic amount of iodine in an argon gas atmosphere, whereby a Grignard reagent was prepared. The Grignard reagent was added dropwise to a solution of diethyl oxalate (8.37 g, 57.3 mmol) in THF at −50° C., and the temperature was slowly raised to room temperature, followed by stirring for 18 hours. After the reaction was completed, the reaction solution was poured into ice, then, acidified with concentrated hydrochloric acid, and the resultant product was extracted with ether (100 mL×2, 50 mL×1). The organic layer was dried over anhydrous magnesium sulfate, and concentrated under reduced pressure, whereby an orange oily crude product (12.9 g) was obtained. This was purified by silica gel column chromatography (hexane:ethyl acetate=10:1), whereby ethyl 2-(4-chloro-2-fluorophenyl)-2-oxoacetate (4.17 g, yield: 41%) was obtained as a yellow oily material. $^1$H-NMR (400 MHz, CDCl$_3$): δ1.40 (t, J=7.1 Hz, 3H), 4.43 (q, J=7.1 Hz, 2H), 7.22 (dd, J=1.8 and 10.2 Hz, 1H), 7.31 (dd, J=1.8 and 8.4 Hz, 1H), 7.89 (dd, J=7.6 and 8.4 Hz, 1H). $^{19}$F-NMR (376 MHz, CDCl$_3$): δ−109 (s, 1F).

Carbon tetrachloride (2.29 g, 14.9 mmol) and ethyl 2-(4-chloro-2-fluorophenyl)-2-oxoacetate (1.60 g, 7.46 mmol) were added to a solution of triphenylphosphine (5.87 g, 22.4 mmol) in dichloromethane under ice-cooling, followed by stirring at room temperature for 22 hours. After the reaction was completed, water (50 mL) was added to the reaction solution, and the resultant product was extracted with chloroform (30 mL×2, 20 mL×1). The organic layer was washed with a saturated saline solution (10 mL), dried over anhydrous magnesium sulfate, and concentrated under reduced pressure, whereby an orange oily crude product was obtained. This was purified by silica gel column chromatography (hexane:chloroform=1:8), whereby ethyl 3,3-dichloro-2-(4-chloro-2-fluorophenyl)acrylate (2.22 g, yield: quantitative) was obtained as a colorless oily material. $^1$H-NMR (400 MHz, CDCl$_3$): δ1.25 (t, J=7.1 Hz, 3H), 4.24 (q, J=7.1 Hz, 2H), 7.13-7.20 (m, 2H), 7.27 (m, 1H). $^{19}$F-NMR (376 MHz, CDCl$_3$): δ−110.0 (s, 1F).

Reference Example-11

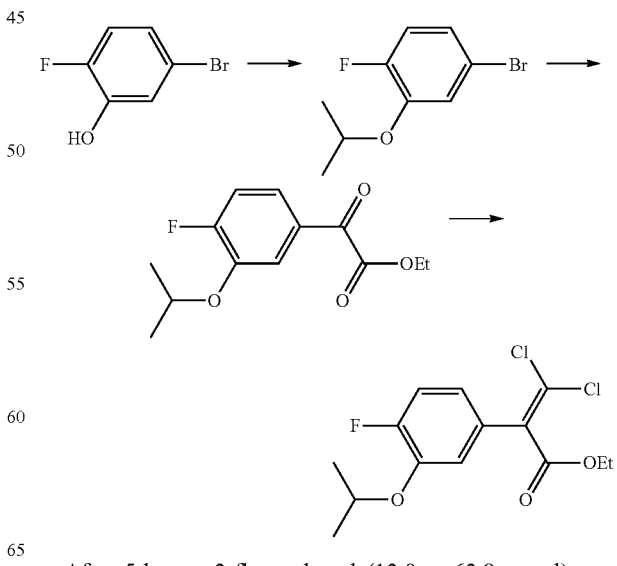

After 5-bromo-2-fluorophenol (12.0 g, 62.8 mmol) was dissolved in DMF (120 mL), cesium carbonate (40.9 g, 126 mmol) was added thereto, and isopropyl bromide (15.5 g, 126 mmol) was added thereto, followed by stirring at room temperature for 22 hours. After the reaction was completed, water (150 mL) was added to the reaction solution, and the resultant product was extracted with ethyl acetate (100 mL×2, 50 mL×1). The organic layer was washed with a saturated saline solution (30 mL), dried over anhydrous magnesium sulfate, and concentrated under reduced pressure, whereby a pale yellow oily crude product (25.5 g) was obtained. This was purified by silica gel column chromatography (hexane:ethyl acetate=10:1), whereby 5-bromo-2-fluoro-1-(isopropyloxy)benzene (13.9 g, yield: 95%) was obtained as a colorless oily material. $^1$H-NMR (400 MHz, CDCl$_3$): δ1.36 (d, J=6.1 Hz, 6H), 4.52 (sept, J=6.1 Hz, 1H), 6.91-7.02 (m, 2H), 7.31 (dd, J=2.3 and 7.4 Hz, 1H). $^{19}$F-NMR (376 MHz, CDCl$_3$): δ−135 (s, 1F).

A solution of 5-bromo-2-fluoro-1-(isopropyloxy)benzene (13.9 g, 59.7 mmol) in THF was added dropwise to a suspension of magnesium (2.79 g, 115 mmol) in THF at 40° C. (oil bath temperature) in the presence of a catalytic amount of iodine in an argon gas atmosphere, whereby a Grignard reagent was prepared. The Grignard reagent was added dropwise to a solution of diethyl oxalate (18.3 g, 125 mmol) in THF at −50° C., and the temperature was slowly raised to room temperature, followed by stirring for 18 hours. After the reaction was completed, the reaction solution was added little by little to saturated ammonium chloride aqueous solution under ice-cooling, and the resultant product was extracted with ether (100 mL×2, 50 mL×1). The organic layer was dried over anhydrous magnesium sulfate, and concentrated under reduced pressure, whereby an orange oily crude product (14.3 g) was obtained. This was purified by silica gel column chromatography (hexane:ethyl acetate=10:1), whereby ethyl 2-[4-fluoro-3-(isopropyloxy)phenyl]-2-oxoacetate (3.49 g, yield: 23%) was obtained as a yellow oily material. $^1$H-NMR (400 MHz, CDCl$_3$): δ1.40 (d, J=6.1 Hz, 6H), 1.43 (t, J=7.2 Hz, 3H), 4.45 (q, J=7.2 Hz, 2H), 4.65 (sept, J=6.1 Hz, 1H), 7.18 (dd, J=8.4 and 10.4 Hz, 1H), 7.31 (ddd, J=2.1, 4.4 and 8.4 Hz, 2H), 7.68 (dd, J=2.1 and 8.0 Hz, 1H). $^{19}$F-NMR (376 MHz, CDCl$_3$): δ−121 (s, 1F).

Carbon tetrachloride (1.82 g, 11.8 mmol) and ethyl 2-[4-fluoro-3-(isopropyloxy)phenyl]-2-oxoacetate (1.50 g, 5.90 mmol) were added to a solution of triphenylphosphine (4.64 g, 17.7 mmol) in dichloromethane under ice-cooling, followed by stirring at room temperature for 22 hours. After the reaction was completed, water (50 mL) was added to the reaction solution, and the resultant product was extracted with chloroform (30 mL×2, 20 mL×1). The organic layer was dried over anhydrous magnesium sulfate, and concentrated under reduced pressure, whereby a crude product (7.1 g) was obtained as an orange solid. This was purified by silica gel column chromatography (hexane:chloroform=1:10), whereby ethyl 3,3-dichloro-2-[4-fluoro-3-(isopropyloxy)phenyl]acrylate (1.69 g, yield: 89%) was obtained as a colorless oily material. $^1$H-NMR (400 MHz, CDCl$_3$): δ1.30 (t, J=7.12 Hz, 3H), 1.37 (d, J=6.1 Hz, 6H), 4.28 (q, J=7.12 Hz, 2H), 4.54 (sept, J=6.1 Hz, 1H), 6.92 (ddd, J=2.16, 4.24 and 8.40 Hz, 1H), 7.02 (dd, J=2.16 and 7.88 Hz, 1H), 7.08 (dd, J=8.40 and 10.9 Hz, 1H). $^{19}$F-NMR (376 MHz, CDCl$_3$): δ−132 (s, 1F).

Reference Example-12

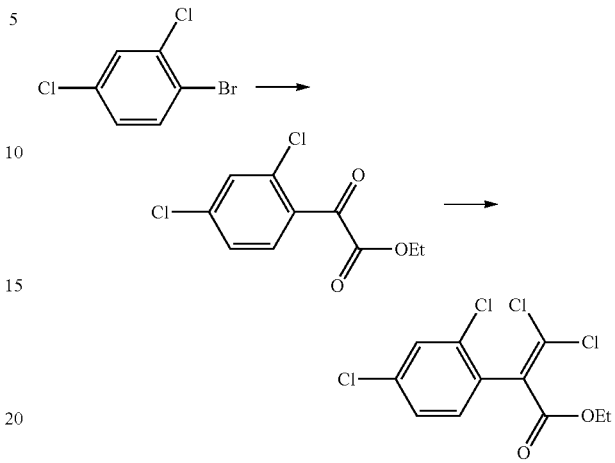

A solution of 1-bromo-2,4-dichlorobenzene (9.0 g, 39.8 mmol) in THF was added dropwise to a suspension of magnesium (1.07 g, 43.8 mmol) in THF at 40° C. (oil bath temperature) in the presence of a catalytic amount of iodine in an argon gas atmosphere, whereby a Grignard reagent was prepared. The Grignard reagent was added dropwise to a solution of diethyl oxalate (6.99 g, 47.8 mmol) in THF at −50° C., and the temperature was slowly raised to room temperature, followed by stirring for 43 hours. After the reaction was completed, the reaction solution was added little by little to saturated ammonium chloride aqueous solution under ice-cooling, and the resultant product was extracted with ether (100 mL×2, 50 mL×1). The organic layer was dried over anhydrous magnesium sulfate, and concentrated under reduced pressure, whereby a brown oily crude product (10.8 g) was obtained. This was purified by silica gel column chromatography (hexane:ethyl acetate=10:1), whereby ethyl 2-(2,4-dichlorophenyl)-2-oxoacetate (850 mg, yield: 9%) was obtained as a yellow oily material. $^1$H-NMR (400 MHz, CDCl$_3$): δ1.40 (t, J=7.1 Hz, 3H), 4.42 (q, J=7.1 Hz, 2H), 7.39 (dd, J=2.0 and 8.4 Hz, 1H), 7.48 (d, J=2.0 Hz, 2H), 7.73 (d, J=8.4 Hz, 1H).

Carbon tetrachloride (1.05 g, 6.88 mmol) and ethyl 2-(2,4-dichlorophenyl)-2-oxoacetate (850 mg, 3.44 mmol) were added to a solution of triphenylphosphine (2.71 g, 10.3 mmol) in dichloromethane under ice-cooling, followed by stirring at room temperature for 20 hours. After the reaction was completed, water (20 mL) was added to the reaction solution, and the resultant product was extracted with chloroform (30 mL×1, 20 mL×2). The organic layer was washed with a saturated saline solution (20 mL), dried over anhydrous magnesium sulfate, and concentrated under reduced pressure, whereby a crude product (4.60 g) was obtained as a yellow solid. This was purified by silica gel column chromatography (hexane:chloroform=1:5), whereby ethyl 3,3-dichloro-2-(2,4-dichlorophenyl)acrylate (760 mg, yield: 71%) was obtained as a pale yellow oily material. $^1$H-NMR (400 MHz, CDCl$_3$): δ1.24 (t, J=7.1 Hz, 3H), 4.28 (q, J=7.1 Hz, 2H), 7.24 (d, J=8.3 Hz, 2H), 7.30 (dd, J=2.0 and 8.3 Hz, 1H), 7.46 (d, J=2.0 Hz, 1H).

Reference Example-13

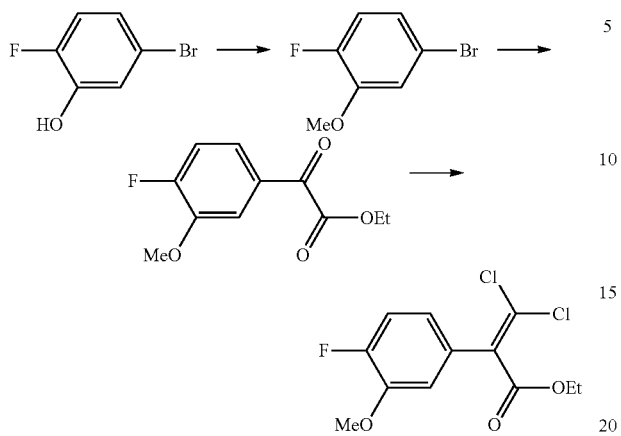

Potassium carbonate (18.8 g, 136 mmol) and methyl iodide (19.3 g, 136 mmol) were added to a solution of 5-bromo-2-fluorophenol (13.0 g, 68.1 mmol) in DMF (120 mL), followed by stirring at room temperature for 65 hours. After the reaction was completed, water (150 mL) was added to the reaction solution, and the resultant product was extracted with ethyl acetate (100 mL×1, 50 mL×2). The organic layer was dried over anhydrous magnesium sulfate, and concentrated under reduced pressure, whereby a pale yellow oily crude product (29.0 g) was obtained. This was purified by silica gel column chromatography (hexane:ethyl acetate=10:1), whereby 5-bromo-2-fluoroanisole (14.2 g, yield: quantitative) was obtained as a colorless oily material. $^1$H-NMR (400 MHz, CDCl$_3$): δ3.88 (s, 3H), 6.95 (dd, J=8.6 and 10.8 Hz, 1H), 7.02 (ddd, J=2.2, 4.2 and 8.6 Hz, 1H), 7.08 (dd, J=2.2 and 7.6 Hz, 1H). $^{19}$F-NMR (376 MHz, CDCl$_3$): δ−137 (s, 1F).

A solution of 5-bromo-2-fluoroanisole (14.2 g, 69.2 mmol) in THF was added dropwise to a suspension of magnesium (1.85 g, 76.1 mmol) in THF at 40° C. (oil bath temperature) in the presence of a catalytic amount of iodine in an argon gas atmosphere, whereby a Grignard reagent was prepared. The Grignard reagent was added dropwise to a solution of diethyl oxalate (12.1 g, 83.0 mmol) in THF at −50° C., and the temperature was slowly raised to room temperature, followed by stirring for 17 hours. After the reaction was completed, the reaction solution was added little by little to saturated ammonium chloride aqueous solution under ice-cooling, and the resultant product was extracted with ether (100 mL×2, 50 mL×1). The organic layer was dried over anhydrous magnesium sulfate, and concentrated under reduced pressure, whereby an orange oily crude product (15.5 g) was obtained. This was purified by silica gel column chromatography (hexane:ethyl acetate=10:1), whereby ethyl 2-(4-fluoro-3-methoxyphenyl)-2-oxoacetate (4.51 g, yield: 29%) was obtained as a pale yellow oily material. $^1$H-NMR (400 MHz, CDCl$_3$): δ1.43 (t, J=7.1 Hz, 3H), 3.96 (s, 3H), 4.44 (q, J=7.1 Hz, 2H), 7.19 (dd, J=8.4 and 10.5 Hz, 1H), 7.61 (ddd, J=2.0, 4.3 and 8.4 Hz, 1H), 7.68 (dd, J=2.0 and 8.2 Hz, 1H). $^{19}$F-NMR (376 MHz, CDCl$_3$): δ−123 (s, 1F).

Carbon tetrachloride (5.10 g, 33.2 mmol) and ethyl 2-(4-fluoro-3-methoxyphenyl)-2-oxoacetate (2.50 g, 11.1 mmol) were added to a solution of triphenylphosphine (8.70 g, 33.2 mmol) in dichloromethane under ice-cooling, followed by stirring at room temperature for 5 hours. After the reaction was completed, water (50 mL) was added to the reaction solution, and the resultant product was extracted with chloroform (30 mL×1, 20 mL×2). The organic layer was dried over anhydrous magnesium sulfate, and concentrated under reduced pressure, whereby a crude product (5.41 g) was obtained as a pale yellow semi-solid. This was purified by silica gel column chromatography (hexane:chloroform=1:5), whereby ethyl 3,3-dichloro-2-(4-fluoro-3-methoxyphenyl)acrylate (2.67 g, yield: 82%) was obtained as a colorless oily material. $^1$H-NMR (400 MHz, CDCl$_3$): δ1.31 (t, J=7.14 Hz, 3H), 3.89 (s, 3H), 4.28 (q, J=7.1 Hz, 2H), 6.93 (ddd, J=2.1, 4.3 and 8.3 Hz, 1H), 7.01 (dd, J=2.1 and 8.0 Hz, 1H), 7.09 (dd, J=8.4 and 11.0 Hz, 1H). $^{19}$F-NMR (376 MHz, CDCl$_3$): δ−134 (s, 1F).

Reference Example-14

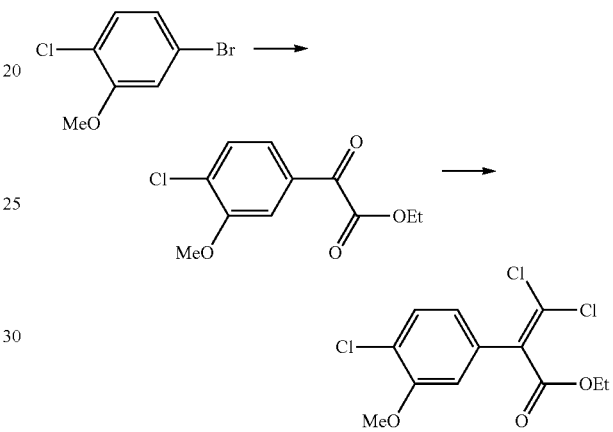

A solution of 5-bromo-2-chloroanisole (10.0 g, 45.2 mmol) in THF was added dropwise to a suspension of magnesium (1.23 g, 49.7 mmol) in THF in the presence of a catalytic amount of iodine in an argon gas atmosphere, whereby a Grignard reagent was prepared. The Grignard reagent was added dropwise to a solution of diethyl oxalate (7.93 g, 54.2 mmol) in THF at −50° C., and the temperature was slowly raised to room temperature, followed by stirring for 17 hours. After the reaction was completed, the reaction solution was added little by little to saturated ammonium chloride aqueous solution under ice-cooling, and the resultant product was extracted with ether (50 mL×3). The organic layer was dried over anhydrous magnesium sulfate, and concentrated under reduced pressure, whereby a crude product (9.93 g) was obtained as a yellow solid. This was purified by silica gel column chromatography (hexane:ethyl acetate=10:1), whereby ethyl 2-(4-chloro-3-methoxyphenyl)-2-oxoacetate (6.98 g, yield: 64%) was obtained as a yellow solid. $^1$H-NMR (400 MHz, CDCl$_3$): δ1.43 (t, J=7.1 Hz, 3H), 3.97 (s, 3H), 4.45 (q, J=7.1 Hz, 2H), 7.50 (d, J=8.2 Hz, 1H), 7.55 (dd, J=1.8 and 8.2 Hz, 1H), 7.61 (d, J=1.8 Hz, 1H).

Carbon tetrachloride (7.58 g, 49.3 mmol) and ethyl 2-(4-chloro-3-methoxyphenyl)-2-oxoacetate (5.98 g, 24.6 mmol) were added to a solution of triphenylphosphine (21.0 g, 79.9 mmol) in dichloromethane under ice-cooling, followed by stirring at room temperature for 4 hours. After the reaction was completed, water (100 mL) was added to the reaction solution, and the resultant product was extracted with chloroform (50 mL×3). The organic layer was washed with a saturated saline solution (10 mL), dried over anhydrous magnesium sulfate, and concentrated under reduced pressure, whereby a crude product (10.9 g) was obtained as a yellow semi-solid. This was purified by silica gel column chromatography (hexane:chloroform=1:1), whereby ethyl 3,3-dichloro-2-(4-chloro-3-methoxyphenyl)acrylate (6.35 g, yield: 83%) was obtained as a colorless oily material. ¹H-NMR (400 MHz, CDCl₃): δ1.30 (t, J=7.1 Hz, 3H), 3.97 (s, 3H), 4.28 (q, J=7.1 Hz, 2H), 6.92 (dd, J=1.9 and 8.2 Hz, 1H), 6.96 (d, J=1.9 Hz, 1H), 7.63 (d, J=8.2 Hz, 1H).

Reference Example-15

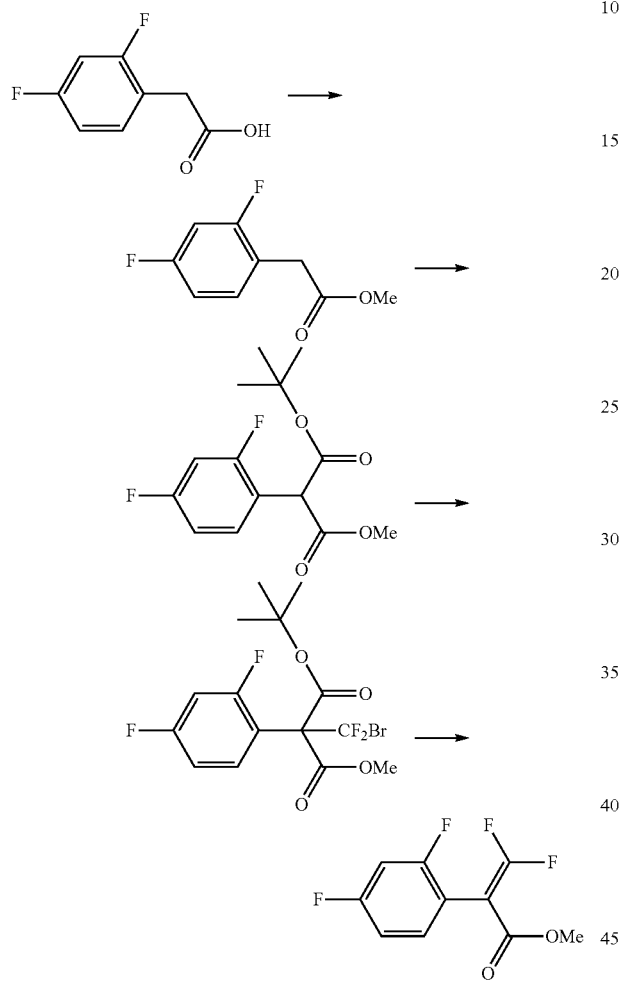

Potassium carbonate (3.89 g, 28.2 mmol) and methyl iodide (12.6 g, 84.5 mmol) were added to a solution of 2,4-dichlorophenylacetic acid (4.85 g, 28.2 mmol) in DMF (30 mL), followed by stirring at room temperature for 22 hours. After the reaction was completed, 2N hydrochloric acid (50 mL) was added to the reaction solution, and the resultant product was extracted with ethyl acetate (50 mL×2, 30 mL×1). The organic layer was dried over anhydrous magnesium sulfate, and concentrated under reduced pressure, whereby an orange oily crude product (8.19 g) was obtained. This was purified by silica gel column chromatography (hexane:ethyl acetate=5:1), whereby methyl 2-(2,4-dichlorophenyl) acetate (5.56 g, yield: quantitative) was obtained as a pale orange oily material. ¹H-NMR (400 MHz, CDCl₃): δ3.64 (s, 2H), 3.71 (s, 3H), 6.80-6.88 (m, 2H), 7.20-7.24 (m, 1H). ¹⁹F-NMR (376 MHz, CDCl₃): δ−113 (d, J=7.5 Hz, 1F), −111 (d, J=7.5 Hz, 1F).

Methyl 2-(2,4-dichlorophenyl) acetate (5.56 g, 29.9 mmol) was dissolved in THF (60 mL), and sodium hydride (60% w/w, 2.5 g, 62.7 mmol) was added little by little thereto under ice-cooling, followed by stirring 3 minutes. After the temperature of the reaction solution was returned to room temperature, tert-butyl dicarbonate (7.2 g, 31.4 mmol) was added thereto, and then, tetrabutyl ammonium chloride (6.16 g, 22.2 mmol) was added thereto, followed by refluxing for 17 hours. After the reaction was completed, the reaction solution was added little by little to saturated ammonium chloride aqueous solution (100 mL) under ice-cooling, and the resultant product was extracted with ethyl acetate (50 mL×2, 30 mL×1). The organic layer was dried over anhydrous magnesium sulfate, and concentrated under reduced pressure, whereby a dark brown oily crude product (9.7 g) was obtained. This was purified by silica gel column chromatography (hexane:ethyl acetate=10:1), whereby tert-butyl 2-(2,4-dichlorophenyl) malonate (5.73 g, yield: 67%) was obtained as a pale yellow oily material. ¹H-NMR (400 MHz, CDCl₃): δ1.46 (s, 9H), 3.77 (s, 3H), 6.82 (ddd, J=2.8, 7.8 and 9.3 Hz, 1H), 6.90 (dddd, J=1.2, 2.7, 6.4 and 11.6 Hz, 2H), 7.46 (dt, J=2.7, 7.8 and 9.3 Hz, 1H). ¹⁹F-NMR (376 MHz, CDCl₃): δ−113 (d, J=7.5 Hz, 1F), −110 (d, J=7.5 Hz, 1F).

tert-Butyl 2-(2,4-dichlorophenyl) malonate (14.5 g, 50.9 mmol) was dissolved in THF (60 mL), and sodium hydride (60% w/w, 1.10 g, 40.4 mmol) was added little by little thereto under ice-cooling. After the temperature of the reaction solution was returned to room temperature, dibromodifluoromethane (12.6 g, 60.6 mmol) was added thereto, followed by stirring for 22 hours. After the reaction was completed, the reaction solution was added little by little to saturated ammonium chloride aqueous solution (100 mL) under ice-cooling, and the resultant product was extracted with ethyl acetate (50 mL×2). The organic layer was dried over anhydrous magnesium sulfate, and concentrated under reduced pressure, whereby an orange oily crude product (6.44 g) was obtained. This was purified by silica gel column chromatography (hexane:ethyl acetate=5:1), whereby tert-butyl 2-(bromodifluoromethyl)-2-(2,4-difluorophenyl)malonate (2.47 g, yield: 30%) was obtained as an yellow oily material. Furthermore, the resultant product was distilled under reduced pressure, whereby methyl 2-(2,4-difluorophenyl)-3,3-difluoroacrylate (1.02 g, yield: 73%) was obtained as a colorless oily material.

Reference Example-16

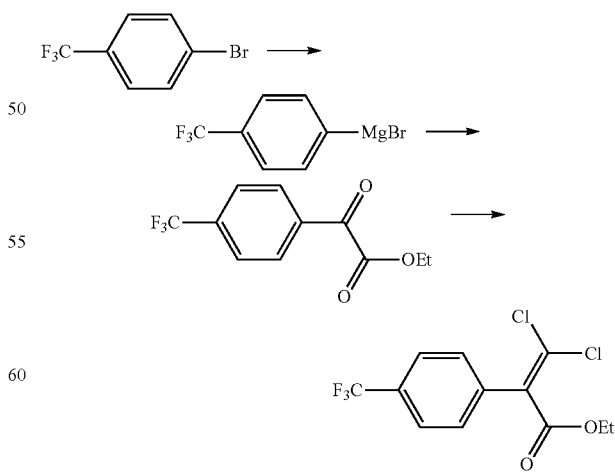

A catalytic amount of iodine was added to a suspension (20.0 mL) of magnesium (0.92 g, 37.8 mmol) in THF, and a solution (20.0 mL) of 4-bromobenzotrifluoride (8.10 g, 36.0 mmol) in THF was slowly added dropwise thereto at room temperature in an argon atmosphere, whereby a Grignard reagent (about 1 mol/L) was prepared. The Grignard reagent was added dropwise to a solution (40.0 mL) of diethyl oxalate (5.52 g, 37.8 mmol) in THF at −78° C. in an argon atmosphere, followed by stirring for 18 hours while slowly raising the temperature to room temperature. After the reaction was completed, saturated ammonium chloride aqueous solution was added thereto, and extraction thereof was performed with ethyl acetate. The organic layer was dried over anhydrous magnesium sulfate, the desiccant was separated by filtration, the solvent was distilled off under reduced pressure, and the obtained mixture was purified by an automatic setting medium pressure column chromatography system (manufactured by Yamazen Corporation), whereby ethyl 2-[4-(trifluoromethyl)phenyl]-2-oxoacetate (4.91 g, yield: 55%) was obtained as pale yellow oil. $^1$H-NMR (CDCl$_3$, TMS, ppm): δ1.44 (t, J=7.2 Hz, 3H), 4.48 (q, J=7.2 Hz, 2H), 7.79 (d, J=8.4 Hz, 2H), 8.17 (d, J=8.4 Hz, 2H).

Carbon tetrachloride (5.3 mL, 55.1 mmol) was added dropwise to a solution of triphenylphosphine (14.4 g, 55.1 mmol) in dichloromethane (92 mL) under ice-cooling, followed by stirring for 0.5 hours. Thereafter, a solution of ethyl 2-[4-(trifluoromethyl)phenyl]-2-oxoacetate (4.52 g, 18.4 mmol) in dichloromethane (50.0 mL) was added dropwise thereto, followed by stirring at room temperature for 24 hours in an argon atmosphere. After the reaction was completed, the solvent was distilled off under reduced pressure, and chloroform (10 mL) and hexane (150 mL) were added thereto, and after precipitating the insoluble solid, the solid was separated by filtration, and the solvent was distilled off under reduced pressure. A mixed solution (250 mL, 9:1) of hexane and chloroform was added to the obtained mixture, and after precipitating the insoluble solid, the solid was separated by filtration, and the solvent was distilled off under reduced pressure. The obtained crude product was purified by an automatic setting medium pressure column chromatography system (manufactured by Yamazen Corporation), whereby ethyl 3,3-dichloro-2-[4-(trifluoromethyl)phenyl] acrylate (4.87 g, yield: 85%) was obtained as yellow oil. $^1$H-NMR (CDCl$_3$, TMS, ppm): δ1.30 (t, J=7.2 Hz, 3H), 4.28 (q, J=7.2 Hz, 2H), 7.51 (d, J=8.0 Hz, 2H), 7.66 (d, J=8.0 Hz, 2H).

Example-1

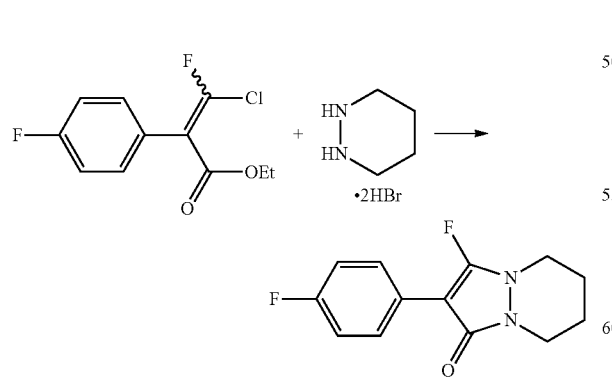

Tetrahydropyridazine dihydrobromide (40 mg, 1.6 mmol) and triethylamine (492 mg, 4.9 mmol) were added to a solution of ethyl 3-chloro-3-fluoro-2-(4-fluorophenyl)acrylate (400 mg, 1.6 mmol) in 1,4-dioxane (10 mL) at room temperature, followed by stirring for 24 hours while heating to reflux. After the reaction was completed, resultant product was concentrated under reduced pressure, then, distilled water (20 mL) was added thereto, and the resultant product was extracted with ethyl acetate (30 mL×2), dried over anhydrous magnesium sulfate, and concentrated under reduced pressure. The obtained residue was purified by silica gel column chromatography (ethyl acetate), whereby 5-fluoro-4-(4-fluorophenyl)-1,2-tetramethylene-4-pyrazolin-3-one (66.7 mg, yield: 17%) was obtained as a white solid. $^1$H-NMR (400 MHz, CDCl$_3$): δ1.83-1.90 (m, 2H), 1.95-2.04 (m, 2H), 3.49 (t, J=5.6 Hz, 2H), 3.77-3.80 (m, 2H), 7.07 (t, J=8.9 Hz, 2H), 7.88 (dd, J=5.5 and 8.6 Hz, 2H). $^{19}$F-NMR (376 MHz, CDCl$_3$): δ−121.6 (s, 1F), −114.8 (s, 1F).

Example-2

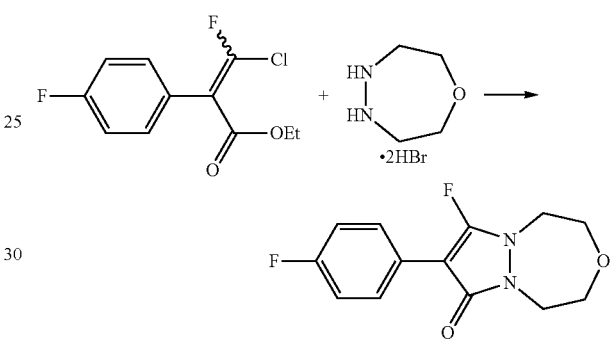

In the same manner as in Example-1, ethyl 3-chloro-3-fluoro-2-(4-fluorophenyl)acrylate was reacted with 1,4,5-oxadiazepane dihydrobromide, whereby 5-fluoro-4-(4-fluorophenyl)-1,2-oxadiethylene-4-pyrazolin-3-one was obtained as a white solid with a yield of 21%. $^1$H-NMR (400 MHz, CDCl$_3$): δ3.91-3.97 (m, 6H), 4.15-4.18 (m, 2H), 7.07 (t, J=8.9 Hz, 2H), 7.87 (dd, J=1.4 and 8.9 Hz, 2H). $^{19}$F-NMR (376 MHz, CDCl$_3$): δ−120.9 (s, 1F), −114.9 (s, 1F).

Example-3

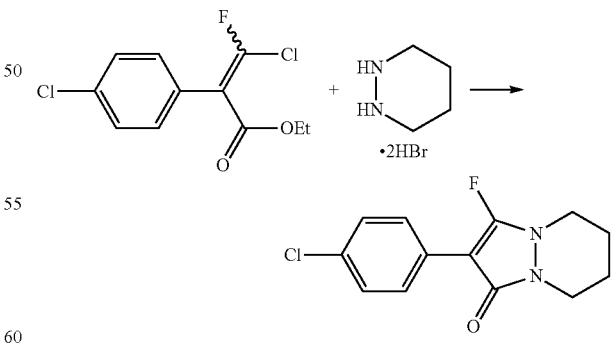

1,4-Dioxane (20 mL) and triethylamine (923 mg, 9.12 mmol) were added to ethyl 3-chloro-2-(4-chlorophenyl)-3-fluoroacrylate (600 mg, 2.28 mmol), and hexahydropyridazine dihydrobromide (721 mg, 2.91 mmol) was added thereto, followed by refluxing for 17 hours. After the reaction was completed, water (50 mL) was added to the reaction solution, and the resultant product was extracted with ethyl acetate (50 mL×1, 20 mL×2). The organic layer was dried over anhydrous magnesium sulfate, and concentrated under reduced pressure, whereby a dark brown oily crude product (566 mg) was obtained. This was purified by silica gel column chromatography (ethyl acetate), whereby 4-(4-chlorophenyl)-5-fluoro-1,2-tetramethylene-4-pyrazolin-3-one (191 mg, yield: 31%) was obtained as a brown solid. $^1$H-NMR (400 MHz, CDCl$_3$): δ1.84-1.89 (m, 2H), 1.95-2.00 (m, 2H), 3.50-3.52 (m, 2H), 3.76-3.80 (m, 2H), 7.34 (d, J=8.4 Hz, 2H), 7.85 (d, J=8.4 Hz, 2H). $^{19}$F-NMR (376 MHz, CDCl$_3$): δ−120 (s, 1F).

Example-4

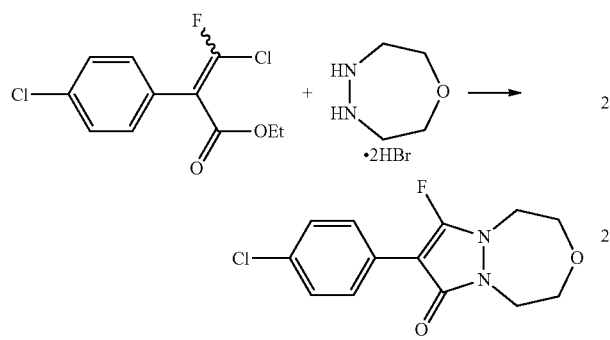

1,4-Dioxane (25 mL) and triethylamine (1.11 mg, 11.0 mmol) were added to ethyl 3-chloro-2-(4-chlorophenyl)-3-fluoroacrylate (723 mg, 2.75 mmol), and 1,4,5-oxadiazepane dihydrobromide (719 mg, 2.72 mmol) was added thereto, followed by refluxing for 20 hours. After the reaction was completed, water (100 mL) was added to the reaction mixture, and the resultant product was extracted with ethyl acetate (50 mL×2, 30 mL×1). The organic layer was dried over anhydrous magnesium sulfate, and concentrated under reduced pressure, whereby a crude product (1.02 g) was obtained as an orange solid. This was purified by silica gel column chromatography (ethyl acetate), whereby 4-(4-chlorophenyl)-5-fluoro-1,2-oxadiethylene-4-pyrazolin-3-one (227 mg, yield: 29%) was obtained as an orange solid. $^1$H-NMR (400 MHz, CDCl$_3$): δ3.91-3.94 (m, 4H), 3.98-4.00 (m, 2H), 4.16-4.19 (m, 2H), 7.35 (d, J=8.6 Hz, 2H), 7.85 (d, J=8.6 Hz, 2H). $^{19}$F-NMR (376 MHz, CDCl$_3$): δ−120 (s, 1F).

Example-5

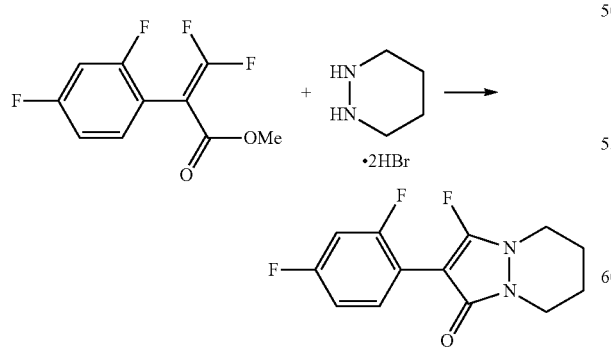

1,4-Dioxane (25 mL) and triethylamine (882 mg, 8.72 mmol) were added to methyl 2-(2,4-difluorophenyl)-3,3-difluoroacrylate (510 mg, 2.18 mmol), and hexahydropyridazine dihydrobromide (689 mg, 2.78 mmol) was added thereto, followed by refluxing for 19 hours. After the reaction was completed, water (50 mL) was added to the reaction solution, and the resultant product was extracted with ethyl acetate (30 mL×2, 20 mL×1). The organic layer was dried over anhydrous magnesium sulfate, and concentrated under reduced pressure, whereby a brown oily crude product (1.08 g) was obtained. This was purified by silica gel column chromatography (ethyl acetate:methanol=8:1) (two times), whereby 5-fluoro-4-(2,4-difluorophenyl)-1,2-tetramethylene-4-pyrazolin-3-one (151 mg, yield: 26%) was obtained as a brown solid. $^1$H-NMR (400 MHz, CDCl$_3$): δ1.88-2.01 (m, 4H), 3.51-3.53 (m, 2H), 3.78-3.81 (m, 2H), 6.84 (ddd, J=2.3, 8.9 and 10.9 Hz, 1H), 7.04 (dddd, J=1.0, 2.3, 7.3 and 9.6 Hz, 1H), 7.48 (ddd, J=7.3, 8.0 and 8.5 Hz, 1H). $^{19}$F-NMR (376 MHz, CDCl$_3$): δ−116 (d, J=4.0 Hz, 1F), −111 (d, J=4.0 Hz, 1F).

Example-6

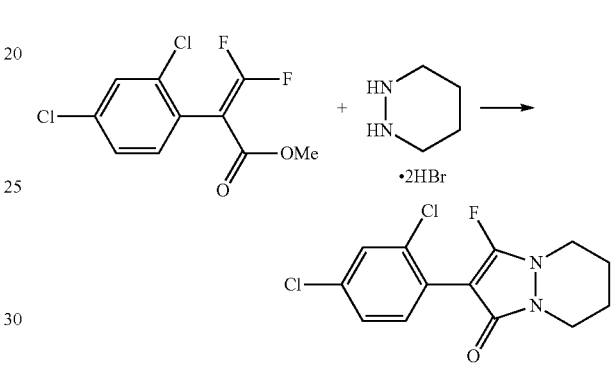

1,4-Dioxane (20 mL) and triethylamine (911 mg, 9.00 mmol) were added to methyl 2-(2,4-dichlorophenyl)-3,3-difluoroacrylate (600 mg, 2.25 mmol), and hexahydropyridazine dihydrobromide (721 mg, 2.87 mmol) was added thereto, followed by refluxing for 19 hours. After the reaction was completed, water (50 mL) was added to the reaction solution, and the resultant product was extracted with ethyl acetate (30 mL×1, 20 mL×2). The organic layer was dried over anhydrous magnesium sulfate, and concentrated under reduced pressure, whereby an orange oily crude product (828 mg) was obtained. This was purified by silica gel column chromatography (ethyl acetate:methanol=4:1), whereby 4-(2,4-dichlorophenyl)-5-fluoro-1,2-tetramethylene-4-pyrazolin-3-one (182 mg, yield: 27%) was obtained as a yellow solid. $^1$H-NMR (400 MHz, CDCl$_3$): δ1.86-1.91 (m, 2H), 1.96-2.02 (m, 2H), 3.52-3.55 (m, 2H), 3.78-3.82 (m, 2H), 7.27-7.48 (m, 3H). $^{19}$F-NMR (376 MHz, CDCl$_3$): δ−113 (s, 1F).

Example-7

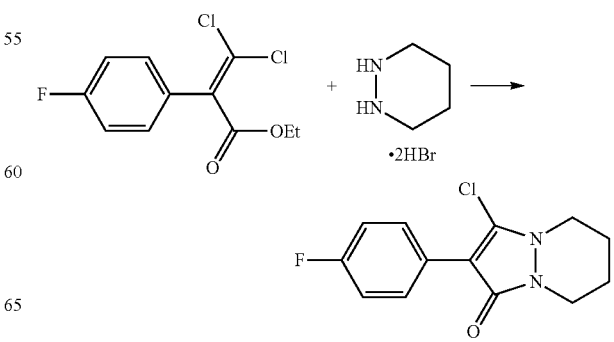

1,4-Dioxane (20 mL) and triethylamine (769 mg, 7.60 mmol) were added to ethyl 3,3-dichloro-2-(4-fluorophenyl)acrylate (500 mg, 1.90 mmol), and hexahydropyridazine dihydrobromide (383 mg, 1.54 mmol) was added thereto, followed by refluxing for 22 hours. After the reaction was completed, water (50 mL) was added to the reaction mixture, and the resultant product was extracted with ethyl acetate (30 mL×1, 20 mL×2). The organic layer was dried over anhydrous magnesium sulfate, and concentrated under reduced pressure, whereby a crude product (528 mg) was obtained as a yellow solid. This was purified by silica gel column chromatography (ethyl acetate:methanol=8:1), and purified by preparative thin layer chromatography (ethyl acetate:methanol=10:1), whereby 5-chloro-4-(4-fluorophenyl)-1,2-tetramethylene-4-pyrazolin-3-one (105 mg, yield: 21%) was obtained as a white solid. $^1$H-NMR (400 MHz, CDCl$_3$): δ1.86-1.91 (m, 2H), 1.98-2.04 (m, 2H), 3.54 (m, 2H), 3.81-3.84 (m, 2H), 7.09 (dd, J=8.9 and 8.9 Hz, 2H), 7.80 (dd, J=5.4 and 8.9 Hz, 2H). $^{19}$F-NMR (376 MHz, CDCl$_3$): δ−114 (s, 1F).

Example-8

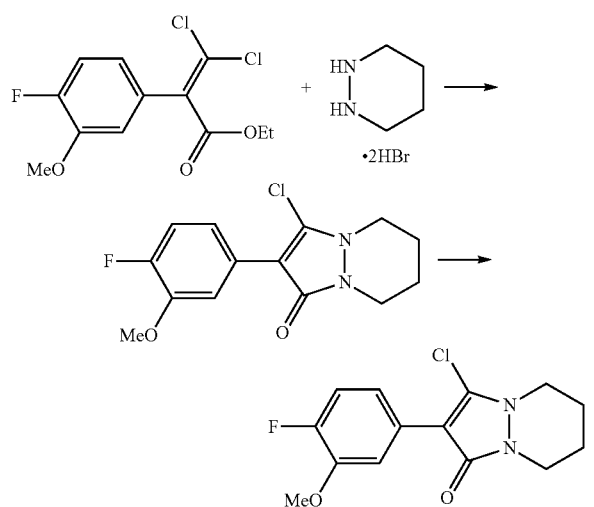

1,4-Dioxane (40 mL) and triethylamine (2.07 g, 20.5 mmol) were added to ethyl 3,3-dichloro-2-(4-fluoro-3-methoxyphenyl)acrylate (1.5 g, 5.12 mmol), and hexahydropyridazine dihydrobromide (1.20 g, 4.83 mmol) was added thereto, followed by refluxing for 16 hours. After the reaction was completed, water (80 mL) was added to the reaction solution, and the resultant product was extracted with ethyl acetate (50 mL×2, 30 mL×1). The organic layer was dried over anhydrous magnesium sulfate, and concentrated under reduced pressure, whereby a crude product (1.44 g) was obtained as a pale yellow solid. This was purified by silica gel column chromatography (ethyl acetate:methanol=10:1), whereby 5-chloro-4-(4-fluoro-3-methoxyphenyl)-1,2-tetramethylene-4-pyrazolin-3-one (659 mg, yield: 46%) was obtained as a pale yellow solid. $^1$H-NMR (400 MHz, CDCl$_3$): δ1.86-1.92 (m, 2H), 1.99-2.04 (m, 2H), 3.56-3.58 (m, 2H), 3.82-3.84 (m, 2H), 3.92 (s, 3H), 7.09 (dd, J=8.5 and 11.2 Hz, 1H), 7.33 (ddd, J=2.1, 4.3 and 8.5 Hz, 1H), 7.62 (dd, J=2.1 and 8.4 Hz, 1H). $^{19}$F-NMR (376 MHz, CDCl$_3$): δ−136 (s, 1F).

Boron tribromide (1 mol/L, 3.62 mL) was added dropwise to a solution of 5-chloro-4-(4-fluoro-3-methoxyphenyl)-1,2-tetramethylene-4-pyrazolin-3-one (537 mg, 1.81 mmol) in dichloromethane (5 mL) at −80° C. in an argon gas atmosphere, and the temperature was slowly raised to room temperature, followed by stirring for 23 hours. After the reaction was completed, the reaction solution was added little by little to 2N hydrochloric acid (50 mL) under ice-cooling, and the resultant product was extracted with chloroform (50 mL×3). The organic layer was washed with a saturated saline solution (20 mL), dried over anhydrous magnesium sulfate, and concentrated under reduced pressure, whereby 5-chloro-4-(4-fluoro-3-hydroxyphenyl)-1,2-tetramethylene-4-pyrazolin-3-one (376 mg, yield: 73%) was obtained as a white solid.

Example-9

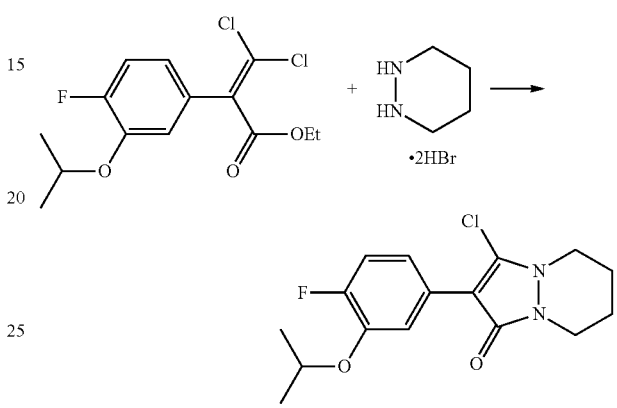

1,4-Dioxane (20 mL) and triethylamine (1.13 g, 11.2 mmol) were added to ethyl 3,3-dichloro-2-[4-fluoro-3-(isopropyloxy)phenyl]acrylate (900 mg, 2.80 mmol), and hexahydropyridazine dihydrobromide (664 mg, 2.68 mmol) was added thereto, followed by refluxing for 18 hours. After the reaction was completed, water (50 mL) was added to the reaction solution, and the resultant product was extracted with ethyl acetate (30 mL×2, 20 mL×1). The organic layer was dried over anhydrous magnesium sulfate, and concentrated under reduced pressure, whereby a brown oily crude product (916 mg) was obtained. This was purified by silica gel column chromatography (ethyl acetate:methanol=8:1), whereby 5-chloro-4-[4-fluoro-3-(isopropyloxy)phenyl]-1,2-tetramethylene-4-pyrazolin-3-one (711 mg, yield: 82%) was obtained as a yellow solid. $^1$H-NMR (400 MHz, CDCl$_3$): δ1.38 (d, J=6.1 Hz, 6H), 1.86-1.92 (m, 2H), 1.99-2.03 (m, 2H), 3.55-3.58 (m, 2H), 3.81-3.89 (m, 2H), 4.60 (sept, J=6.1 Hz, 1H), 7.08 (dd, J=8.5 and 11.2 Hz, 1H), 7.34 (ddd, J=2.1, 4.4 and 8.5 Hz, 1H), 7.62 (dd, J=2.1 and 8.3 Hz, 1H). $^{19}$F-NMR (376 MHz, CDCl$_3$): δ−134 (s, 1F).

Example-10

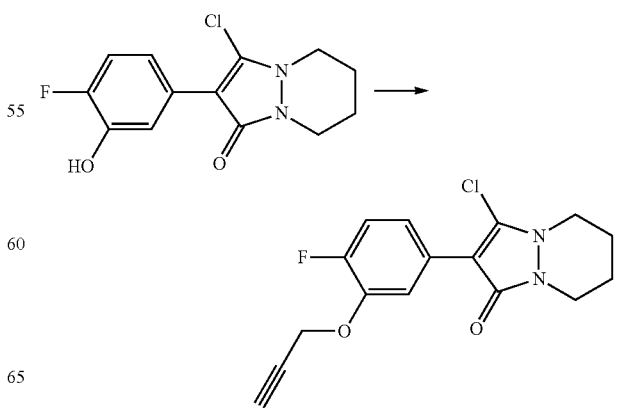

Cesium carbonate (867 mg, 2.66 mmol) and propargyl bromide (333 mg, 2.66 mmol) were added to a solution of 5-chloro-4-(4-fluoro-3-hydroxyphenyl)-1,2-tetramethylene-4-pyrazolin-3-one (376 mg, 1.33 mmol) in DMF (5 mL), followed by stirring at room temperature for 2 hours. After the reaction was completed, water (20 mL) was added to the reaction mixture, and the resultant product was extracted with ethyl acetate (20 mL×2, 10 mL×1). The organic layer was washed with a saturated saline solution (10 mL), dried over anhydrous magnesium sulfate, and was concentrated under reduced pressure, whereby a pale yellow oily crude product (4.10 g) was obtained. This was purified by silica gel column chromatography (ethyl acetate:methanol=8:1), and recrystallized from a mixed solvent of chloroform and hexane, whereby 5-chloro-4-[4-fluoro-3-(propargyloxy)phenyl]-1,2-tetramethylene-4-pyrazolin-3-one (135 mg, yield: 32%) was obtained as a white solid. $^1$H-NMR (400 MHz, CDCl$_3$): δ1.86-1.92 (m, 2H), 1.99-2.04 (m, 2H), 2.55 (t, J=2.4 Hz, 1H), 3.56-3.59 (m, 2H), 3.82-3.84 (m, 2H), 4.80 (d, J=2.4 Hz, 2H), 7.11 (dd, J=8.5 and 11.0 Hz, 1H), 7.45 (ddd, J=2.1, 3.8 and 8.5 Hz, 1H), 7.70 (dd, J=3.8 and 8.2 Hz, 1H). $^{19}$F-NMR (376 MHz, CDCl$_3$): δ−135 (s, 1F).

Example-11

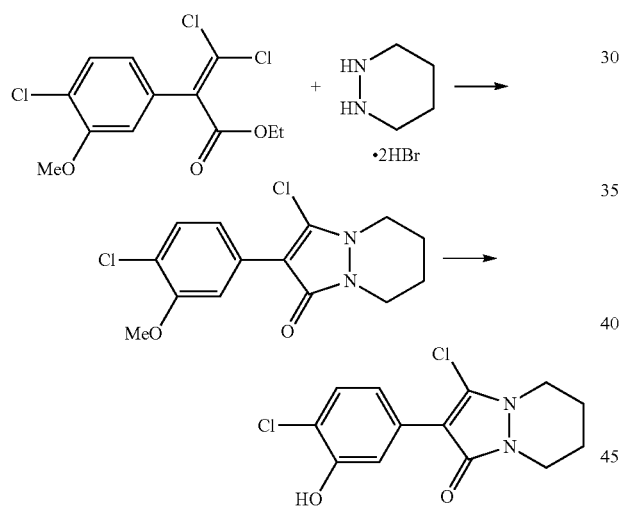

Triethylamine (7.16 g, 70.8 mmol) and hexahydropyridazine dihydrobromide (4.20 g, 16.9 mmol) were added to a solution of ethyl 3,3-dichloro-2-(4-chloro-3-methoxyphenyl)acrylate (5.48 g, 17.7 mmol) in 1,4-dioxane (50 mL), followed by refluxing for 19 hours. After the reaction was completed, water (50 mL) was added to the reaction solution, and the resultant product was extracted with ethyl acetate (50 mL×2, 30 mL×1). The organic layer was washed with a saturated saline solution (20 mL), dried over anhydrous magnesium sulfate, and concentrated under reduced pressure, whereby a crude product (9.16 g) was obtained as a pale yellow solid. This was purified by silica gel column chromatography (ethyl acetate), whereby 5-chloro-4-(4-chloro-3-methoxyphenyl)-1,2-tetramethylene-4-pyrazolin-3-one (4.01 g, yield: 76%) was obtained as a white solid. $^1$H-NMR (400 MHz, CDCl$_3$): δ1.89-1.93 (m, 2H), 1.99-2.06 (m, 2H), 3.58-3.61 (m, 2H), 3.82-3.85 (m, 2H), 3.94 (s, 3H), 7.35 (d, J=1.3 Hz, 1H), 7.36 (d, J=0.7 Hz, 1H), 7.63 (d, J=1.3 Hz, 1H).

Boron tribromide (1 mol/L, 24.7 mL) was added dropwise to a solution of 5-chloro-4-(4-chloro-3-methoxyphenyl)-1,2-tetramethylene-4-pyrazolin-3-one (3.87 g, 12.4 mmol) in dichloromethane (30 mL) at −80° C. in an argon gas atmosphere, and the temperature was slowly raised to room temperature, followed by stirring for 21 hours. After the reaction was completed, the reaction solution was added little by little to 2N hydrochloric acid (50 mL) under ice-cooling, and the resultant product was filtered, whereby a filtrate and a white solid were obtained. 2N hydrochloric acid (20 mL) was added to the white solid, and the resultant product was stirred for 137 hours, and filtered, whereby a white solid was obtained. On the other hand, the filtrate was extracted with chloroform (50 mL×3), and the organic layer was washed with a saturated saline solution (20 mL), dried over anhydrous magnesium sulfate, concentrated under reduced pressure, and recrystallized from chloroform, whereby a white solid was obtained. By combining with the previously obtained white solid, 5-chloro-4-(4-chloro-3-hydroxyphenyl)-1,2-tetramethylene-4-pyrazolin-3-one (3.52 g, yield: 95%) was obtained as a white solid. $^1$H-NMR (400 MHz, DMSO): δ1.76-1.82 (m, 2H), 1.89-1.94 (m, 2H), 3.60-3.63 (m, 2H), 3.66-3.69 (m, 2H), 7.22 (dd, J=2.0 and 8.3 Hz, 1H), 7.34 (d, J=8.3 Hz, 1H), 7.52 (d, J=2.0 Hz, 1H), 10.2 (s, 1H).

Example-12

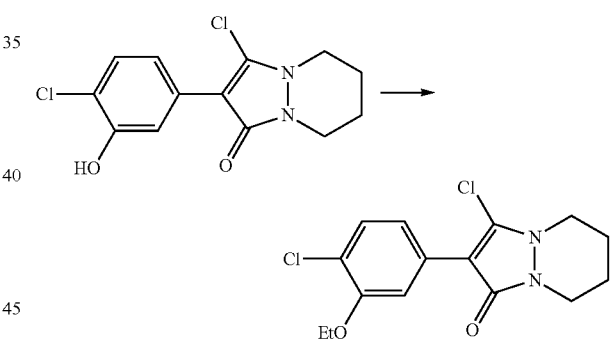

Cesium carbonate (547 mg, 1.68 mmol) and ethyl iodide (262 mg, 1.68 mmol) were added to a solution of 5-chloro-4-(4-chloro-3-hydroxyphenyl)-1,2-tetramethylene-4-pyrazolin-3-one (250 mg, 0.84 mmol) in DMF (3 mL), followed by stirring at room temperature for 2 hours. After the reaction was completed, water (20 mL) was added to the reaction solution, and the resultant product was extracted with ethyl acetate (20 mL×3). The organic layer was washed with a saturated saline solution, dried over anhydrous magnesium sulfate, and concentrated under reduced pressure. The obtained white yellow solid was washed with ether and chloroform, and purified by silica gel column chromatography, whereby 5-chloro-4-(4-chloro-3-ethoxyphenyl)-1,2-tetramethylene-4-pyrazolin-3-one (60 mg, yield: 22%) was obtained as a white solid. $^1$H-NMR (400 MHz, CDCl$_3$): δ1.47 (t, J=7.0 Hz, 3H), 1.86-1.92 (m, 2H), 1.99-2.03 (m, 2H), 3.57-3.60 (m, 2H), 3.81-3.84 (m, 2H), 4.17 (q, J=7.0 Hz, 2H), 7.32-7.35 (m, 2H), 7.62 (d, J=1.4 Hz, 1H).

Example-13

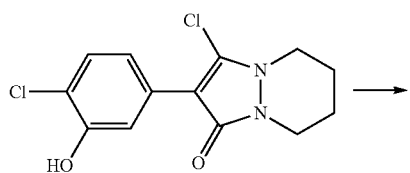

After 5-chloro-4-(4-chloro-3-hydroxyphenyl)-1,2-tetramethylene-4-pyrazolin-3-one (250 mg, 0.84 mmol) was dissolved in anhydrous DMF (3 mL), cesium carbonate (547 mg, 1.68 mmol) was added thereto, and propyl iodide (286 mg, 1.68 mmol) was added thereto, followed by stirring at room temperature for 2 hours. After the reaction was completed, water (20 mL) was added to the reaction solution, and the resultant product was extracted with ethyl acetate (20 mL×3). The organic layer was washed with a saturated saline solution, dried over anhydrous magnesium sulfate, and concentrated under reduced pressure, whereby a crude product was obtained as a white yellow solid. This was washed with ether, and dried, whereby 5-chloro-4-[4-chloro-3-(propyloxy)phenyl]-1,2-tetramethylene-4-pyrazolin-3-one (110 mg, yield: 39%) was obtained as a white solid. $^1$H-NMR (400 MHz, CDCl$_3$): δ1.06 (t, J=7.0 Hz, 3H), 1.83-1.92 (m, 4H), 1.99-2.04 (m, 2H), 3.57-3.59 (m, 2H), 3.81-3.85 (m, 2H), 4.05 (t, J=7.0 Hz, 2H), 7.31-7.37 (m, 2H), 7.61 (d, J=1.6 Hz, 1H).

Example-14

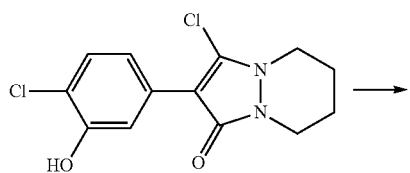

Cesium carbonate (652 mg, 2.00 mmol) and isopropyl bromide (245 mg, 2.00 mmol) were added to a solution of 5-chloro-4-(4-chloro-3-hydroxyphenyl)-1,2-tetramethylene-4-pyrazolin-3-one (300 mg, 1.00 mmol) in DMF (5 mL), followed by stirring at room temperature for 22 hours. After the reaction was completed, water (20 mL) was added to the reaction mixture, and the resultant product was extracted with ethyl acetate (30 mL×1, 20 mL×2). The organic layer was dried over anhydrous magnesium sulfate, and concentrated under reduced pressure, whereby a colorless oily crude product (3.38 g) was obtained. This was purified by silica gel column chromatography (ethyl acetate:methanol=10:1), and recrystallized from ether, whereby 5-chloro-4-[4-chloro-3-(isopropoxy)phenyl]-1,2-tetramethylene-4-pyrazolin-3-one (118 mg, yield: 35%) was obtained as a white solid. $^1$H-NMR (400 MHz, CDCl$_3$): δ1.39 (d, J=6.1 Hz, 6H), 1.68-1.92 (m, 2H), 1.99-2.04 (m, 2H), 3.57 (m, 2H), 3.81-3.84 (m, 2H), 4.63 (sept, J=6.1 Hz, 1H), 7.34-7.35 (m, 2H), 7.62 (m, 1H).

Example-15

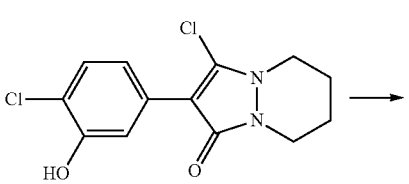

Cesium carbonate (652 mg, 2.00 mmol) and cyclopentyl bromide (302 mg, 2.00 mmol) were added to a solution of 5-chloro-4-(4-chloro-3-hydroxyphenyl)-1,2-tetramethylene-4-pyrazolin-3-one (300 mg, 1.00 mmol) in DMF (5 mL), followed by stirring at room temperature for 22 hours. After the reaction was completed, water (20 mL) was added to the reaction mixture, and the resultant product was extracted with ethyl acetate (30 mL×1, 20 mL×2). The organic layer was dried over anhydrous magnesium sulfate, and concentrated under reduced pressure, whereby a colorless oily crude product (2.83 g) was obtained. This was purified by silica gel column chromatography (ethyl acetate:methanol=9:1), and recrystallized from ether, whereby 5-chloro-4-[4-chloro-3-(cyclopentyloxy)phenyl]-1,2-tetramethylene-4-pyrazolin-3-one (167 mg, yield: 45%) was obtained as a white solid. $^1$H-NMR (400 MHz, CDCl$_3$): δ1.63-1.66 (m, 2H), 1.79-2.04 (m, 10H), 3.56-3.92 (m, 2H), 3.81-3.84 (m, 2H), 4.85-4.89 (m, 1H), 7.31-7.36 (m, 2H), 7.63 (m, 1H).

Example-16

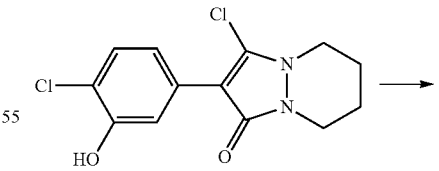

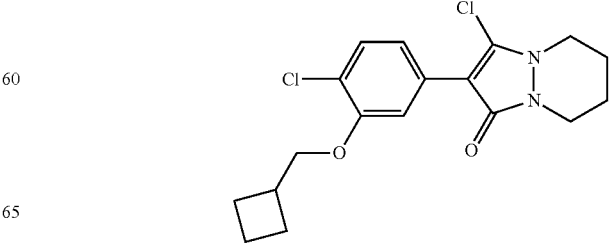

Cesium carbonate (652 mg, 2.00 mmol) and bromomethyl cyclobutane (298 mg, 2.00 mmol) were added to a solution of 5-chloro-4-(4-chloro-3-hydroxyphenyl)-1,2-tetramethylene-4-pyrazolin-3-one (300 mg, 1.00 mmol) in DMF (10 mL), followed by stirring at room temperature for 23 hours. After the reaction was completed, water (20 mL) was added to the reaction mixture, and the resultant product was extracted with ethyl acetate (30 mL×1, 20 mL×2). The organic layer was dried over anhydrous magnesium sulfate, and concentrated under reduced pressure, whereby a pale yellow oily crude product (1.63 g) was obtained. This was purified by silica gel column chromatography (ethyl acetate:methanol=9:1), and recrystallized from ether, whereby 5-chloro-4-[4-chloro-3-(cyclobutylmethyloxy)phenyl]-1,2-tetramethylene-4-pyrazolin-3-one (139 mg, yield: 38%) was obtained as a white solid. $^1$H-NMR (400 MHz, CDCl$_3$): δ1.86-1.96 (m, 6H), 1.97-2.05 (m, 2H), 2.10-2.17 (m, 2H), 2.77-2.86 (m, 1H), 3.57-3.60 (m, 2H), 3.82-3.84 (m, 2H), 4.05 (d, J=6.4 Hz, 2H), 7.31-7.36 (m, 2H), 7.60 (d, J=1.7 Hz, 1H).

Example-17

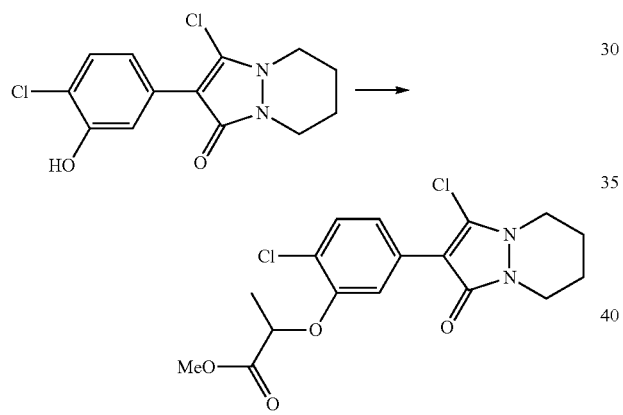

Cesium carbonate (202 mg, 2.00 mmol) and methyl 2-bromopropionate (334 mg, 2.00 mmol) were added to a solution of 5-chloro-4-(4-chloro-3-hydroxyphenyl)-1,2-tetramethylene-4-pyrazolin-3-one (300 mg, 1.00 mmol) in DMF (10 mL), followed by stirring at room temperature for 23 hours. After the reaction was completed, water (20 mL) was added thereto, and the resultant product was extracted with ethyl acetate (30 mL×1, 20 mL×1). The organic layer was dried over anhydrous magnesium sulfate, and concentrated under reduced pressure, whereby a pale yellow oily crude product (1.64 g) was obtained. This was purified by silica gel column chromatography (ethyl acetate:methanol=9:1), and recrystallized from ether, whereby 5-chloro-4-[4-chloro-3-[1-(methoxycarbonyl)ethyloxy]phenyl]-1,2-tetramethylene-4-pyrazolin-3-one (182 mg, yield: 47%) was obtained as a white solid. $^1$H-NMR (400 MHz, CDCl$_3$): δ1.68 (d, J=6.8 Hz, 3H), 1.86-1.91 (m, 2H), 1.98-2.04 (m, 2H), 3.56-3.59 (m, 2H), 3.77 (s, 3H), 3.80-3.83 (m, 2H), 4.86 (q, J=6.8 Hz, 1H), 7.38 (d, J=8.2 Hz, 1H), 7.46 (d, J=1.9 Hz, 1H), 7.48 (m, 1H).

Example-18

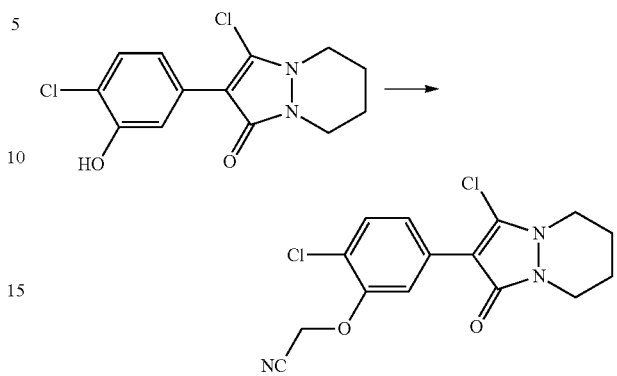

Cesium carbonate (652 mg, 2.00 mmol) and bromoacetonitrile (240 mg, 2.00 mmol) were added to a solution of 5-chloro-4-(4-chloro-3-hydroxyphenyl)-1,2-tetramethylene-4-pyrazolin-3-one (300 mg, 1.00 mmol) in DMF (10 mL), followed by stirring at room temperature for 17 hours. After the reaction was completed, water (20 mL) was added to the reaction mixture, and the resultant product was extracted with ethyl acetate (20 mL×3). The organic layer was washed with a saturated saline solution (10 mL), dried over anhydrous magnesium sulfate, and concentrated under reduced pressure, whereby a crude product (1.40 g) was obtained as a brown solid. This was recrystallized from ether, whereby 5-chloro-4-[4-chloro-3-(cyanomethyloxy)phenyl]-1,2-tetramethylene-4-pyrazolin-3-one (268 mg, yield: 79%) was obtained as a white solid. $^1$H-NMR (400 MHz, CDCl$_3$): δ1.88-1.94 (m, 2H), 2.00-2.06 (m, 2H), 3.61-3.63 (m, 2H), 3.82-3.85 (m, 2H), 4.88 (s, 2H), 7.42 (d, J=8.4 Hz, 1H), 7.56 (dd, J=1.9 and 8.4 Hz, 1H), 7.77 (d, J=1.9 Hz, 1H).

Example-19

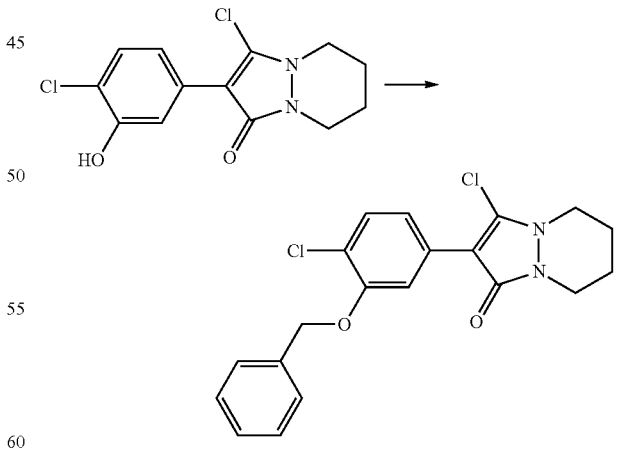

Cesium carbonate (652 mg, 2.00 mmol) and benzyl bromide (342 mg, 2.00 mmol) were added to a solution of 5-chloro-4-(4-chloro-3-hydroxyphenyl)-1,2-tetramethylene-4-pyrazolin-3-one (300 mg, 1.00 mmol) in DMF (10 mL), followed by stirring at room temperature for 23 hours. After the reaction was completed, water (20 mL) was added to the reaction mixture, and the resultant product was extracted with ethyl acetate (20 mL×2, 10 mL×1). The organic layer was washed with a saturated saline solution (10 mL), dried over anhydrous magnesium sulfate, and concentrated under reduced pressure, whereby a crude product (1.40 g) was obtained as a brown solid. This was recrystallized from ether, whereby 4-(3-benzyloxy-4-chlorophenyl)-5-chloro-1,2-tetramethylene-4-pyrazolin-3-one (113 mg, yield: 29%) was obtained as a pale yellow oily material. $^1$H-NMR (400 MHz, CDCl$_3$): δ1.86-1.92 (m, 2H), 1.98-2.04 (m, 2H), 3.56-3.59 (m, 2H), 3.81-3.84 (m, 2H), 5.21 (s, 2H), 7.29-7.40 (m, 5H), 7.48-7.51 (m, 2H), 7.66 (s, 1H).

Example-20

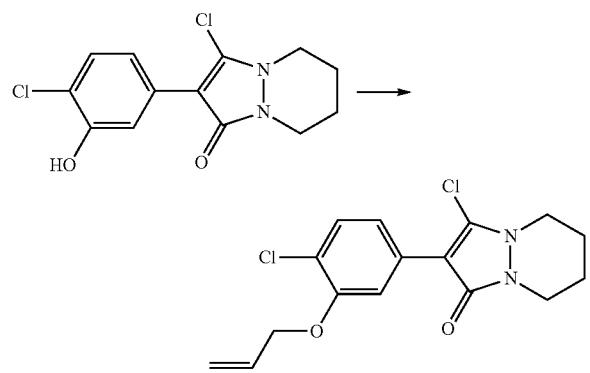

Cesium carbonate (652 mg, 2.00 mmol) and allyl bromide (242 mg, 2.00 mmol) were added to a solution of 5-chloro-4-(4-chloro-3-hydroxyphenyl)-1,2-tetramethylene-4-pyrazolin-3-one (300 mg, 1.00 mmol) in DMF (10 mL), followed by stirring at room temperature for 5 hours. After the reaction was completed, water (20 mL) was added to the reaction mixture, and the resultant product was extracted with ethyl acetate (30 mL×1, 20 mL×1). The organic layer was washed with a saturated saline solution (10 mL), dried over anhydrous magnesium sulfate, and concentrated under reduced pressure, whereby a colorless oily crude product (1.40 g) was obtained. This was purified by silica gel column chromatography (ethyl acetate:methanol=8:1), and recrystallized from ether, whereby 4-(3-allyloxy-4-chlorophenyl)-5-chloro-1,2-tetramethylene-4-pyrazolin-3-one (149 mg, yield: 44%) was obtained as a white solid. $^1$H-NMR (400 MHz, CDCl$_3$): δ1.87-1.92 (m, 2H), 1.99-2.05 (m, 2H), 3.57-3.60 (m, 2H), 3.81-3.84 (m, 2H), 4.67 (dt, J=1.5 and 5.2 Hz, 2H), 5.31 (dq, J=1.5 and 10.5 Hz, 1H), 5.49 (dq, J=1.5 and 17.2 Hz, 1H), 6.19 (ddt, J=5.2, 10.5 and 17.2 Hz, 1H), 7.34-7.39 (m, 2H), 7.62 (m, 1H).

Example-21

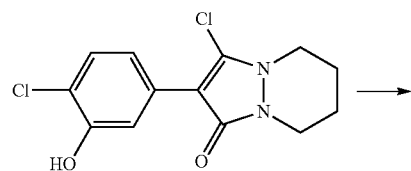

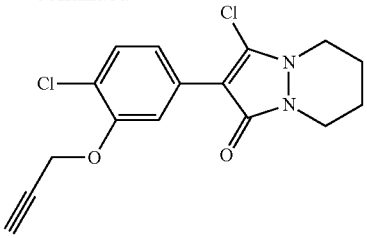

Cesium carbonate (652 mg, 2.00 mmol) and propargyl bromide (250 mg, 2.00 mmol) were added to a solution of 5-chloro-4-(4-chloro-3-hydroxyphenyl)-1,2-tetramethylene-4-pyrazolin-3-one (300 mg, 1.00 mmol) in DMF (5 mL), followed by stirring at room temperature for 22 hours. After the reaction was completed, water (20 mL) was added to the reaction mixture, and the resultant product was extracted with ethyl acetate (30 mL×3). The organic layer was dried over anhydrous magnesium sulfate, and concentrated under reduced pressure, whereby a yellow semi-oily crude product (1.76 g) was obtained. This was recrystallized from ether, whereby 5-chloro-4-[4-chloro-3-(propargyloxy)phenyl]-1,2-tetramethylene-4-pyrazolin-3-one (181 mg, yield: 54%) was obtained as a white solid. $^1$H-NMR (400 MHz, CDCl$_3$): δ1.87-1.93 (m, 2H), 2.01-2.05 (m, 2H), 2.55 (t, J=2.4 Hz, 1H), 3.58-3.61 (m, 2H), 3.82-3.85 (m, 2H), 4.82 (d, J=2.4 Hz, 2H), 7.39 (d, J=8.3 Hz, 1H), 7.45 (dd, J=1.9 and 8.3 Hz, 1H), 7.72 (d, J=1.9 Hz, 1H).

Example-22

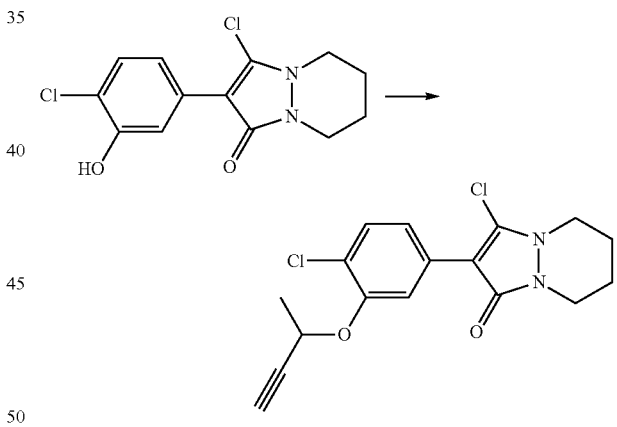

Cesium carbonate (652 mg, 2.00 mmol) and 3-chloro-1-butyne (181 mg, 2.00 mmol) were added to a solution of 5-chloro-4-(4-chloro-3-hydroxyphenyl)-1,2-tetramethylene-4-pyrazolin-3-one (300 mg, 1.00 mmol) in DMF (10 mL), followed by stirring at room temperature for 27 hours. After the reaction was completed, water (20 mL) was added to the reaction mixture, and the resultant product was extracted with ethyl acetate (30 mL×2). The organic layer was washed with a saturated saline solution (10 mL), dried over anhydrous magnesium sulfate, and concentrated under reduced pressure, whereby a pale orange oily crude product (1.04 g) was obtained. This was purified by silica gel column chromatography (ethyl acetate:methanol=9:1), and recrystallized from ether, whereby 4-[3-(1-butyn-3-yloxy)-4-chlorophenyl]-5-chloro-1,2-tetramethylene-4-pyrazolin-3-one (52 mg, yield: 15%) was obtained as a white solid. $^1$H-NMR (400 MHz, CDCl₃): δ1.73 (d, J=6.6 Hz, 3H), 1.86-1.88 (m, 2H), 1.99-2.04 (m, 2H), 2.51 (d, J=2.0 Hz, 1H), 3.53-3.63 (m, 2H), 3.78-3.88 (m, 2H), 4.96 (dq, J=2.0 and 6.6 Hz, 1H), 7.38 (d, J=8.3 Hz, 1H), 7.67 (dd, J=1.9 and 8.3 Hz, 1H), 7.76 (d, J=1.9 Hz, 1H).

Example-23

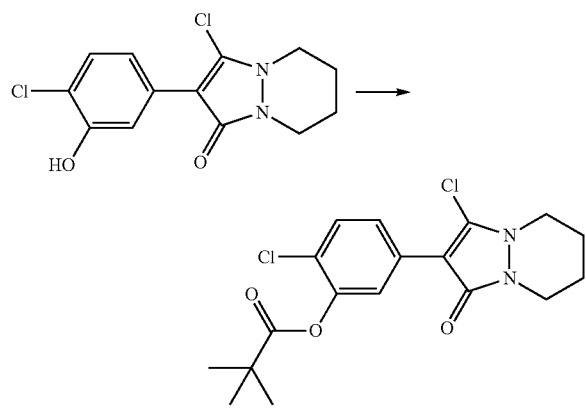

Triethylamine (202 mg, 2.00 mmol) and pivaloyl chloride (241 mg, 2.00 mmol) were added to a solution of 5-chloro-4-(4-chloro-3-hydroxyphenyl)-1,2-tetramethylene-4-pyrazolin-3-one (300 mg, 1.00 mmol) in dichloromethane (10 mL) under ice-cooling, followed by stirring at room temperature for 22 hours. After the reaction was completed, water (20 mL) was added to the reaction mixture, and the resultant product was extracted with chloroform (20 mL×2). The organic layer was washed with a saturated saline solution (10 mL), dried over anhydrous magnesium sulfate, and concentrated under reduced pressure, whereby a crude product (430 mg) was obtained as a pale orange solid. This was recrystallized from ether, whereby 5-chloro-4-[4-chloro-3-(pivaloyloxy)phenyl]-1,2-tetramethylene-4-pyrazolin-3-one (268 mg, yield: 70%) was obtained as a white solid. ¹H-NMR (400 MHz, CDCl₃): δ1.39 (s, 9H), 1.86-1.92 (m, 2H), 1.98-2.04 (m, 2H), 3.57-3.60 (m, 2H), 3.80-3.83 (m, 2H), 7.43 (m, 1H), 7.68-7.71 (m, 2H).

Example-24

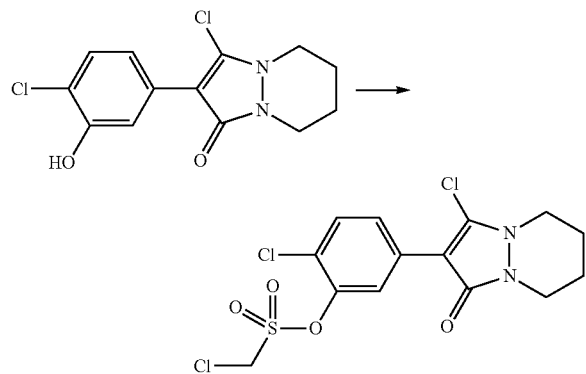

Triethylamine (202 mg, 2.00 mmol) and chloromethyl sulfonyl chloride (298 mg, 2.00 mmol) were added to a solution of 5-chloro-4-(4-chloro-3-hydroxyphenyl)-1,2-tetramethylene-4-pyrazolin-3-one (300 mg, 1.00 mmol) in dichloromethane (10 mL) under ice-cooling, followed by stirring at room temperature for 5 days. Chloromethyl sulfonyl chloride (298 mg, 2.00 mmol) was further added thereto, followed by stirring at room temperature for 42 hours. After the reaction was completed, water (30 mL) was added to the reaction mixture, and the resultant product was extracted with chloroform (30 mL×1, 20 mL×2). The organic layer was washed with a saturated saline solution (10 mL), dried over anhydrous magnesium sulfate, and concentrated under reduced pressure, whereby a crude product (1.03 g) was obtained as a pale yellow solid. This was purified by silica gel column chromatography (ethyl acetate:methanol=9:1), washed with a potassium carbonate aqueous solution, dried over anhydrous magnesium sulfate, and concentrated under reduced pressure, whereby 5-chloro-4-[4-chloro-3-(chloromethyl sulfonyl oxy)phenyl]-1,2-tetramethylene-4-pyrazolin-3-one (169 mg, yield: 41%) was obtained as a pale yellow solid. ¹H-NMR (400 MHz, CDCl₃): δ1.88-1.94 (m, 2H), 2.00-2.06 (m, 2H), 3.62-3.64 (m, 2H), 3.82-3.84 (m, 2H), 4.86 (s, 2H), 7.50 (d, J=8.5 Hz, 1H), 7.89 (dd, J=2.0 and 8.5 Hz, 1H), 8.04 (d, J=2.0 Hz, 1H).

Example-25

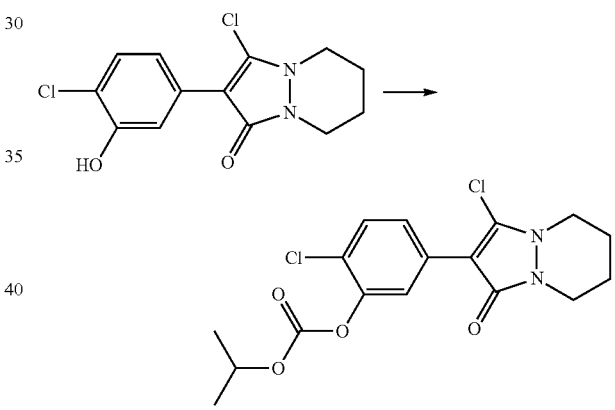

A 3 M sodium hydroxide aqueous solution (1 mL) and isopropyl chloroformate (245 mg, 2.00 mmol) were added to a solution of 5-chloro-4-(4-chloro-3-hydroxyphenyl)-1,2-tetramethylene-4-pyrazolin-3-one (300 mg, 1.00 mmol) in DMF (10 mL), followed by stirring at room temperature for 17 hours. After the reaction was completed, water (20 mL) was added to the reaction mixture, and the resultant product was extracted with ethyl acetate (20 mL×2). The organic layer was washed with a saturated saline solution (10 mL), dried over anhydrous magnesium sulfate, and concentrated under reduced pressure, whereby a pale yellow oily crude product (1.13 g) was obtained. This was purified by silica gel column chromatography (ethyl acetate:methanol=9:1), and recrystallized from ether, whereby 5-chloro-4-[4-chloro-3-(isopropoxycarbonyloxy)phenyl]-1,2-tetramethylene-4-pyrazolin-3-one (45 mg, yield: 12%) was obtained as a white solid. ¹H-NMR (400 MHz, CDCl₃): δ1.39 (d, J=6.3 Hz, 6H), 1.86-1.92 (m, 2H), 1.98-2.04 (m, 2H), 3.57-3.61 (m, 2H), 3.81-3.83 (m, 2H), 5.00 (sept, J=6.3 Hz, 1H), 7.45 (d, J=8.5 Hz, 1H), 7.79 (d d, J=2.0 and 8.5 Hz, 1H), 7.83 (d, J=2.0 Hz, 1H).

Example-26

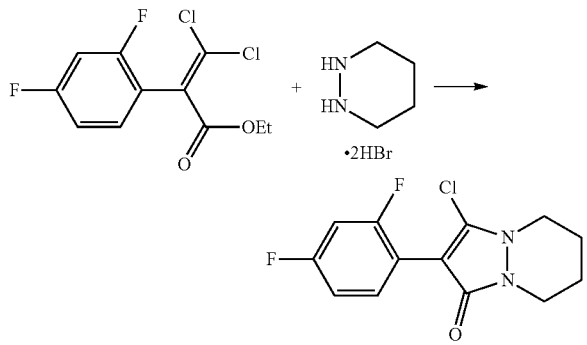

Triethylamine (8.9 mL, 64.0 mmol), and hexahydropyridazine dihydrobromide (5.8 g, 23.4 mmol) were added to a solution of ethyl 3,3-dichloro-2-(2,4-difluorophenyl)acrylate (6.0 g, 21.4 mmol) in 1,4-dioxane (80 mL) in an argon atmosphere, followed by heating to reflux for 20 hours. After the reaction was completed, water (80 mL) was added to the reaction solution, and the resultant product was extracted with ethyl acetate (100 mL×3). The organic layer was dried over anhydrous magnesium sulfate, and concentrated under reduced pressure, and the obtained crude product was purified by silica gel column chromatography (ethyl acetate), whereby 5-chloro-4-(2,4-difluorophenyl)-1,2-tetramethylene-4-pyrazolin-3-one (5.6 g, yield: 93%) was obtained as a pale yellow solid. $^1$H-NMR (400 MHz, CDCl$_3$): δ1.89-1.92 (m, 2H), 2.00-2.05 (m, 2H), 3.59-3.62 (m, 2H), 3.82-3.85 (m, 2H), 6.86-6.96 (m, 2H), 7.48 (dt, J=6.5 and 8.4 Hz, 1H). $^{19}$F-NMR (376 MHz, CDCl$_3$): δ−110 (d, J=7.8 Hz, 1F), −107 (d, J=7.8 Hz, 1F).

Example-27

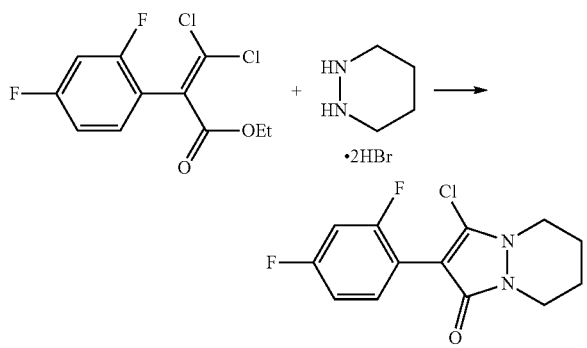

Triethylamine (378 g, 3.70 mol) was added to a solution of hexahydropyridazine dihydrobromide (306 g, 1.23 mol) and ethyl 3,3-dichloro-2-(2,4-difluorophenyl)acrylate (315 g, 1.12 mol) in 1,4-dioxane (1.12 L), followed by heating to reflux for 15 hours. After the reaction was completed, the solvent was distilled off from the reaction solution under reduced pressure, then, water (1.0 L) was added to the obtained residue, and the precipitated solid was collected by filtration. The obtained solid was washed with water (1.0 L) and ether (1.0 L), and dried under reduced pressure, whereby 5-chloro-4-(2,4-difluorophenyl)-1,2-tetramethylene-4-pyrazolin-3-one (241 g, yield: 76%) was obtained as a pale yellow solid.

Reference Example-17

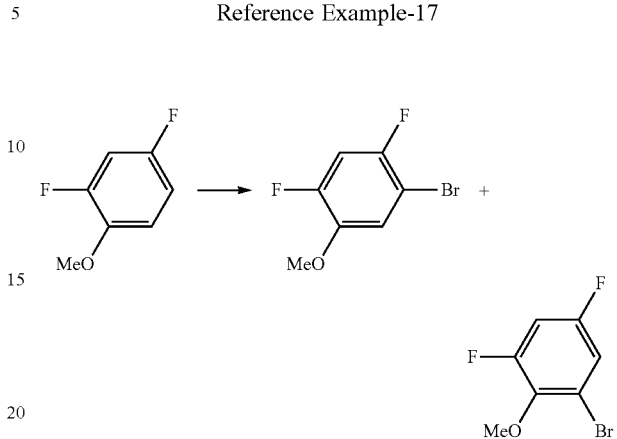

Bromine (11.6 mL, 226 mmol) was added to a solution of 2,4-difluoroanisole (25.0 g, 173 mmol) in concentrated sulfuric acid (140 mL) under ice-cooling, followed by stirring for 2 hours. After the reaction was completed, the reaction solution was added little by little to ice water, and the resultant product was extracted with ether (300 mL×3). After the organic layer was washed with a 5% sodium thiosulfate aqueous solution (300 mL), the organic layer was dried over anhydrous magnesium sulfate, filtered, and concentrated under reduced pressure, and the obtained crude product was purified by silica gel chromatography (hexane:ethyl acetate=10:1), whereby 5-bromo-2,4-difluoroanisole (7.0 g, yield: 18%) was obtained as a white solid. $^1$H-NMR (400 MHz, CDCl$_3$): δ3.87 (s, 3H), 6.94 (dd, J=8.2 and 10.8 Hz, 1H), 7.11 (dd, J=6.5 and 8.6 Hz, 1H). $^{19}$F-NMR (376 MHz, CDCl$_3$): δ−131.0 (d, J=2.8 Hz, 1F), −114.1 (d, J=2.8 Hz, 1F).

Reference Example-18

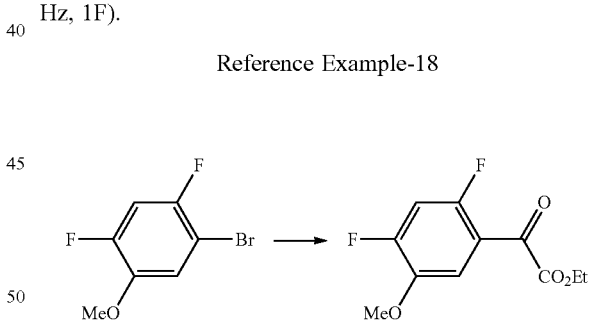

THF (50 mL) was added to magnesium (686 mg, 28.2 mmol), and 5-bromo-2,4-difluoroanisole (6.00 g, 26.9 mmol) was slowly added thereto, whereby a Grignard reagent was prepared. The Grignard reagent was added dropwise to a solution of diethyl oxalate (3.28 mL, 24.2 mmol) in THF (60 mL) at −40° C. or lower, followed by stirring for 2 hours at 0° C., and a saturated ammonium chloride aqueous solution and water (200 mL) were added to the reaction solution, and the resultant product was extracted with ethyl acetate (200 mL×2). The organic layer was dried over magnesium sulfate, filtered, and concentrated under reduced pressure, and the resultant product was purified by silica gel column chromatography (hexane:ethyl acetate=10:1), whereby ethyl 2-(2,4-difluoro-5-methoxyphenyl)-2-oxoacetate (1.0 g, yield: 15%) was obtained as a colorless liquid. $^1$H-NMR (400 MHz, CDCl$_3$): δ1.40 (t, J=7.2 Hz, 3H), 3.93 (s, 3H), 4.43 (q, J=7.2 Hz, 2H), 6.94 (dd, J=10.1 and 10.1 Hz, 1H), 7.49 (dd, J=6.4 and 9.2 Hz, 1H). $^{19}$F-NMR (376 MHz, CDCl$_3$): δ−117.1 (d, J=8.6 Hz, 1F), −116.6 (d, J=8.6 Hz, 1F).

Reference Example-19

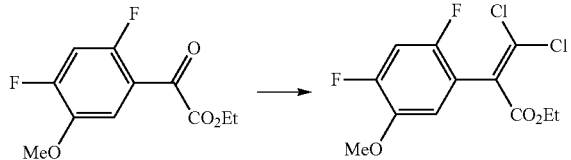 [SMILES: CCOC(=O)C(=O)c1cc(OC)c(F)cc1F ; CCOC(=O)C(=C(Cl)Cl)c1cc(OC)c(F)cc1F]

Carbon tetrachloride (1.18 mL, 12.2 mmol) was added to a solution of triphenylphosphine (3.2 g, 12.2 mmol) in dichloromethane (20 mL) under ice-cooling, followed by stirring for 15 minutes. To the solution, ethyl 2-(2,4-difluoro-5-methoxyphenyl)-2-oxoacetate (0.994 g, 4.07 mmol) was added, followed by stirring at room temperature for 24 hours. The solvent was removed from the reaction mixture under reduced pressure, then, a mixed solvent of chloroform and ether was added to the residue, and the solid was separated by filtration. The filtrate was concentrated under reduced pressure, and the obtained crude product was purified by silica gel column chromatography (hexane:ethyl acetate=10:1), whereby ethyl 3,3-dichloro-2-(2,4-difluoro-5-methoxyphenyl)acrylate (0.99 g, yield: 78%) was obtained as a colorless liquid. $^1$H-NMR (400 MHz, CDCl$_3$): δ1.27 (t, J=7.1 Hz, 3H), 3.88 (s, 3H), 4.26 (q, J=7.1 Hz, 2H), 6.89 (dd, J=1.0 and 9.0 Hz, 1H), 6.91 (dd, J=5.3 and 9.0 Hz, 1H). $^{19}$F-NMR (376 MHz, CDCl$_3$): δ−128.3 (d, J=4.2 Hz, 1F), −118.9 (d, J=4.2 Hz, 1F).

Reference Example-20

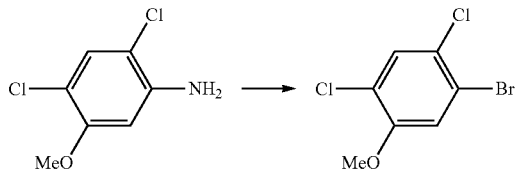 [SMILES: COc1cc(N)c(Cl)cc1Cl ; COc1cc(Br)c(Cl)cc1Cl]

A solution of sodium nitrite (2.69 g, 39.0 mmol) in concentrated sulfuric acid (20 mL) was added dropwise to a solution of 5-amino-2,4-dichloroanisole (5.00 g, 26.0 mmol) in acetic acid (26 mL) under ice-cooling, followed by stirring at the same temperature for 30 minutes. Copper (I) bromide and a 25% hydrogen bromide-acetic acid solution (17 mL) were sequentially added to the reaction solution, followed by heating at 50° C. for 1 hour. After the reaction was completed, the reaction solution was cooled in an ice bath, sodium hydroxide was added thereto, and the resultant product was extracted with chloroform (50 mL×3). The combined organic layer was washed with a saturated saline solution, dried over anhydrous magnesium sulfate, and concentrated under reduced pressure, and the obtained crude product was purified by silica gel column chromatography (hexane), whereby 5-bromo-2,4-dichloroanisole (2.85 g, yield: 43%) was obtained as a white solid. $^1$H-NMR (400 MHz, CDCl$_3$): δ3.89 (s, 3H), 7.14 (s, 1H), 7.45 (s, 1H).

Reference Example-21

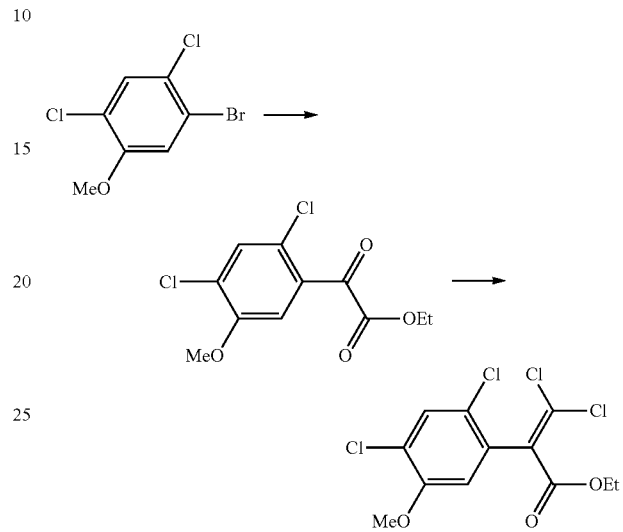

An isopropyl magnesium chloride solution (15 mL, 2M-THF solution) was added to a solution of 5-bromo-2,4-dichloroanisole (5.12 g, 20.0 mmol) in THF (20 mL) at −78° C., followed by stirring at room temperature for 30 minutes. A solution of the obtained Grignard reagent in THF was added dropwise to a solution of diethyl oxalate (2.84 mL, 21.0 mmol) in THF (20 mL) at −78° C., followed by stirring at room temperature for 12 hours. A saturated ammonium chloride aqueous solution (50 mL) was added to the reaction solution, and the resultant product was extracted with ethyl acetate (100 mL×3). The organic layer was dried over anhydrous magnesium sulfate, and concentrated under reduced pressure, and the obtained crude product was eluted by silica gel column chromatography (hexane:ethyl acetate=9:1), whereby ethyl 2-(2,4-dichloro-5-methoxyphenyl)-2-oxoacetate was obtained as a colorless oily material.

Carbon tetrachloride (3.38 mL) was added to a solution of triphenylphosphine (9.20 g, 35.0 mmol) in dichloromethane (15 mL) under ice-cooling, and the previously prepared solution of ethyl 2-(2,4-dichloro-5-methoxyphenyl)-2-oxoacetate in dichloromethane (10 mL) was added thereto, followed by stirring at room temperature for 17 hours. The solvent was removed from the reaction solution under reduced pressure, then, a 1:1 mixed solvent of hexane and ether was added to the precipitated solid, and the precipitated solid was separated by filtration. The filtrate was concentrated under reduced pressure, and the obtained crude product was purified by silica gel column chromatography (hexane:ethyl acetate=9:1), whereby ethyl 3,3-dichloro-2-(2,4-dichloro-5-methoxyphenyl)acrylate (1.52 g, yield: 22%) was obtained as a yellow oily material. $^1$H-NMR (400 MHz, CDCl$_3$): δ1.25 (t, J=7.2 Hz, 3H), 3.90 (s, 3H), 4.24 (q, J=7.2 Hz, 2H), 6.84 (s, 1H), 7.44 (s, 1H).

Reference Example-22

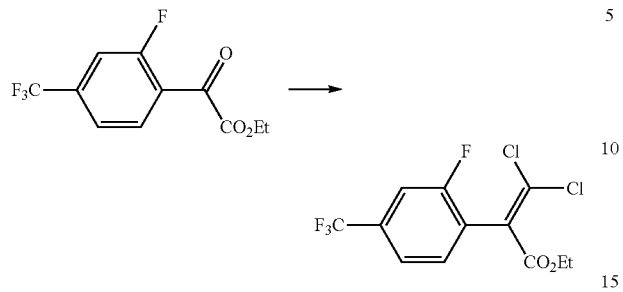

In the same manner as in Reference Example-21, from ethyl 2-[2-fluoro-4-(trifluoromethyl)phenyl]-2-oxoacetate, ethyl 3,3-dichloro-2-[2-fluoro-4-(trifluoromethyl)phenyl]acrylate was obtained with a yield of 71%. $^1$H-NMR (400 MHz, CDCl$_3$): δ1.26 (t, J=7.1 Hz, 3H), 4.25 (q, J=7.1 Hz, 2H), 7.39 (m, 1H), 7.44-7.50 (m, 2H). $^{19}$F-NMR (376 MHz, CDCl$_3$): δ−110.2 (s, 1F), −63.0 (s, 3F).

Example-28

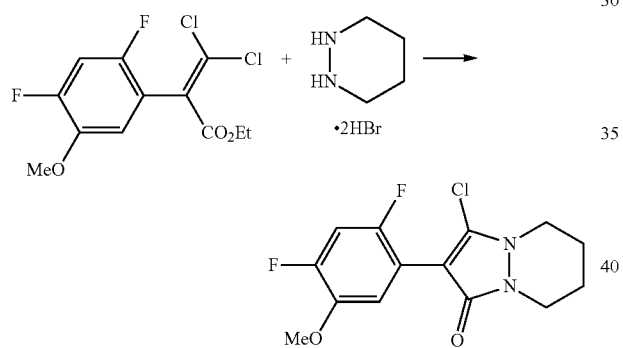

Triethylamine (0.97 g, 9.55 mmol) and hexahydropyridazine dihydrobromide (0.87 g, 3.50 mmol) were added to a solution of ethyl 3,3-dichloro-2-(2,4-difluoro-5-methoxyphenyl)acrylate (0.99 g, 3.18 mmol) in 1,4-dioxane (20 mL), followed by refluxing for 24 hours. After the reaction was completed, water (30 mL) was added to the reaction solution, and the resultant product was extracted with ethyl acetate (20 mL×3). The organic layer was washed with a saturated saline solution (20 mL), dried over anhydrous magnesium sulfate, and concentrated under reduced pressure, whereby a crude product was obtained. This was purified by silica gel column chromatography (ethyl acetate: methanol=10:1), whereby 5-chloro-4-(2,4-difluoro-5-methoxyphenyl)-1,2-tetramethylene-4-pyrazolin-3-one (0.78 g, yield: 78%) was obtained as a white solid. $^1$H-NMR (400 MHz, CDCl$_3$): δ1.86-1.94 (m, 2H), 1.98-2.06 (m, 2H), 3.59-3.66 (m, 2H), 3.81-3.87 (m, 2H), 3.88 (s, 3H), 6.92 (dd, J=9.3 and 10.9 Hz, 1H), 7.12 (dd, J=6.9 and 9.2 Hz, 1H). $^{19}$F-NMR (376 MHz, CDCl$_3$): δ−130.8 (d, J=4.1 Hz, 1F), −117.9 (d, J=4.1 Hz, 1F).

Example-29

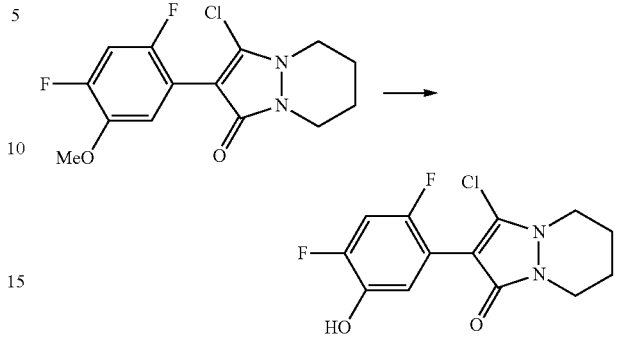

A solution (4.0 mL) of 1M boron tribromide in dichloromethane was added to a solution of 5-chloro-4-(2,4-difluoro-5-methoxyphenyl)-1,2-tetramethylene-4-pyrazolin-3-one (629 mg, 2.0 mmol) in dichloromethane (8 mL) at −78° C. The resultant product was stirred for 10 hours while slowly raising the reaction temperature to room temperature. After the reaction solution was added to ice water, a 1N HCl aqueous solution (20 mL) was added thereto. The precipitated solid was filtered, and sufficiently dried, whereby 5-chloro-4-(2,4-difluoro-5-hydroxyphenyl)-1,2-tetramethylene-4-pyrazolin-3-one (544 mg, yield: 90%) was obtained as a white solid. $^1$H-NMR (400 MHz, CDCl$_3$): δ1.89-1.98 (m, 2H), 2.00-2.08 (m, 2H), 3.63-3.69 (m, 2H), 3.86-3.92 (m, 2H), 6.83 (dd, J=9.9 and 10.6 Hz, 1H), 7.25 (dd, J=7.2 and 9.4 Hz, 1H). $^{19}$F-NMR (376 MHz, CDCl$_3$): δ−132.9 (s, 1F), −120.4 (s, 1F).

Example-30

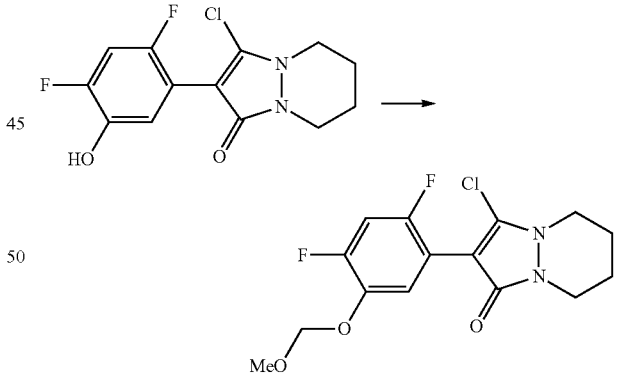

In the same manner as in Example-12, 5-chloro-4-(2,4-difluoro-5-hydroxyphenyl)-1,2-tetramethylene-4-pyrazolin-3-one was reacted with chloromethyl methyl ether, whereby 5-chloro-4-[2,4-difluoro-5-(methoxymethoxy)phenyl]-1,2-tetramethylene-4-pyrazolin-3-one was obtained with a yield of 53%. $^1$H-NMR (400 MHz, CDCl$_3$): δ1.85-1.93 (m, 2H), 1.98-2.05 (m, 2H), 3.52 (s, 3H), 3.58-3.62 (m, 2H), 3.80-3.85 (m, 2H), 5.18 (s, 2H), 6.92 (dd, J=9.4 and 10.7 Hz, 1H), 7.33 (dd, J=6.9 and 9.2 Hz, 1H). $^{19}$F-NMR (376 MHz, CDCl$_3$): δ−128.9 (d, J=5.5 Hz, 1F), −115.6 (d, J=5.5 Hz, 1F).

Example-31

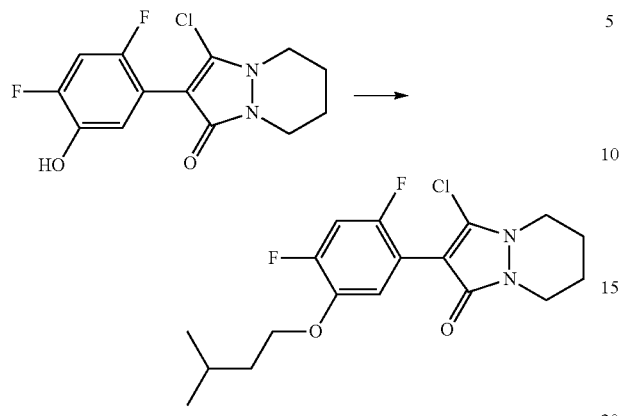

In the same manner as in Example-12, 5-chloro-4-(2,4-difluoro-5-hydroxyphenyl)-1,2-tetramethylene-4-pyrazolin-3-one was reacted with isopentyl bromide, whereby 5-chloro-4-[2,4-difluoro-5-(isopentyloxy)phenyl]-1,2-tetramethylene-4-pyrazolin-3-one was obtained with a yield of 95%. $^1$H-NMR (400 MHz, CDCl$_3$): δ0.95 (d, J=6.7 Hz, 6H), 1.69 (q, J=6.7 Hz, 2H), 1.83 (sept. J=6.7 Hz, 1H), 1.86-1.93 (m, 2H), 1.98-2.05 (m, 2H), 3.58-3.63 (m, 2H), 3.81-3.86 (m, 2H), 4.04 (t, J=6.7 Hz, 2H), 6.90 (dd, J=9.4 and 10.9 Hz, 1H), 7.12 (dd, J=6.8 and 9.3 Hz, 1H). $^{19}$F-NMR (376 MHz, CDCl$_3$): δ−130.1 (d, J=4.1 Hz, 1F), −118.1 (d, J=4.1 Hz, 1F).

Example-32

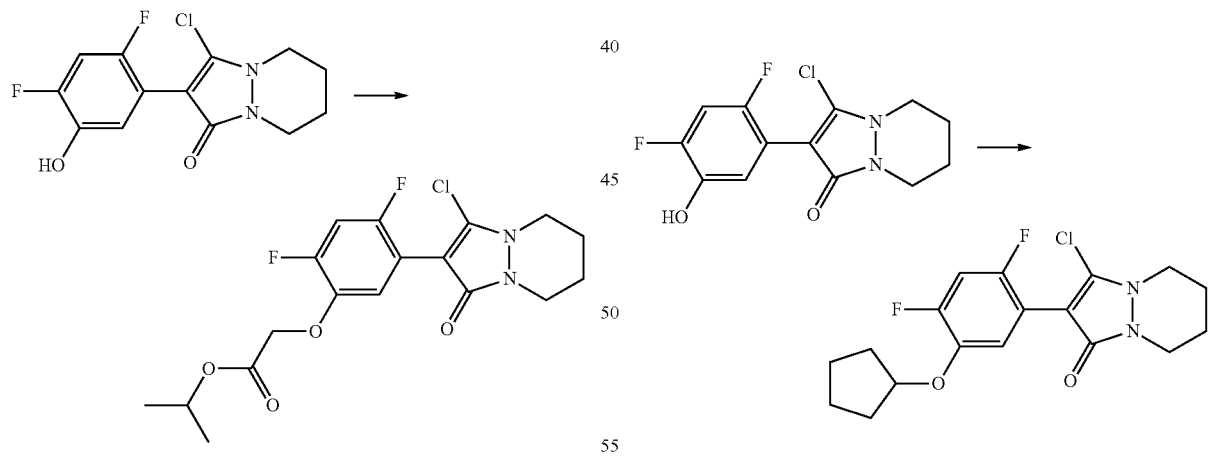

In the same manner as in Example-12, 5-chloro-4-(2,4-difluoro-5-hydroxyphenyl)-1,2-tetramethylene-4-pyrazolin-3-one was reacted with isopropyl chloroacetate, whereby isopropyl 2-[5-(5-chloro-3-oxo-1,2-tetramethylene-4-pyrazolin-4-yl)-2,4-difluorophenyloxy]acetate was obtained with a yield of 91%. $^1$H-NMR (400 MHz, CDCl$_3$): δ1.26 (d, J=6.3 Hz, 6H), 1.86-1.93 (m, 2H), 1.98-2.05 (m, 2H), 3.58-3.63 (m, 2H), 3.80-3.84 (m, 2H), 4.64 (s, 2H), 5.12 (sept, J=6.3 Hz, 1H), 6.94 (dd, J=9.4 and 10.8 Hz, 1H), 7.13 (dd, J=6.6 and 9.2 Hz, 1H). $^{19}$F-NMR (376 MHz, CDCl$_3$): δ−128.5 (d, J=4.2 Hz, 1F), −115.6 (d, J=4.2H, 1F).

Example-33

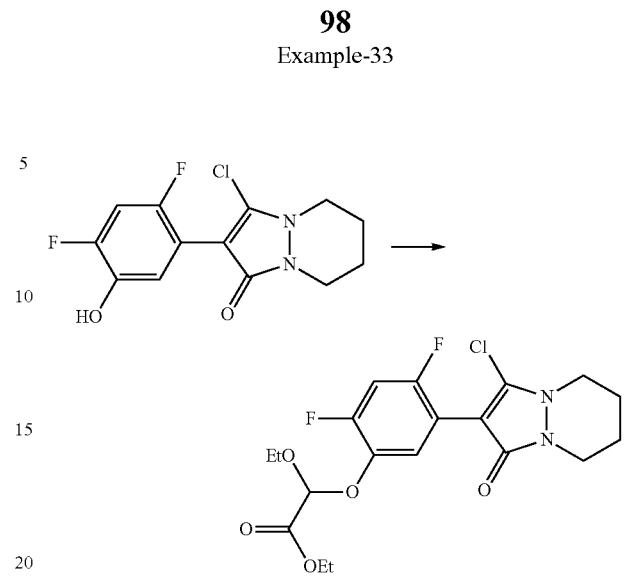

In the same manner as in Example-12, 5-chloro-4-(2,4-difluoro-5-hydroxyphenyl)-1,2-tetramethylene-4-pyrazolin-3-one was reacted with ethyl 2-chloro-2-ethoxy acetate, whereby ethyl 2-[5-(5-chloro-3-oxo-1,2-tetramethylene-4-pyrazolin-4-yl)-2,4-difluorophenyloxy]-2-ethoxy acetate was obtained with a yield of 77%. $^1$H-NMR (400 MHz, CDCl$_3$): δ1.28 (d, J=7.0 Hz, 3H), 1.30 (d, J=7.2 Hz, 3H), 1.86-1.94 (m, 2H), 1.98-2.05 (m, 2H), 3.58-3.64 (m, 2H), 3.77-3.98 (m, 4H), 4.29 (q, J=7.2 Hz, 2H), 5.44 (s, 1H), 6.94 (dd, J=9.5 and 10.5 Hz, 1H), 7.34 (dd, J=7.0 and 9.0 Hz, 1H). $^{19}$F-NMR (376 MHz, CDCl$_3$): δ−126.8 (d, J=5.5 Hz, 1F), −113.4 (d, J=5.5 Hz, 1F).

Example-34

In the same manner as in Example-12, 5-chloro-4-(2,4-difluoro-5-hydroxyphenyl)-1,2-tetramethylene-4-pyrazolin-3-one was reacted with cyclopentyl bromide, whereby 5-chloro-4-[5-(cyclopentyloxy)-2,4-difluorophenyl]-1,2-tetramethylene-4-pyrazolin-3-one was obtained with a yield of 73%. $^1$H-NMR (400 MHz, CDCl$_3$): δ1.58-1.66 (m, 2H), 1.75-1.92 (m, 8H), 1.98-2.06 (m, 2H), 3.58-3.63 (m, 2H), 3.80-3.86 (m, 2H), 4.77 (m, 1H), 6.89 (dd, J=9.5 and 10.9 Hz, 1H), 7.11 (dd, J=6.9 and 9.2 Hz, 1H). $^{19}$F-NMR (376 MHz, CDCl$_3$): δ−129.4 (d, J=4.1 Hz, 1F), −118.0 (d, J=4.1 Hz, 1F).

Example-35

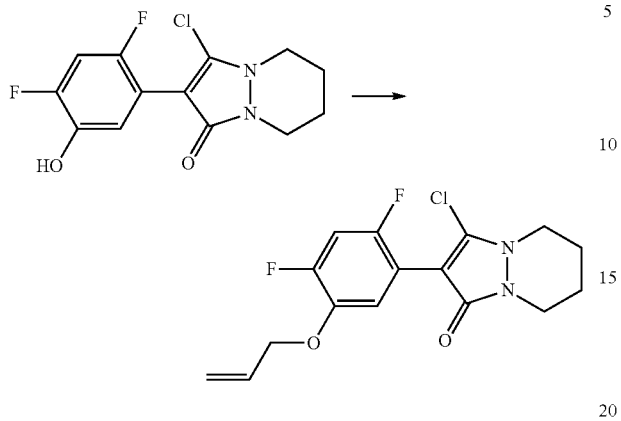

In the same manner as in Example-12, 5-chloro-4-(2,4-difluoro-5-hydroxyphenyl)-1,2-tetramethylene-4-pyrazolin-3-one was reacted with allyl bromide, whereby 4-(5-allyloxy-2,4-difluorophenyl)-5-chloro-1,2-tetramethylene-4-pyrazolin-3-one was obtained with a yield of 74%. $^1$H-NMR (400 MHz, CDCl$_3$): δ1.86-1.94 (m, 2H), 1.98-2.06 (m, 2H), 3.58-3.63 (m, 2H), 3.81-3.85 (m, 2H), 4.59 (td, J=1.3 and 5.5 Hz, 2H), 5.29 (qd, J=1.3 and 10.5 Hz, 1H), 5.42 (qd, J=1.3 and 17.2 Hz, 1H), 6.06 (ddt, J=5.4, 10.5 and 17.2 Hz, 1H), 6.92 (dd, J=9.4 and 10.8 Hz, 1H), 7.14 (dd, J=6.8 and 9.3 Hz, 1H). $^{19}$F-NMR (376 MHz, CDCl$_3$): δ−129.6 (d, J=4.1 Hz, 1F), −117.2 (d, J=4.1 Hz, 1F).

Example-36

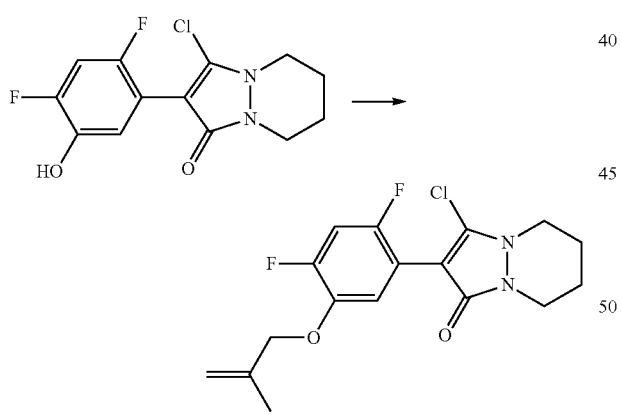

In the same manner as in Example-12, 5-chloro-4-(2,4-difluoro-5-hydroxyphenyl)-1,2-tetramethylene-4-pyrazolin-3-one was reacted with methallyl chloride, whereby 5-chloro-4-[2,4-difluoro-5-(methallyloxy)phenyl]-1,2-tetramethylene-4-pyrazolin-3-one was obtained with a yield of 83%. $^1$H-NMR (400 MHz, CDCl$_3$): δ1.83 (s, 3H), 1.86-1.94 (m, 2H), 1.98-2.05 (m, 2H), 3.58-3.63 (m, 2H), 3.80-3.86 (m, 2H), 4.48 (s, 2H), 4.99 (s, 1H), 5.10 (s, 1H), 6.91 (dd, J=9.5 and 10.8 Hz, 1H), 7.13 (dd, J=6.8 and 9.3 Hz, 1H). $^{19}$F-NMR (376 MHz, CDCl$_3$): δ−129.6 (d, J=4.1 Hz, 1F), −117.3 (d, J=4.1 Hz, 1F).

Example-37

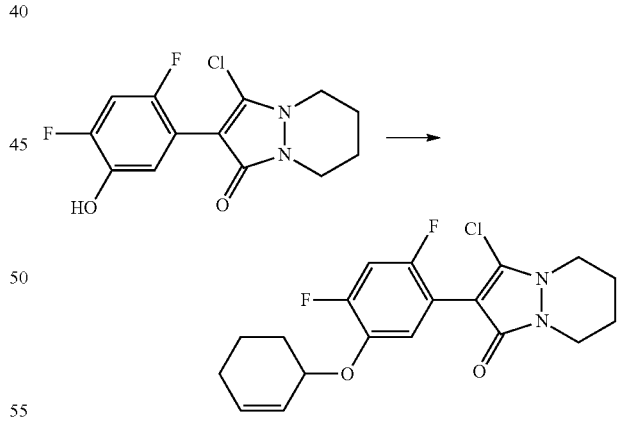

In the same manner as in Example-12, 5-chloro-4-(2,4-difluoro-5-hydroxyphenyl)-1,2-tetramethylene-4-pyrazolin-3-one was reacted with 4-bromo-1-butene, whereby 5-chloro-4-[5-(3-butenyloxy)-2,4-difluorophenyl]-1,2-tetramethylene-4-pyrazolin-3-one was obtained with a yield of 29%. $^1$H-NMR (400 MHz, CDCl$_3$): δ1.86-1.94 (m, 2H), 1.98-2.06 (m, 2H), 2.56 (ttd, J=1.4, 6.8 and 6.8 Hz, 2H), 3.58-3.63 (m, 2H), 3.80-3.85 (m, 2H), 4.07 (t, J=6.8 Hz, 2H), 5.10 (qd, J=1.4 and 10.3 Hz, 1H), 5.16 (qd, J=1.4 and 17.2 Hz, 1H), 5.88 (ddt, J=6.8, 10.3 and 17.2 Hz, 1H), 6.91 (dd, J=9.4 and 10.8 Hz, 1H), 7.13 (dd, J=6.7 and 9.2 Hz, 1H). $^{19}$F-NMR (376 MHz, CDCl$_3$): δ−129.8 (d, J=4.1 Hz, 1F), −117.5 (d, J=4.1 Hz, 1F).

Example-38

In the same manner as in Example-12, 5-chloro-4-(2,4-difluoro-5-hydroxyphenyl)-1,2-tetramethylene-4-pyrazolin-3-one was reacted with 3-bromocyclohexene, whereby 5-chloro-4-[5-(2-cyclohexenyloxy)-2,4-difluorophenyl]-1,2-tetramethylene-4-pyrazolin-3-one was obtained with a yield of 88%. $^1$H-NMR (400 MHz, CDCl$_3$): δ1.56-2.18 (m, 10H), 3.57-3.63 (m, 2H), 3.80-3.86 (m, 2H), 4.72 (m, 1H), 5.86-6.00 (m, 2H), 6.91 (dd, J=9.3 and 10.7 Hz, 1H), 7.18 (dd, J=6.9 and 9.0 Hz, 1H). $^{19}$F-NMR (376 MHz, CDCl$_3$): δ−129.4 (d, J=4.1 Hz, 1F), −118.0 (d, J=4.1 Hz, 1F).

Example-39

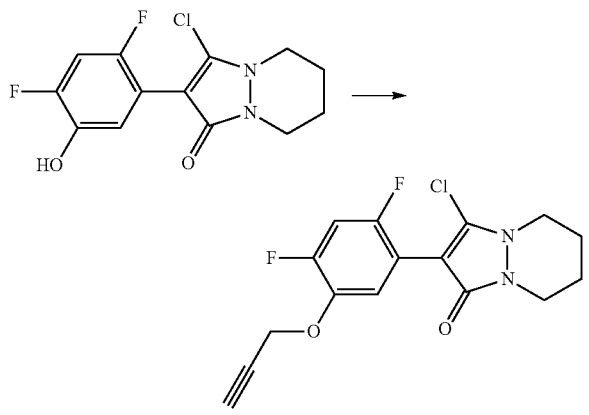

Propargyl bromide (79 μL, 1.00 mmol) was added to a solution of 5-chloro-4-(2,4-difluoro-5-hydroxyphenyl)-1,2-tetramethylene-4-pyrazolin-3-one (200 mg, 0.67 mmol) and cesium carbonate (0.326 g, 1.00 mmol) in DMF (3 mL), followed by stirring at 80° C. for 5 hours. After the reaction was completed, water (10 mL) was added to the reaction solution, and the resultant product was extracted with ethyl acetate (20 mL×2). The combined organic layer was dried over anhydrous magnesium sulfate, and concentrated under reduced pressure. The obtained crude product was purified by silica gel column chromatography (ethyl acetate), whereby 5-chloro-4-[2,4-difluoro-5-(propargyloxy)phenyl]-1,2-tetramethylene-4-pyrazolin-3-one (204 mg, yield: 91%) was obtained as a white solid. $^1$H-NMR (400 MHz, CDCl$_3$): δ1.86-1.95 (m, 2H), 1.98-2.06 (m, 2H), 2.55 (t, J=2.4 Hz, 1H), 3.58-3.65 (m, 2H), 3.80-3.86 (m, 2H), 4.75 (d, J=2.4 Hz, 2H), 6.94 (dd, J=9.4 and 10.8 Hz, 1H), 7.25 (dd, J=6.8 and 9.3 Hz, 1H). $^{19}$F-NMR (376 MHz, CDCl$_3$): δ−128.9 (d, J=4.2 Hz, 1F), −115.7 (d, J=4.2 Hz, 1F).

Example-40

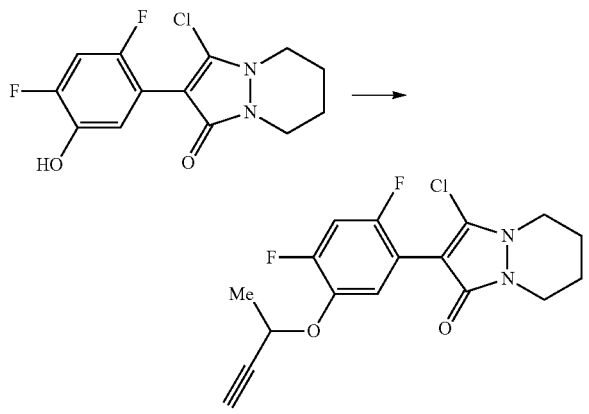

3-Chloro-1-butyne (94 μL, 1.00 mmol) was added to a solution of 5-chloro-4-(2,4-difluoro-5-hydroxyphenyl)-1,2-tetramethylene-4-pyrazolin-3-one (200 mg, 0.67 mmol) and cesium carbonate (0.326 g, 1.00 mmol) in DMF (3 mL), followed by stirring at 80° C. for 5 hours. After the reaction was completed, water (10 mL) was added to the reaction solution, and the resultant product was extracted with ethyl acetate (20 mL×2). The combined organic layer was dried over anhydrous magnesium sulfate, and concentrated under reduced pressure. The obtained crude product was purified by silica gel column chromatography (ethyl acetate), whereby 4-[5-(1-butyn-3-yloxy)-2,4-difluorophenyl]-5-chloro-1,2-tetramethylene-4-pyrazolin-3-one (121 mg, yield: 52%) was obtained as a white solid. $^1$H-NMR (400 MHz, CDCl$_3$): δ1.67 (d, J=6.6 Hz, 3H), 1.86-1.94 (m, 2H), 1.98-2.05 (m, 2H), 2.51 (d, J=2.0 Hz, 1H), 3.57-3.64 (m, 2H), 3.80-3.86 (m, 2H), 4.88 (dq, J=2.0 and 6.6 Hz, 1H), 6.92 (dd, J=9.4 and 10.8 Hz, 1H), 7.30 (dd, J=6.8 and 9.1 Hz, 1H). $^{19}$F-NMR (376 MHz, CDCl$_3$): δ−128.2 (d, J=4.2 Hz, 1F), −115.5 (d, J=4.2 Hz, 1F).

Example-41

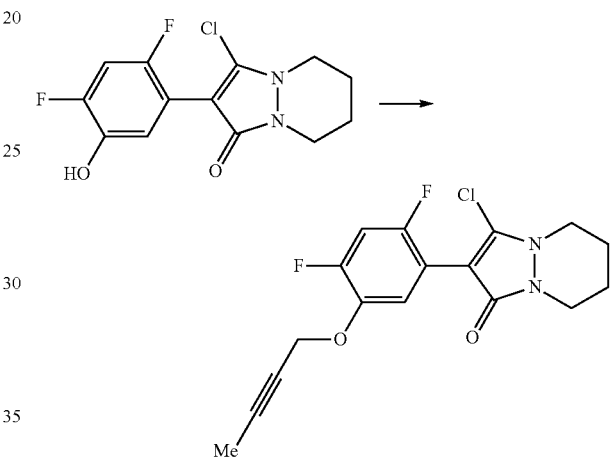

In the same manner as in Example-39, 5-chloro-4-(2,4-difluoro-5-hydroxyphenyl)-1,2-tetramethylene-4-pyrazolin-3-one was reacted with 1-bromo-2-butyne, whereby 4-[5-(2-butynyloxy)-2,4-difluorophenyl]-5-chloro-1,2-tetramethylene-4-pyrazolin-3-one was obtained with a yield of 74%. $^1$H-NMR (400 MHz, CDCl$_3$): δ1.86 (t, J=2.3 Hz, 3H), 1.88-1.94 (m, 2H), 1.98-2.06 (m, 2H), 3.59-3.63 (m, 2H), 3.81-3.86 (m, 2H), 4.70 (q, J=2.3 Hz, 2H), 6.92 (dd, J=9.3 and 10.8 Hz, 1H), 7.20 (dd, J=6.8 and 9.2 Hz, 1H). $^{19}$F-NMR (376 MHz, CDCl$_3$): δ−129.1 (d, J=4.1 Hz, 1F), −116.4 (d, J=4.1 Hz, 1F).

Example-42

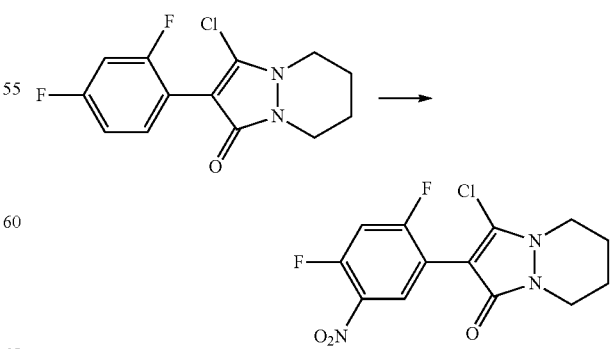

A mixed acid prepared from 69% nitric acid (0.34 g, 3.69 mmol) and concentrated sulfuric acid (1 mL) was slowly added to a suspension of 5-chloro-4-(2,4-difluorophenyl)-1,2-tetramethylene-4-pyrazolin-3-one (1.0 g, 3.51 mmol) in concentrated sulfuric acid (10 mL) over 30 minutes under ice-cooling, followed by stirring at the same temperature for 3 hours. After the reaction was completed, the reaction solution was poured into ice water (50 g), and the resultant product was extracted with ethyl acetate (50 mL×3). The organic layer was washed with a saturated saline solution (50 mL), dried over anhydrous magnesium sulfate, and concentrated under reduced pressure, whereby a crude product was obtained as a brown solid. This was purified by silica gel column chromatography (chloroform:methanol=50:1), whereby 5-chloro-4-(2,4-difluoro-5-nitrophenyl)-1,2-tetramethylene-4-pyrazolin-3-one (1.01 g, yield: 87%) was obtained as a yellow solid. $^1$H-NMR (400 MHz, CDCl$_3$): δ1.91-1.96 (m, 2H), 2.02-2.07 (m, 2H), 3.66-3.69 (m, 2H), 3.83-3.86 (m, 2H), 7.10 (dd, J=9.1 and 10.4 Hz, 1H), 8.34 (dd, J=7.2 and 8.3 Hz, 1H). $^{19}$F-NMR (376 MHz, CDCl$_3$): δ−112 (d, J=15.8 Hz, 1F), −95.6 (d, J=15.8 Hz, 1F).

Example-43

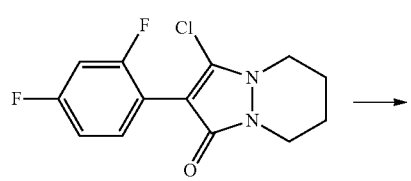

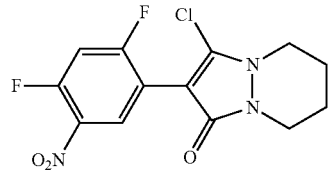

A mixed acid prepared from 69% nitric acid (92.4 g, 1.01 mol) and concentrated sulfuric acid (56.3 mL) was slowly added to a suspension of 5-chloro-4-(2,4-difluorophenyl)-1,2-tetramethylene-4-pyrazolin-3-one (240 g, 0.843 mol) in concentrated sulfuric acid (1.69 L) over 1 hour or longer under ice-cooling, followed by stirring at the same temperature for 4 hours. After the reaction was completed, the reaction solution was poured into ice water (7.5 kg), and the product was extracted with chloroform (0.6 L×6). The combined organic layer was washed with a 5% sodium hydroxide aqueous solution (0.5 L×3). The obtained organic layer was dried over anhydrous magnesium sulfate, and concentrated under reduced pressure, whereby 5-chloro-4-(2,4-difluoro-5-nitrophenyl)-1,2-tetramethylene-4-pyrazolin-3-one (202 g, yield: 73%) was obtained as a yellow solid.

Example-44

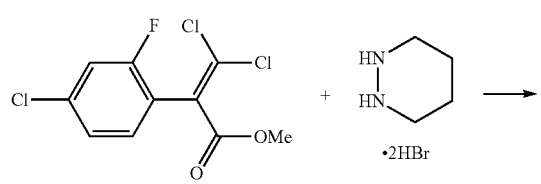

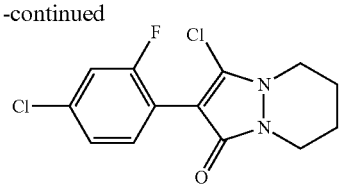

1,4-Dioxane (30 mL) and triethylamine (3.74 g, 37.0 mmol) were added to ethyl 3,3-dichloro-2-(4-chloro-2-fluorophenyl) acrylate (2.75 g, 9.24 mmol), and hexahydropyridazine dihydrobromide (2.19 g, 8.83 mmol) was added thereto, followed by refluxing for 17 hours. After the reaction was completed, water (50 mL) was added to the reaction solution, and the resultant product was extracted with ethyl acetate (30 mL×2, 20 mL×1). The organic layer was dried over anhydrous magnesium sulfate, and concentrated under reduced pressure, whereby an orange oily crude product (13.1 g) was obtained. This was purified by silica gel column chromatography (ethyl acetate), whereby 5-chloro-4-(4-chloro-2-fluorophenyl)-1,2-tetramethylene-4-pyrazolin-3-one (1.16 g, yield: 44%) was obtained as a white solid. $^1$H-NMR (400 MHz, CDCl$_3$): δ1.89-1.93 (m, 2H), 1.99-2.63 (m, 2H), 3.60-3.62 (m, 2H), 3.81-3.84 (m, 2H), 7.15-7.20 (m, 2H), 7.46 (m, 1H). $^{19}$F-NMR (376 MHz, CDCl$_3$): δ−107 (s, 1F).

Example-45

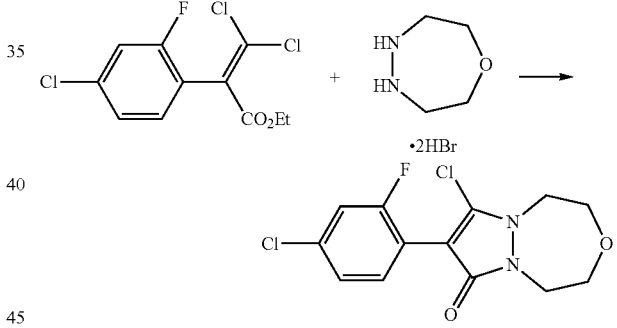

In the same manner as in Example-4, ethyl 3,3-dichloro-2-(4-chloro-2-fluorophenyl)acrylate was reacted with 1,4,5-oxadiazepane dihydrobromide, whereby 5-chloro-4-(4-chloro-2-fluorophenyl)-1,2-oxadiethylene-4-pyrazolin-3-one was obtained with a yield of 72%. $^1$H-NMR (400 MHz, CDCl$_3$): δ3.91-3.96 (m, 4H), 4.20-4.24 (m, 2H), 4.25-4.29 (m, 2H), 7.13-7.22 (m, 2H), 7.46 (t, J=8.0 Hz, 1H). $^{19}$F-NMR (376 MHz, CDCl$_3$): δ−109.1 (s, 1F).

Reference Example-23

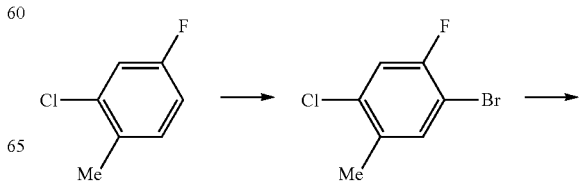

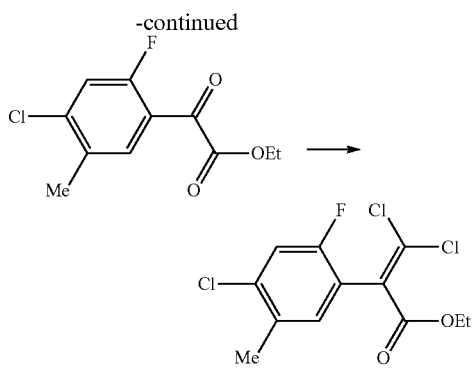

After 2-chloro-4-fluorotoluene (10.0 g, 69.2 mmol) was heated and stirred at 60° C., reduced iron (265 mg, 4.75 mmol) was added thereto, and bromine (11.1 g, 69.2 mmol) was added little by little thereto over 4 hours, followed by stirring at the same temperature for 1 hour. After the reaction was completed, the temperature was returned to room temperature, then, the reaction solution was added little by little to a 2N sodium hydroxide aqueous solution under ice-cooling, and the resultant product was extracted with hexane (50 mL×2, 30 mL×1). The organic layer was washed with water, washed with a saturated saline solution, dried over anhydrous magnesium sulfate, and concentrated under reduced pressure, whereby an orange oily crude product (13.8 g) was obtained. This was purified by silica gel column chromatography (hexane), whereby 5-bromo-2-chloro-4-fluorotoluene (10.8 g, yield: 70%) was obtained as a colorless oily material. $^1$H-NMR (400 MHz, CDCl$_3$): δ2.32 (s, 3H), 4.43 (d, J=8.2 Hz, 1H), 7.41 (dd, J=0.6 and 7.3 Hz, 1H). $^{19}$F-NMR (376 MHz, CDCl$_3$): δ−110 (s, 1F).

A solution of 5-bromo-2-chloro-4-fluorotoluene (10 g, 44.7 mmol) in THF was added dropwise to a suspension of magnesium (1.20 g, 49.2 mmol) in THF in the presence of a catalytic amount of iodine in an argon gas atmosphere, whereby a Grignard reagent was prepared. The Grignard reagent was added dropwise to a solution of diethyl oxalate (7.84 g, 53.6 mmol) in THF at −60° C., and the temperature was slowly raised to room temperature, followed by stirring for 19 hours. After the reaction was completed, the reaction solution was added little by little to saturated ammonium chloride aqueous solution under ice-cooling, and the resultant product was extracted with ether (150 mL×1, 100 mL×2). The organic layer was dried over anhydrous magnesium sulfate, and concentrated under reduced pressure, whereby an orange oily crude product (12.2 g) was obtained. This was purified by silica gel column chromatography (hexane:ethyl acetate=15:1), whereby ethyl 2-(4-chloro-2-fluoro-5-methylphenyl)-2-oxoacetate (5.52 g, yield: 50%) was obtained as a yellow oily material. $^1$H-NMR (400 MHz, CDCl$_3$): δ1.40 (t, J=7.2 Hz, 3H), 2.40 (s, 3H), 4.42 (q, J=7.2 Hz, 2H), 7.21 (d, J=10.1 Hz, 1H), 7.22 (dd, J=0.5 and 7.4 Hz, 1H). $^{19}$F-NMR (376 MHz, CDCl$_3$): δ−114 (s, 1F).

Carbon tetrachloride (6.27 g, 40.8 mmol) and ethyl 2-(4-chloro-2-fluoro-5-methylphenyl)-2-oxoacetate (5.0 g, 20.4 mmol) were added to a solution of triphenylphosphine (16.1 g, 61.2 mmol) in dichloromethane (40 mL) under ice-cooling, followed by stirring at room temperature for 17 hours. After the reaction was completed, water (150 mL) was added to the reaction solution, and the resultant product was extracted with chloroform (100 mL×1, 50 mL×2). The organic layer was dried over anhydrous magnesium sulfate, and concentrated under reduced pressure, whereby a crude product (28.8 g) was obtained as an orange solid. This was purified by silica gel column chromatography (hexane:ethyl acetate=20:1), whereby ethyl 3,3-dichloro-2-(4-chloro-2-fluoro-5-methylphenyl)acrylate (5.65 g, yield: 89%) was obtained as a yellow oily material. $^1$H-NMR (400 MHz, CDCl$_3$): δ1.26 (t, J=7.1 Hz, 3H), 2.35 (s, 3H), 4.25 (q, J=7.1 Hz, 2H), 7.15 (d, J=9.1 Hz, 1H), 7.18 (d, J=7.6 Hz, 1H). $^{19}$F-NMR (376 MHz, CDCl$_3$): δ−115 (s, 1F).

Example-46

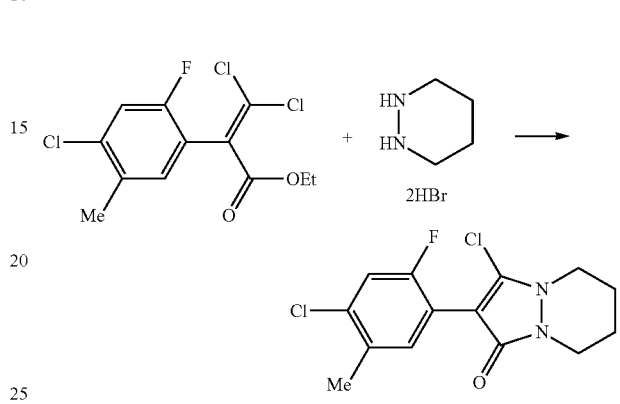

1,4-Dioxane (70 mL) and triethylamine (6.01 g, 59.4 mmol) were added to ethyl 3,3-dichloro-2-(4-chloro-2-fluoro-5-methylphenyl)acrylate (5.0 g, 16.1 mmol), and hexahydropyridazine dihydrobromide (4.32 g, 17.4 mmol) was added thereto, followed by refluxing for 17 hours. After the reaction was completed, the temperature was returned to room temperature, then, water (150 mL) was added to the reaction solution, and the resultant product was extracted with ethyl acetate (70 mL×2, 50 mL×1). The organic layer was washed with a saturated saline solution, dried over anhydrous magnesium sulfate, and concentrated under reduced pressure, whereby a dark brown oily crude product (5.34 g) was obtained. This was purified by silica gel column chromatography (ethyl acetate:methanol=10:1), whereby 5-chloro-4-(4-chloro-2-fluoro-5-methylphenyl)-1,2-tetramethylene-4-pyrazolin-3-one (3.39 g, yield: 67%) was obtained as a white yellow solid. $^1$H-NMR (400 MHz, CDCl$_3$): δ1.87-1.92 (m, 2H), 1.99-2.04 (m, 2H), 2.34 (s, 3H), 3.58-3.61 (m, 2H), 3.81-3.84 (m, 2H), 7.18 (d, J=9.5 Hz, 1H), 7.38 (d, J=7.6 Hz, 1H). $^{19}$F-NMR (376 MHz, CDCl$_3$): δ−114 (s, 1F).

Reference Example-24

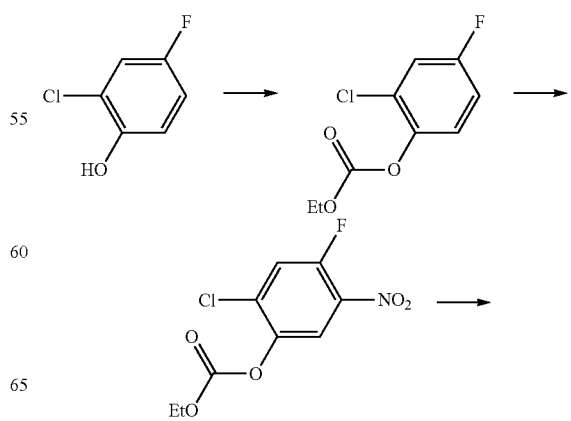

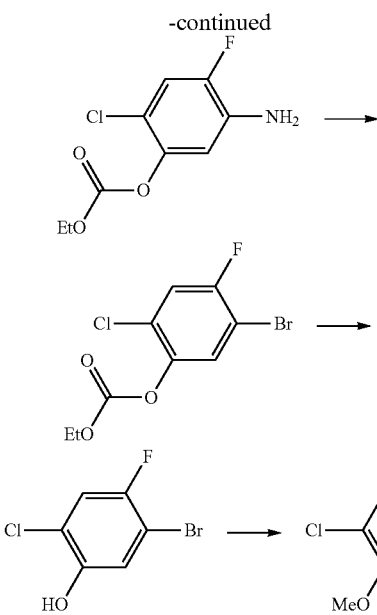

2-Chloro-4-fluorophenol (2.88 kg, 19.7 mol) was measured and put into a three-neck flask (20 L) provided with a stirrer, and a 2.5N sodium hydroxide aqueous solution (8 L) was slowly added thereto over 30 minutes while stirring at room temperature. Ethyl chloroformate (2.11 kg, 19.4 mol) was added dropwise to the solution at room temperature, followed by further stirring for 2 hours. After the reaction was completed, the organic layer was separated, and the aqueous layer was extracted with dichloromethane (3.0 L×2). The organic layers were combined, and the resultant product was washed with water (2.0 L), and dried over anhydrous magnesium sulfate. After the desiccant was separated by filtration, the solvent was distilled off from the filtrate under reduced pressure, whereby (2-chloro-4-fluorophenyl)ethyl carbonate (3.98 kg, yield: 93.9%) was obtained as a oily material. $^1$H-NMR (400 MHz, CDCl$_3$): δ1.40 (t, J=7.1 Hz, 3H), 4.35 (q, J=7.1 Hz, 2H), 7.00 (ddd, J=3.0, 7.7 and 9.1 Hz, 1H), 7.18-7.22 (m, 2H). $^{19}$F-NMR (376 MHz, CDCl$_3$): δ−113.9 (s, 1F).

Synthesis 1 of
(2-chloro-4-fluoro-5-nitrophenyl)ethyl carbonate (2-Chloro-4-fluorophenyl)ethyl carbonate (656 g, 3.0 mol) was put into a three-neck flask (2 L) provided with a dropping funnel and a stirrer, and concentrated sulfuric acid (300 mL) was added thereto under ice-cooling, followed by sufficiently stirring to suspend. Next, a mixed acid prepared from nitric acid (240 mL, 60% to 70%) and concentrated sulfuric acid (240 mL, 98%) was slowly added thereto with the dropping funnel over 2 hours to the extent that the reaction temperature does not rise (20° C. to 30° C.) while stirring vigorously. After the dropping was completed, the resultant product was further stirred vigorously for 2 hours, and after ice water (5.0 L) was added thereto, the precipitated white solid was filtered, washed with water, and sufficiently dried, whereby (2-chloro-4-fluoro-5-nitrophenyl)ethyl carbonate (791 g, 3.0 mol, yield: quantitative) was obtained as a white solid.

Synthesis 2 of
(2-chloro-4-fluoro-5-nitrophenyl)ethyl carbonate

90% fuming nitric acid (4.2 mL) was slowly added to a solution of (2-chloro-4-fluorophenyl)ethyl carbonate (18.6 g, 85 mmol) in concentrated sulfuric acid (21 mL) such that the temperature does not exceed 30° C. The mixed solution was stirred at room temperature for 2 hours, and poured into ice, and the resultant product was extracted with toluene. The organic layer was washed with water, and dried over anhydrous magnesium sulfate, and the solvent was distilled off under reduced pressure, whereby a crude product was obtained. This was purified by silica gel column chromatography (hexane:ethyl acetate=10:1), whereby (2-chloro-4-fluoro-5-nitrophenyl)ethyl carbonate (16.7 g, 63.8 mmol, yield: 75%) was obtained as a pale yellow solid. $^1$H-NMR (400 MHz, CDCl$_3$): δ8.05 (d, J=6.7 Hz, 1H), 7.45 (d, J=10.0 Hz, 1H), 4.39 (q, J=7.1 Hz, 2H), 1.43 (t, J=7.1 Hz, 3H); $^{19}$F-NMR (377 MHz, CDCl$_3$): δ−117.2 (s, 1F).

Synthesis 1 of
(5-amino-2-chloro-4-fluorophenyl)ethyl carbonate (2-Chloro-4-fluoro-5-nitrophenyl)ethyl carbonate (395.4 g, 1.5 mol), 5% palladium carbon (15 g), and toluene (1000 mL) were put into a three-neck separable flask (3000 cc) provided with a stirrer, and hydrogen gas was introduced thereinto while stirring vigorously. Although heat was generated with the progress of the reaction, the reaction temperature was maintained at 50° C. to 60° C. by introducing hydrogen at a rate that the hydrogen is not discharged from the system. After the reaction was completed, water (100 mL to 200 mL) was added thereto, the catalyst was separated by filtering the reaction mixture. The organic layer of the filtrate was separated, and dried over anhydrous magnesium sulfate. After the desiccant was separated by filtration, the solvent was distilled off under reduced pressure, whereby (5-amino-2-chloro-4-fluorophenyl)ethyl carbonate was obtained almost quantitatively as a pale yellow oily material.

Synthesis 2 of
(5-amino-2-chloro-4-fluorophenyl)ethyl carbonate

5% palladium/carbon (2.7 g) was added to a solution of (2-chloro-4-fluoro-5-nitrophenyl)ethyl carbonate (16.7 g, 63.4 mmol) in toluene (250 mL), followed by stirring at 70° C. for 24 hours in a hydrogen atmosphere. After the reaction was completed, the catalyst was removed by filtration using Celite, and the solvent was distilled off from the filtrate under reduced pressure, whereby (5-amino-2-chloro-4-fluorophenyl)ethyl carbonate (14.8 g, 63.4 mmol, quantitative) was obtained as a brown solid. $^1$H-NMR (400 MHz, CDCl$_3$): δ7.07 (d, J=10.3 Hz, 1H), 6.64 (d, J=8.2 Hz, 1H), 4.33 (q, J=7.1 Hz, 2H), 3.73 (brs, 2H), 1.39 (t, J=7.1 Hz, 3H); $^{19}$F-NMR (377 MHz, CDCl$_3$): δ−135.5 (s, 1F).

A solution of (5-amino-2-chloro-4-fluorophenyl)ethyl carbonate (1.0 g, 4.3 mmol) in acetic acid (4.3 mL) was cooled by ice, and a solution of sodium nitrite (0.44 g, 6.4 mmol) in concentrated sulfuric acid (3.3 mL) was slowly added thereto over 30 minutes to the extent that the reaction temperature does not rise (10° C.), followed by stirring at the same temperature for 30 minutes. Copper (I) bromide (0.97 g, 6.4 mmol) and a 25% hydrobromic acid-acetic acid solution (2.8 mL) were added to the mixed solution, followed by stirring at 50° C. for 1 hour. After the reaction was completed, the resultant product was cooled in an ice bath, and neutralized by adding a 10% sodium hydroxide aqueous solution. The solution was extracted with ethyl acetate (50 mL×3), and the organic layer was washed with a saturated saline solution, and dried over anhydrous magnesium sulfate. The crude product obtained by distilling off the solvent was purified by silica gel column chromatography (hexane:

ethyl acetate=9:1), whereby (5-bromo-2-chloro-4-fluorophenyl)ethyl carbonate (0.84 g, 2.8 mmol, yield: 66%) was obtained as a white solid. $^1$H-NMR (400 MHz, CDCl$_3$): δ7.47 (d, J=6.3 Hz, 1H), 7.26 (d, J=7.7 Hz, 1H), 4.35 (q, J=7.1 Hz, 2H), 1.41 (t, J=7.1 Hz, 3H); $^{19}$F-NMR (377 MHz, CDCl$_3$): δ−107.6 (s, 1F).

A 23% sodium hydroxide aqueous solution (2.1 mL) was added dropwise to a solution of (5-bromo-2-chloro-4-fluorophenyl)ethyl carbonate (3.0 g, 10 mmol) in ethanol (5 mL). The mixture was stirred at room temperature for 2 hours. After the reaction was completed, the resultant product was neutralized with concentrated hydrochloric acid, and extracted with ether (20 mL×3). The organic layer was washed with a saturated saline solution, and dried over anhydrous magnesium sulfate, and the solvent was distilled off under reduced pressure, whereby 5-bromo-2-chloro-4-fluorophenol (1.9 g, yield: 82%) was obtained as a brown solid. $^1$H-NMR (400 MHz, CDCl$_3$): δ5.39 (s, 1H), 7.14 (d, J=7.7 Hz, 1H), 7.23 (d, J=6.3 Hz, 1H). $^{19}$F-NMR (376 MHz, CDCl$_3$): δ−116.0 (s, 1F).

A solution of 5-bromo-2-chloro-4-fluorophenol (1.0 g, 4.4 mmol) in DMF (5 mL) and methyl iodide (0.55 mL, 8.8 mmol) were added to potassium carbonate (1.2 g, 8.9 mmol), followed by stirring at room temperature for 20 hours. After the reaction was completed, water (20 mL) was added to the reaction mixture, and the resultant product was extracted with ether (20 mL×3). The organic layer was washed with a saturated saline solution (20 mL), and dried over anhydrous magnesium sulfate, and the solvent was distilled off under reduced pressure, whereby 5-bromo-2-chloro-4-fluoroanisole (0.951 g, yield: 90%) was obtained as a white solid. $^1$H-NMR (400 MHz, CDCl$_3$): δ3.88 (s, 3H), 7.07 (d, J=5.8 Hz, 1H), 7.19 (d, J=8.0 Hz, 1H). $^{19}$F-NMR (376 MHz, CDCl$_3$): δ−116.1 (s, 1F).

Reference Example-25

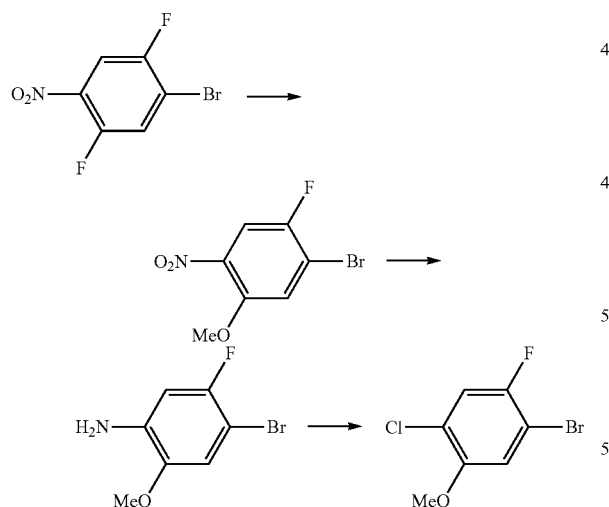

A suspension of a 55% oil dispersion (12.3 g, 282 mmol) of sodium hydride in THF (470 mL) was cooled in an ice bath, then, 4-bromo-2,5-difluoronitrobenzene (56 g, 236 mmol) was added thereto, and methanol (24 mL, 588 mmol) was slowly added thereto. The mixed solution was stirred at room temperature for 30 minutes, and poured into ice water (500 g), and the resultant product was extracted with chloroform (100 mL×3). The organic layer was dried over anhydrous magnesium sulfate, and the solvent was distilled off under reduced pressure, whereby 5-bromo-4-fluoro-2-nitroanisole (59 g, yield: quantitative) was obtained as a brown solid. $^1$H-NMR (400 MHz, CDCl$_3$): δ3.97 (s, 3H), 7.30 (d, J=5.5 Hz, 1H), 7.71 (dd, J=1.8 and 7.7 Hz, 1H). $^{19}$F-NMR (376 MHz, CDCl$_3$): δ−114.8 (s, 1F).

Ethyl acetate (470 mL), acetic acid (230 mL), and water (42.4 g) were added to 5-bromo-4-fluoro-2-nitroanisole (59 g, 235 mmol), then, the resultant product was cooled in an ice bath, and reduced iron (67.8 g, 1.21 mmol) was added thereto. The mixed liquid was stirred at 80° C. for 1 hour and cooled to room temperature, and filtration was performed using Celite, whereby the insoluble iron acetate was removed. The filtrate was diluted with ethyl acetate (200 mL), and the resultant product was washed sequentially with water (300 mL), a saturated sodium hydrogencarbonate aqueous solution (300 mL), and a saturated saline solution (300 mL). The resultant product was dried over anhydrous magnesium sulfate, and the solvent was distilled off under reduced pressure, whereby 4-bromo-5-fluoro-2-methoxyaniline (46 g, 209 mmol, yield: 89%) was obtained. $^1$H-NMR (400 MHz, CDCl$_3$): δ3.82 (s, 3H), 3.90 (brs, 2H), 6.50 (d, J=9.5 Hz, 1H), 6.84 (d, J=6.2 Hz, 1H). $^{19}$F-NMR (376 MHz, CDCl$_3$): δ−117.8 (s, 1F).

A solution of isoamyl nitrite (17.6 mL, 126 mmol) in acetonitrile (60 mL) was added dropwise to a solution of 4-bromo-5-fluoro-2-methoxyaniline (9.2 g, 41.8 mmol), copper(I) chloride (8.28 g, 83.6 mmol), and copper(II) chloride (16.86 g, 125 mmol) in acetonitrile (200 mL) at room temperature. The mixed solution was stirred at room temperature for 4 hours, and poured into 2N hydrochloric acid (100 mL), and the resultant product was extracted with ethyl acetate (50 mL×3). The organic layer was washed with a saturated saline solution and dried over anhydrous magnesium sulfate, and the solvent was distilled off under reduced pressure, whereby a crude product was obtained as a brown solid. This was purified by silica gel column (hexane), whereby 5-bromo-2-chloro-4-fluoroanisole (6.6 g, yield: 66%) was obtained as a white solid. $^1$H-NMR (400 MHz, CDCl$_3$): δ3.88 (s, 3H), 7.07 (d, J=5.8 Hz, 1H), 7.19 (d, J=8.0 Hz, 1H). $^{19}$F-NMR (376 MHz, CDCl$_3$): δ−116.1 (s, 1F).

Reference Example-26

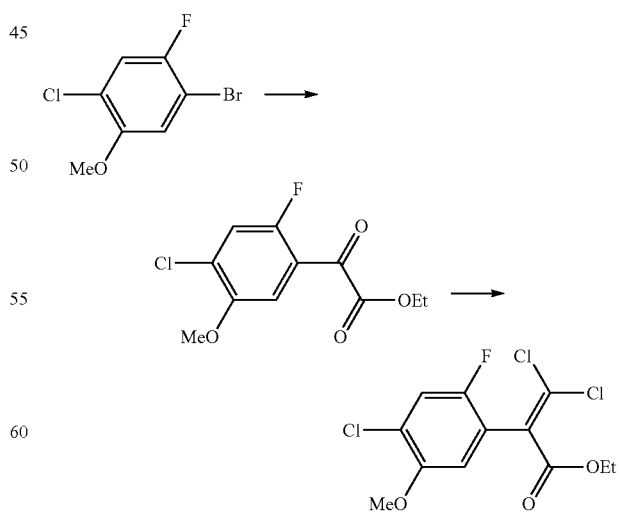

After THF (25 mL) was added to magnesium (2.55 g, 105 mmol) at room temperature, iodine (10 mg) was added thereto, then, a solution of 5-bromo-2-chloro-4-fluoroanisole (23.9 g, 100 mmol) in THF (50 mL) was slowly added thereto, and the resultant product was stirred for 1 hour, whereby a Grignard reagent was prepared. The Grignard reagent was added dropwise to a solution of diethyl oxalate (14.5 mL, 105 mmol) in THF (14.5 mL) at −40° C. or lower. After the dropping was completed, the temperature of the reaction solution was raised to 0° C., followed by stirring 1 hour. After the reaction was completed, a saturated ammonium chloride aqueous solution (100 mL) was added to the reaction solution, and the resultant product was diluted with water (100 mL) and extracted with ethyl acetate (200 L×2). After the organic layer was dried over anhydrous magnesium sulfate, the solvent was distilled off under reduced pressure. The crude product was distilled under reduced pressure (125° C. to 130° C./4 mmHg), whereby ethyl 2-(4-chloro-2-fluoro-5-methoxyphenyl)-2-oxoacetate (17.8 g, yield: 68%) was obtained as a pale yellow oily material. $^1$H-NMR (400 MHz, CDCl$_3$): δ1.40 (t, J=7.2 Hz, 3H). 3.95 (s, 3H), 4.43 (q, J=7.2 Hz, 2H), 7.25 (d, J=9.9 Hz, 1H), 7.42 (d, J=5.9 Hz, 1H). $^{19}$F-NMR (376 MHz, CDCl$_3$): δ−119.7 (s, 1F).

Carbon tetrachloride (5.1 g, 32.8 mmol) was added to a solution of triphenylphosphine (8.6 g, 32.8 mmol) in dichloromethane (60 mL) under ice-cooling, followed by stirring for 15 minutes. Thereafter, ethyl 2-(4-chloro-2-fluoro-5-methoxyphenyl)-2-oxoacetate (4.27 g, 16.4 mmol) was added thereto, followed by stirring at room temperature for 24 hours. After the reaction was completed, the solvent was removed from the reaction solution under reduced pressure, and after a mixed solvent of chloroform (15 mL) and ether (90 mL) was added to the precipitated solid, the insoluble matters were separated by filtration, and washed with a mixed solvent of chloroform (5 mL) and ether (30 mL). The filtrate and the reaction solution were combined, and the crude product obtained by concentrating under reduced pressure was purified by silica gel column chromatography (hexane:ethyl acetate=10:1), whereby ethyl 3,3-dichloro-2-(4-chloro-2-fluoro-5-methoxyphenyl)acrylate (4.4 g, yield: 82%) was obtained as a colorless oily material. $^1$H-NMR (400 MHz, CDCl$_3$): δ1.27 (t, J=7.2 Hz, 3H), 3.89 (s, 3H), 4.26 (q, J=7.2 Hz, 2H), 6.85 (d, J=6.2 Hz, 1H), 7.18 (d, J=8.7 Hz, 1H). $^{19}$F-NMR (376 MHz, CDCl$_3$): δ−121.6 (s, 1F).

Example-47

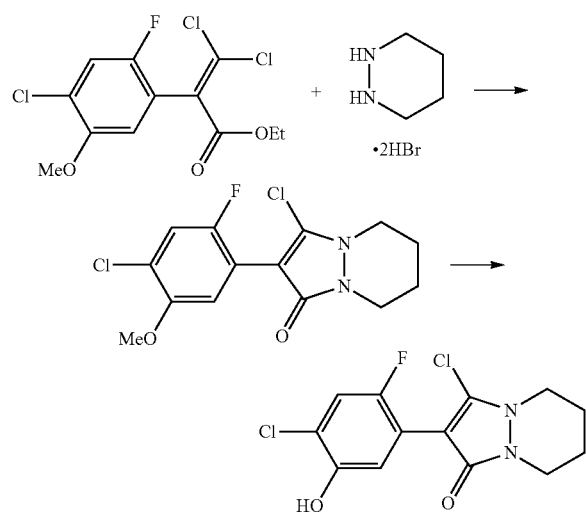

1,4-Dioxane (20 mL) and triethylamine (2.64 g, 26.1 mmol) were added to ethyl 3,3-dichloro-2-(4-chloro-2-fluoro-5-methoxyphenyl)acrylate (2.14 g, 6.53 mmol), and hexahydropyridazine dihydrobromide (1.92 g, 7.74 mmol) was added thereto, followed by refluxing for 17 hours. After the reaction was completed, water (30 mL) was added to the reaction solution, and the resultant product was extracted with ethyl acetate (30 mL×1, 20 mL×2). The organic layer was washed with a saturated saline solution (20 mL), dried over anhydrous magnesium sulfate, and concentrated under reduced pressure, whereby a crude product (2.76 g) was obtained as a brown solid. This was purified by silica gel column chromatography (ethyl acetate:methanol=10:1), whereby 5-chloro-4-(2-fluoro-4-chloro-5-methoxyphenyl)-1,2-tetramethylene-4-pyrazolin-3-one (1.79 g, yield: 83%) was obtained as a white brown solid. $^1$H-NMR (400 MHz, CDCl$_3$): δ1.92-1.94 (m, 2H), 2.00-2.05 (m, 2H), 3.61 (m, 2H), 3.82-3.85 (m, 2H), 3.89 (s, 3H), 7.09 (d, J=6.2 Hz, 1H), 7.33 (d, J=9.9 Hz, 1H). $^{19}$F-NMR (376 MHz, CDCl$_3$): δ−120 (s, 1F).

A solution (3.0 mL) of 1M boron tribromide in dichloromethane was added to a solution of 5-chloro-4-(4-chloro-2-fluoro-5-methoxyphenyl)-1,2-tetramethylene-4-pyrazolin-3-one (500 mg, 1.5 mmol) in dichloromethane (10 mL) at −40° C. The resultant product was stirred for 10 hours while slowly raising the reaction temperature to room temperature. After the reaction solution was added to ice water, a 1N HCl aqueous solution (50 mL) was added thereto. The precipitated solid was filtered, whereby 5-chloro-4-(4-chloro-2-fluoro-5-hydroxyphenyl)-1,2-tetramethylene-4-pyrazolin-3-one (456 mg, yield: 95%) was obtained as a white solid. $^1$H-NMR (400 MHz, CDCl$_3$): δ1.88-1.96 (m, 2H), 1.99-2.07 (m, 2H), 3.61-3.67 (m, 2H), 3.77-3.84 (m, 2H), 7.09 (d, J=9.3 Hz, 1H), 7.10 (d, J=6.6 Hz, 1H), 9.61 (brs, 1H). $^{19}$F-NMR (376 MHz, CDCl$_3$): δ−117.4 (s, 1F).

Example-48

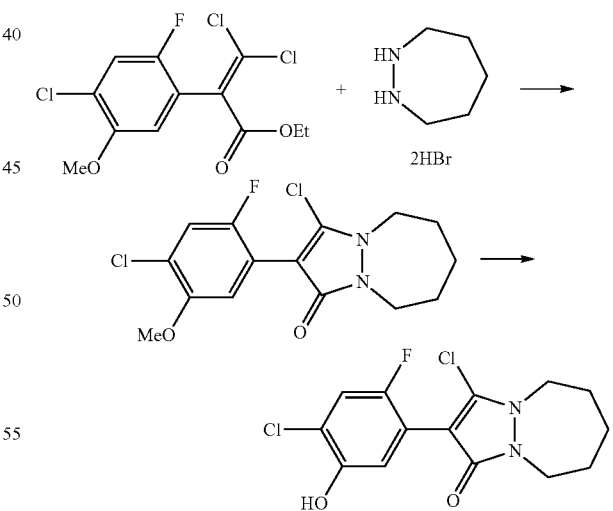

1,2-Diazepane dihydrobromide (650 mg, 2.48 mmol) and triethylamine (890 μL, 6.38 mmol) were added to a solution of ethyl 3,3-dichloro-2-(4-chloro-2-fluoro-5-methoxyphenyl)acrylate (700 mg, 2.14 mmol) in 1,4-dioxane (15 mL) at room temperature, followed by stirring for 24 hours while heating to reflux. After the reaction was completed, the resultant product was concentrated under reduced pressure, then, distilled water (40 mL) was added thereto, and the resultant product was extracted with ethyl acetate (60 mL×2), dried over anhydrous magnesium sulfate, and concentrated under reduced pressure. The residue was purified by silica gel column chromatography (ethyl acetate:methanol=10:1), whereby 5-chloro-4-(4-chloro-2-fluoro-5-methoxyphenyl)-1,2-pentamethylene-4-pyrazolin-3-one (550 mg, yield: 75%) was obtained as a white solid. $^1$H-NMR (400 MHz, CDCl$_3$): δ1.84 (brs, 6H), 3.90 (s, 3H), 4.10-4.13 (m, 4H), 7.14 (d, J=6.3 Hz, 1H), 7.17 (d, J=9.2 Hz, 1H). $^{19}$F-NMR (376 MHz, CDCl$_3$): δ−120.6 (s, 1F).

A solution (2.6 mL) of 1M boron tribromide in dichloromethane was added to a solution of 5-chloro-4-(4-chloro-2-fluoro-5-methoxyphenyl)-1,2-pentamethylene-4-pyrazolin-3-one (450 mg, 1.3 mmol) in dichloromethane (10 mL) at −40° C. The resultant product was stirred for 10 hours while slowly raising the reaction temperature to room temperature. After the reaction solution was added to ice water, a 1N HCl aqueous solution (50 mL) was added thereto. The precipitated solid was filtered, whereby 5-chloro-4-(4-chloro-2-fluoro-5-hydroxyphenyl)-1,2-pentamethylene-4-pyrazolin-3-one (430 mg, yield: 99%) was obtained as a white solid. $^1$H-NMR (400 MHz, d$_6$-DMSO): δ1.68-1.71 (m, 6H), 4.00-4.06 (m, 2H), 4.12-4.19 (m, 2H), 7.04 (d, J=6.8 Hz, 1H), 7.34 (d, J=9.5 Hz, 1H). $^{19}$F-NMR (376 MHz, d$_6$-DMSO): δ−122.1 (s, 1F).

Example-49

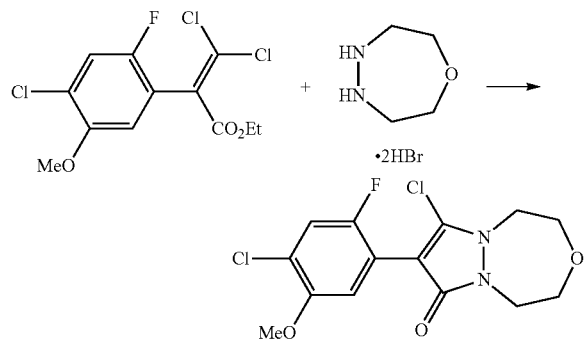

In the same manner as in Example-4, ethyl 3,3-dichloro-2-(4-chloro-2-fluoro-5-methoxyphenyl]acrylate was reacted with 1,4,5-oxadiazepane dihydrobromide, whereby 5-chloro-4-[4-chloro-2-fluoro-5-methoxyphenyl]-1,2-oxadiethylene-4-pyrazolin-3-one was obtained with a yield of 58%. $^1$H-NMR (400 MHz, CDCl$_3$): δ3.90 (s, 3H), 3.92-3.96 (m, 4H), 4.21-4.25 (m, 2H), 4.26-4.30 (m, 2H), 7.11 (d, J=6.2 Hz, 1H), 7.18 (d, J=9.1 Hz, 1H). $^{19}$F-NMR (376 MHz, CDCl$_3$): δ−120.0 (s, 1F).

Example-50

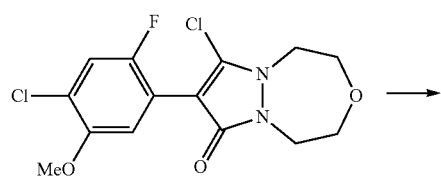

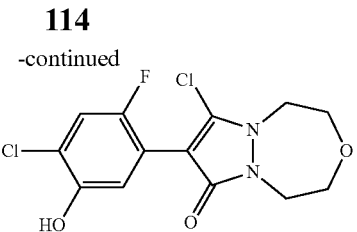

In the same manner as in Example-29, from 5-chloro-4-[4-chloro-2-fluoro-5-methoxyphenyl]-1,2-oxadiethylene-4-pyrazolin-3-on, 5-chloro-4-[4-chloro-2-fluoro-5-hydroxyphenyl]-1,2-oxadiethylene-4-pyrazolin-3-one was obtained with a yield of 67%. $^1$H-NMR (400 MHz, DMSO-d$_6$): δ3.79-3.87 (m, 4H), 4.13-4.18 (m, 2H), 4.26-4.30 (m, 2H), 7.04 (d, J=6.5 Hz, 1H), 7.36 (d, J=9.5 Hz, 1H), 10.2 (s, 1H). $^{19}$F-NMR (376 MHz, DMSO-d$_6$): δ−122.0 (s, 1F).

Example-51

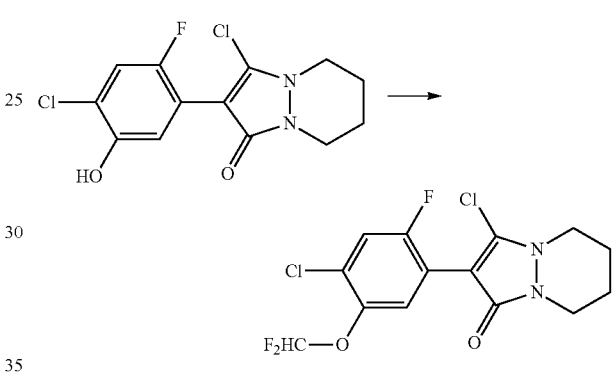

Ethyl bromodifluoroacetate (122 μL, 0.947 mmol) was added to a solution of 5-chloro-4-(4-chloro-2-fluoro-5-hydroxyphenyl)-1,2-tetramethylene-4-pyrazolin-3-one (200 mg, 0.63 mmol) and potassium carbonate (0.126 g, 1.24 mmol) in DMF (3 mL), followed by stirring at 50° C. for 24 hours. After the reaction was completed, water (10 mL) was added to the reaction solution, and the resultant product was extracted with ethyl acetate (15 mL×3). The combined organic layer was dried over anhydrous magnesium sulfate, and concentrated under reduced pressure. The obtained crude product was purified by silica gel column chromatography (ethyl acetate), whereby 5-chloro-4-[4-chloro-5-(difluoromethoxy)-2-fluorophenyl]-1,2-tetramethylene-4-pyrazolin-3-one (55 mg, yield: 23%) was obtained as a white solid. $^1$H-NMR (400 MHz, CDCl$_3$): δ1.87-1.95 (m, 2H), 1.99-2.06 (m, 2H), 3.61-3.67 (m, 2H), 3.80-3.86 (m, 2H), 6.52 (t, J=73.5 Hz, 1H), 7.26 (d, J=9.0 Hz, 1H), 7.44 (d, J=6.5 Hz, 1H). $^{19}$F-NMR (376 MHz, CDCl$_3$): δ−112.0 (s, 1F), −81.4 (s, 2F).

Example-52

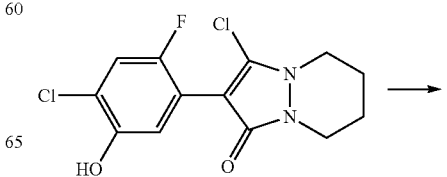

-continued

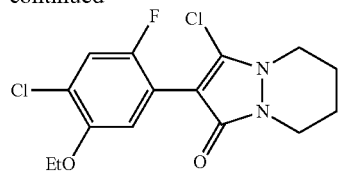

Cesium carbonate (619 mg, 1.90 mmol) and ethyl iodide (296 mg, 1.90 mmol) were added to a solution of 5-chloro-4-(4-chloro-2-fluoro-5-hydroxyphenyl)-1,2-tetramethylene-4-pyrazolin-3-one (300 mg, 0.95 mmol) in DMF (3 mL), followed by stirring at room temperature for 22 hours. After the reaction was completed, water (20 mL) was added thereto, and the resultant product was extracted with ethyl acetate (20 mL×3). The organic layer was washed with a saturated saline solution (20 mL), dried over anhydrous magnesium sulfate, and was concentrated under reduced pressure, whereby a pale yellow oily crude product (392 mg) was obtained. This was purified by silica gel column chromatography (ethyl acetate:methanol=10:1), and recrystallized from a mixed solvent of ether and hexane, whereby 5-chloro-4-(4-chloro-5-ethoxy-2-fluorophenyl)-1,2-tetramethylene-4-pyrazolin-3-one (116 mg, yield: 35%) was obtained as a white solid. $^1$H-NMR (400 MHz, CDCl$_3$): δ1.44 (t, J=7.0 Hz, 3H), 1.87-1.93 (m, 2H), 1.99-2.05 (m, 2H), 3.61-3.63 (m, 2H), 3.82-3.85 (m, 2H), 4.11 (q, J=7.0 Hz, 1H), 7.10 (d, J=6.3 Hz, 1H), 7.18 (d, J=9.2 Hz, 1H). $^{19}$F-NMR (376 MHz, CDCl$_3$): δ−120 (s, 1F).

Example-53

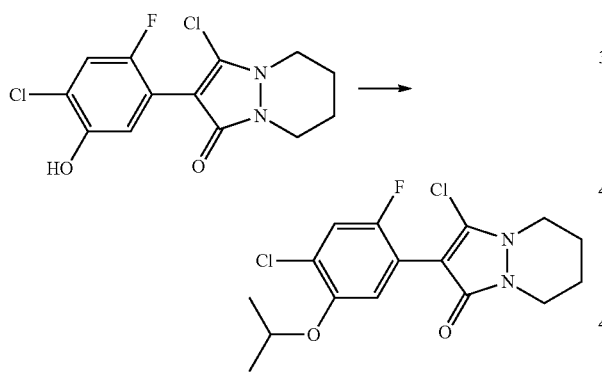

Cesium carbonate (154 mg, 0.47 mmol) and 2-iodopropane (80 mg, 0.47 mmol) were added to a solution of 5-chloro-4-(4-chloro-2-fluoro-5-hydroxyphenyl)-1,2-tetramethylene-4-pyrazolin-3-one (100 mg, 0.32 mmol) in DMF (1.5 mL), followed by stirring at room temperature for 22 hours. After the reaction was completed, water (20 mL) was added thereto, and the resultant product was extracted with ethyl acetate (20 mL×3). The organic layer was washed with a saturated saline solution (20 mL), dried over anhydrous magnesium sulfate, and was concentrated under reduced pressure, whereby a pale yellow oily crude product was obtained. This was purified by silica gel column chromatography (ethyl acetate:methanol=10:1), whereby 5-chloro-4-[4-chloro-2-fluoro-5-(isopropyloxy)phenyl]-1,2-tetramethylene-4-pyrazolin-3-one (50 mg, yield: 44%) was obtained as a white solid. $^1$H-NMR (400 MHz, CDCl$_3$): δ1.37 (d, J=6.1 Hz, 6H), 1.86-1.94 (m, 2H), 1.98-2.06 (m, 2H), 3.59-3.64 (m, 2H), 3.80-3.85 (m, 2H), 4.51 (sept, J=6.1 Hz, 1H), 7.13 (d, J=6.4 Hz, 1H), 7.17 (d, J=9.2 Hz, 1H). $^{19}$F-NMR (376 MHz, CDCl$_3$): δ−119.3 (s, 1F).

Example-54

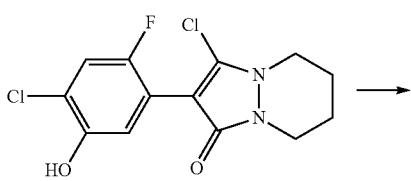

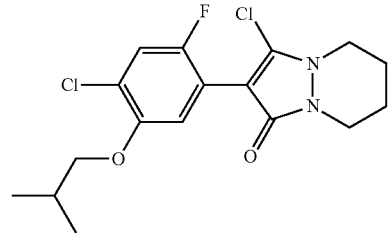

Cesium carbonate (411 mg, 1.26 mmol) and isobutyl chloride (173 mg, 1.26 mmol) were added to a solution of 5-chloro-4-(4-chloro-2-fluoro-5-hydroxyphenyl)-1,2-tetramethylene-4-pyrazolin-3-one (200 mg, 0.63 mmol) in DMF (2 mL), followed by stirring at room temperature for 66 hours. After the reaction was completed, water (20 mL) was added thereto, and the resultant product was extracted with ethyl acetate (20 mL×1, 10 mL×2). The organic layer was washed with a saturated saline solution, dried over anhydrous magnesium sulfate, and concentrated under reduced pressure, whereby a crude product (141 mg) was obtained as a white yellow solid. This was purified by silica gel column chromatography (ethyl acetate), whereby 5-chloro-4-[4-chloro-2-fluoro-5-(isobutyloxy)phenyl]-1,2-tetramethylene-4-pyrazolin-3-one (122 mg, yield: 52%) was obtained as a white solid. $^1$H-NMR (400 MHz, CDCl$_3$): δ1.03 (d, J=6.7 Hz, 6H), 1.87-1.93 (m, 2H), 1.99-2.05 (m, 2H), 2.13 (t and sept, J=6.7 and 6.7 Hz, 1H), 3.60-3.63 (m, 2H), 3.77 (d, J=6.7 Hz, 2H), 3.82-3.85 (m, 2H), 7.07 (d, J=6.3 Hz, 1H), 7.17 (d, J=9.2 Hz, 1H). $^{19}$F-NMR (376 MHz, CDCl$_3$): δ−120 (s, 1F).

Example-55

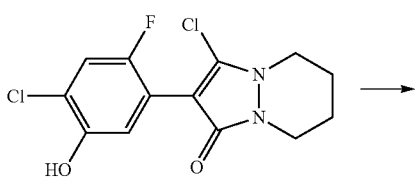

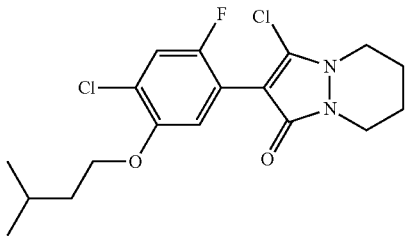

Cesium carbonate (411 mg, 1.26 mmol) and 1-bromo-3-methylbutane (190 mg, 1.26 mmol) were added to a solution of 5-chloro-4-(4-chloro-2-fluoro-5-hydroxyphenyl)-1,2-tetramethylene-4-pyrazolin-3-one (200 mg, 0.63 mmol) in DMF (2 mL), followed by stirring at 50° C. for 18 hours.

After the reaction was completed, water (20 mL) was added thereto, and the resultant product was extracted with ethyl acetate (20 mL×2, 10 mL×1). The organic layer was washed with a saturated saline solution, dried over anhydrous magnesium sulfate, and was concentrated under reduced pressure, whereby a pale yellow oily crude product (176 mg) was obtained. This was purified by silica gel column chromatography (ethyl acetate), whereby 5-chloro-4-[4-chloro-2-fluoro-5-(isopentyloxy)phenyl]-1,2-tetramethylene-4-pyrazolin-3-one (151 mg, yield: 62%) was obtained as a white solid. ¹H-NMR (400 MHz, CDCl₃): δ0.96 (d, J=6.6 Hz, 6H), 1.71 (dt, J=6.6 and 6.6 Hz, 2H), 1.86 (t and sept, J=6.6 and 6.6 Hz, 1H), 1.81-1.93 (m, 2H), 1.99-2.06 (m, 2H), 3.60-3.63 (m, 2H), 3.82-3.85 (m, 2H), 4.04 (t, J=6.6 Hz, 2H), 7.09 (d, J=6.3 Hz, 1H), 7.17 (d, J=9.2 Hz, 1H). ¹⁹F-NMR (376 MHz, CDCl₃): δ−120 (s, 1F).

Example-56

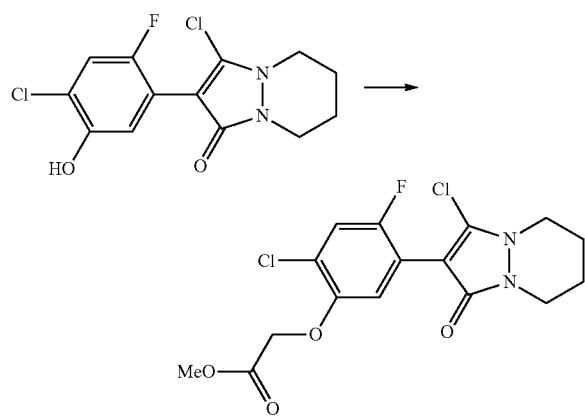

Cesium carbonate (263 mg, 1.90 mmol) and methyl chloroacetate (114 mg, 1.10 mmol) were added to a solution of 5-chloro-4-(4-chloro-2-fluoro-5-hydroxyphenyl)-1,2-tetramethylene-4-pyrazolin-3-one (300 mg, 0.95 mmol) in DMF (3 mL), followed by stirring at 50° C. for 19 hours. After the reaction was completed, the reaction mixture was filtered, and the filtrate was concentrated under reduced pressure. The obtained crude product was purified by silica gel column chromatography (ethyl acetate). The obtained product was recrystallized from a mixed solvent of hexane and ether, whereby methyl 2-[2-chloro-5-(5-chloro-3-oxo-1,2-tetramethylene-4-pyrazolin-4-yl)-4-fluorophenyloxy]acetate (220 mg, yield: 59%) was obtained as a white solid. ¹H-NMR (400 MHz, CDCl₃): δ1.87-1.93 (m, 2H), 1.99-2.05 (m, 2H), 3.61-3.64 (m, 2H), 3.80 (s, 3H), 3.80-3.84 (m, 2H), 4.71 (s, 2H), 7.07 (d, J=4.0 Hz, 1H), 7.21 (d, J=12.0 Hz, 1H). ¹⁹F-NMR (376 MHz, CDCl₃): δ−118 (s, 1F).

Example-57

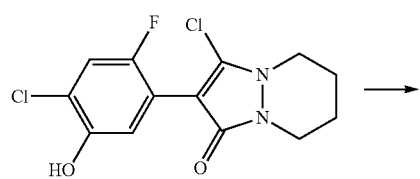

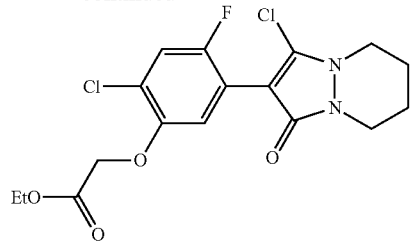

Cesium carbonate (154 mg, 0.47 mmol) and ethyl 2-bromoacetate (50.6 μL, 0.47 mmol) were added to a solution of 5-chloro-4-(4-chloro-2-fluoro-5-hydroxyphenyl)-1,2-tetramethylene-4-pyrazolin-3-one (100 mg, 0.32 mmol) in DMF (1.5 mL), followed by stirring at 80° C. for 3 hours. Water (10 mL) was added to the reaction mixture, and the resultant product was extracted with ethyl acetate (10 mL×2). The organic layer was dried over anhydrous magnesium sulfate, and concentrated under reduced pressure. The obtained residue was purified by silica gel column chromatography (ethyl acetate:methanol=10:1), whereby ethyl 2-[2-chloro-5-(5-chloro-3-oxo-1,2-tetramethylene-4-pyrazolin-4-yl)-4-fluorophenyloxy]acetate (110 mg, yield: 87%) was obtained as a white solid. ¹H-NMR (400 MHz, CDCl₃): δ1.29 (t, J=7.2, 3H), 1.87-1.93 (m, 2H), 1.99-2.05 (m, 2H), 3.59-3.64 (m, 2H), 3.80-3.84 (m, 2H), 4.26 (q, J=7.2 Hz, 2H), 4.69 (s, 2H), 7.08 (d, J=6.2 Hz, 1H), 7.20 (d, J=9.1 Hz, 1H). ¹⁹F-NMR (376 MHz, CDCl₃): δ−117.7 (s, 1F).

Example-58

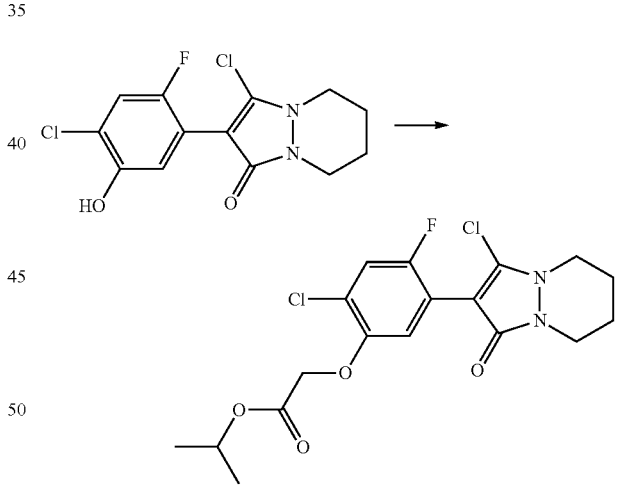

DMF (3 mL), cesium carbonate (263 mg, 1.90 mmol), and isopropyl chloroacetate (143 mg, 1.05 mmol) were added to 5-chloro-4-(4-chloro-2-fluoro-5-hydroxyphenyl)-1,2-tetramethylene-4-pyrazolin-3-one (300 mg, 0.95 mmol), followed by stirring at 50° C. for 22 hours. After the reaction was completed, the reaction mixture was loaded on the upper portion of a silica gel column, and eluted with ethyl acetate, whereby a crude product was obtained. This was recrystallized from a mixed solvent of hexane and ether, whereby isopropyl 2-[2-chloro-5-(5-chloro-3-oxo-1,2-tetramethylene-4-pyrazolin-4-yl)-4-fluorophenyloxy]acetate (153 mg, yield: 39%) was obtained as a white solid. ¹H-NMR (400 MHz, CDCl₃): δ1.26 (d, J=8.0H, 6H), 1.87-

1.93 (m, 2H), 1.99-2.05 (m, 2H), 3.60-3.61 (m, 2H), 3.81-3.84 (m, 2H), 4.66 (s, 2H), 5.12 (sept, J=8.0 Hz, 1H), 7.07 (d, J=8.0 Hz, 1H), 7.20 (d, J=8.0 Hz, 1H). $^{19}$F-NMR (376 MHz, CDCl$_3$): δ−118 (s, 1F).

Example-59

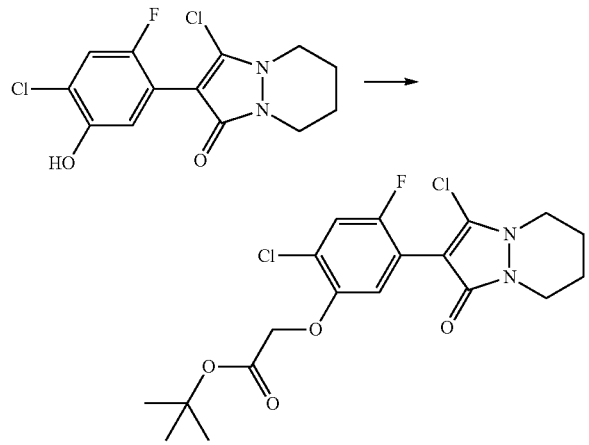

Cesium carbonate (263 mg, 1.90 mmol) and tert-butyl chloroacetate (158 mg, 1.05 mmol) were added to a solution of 5-chloro-4-(4-chloro-2-fluoro-5-hydroxyphenyl)-1,2-tetramethylene-4-pyrazolin-3-one (300 mg, 0.95 mmol) in DMF (3 mL), followed by stirring at 50° C. for 22 hours. After the reaction was completed, the reaction solution was loaded on the upper portion of a silica gel column, purified by eluting with ethyl acetate, and recrystallized from a mixed solvent of hexane and ether, whereby tert-butyl 2-[2-chloro-5-(5-chloro-3-oxo-1,2-tetramethylene-4-pyrazolin-4-yl)-4-fluorophenyloxy]acetate (296 mg, yield: 72%) was obtained as a white solid. $^1$H-NMR (400 MHz, CDCl$_3$): δ1.47 (s, 9H), 1.87-1.93 (m, 2H), 1.99-2.05 (m, 2H), 3.60-3.63 (m, 2H), 3.81-3.84 (m, 1H), 4.58 (s, 2H), 7.05 (d, J=8.0 Hz, 1H), 7.20 (d, J=8.0 Hz, 1H). $^{19}$F-NMR (376 MHz, CDCl$_3$): δ−118 (s, 1F).

Example-60

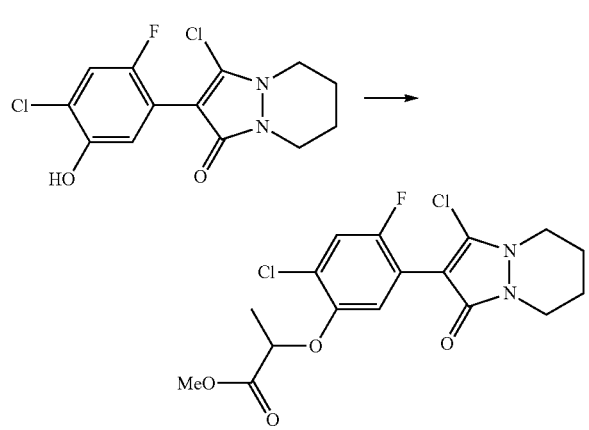

Methyl 2-bromopropionate (141 μL, 1.27 mmol) was added to a solution of 5-chloro-4-(4-chloro-2-fluoro-5-hydroxyphenyl)-1,2-tetramethylene-4-pyrazolin-3-one (200 mg, 0.63 mmol) and potassium carbonate (0.174 g, 1.24 mmol) in DMF (3 mL), followed by stirring at room temperature for 24 hours. After the reaction was completed, water (10 mL) was added to the reaction solution, and the resultant product was extracted with ethyl acetate (15 mL×3). The combined organic layer was dried over anhydrous magnesium sulfate, and concentrated under reduced pressure. The obtained crude product was purified by silica gel column chromatography (ethyl acetate), whereby methyl 2-[2-chloro-5-(5-chloro-3-oxo-1,2-tetramethylene-4-pyrazolin-4-yl)-4-fluorophenyloxy]propionate (186 mg, yield: 73%) was obtained as a white solid. $^1$H-NMR (400 MHz, CDCl$_3$): δ1.66 (d, J=6.8 Hz, 3H), 1.86-1.94 (m, 2H), 1.97-2.06 (m, 2H), 3.59-3.64 (m, 2H), 3.77 (s, 3H), 3.79-3.85 (m, 2H), 4.78 (q, J=6.8 Hz, 1H), 7.05 (d, J=6.3 Hz, 1H), 7.19 (d, J=9.1 Hz, 1H). $^{19}$F-NMR (376 MHz, CDCl$_3$): δ−117.5 (s, 1F).

Example-61

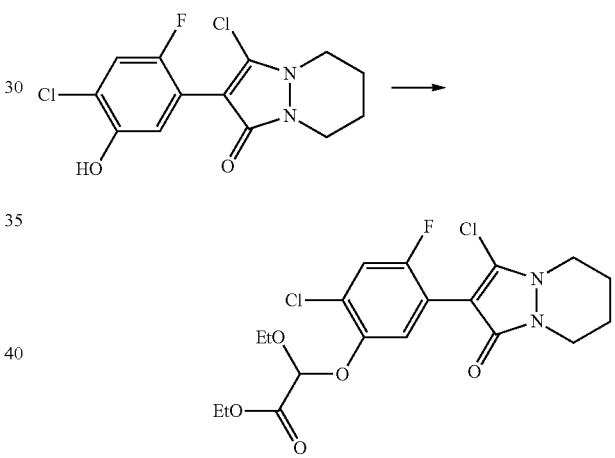

Potassium carbonate (263 mg, 1.90 mmol) and ethyl 2-chloro-2-ethoxy acetate (194 mg, 1.05 mmol) were added to a solution of 5-chloro-4-(4-chloro-2-fluoro-5-hydroxyphenyl)-1,2-tetramethylene-4-pyrazolin-3-one (300 mg, 0.95 mmol) in DMF (3 mL), followed by stirring at room temperature for 17 hours. After the reaction was completed, the reaction solution was filtered using a silica pad, and eluted with a mixed solvent of hexane and ethyl acetate. The eluate was concentrated under reduced pressure, and the obtained crude product was purified by silica gel column chromatography (ethyl acetate), whereby ethyl 2-[2-chloro-5-(5-chloro-3-oxo-1,2-tetramethylene-4-pyrazolin-4-yl)-4-fluorophenyloxy]-2-ethoxyacetate (291 mg, yield: 67%) was obtained as a pale yellow oily material. $^1$H-NMR (400 MHz, CDCl$_3$): δ1.28 (d, J=7.0 Hz, 3H), 1.30 (d, J=7.2 Hz, 3H), 1.89-1.93 (m, 2H), 1.99-2.05 (m, 2H), 3.60-3.63 (m, 2H), 3.75-3.95 (m, 2H), 3.81-3.83 (m, 2H), 4.29 (q, J=7.2 Hz, 1H), 5.49 (s, 1H), 7.20 (d, J=9.2 Hz, 1H), 7.33 (d, J=6.4 Hz, 1H). $^{19}$F-NMR (376 MHz, CDCl$_3$): δ−116 (s, 1F).

Example-62

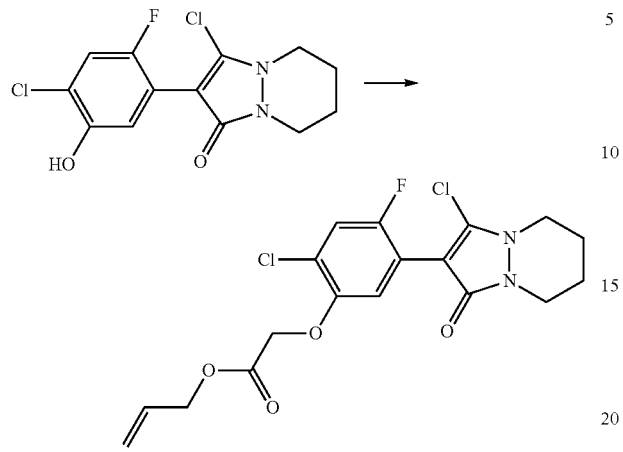

Cesium carbonate (263 mg, 1.90 mmol) and allyl chloroacetate (141 mg, 1.05 mmol) were added to a solution of 5-chloro-4-(4-chloro-2-fluoro-5-hydroxyphenyl)-1,2-tetramethylene-4-pyrazolin-3-one (300 mg, 0.95 mmol) in DMF (3 mL), followed by stirring at 50° C. for 20 hours. After the reaction was completed, the reaction solution was loaded on the upper portion of a silica gel column and eluted with ethyl acetate, and the eluate was concentrated under reduced pressure. The obtained residue was recrystallized from a mixed solvent of hexane and ether, whereby allyl 2-[2-chloro-5-(5-chloro-3-oxo-1,2-tetramethylene-4-pyrazolin-4-yl)-4-fluorophenyloxy]acetate (235 mg, yield: 62%) was obtained as a white solid. $^1$H-NMR (400 MHz, CDCl$_3$): δ1.89-1.93 (m, 2H), 1.99-2.03 (m, 2H), 3.61-3.63 (m, 2H), 3.81-3.84 (m, 2H), 4.70 (dt, J=1.4 and 5.8 Hz, 2H), 4.73 (s, 2H), 5.25 (dq, J=1.4 and 10.4 Hz, 1H), 5.33 (dq, J=1.4 and 17.2 Hz, 1H), 5.92 (ddt, J=5.8, 10.4 and 17.2 Hz, 1H), 7.08 (d, J=8.0 Hz, 1H), 7.21 (d, J=12.0 Hz, 1H). $^{19}$F-NMR (376 MHz, CDCl$_3$): δ−118 (s, 1F).

Example-63

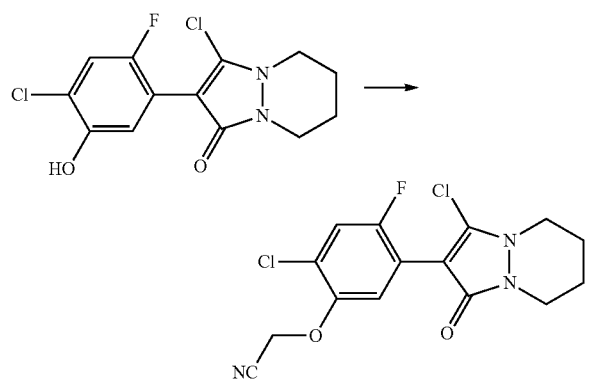

5-Chloro-4-(4-chloro-2-fluoro-5-hydroxyphenyl)-1,2-tetramethylene-4-pyrazolin-3-one (200 mg, 0.63 mmol) and cesium carbonate (0.31 g, 0.95 mmol) were measured and mixed, and DMF (3 mL) and bromoacetonitrile (66 μL, 0.95 mmol) were added thereto, followed by stirring at 80° C. for 24 hours. After the reaction was completed, water (10 mL) was added to the reaction solution, and the resultant product was extracted with ethyl acetate (15 mL×3). The combined organic layer was dried over anhydrous magnesium sulfate, and concentrated under reduced pressure. The obtained crude product was purified by silica gel column chromatography (ethyl acetate), whereby 5-chloro-4-[4-chloro-3-(cyanomethyloxy)-2-fluorophenyl]-1,2-tetramethylene-4-pyrazolin-3-one (157 mg, yield: 70%) was obtained as a white solid. $^1$H-NMR (400 MHz, CDCl$_3$): δ1.88-1.96 (m, 2H), 2.00-2.07 (m, 2H), 3.63-3.68 (m, 2H), 3.81-3.86 (m, 2H), 4.84 (s, 2H), 7.24 (d, J=8.9 Hz, 1H), 7.29 (d, J=6.0 Hz, 1H). $^{19}$F-NMR (376 MHz, CDCl$_3$): δ−115.0 (s, 1F).

Example-64

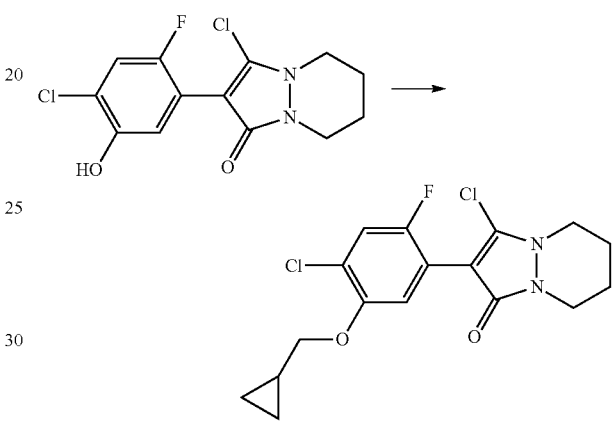

Cesium carbonate (411 mg, 1.26 mmol) and bromomethyl cyclopropane (170 mg, 1.26 mmol) were added to a solution of 5-chloro-4-(4-chloro-2-fluoro-5-hydroxyphenyl)-1,2-tetramethylene-4-pyrazolin-3-one (200 mg, 0.63 mmol) in DMF (2 mL), followed by stirring at 50° C. for 3 hours. After the reaction was completed, water (20 mL) was added thereto, and the resultant product was extracted with ethyl acetate (20 mL×1, 10 mL×2). The organic layer was washed with a saturated saline solution, dried over anhydrous magnesium sulfate, and concentrated under reduced pressure, whereby a milky-white oily crude product was obtained. This was purified by silica gel column chromatography (ethyl acetate), whereby 5-chloro-4-(4-chloro-5-cyclopropylmethyloxy-2-fluorophenyl)-1,2-tetramethylene-4-pyrazolin-3-one (128 mg, yield: 55%) was obtained as a milky-white oily material. $^1$H-NMR (400 MHz, CDCl$_3$): δ0.34-0.38 (m, 2H), 0.60-0.65 (m, 2H), 1.23-1.36 (m, 1H), 1.87-1.93 (m, 2H), 1.99-2.04 (m, 2H), 3.60-3.62 (m, 2H), 3.81-3.84 (m, 2H), 3.86-3.90 (m, 2H), 7.10 (d, J=6.4 Hz, 1H), 7.17 (d, J=9.2 Hz, 1H). $^{19}$F-NMR (376 MHz, CDCl$_3$): δ−120 (s, 1F).

Example-65

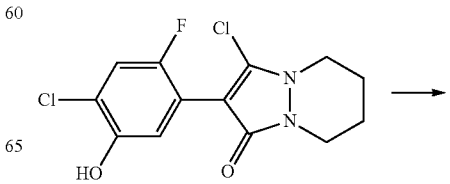

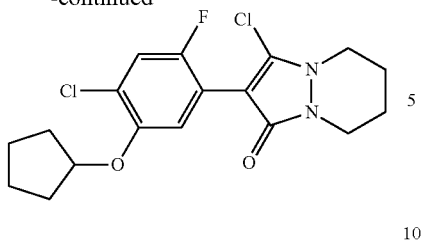

Cesium carbonate (231 mg, 0.71 mmol) and cyclopentyl bromide (116 mg, 0.71 mmol) were added to a solution of 5-chloro-4-(4-chloro-2-fluoro-5-hydroxyphenyl)-1,2-tetramethylene-4-pyrazolin-3-one (150 mg, 0.47 mmol) in DMF (3.0 mL), followed by stirring at 80° C. for 5 hours. After the reaction was completed, distilled water (10 mL) was added thereto, and the resultant product was extracted with ethyl acetate (10 mL×2). The mixed organic layer was dried over anhydrous magnesium sulfate, and concentrated under reduced pressure, and the residue was purified by silica gel column chromatography (ethyl acetate:methanol=10:1), whereby 5-chloro-4-[4-chloro-5-(cyclopentyloxy)-2-fluorophenyl]-1,2-tetramethylene-4-pyrazolin-3-one (135 mg, yield: 74%) was obtained as a white solid. $^1$H-NMR (400 MHz, CDCl$_3$): δ1.59-2.03 (m, 12H), 3.56-3.66 (m, 2H), 3.80-3.87 (m, 2H), 4.79 (m, 1H), 7.10 (d, J=6.4 Hz, 1H), 7.15 (d, J=9.2 Hz, 1H). $^{19}$F-NMR (376 MHz, CDCl$_3$): δ−120.6 (s, 1F).

Example-66

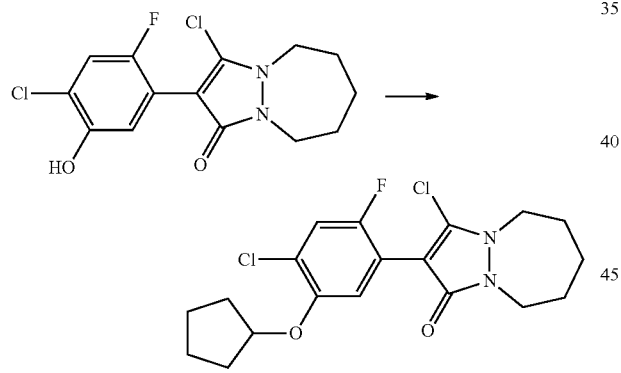

Cesium carbonate (133 mg, 0.82 mmol) and cyclopentyl bromide (133 mg, 0.82 mmol) were added to a solution of 5-chloro-4-(4-chloro-2-fluoro-5-hydroxyphenyl)-1,2-pentamethylene-4-pyrazolin-3-one (180 mg, 0.54 mmol) in DMF (3.0 mL), followed by stirring at 80° C. for 2 hours. After the reaction was completed, distilled water (10 mL) was added thereto, and the resultant product was extracted with ethyl acetate (10 mL×2). The mixed organic layer was dried over anhydrous magnesium sulfate, and concentrated under reduced pressure, and the residue was purified by silica gel column chromatography (ethyl acetate:methanol=10:1), whereby 5-chloro-4-[4-chloro-5-(cyclopentyloxy)-2-fluorophenyl]-1,2-pentamethylene-4-pyrazolin-3-one (195 mg, yield: 90%) was obtained as a white solid. $^1$H-NMR (400 MHz, CDCl$_3$): δ1.92-1.58 (m, 14H), 4.13-4.09 (m, 4H), 4.80 (m, 1H), 7.13-7.15 (m, 2H). $^{19}$F-NMR (376 MHz, CDCl$_3$): δ−120.3 (s, 1F).

Example-67

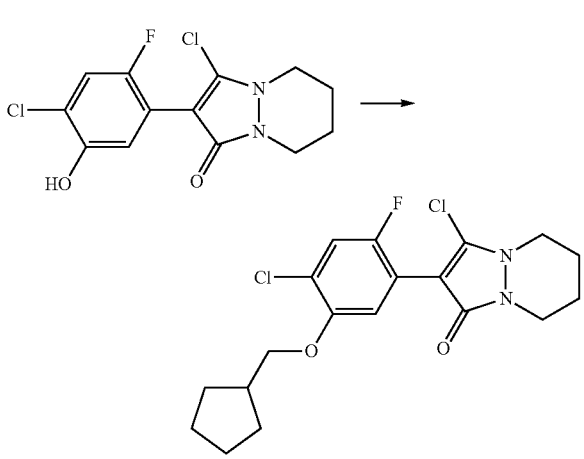

Potassium carbonate (96 mg, 0.70 mmol) and bromomethyl cyclopentane (113 mg, 0.69 mmol) were added to a solution of 5-chloro-4-(4-chloro-2-fluoro-5-hydroxyphenyl)-1,2-tetramethylene-4-pyrazolin-3-one (200 mg, 0.63 mmol) in DMF (2 mL), followed by stirring at 50° C. for 24 hours. After the reaction was completed, water (20 mL) was added thereto, and the resultant product was extracted with ethyl acetate (20 mL×3). The organic layer was washed with a saturated saline solution, dried over anhydrous magnesium sulfate, and concentrated under reduced pressure, whereby a crude product was obtained. This was purified by silica gel column chromatography (ethyl acetate), whereby 5-chloro-4-[4-chloro-5-(cyclopentylmethoxy)-2-fluorophenyl]-1,2-tetramethylene-4-pyrazolin-3-one (212 mg, yield: 84%) was obtained as a white solid. $^1$H-NMR (400 MHz, CDCl$_3$): δ1.33-1.44 (m, 2H), 1.54-1.70 (m, 5H), 1.78-1.94 (m, 4H), 1.98-2.06 (m, 2H), 2.40 (t and quint, J=7.4 and 7.4 Hz, 1H), 3.58-3.63 (m, 2H), 3.81-3.86 (m, 2H), 3.89 (d, J=7.4 Hz, 1H), 7.08 (d, J=6.3 Hz, 1H), 7.18 (d, J=9.1 Hz, 1H). $^{19}$F-NMR (376 MHz, CDCl$_3$): δ−120.1 (s, 1F).

Example-68

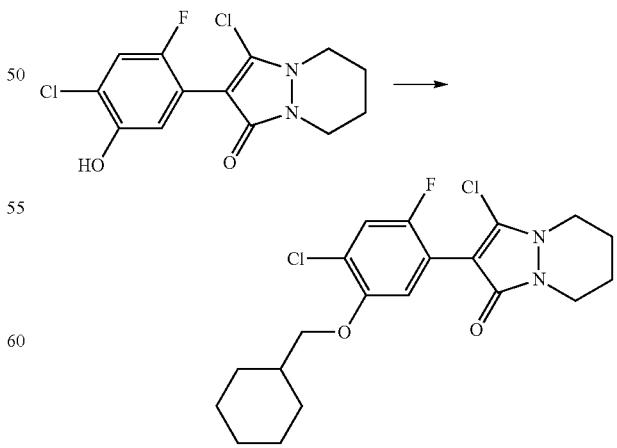

Cesium carbonate (411 mg, 1.26 mmol) and bromomethyl cyclohexane (223 mg, 1.26 mmol) were added to a solution of 5-chloro-4-(4-chloro-2-fluoro-5-hydroxyphenyl)-1,2-tetramethylene-4-pyrazolin-3-one (200 mg, 0.63 mmol) in DMF (2 mL), followed by stirring at 50° C. for 18 hours. After the reaction was completed, water (20 mL) was added thereto, and the resultant product was extracted with ethyl acetate (20 mL×2, 10 mL×1). The organic layer was washed with a saturated saline solution, dried over anhydrous magnesium sulfate, and concentrated under reduced pressure, whereby a pale yellow oily crude product (323 mg) was obtained. This was purified by silica gel column chromatography (ethyl acetate), whereby 5-chloro-4-[4-chloro-5-(cyclohexylmethyloxy)-2-fluorophenyl]-1,2-tetramethylene-4-pyrazolin-3-one (159 mg, yield: 61%) was obtained as a white solid. $^1$H-NMR (400 MHz, CDCl$_3$): δ1.01-1.39 (m, 6H), 1.65-1.95 (m, 7H), 1.99-2.04 (m, 2H), 3.58-3.64 (m, 2H), 3.80 (d, J=6.2 Hz, 2H), 3.81-3.86 (m, 2H), 7.07 (d, J=6.3 Hz, 1H), 7.16 (d, J=9.2 Hz, 1H). $^{19}$F-NMR (376 MHz, CDCl$_3$): δ−120 (s, 1F).

Example-69

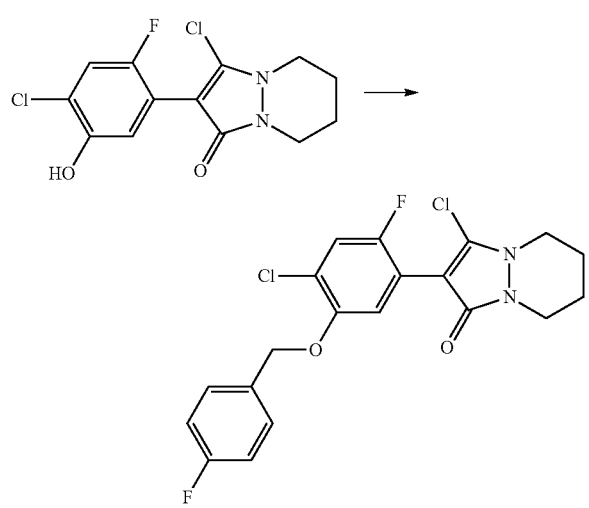

Potassium carbonate (95 mg, 0.69 mmol) and 4-fluorobenzyl bromide (130 mg, 0.69 mmol) were added to a solution of 5-chloro-4-(4-chloro-2-fluoro-5-hydroxyphenyl)-1,2-tetramethylene-4-pyrazolin-3-one (200 mg, 0.63 mmol) in DMF (2 mL), followed by stirring at 50° C. for 76 hours. After the reaction was completed, water (20 mL) was added to the reaction mixture, and the resultant product was extracted with ethyl acetate (20 mL×2, 10 mL×1). The organic layer was washed with a saturated saline solution, dried over anhydrous magnesium sulfate, and concentrated under reduced pressure, whereby a pale yellow oily crude product (219 mg) was obtained. This was purified by silica gel column chromatography (ethyl acetate), whereby 5-chloro-4-[4-chloro-2-fluoro-5-(4-fluorobenzyloxy)phenyl]-1,2-tetramethylene-4-pyrazolin-3-one (113 mg, yield: 42%) was obtained as a white yellow solid. $^1$H-NMR (400 MHz, CDCl$_3$): δ1.88-1.94 (m, 2H), 2.00-2.05 (m, 2H), 3.61-3.64 (m, 2H), 3.82-3.85 (m, 2H), 5.08 (s, 2H), 7.07 (dd, J=8.7 and 8.7 Hz, 2H), 7.19 (d, J=1.9 Hz, 1H), 7.21 (d, J=1.9 Hz, 1H), 7.44 (dd, J=5.4 and 8.7 Hz, 2H). $^{19}$F-NMR (376 MHz, CDCl$_3$): δ−114 (s, 1F), −119 (s, 1F).

Example-70

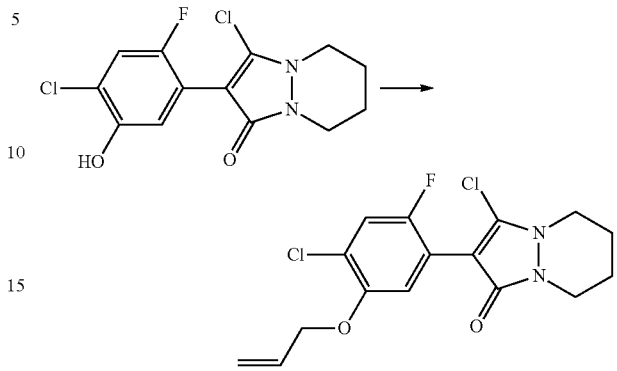

Cesium carbonate (411 mg, 1.26 mmol) and allyl bromide (152 mg, 1.26 mmol) were added to a solution of 5-chloro-4-(4-chloro-2-fluoro-5-hydroxyphenyl)-1,2-tetramethylene-4-pyrazolin-3-one (200 mg, 0.63 mmol) in DMF (2 mL), followed by stirring at room temperature for 69 hours. After the reaction was completed, water (20 mL) was added to the reaction mixture, and the resultant product was extracted with ethyl acetate (20 mL×1, 10 mL×2). The organic layer was washed with a saturated saline solution, dried over anhydrous magnesium sulfate, and concentrated under reduced pressure, whereby a crude product (152 mg) was obtained as a milky-white solid. This was recrystallized from ether, whereby 4-(5-allyloxy-4-chloro-2-fluorophenyl)-5-chloro-1,2-tetramethylene-4-pyrazolin-3-one (89 mg, yield: 40%) was obtained as a white solid. $^1$H-NMR (400 MHz, CDCl$_3$): δ1.87-1.93 (m, 2H), 1.99-2.05 (m, 2H), 3.60-3.63 (m, 2H), 3.82-3.84 (m, 2H), 4.60 (dt, J=1.5 and 5.2 Hz, 2H), 5.30 (dq, J=1.46 and 10.5 Hz, 1H), 5.46 (dq, J=1.5 and 17.2 Hz, 1H), 6.06 (ddt, J=5.2, 10.5 and 17.2 Hz, 1H), 7.11 (d, J=6.3 Hz, 1H), 7.18 (d, J=9.2 Hz, 1H). $^{19}$F-NMR (376 MHz, CDCl$_3$): δ−119 (s, 1F).

Example-71

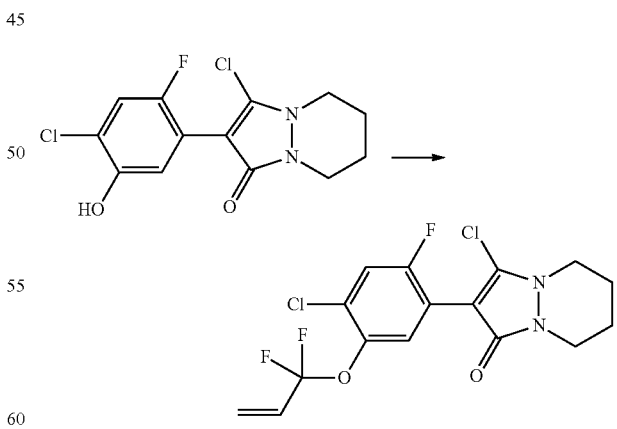

Potassium carbonate (96 mg, 0.70 mmol) and 1-bromo-1,1-difluoro-2-propene (0.128 mL, 1.26 mmol) were added to a solution of 5-chloro-4-(4-chloro-2-fluoro-5-hydroxyphenyl)-1,2-tetramethylene-4-pyrazolin-3-one (200 mg, 0.63 mmol) in DMF (2 mL), followed by stirring at 50° C. for 48 hours. After the reaction was completed, water (20 mL) was added thereto, and the resultant product was extracted with ethyl acetate (20 mL×3). The organic layer was washed with a saturated saline solution, dried over anhydrous magnesium sulfate, and concentrated under reduced pressure, whereby a crude product was obtained. This was purified by silica gel column chromatography (ethyl acetate), whereby 5-chloro-4-[4-chloro-5-(1,1-difluoroallyloxy)-2-fluorophenyl]-1,2-tetramethylene-4-pyrazolin-3-one (100 mg, yield: 40%) was obtained as a white solid. $^1$H-NMR (400 MHz, CDCl$_3$): δ1.87-1.94 (m, 2H), 1.98-2.05 (m, 2H), 3.61-3.65 (m, 2H), 3.80-3.86 (m, 2H), 5.63 (dd, J=1.0 and 10.5 Hz, 1H), 5.95-6.14 (m, 2H), 7.23 (d, J=9.1 Hz, 1H), 7.54 (m, 1H). $^{19}$F-NMR (376 MHz, CDCl$_3$): δ−112.3 (s, 1F), −68.6 (s, 1F).

Example-72

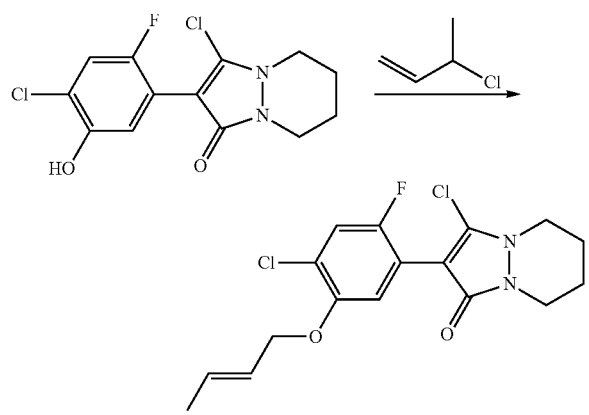

Cesium carbonate (411 mg, 1.26 mmol) and 3-chloro-1-butene (114 mg, 1.26 mmol) were added to a solution of 5-chloro-4-(4-chloro-2-fluoro-5-hydroxyphenyl)-1,2-tetramethylene-4-pyrazolin-3-one (200 mg, 0.63 mmol) in DMF (2 mL), followed by stirring at room temperature for 69 hours. After the reaction was completed, water (20 mL) was added to the reaction mixture, and the resultant product was extracted with ethyl acetate (20 mL×1, 10 mL×2). The organic layer was washed with a saturated saline solution, dried over anhydrous magnesium sulfate, and was concentrated under reduced pressure, whereby a pale yellow oily crude product (180 mg) was obtained. This was purified by silica gel column chromatography (ethyl acetate), whereby 5-chloro-4-(4-chloro-5-crotyloxy-2-fluorophenyl)-1,2-tetramethylene-4-pyrazolin-3-one (153 mg, yield: 65%) was obtained as a white solid. $^1$H-NMR (400 MHz, CDCl$_3$): δ1.75 (dq, J=1.1 and 6.4 Hz, 3H), 1.87-1.93 (m, 2H), 1.99-2.04 (m, 2H), 3.60-3.63 (m, 2H), 3.82-3.85 (m, 2H), 4.51 (dt, J=1.1 and 5.9 Hz, 2H), 5.70-5.77 (m, 1H), 5.83-5.92 (m, 1H), 7.10 (d, J=6.3 Hz, 1H), 7.18 (d, J=9.2 Hz, 1H). $^{19}$F-NMR (376 MHz, CDCl$_3$): δ−120 (s, 1F).

Example-73

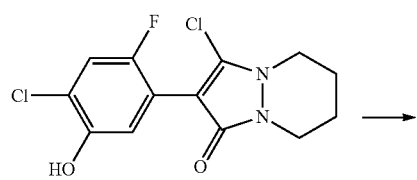

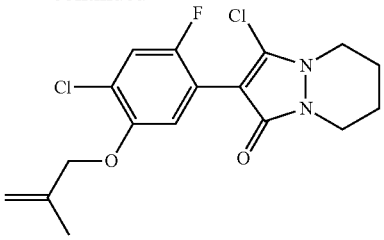

Cesium carbonate (717 mg, 2.20 mmol) and methallyl chloride (199 mg, 2.20 mmol) were added to a solution of 5-chloro-4-(4-chloro-2-fluoro-5-hydroxyphenyl)-1,2-tetramethylene-4-pyrazolin-3-one (350 mg, 1.10 mmol) in DMF (3 mL), followed by stirring at room temperature for 17 hours. After the reaction was completed, water (20 mL) was added to the reaction mixture, and the resultant product was extracted with ethyl acetate (20 mL×3). The organic layer was washed with a saturated saline solution, dried over anhydrous magnesium sulfate, and concentrated under reduced pressure, whereby a pale yellow oily crude product (440 mg) was obtained. This was purified by silica gel column chromatography (ethyl acetate), whereby 5-chloro-4-[4-chloro-2-fluoro-5-(methallyloxy)phenyl]-1,2-tetramethylene-4-pyrazolin-3-one (286 mg, yield: 70%) was obtained as a white solid. $^1$H-NMR (400 MHz, CDCl$_3$): δ1.84 (d, J=0.4 Hz, 3H), 1.73-1.93 (m, 2H), 1.99-2.05 (m, 2H), 3.62 (t, J=5.67 Hz, 2H), 3.83 (t, J=5.67 Hz, 2H), 4.48 (s, 2H), 5.00-5.15 (m, 2H), 7.10 (d, J=6.4 Hz, 1H), 7.17 (d, J=9.2 Hz, 1H). $^{19}$F-NMR (376 MHz, CDCl$_3$): δ−119 (s, 1F).

Example-74

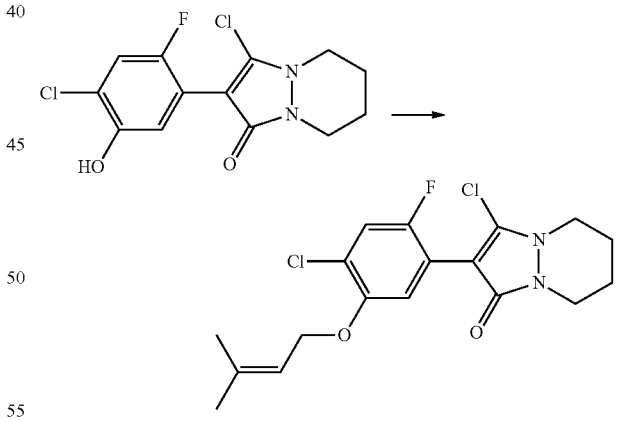

Cesium carbonate (411 mg, 1.26 mmol) and 1-bromo-3-methyl-2-butene (188 mg, 1.26 mmol) were added to a solution of 5-chloro-4-(4-chloro-2-fluoro-5-hydroxyphenyl)-1,2-tetramethylene-4-pyrazolin-3-one (200 mg, 0.63 mmol) in DMF (2 mL), followed by stirring at room temperature for 66 hours. After the reaction was completed, water (20 mL) was added to the reaction mixture, and the resultant product was extracted with ethyl acetate (20 mL×1, 10 mL×2). The organic layer was washed with a saturated saline solution, dried over anhydrous magnesium sulfate, and concentrated under reduced pressure, whereby a pale brown oily crude product (186 mg) was obtained. This was purified by silica gel column chromatography (ethyl acetate), whereby 5-chloro-4-[4-chloro-2-fluoro-5-(prenyloxy)phenyl]-1,2-tetramethylene-4-pyrazolin-3-one (169 mg, yield: 70%) was obtained as a pale yellow oily material. $^1$H-NMR (400 MHz, CDCl$_3$): δ1.72 (d, J=0.8 Hz, 3H), 1.79 (d, J=0.8 Hz, 3H), 1.87-1.93 (m, 2H), 1.99-2.04 (m, 2H), 3.60-3.63 (m, 2H), 3.82-3.85 (m, 2H), 4.57 (d, J=6.8 Hz, 2H), 5.51 (tt, J=2.8 and 6.8 Hz, 1H), 7.11 (d, J=6.3 Hz, 1H), 7.18 (d, J=9.2 Hz, 1H). $^{19}$F-NMR (376 MHz, CDCl$_3$): δ−120 (s, 1F).

Example-75

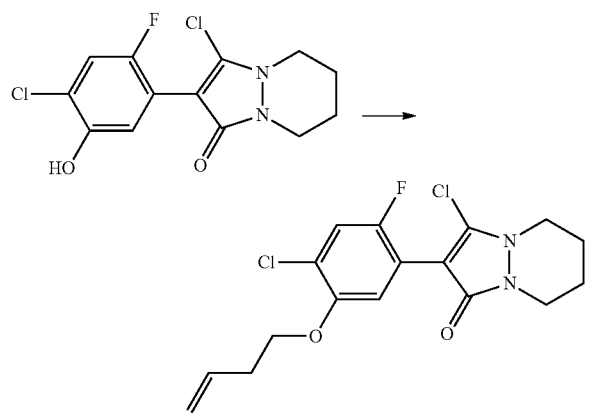

4-Bromo-1-butene (87 μL, 0.94 mmol) was added to a solution of 5-chloro-4-(4-chloro-2-fluoro-5-hydroxyphenyl)-1,2-tetramethylene-4-pyrazolin-3-one (200 mg, 0.63 mmol) and cesium carbonate (0.31 g, 0.95 mmol) in DMF (3 mL), followed by stirring at 80° C. for 24 hours. After the reaction was completed, water (10 mL) was added to the reaction solution, and the resultant product was extracted with ethyl acetate (15 mL×3). The combined organic layer was dried over anhydrous magnesium sulfate, and concentrated under reduced pressure. The obtained crude product was purified by silica gel column chromatography (ethyl acetate), whereby 5-chloro-4-[5-(3-butenyloxy)phenyl-4-chloro-2-fluoro]-1,2-tetramethylene-4-pyrazolin-3-one (44 mg, yield: 8%) was obtained as a white solid. $^1$H-NMR (400 MHz, CDCl$_3$): δ1.86-1.94 (m, 2H), 1.98-2.06 (m, 2H), 2.54-2.61 (m, 2H), 3.59-3.64 (m, 2H), 3.81-3.86 (m, 2H), 4.04-4.10 (m, 2H), 5.06-5.22 (m, 2H), 5.91 (m, 1H), 7.10 (d, J=6.3 Hz, 1H), 7.17 (d, J=9.2 Hz, 1H). $^{19}$F-NMR (376 MHz, CDCl$_3$): δ−119.6 (s, 1F).

Example-76

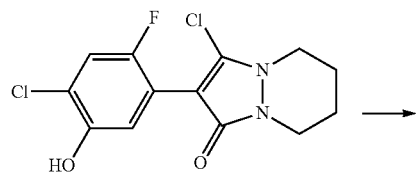

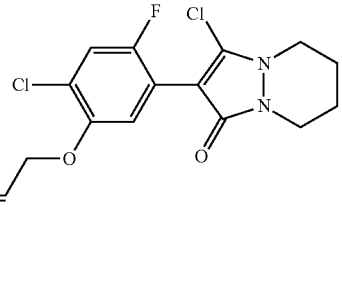

Potassium carbonate (145 mg, 1.05 mmol) and cinnamyl bromide (207 mg, 1.05 mmol) were added to a solution of 5-chloro-4-(4-chloro-2-fluoro-5-hydroxyphenyl)-1,2-tetramethylene-4-pyrazolin-3-one (300 mg, 0.95 mmol) in DMF (3 mL), followed by stirring at room temperature for 18 hours. After the reaction was completed, water (20 mL) was added to the reaction mixture, and the resultant product was extracted with ethyl acetate (20 mL×1, 10 mL×2). The organic layer was dried over anhydrous magnesium sulfate, and concentrated under reduced pressure. The obtained crude product was purified by silica gel column chromatography (ethyl acetate), whereby 5-chloro-4-[4-chloro-5-(cinnamyl oxy)-2-fluorophenyl]-1,2-tetramethylene-4-pyrazolin-3-one (246 mg, yield: 60%) was obtained as a white solid. $^1$H-NMR (400 MHz, CDCl$_3$): δ1.87-1.93 (m, 2H), 1.99-2.05 (m, 2H), 3.60-3.63 (m, 2H), 3.82-3.85 (m, 2H), 4.77 (dd, J=1.4 and 4.0 Hz, 2H), 6.42 (dt, J=4.0 and 8.0 Hz, 1H), 6.72 (d, J=12.0 Hz, 1H), 7.17 (d, J=8.0 Hz, 1H), 7.20 (d, J=8.0 Hz, 1H), 7.23-7.43 (m, 5H). $^{19}$F-NMR (376 MHz, CDCl$_3$): δ−119 (s, 1F).

Example-77

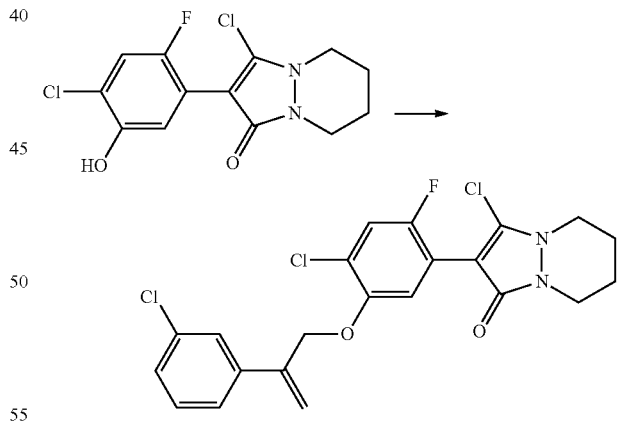

Potassium carbonate (96 mg, 0.70 mmol) and 2-(3-chlorophenyl)allyl chloride (0.130 g, 0.70 mmol) were added to a solution of 5-chloro-4-(4-chloro-2-fluoro-5-hydroxyphenyl)-1,2-tetramethylene-4-pyrazolin-3-one (200 mg, 0.63 mmol) in DMF (2 mL), followed by stirring at 50° C. for 48 hours. After the reaction was completed, water (20 mL) was added thereto, and the resultant product was extracted with ethyl acetate (20 mL×3). The organic layer was washed with a saturated saline solution, dried over anhydrous magnesium sulfate, and concentrated under reduced pressure, whereby a crude product was obtained. This was purified by silica gel column chromatography (ethyl acetate), whereby 5-chloro-4-[4-chloro-5-{2-(3-chlorophenyl)allyloxy}-2-fluorophenyl]-1,2-tetramethylene-4-pyrazolin-3-one (188 mg, yield: 64%) was obtained as a white solid. $^1$H-NMR (400 MHz, CDCl$_3$): δ1.86-1.94 (m, 2H), 1.98-2.06 (m, 2H), 3.59-3.65 (m, 2H), 3.81-3.86 (m, 2H), 4.90 (s, 2H), 5.60 (s, 1H), 5.62 (s, 1H), 7.16-7.21 (m, 2H), 7.27-7.30 (m, 2H), 7.36 (m, 1H), 7.48 (m, 1H). $^{19}$F-NMR (376 MHz, CDCl$_3$): δ−118.7 (s, 1F).

Example-78

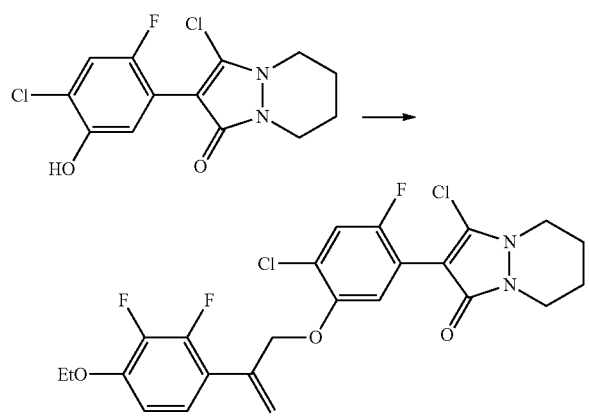

Potassium carbonate (96 mg, 0.70 mmol) and 2-(4-ethoxy-2,3-difluorophenyl)allyl chloride (0.161 g, 0.69 mmol) were added to a solution of 5-chloro-4-(4-chloro-2-fluoro-5-hydroxyphenyl)-1,2-tetramethylene-4-pyrazolin-3-one (200 mg, 0.63 mmol) in DMF (2 mL), followed by stirring at 50° C. for 48 hours. After the reaction was completed, water (20 mL) was added thereto, and the resultant product was extracted with ethyl acetate (20 mL×3). The organic layer was washed with a saturated saline solution, dried over anhydrous magnesium sulfate, and concentrated under reduced pressure, whereby a crude product was obtained. This was purified by silica gel column chromatography (ethyl acetate), whereby 5-chloro-4-[4-chloro-5-{2-(4-ethoxy-2,3-difluorophenyl)allyloxy}-2-fluorophenyl]-1,2-tetramethylene-4-pyrazolin-3-one (192 mg, yield: 59%) was obtained as a white solid. $^1$H-NMR (400 MHz, CDCl$_3$): δ1.46 (t, J=7.0 Hz, 3H), 1.86-1.94 (m, 2H), 1.98-2.06 (m, 2H), 3.59-3.64 (m, 2H), 3.81-3.85 (m, 2H), 4.13 (q, J=7.0 Hz, 2H), 4.86 (s, 2H), 5.50 (s, 1H), 5.68 (s, 1H), 6.70 (ddd, J=1.9, 7.8 and 9.1 Hz, 1H), 7.05 (ddd, J=2.4, 7.8 and 10.3 Hz, 1H), 7.36 (d, J=6.2 Hz, 1H), 7.48 (d, J=9.2 Hz, 1H). $^{19}$F-NMR (376 MHz, CDCl$_3$): δ−159.3 (d, J=19.1 Hz, 1F), −138.8 (d, J=19.1 Hz, 1F), −119.0 (s, 1F).

Example-79

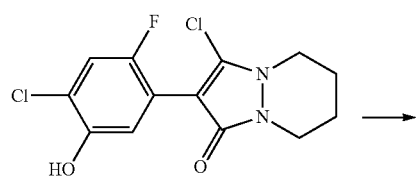

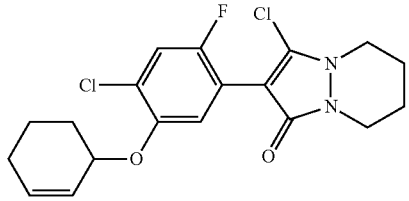

Potassium carbonate (96 mg, 0.70 mmol) and 3-bromocyclohexene (89 μL, 0.70 mmol) were added to a solution of 5-chloro-4-(4-chloro-2-fluoro-5-hydroxyphenyl)-1,2-tetramethylene-4-pyrazolin-3-one (200 mg, 0.63 mmol) in DMF (2 mL), followed by stirring at 50° C. for 48 hours. After the reaction was completed, water (20 mL) was added thereto, and the resultant product was extracted with ethyl acetate (20 mL×3). The organic layer was washed with a saturated saline solution, dried over anhydrous magnesium sulfate, and concentrated under reduced pressure, whereby a crude product was obtained. This was purified by silica gel column chromatography (ethyl acetate), whereby 5-chloro-4-[4-chloro-5-{(2-cyclohexenyl)oxy}-2-fluorophenyl]-1,2-tetramethylene-4-pyrazolin-3-one (128 mg, yield: 51%) was obtained as a colorless oily material. $^1$H-NMR (400 MHz, CDCl$_3$): δ1.63 (m, 1H), 1.84-2.19 (m, 9H), 3.59-3.64 (m, 2H), 3.81-3.86 (m, 2H), 4.75 (m, 1H), 5.88-6.01 (m, 2H), 7.16-7.19 (m, 2H). $^{19}$F-NMR (376 MHz, CDCl$_3$): δ−119.1 (s, 1F).

Example-80

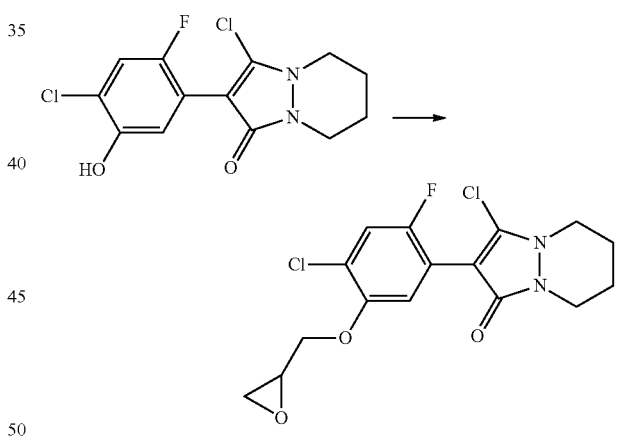

5-Chloro-4-(4-chloro-2-fluoro-5-hydroxyphenyl)-1,2-tetramethylene-4-pyrazolin-3-one (200 mg, 0.63 mmol) and cesium carbonate (0.31 g, 0.95 mmol) were measured and mixed, and DMF (3 mL) and epibromohydrin (78 μL, 0.95 mmol) were added thereto, followed by stirring at 80° C. for 24 hours. After the reaction was completed, water (10 mL) was added to the reaction solution, and the resultant product was extracted with ethyl acetate (15 mL×3). The combined organic layer was dried over anhydrous magnesium sulfate, and concentrated under reduced pressure. The obtained crude product was purified by silica gel column chromatography (ethyl acetate), whereby 5-chloro-4-[4-chloro-2-fluoro-5-(glycidyloxy)phenyl]-1,2-tetramethylene-4-pyrazolin-3-one (131 mg, yield: 22%) was obtained as a white solid. $^1$H-NMR (400 MHz, CDCl$_3$): δ1.87-1.94 (m, 2H), 1.98-2.06 (m, 2H), 2.80 (m, 1H), 2.90 (m, 1H), 3.38 (m, 1H), 3.59-3.65 (m, 2H), 3.79-3.86 (m, 2H), 4.04 (m, 1H), 4.29 (m, 1H), 7.15 (d, J=6.2 Hz, 1H), 7.18 (d, J=9.1 Hz, 1H). $^{19}$F-NMR (376 MHz, CDCl$_3$): δ–118.5 (s, 1F).

Example-81

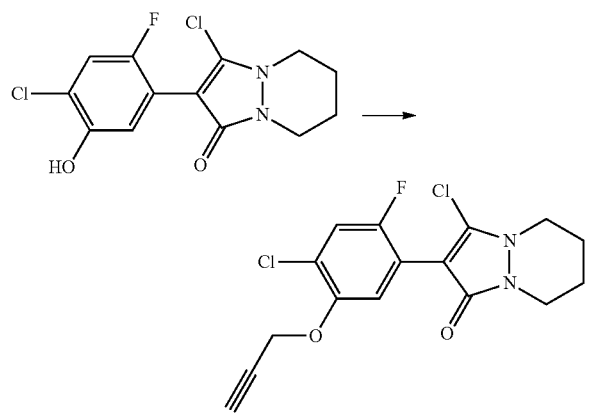

Cesium carbonate (154 mg, 0.47 mmol) and propargyl bromide (56 mg, 0.47 mmol) were added to a solution of 5-chloro-4-(4-chloro-2-fluoro-5-hydroxyphenyl)-1,2-tetramethylene-4-pyrazolin-3-one (100 mg, 0.32 mmol) in DMF (1.5 mL), followed by stirring at 80° C. for 5 hours. After the reaction was completed, water (10 mL) was added to the reaction mixture, and the resultant product was extracted with ethyl acetate (10 mL×2). The mixed organic layer was dried over anhydrous magnesium sulfate, and concentrated under reduced pressure, and the residue was purified by silica gel column chromatography (ethyl acetate: methanol=10:1), whereby 5-chloro-4-[4-chloro-2-fluoro-5-(propargyloxy)phenyl]-1,2-tetramethylene-4-pyrazolin-3-one (93 mg, yield: 83%) was obtained as a yellow solid. $^1$H-NMR (400 MHz, CDCl$_3$): δ1.87-1.94 (m, 2H), 1.99-2.06 (m, 2H), 2.56 (t, J=2.4 Hz, 1H), 3.60-3.65 (m, 2H), 3.81-3.86 (m, 2H), 4.77 (d, J=2.4 Hz, 2H), 7.20 (d, J=9.1 Hz, 1H), 7.24 (d, J=6.2 Hz, 1H). $^{19}$F-NMR (376 MHz, CDCl$_3$): δ–118.0 (s, 1F).

Example-82

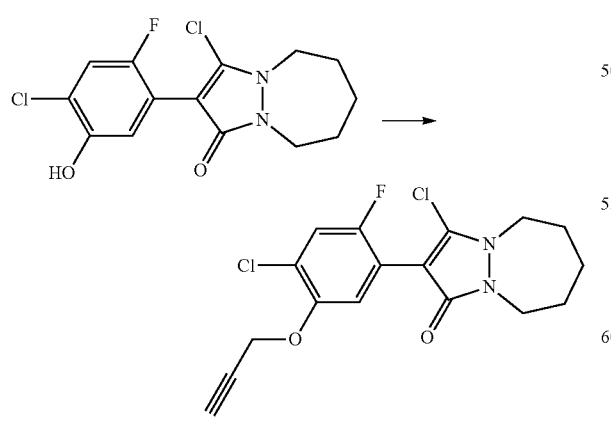

Cesium carbonate (266 mg, 0.82 mmol) and propargyl bromide (97 mg, 0.82 mmol) were added to a solution of 5-chloro-4-(4-chloro-2-fluoro-5-hydroxyphenyl)-1,2-pentamethylene-4-pyrazolin-3-one (180 mg, 0.54 mmol) in DMF (3.0 mL), followed by stirring at 80° C. for 2 hours. After the reaction was completed, water (10 mL) was added to the reaction mixture, and the resultant product was extracted with ethyl acetate (10 mL×2). The mixed organic layer was dried over anhydrous magnesium sulfate, and concentrated under reduced pressure, and the residue was purified by silica gel column chromatography (ethyl acetate: methanol=10:1), whereby 5-chloro-4-[4-chloro-2-fluoro-5-(propargyloxy)phenyl]-1,2-pentamethylene-4-pyrazolin-3-one (132 mg, yield: 66%) was obtained as a white solid. $^1$H-NMR (400 MHz, CDCl$_3$): δ1.81-1.90 (m, 6H), 2.55 (t, J=2.4 Hz, 1H), 4.06-4.18 (m, 4H), 4.77 (d, J=2.4 Hz, 2H), 7.18 (d, J=9.2 Hz, 1H), 7.26 (d, J=6.1 Hz, 1H). $^{19}$F-NMR (376 MHz, CDCl$_3$): δ–118.6 (s, 1F).

Example-83

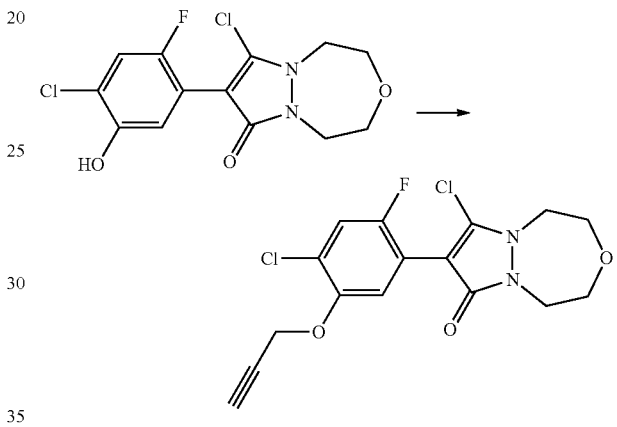

In the same manner as in Example-39, 5-chloro-4-[4-chloro-2-fluoro-5-hydroxyphenyl]-1,2-oxadiethylene-4-pyrazolin-3-one was reacted with propargyl bromide, whereby 5-chloro-4-[4-chloro-2-fluoro-5-(propargyloxy)phenyl]-1,2-oxadiethylene-4-pyrazolin-3-one was obtained with a yield of 74%. $^1$H-NMR (400 MHz, CDCl$_3$): δ2.55 (t, J=2.4 Hz, 1H), 3.92-3.96 (m, 4H), 4.21-4.25 (m, 2H), 4.26-4.30 (m, 2H), 4.77 (d, J=2.4 Hz, 2H), 7.20 (d, J=9.2 Hz, 1H), 7.24 (d, J=6.3 Hz, 1H). $^{19}$F-NMR (376 MHz, CDCl$_3$): δ–118.1 (s, 1F).

Example-84

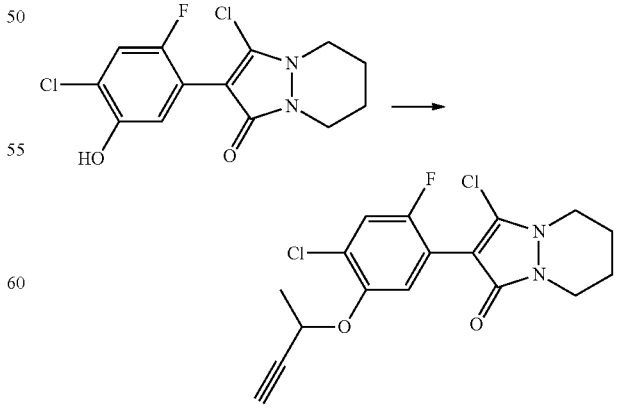

Cesium carbonate (619 mg, 1.90 mmol) and 3-chloro-1-butyne (172 mg, 1.90 mmol) were added to a solution of 5-chloro-4-(4-chloro-2-fluoro-5-hydroxyphenyl)-1,2-tetramethylene-4-pyrazolin-3-one (300 mg, 0.95 mmol) in DMF (3 mL), followed by stirring at room temperature for 22 hours. After the reaction was completed, water (20 mL) was added to the reaction mixture, and the resultant product was extracted with ethyl acetate (20 mL×3). The organic layer was washed with a saturated saline solution (20 mL), dried over anhydrous magnesium sulfate, and concentrated under reduced pressure, whereby a yellow oily crude product (448 mg) was obtained. This was purified by silica gel column chromatography (ethyl acetate:methanol=10:1), and recrystallized from ether, whereby 5-chloro-4-[3-(1-butyn-3-yloxy)-4-chloro-2-fluorophenyl]-1,2-tetramethylene-4-pyrazolin-3-one (110 mg, yield: 31%) was obtained as a white solid. $^1$H-NMR (400 MHz, CDCl$_3$): δ1.70 (d, J=6.6 Hz, 3H), 1.87-1.93 (m, 2H), 2.00-2.05 (m, 2H), 2.52 (d, J=2.0 Hz, 1H), 3.60-3.64 (m, 2H), 3.81-3.85 (m, 2H), 4.88 (dq, J=2.0 and 6.6 Hz, 1H), 7.19 (d, J=9.2 Hz, 1H), 7.30 (d, J=6.4 Hz, 1H). $^{19}$F-NMR (376 MHz, CDCl$_3$): δ−118 (s, 1F).

Example-85

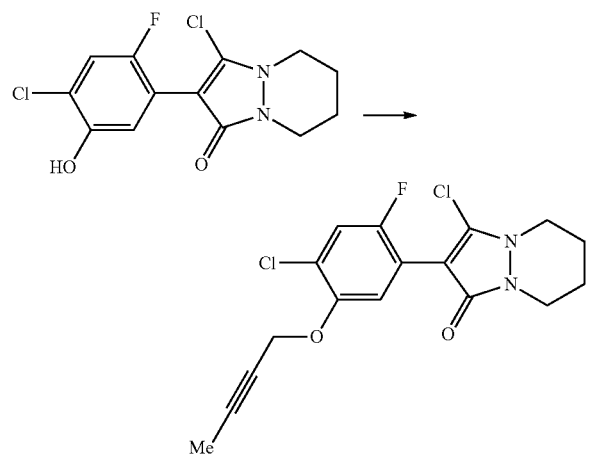

Potassium carbonate (96 mg, 0.70 mmol) and 1-bromo-2-butyne (0.114 mL, 1.26 mmol) were added to a solution of 5-chloro-4-(4-chloro-2-fluoro-5-hydroxyphenyl)-1,2-tetramethylene-4-pyrazolin-3-one (200 mg, 0.63 mmol) in DMF (2 mL), followed by stirring at 50° C. for 6 hours. After the reaction was completed, water (20 mL) was added to the reaction solution, and the resultant product was extracted with ethyl acetate (20 mL×3). The organic layer was washed with a saturated saline solution, dried over anhydrous magnesium sulfate, and concentrated under reduced pressure, whereby a crude product was obtained. This was purified by silica gel column chromatography (ethyl acetate), whereby 5-chloro-4-[5-(2-butynyloxy)-4-chloro-2-fluorophenyl]-1,2-tetramethylene-4-pyrazolin-3-one (143 mg, yield: 61%) was obtained as a white solid. $^1$H-NMR (400 MHz, CDCl$_3$): δ1.86 (t, J=2.3 Hz, 3H), 1.88-1.94 (m, 2H), 1.98-2.06 (m, 2H), 3.60-3.65 (m, 2H), 3.81-3.86 (m, 2H), 4.72 (q, J=2.3 Hz, 1H), 7.19 (d, J=9.2 Hz, 1H), 7.20 (d, J=6.3 Hz, 1H). $^{19}$F-NMR (376 MHz, CDCl$_3$): δ−118.6 (s, 1F).

Example-86

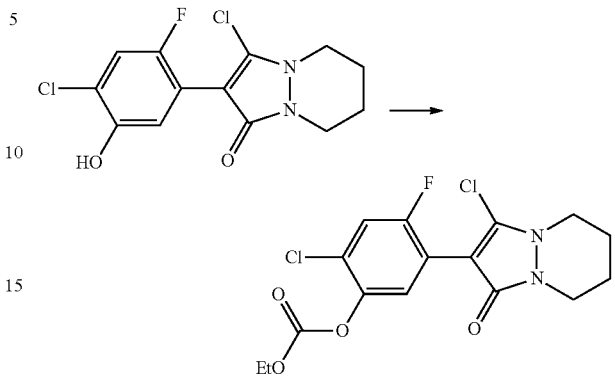

A 37% sodium hydroxide aqueous solution (97 µL) and ethyl chloroformate (122 µL, 1.26 mmol) were added to a solution of 5-chloro-4-(4-chloro-2-fluoro-5-hydroxyphenyl)-1,2-tetramethylene-4-pyrazolin-3-one (200 mg, 0.63 mmol) in DMF (3 mL), followed by stirring at room temperature for 24 hours. After the reaction was completed, water (10 mL) was added to the reaction solution, and the resultant product was extracted with ethyl acetate (15 mL×3). The combined organic layer was dried over anhydrous magnesium sulfate, and concentrated under reduced pressure. The obtained crude product was purified by silica gel column chromatography (ethyl acetate), whereby 5-chloro-4-[4-chloro-5-(ethoxycarbonyloxy)-2-fluorophenyl]-1,2-tetramethylene-4-pyrazolin-3-one (162 mg, yield: 66%) was obtained as a white solid. $^1$H-NMR (400 MHz, CDCl$_3$): δ1.39 (t, J=7.2 Hz, 3H), 1.86-1.94 (m, 2H), 1.98-2.06 (m, 2H), 3.60-3.65 (m, 2H), 3.79-3.85 (m, 2H), 4.34 (q, J=7.2 Hz, 2H), 7.24 (d, J=9.0 Hz, 1H), 7.46 (d, J=6.5 Hz, 1H). $^{19}$F-NMR (376 MHz, CDCl$_3$): δ−111.6 (s, 1F).

Example-87

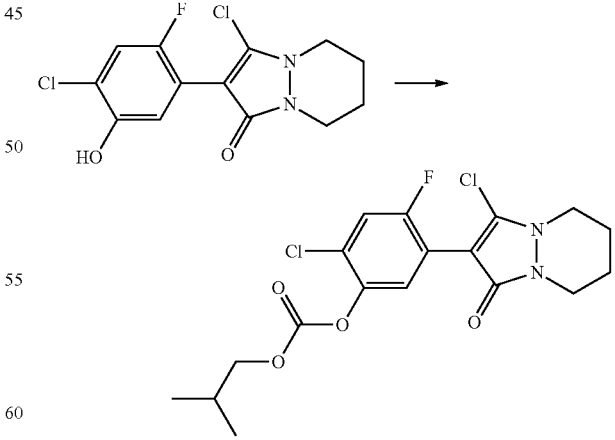

A 37% sodium hydroxide aqueous solution (97 µL) and isobutyl chloroformate (166 µL, 1.26 mmol) were added to a solution of 5-chloro-4-(4-chloro-2-fluoro-5-hydroxyphenyl)-1,2-tetramethylene-4-pyrazolin-3-one (200 mg, 0.63 mmol) in DMF (3 mL), followed by stirring at room temperature for 24 hours. After the reaction was completed, water (10 mL) was added to the reaction solution, and the resultant product was extracted with ethyl acetate (15 mL×3). The combined organic layer was dried over anhydrous magnesium sulfate, and concentrated under reduced pressure. The obtained crude product was purified by silica gel column chromatography (ethyl acetate), whereby 5-chloro-4-[4-chloro-2-fluoro-5-(isobutyloxycarbonyloxy)phenyl]-1,2-tetramethylene-4-pyrazolin-3-one (173 mg, yield: 66%) was obtained as a white solid. $^1$H-NMR (400 MHz, CDCl$_3$): δ0.99 (d, J=6.7 Hz, 6H), 1.86-1.94 (m, 2H), 1.98-2.04 (m, 2H), 2.04 (t and sept, J=6.7 and 6.7 Hz, 1H), 3.59-3.65 (m, 2H), 3.79-3.84 (m, 2H), 4.06 (d, J=6.7 Hz, 2H), 7.24 (d, J=9.0 Hz, 1H), 7.46 (d, J=6.5 Hz, 1H). $^{19}$F-NMR (376 MHz, CDCl$_3$): δ−111.6 (s, 1F).

Example-88

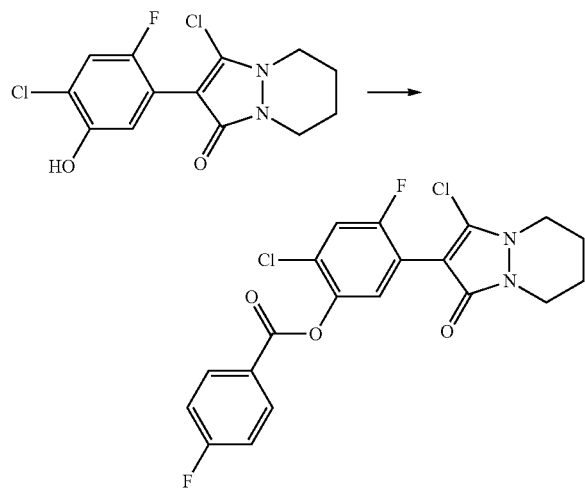

Triethylamine (106 mg, 1.05 mmol) and 4-fluorobenzoyl chloride (166 mg, 1.05 mmol) were added to a solution of 5-chloro-4-(4-chloro-2-fluoro-5-hydroxyphenyl)-1,2-tetramethylene-4-pyrazolin-3-one (300 mg, 0.95 mmol) in dichloromethane (3 mL), followed by stirring at room temperature for 18 hours. After the reaction was completed, the reaction solution was concentrated under reduced pressure, and the obtained residue was purified by silica gel column chromatography (ethyl acetate:methanol=10:1), whereby 5-chloro-4-[4-chloro-2-fluoro-5-(4-fluorobenzoyloxy)phenyl]-1,2-tetramethylene-4-pyrazolin-3-one (293 mg, yield: 70%) was obtained as a white solid. $^1$H-NMR (400 MHz, CDCl$_3$): δ1.87-1.93 (m, 2H), 1.99-2.05 (m, 2H), 3.62-3.64 (m, 2H), 3.81-3.84 (m, 2H), 7.20-7.22 (m, 2H), 7.30 (d, J=8.0 Hz, 1H), 7.51 (d, J=8.0 Hz, 1H), 8.21-8.26 (m, 2H). $^{19}$F-NMR (376 MHz, CDCl$_3$): δ−112 (s, 1F), −104 (s, 1F).

Example-89

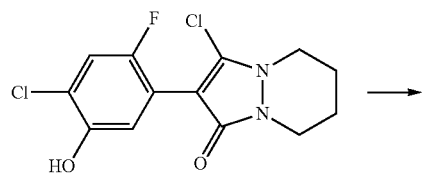

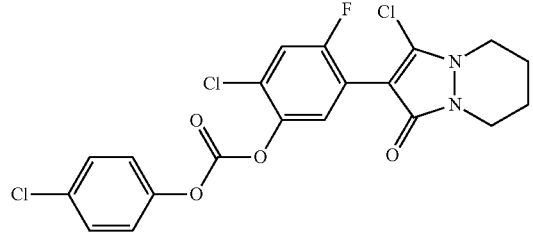

A 37% sodium hydroxide aqueous solution (97 μL) and 4-chlorophenyl chloroformate (166 μL, 1.26 mmol) were added to a solution of 5-chloro-4-(4-chloro-2-fluoro-5-hydroxyphenyl)-1,2-tetramethylene-4-pyrazolin-3-one (200 mg, 0.63 mmol) in DMF (3 mL), followed by stirring at room temperature for 24 hours. After the reaction was completed, water (10 mL) was added to the reaction solution, and the resultant product was extracted with ethyl acetate (15 mL×3). The combined organic layer was dried over anhydrous magnesium sulfate, and concentrated under reduced pressure. The obtained crude product was purified by silica gel column chromatography (ethyl acetate), whereby 5-chloro-4-[4-chloro-5-{(4-chlorophenoxy)carbonyloxy}-2-fluorophenyl]-1,2-tetramethylene-4-pyrazolin-3-one (173 mg, yield: 66%) was obtained as a white solid. $^1$H-NMR (400 MHz, CDCl$_3$): δ1.87-1.95 (m, 2H), 1.98-2.06 (m, 2H), 3.60-3.67 (m, 2H), 3.80-3.87 (m, 2H), 7.23 (d, J=9.1 Hz, 2H), 7.28 (d, J=9.1 Hz, 1H), 7.38 (d, J=9.1 Hz, 2H), 7.57 (d, J=6.6 Hz, 1H). $^{19}$F-NMR (376 MHz, CDCl$_3$): δ−110.6 (s, 1F).

Example-90

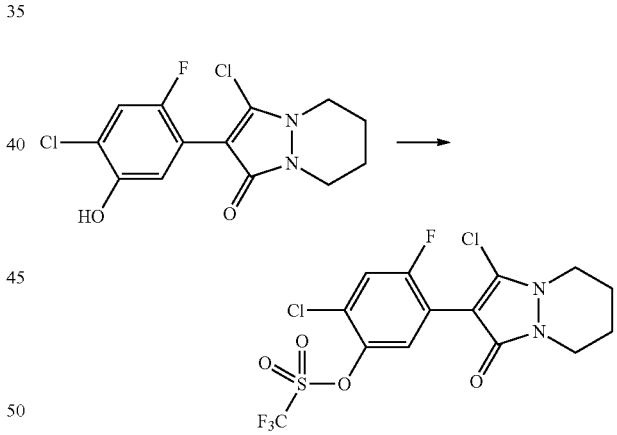

N,N-diisopropyl ethylamine (1.07 mL, 6.29 mmol) and trifluoromethyl sulfonyl chloride (1.03 mL, 6.28 mmol) were added to a solution of 5-chloro-4-(4-chloro-2-fluoro-5-hydroxyphenyl)-1,2-tetramethylene-4-pyrazolin-3-one (1.00 g, 3.15 mmol) in dichloromethane (15 mL) under ice-cooling, followed by stirring at room temperature for 48 hours. After the reaction was completed, the solvent was removed from the reaction mixture under reduced pressure, then, chloroform was added to the residue, and the resultant product was washed sequentially with 2N hydrochloric acid and sodium hydrogencarbonate. The organic layer was dried over anhydrous magnesium sulfate, and concentrated under reduced pressure, and the obtained product was concentrated under reduced pressure, whereby 5-chloro-4-[4-chloro-2-fluoro-5-(trifluoromethyl sulfonyl oxy)phenyl]-1,2-tetramethylene-4-pyrazolin-3-one (994 mg, yield: 70%) was obtained as a white solid. ¹H-NMR (400 MHz, CDCl₃): δ1.89-1.96 (m, 2H), 2.00-2.08 (m, 2H), 3.64-3.69 (m, 2H), 3.81-3.86 (m, 2H), 7.32 (d, J=9.0 Hz, 1H), 7.61 (d, J=6.2 Hz, 1H). ¹⁹F-NMR (376 MHz, CDCl₃): δ−107.5 (s, 1F), −73.2 (s, 3F).

Example-91

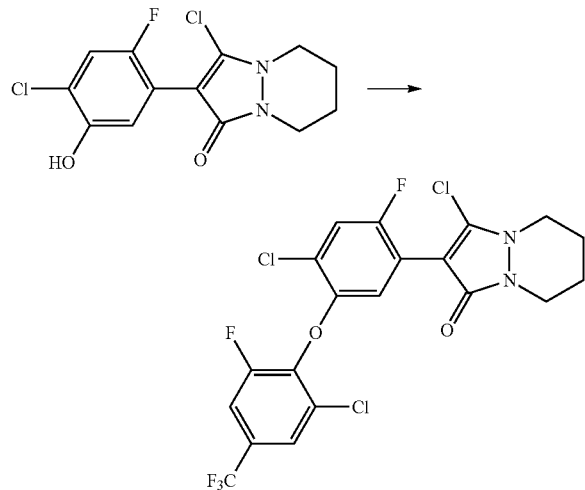

A 55% oil dispersion (0.65 g, 1.49 mmol) of sodium hydride was added to a solution of 5-chloro-4-(4-chloro-2-fluoro-5-hydroxyphenyl)-1,2-tetramethylene-4-pyrazolin-3-one (200 mg, 0.63 mmol) and 3-chloro-4,5-difluorobenzotrifluoride (205 mg, 0.95 mmol) in DMF (3 mL), followed by stirring at room temperature for 24 hours. After the reaction was completed, water (10 mL) was added to the reaction solution, and the resultant product was extracted with ethyl acetate (15 mL×3). The combined organic layer was dried over anhydrous magnesium sulfate, and concentrated under reduced pressure. The obtained crude product was purified by silica gel column chromatography (ethyl acetate), whereby 5-chloro-4-[4-chloro-5-{2-chloro-6-fluoro-4-(trifluoromethyl)phenoxy}-2-fluorophenyl]-1,2-tetramethylene-4-pyrazolin-3-one (84 mg, yield: 26%) was obtained as a white solid. ¹H-NMR (400 MHz, CDCl₃): δ1.83-1.90 (m, 2H), 1.95-2.02 (m, 2H), 3.56-3.61 (m, 2H), 3.74-3.79 (m, 2H), 6.85 (dd, J=0.7 and 6.1 Hz, 1H), 7.28 (d, J=9.0 Hz, 1H), 7.38 (dd, J=1.9 and 9.6 Hz), 7.56 (d, J=1.9 Hz, 1H). ¹⁹F-NMR (376 MHz, CDCl₃): δ−121.8 (s, 1F), −115.1 (s, 1F), −62.6 (s, 3F).

Example-92

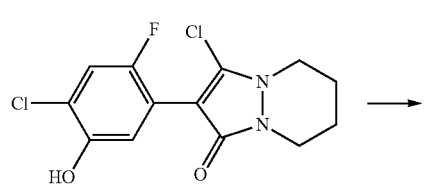

-continued

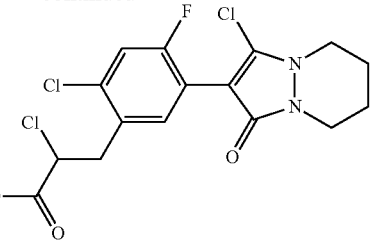

Concentrated hydrochloric acid (0.5 g) was added to a solution of 5-chloro-4-(5-amino-4-chloro-2-fluorophenyl)-1,2-tetramethylene-4-pyrazolin-3-one (659 mg, 2.20 mmol) and copper(I) chloride (28 mg, 1.3 mol %) in acetone (5 mL), and a solution of methyl acrylate (2.27 mL, 25.3 mmol) and sodium nitrite (197 mg, 2.86 mmol) in water (1 mL) was added thereto under ice-cooling, followed by stirring at the same temperature for 3 hours. After the reaction was completed, ice water was added to the reaction solution, and the resultant product was extracted with ethyl acetate (30 mL×3). The combined organic layer was dried over anhydrous magnesium sulfate, and concentrated under reduced pressure. The obtained crude product was purified by silica gel column chromatography (ethyl acetate), whereby methyl 2-chloro-3-[2-chloro-5-(5-chloro-3-oxo-1,2-tetramethylene-4-pyrazolin-4-yl)-4-fluorophenyl]propionate (648 mg, yield: 70%) was obtained as a white solid. ¹H-NMR (400 MHz, CDCl₃): δ1.86-1.94 (m, 2H), 1.98-2.05 (m, 2H), 3.28 (dd, J=6.8 and 14.1 Hz, 1H), 3.49 (dd, J=8.2 and 14.1 Hz, 1H), 3.59-3.64 (m, 2H), 3.78 (s, 3H), 3.80-3.85 (m, 2H), 4.58 (dd, J=6.8 and 8.2 Hz, 1H), 7.20 (d, J=9.3 Hz, 1H), 7.44 (d, J=7.5 Hz, 1H). ¹⁹F-NMR (376 MHz, CDCl₃): δ−110.4 (s, 1F).

Example-93

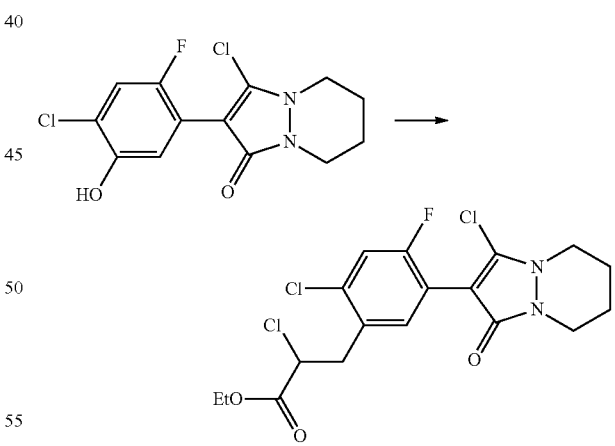

Concentrated hydrochloric acid (0.5 g) was added to a solution of 5-chloro-4-(5-amino-4-chloro-2-fluorophenyl)-1,2-tetramethylene-4-pyrazolin-3-one (659 mg, 2.20 mmol) and copper(I) chloride (28 mg, 1.3 mol %) in acetone (5 mL), and a solution of ethyl acrylate (2.75 mL, 25.3 mmol) and sodium nitrite (197 mg, 2.86 mmol) in water (1 mL) was added thereto under ice-cooling, followed by stirring at the same temperature for 3 hours. After the reaction was completed, ice water was added to the reaction solution, and the resultant product was extracted with ethyl acetate (30 mL×3). The combined organic layer was dried over anhydrous magnesium sulfate, and concentrated under reduced pressure. The obtained crude product was purified by silica gel column chromatography (ethyl acetate), whereby ethyl 2-chloro-3-[2-chloro-5-(5-chloro-3-oxo-1,2-tetramethylene-4-pyrazolin-4-yl)-4-fluorophenyl]propionate (612 mg, yield: 64%) was obtained as a white solid. $^1$H-NMR (400 MHz, CDCl$_3$): δ1.25 (t, J=7.2 Hz, 3H), 1.86-1.94 (m, 2H), 1.98-2.05 (m, 2H), 3.27 (dd, J=8.1 and 14.5 Hz, 1H), 3.49 (dd, J=6.8 and 14.5 Hz, 1H), 3.59-3.64 (m, 2H), 3.80-3.85 (m, 2H), 4.21 (m, 2H), 4.56 (dd, J=6.8 and 8.1 Hz, 1H), 7.20 (d, J=9.4 Hz, 1H), 7.44 (d, J=7.6 Hz, 1H). $^{19}$F-NMR (376 MHz, CDCl$_3$): δ−110.5 (s, 1F).

Example-94

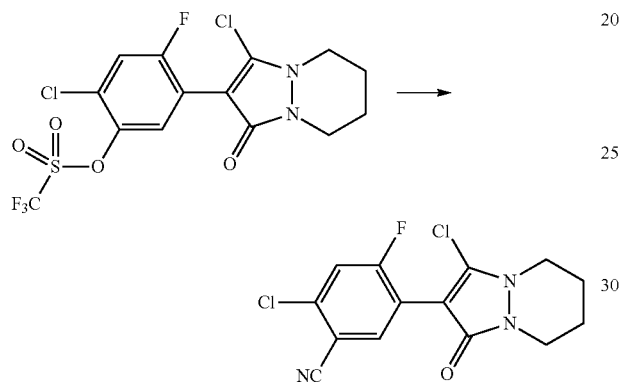

Tetrakistriphenylphosphine palladium (39 mg, 5 mol %) and zinc cyanide (157 mg, 1.34 mmol) was added to a solution of 5-chloro-4-[4-chloro-2-fluoro-5-(trifluoromethyl sulfonyl oxy)phenyl]-1,2-tetramethylene-4-pyrazolin-3-one (300 mg, 0.668 mmol) in DMF (3 mL) in an argon atmosphere, followed by stirring at 120° C. (oil bath temperature) for 12 hours. After the reaction was completed, water (10 mL) was added to the reaction solution, and the resultant product was extracted with ethyl acetate (15 mL×3). The combined organic layer was dried over anhydrous magnesium sulfate, and concentrated under reduced pressure. The obtained crude product was purified by silica gel column chromatography (ethyl acetate), whereby 5-chloro-4-(4-chloro-5-cyano-2-fluorophenyl)-1,2-tetramethylene-4-pyrazolin-3-one (146 mg, yield: 67%) was obtained as a white solid. $^1$H-NMR (400 MHz, CDCl$_3$): δ1.89-1.96 (m, 2H), 2.00-2.08 (m, 2H), 3.64-3.70 (m, 2H), 3.81-3.86 (m, 2H), 7.32 (d, J=9.2 Hz, 1H), 7.91 (d, J=7.0 Hz, 1H). $^{19}$F-NMR (376 MHz, CDCl$_3$): δ−98.8 (s, 1F).

Example-95

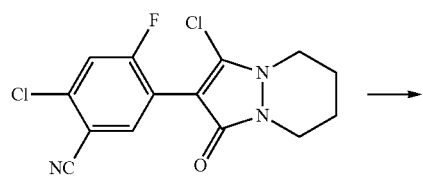

-continued

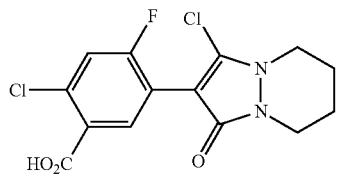

A suspension of 5-chloro-4-(4-chloro-5-cyano-2-fluorophenyl)-1,2-tetramethylene-4-pyrazolin-3-one (100 mg, 0.307 mmol) in 60% sulfuric acid (2 mL) was stirred at 140° C. (oil bath temperature) for 3 hours. After the reaction was completed, water (20 mL) was added to the reaction solution, and the resultant product was extracted with chloroform (15 mL×3). The combined organic layer was dried over anhydrous magnesium sulfate, and concentrated under reduced pressure. The obtained product was concentrated under reduced pressure, whereby 2-chloro-5-(5-chloro-3-oxo-1,2-tetramethylene-4-pyrazolin-4-yl)-4-fluorobenzoic acid (91 mg, yield: 86%) was obtained as a white solid. $^1$H-NMR (400 MHz, CDCl$_3$): δ1.93-2.00 (m, 2H), 2.02-2.10 (m, 2H), 3.70-3.75 (m, 2H), 3.94-3.99 (m, 2H), 7.24 (d, J=9.0 Hz, 1H), 8.23 (d, J=7.7 Hz, 1H). $^{19}$F-NMR (376 MHz, CDCl$_3$): δ−104.7 (s, 1F).

Example-96

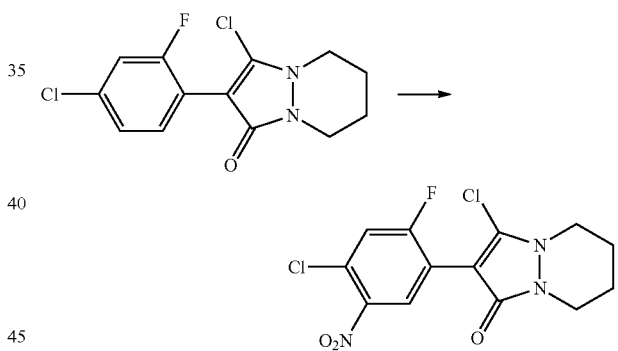

5-Chloro-4-(4-chloro-2-fluorophenyl)-1,2-tetramethylene-4-pyrazolin-3-one (630 mg, 2.09 mmol) was susp was completed in concentrated sulfuric acid (3 mL), and a mixed acid prepared from concentrated nitric acid (0.18 mL, 4.18 mmol) and concentrated sulfuric acid (1 mL) was slowly added thereto under ice-cooling, followed by stirring for 1.5 hours. After the reaction was completed, the reaction solution was poured into ice water, and the resultant product was extracted with ethyl acetate (30 mL×2, 20 mL×1). The organic layer was dried over anhydrous magnesium sulfate, and concentrated under reduced pressure, whereby a crude product (723 mg) was obtained as a brown solid. This was purified by silica gel column chromatography (ethyl acetate), whereby 5-chloro-4-(4-chloro-2-fluoro-5-nitrophenyl)-1,2-tetramethylene-4-pyrazolin-3-one (441 mg, yield: 61%) was obtained as a yellow solid. $^1$H-NMR (400 MHz, CDCl$_3$): δ1.90-1.96 (m, 2H), 2.01-2.07 (m, 2H), 3.67-3.69 (m, 2H), 3.83-3.86 (m, 2H), 7.32 (d, J=9.0 Hz, 1H), 8.22 (d, J=6.6 Hz, 1H). $^{19}$F-NMR (376 MHz, CDCl$_3$): δ−101 (s, 1F).

Example-97

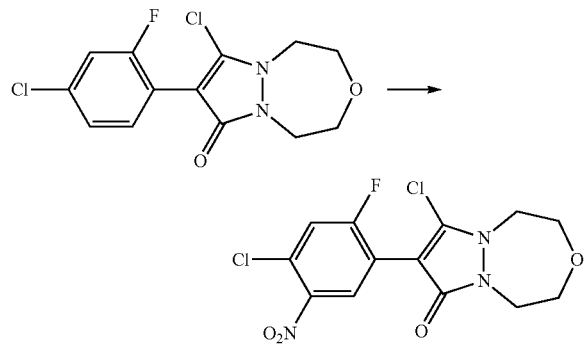

In the same manner as in Example-42, from 5-chloro-4-(4-chloro-2-fluorophenyl)-1,2-oxadiethylene-4-pyrazolin-3-on, 5-chloro-4-(4-chloro-2-fluoro-5-nitrophenyl)-1,2-oxadiethylene-4-pyrazolin-3-one was obtained with a yield of 57%. $^1$H-NMR (400 MHz, CDCl$_3$): δ3.92-3.97 (m, 4H), 4.27-4.31 (m, 4H), 7.34 (d, J=9.1 Hz, 1H), 8.22 (d, J=6.7 Hz, 1H). $^{19}$F-NMR (376 MHz, CDCl$_3$): δ−100.9 (s, 1F).

Example-98

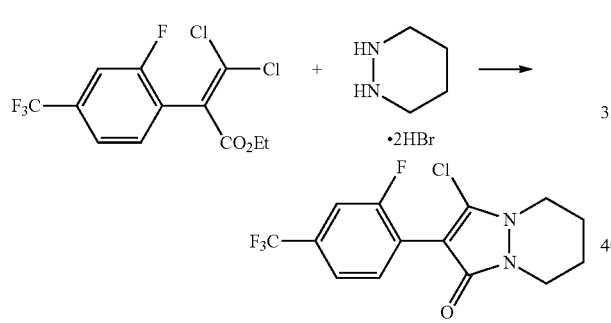

In the same manner as in Example-7, ethyl 3,3-dichloro-2-[2-fluoro-4-(trifluoromethyl)phenyl] acrylate was reacted with hexahydropyridazine dihydrobromide, whereby 5-chloro-4-[2-fluoro-4-(trifluoromethyl)phenyl]-1,2-tetramethylene-4-pyrazolin-3-one was obtained with a yield of 68%. $^1$H-NMR (400 MHz, CDCl$_3$): δ1.88-1.95 (m, 2H), 2.00-2.07 (m, 2H), 3.63-3.68 (m, 2H), 3.82-3.87 (m, 2H), 7.40 (d, J=10.0 Hz, 1H), 7.46 (d, J=7.4 Hz, 1H), 7.68 (t, J=7.4 Hz, 1H). $^{19}$F-NMR (376 MHz, CDCl$_3$): δ−109.1 (s, 1F), −62.8 (s, 3F).

Example-99

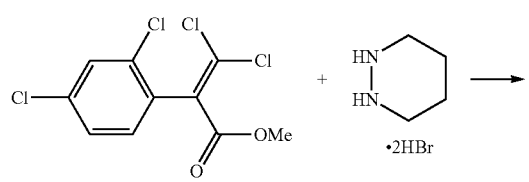

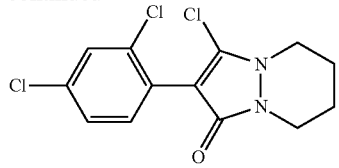

1,4-Dioxane (20 mL) and triethylamine (776 mg, 7.68 mmol) were added to ethyl 3,3-dichloro-2-(2,4-dichlorophenyl)acrylate (600 mg, 1.92 mmol), and hexahydropyridazine dihydrobromide (455 mg, 1.83 mmol) was added thereto, followed by refluxing for 19 hours. After the reaction was completed, water (30 mL) was added to the reaction solution, and the resultant product was extracted with ethyl acetate (30 mL×2, 20 mL×1). The organic layer was dried over anhydrous magnesium sulfate, and concentrated under reduced pressure, whereby an ocherous oily crude product (532 mg) was obtained. This was purified by silica gel column chromatography (ethyl acetate:methanol=10:1), whereby 5-chloro-4-(2,4-dichlorophenyl)-1,2-tetramethylene-4-pyrazolin-3-one (181 mg, yield: 31%) was obtained as a yellow solid. $^1$H-NMR (400 MHz, CDCl$_3$): δ1.88-1.93 (m, 2H), 1.99-2.75 (m, 2H), 3.59-3.62 (m, 2H), 3.82-3.85 (m, 2H), 7.29 (d, J=1.6 Hz, 2H), 7.48 (dd, J=0.9 and 1.6 Hz, 1H).

Example-100

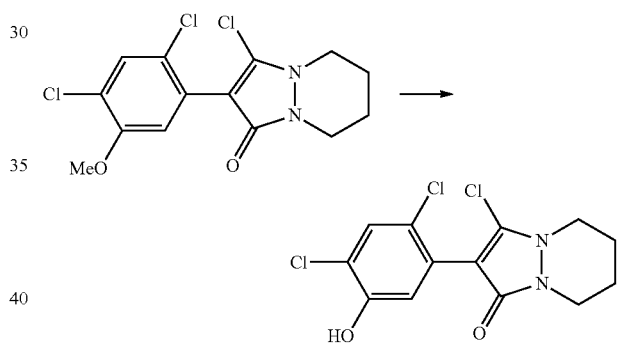

A solution (5.8 mL, 5.8 mmol) of 1M boron tribromide in dichloromethane was added dropwise to a solution of 5-chloro-4-(2,4-dichloro-5-methoxyphenyl)-1,2-tetramethylene-4-pyrazolin-3-one (1.00 g, 2.88 mmol) in dichloromethane (12 mL) at −78° C., followed by stirring at room temperature for 2 hours. After the reaction was completed, the reaction solution was added to ice water, followed by stirring for 1 hour. The precipitated solid was filtered, whereby 5-chloro-4-(2,4-dichloro-5-hydroxyphenyl)-1,2-tetramethylene-4-pyrazolin-3-one (853 mg, yield: 89%) was obtained as a white solid. $^1$H-NMR (400 MHz, DMSO-d$_6$): δ1.76-1.84 (m, 2H), 1.88-1.96 (m, 2H), 3.59-3.70 (m, 4H), 6.91 (s, 1H), 7.56 (s, 1H), 10.6 (s, 1H).

Example-101

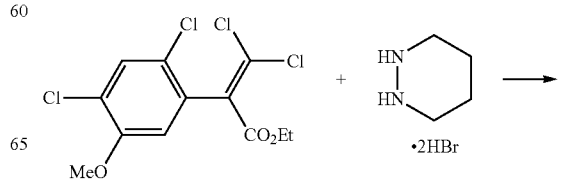

-continued

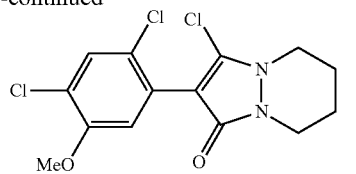

Hexahydropyridazine dihydrobromide (1.21 g, 4.87 mmol) and triethylamine (1.85 mL, 13.3 mmol) were added to a solution of ethyl 3,3-dichloro-2-(2,4-dichloro-5-methoxyphenyl)acrylate (1.52 g, 4.43 mmol) in 1,4-dioxane (25 mL) at room temperature, followed by stirring for 15 hours while heating to reflux. After the reaction was completed, water (100 mL) was added to the reaction solution, and the resultant product was extracted with ethyl acetate (100 mL×3). The organic layer was dried over anhydrous magnesium sulfate, and concentrated under reduced pressure. The obtained crude product was purified by silica gel column chromatography (ethyl acetate), whereby 5-chloro-4-(2,4-dichloro-5-methoxyphenyl)-1,2-tetramethylene-4-pyrazolin-3-one (1.13 g, yield: 74%) was obtained as a white solid. $^1$H-NMR (400 MHz, CDCl$_3$): δ1.87-1.95 (m, 2H), 1.99-2.06 (m, 2H), 3.59-3.64 (m, 2H), 3.82-3.87 (m, 2H), 3.89 (s, 3H), 6.92 (s, 1H), 7.46 (s, 1H).

Example-102

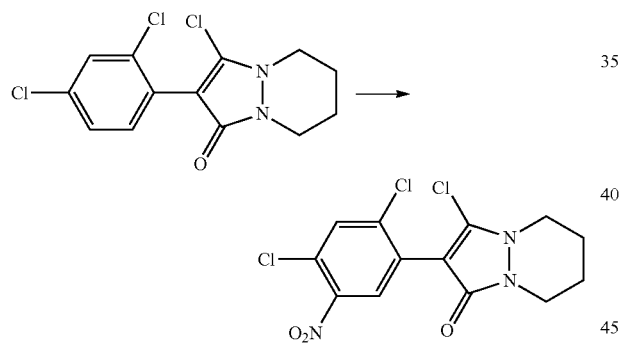

5-Chloro-4-(2,4-dichlorophenyl)-1,2-tetramethylene-4-pyrazolin-3-one (1.0 g, 3.15 mmol) was susp was completed in concentrated sulfuric acid (3 mL), and a mixed acid prepared from concentrated nitric acid (567 mg, 6.30 mmol) and concentrated sulfuric acid (0.2 mL) was slowly added thereto at room temperature, followed by stirring for 4 hours. After the reaction was completed, the reaction solution was poured into ice water, and the resultant product was extracted with ethyl acetate (50 mL×1, 20 mL×2). The organic layer was washed with a saturated saline solution (10 mL), dried over anhydrous magnesium sulfate, and concentrated under reduced pressure, whereby a brown oily crude product (1.10 g) was obtained. This was purified by silica gel column chromatography (ethyl acetate:methanol=10:1), whereby 5-chloro-4-(2,4-dichloro-5-nitrophenyl)-1,2-tetramethylene-4-pyrazolin-3-one (527 mg, yield: 46%) was obtained as a brown solid. $^1$H-NMR (400 MHz, CDCl$_3$): δ1.91-1.96 (m, 2H), 2.02-2.08 (m, 2H), 3.66-3.69 (m, 2H), 3.83-3.86 (m, 2H), 7.68 (s, 1H), 8.00 (s, 1H).

Example-103

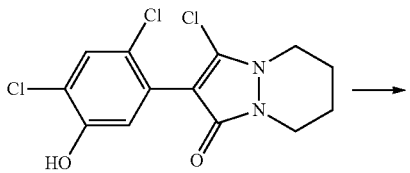

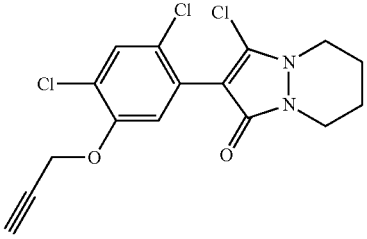

Potassium carbonate (129 mg, 0.90 mmol) and propargyl bromide (0.113 g, 0.90 mmol) were added to a solution of 5-chloro-4-(2,4-dichloro-5-hydroxyphenyl)-1,2-tetramethylene-4-pyrazolin-3-one (200 mg, 0.60 mmol) in DMF (3 mL), followed by stirring at room temperature for 24 hours. After the reaction was completed, water (20 mL) was added to the reaction solution, and the resultant product was extracted with toluene (20 mL×3). The organic layer was washed with a saturated saline solution, dried over anhydrous magnesium sulfate, and concentrated under reduced pressure, whereby a crude product was obtained. This was purified by silica gel column chromatography (ethyl acetate: methanol=9:1), whereby 5-chloro-4-[2,4-dichloro-5-(propargyloxy)phenyl]-1,2-tetramethylene-4-pyrazolin-3-one (204 mg, yield: 92%) was obtained as a white solid. $^1$H-NMR (400 MHz, CDCl$_3$): δ1.88-1.95 (m, 2H), 1.99-2.07 (m, 2H), 2.56 (t, J=2.4 Hz, 1H), 3.60-3.66 (m, 2H), 3.82-3.87 (m, 2H), 4.77 (d, J=2.4 Hz, 2H), 7.05 (s, 1H), 7.49 (s, 1H).

Example-104

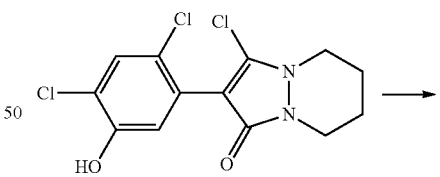

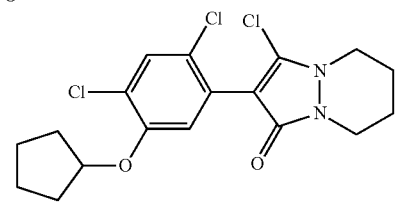

In the same manner as in Example-12, 5-chloro-4-(2,4-dichloro-5-hydroxyphenyl)-1,2-tetramethylene-4-pyrazolin-3-one was reacted with cyclopentyl bromide, whereby 5-chloro-4-[5-(cyclopentyloxy)-2,4-dichlorophenyl]-1,2-tetramethylene-4-pyrazolin-3-one was obtained with a yield of 91%. $^1$H-NMR (400 MHz, CDCl$_3$): δ1.59-1.66 (m, 2H), 1.77-1.94 (m, 8H), 1.98-2.06 (m, 2H), 3.58-3.63 (m, 2H), 3.82-3.86 (m, 2H), 4.78 (m, 1H), 6.90 (s, 1H), 7.44 (s, 1H).

Reference Example-27

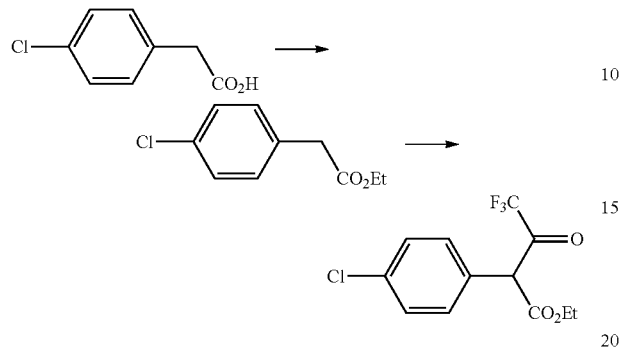

Concentrated sulfuric acid (287 mg) and ethanol (10.8 g, 234 mmol) were added to a solution of 2-(4-chlorophenyl) acetic acid (10.0 g, 59.6 mmol) in benzene (10 mL), followed by stirring for 6 hours while heating to reflux. After the reaction was completed, distilled water (100 mL) was added thereto, and the resultant product was extracted with ether (50 mL×3). The mixed organic layer was dried over anhydrous magnesium sulfate, and the solvent was distilled off under reduced pressure, whereby ethyl 2-(4-chlorophenyl)acetate (yield: quantitative) was obtained as a colorless oily material. $^1$H-NMR (400 MHz, CDCl$_3$): δ3.54 (s, 2H), 3.70 (s, 3H), 7.21-7.33 (m, 4H).

Ethyl trifluoroacetate (3.57 g, 25.2 mmol) and sodium (580 mg, 25.2 mmol) were added to a solution of ethyl 2-(4-chlorophenyl)acetate (5.0 g, 25.2 mmol) in ether (8 mL), followed by heating to reflux for 24 hours. After the reaction was completed, 2N hydrochloric acid (50 mL) was added thereto, and the resultant product was extracted with ether (20 mL×3). The mixed organic layer was washed with water (20 mL×3), and dried over anhydrous magnesium sulfate, and the solvent was concentrated under reduced pressure. The obtained residue was purified by silica gel column chromatography (hexane:ethyl acetate=4:1), whereby ethyl 2-(4-chlorophenyl)-4,4,4-trifluoro-3-oxobutanoate (2.42 g, yield: 34%) was obtained as a yellow solid.

Example-105

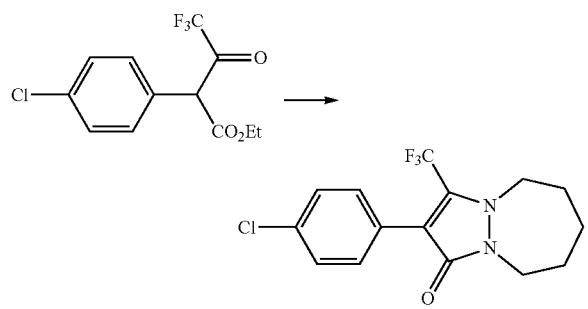

1,2-Diazepane dihydrobromide (427 mg, 1.63 mmol) and triethylamine (235 mg, 2.32 mmol) were added to a solution of ethyl 2-(4-chlorophenyl)-4,4,4-trifluoro-3-oxobutanoate (400 mg, 1.36 mmol) in 1,4-dioxane (5 mL) at room temperature, followed by stirring for 12 hours while heating to reflux. After the reaction was completed, the resultant product was diluted with ethyl acetate (20 mL), washed with distilled water (10 mL×2), and dried over anhydrous magnesium sulfate, and the solvent was concentrated under reduced pressure. The concentrated residue was purified by silica gel column chromatography (ethyl acetate), whereby 4-(4-chlorophenyl)-1,2-pentamethylene-5-trifluoromethyl-4-pyrazolin-3-one (100 mg, yield: 22%) was obtained as a yellow solid. $^1$H-NMR (400 MHz, CDCl$_3$): δ1.79-1.92 (m, 6H), 4.03-4.10 (m, 2H), 4.14-4.20 (m, 2H), 7.35 (brs, 4H). $^{19}$F-NMR (376 MHz, CDCl$_3$): δ−57.3 (s, 3F).

Reference Example-28

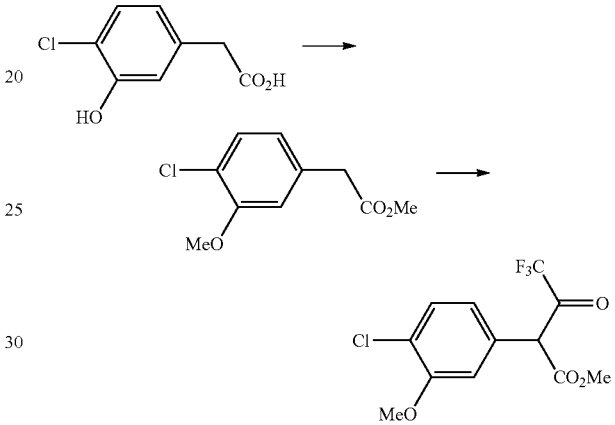

Potassium carbonate (22.2 g, 161 mmol) and dimethyl sulfate (15.2 g, 121 mmol) were added to a solution of 2-(4-chloro-3-hydroxyphenyl) acetic acid (15.0 g, 80.4 mmol) in acetone (200 mL), followed by stirring at room temperature for 4 hours. After the reaction was completed, water (100 mL) was added to the reaction mixture, and the resultant product was extracted with ether (50 mL×2). The mixed organic layer was dried over anhydrous magnesium sulfate, and concentrated under reduced pressure. To a solution of this in DMF (50 mL), potassium carbonate (7.4 g, 53.6 mmol) and methyl iodide (3.80 g, 26.8 mmol) were added, followed by stirring at room temperature for 12 hours. After the reaction was completed, water (100 mL) was added thereto, and the resultant product was extracted with ether (50 mL×2). The mixed organic layer was washed with water (20 mL×4), and dried over anhydrous magnesium sulfate, and the solvent was distilled off under reduced pressure, whereby methyl 2-(4-chloro-3-methoxyphenyl)acetate was obtained as a yellow oily material. $^1$H-NMR (400 MHz, CDCl$_3$): δ3.54 (s, 2H), 3.70 (s, 3H), 3.89 (s, 3H), 6.88 (d, J=8.4 Hz, 1H), 7.14 (dd, J=2.1 and 8.4 Hz, 1H), 7.30 (d, J=2.1 Hz, 1H).

Ethyl trifluoroacetate (4.69 g, 25.5 mmol) and sodium (391 mg, 17.0 mmol) were added to a solution of methyl 2-(4-chloro-3-methoxyphenyl)acetate (5.0 g, 17.0 mmol) in ether (10 mL), followed by heating to reflux for 24 hours. After the reaction was completed, 2N hydrochloric acid (50 mL) was added thereto, and the resultant product was extracted with ether (20 mL×3). The mixed organic layer was washed with water (20 mL×3), and dried over anhydrous magnesium sulfate, and the solvent was distilled off under reduced pressure. The obtained residue was purified by silica gel column chromatography (hexane:ethyl acetate=4:1), whereby methyl 2-(4-chloro-3-methoxyphenyl)-4,4,4-trifluoro-3-oxobutanoate (1.58 g, yield: 30%) was obtained as a yellow solid.

Example-106

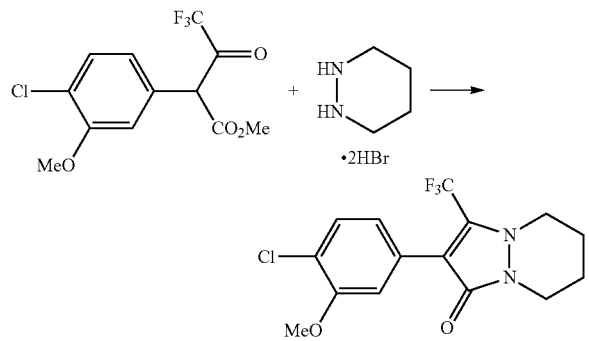

Tetrahydropyridazine dihydrobromide (1.51 g, 6.10 mmol) and triethylamine (1.24 g, 12.2 mmol) were added to a solution of methyl 2-(4-chloro-3-methoxyphenyl)-4,4,4-trifluoro-3-oxobutanoate (1.58 g, 5.09 mmol) in 1,4-dioxane (15 mL) at room temperature, followed by stirring for 24 hours while heating to reflux. After the reaction was completed, the resultant product was diluted with ethyl acetate (100 mL), washed with distilled water (50 mL×2), and dried over anhydrous magnesium sulfate, and the solvent was distilled off under reduced pressure. To this, 1,4-dioxane and a catalytic amount of p-toluene sulfonic acid were added, followed by stirring for 12 hours while heating to reflux again. After the reaction was completed, the resultant product was concentrated under reduced pressure. The concentrated residue was purified by silica gel column chromatography (ethyl acetate:methanol=95:5), whereby 4-(4-chloro-3-methoxyphenyl)-1,2-tetramethylene-5-trifluoromethyl-4-pyrazolin-3-one (752 mg, yield: 43%) was obtained as a white solid. $^1$H-NMR (400 MHz, CDCl$_3$): δ1.86-1.93 (m, 2H), 2.01-2.08 (m, 2H), 3.58-3.63 (m, 2H), 3.88-3.93 (m, 2H), 3.92 (s, 3H), 6.95 (d, J=8.6 Hz, 1H), 7.31 (dd, J=2.0 and 8.6 Hz, 1H), 7.44 (d, J=2.0 Hz, 1H). $^{19}$F-NMR (376 MHz, CDCl$_3$): δ−58.5 (s, 1F).

Reference Example-29

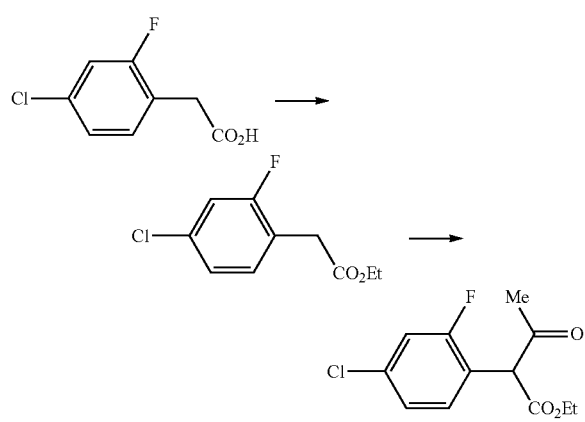

Concentrated sulfuric acid (260 mg) was added to a solution of 2-(4-chloro-2-fluorophenyl) acetic acid (10.0 g, 53.0 mmol) in ethanol (24.8 mL), followed by stirring for 12 hours while heating to reflux. After the reaction was completed, distilled water (100 mL) was added thereto, and the resultant product was extracted with ether (50 mL×3). The mixed organic layer was dried over anhydrous magnesium sulfate, and the solvent was distilled off under reduced pressure, whereby ethyl 2-(4-chloro-2-fluorophenyl)acetate (yield: quantitative) was obtained as a white solid.

n-Butyl lithium (2.6 M hexane solution, 7.7 mL) was added to a solution of N,N-diisopropylamine (2.01 g, 19.9 mmol) in THF (15 mL) in a dry ice/acetone bath, and the temperature was raised to 0° C., whereby a lithium diisopropylamide solution was prepared. To this solution, a solution of ethyl 2-(4-chloro-2-fluorophenyl)acetate (3.60 g, 16.6 mmol) in THF (5 mL) and acetyl chloride (1.56 g, 19.9 mmol) were added while cooling to −20° C., followed by stirring at room temperature for 12 hours. After the reaction was completed, water (100 mL) was added to the reaction mixture, and the resultant product was extracted with ether (50 mL×2). The mixed organic layer was dried over anhydrous magnesium sulfate, and concentrated under reduced pressure. The concentrated residue was purified by silica gel column chromatography (hexane:ethyl acetate=4:1), whereby ethyl 2-(4-chloro-2-fluorophenyl)-3-oxobutanoate (1.62 g, yield: 38%) was obtained as a yellow solid.

Example-107

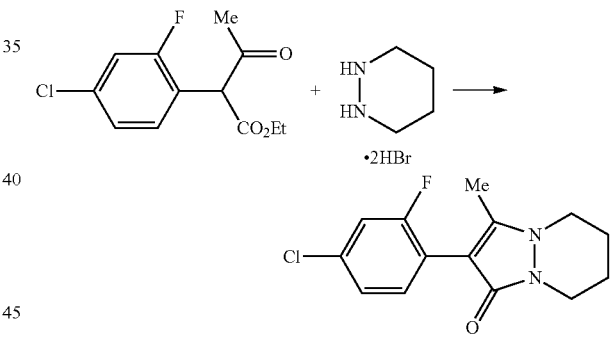

Tetrahydropyridazine dihydrobromide (919 mg, 3.71 mmol) and triethylamine (375 mg, 3.71 mmol) were added to a solution of ethyl 2-(4-chloro-2-fluorophenyl)-3-oxobutanoate (800 mg, 3.09 mmol) in 1,4-dioxane (8 mL) at room temperature, followed by stirring for 12 hours while heating to reflux. After the reaction was completed, the resultant product was diluted with ethyl acetate (20 mL), washed with distilled water (10 mL×2), and dried over anhydrous magnesium sulfate, and the solvent was concentrated under reduced pressure. The concentrated residue was purified by silica gel column chromatography (ethyl acetate), whereby 4-(4-chloro-2-fluorophenyl)-5-methyl-1,2-tetramethylene-4-pyrazolin-3-one (292 mg, yield: 34%) was obtained as a white solid. $^1$H-NMR (400 MHz, CDCl$_3$): δ1.85-1.93 (m, 2H), 1.95-2.02 (m, 2H), 2.10 (d, J=2.5 Hz, 3H), 3.49-3.55 (m, 2H), 3.77-3.83 (m, 2H), 7.13 (dd, J=2.1 and 9.9 Hz, 1H), 7.18 (ddd, J=0.5, 2.1 and 8.2 Hz, 1H), 7.49 (dd, J=8.2 and 8.2 Hz, 1H). $^{19}$F-NMR (376 MHz, CDCl$_3$): δ−112.0 (s, 1F).

Reference Example-30

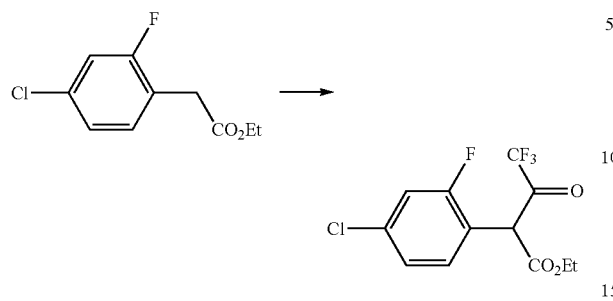

Ethyl trifluoroacetate (8.03 g, 43.6 mmol) and sodium (669 mg, 29.1 mmol) were added to a solution of ethyl 2-(4-chloro-2-fluorophenyl)acetate (6.3 g, 29.1 mmol) in ether (15 mL), followed by heating to reflux for hours. After the reaction was completed, 2N hydrochloric acid (20 mL) was added thereto, and the resultant product was extracted with ether (20 mL×3). The mixed organic layer was washed with water (20 mL×3), and dried over anhydrous magnesium sulfate, and the solvent was concentrated under reduced pressure. The obtained residue was purified by silica gel column chromatography (hexane:ethyl acetate=4:1), whereby ethyl 2-(4-chloro-2-fluorophenyl)-4,4,4-trifluoro-3-oxobutanoate (1.06 g, yield: 15%) was obtained as a red brown oily material.

Example-108

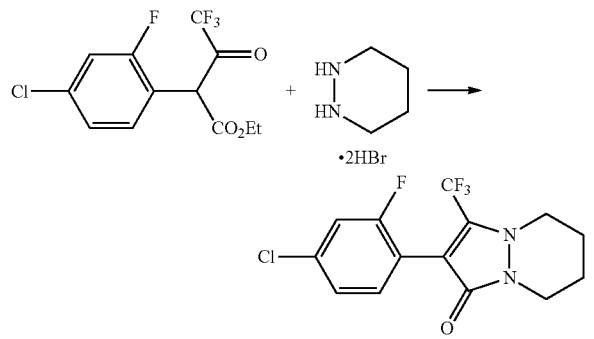

Tetrahydropyridazine dihydrobromide (1.01 g, 4.07 mmol) and triethylamine (823 mg, 8.14 mmol) were added to a solution of ethyl 2-(4-chloro-2-fluorophenyl)-4,4,4-trifluoro-3-oxobutanoate (1.06 g, 3.39 mmol) in 1,4-dioxane (10 mL) at room temperature, followed by stirring for 24 hours while heating to reflux. After the reaction was completed, distilled water (50 mL) was added thereto, and the resultant product was extracted with ethyl acetate (30 mL×3). The mixed organic layer was washed with water (20 mL×3), and dried over anhydrous magnesium sulfate, and the solvent was concentrated under reduced pressure. The obtained residue was purified by silica gel column chromatography (hexane:ethyl acetate=1:1), whereby 4-(4-chloro-2-fluorophenyl)-1,2-tetramethylene-5-trifluoromethyl-4-pyrazolin-3-one (253 mg, yield: 21%) was obtained as a pale yellow solid. $^{1}$H-NMR (400 MHz, CDCl$_3$): δ1.89-1.97 (m, 2H), 2.01-2.10 (m, 2H), 3.66-3.72 (m, 2H), 3.89-3.95 (m, 2H), 7.15 (dd, J=2.0 and 9.4 Hz, 1H), 7.20 (ddd, J=0.6, 2.0 and 8.0 Hz, 1H), 7.37 (dd, J=8.0 Hz, 1H). $^{19}$F-NMR (376 MHz, CDCl$_3$): δ−111.5 (m, 1F). −61.5 (m, 3F).

Example-109

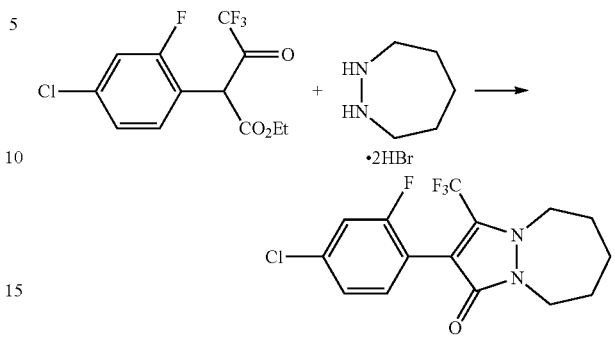

1,2-Diazepane dihydrobromide (503 mg, 1.92 mmol) and triethylamine (388 mg, 3.84 mmol) were added to a solution of ethyl 2-(4-chloro-2-fluorophenyl)-4,4,4-trifluoro-3-oxobutanoate (500 mg, 1.60 mmol) in 1,4-dioxane (10 mL) at room temperature, followed by stirring for 3 hours while heating to reflux. After the reaction was completed, distilled water (30 mL) was added thereto, and the resultant product was extracted with ethyl acetate (30 mL×3). The mixed organic layer was washed with water (20 mL×3), and dried over anhydrous magnesium sulfate, and the solvent was concentrated under reduced pressure. To this, 1,4-dioxane and a catalytic amount of p-toluene sulfonic acid were added, followed by stirring for 3 hours while heating to reflux again. After the reaction was completed, distilled water (30 mL) was added thereto, and the resultant product was extracted with ethyl acetate (30 mL×3). The mixed organic layer was washed with water (20 mL×3), and dried over anhydrous magnesium sulfate, and the solvent was concentrated under reduced pressure. The concentrated residue was purified by silica gel column chromatography (ethyl acetate:methanol=95:5), whereby 4-(4-chloro-2-fluorophenyl)-1,2-pentamethylene-5-trifluoromethyl-4-pyrazolin-3-one (226 mg, yield: 40%) was obtained as a pale yellow solid. $^{1}$H-NMR (400 MHz, CDCl$_3$): δ1.81-1.92 (m, 6H), 4.06-4.12 (m, 2H), 4.16-4.22 (m, 2H), 7.13 (dd, J=2.0 and 9.5 Hz, 1H), 7.18 (ddd, J=0.8, 2.0 and 8.0 Hz, 1H), 7.41 (dd, J=8.0 Hz, 1H). $^{19}$F-NMR (376 MHz, CDCl$_3$): δ−111.9 (m, 1F). −60.3 (m, 3F).

Example-110

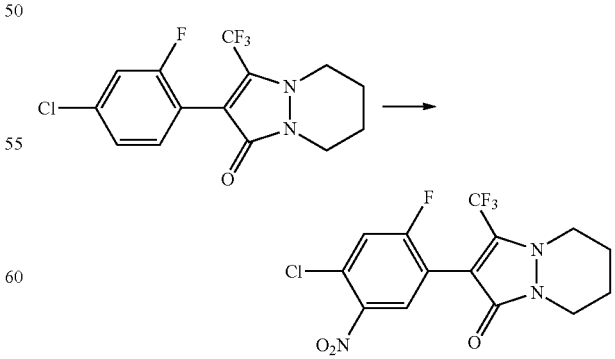

69% nitric acid (108 mg, 1.71 mmol) was added to a suspension of 4-(4-chloro-2-fluorophenyl)-1,2-tetramethylene-5-trifluoromethyl-4-pyrazolin-3-one (300 mg, 0.857 mmol) in concentrated sulfuric acid (3 mL) under ice-cooling, followed by stirring at the same temperature for 1 hour. After the reaction was completed, the reaction solution was poured into ice water (30 g), and the product was extracted with ethyl acetate (20×3). The mixed organic layer was washed with water. The obtained organic layer was dried over anhydrous magnesium sulfate, and concentrated under reduced pressure, whereby 4-(4-chloro-2-fluoro-5-nitrophenyl)-1,2-tetramethylene-5-trifluoromethyl-4-pyrazolin-3-one (272 mg, yield: 83%) was obtained as a yellow solid. $^1$H-NMR (400 MHz, CDCl$_3$): δ1.89-1.97 (m, 2H), 2.01-2.10 (m, 2H), 3.66-3.72 (m, 2H), 3.89-3.95 (m, 2H), 7.15 (dd, J=2.0 and 9.4 Hz, 1H), 7.20 (ddd, J=0.6, 2.0 and 8.0 Hz, 1H), 7.37 (dd, J=8.0 Hz, 1H). $^{19}$F-NMR (376 MHz, CDCl$_3$): δ−111.5 (q, J=7.8 Hz, 1F). −61.5 (d, J=7.8 Hz, 3F).

Example-111

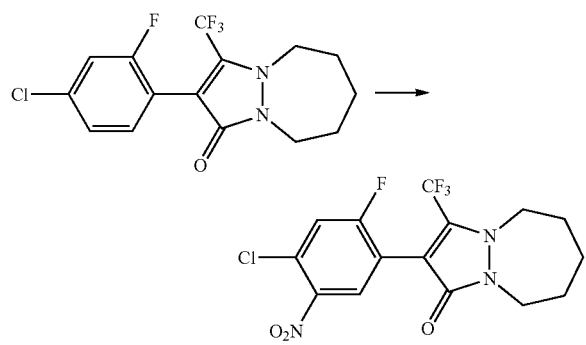

69% nitric acid (54 mg, 0.602 mmol) was added to a suspension of 4-(4-chloro-2-fluorophenyl)-1,2-pentamethylene-5-trifluoromethyl-4-pyrazolin-3-one (110 mg, 0.301 mmol) in concentrated sulfuric acid (1.5 mL) under ice-cooling, followed by stirring at the same temperature for 1 hour. After the reaction was completed, the reaction solution was poured into ice water (30 g), and the product was extracted with ethyl acetate (20×3). The mixed organic layer was washed with water. The obtained organic layer was dried over anhydrous magnesium sulfate, and concentrated under reduced pressure, whereby 4-(4-chloro-2-fluoro-5-nitrophenyl)-1,2-pentamethylene-5-trifluoromethyl-4-pyrazolin-3-one (115 mg, yield: 97%) was obtained as a yellow solid. $^1$H-NMR (400 MHz, CDCl$_3$): δ1.84-1.95 (m, 6H), 4.12-4.24 (m, 2H), 7.32 (d, J=8.8 Hz, 1H), 8.17 (d, J=6.8 Hz, 1H). $^{19}$F-NMR (376 MHz, CDCl$_3$): δ−104.1 (q, J=8.4 Hz, 1F). −60.3 (d, J=8.4 Hz, 3F).

Reference Example-31

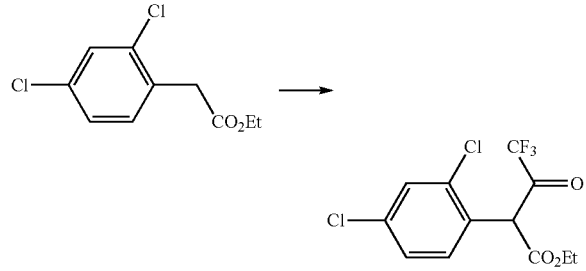

Ethyl trifluoroacetate (3.05 g, 21.5 mmol) and sodium (495 mg, 21.5 mmol) were added to a solution of ethyl 2-(2,4-dichlorophenyl)acetate (5.0 g, 21.5 mmol) in ether (8 mL), followed by heating to reflux for 12 hours. After the reaction was completed, 2N hydrochloric acid (20 mL) was added thereto, and the resultant product was extracted with ether (20 mL×3). The mixed organic layer was washed with water (20 mL×3), and dried over anhydrous magnesium sulfate, and the solvent was concentrated under reduced pressure. The obtained residue was purified by silica gel column chromatography (hexane:ethyl acetate=4:1), whereby ethyl 2-(2,4-dichlorophenyl)-4,4,4-trifluoro-3-oxobutanoate (482 g, yield: 7%) was obtained as a yellow oily material.

Example-112

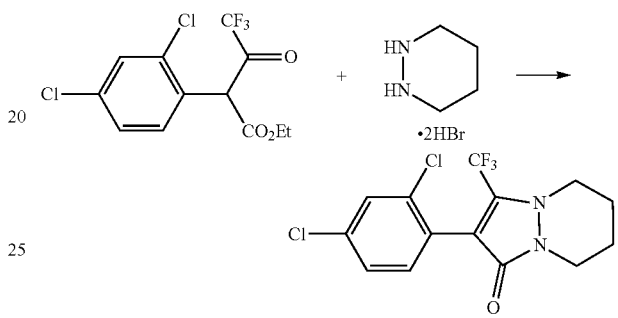

Tetrahydropyridazine dihydrobromide (434 mg, 1.75 mmol) and triethylamine (365 mg, 3.50 mmol) were added to a solution of ethyl 2-(2,4-dichlorophenyl)-4,4,4-trifluoro-3-oxobutanoate (480 mg, 1.46 mmol) in 1,4-dioxane (5 mL) at room temperature, followed by stirring for 2 hours while heating to reflux. After the reaction was completed, distilled water (50 mL) was added thereto, and the resultant product was extracted with ethyl acetate (30 mL×3). The mixed organic layer was washed with water (20 mL×3), and dried over anhydrous magnesium sulfate, and the solvent was concentrated under reduced pressure. The obtained residue was purified by silica gel column chromatography (hexane:ethyl acetate=1:1), whereby 4-(2,4-dichlorophenyl)-1,2-tetramethylene-5-trifluoromethyl-4-pyrazolin-3-one (125 mg, yield: 24%) was obtained as a pale yellow solid. $^1$H-NMR (400 MHz, CDCl$_3$): δ1.89-1.98 (m, 2H), 2.03-2.11 (m, 2H), 3.63-3.75 (m, 2H), 3.82-4.02 (m, 2H), 7.21 (d, J=8.2 Hz, 1H), 7.28 (dd, J=2.1 and 8.2 Hz, 1H), 7.48 (d, J=2.1 Hz, 1H). $^{19}$F-NMR (376 MHz, CDCl$_3$): δ−60.4 (m, 3F).

Reference Example-32

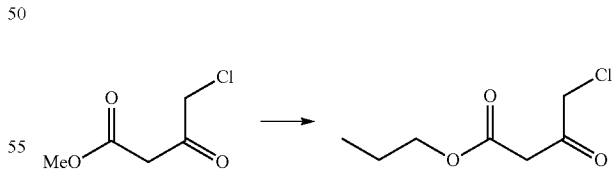

Methyl 4-chloroacetoacetate (5 g, 33.3 mmol) was added to a solution of propyl alcohol (15.5 g, 258 mmol) and 4-(dimethylamino)pyridine (500 mg, 4.09 mmol) in toluene (50 mL), followed by refluxing for 19 hours. After the reaction was completed, the reaction solution was concentrated under reduced pressure, and the residue was purified by silica gel column chromatography (hexane:ethyl acetate=8:2), whereby propyl 4-chloroacetoacetate (2.88 g, yield: 48%) was obtained as an orange oily material. $^1$H-NMR (400 MHz, CDCl$_3$): δ0.95 (keto t, J=4.0 Hz, 2.7H), 0.96 (enol t, J=4.0 Hz, 0.3H), 1.68 (keto sext, J=4.0 Hz, 1.8H), 1.69 (enol sext, J=4.0 Hz, 0.2H), 3.67 (keto s, 1.8H), 4.12 (keto t, J=4.0 Hz, 1.8H), 4.12 (enol, J=4.0 Hz, 0.2H), 4.23 (s, 2H), 5.34 (en of s, 0.1H), 12.1 (enol s, 0.1H).

Reference Example-33

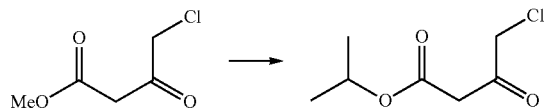

Methyl 4-chloroacetoacetate (5 g, 33.3 mmol) was added to a solution of isopropyl alcohol (15.5 g, 258 mmol) and 4-(dimethylamino)pyridine (500 mg, 4.09 mmol) in toluene (50 mL), followed by refluxing for 18 hours. After the reaction was completed, the reaction solution was concentrated under reduced pressure, and the residue was purified by silica gel column chromatography (hexane:ethyl acetate=8:1), whereby isopropyl 4-chloroacetoacetate (2.27 g, yield: 38%) was obtained as an orange oily material. $^1$H-NMR (400 MHz, CDCl$_3$): δ1.27 (keto d, J=6.3 Hz, 5.4H), 1.28 (enol d, J=6.3 Hz, 0.6H), 3.63 (keto s, 1.8H), 4.22 (s, 2H), 5.08 (keto sept, J=6.3 Hz, 0.9H), 5.09 (enol sept, J=6.3 Hz, 0.1H), 5.29 (enol s, 0.1H), 12.1 (enol brs, 0.1H).

Reference Example-34

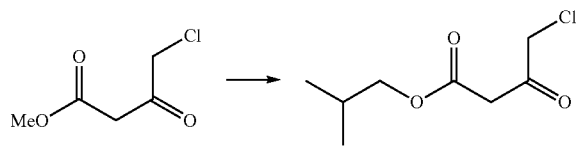

Methyl 4-chloroacetoacetate (7 g, 46.5 mmol) was added to a solution of isobutyl alcohol (26.5 g, 358 mmol) and 4-(dimethyl amino) pyridine (682 mg, 5.58 mmol) in toluene (60 mL), followed by refluxing for 18 hours. After the reaction was completed, the reaction solution was concentrated under reduced pressure, and the residue was purified by silica gel column chromatography (hexane:ethyl acetate=8:2), whereby isobutyl 4-chloroacetoacetate (5.7 g, yield: 64%) was obtained as an orange oily material. $^1$H-NMR (400 MHz, CDCl$_3$): δ0.94 (keto d, J=6.7 Hz, 5.4H), 0.95 (enol d, J=6.7 Hz, 0.6H), 1.96 (keto h, J=6.7 Hz, 0.9H), 1.98 (enol h, J=6.7 Hz, 0.1H), 3.68 (keto s, 1.8H), 3.95 (keto d, J=6.7 Hz, 1.8H), 3.96 (enol d, J=6.7 Hz, 0.2H), 4.23 (s, 2H), 5.35 (enol s, 0.1H), 12.0 (enol s, 0.1H).

Reference Example-35

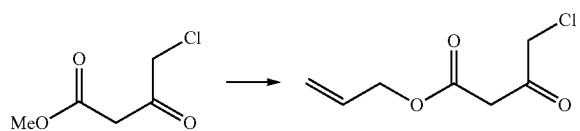

Methyl 4-chloroacetoacetate (5 g, 33.3 mmol) was added to a solution of allyl alcohol (15 g, 258 mmol) and 4-(dimethyl amino) pyridine (500 mg, 4.09 mmol) in toluene (50 mL), followed by refluxing for 25 hours. After the reaction was completed, the reaction solution was concentrated under reduced pressure, and the residue was purified by silica gel column chromatography (hexane:ethyl acetate=8:2), whereby allyl 4-chloroacetoacetate (2.6 g, yield: 44%) was obtained as a pale yellow oily material. $^1$H-NMR (400 MHz, CDCl$_3$): δ3.70 (s, 2H), 4.23 (s, 2H), 4.67 (dt, J=4.0 and 8.0 Hz, 2H), 5.26-5.38 (m, 2H), 5.87-5.95 (m, 1H).

Reference Example-36

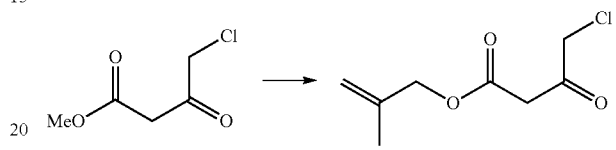

Methyl 4-chloroacetoacetate (7 g, 46.5 mmol) was added to a solution of 2-methyl-2-propen-1-ol (26.3 g, 358 mmol) and 4-(dimethyl amino) pyridine (682 mg, 5.58 mmol) in toluene (60 mL), followed by refluxing for 18 hours. After the reaction was completed, the reaction solution was concentrated under reduced pressure, and the residue was purified by silica gel column chromatography (hexane:ethyl acetate=8:2), whereby methallyl 4-chloroacetoacetate (6.2 g, yield: 70%) was obtained as an orange oily material. $^1$H-NMR (400 MHz, CDCl$_3$): δ1.77 (keto s, 2.7H), 1.78 (enol s, 0.3H), 3.71 (keto s, 1.8H), 4.28 (s, 2H), 4.58 (keto s, 1.8H), 4.60 (enol s, 0.2H), 4.97-5.01 (m, 2H), 5.40 (enol s, 0.1H), 12.0 (enol brs, 0.1H).

Reference Example-37

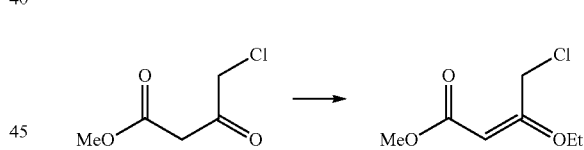

Concentrated sulfuric acid (one drop) was added to a mixture of methyl 4-chloroacetoacetate (1.10 g, 7.0 mmol) and triethyl orthoformate (1.16 g, 7.7 mmol), followed by stirring at room temperature for 90 hours. After the reaction was completed, the reaction solution was filtered using a silica pad, and eluted with a 4:1 mixed solvent of hexane and ethyl acetate, and the eluate was concentrated under reduced pressure, whereby a pale yellow oily material (1.37 g) was obtained. To this, chloroform (40 mL) and phosphorus pentaoxide (1.04 g, 7.32 mmol) were added, followed by refluxing for 2 hours. After the reaction was completed, the reaction solution was filtered using a silica pad, and eluted with a 4:1 mixed solvent of hexane and ethyl acetate, and the eluate was concentrated under reduced pressure, whereby methyl (E)-4-chloro-3-ethoxy-2-butenoate (881 mg, yield: 70%) was obtained as a colorless oily material. $^1$H-NMR (400 MHz, CDCl$_3$): δ1.39 (t, J=6.9 Hz, 3H), 3.71 (s, 3H), 3.89 (q, J=6.9 Hz, 2H), 4.64 (s, 2H), 5.11 (s, 1H).

Reference Example-38

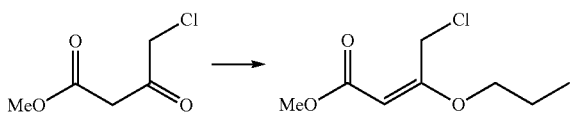

Concentrated sulfuric acid (one drop) was added to a mixture of methyl 4-chloroacetoacetate (1.10 g, 7.0 mmol) and tripropyl orthoformate (1.50 g, 7.7 mmol), followed by stirring at room temperature for 72 hours. After the reaction was completed, the reaction solution was filtered using a silica pad, and eluted with a 4:1 mixed solvent of hexane and ethyl acetate, and the eluate was concentrated under reduced pressure, whereby a colorless oily material (1.85 g) was obtained. To this, chloroform (40 mL) and phosphorus pentaoxide (1.43 g, 10.1 mmol) were added, followed by refluxing for 2 hours. After the reaction was completed, the reaction solution was filtered using a silica pad, and eluted with a 4:1 mixed solvent of hexane and ethyl acetate, and the eluate was concentrated under reduced pressure, whereby methyl (E)-4-chloro-3-propoxy-2-butenoate (1.07 g, yield: 79%) was obtained as a pale yellow oily material. $^1$H-NMR (400 MHz, CDCl$_3$): δ1.01 (t, J=6.9 Hz, 3H), 1.79 (sext, J=6.9 Hz, 2H), 3.71 (s, 3H), 3.78 (t, J=6.9 Hz, 2H), 4.65 (s, 2H), 5.11 (s, 1H).

Reference Example-39

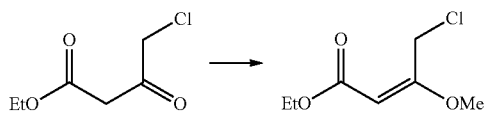 [SMILES: CCOC(=O)CC(=O)CCl ; CCOC(=O)/C=C(\CCl)OC]

Concentrated sulfuric acid (one drop) was added to a mixture of ethyl 4-chloroacetoacetate (1.21 g, 7.0 mmol) and trimethyl orthoformate (880 mg, 7.7 mmol), followed by stirring at room temperature for 66 hours. After the reaction was completed, the reaction solution was filtered using a silica pad, and eluted with a 4:1 mixed solvent of hexane and ethyl acetate, and the eluate was concentrated under reduced pressure, whereby a pale yellow oily material (1.36 g) was obtained. To this, chloroform (40 mL) and phosphorus pentaoxide (1.10 g, 7.74 mmol) were added, followed by refluxing for 2 hours. After the reaction was completed, the reaction solution was filtered using a silica pad, and eluted with a 4:1 mixed solvent of hexane and ethyl acetate, and the eluate was concentrated under reduced pressure. The obtained crude product was purified by silica gel column chromatography (hexane:ethyl acetate=8:2), whereby ethyl (E)-4-chloro-3-methoxy-2-butenoate (304 mg, yield: 24%) was obtained as a colorless oily material. $^1$H-NMR (400 MHz, CDCl$_3$): δ1.29 (t, J=6.9 Hz, 3H), 3.71 (s, 3H), 4.18 (q, J=6.9 Hz, 2H), 4.66 (s, 2H), 5.14 (s, 1H).

Reference Example-40

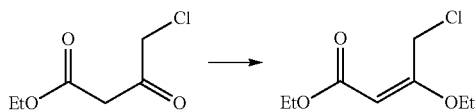 [SMILES: CCOC(=O)CC(=O)CCl ; CCOC(=O)/C=C(\CCl)OCC]

Concentrated sulfuric acid (one drop) was added to a mixture of ethyl 4-chloroacetoacetate (1.21 g, 7.0 mmol) and triethyl orthoformate (1.16 g, 7.7 mmol), followed by stirring at room temperature for 67 hours. After the reaction was completed, the reaction solution was filtered using a silica pad, and eluted with a 4:1 mixed solvent of hexane and ethyl acetate, and the eluate was concentrated under reduced pressure, whereby a pale orange oily material (1.50 g) was obtained. To this, chloroform (40 mL) and phosphorus pentaoxide (1.07 g, 7.56 mmol) were added, followed by refluxing for 2 hours. After the reaction was completed, the reaction solution was filtered using a silica pad, and eluted with a 4:1 mixed solvent of hexane and ethyl acetate, and the eluate was concentrated under reduced pressure, whereby ethyl (E)-4-chloro-3-ethoxy-2-butenoate (624 mg, yield: 46%) was obtained as a colorless oily material. $^1$H-NMR (400 MHz, CDCl$_3$): δ1.28 (t, J=6.9 Hz, 3H), 1.39 (t, J=6.9 Hz, 3H), 3.89 (q, J=6.9 Hz, 2H), 4.17 (q, J=6.9 Hz, 2H), 4.64 (s, 2H), 5.10 (s, 1H).

Reference Example-41

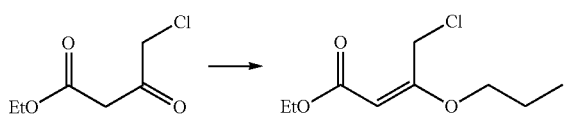

Concentrated sulfuric acid (one drop) was added to a mixture of ethyl 4-chloroacetoacetate (1.21 g, 7.0 mmol) and tripropyl orthoformate (1.50 g, 7.7 mmol), followed by stirring at room temperature for 3 days. After the reaction was completed, the reaction solution was filtered using a silica pad, and eluted with a 4:1 mixed solvent of hexane and ethyl acetate, and the eluate was concentrated under reduced pressure, whereby a colorless oily material (1.94 g) was obtained. To this, chloroform (40 mL) and phosphorus pentaoxide (1.41 g, 9.9 mmol) were added, followed by refluxing for 2 hours. After the reaction was completed, the reaction solution was filtered using a silica pad, and eluted with a 4:1 mixed solvent of hexane and ethyl acetate, and the eluate was concentrated under reduced pressure, whereby ethyl (E)-4-chloro-3-propoxy-2-butenoate (1.07 mg, yield: 74%) was obtained as a colorless oily material. $^1$H-NMR (400 MHz, CDCl$_3$): δ1.01 (t, J=7.2 Hz, 3H), 1.28 (t, J=7.0 Hz, 3H), 1.79 (sext, J=7.0 Hz, 2H), 3.78 (t, J=7.0 Hz, 2H), 4.17 (q, J=7.2 Hz, 2H), 4.65 (s, 2H), 5.11 (s, 1H).

Reference Example-42

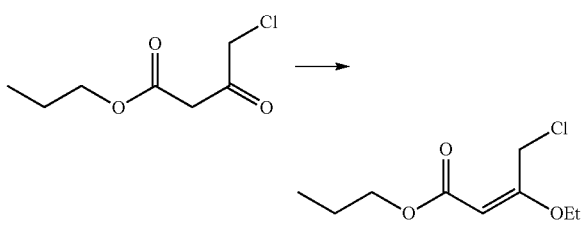

Concentrated sulfuric acid (one drop) was added to a mixture of propyl 4-chloroacetoacetate (1.20 g, 6.72 mmol) and triethyl orthoformate (1.12 g, 7.39 mmol), followed by stirring at room temperature for 45 hours. After the reaction was completed, the reaction solution was filtered using a silica pad, and eluted with a 8:1 mixed solvent of hexane and ethyl acetate, and the eluate was concentrated under reduced pressure, whereby a pale orange oily material (1.39 g) was obtained. To this, chloroform (40 mL) and phosphorus pentaoxide (937 mg, 6.6 mmol) were added, followed by refluxing for 1 hour. After the reaction was completed, the reaction solution was filtered using a silica pad, and eluted with a 8:1 mixed solvent of hexane and ethyl acetate, and the eluate was concentrated under reduced pressure, whereby propyl (E)-4-chloro-3-ethoxy-2-butenoate (1.04 g, yield: 80%) was obtained as a light yellow oily material. $^1$H-NMR (400 MHz, CDCl$_3$): δ0.96 (t, J=7.2 Hz, 3H), 1.39 (t, J=7.2 Hz, 3H), 1.68 (sext, J=7.2 Hz, 2H), 3.90 (q, J=7.2 Hz, 2H), 4.07 (t, J=6.7 Hz, 2H), 4.64 (s, 2H), 5.11 (s, 1H).

Reference Example-43

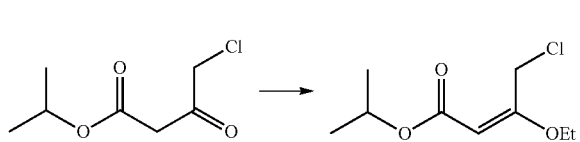

Concentrated sulfuric acid (one drop) was added to a mixture of isopropyl 4-chloroacetoacetate (1.14 g, 6.35 mmol) and triethyl orthoformate (760 mg, 6.99 mmol), followed by stirring at room temperature for 68 hours. After the reaction was completed, the reaction solution was filtered using a silica pad, and eluted with a 8:1 mixed solvent of hexane and ethyl acetate, and the eluate was concentrated under reduced pressure, whereby a colorless oily material (1.28 g) was obtained. To this, chloroform (40 mL) and phosphorus pentaoxide (863 mg, 6.08 mmol) were added, followed by refluxing for 2 hours. After the reaction was completed, the reaction solution was filtered using a silica pad, and eluted with a 4:1 mixed solvent of hexane and ethyl acetate, and the eluate was concentrated under reduced pressure, whereby isopropyl (E)-4-chloro-3-ethoxy-2-butenoate (907 mg, yield: 69%) was obtained as a light yellow oily material. $^1$H-NMR (400 MHz, CDCl$_3$): δ1.26 (d, J=6.6 Hz, 6H), 1.39 (t, J=7.2 Hz, 3H), 3.88 (q, J=7.2 Hz, 2H), 4.64 (s, 2H), 5.05 (sept, J=6.6 Hz, 2H), 5.08 (s, 1H).

Reference Example-44

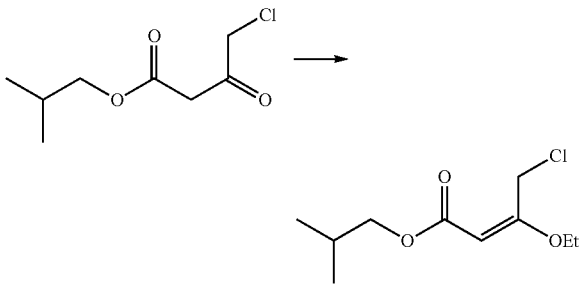

Concentrated sulfuric acid (one drop) was added to a mixture of isobutyl 4-chloroacetoacetate (1.35 g, 7.0 mmol) and triethyl orthoformate (1.16 g, 7.7 mmol), followed by stirring at room temperature for 47 hours. After the reaction was completed, the reaction solution was filtered using a silica pad, and eluted with a 4:1 mixed solvent of hexane and ethyl acetate, and the eluate was concentrated under reduced pressure, whereby a colorless oily material (2.05 g) was obtained. To this, chloroform (40 mL) and phosphorus pentaoxide (1.31 g, 9.22 mmol) were added, followed by refluxing for 2 hours. After the reaction was completed, the reaction solution was filtered using a silica pad, and eluted with a 9:1 mixed solvent of hexane and ethyl acetate, and the eluate was concentrated under reduced pressure, whereby isobutyl (E)-4-chloro-3-ethoxy-2-butenoate (1.28 g, yield: 83%) was obtained as a yellow oily material. $^1$H-NMR (400 MHz, CDCl$_3$): δ0.95 (d, J=6.9 Hz, 6H), 1.39 (t, J=6.9 Hz, 3H), 1.93 (h, J=6.9 Hz, 1H), 3.89 (t, J=6.9 Hz, 2H), 3.91 (t, J=6.9 Hz, 2H), 4.64 (s, 2H), 5.12 (s, 1H).

Reference Example-45

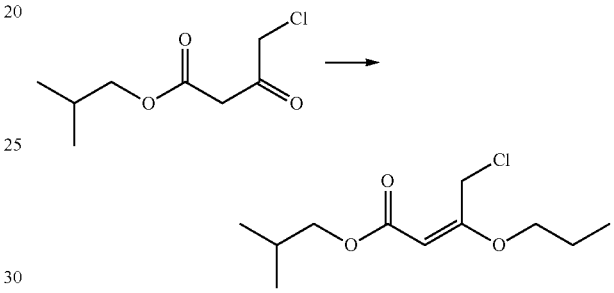

Concentrated sulfuric acid (one drop) was added to a mixture of isobutyl 4-chloroacetoacetate (1.35 g, 7.0 mmol) and tripropyl orthoformate (1.50 g, 7.7 mmol), followed by stirring at room temperature for 1 day and 18 hours. After the reaction was completed, the reaction solution was filtered using a silica pad, and washed with a 8:2 mixed solvent of hexane and ethyl acetate, and concentrated under reduced pressure, whereby a colorless oily material (2.06 g) was obtained. To this, chloroform (40 mL) and phosphorus pentaoxide (1.19 g, 8.39 mmol) were added, followed by refluxing for 2 hours. After the reaction was completed, the reaction solution was filtered using a silica pad, and washed with a 8:2 mixed solvent of hexane and ethyl acetate, and concentrated under reduced pressure, whereby isobutyl (E)-4-chloro-3-propyloxy-2-butenoate (1.29 g, yield: 79%) was obtained as a colorless oily material. $^1$H-NMR (400 MHz, CDCl$_3$): δ0.95 (d, J=6.7 Hz, 6H), 1.01 (t, J=7.2 Hz, 3H), 1.79 (sext, J=7.2 Hz, 2H), 1.95 (h, J=6.7 Hz, 1H), 3.79 (t, J=6.6 Hz, 2H), 3.90 (d, J=6.7 Hz, 2H), 4.65 (s, 2H), 5.12 (s, 1H).

Reference Example-46

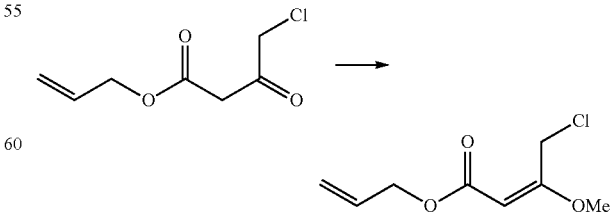

Concentrated sulfuric acid (one drop) was added to a mixture of allyl 4-chloroacetoacetate (1.2 g, 6.8 mmol) and trimethyl orthoformate (810 mg, 7.48 mmol), followed by stirring at room temperature for 67 hours. After the reaction was completed, the reaction solution was filtered using a silica pad, and eluted with a 4:1 mixed solvent of hexane and ethyl acetate, and the eluate was concentrated under reduced pressure, whereby a pale yellow oily material (1.58 g) was obtained. To this, chloroform (40 mL) and phosphorus pentaoxide (1.16 g, 8.1 mmol) were added, followed by refluxing for 2 hours. After the reaction was completed, the reaction solution was filtered using a silica pad, and eluted with a 4:1 mixed solvent of hexane and ethyl acetate, and the eluate was concentrated under reduced pressure, whereby allyl (E)-4-chloro-3-methoxy-2-butenoate (1.02 g, yield: 79%) was obtained as a pale yellow oily material. $^1$H-NMR (400 MHz, CDCl$_3$): δ3.72 (s, 3H), 4.64 (dt, J=1.4 and 5.8 Hz, 2H), 4.66 (s, 2H), 5.18 (s, 1H), 5.35 (dq, J=1.4 and 10.4 Hz, 1H), 5.35 (dq, J=1.4 and 17.4 Hz, 1H), 5.95 (ddt, J=5.8, 10.4 and 17.4 Hz, 1H).

Reference Example-47

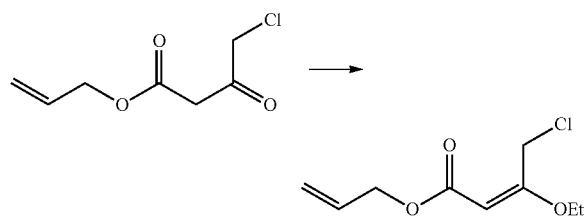

Concentrated sulfuric acid (one drop) was added to a mixture of allyl 4-chloroacetoacetate (1.2 g, 6.8 mmol) and triethyl orthoformate (1.13 g, 7.48 mmol), followed by stirring at room temperature for 67 hours. After the reaction was completed, the reaction solution was filtered using a silica pad, and eluted with a 4:1 mixed solvent of hexane and ethyl acetate, and the eluate was concentrated under reduced pressure, whereby a pale yellow oily material (1.29 g) was obtained. To this, chloroform (40 mL) and phosphorus pentaoxide (1.16 g, 8.1 mmol) were added, followed by refluxing for 2 hours. After the reaction was completed, the reaction solution was filtered using a silica pad, and eluted with a 4:1 mixed solvent of hexane and ethyl acetate, and the eluate was concentrated under reduced pressure, whereby allyl (E)-4-chloro-3-ethoxy-2-butenoate (1.30 g, yield: 93%) was obtained as a pale yellow oily material. $^1$H-NMR (400 MHz, CDCl$_3$): δ1.39 (t, J=7.0 Hz, 3H), 3.90 (q, J=7.0 Hz, 2H), 4.63 (dt, J=1.4 and 5.6 Hz, 2H), 4.64 (s, 2H), 5.14 (s, 1H), 5.25 (dq, J=1.4 and 10.4 Hz, 1H), 5.34 (dq, J=1.4 and 17.2 Hz, 1H), 5.95 (ddt, J=5.8, 10.4 and 17.2 Hz, 1H).

Reference Example-48

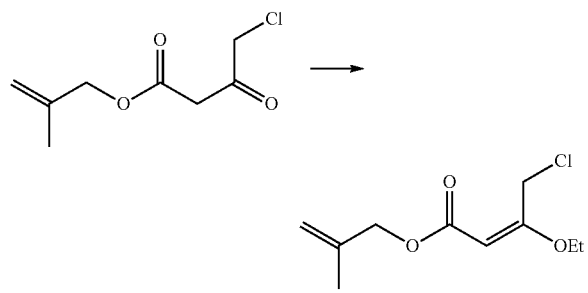

Concentrated sulfuric acid (one drop) was added to a mixture of methallyl 4-chloroacetoacetate (1.33 g, 7.0 mmol) and triethyl orthoformate (1.16 g, 7.7 mmol), followed by stirring at room temperature for 47 hours. After the reaction was completed, the reaction solution was filtered using a silica pad, and eluted with a 4:1 mixed solvent of hexane and ethyl acetate, and the eluate was concentrated under reduced pressure, whereby a yellow oily material (1.75 g) was obtained. To this, chloroform (40 mL) and phosphorus pentaoxide (1.06 g, 7.52 mmol) were added, followed by refluxing for 2 hours. After the reaction was completed, the reaction solution was filtered using a silica pad, and eluted with a 4:1 mixed solvent of hexane and ethyl acetate, and the eluate was concentrated under reduced pressure, whereby methallyl (E)-4-chloro-3-ethoxy-2-butenoate (976 mg, yield: 63%) was obtained as a yellow oily material. $^1$H-NMR (400 MHz, CDCl$_3$): δ1.40 (d, J=6.86 Hz, 3H), 1.78 (s, 3H), 3.91 (q, J=6.80 Hz, 2H), 4.55 (s, 2H), 4.64 (s, 2H), 4.94-5.00 (m, 2H), 5.16 (s, 1H).

Reference Example-49

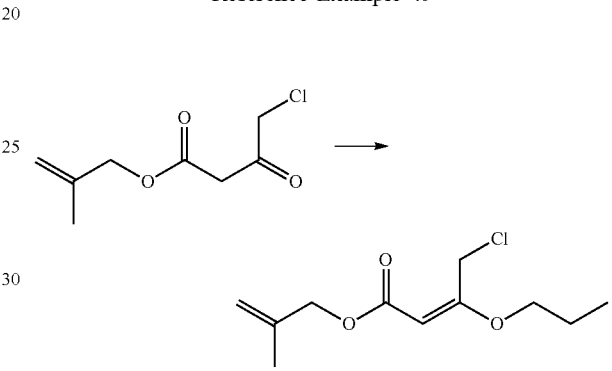

Concentrated sulfuric acid (one drop) was added to a mixture of methallyl 4-chloroacetoacetate (1.33 g, 7.0 mmol) and tripropyl orthoformate (1.50 g, 7.7 mmol), followed by stirring at room temperature for 1 day and 18 hours. After the reaction was completed, the reaction solution was filtered using a silica pad, and washed with a 8:2 mixed solvent of hexane and ethyl acetate, and concentrated under reduced pressure, whereby a pale yellow oily material (1.83 g) was obtained. To this, chloroform (40 mL) and phosphorus pentaoxide (1.06 g, 7.52 mmol) were added, followed by refluxing for 2 hours. After the reaction was completed, the reaction solution was filtered using a silica pad, and washed with a 8:2 mixed solvent of hexane and ethyl acetate, and concentrated under reduced pressure, whereby methallyl (E)-4-chloro-3-propyloxy-2-butenoate (976 mg, yield: 63%) was obtained as a yellow oily material. $^1$H-NMR (400 MHz, CDCl$_3$): δ1.01 (t, J=7.3 Hz, 3H), 1.78 (s, 3H), 1.79 (sext, J=7.3 Hz, 2H), 3.79 (t, J=6.5 Hz, 2H), 4.65 (s, 2H), 4.94 (s, 2H), 4.99 (s, 2H), 5.16 (s, 1H).

Example-113

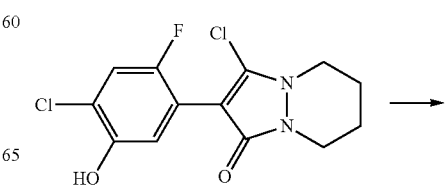

-continued

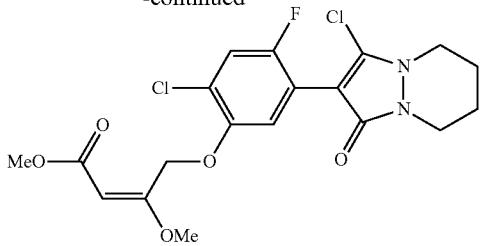

Potassium carbonate (95 mg, 0.69 mmol) and methyl (E)-4-chloro-3-methoxy-2-butenoate (114 mg, 0.69 mmol) were added to a solution of 5-chloro-4-(4-chloro-2-fluoro-5-hydroxyphenyl)-1,2-tetramethylene-4-pyrazolin-3-one (200 mg, 0.63 mmol) in DMF (2 mL), followed by stirring at 50° C. for 5 hours. After the reaction was completed, water (20 mL) was added to the reaction solution, and the resultant product was extracted with ethyl acetate (20 mL×2, 10 mL×1). The organic layer was washed with a saturated saline solution, dried over anhydrous magnesium sulfate, and was concentrated under reduced pressure, whereby a pale yellow oily crude product (319 mg) was obtained. This was purified by silica gel column chromatography (ethyl acetate), whereby methyl (E)-4-[2-chloro-5-(5-chloro-3-oxo-1,2-tetramethylene-4-pyrazolin-4-yl)-4-fluorophenyloxy]-3-methoxy-2-butenoate (283 mg, yield: quantitative) was obtained as a pale yellow oily material. $^1$H-NMR (400 MHz, CDCl$_3$): δ1.87-1.92 (m, 2H), 1.99-2.03 (m, 2H), 3.60-3.62 (m, 2H), 3.69 (s, 3H), 3.72 (s, 3H), 3.80-3.83 (m, 2H), 5.21 (s, 1H), 5.27 (s, 2H), 7.13 (d, J=6.3 Hz, 1H), 7.17 (d, J=9.1 Hz, 1H). $^{19}$F-NMR (376 MHz, CDCl$_3$): δ−119 (s, 1F).

Example-114

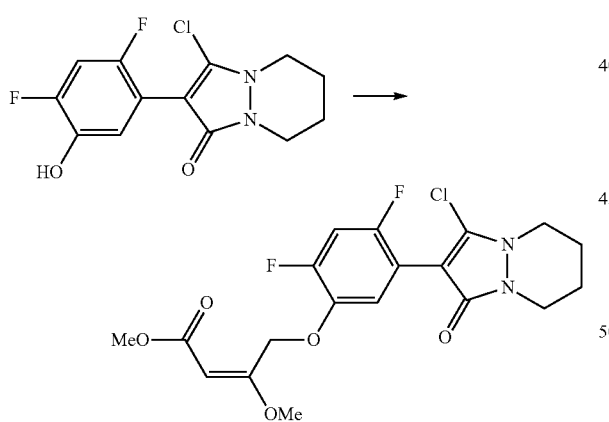

Potassium carbonate (138 mg, 1.00 mmol) and methyl (E)-4-chloro-3-methoxy-2-butenoate (174 mg, 1.00 mmol) were added to a solution of 5-chloro-4-(2,4-difluoro-5-hydroxyphenyl)-1,2-tetramethylene-4-pyrazolin-3-one (200 mg, 0.665 mmol) in DMF (2 mL), followed by stirring at room temperature for 24 hours. After the reaction was completed, water (10 mL) was added to the reaction solution, and the resultant product was extracted with ethyl acetate (20 mL×3). The organic layer was washed with a saturated saline solution, dried over anhydrous magnesium sulfate, and concentrated under reduced pressure, whereby a crude product was obtained. This was purified by silica gel column chromatography (ethyl acetate), whereby methyl (E)-4-[5-(5-chloro-3-oxo-1,2-tetramethylene-4-pyrazolin-4-yl)-2,4-difluorophenyloxy]-3-methoxy-2-butenoate (178 mg, yield: 62%) was obtained as a pale yellow oily material. $^1$H-NMR (400 MHz, CDCl$_3$): δ1.86-1.94 (m, 2H), 1.98-2.06 (m, 2H), 3.57-3.62 (m, 2H), 3.68 (s, 3H), 3.71 (s, 3H), 3.79-3.85 (m, 2H), 5.20 (s, 1H), 5.24 (s, 2H), 6.91 (dd, J=9.3 and 10.8 Hz, 1H), 7.16 (dd, J=6.7 and 9.2 Hz, 1H). $^{19}$F-NMR (376 MHz, CDCl$_3$): δ−129.0 (d, J=4.1 Hz, 1F), −116.6 (d, J=4.1H, 1F).

Example-115

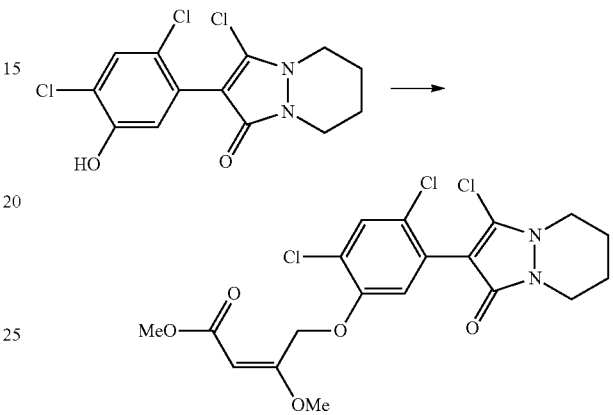

In the same manner as in Example-12 except that cesium carbonate was used instead of potassium carbonate, from 5-chloro-4-(2,4-dichloro-5-hydroxyphenyl)-1,2-tetramethylene-4-pyrazolin-3-one and methyl (E)-4-chloro-3-methoxy-2-butenoate, methyl (E)-4-[5-(5-chloro-3-oxo-1,2-tetramethylene-4-pyrazolin-4-yl)-2,4-dichlorophenyloxy]-3-methoxy-2-butenoate was obtained with a yield of 86%. $^1$H-NMR (400 MHz, CDCl$_3$): δ1.87-1.94 (m, 8H), 1.99-2.06 (m, 2H), 3.58-3.63 (m, 2H), 3.69 (s, 3H), 3.70 (s, 3H), 3.80-3.85 (m, 2H), 5.20 (s, 1H), 5.28 (s, 2H), 6.97 (s, 1H), 7.46 (s, 1H).

Example-116

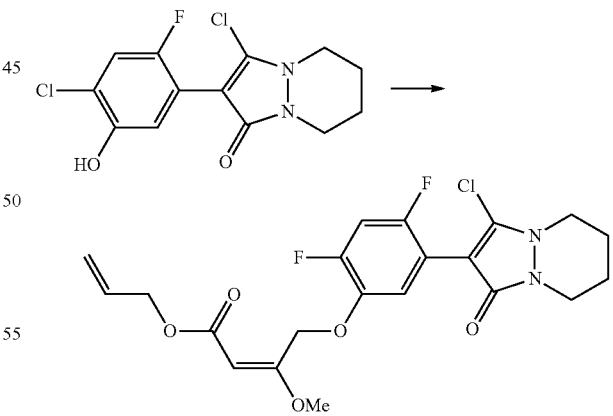

Potassium carbonate (263 mg, 1.90 mmol) and allyl (E)-4-chloro-3-methoxy-2-butenoate (217 mg, 1.14 mmol) were added to a solution of 5-chloro-4-(4-chloro-2-fluoro-5-hydroxyphenyl)-1,2-tetramethylene-4-pyrazolin-3-one (300 mg, 0.95 mmol) in DMF (3 mL), followed by stirring at room temperature for 18 hours. After the reaction was completed, the reaction solution was filtered using a silica pad, and eluted with a mixed solvent of hexane and ethyl acetate, and the eluate was concentrated under reduced pressure. The obtained crude product was purified by silica gel column chromatography (ethyl acetate), whereby allyl (E)-4-[2-chloro-5-(5-chloro-3-oxo-1,2-tetramethylene-4-pyrazolin-4-yl)-4-fluorophenyloxy]-3-methoxy-2-butenoate (156 mg, yield: 31%) was obtained as a pale yellow oily material. $^1$H-NMR (400 MHz, CDCl$_3$): δ1.88-1.92 (m, 2H), 1.99-2.04 (m, 2H), 3.59-3.62 (m, 2H), 3.72 (s, 3H), 3.80-3.83 (m, 2H), 4.60 (dt, J=1.4 and 5.6 Hz, 2H), 5.23 (dq, J=1.4 and 10.5 Hz, 1H), 5.24 (s, 1H), 5.27 (s, 2H), 5.32 (dq, J=1.4 and 17.2 Hz, 1H), 5.94 (ddt, J=5.6, 10.5 and 17.2 Hz, 1H), 7.13 (d, J=6.1 Hz, 1H), 7.17 (d, J=9.3 Hz, 1H). $^{19}$F-NMR (376 MHz, CDCl$_3$): δ−119 (s, 1F).

Example-117

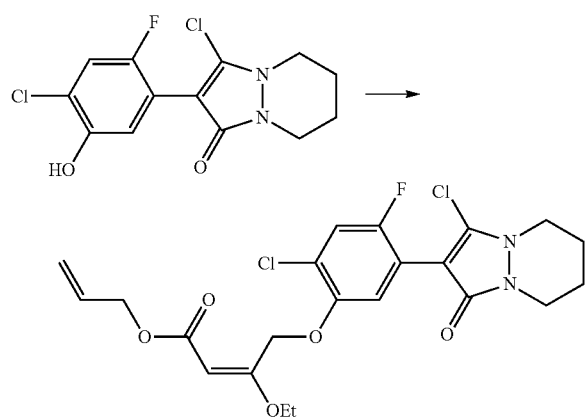

Potassium carbonate (263 mg, 1.90 mmol) and allyl (E)-4-chloro-3-ethoxy-2-butenoate (233 mg, 1.14 mmol) were added to a solution of 5-chloro-4-(4-chloro-2-fluoro-5-hydroxyphenyl)-1,2-tetramethylene-4-pyrazolin-3-one (300 mg, 0.95 mmol) in DMF (3 mL), followed by stirring at room temperature for 18 hours. After the reaction was completed, the reaction solution was filtered using a silica pad, and eluted with a mixed solvent of hexane and ethyl acetate, and the eluate was concentrated under reduced pressure. The obtained crude product was purified by silica gel column chromatography (ethyl acetate), whereby allyl (E)-4-[2-chloro-5-(5-chloro-3-oxo-1,2-tetramethylene-4-pyrazolin-4-yl)-4-fluorophenyloxy]-3-ethoxy-2-butenoate (90 mg, yield: 20%) was obtained as a pale yellow oily material. $^1$H-NMR (400 MHz, CDCl$_3$): δ1.32 (t, J=6.8 Hz, 3H), 1.86-1.92 (m, 2H), 1.98-2.04 (m, 2H), 3.59-3.61 (m, 2H), 3.80-3.83 (m, 2H), 3.89 (q, J=6.8 Hz, 2H), 4.60 (dt, J=1.4 and 5.7 Hz, 2H), 5.20 (s, 1H), 5.22 (dq, J=10.4 and 1.4 Hz, 1H), 5.26 (s, 2H), 5.32 (dq, J=17.3 and 1.4 Hz, 1H), 5.93 (ddt, J=17.3, 10.4 and 5.7 Hz, 1H), 7.12 (d, J=6.3 Hz, 1H), 7.17 (d, J=9.0 Hz, 1H). $^{19}$F-NMR (376 MHz, CDCl$_3$): δ−119 (s, 1F).

Example-118

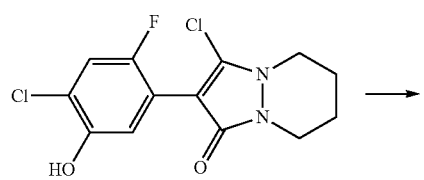

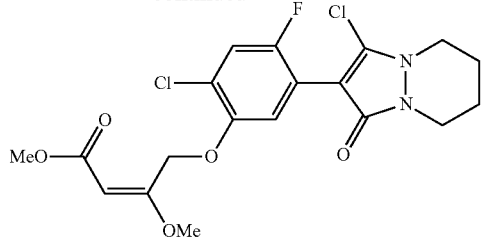

Cesium carbonate (411 mg, 1.26 mmol) and methyl (E)-4-chloro-3-ethoxy-2-butenoate (170 mg, 0.95 mmol) were added to a solution of 5-chloro-4-(4-chloro-2-fluoro-5-hydroxyphenyl)-1,2-tetramethylene-4-pyrazolin-3-one (200 mg, 0.63 mmol) in DMF (2 mL), followed by stirring at 50° C. for 3 hours. After the reaction was completed, the reaction solution was loaded on the upper portion of a silica gel column, and purified by eluting with a mixed solvent (hexane:ethyl acetate=4:1 to 0:1) of hexane and ethyl acetate, whereby methyl (E)-4-[2-chloro-5-(5-chloro-3-oxo-1,2-tetramethylene-4-pyrazolin-4-yl)-4-fluorophenyloxy]-3-ethoxy-2-butenoate (187 mg, yield: 64%) was obtained as a yellow oily material. $^1$H-NMR (400 MHz, CDCl$_3$): δ1.32 (t, J=7.1 Hz, 3H), 1.86-1.92 (m, 2H), 1.98-2.05 (m, 2H), 3.59-3.62 (m, 2H), 3.68 (s, 3H), 3.80-3.83 (m, 2H), 3.88 (q, J=7.2 Hz, 2H), 5.17 (s, 1H), 5.26 (s, 2H), 7.13 (d, J=6.2 Hz, 1H), 7.17 (d, J=9.0 Hz, 1H). $^{19}$F-NMR (376 MHz, CDCl$_3$): δ−119 (s, 1F).

Example-119

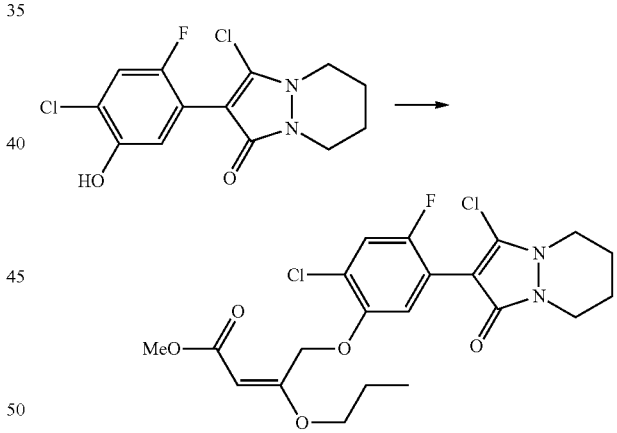

Cesium carbonate (411 mg, 1.26 mmol) and methyl (E)-4-chloro-3-propoxy-2-butenoate (183 mg, 0.95 mmol) were added to a solution of 5-chloro-4-(4-chloro-2-fluoro-5-hydroxyphenyl)-1,2-tetramethylene-4-pyrazolin-3-one (200 mg, 0.63 mmol) in DMF (2 mL), followed by stirring at 50° C. for 2 hours. After the reaction was completed, water (20 mL) was added to the reaction solution, and the resultant product was extracted with ethyl acetate (10 mL×3), and the organic layer was washed with water (20 mL), and then, a saturated saline solution, dried over anhydrous magnesium sulfate, and concentrated under reduced pressure. The obtained crude product was purified by silica gel column chromatography (hexane:ethyl acetate=8:2 to 0:10), whereby methyl (E)-4-[2-chloro-5-(5-chloro-3-oxo-1,2-tetramethylene-4-pyrazolin-4-yl)-4-fluorophenyloxy]-

3-propyloxy-2-butenoate (161 mg, yield: 52%) was obtained as a yellow oily material. $^1$H-NMR (400 MHz, CDCl$_3$): δ0.90 (t, J=7.1 Hz, 3H), 1.71 (sext, J=7.1 Hz, 2H), 1.86-1.92 (m, 2H), 1.98-2.04 (m, 2H), 3.59-3.62 (m, 2H), 3.68 (s, 3H), 3.76 (t, J=6.5 Hz, 2H), 3.80-3.83 (m, 2H), 5.17 (s, 1H), 5.28 (s, 2H), 7.11 (d, J=6.2 Hz, 1H), 7.17 (d, J=9.3 Hz, 1H). $^{19}$F-NMR (376 MHz, CDCl$_3$): δ−119 (s, 1F).

Example-120

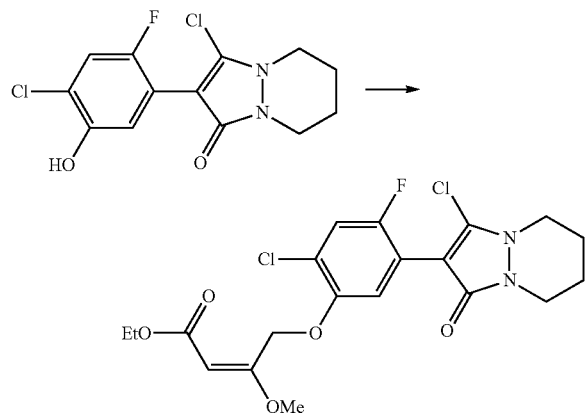

Cesium carbonate (411 mg, 1.26 mmol) and ethyl (E)-4-chloro-3-methoxy-2-butenoate (170 mg, 0.95 mmol) were added to a solution of 5-chloro-4-(4-chloro-2-fluoro-5-hydroxyphenyl)-1,2-tetramethylene-4-pyrazolin-3-one (200 mg, 0.63 mmol) in DMF (2 mL), followed by stirring at 50° C. for 3 hours. After the reaction was completed, the reaction solution was loaded on the upper portion of a silica gel column, and purified by eluting with a mixed solution (hexane:ethyl acetate=4:1 to 0:1) of hexane and ethyl acetate, whereby ethyl (E)-4-[2-chloro-5-(5-chloro-3-oxo-1,2-tetramethylene-4-pyrazolin-4-yl)-4-fluorophenyloxy]-3-methoxy-2-butenoate (187 mg, yield: 65%) was obtained as a white solid. $^1$H-NMR (400 MHz, CDCl$_3$): δ1.26 (t, J=7.3 Hz, 3H), 1.86-1.92 (m, 2H), 1.98-2.05 (m, 2H), 3.59-3.62 (m, 2H), 3.71 (s, 3H), 3.80-3.83 (m, 2H), 4.14 (q, J=7.2 Hz, 2H), 5.20 (s, 1H), 5.27 (s, 2H), 7.13 (d, J=6.4 Hz, 1H), 7.17 (d, J=9.0 Hz, 1H). $^{19}$F-NMR (376 MHz, CDCl$_3$): δ−119 (s, 1F).

Example-121

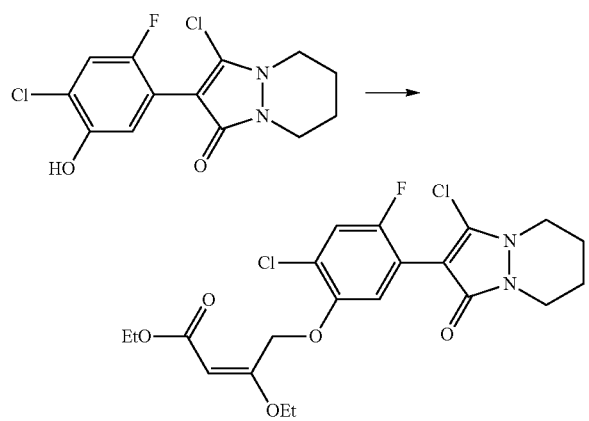

Cesium carbonate (411 mg, 1.26 mmol) and ethyl (E)-4-chloro-3-ethoxy-2-butenoate (183 mg, 0.95 mmol) were added to a solution of 5-chloro-4-(4-chloro-2-fluoro-5-hydroxyphenyl)-1,2-tetramethylene-4-pyrazolin-3-one (200 mg, 0.63 mmol) in DMF (2 mL), followed by stirring at 50° C. for 2 hours. After the reaction was completed, water (20 mL) was added to the reaction solution, and the resultant product was extracted with ethyl acetate (10 mL×3). The organic layer was washed with water (20 mL), and then, a saturated saline solution, dried over anhydrous magnesium sulfate, and concentrated under reduced pressure. The obtained crude product was purified by silica gel column chromatography (hexane:ethyl acetate=8:2 to 0:10), whereby ethyl (E)-4-[2-chloro-5-(5-chloro-3-oxo-1,2-tetramethylene-4-pyrazolin-4-yl)-4-fluorophenyloxy]-3-ethoxy-2-butenoate (88 mg, yield: 30%) was obtained as a yellow oily material. $^1$H-NMR (400 MHz, CDCl$_3$): δ1.26 (t, J=7.3 Hz, 3H), 1.32 (t, J=6.8 Hz, 3H), 1.86-1.92 (m, 2H), 1.98-2.04 (m, 2H), 3.59-3.62 (m, 2H), 3.80-3.83 (m, 2H), 3.88 (q, J=6.8 Hz, 2H), 4.13 (q, J=7.3 Hz, 2H), 5.16 (s, 1H), 5.26 (s, 2H), 7.12 (d, J=6.4 Hz, 1H), 7.17 (d, J=9.0 Hz, 1H). $^{19}$F-NMR (376 MHz, CDCl$_3$): δ−119 (s, 1F).

Example-122

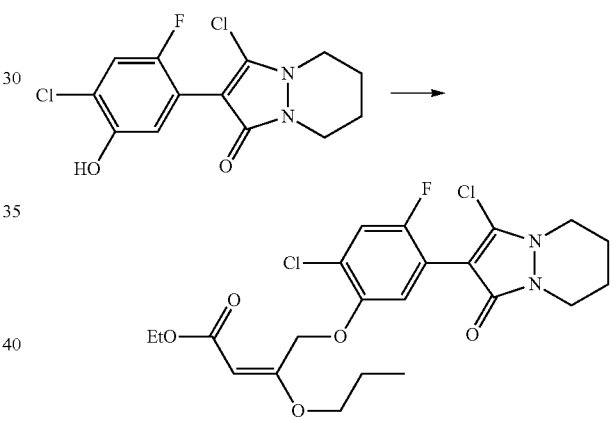

Cesium carbonate (411 mg, 1.26 mmol) and ethyl (E)-4-chloro-3-propoxy-2-butenoate (169 mg, 0.95 mmol) were added to a solution of 5-chloro-4-(4-chloro-2-fluoro-5-hydroxyphenyl)-1,2-tetramethylene-4-pyrazolin-3-one (200 mg, 0.63 mmol) in DMF (2 mL), followed by stirring at 50° C. for 2 hours. After the reaction was completed, water (20 mL) was added to the reaction solution, and the resultant product was extracted with ethyl acetate (10 mL×3). The organic layer was washed with water (20 mL), and then, a saturated saline solution, dried over anhydrous magnesium sulfate, and concentrated under reduced pressure. The obtained crude product was purified by silica gel column chromatography (hexane:ethyl acetate=8:2 to 0:10), whereby ethyl (E)-4-[2-chloro-5-(5-chloro-3-oxo-1,2-tetramethylene-4-pyrazolin-4-yl)-4-fluorophenyloxy]-3-propyloxy-2-butenoate (164 mg, yield: 52%) was obtained as a yellow oily material. $^1$H-NMR (400 MHz, CDCl$_3$): δ0.90 (t, J=7.7 Hz, 3H), 1.26 (t, J=7.2 Hz, 3H), 1.71 (sext, J=7.3 Hz, 2H), 1.86-1.92 (m, 2H), 1.98-2.02 (m, 2H), 3.59-3.61 (m, 2H), 3.76 (t, J=6.4 Hz, 2H), 3.80-3.83 (m, 2H), 4.14 (q, J=7.7 Hz, 2H), 5.16 (s, 1H), 5.28 (s, 2H), 7.11 (d, J=6.0 Hz, 1H), 7.17 (d, J=9.0 Hz, 1H). $^{19}$F-NMR (376 MHz, CDCl$_3$): δ−119 (s, 1F).

Example-123

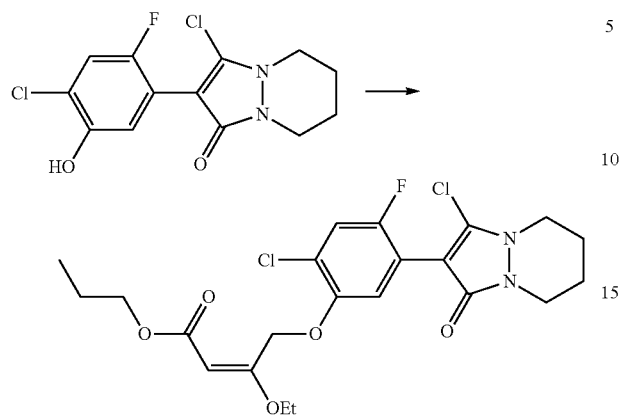

Cesium carbonate (411 mg, 1.26 mmol) and propyl (E)-4-chloro-3-ethoxy-2-butenoate (196 mg, 0.95 mmol) were added to a solution of 5-chloro-4-(4-chloro-2-fluoro-5-hydroxyphenyl)-1,2-tetramethylene-4-pyrazolin-3-one (200 mg, 0.63 mmol) in acetonitrile (3 mL), followed by stirring at 50° C. for 4 hours. After the reaction was completed, the reaction solution was loaded on the upper portion of a silica gel column, and purified by eluting with a mixed solution (hexane:ethyl acetate=20:1 to 0:1) of hexane and ethyl acetate, whereby propyl (E)-4-[2-chloro-5-(5-chloro-3-oxo-1,2-tetramethylene-4-pyrazolin-4-yl)-4-fluorophenyloxy]-3-ethoxy-2-butenoate (106 mg, yield: 36%) was obtained as a pale yellow oily material. $^1$H-NMR (400 MHz, CDCl$_3$): δ0.94 (t, J=7.3 Hz, 3H), 1.32 (t, J=7.3 Hz, 3H), 1.65 (sext, J=7.3 Hz, 2H), 1.86-1.92 (m, 2H), 1.98-2.04 (m, 2H), 3.58-3.61 (m, 2H), 3.80-3.83 (m, 2H), 3.88 (q, J=7.3 Hz, 2H), 4.03 (t, J=7.3 Hz, 2H), 5.17 (s, 1H), 5.26 (s, 2H), 7.12 (d, J=6.4 Hz, 1H), 7.17 (d, J=9.3 Hz, 1H). $^{19}$F-NMR (376 MHz, CDCl$_3$): δ–119 (s, 1F).

Example-124

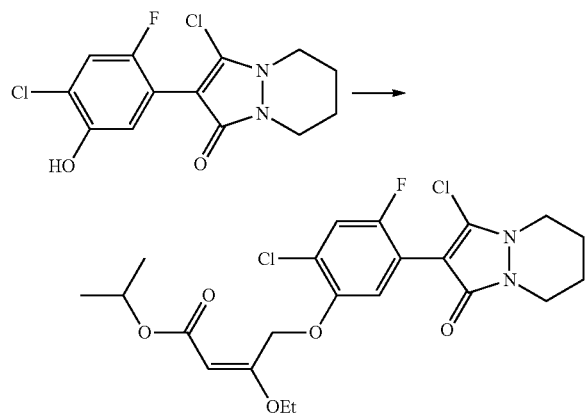

Cesium carbonate (411 mg, 1.26 mmol) and isopropyl (E)-4-chloro-3-ethoxy-2-butenoate (196 mg, 0.95 mmol) were added to a solution of 5-chloro-4-(4-chloro-2-fluoro-5-hydroxyphenyl)-1,2-tetramethylene-4-pyrazolin-3-one (200 mg, 0.63 mmol) in acetonitrile (3 mL), followed by stirring at 50° C. for 4 hours. After the reaction was completed, the reaction solution was loaded on the upper portion of a silica gel column, and purified by eluting with a mixed solution (hexane:ethyl acetate=20:1 to 0:1) of hexane and ethyl acetate, whereby isopropyl (E)-4-[2-chloro-5-(5-chloro-3-oxo-1,2-tetramethylene-4-pyrazolin-4-yl)-4-fluorophenyloxy]-3-ethoxy-2-butenoate (106 mg, yield: 34%) was obtained as a pale yellow oily material. $^1$H-NMR (400 MHz, CDCl$_3$): δ1.23 (d, J=6.2 Hz, 6H), 1.32 (t, J=6.9 Hz, 3H), 1.86-1.92 (m, 2H), 1.98-2.06 (m, 2H), 3.58-3.61 (m, 2H), 3.80-3.82 (m, 1H), 3.87 (q, J=6.9 Hz, 2H), 5.01 (sept, J=6.0 Hz, 1H), 5.13 (s, 1H), 5.26 (s, 2H), 7.12 (d, J=6.0 Hz, 1H), 7.17 (d, J=9.1 Hz, 1H). $^{19}$F-NMR (376 MHz, CDCl$_3$): δ–119 (s, 1F).

Example-125

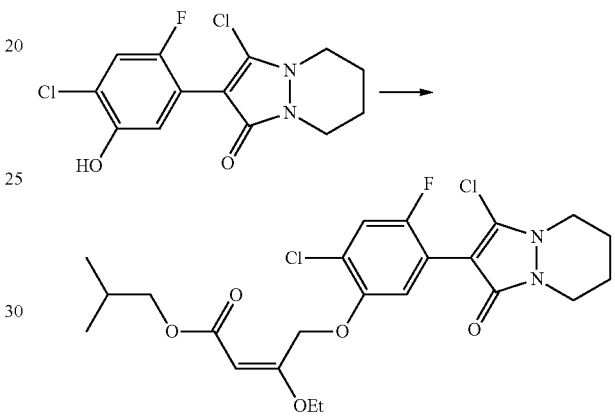

Cesium carbonate (411 mg, 1.26 mmol) and isobutyl (E)-4-chloro-3-ethoxy-2-butenoate (210 mg, 0.95 mmol) were added to a solution of 5-chloro-4-(4-chloro-2-fluoro-5-hydroxyphenyl)-1,2-tetramethylene-4-pyrazolin-3-one (200 mg, 0.63 mmol) in acetonitrile (3 mL), followed by stirring at 50° C. for 5 hours. After the reaction was completed, the reaction solution was loaded on the upper portion of a silica gel column, and purified by eluting with a mixed solution (hexane:ethyl acetate=20:1 to 0:1) of hexane and ethyl acetate, whereby isobutyl (E)-4-[2-chloro-5-(5-chloro-3-oxo-1,2-tetramethylene-4-pyrazolin-4-yl)-4-fluorophenyloxy]-3-ethoxy-2-butenoate (115 mg, yield: 36%) was obtained as a light yellow oily material. $^1$H-NMR (400 MHz, CDCl$_3$): δ0.93 (d, J=6.8 Hz, 6H), 1.26 (t, J=6.9 Hz, 2H), 1.32 (t, J=6.9 Hz, 3H), 1.86-1.96 (m, 3H), 1.98-2.05 (m, 2H), 3.58-3.61 (m, 2H), 3.80-3.83 (m, 2H), 3.86 (d, J=6.5 Hz, 2H), 3.89 (q, J=6.9 Hz, 2H), 4.12 (q, J=6.9 Hz, 1H), 5.18 (s, 1H), 5.26 (s, 2H), 7.12 (d, J=6.5 Hz, 1H), 7.17 (d, J=9.1 Hz, 1H). $^{19}$F-NMR (376 MHz, CDCl$_3$): δ–119 (s, 1F).

Example-126

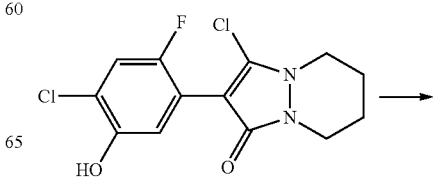

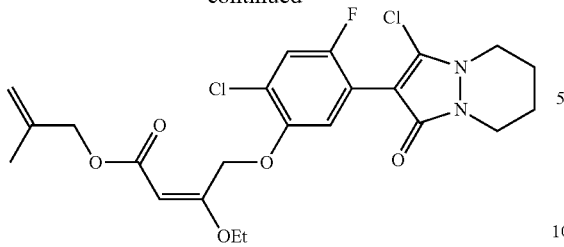

Cesium carbonate (411 mg, 1.26 mmol) and methallyl (E)-4-chloro-3-ethoxy-2-butenoate (208 mg, 0.95 mmol) were added to a solution of 5-chloro-4-(4-chloro-2-fluoro-5-hydroxyphenyl)-1,2-tetramethylene-4-pyrazolin-3-one (200 mg, 0.63 mmol) in acetonitrile (3 mL), followed by stirring at 50° C. for 3 hours. After the reaction was completed, the reaction solution was loaded on the upper portion of a silica gel column, and purified by eluting with a mixed solution (hexane:ethyl acetate=20:1 to 0:1) of hexane and ethyl acetate, whereby methallyl (E)-4-[2-chloro-5-(5-chloro-3-oxo-1,2-tetramethylene-4-pyrazolin-4-yl)-4-fluorophenyloxy]-3-ethoxy-2-butenoate (203 mg, yield: 65%) was obtained as a light yellow oily material. ¹H-NMR (400 MHz, CDCl₃): δ1.33 (t, J=6.9 Hz, 3H), 1.76 (s, 3H), 1.86-1.92 (m, 2H), 1.98-2.05 (m, 2H), 3.58-3.61 (m, 2H), 3.80-3.83 (m, 2H), 3.90 (q, J=6.9 Hz, 2H), 4.51 (s, 2H), 4.91 (s, 1H), 4.97 (s, 1H), 5.21 (s, 1H), 5.27 (s, 2H), 7.12 (d, J=6.5 Hz, 1H), 7.17 (d, J=9.1 Hz, 1H). ¹⁹F-NMR (376 MHz, CDCl₃): δ−119 (s, 1F).

Example-127

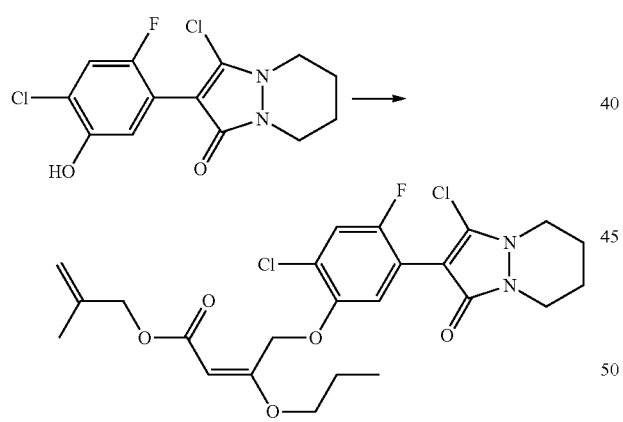

Cesium carbonate (515 mg, 1.58 mmol) and methallyl (E)-4-chloro-3-propoxy-2-butenoate (275 mg, 1.18 mmol) were added to a solution of 5-chloro-4-(4-chloro-2-fluoro-5-hydroxyphenyl)-1,2-tetramethylene-4-pyrazolin-3-one (250 mg, 0.79 mmol) in acetonitrile (3 mL), followed by stirring at 50° C. for 4 hours. After the reaction was completed, the reaction solution was purified by silica gel column chromatography (ethyl acetate:methanol=20:1), whereby methallyl (E)-4-[2-chloro-5-(5-chloro-3-oxo-1,2-tetramethylene-4-pyrazolin-4-yl)-4-fluorophenyloxy]-3-propoxy-2-butenoate (260 mg, yield: 64%) was obtained as a pale yellow oily material. ¹H-NMR (400 MHz, CDCl₃): δ0.90 (t, J=7.4 Hz, 3H), 1.71 (sext, J=7.4 Hz, 2H), 1.76 (s, 3H), 1.87-1.92 (m, 2H), 1.99-2.05 (m, 2H), 3.59-3.62 (m, 2H), 3.78 (t, J=6.4 Hz, 2H), 3.82-3.83 (m, 2H), 4.51 (s, 2H), 4.92-4.98 (s, 2H), 5.21 (s, 1H), 5.29 (s, 2H), 7.10 (d, J=6.1 Hz, 1H), 7.17 (d, J=9.2 Hz, 1H). ¹⁹F-NMR (376 MHz, CDCl₃): δ−119 (s, 1F).

Example-128

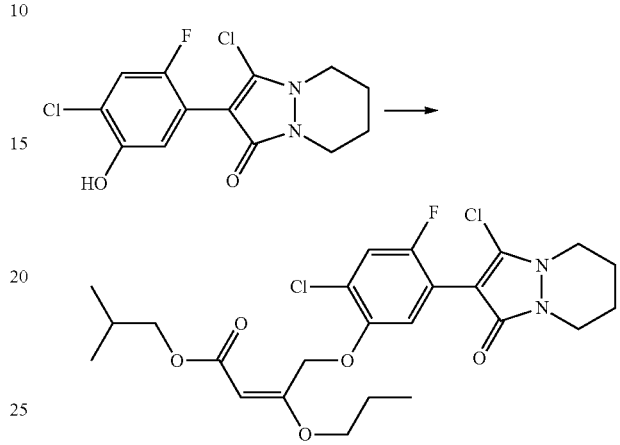

Cesium carbonate (515 mg, 1.58 mmol) and isobutyl (E)-4-chloro-3-propyloxy-2-butenoate (277 mg, 1.18 mmol) were added to a solution of 5-chloro-4-(4-chloro-2-fluoro-5-hydroxyphenyl)-1,2-tetramethylene-4-pyrazolin-3-one (250 mg, 0.79 mmol) in acetonitrile (3 mL), followed by stirring at 50° C. for 4 hours. After the reaction was completed, the reaction solution was purified by silica gel column chromatography (ethyl acetate:methanol=20:1), whereby isobutyl (E)-4-[2-chloro-5-(5-chloro-3-oxo-1,2-tetramethylene-4-pyrazolin-4-yl)-4-fluorophenyloxy]-3-propyloxy-2-butenoate (116 mg, yield: 28%) was obtained as a light yellow oily material. ¹H-NMR (400 MHz, CDCl₃): δ0.90 (t, J=7.2 Hz, 3H), 0.93 (d, J=6.8 Hz, 6H), 1.71 (dt, J=7.2 and 7.2 Hz, 2H), 1.86-1.96 (m, 3H), 1.98-2.03 (m, 2H), 3.59-3.61 (m, 2H), 3.77 (t, J=6.4 Hz, 2H), 3.80-3.83 (m, 2H), 3.86 (d, J=6.4 Hz, 2H), 5.12 (s, 1H), 5.28 (s, 2H), 7.10 (d, J=6.4 Hz, 1H), 7.17 (d, J=9.2 Hz, 1H). ¹⁹F-NMR (376 MHz, CDCl₃): δ−119 (s, 1F).

Reference Example-50

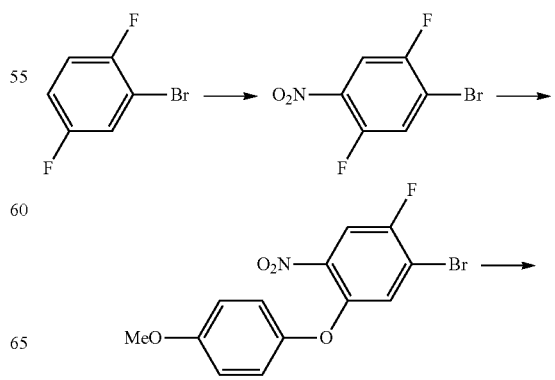

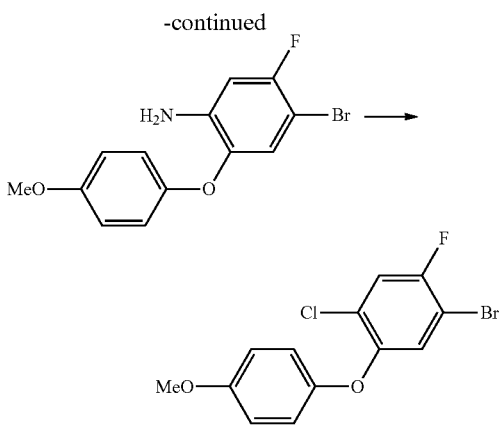

Concentrated sulfuric acid (57 mL) was cooled in an ice bath, and 69% nitric acid (25.5 g, 279 mmol) was added dropwise over 25 minutes, whereby a mixed acid was prepared. To this mixed acid, a solution of 2-bromo-1,4-difluorobenzene (50 g, 254 mmol) in dichloroethane (125 mL) was slowly added dropwise over 1.5 hours under ice-cooling. After the reaction was completed, the reaction solution was further stirred at room temperature for 2 hours. After the reaction was completed, the reaction solution was added little by little to ice water (500 g), and the resultant product was extracted with ether (300 mL×2). The organic layer was washed sequentially with water (300 mL), a saturated sodium hydrogencarbonate aqueous solution (300 mL), and a saturated saline solution (300 mL), and dried over anhydrous magnesium sulfate, and the solvent was distilled off under reduced pressure. The obtained crude product was purified by silica gel chromatography (hexane:chloroform=4:1), whereby 1-bromo-2,5-difluoro-4-nitrobenzene (56 g, yield: 93%) was obtained as a pale yellow solid. $^1$H-NMR (400 MHz, CDCl$_3$): δ7.59 (dd, J=9.5 and 5.5 Hz, 1H), 7.89 (dd, J=7.3 and 6.5 Hz, 1H). $^{19}$F-NMR (376 MHz, CDCl$_3$): δ−120.1 (d, J=15.2 Hz, 1F), −107.9 (d, J=15.2 Hz, 1F).

THF (200 mL) was added to a 55% oil dispersion (5.23 g, 100 mmol) of sodium hydride under ice-cooling, then, 1-bromo-2,5-difluoro-4-nitrobenzene (23.8 g, 100 mmol) was added thereto, followed by stirring for 30 minutes, and a solution of p-methoxyphenol (12.4 g, 100 mmol) in THF (80 mL) was added dropwise thereto, followed by stirring at room temperature for 2 hours. After the reaction was completed, the reaction solution was poured into ice water (50 mL), and the resultant product was extracted with chloroform (100 mL×3). The organic layer was washed with a saturated saline solution (50 mL), dried over anhydrous magnesium sulfate, and concentrated under reduced pressure. The obtained crude product was purified by silica gel column chromatography (hexane:chloroform=1:1), whereby 1-bromo-2-fluoro-5-(4-methoxyphenoxy)-4-nitrobenzene (30.4 g, yield: 89%) was obtained as a yellow solid. $^1$H-NMR (400 MHz, CDCl$_3$) δ3.83 (s, 3H), 6.94 (d, J=9.2 Hz, 2H), 7.01 (d, J=9.2 Hz, 2H), 7.13 (d, J=5.8 Hz, 1H), 7.77 (d, J=7.5 Hz, 1H). $^{19}$F-NMR (376 MHz, CDCl$_3$) δ−112.0 (s, 1F).

Acetic acid (87 mL) and water (16 mL) were added to a solution of 1-bromo-2-fluoro-5-(4-methoxyphenoxy)-4-nitrobenzene (29.9 g, 87.4 mmol) in ethyl acetate (175 mL), and reduced iron (29.3 g, 524 mmol) was added thereto under ice-cooling. After the reaction solution was stirred at 80° C. for 24 hours, the temperature of the reaction solution was returned to room temperature, and the insoluble matters were removed by filtration using Celite. Ethyl acetate was added to the filtrate, and the resultant product was washed sequentially with water (200 mL), a saturated sodium hydrogencarbonate aqueous solution (150 mL), and a saturated saline solution (100 mL). The organic layer was dried over anhydrous magnesium sulfate, and the solvent was distilled off under reduced pressure, whereby 4-bromo-5-fluoro-2-(4-methoxyphenoxy)aniline (21.5 g, yield: 79%) was obtained as a black oily material. $^1$H-NMR (400 MHz, CDCl$_3$) δ3.80 (s, 3H), 3.98 (s, 2H), 6.58 (d, J=9.7 Hz, 1H), 6.87 (d, J=6.6 Hz, 1H), 6.87 (d, J=9.3 Hz, 2H), 6.92 (d, J=9.3 Hz, 2H). $^{19}$F-NMR (376 MHz, CDCl$_3$) δ−114.0 (s, 1F).

A solution of isoamyl nitrite (21 mL, 150 mmol) in acetonitrile (25 mL) was added dropwise to a suspension of 4-bromo-5-fluoro-2-(4-methoxyphenoxy)aniline (15.5 g, 50.0 mmol), copper(I) chloride (9.90 g, 100 mmol), and copper(II) chloride (20.2 g, 150 mmol) in acetonitrile (100 mL) at room temperature. After the reaction solution was stirred at room temperature for 2 hours and poured into 2N hydrochloric acid (100 mL), water (100 mL) was added thereto, and the resultant product was extracted with ethyl acetate (100 mL×3). The organic layer was dried over anhydrous magnesium sulfate, and concentrated under reduced pressure, and the obtained crude product was purified by silica gel column chromatography (hexane), whereby 1-bromo-4-chloro-2-fluoro-5-(4-methoxyphenoxy)benzene (14.4 g, yield: 87%) was obtained as a yellow solid. $^1$H-NMR (400 MHz, CDCl$_3$) δ3.81 (s, 3H), 6.90 (d, J=9.4 Hz, 2H), 6.94 (d, J=9.4 Hz, 2H), 7.02 (d, J=6.3 Hz, 1H), 7.25 (d, J=7.8 Hz, 1H). $^{19}$F-NMR (376 MHz, CDCl$_3$) δ−112.8 (s, 1F).

Reference Example-51

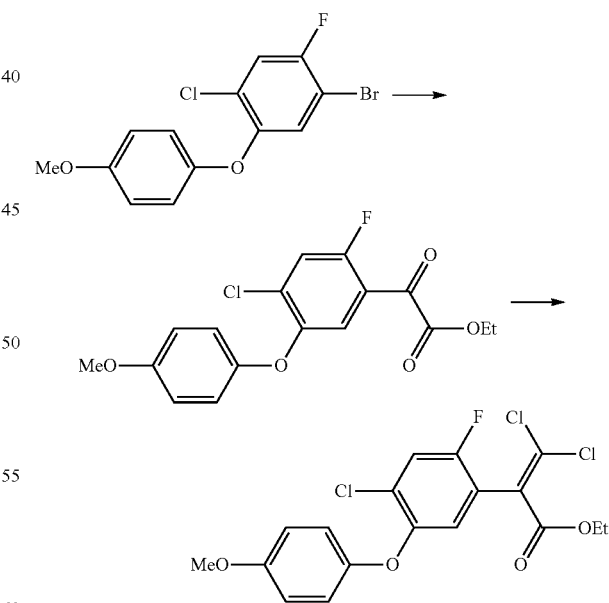

An isopropyl magnesium chloride solution (20 mL, 2M-THF solution) was added to a solution of 1-bromo-4-chloro-2-fluoro-5-(4-methoxyphenoxy)benzene (12.6 g, 38.1 mmol) in THF (25 mL) at −40° C., followed by stirring at room temperature for 1 hour. A solution of the obtained Grignard reagent in THF was added dropwise to a solution of diethyl oxalate (5.4 mL, 40 mmol) in THF (5 mL) at −40° C., followed by stirring at 0° C. for 1 hour. A saturated ammonium chloride aqueous solution (50 mL) was added to the reaction solution, and the resultant product was extracted with ethyl acetate (100 mL×3). The organic layer was dried over anhydrous magnesium sulfate, and concentrated under reduced pressure, and the obtained crude product was purified by silica gel column chromatography (hexane:ethyl acetate=10:1), whereby ethyl 2-[4-chloro-2-fluoro-5-(4-methoxyphenoxy)phenyl]-2-oxoacetate (11.6 g, yield: 87%) was obtained as a white solid. $^1$H-NMR (400 MHz, CDCl$_3$) δ1.37 (t, J=7.2 Hz, 3H), 3.82 (s, 3H), 4.40 (q, J=7.2 Hz, 2H), 6.91 (d, J=9.3 Hz, 2H), 6.96 (d, J=9.3 Hz, 2H), 7.31 (d, J=9.7 Hz, 1H), 7.33 (d, J=6.3 Hz, 1H). $^{19}$F-NMR (376 MHz, CDCl$_3$) δ−117.4 (s, 1F).

Carbon tetrachloride (6.3 mL) was added to a solution of triphenylphosphine (17.6 g, 65.2 mmol) in dichloromethane (33 mL) at 0° C., followed by stirring for 15 minutes. Next, ethyl 2-[4-chloro-2-fluoro-5-(4-methoxyphenoxy)phenyl]-2-oxoacetate (11.5 g, 32.6 mmol) was added thereto, followed by stirring at room temperature for 17 hours. The solvent was removed from the reaction solution under reduced pressure, then, a 1:1 mixed solvent of hexane and ether was added to the precipitated solid, and the solid was separated by filtration. The filtrate was concentrated under reduced pressure, and the obtained crude product was purified by silica gel column chromatography (hexane:ethyl acetate=10:1), whereby ethyl 3,3-dichloro-2-[4-chloro-2-fluoro-5-(4-methoxyphenoxy)phenyl]acrylate (11.3 g, yield: 83%) was obtained as a yellow oily material. $^1$H-NMR (400 MHz, CDCl$_3$) δ1.23 (t, J=7.1 Hz, 3H), 3.81 (s, 3H), 4.22 (q, J=7.1 Hz, 2H), 6.84 (d, J=6.5 Hz, 1H), 6.88 (d, J=9.3 Hz, 2H), 6.93 (d, J=9.3 Hz, 2H), 7.24 (d, J=8.7 Hz, 1H). $^{19}$F-NMR (376 MHz, CDCl$_3$) δ−117.9 (s, 1F).

Reference Example-52

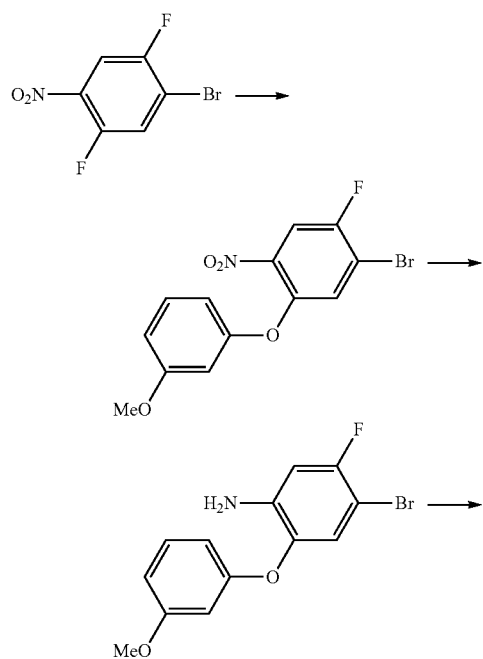

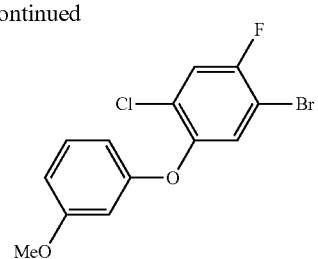

THF (200 mL) and 1-bromo-2,5-difluoro-4-nitrobenzene (23.8 g, 100 mmol) were added to a 55% oil dispersion (5.23 g, 100 mmol) of sodium hydride under ice-cooling, followed by stirring for 30 minutes. Next, a solution of 3-methoxyphenol (12.4 g, 100 mmol) in THF (80 mL) was added dropwise, followed by stirring at room temperature for 1 hour. After the reaction was completed, the reaction solution was poured into ice water (50 g), and the resultant product was extracted with chloroform (100 mL×3). The organic layer was washed with a saturated saline solution (50 mL), dried over anhydrous magnesium sulfate, and concentrated under reduced pressure. The obtained crude product was purified by silica gel column chromatography (hexane:chloroform=1:1), whereby 1-bromo-2-fluoro-5-(3-methoxyphenoxy)-4-nitrobenzene (29.9 g, yield: 87%) was obtained as a yellow oily material. $^1$H-NMR (400 MHz, CDCl$_3$) δ3.81 (s, 3H), 6.62-6.57 (m, 2H), 6.77 (ddd, J=8.4, 2.3 and 1.0 Hz, 1H), 7.32-7.26 (m, 2H), 7.79 (d, J=7.5 Hz, 1H). $^{19}$F-NMR (376 MHz, CDCl$_3$) δ−110.4 (s, 1F).

Acetic acid (87 mL) and water (16 mL) were added to a solution of 1-bromo-2-fluoro-5-(3-methoxyphenoxy)-4-nitrobenzene (29.9 g, 87.4 mmol) in ethyl acetate (175 mL), and reduced iron (29.3 g, 524 mmol) was added thereto under ice-cooling. After the reaction solution was stirred at room temperature for 1 hour, the temperature was returned to room temperature, and the insoluble matters were removed by filtration using Celite. Ethyl acetate was added to the filtrate, and the resultant product was washed sequentially with water (100 mL), a saturated sodium hydrogencarbonate aqueous solution (150 mL), and a saturated saline solution (100 mL). The resultant product was dried over anhydrous magnesium sulfate, and the solvent was distilled off under reduced pressure, whereby 4-bromo-5-fluoro-2-(3-methoxyphenoxy)aniline (23.7 g, yield: 88%) was obtained as a brown solid. $^1$H-NMR (400 MHz, CDCl$_3$) δ3.79 (s, 3H), 3.92 (s, 2H), 6.55-6.49 (m, 2H), 6.60 (d, J=9.7 Hz, 1H), 6.64 (m, 1H), 7.02 (d, J=6.6 Hz, 1H), 7.22 (m, 1H). $^{19}$F-NMR (376 MHz, CDCl$_3$) δ−112.6 (s, 1F).

Copper(I) chloride (9.90 g, 100 mmol) and copper(II) chloride (20.2 g, 150 mmol) were added to a solution of 4-bromo-5-fluoro-2-(3-methoxyphenoxy)aniline (15.5 g, 50.0 mmol) in acetonitrile (100 mL), and a solution of isoamyl nitrite (21 mL, 150 mmol) in acetonitrile (25 mL) was added dropwise thereto at room temperature. After the reaction solution was stirred at room temperature for 2 hours and poured into 2N hydrochloric acid (100 mL), water (100 mL) was added thereto, and the resultant product was extracted with ethyl acetate (100 mL×3). The organic layer was dried over anhydrous magnesium sulfate, and concentrated under reduced pressure. The obtained crude product was purified by silica gel column chromatography (hexane), whereby 1-bromo-4-chloro-2-fluoro-5-(3-methoxyphenoxy)benzene (16.5 g, yield: 99%) was obtained as a colorless and transparent oily material. $^1$H-NMR (400 MHz, CDCl$_3$) δ3.80 (s, 3H), 6.53-6.48 (m, 2H), 6.69 (m, 1H), 7.20

(d, J=6.4 Hz, 1H), 7.25 (m, 1H), 7.27 (d, J=8.1 Hz, 1H). $^{19}$F-NMR (376 MHz, CDCl$_3$) δ−111.2 (s, 1F).

Reference Example-53

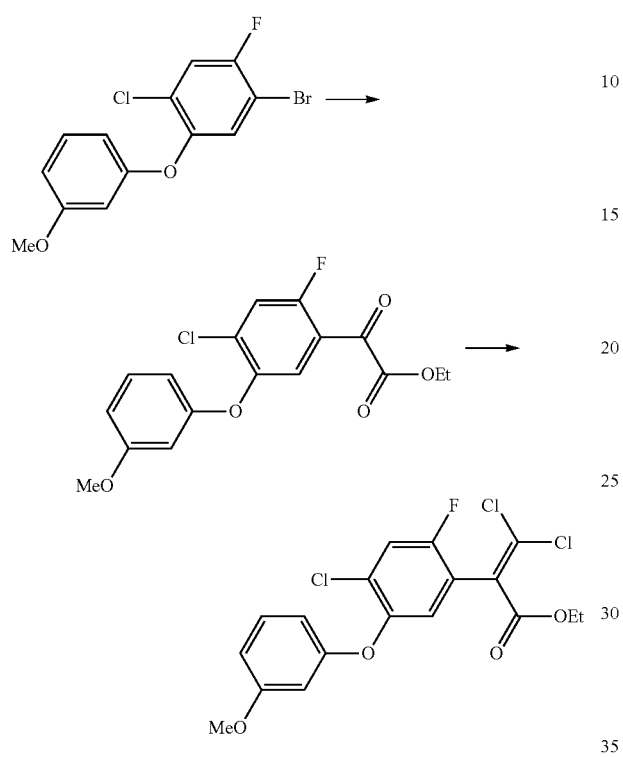

An isopropyl magnesium chloride solution (25 mL, 2M-THF solution) was added to a solution of 1-bromo-4-chloro-2-fluoro-5-(3-methoxyphenoxy)benzene (15.8 g, 47.6 mmol) in THF (30 mL) at −40° C., and the resultant product was stirred at room temperature for 1 hour, whereby a solution of a Grignard reagent in THF was prepared.

The previously prepared Grignard reagent was added dropwise to a solution of diethyl oxalate (6.8 mL, 50 mmol) in THF (7 mL) at −40° C., followed by stirring at 0° C. for 1 hour. A saturated ammonium chloride aqueous solution (100 mL) was added to the reaction solution, and the resultant product was extracted with ethyl acetate (100 mL×3). The organic layer was dried over anhydrous magnesium sulfate, and concentrated under reduced pressure, and the obtained crude product was purified by silica gel column chromatography (hexane:ethyl acetate=10:1), whereby ethyl 2-[4-chloro-2-fluoro-5-(3-methoxyphenoxy)phenyl]-2-oxoacetate (15.4 g, yield: 92%) was obtained as a yellow oily material. $^1$H-NMR (400 MHz, CDCl$_3$) δ1.39 (t, J=7.2 Hz, 3H), 3.80 (s, 3H), 4.42 (q, J=7.2 Hz, 2H), 6.57-6.50 (m, 2H), 6.72 (m, 1H), 7.29-7.23 (m, 1H), 7.34 (d, J=9.6 Hz, 1H), 7.52 (d, J=6.3 Hz, 1H). $^{19}$F-NMR (376 MHz, CDCl$_3$) δ−115.9 (s, 1F).

Carbon tetrachloride (10 mL) was added to a solution of triphenylphosphine (28.1 g, 104 mmol) in dichloromethane (50 mL) at 0° C., followed by stirring for 15 minutes. Thereafter, ethyl 2-[4-chloro-2-fluoro-5-(3-methoxyphenoxy)phenyl]-2-oxoacetate (18.3 g, 51.9 mmol) was added thereto, followed by stirring at room temperature for 17 hours. The solvent was removed from the reaction solution under reduced pressure, then, a 1:1 mixed solvent of hexane and ether was added to the precipitated solid, and the solid was separated by filtration. The filtrate was concentrated under reduced pressure, and the obtained crude product was purified by silica gel column chromatography (hexane:ethyl acetate=10:1), whereby ethyl 3,3-dichloro-2-[4-chloro-2-fluoro-5-(3-methoxyphenoxy)phenyl]acrylate (16.2 g, yield: 74%) was obtained as a yellow oily material. $^1$H-NMR (400 MHz, CDCl$_3$) δ1.24 (t, J=7.1 Hz, 3H), 3.78 (s, 3H), 4.23 (q, J=7.1 Hz, 2H), 6.50 (m, 1H), 6.52 (m, 1H), 6.67 (m, 1H), 7.01 (d, J=6.6 Hz, 1H), 7.22 (dd, J=8.2 and 8.2 Hz, 1H), 7.26 (d, J=8.7 Hz, 1H). $^{19}$F-NMR (376 MHz, CDCl$_3$) δ−116.4 (s, 1F).

Reference Example-54

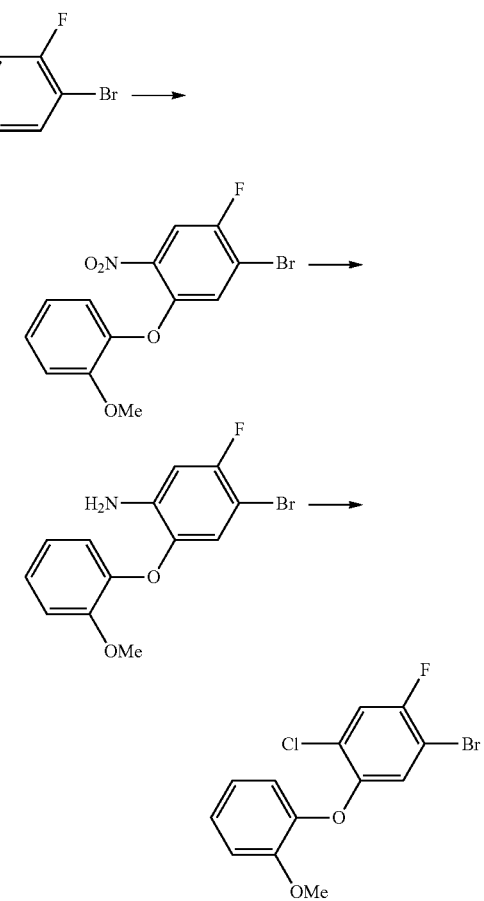

A solution of 2-methoxyphenol (7.45 g, 60.0 mmol) in DMSO (60 mL) was added dropwise to a solution of potassium tert-butoxy (6.73 g, 60.0 mmol) and 18-crown-6 (3.17 g, 12.0 mmol) in THF (60 mL) under ice-cooling, followed by stirring at room temperature for 30 minutes, and a solution of 1-bromo-2,5-difluoro-4-nitrobenzene (14.28 g, 60.0 mmol) in DMSO (45 mL) was added dropwise thereto. The mixed solution was stirred at room temperature for 12 hours. After the reaction was completed, chloroform was added to the reaction solution, and the resultant product was washed with water, dried over anhydrous magnesium sulfate, and concentrated under reduced pressure. The obtained crude product was purified by silica gel column chromatography (hexane:chloroform=4:1), whereby 1-bromo-2-fluoro-5-(2-methoxyphenoxy)-4-nitrobenzene (11.9 g, yield:

58%) was obtained as a yellow solid. ¹H-NMR (400 MHz, CDCl₃) δ3.79 (s, 3H), 6.98-7.05 (m, 3H), 7.11 (dd, J=1.5 and 7.9 Hz, 1H), 7.26 (m, 1H), 7.79 (d, J=7.6 Hz, 1H). ¹⁹F-NMR (376 MHz, CDCl₃) δ−112.6 (s, 1F).

Acetic acid (120 mL) and water (6 mL) were added to a solution of 1-bromo-2-fluoro-5-(2-methoxyphenoxy)-4-nitrobenzene (11.9 g, 34.7 mmol) in ethyl acetate (120 mL), and reduced iron (12.0 g, 215 mmol) was added thereto under ice-cooling. The mixed solution was stirred at room temperature for 2 hours, and the insoluble matters were removed by filtration using Celite. Ethyl acetate was added to the filtrate, and the resultant product was washed sequentially with water (200 mL), a saturated sodium hydrogencarbonate aqueous solution (150 mL), and a saturated saline solution (100 mL). The organic layer was dried over anhydrous magnesium sulfate, and the solvent was distilled off under reduced pressure, whereby 4-bromo-5-fluoro-2-(2-methoxyphenoxy)aniline (10.8 g, yield: quantitative) was obtained as a brown oily material. ¹H-NMR (400 MHz, CDCl₃) δ3.87 (s, 3H), 4.03 (brs, 2H), 6.58 (d, J=9.7 Hz, 1H), 6.84 (d, J=6.4 Hz, 1H), 6.88-6.92 (m, 2H), 7.00 (m, 1H), 7.12 (qd, J=3.0 and 9.0 Hz). ¹⁹F-NMR (376 MHz, CDCl₃) δ−114.1 (s, 1F).

A solution of isoamyl nitrite (9.63 mL, 68.7 mmol) in acetonitrile (30 mL) was added dropwise to a suspension of 4-bromo-5-fluoro-2-(2-methoxyphenoxy)aniline (7.15 g, 22.9 mmol), copper(I) chloride (4.53 g, 45.8 mmol), and copper(II) chloride (9.23 g, 68.7 mmol) in acetonitrile (180 mL) at room temperature. After the reaction solution was stirred at room temperature for 2 hours and poured into 2N hydrochloric acid (100 mL), water (100 mL) was added thereto, and the resultant product was extracted with ethyl acetate (100 mL×3). The organic layer was dried over anhydrous magnesium sulfate, and concentrated under reduced pressure, and the obtained crude product was purified by silica gel column chromatography (hexane), whereby 1-bromo-4-chloro-2-fluoro-5-(2-methoxyphenoxy)benzene (7.12 g, yield: 94%) was obtained as a yellow solid. ¹H-NMR (400 MHz, CDCl₃) δ3.84 (s, 3H), 6.91 (d, J=6.3 Hz, 1H), 6.94-6.96 (m, 2H), 7.02 (m, 1H), 7.19 (m, 1H), 7.25 (d, J=7.9 Hz, 1H). ¹⁹F-NMR (376 MHz, CDCl₃) δ−113.4 (s, 1F).

Reference Example-55

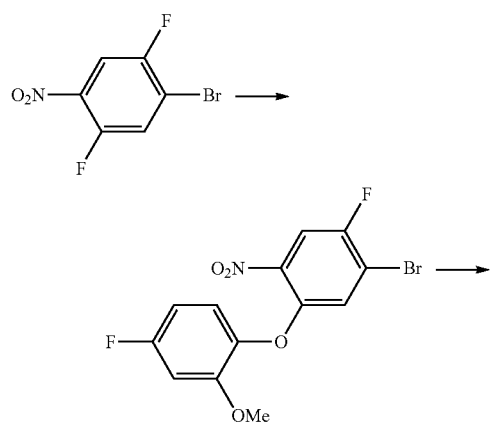

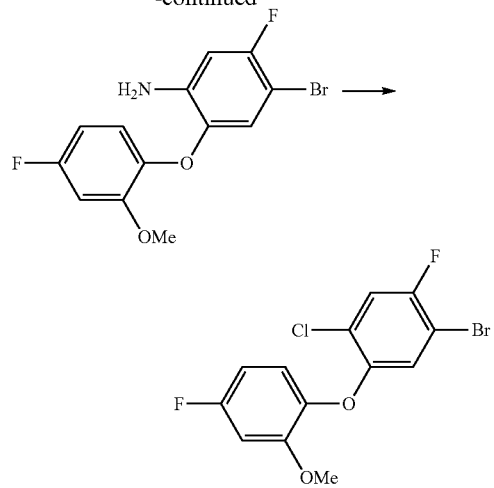

In the same manner as in Reference Example-54, 1-bromo-2,5-difluoro-4-nitrobenzene was reacted with 4-fluoro-2-methoxyphenol, whereby 1-bromo-2-fluoro-5-(4-fluoro-2-methoxyphenoxy)-4-nitrobenzene was obtained with a yield of 47%. ¹H-NMR (400 MHz, CDCl₃) δ3.78 (s, 3H), 6.71 (ddd, J=2.8, 8.8 and 10.6 Hz, 1H), 6.78 (dd, J=2.8 and 10.0 Hz, 1H), 6.97 (d, J=5.7 Hz, 1H), 7.09 (dd, J=5.6 and 8.8 Hz, 1H), 7.78 (d, J=7.5 Hz, 1H). ¹⁹F-NMR (376 MHz, CDCl₃) δ−112.4 (s, 1F), −112.3 (s, 1F).

In the same manner as in Reference Example-54, from 1-bromo-2-fluoro-5-(4-fluoro-2-methoxyphenoxy)-4-nitrobenzene, 4-bromo-5-fluoro-2-(4-fluoro-2-methoxyphenoxy)aniline was obtained with a yield of 89%. ¹H-NMR (400 MHz, CDCl₃) δ3.83 (s, 3H), 4.04 (brs, 2H), 6.57 (d, J=9.6 Hz, 1H), 6.62 (ddd, J=2.8, 8.8 and 10.7 Hz, 1H), 6.73 (dd, J=2.8 and 10.1 Hz, 1H), 6.74 (d, J=6.5 Hz, 1H), 6.90 (dd, J=5.6 and 8.8 Hz, 1H). ¹⁹F-NMR (376 MHz, CDCl₃) δ−115.3 (s, 1F), −114.4 (s, 1F).

In the same manner as in Reference Example-54, from 4-bromo-5-fluoro-2-(4-fluoro-2-methoxyphenoxy)aniline, 1-bromo-4-chloro-2-fluoro-5-(4-fluoro-2-methoxyphenoxy)benzene was obtained with a yield of 88%. ¹H-NMR (400 MHz, CDCl₃) δ3.81 (s, 3H), 6.66 (ddd, J=2.9, 8.8 and 10.7 Hz, 1H), 6.76 (dd, J=2.9 and 10.1 Hz, 1H), 6.83 (d, J=6.2 Hz, 1H), 6.95 (dd, J=5.6 and 8.8 Hz, 1H), 7.24 (d, J=7.8 Hz, 1H). ¹⁹F-NMR (376 MHz, CDCl₃) δ−113.9 (s, 1F), −113.5 (s, 1F).

Reference Example-56

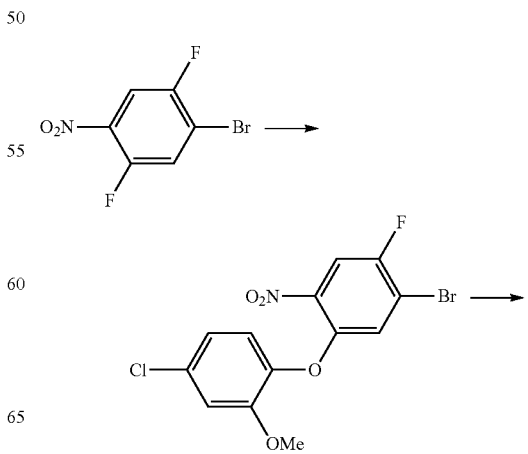

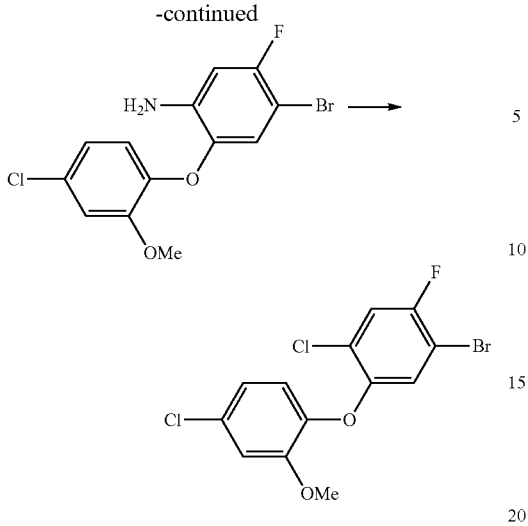

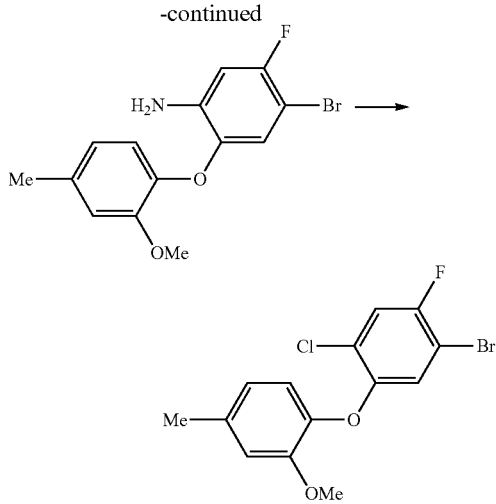

In the same manner as in Reference Example-54, 1-bromo-2,5-difluoro-4-nitrobenzene was reacted with 4-chloro-2-methoxyphenol, whereby 1-bromo-5-(4-chloro-2-methoxyphenoxy)-2-fluoro-4-nitrobenzene was obtained with a yield of 68%. $^1$H-NMR (400 MHz, CDCl$_3$) δ3.79 (s, 3H), 6.96-7.02 (m, 3H), 7.04 (d, J=8.5 Hz, 1H), 7.79 (d, J=7.6 Hz, 1H). $^{19}$F-NMR (376 MHz, CDCl$_3$) δ–111.9 (s, 1F).

In the same manner as in Reference Example-54, from 1-bromo-5-(4-chloro-2-methoxyphenoxy)-2-fluoro-4-nitrobenzene, 4-bromo-2-(4-chloro-2-methoxyphenoxy)-5-fluoroaniline was obtained with a yield of 94%. $^1$H-NMR (400 MHz, CDCl$_3$) δ3.85 (s, 3H), 4.01 (brs, 2H), 6.58 (d, J=9.6 Hz, 1H), 6.81 (d, J=6.3 Hz, 1H), 6.82 (d, J=8.6 Hz, 1H), 6.89 (dd, J=2.4 and 8.6 Hz, 1H), 6.97 (d, J=2.4 Hz, 1H). $^{19}$F-NMR (376 MHz, CDCl$_3$) δ–113.6 (s, 1F).

In the same manner as in Reference Example-54, from 4-bromo-2-(4-chloro-2-methoxyphenoxy)-5-fluoroaniline, 1-bromo-4-chloro-5-(4-chloro-2-methoxyphenoxy)-2-fluorobenzene was obtained with a yield of 94%. $^1$H-NMR (400 MHz, CDCl$_3$) δ3.83 (s, 3H), 6.84-7.02 (m, 4H), 7.25 (d, J=7.9 Hz, 1H). $^{19}$F-NMR (376 MHz, CDCl$_3$) δ–112.7 (s, 1F).

In the same manner as in Reference Example-54, 1-bromo-2,5-difluoro-4-nitrobenzene was reacted with 2-methoxy-4-methylphenol, whereby 1-bromo-2-fluoro-5-(2-methoxy-4-methylphenoxy)-4-nitrobenzene was obtained with a yield of 52%. $^1$H-NMR (400 MHz, CDCl$_3$) δ2.39 (s, 3H), 3.76 (s, 3H), 6.80 (dd, J=1.8 and 8.0 Hz, 1H), 6.83 (d, J=1.8 Hz, 1H), 6.99 (d, J=8.0 Hz, 1H), 7.00 (d, J=5.8 Hz, 1H), 7.77 (d, J=7.6 Hz, 1H). $^{19}$F-NMR (376 MHz, CDCl$_3$) δ–113.1 (s, 1F).

In the same manner as in Reference Example-54, from 1-bromo-2-fluoro-5-(2-methoxy-4-methylphenoxy)-4-nitrobenzene, 4-bromo-5-fluoro-2-(2-methoxy-4-methylphenoxy)aniline was obtained with a yield of 90%. $^1$H-NMR (400 MHz, CDCl$_3$) δ2.35 (s, 3H), 3.83 (s, 3H), 4.04 (brs, 2H), 6.56 (d, J=9.7 Hz, 1H), 6.71 (m, 1H), 6.78-6.82 (m, 3H). $^{19}$F-NMR (376 MHz, CDCl$_3$) δ–114.7 (s, 1F).

In the same manner as in Reference Example-54, from 4-bromo-5-fluoro-2-(2-methoxy-4-methylphenoxy)aniline, 1-bromo-4-chloro-2-fluoro-5-(2-methoxy-4-methylphenoxy)benzene was obtained with a yield of 45%. $^1$H-NMR (400 MHz, CDCl$_3$) δ2.37 (s, 3H), 3.80 (s, 3H), 6.71-6.88 (m, 4H), 7.23 (d, J=7.7 Hz, 1H). $^{19}$F-NMR (376 MHz, CDCl$_3$) δ–114.0 (s, 1F).

Reference Example-57

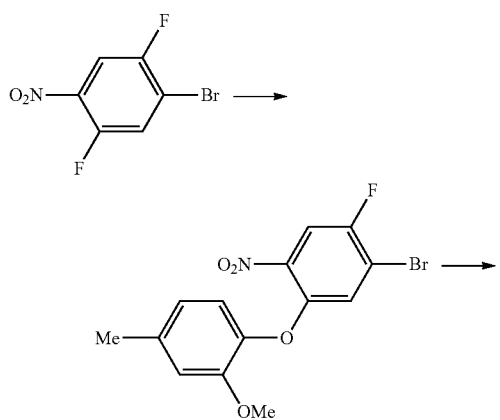

Reference Example-58

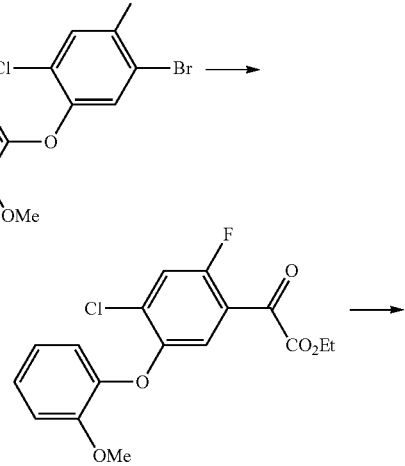

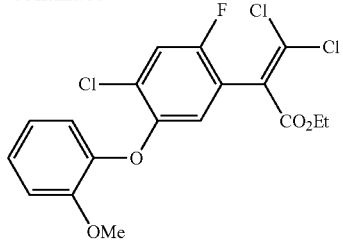

An isopropyl magnesium chloride solution (5.84 mL, 2M-THF solution) was added to a solution of 1-bromo-4-chloro-2-fluoro-5-(2-methoxyphenoxy)benzene (3.69 g, 11.1 mmol) in THF (20 mL) at −78° C., followed by stirring at room temperature for 30 minutes. A solution of the obtained Grignard reagent in THF was added dropwise to a solution of diethyl oxalate (1.58 mL, 11.7 mmol) in THF (20 mL) at −78° C., followed by stirring at room temperature for 12 hours. A saturated ammonium chloride aqueous solution (50 mL) was added to the reaction solution, and the resultant product was extracted with ethyl acetate (100 mL×3). The organic layer was dried over anhydrous magnesium sulfate, and concentrated under reduced pressure, and the obtained crude product was purified by silica gel column chromatography (hexane:ethyl acetate=10:1), whereby ethyl 2-[4-chloro-2-fluoro-5-(2-methoxyphenoxy)phenyl]-2-oxoacetate (2.40 g, yield: 61%) was obtained as a white solid. $^1$H-NMR (400 MHz, CDCl$_3$) δ1.36 (t, J=7.2 Hz, 3H), 3.81 (s, 3H), 4.39 (q, J=7.2 Hz, 2H), 6.94-7.04 (m, 3H), 7.20 (d, J=6.2 Hz, 1H), (ddd, J=1.9, 7.3 and 8.3 Hz, 1H), 7.30 (d, J=9.7 Hz, 1H). $^{19}$F-NMR (376 MHz, CDCl$_3$) δ−118.0 (s, 1F).

Carbon tetrachloride (2.06 mL) was added to a solution of triphenylphosphine (5.59 g, 21.3 mmol) in dichloromethane (21.3 mL) under ice-cooling. Next, ethyl 2-[4-chloro-2-fluoro-5-(2-methoxyphenoxy)phenyl]-2-oxoacetate (2.05 g, 7.10 mmol) was added thereto, followed by stirring at room temperature for 17 hours. The solvent was removed from the reaction solution under reduced pressure, then, a 1:1 mixed solvent of hexane and ether was added to the precipitated solid, and the solid was separated by filtration. The filtrate was concentrated under reduced pressure, and the obtained crude product was purified by silica gel column chromatography (hexane:ethyl acetate=9:1), whereby ethyl 3,3-dichloro-2-[4-chloro-2-fluoro-5-(2-methoxyphenoxy)phenyl]acrylate (2.61 g, yield: 87%) was obtained as a yellow oily material. $^1$H-NMR (400 MHz, CDCl$_3$) δ1.21 (t, J=7.1 Hz, 3H), 3.82 (s, 3H), 4.20 (q, J=7.1 Hz, 2H), 6.74 (d, J=6.4 Hz, 1H), 6.90-6.96 (m, 2H), 7.01 (m, 1H), 7.16 (m, 1H), 7.24 (d, J=8.7 Hz, 1H). $^{19}$F-NMR (376 MHz, CDCl$_3$) δ−118.4 (s, 1F).

Reference Example-59

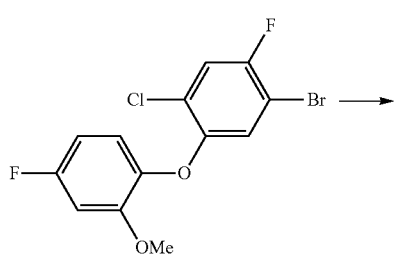

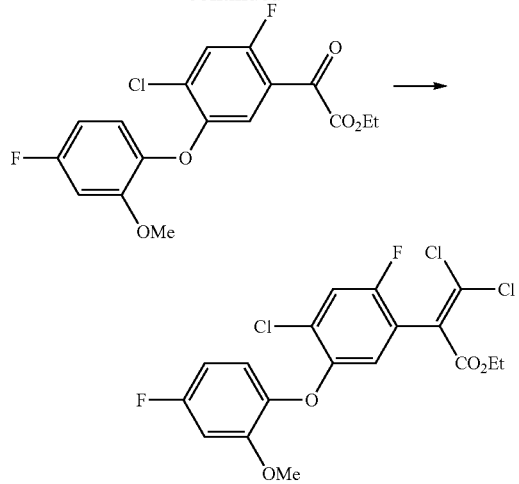

In the same manner as in Reference Example-58, the Grignard reagent prepared from 1-bromo-4-chloro-2-fluoro-5-(4-fluoro-2-methoxyphenoxy)benzene was reacted with diethyl oxalate, whereby ethyl 2-[4-chloro-2-fluoro-5-(4-fluoro-2-methoxyphenoxy)phenyl]-2-oxoacetate was obtained with a yield of 44%. $^1$H-NMR (400 MHz, CDCl$_3$) δ1.37 (t, J=7.1 Hz, 3H), 3.78 (s, 3H), 4.40 (q, J=7.1 Hz, 2H), 6.68 (ddd, J=2.9, 8.8 and 10.7 Hz, 1H), 6.78 (dd, J=2.9 and 10.1 Hz, 1H), 7.01 (dd, J=5.6 and 8.8 Hz, 1H), 7.13 (d, J=6.1 Hz, 1H), 7.30 (d, J=9.6 Hz, 1H). $^{19}$F-NMR (376 MHz, CDCl$_3$) δ−118.0 (s, 1F), −113.3 (s, 1F).

In the same manner as in Reference Example-58, from ethyl 2-[4-chloro-2-fluoro-5-(4-fluoro-2-methoxyphenoxy)phenyl]-2-oxoacetate, ethyl 3,3-dichloro-2-[4-chloro-2-fluoro-5-(4-fluoro-2-methoxyphenoxy)phenyl]acrylate was obtained with a yield of 69%. $^1$H-NMR (400 MHz, CDCl$_3$) δ1.22 (t, J=7.1 Hz, 3H), 3.79 (s, 3H), 4.20 (q, J=7.1 Hz, 2H), 6.64 (ddd, J=2.8, 8.9 and 10.6 Hz, 1H), 6.67 (d, J=6.5 Hz, 1H), 6.74 (dd, J=2.8 and 10.0 Hz, 1H), 6.92 (dd, J=5.6 and 8.9 Hz, 1H), 7.23 (d, J=8.7 Hz, 1H). $^{19}$F-NMR (376 MHz, CDCl$_3$) δ−118.5 (s, 1F), −114.5 (s, 1F).

Reference Example-60

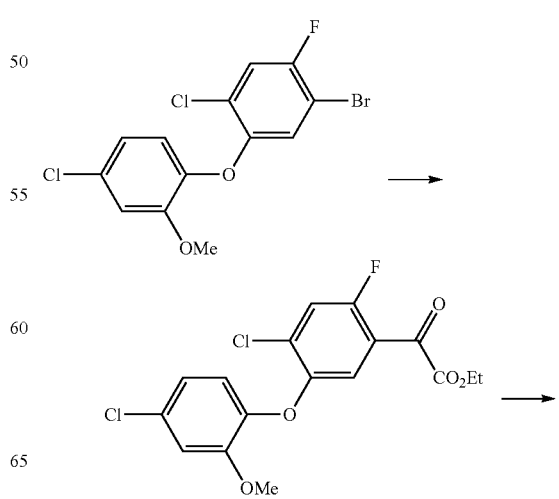

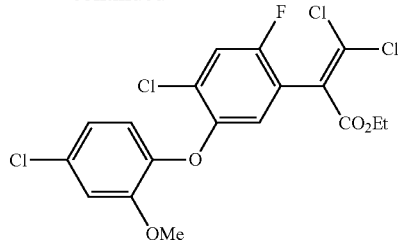

In the same manner as in Reference Example-58, the Grignard reagent prepared from 1-bromo-4-chloro-5-(4-chloro-2-methoxyphenoxy)-2-fluorobenzene was reacted with diethyl oxalate, whereby ethyl 2-[4-chloro-5-(4-chloro-2-methoxyphenoxy)-2-fluorophenyl]-2-oxoacetate was obtained with a yield of 60%. $^1$H-NMR (400 MHz, CDCl$_3$) δ1.37 (t, J=7.1 Hz, 3H), 3.80 (s, 3H), 4.40 (q, J=7.1 Hz, 2H), 6.90-7.04 (m, 3H), 7.19 (d, J=6.4 Hz, 1H), 7.31 (d, J=9.4 Hz, 1H). $^{19}$F-NMR (376 MHz, CDCl$_3$) δ−117.4 (s, 1F).

In the same manner as in Reference Example-58, from ethyl 2-[4-chloro-5-(4-chloro-2-methoxyphenoxy)-2-fluorophenyl]-2-oxoacetate, ethyl 3,3-dichloro-2-[4-chloro-5-(4-chloro-2-methoxyphenoxy)-2-fluorophenyl]acrylate was obtained with a yield of 75%. $^1$H-NMR (400 MHz, CDCl$_3$) δ1.22 (t, J=7.1 Hz, 3H), 3.82 (s, 3H), 4.21 (q, J=7.1 Hz, 2H), 6.74 (d, J=6.5 Hz, 1H), 6.83 (d, J=8.5 Hz, 1H), 6.91 (dd, J=2.3 and 8.5 Hz, 1H), 6.98 (d, J=2.3 Hz, 1H), 7.24 (d, J=8.7 Hz, 1H). $^{19}$F-NMR (376 MHz, CDCl$_3$) δ−117.8 (s, 1F).

Reference Example-61

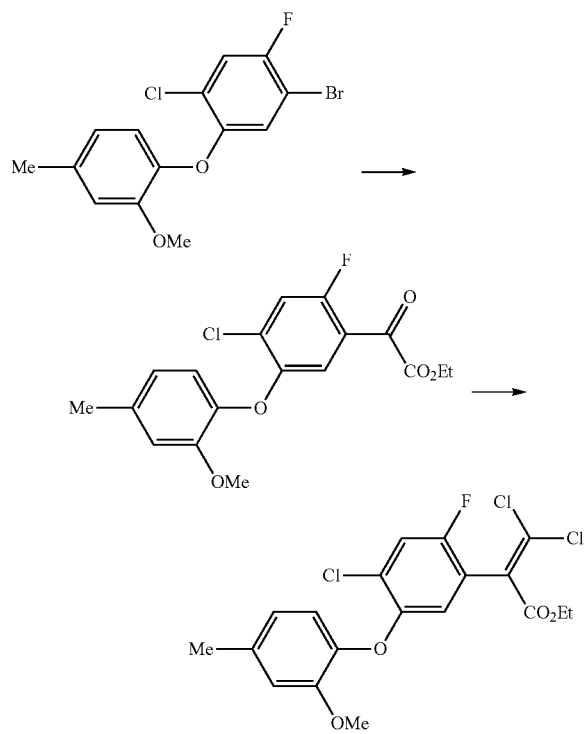

In the same manner as in Reference Example-58, the Grignard reagent prepared from 1-bromo-4-chloro-2-fluoro-5-(2-methoxy-4-methylphenoxy)benzene was reacted with diethyl oxalate, whereby ethyl 2-[4-chloro-2-fluoro-5-(2-methoxy-4-methylphenoxy)phenyl]-2-oxoacetate was obtained with a yield of 65%. $^1$H-NMR (400 MHz, CDCl$_3$) δ1.36 (t, J=7.2 Hz, 3H), 3.77 (s, 3H), 4.39 (q, J=7.2 Hz, 2H), 6.74-6.84 (m, 2H), 6.90 (d, J=8.0 Hz, 1H), 7.16 (d, J=6.2 Hz, 1H), 7.29 (d, J=9.7 Hz, 1H). $^{19}$F-NMR (376 MHz, CDCl$_3$) δ−118.5 (s, 1F).

In the same manner as in Reference Example-58, from ethyl 2-[4-chloro-2-fluoro-5-(2-methoxy-4-methylphenoxy)phenyl]-2-oxoacetate, ethyl 3,3-dichloro-2-[4-chloro-2-fluoro-5-(2-methoxy-4-methylphenoxy)phenyl]acrylate was obtained with a yield of 79%. $^1$H-NMR (400 MHz, CDCl$_3$) δ1.21 (t, J=7.2 Hz, 3H), 2.36 (s, 3H), 3.79 (s, 3H), 4.20 (q, J=7.2 Hz, 2H), 6.68 (d, J=6.5 Hz, 1H), 6.71-6.84 (m, 3H), 7.22 (d, J=8.6 Hz, 1H). $^{19}$F-NMR (376 MHz, CDCl$_3$) δ−119.1 (s, 1F).

Example-129

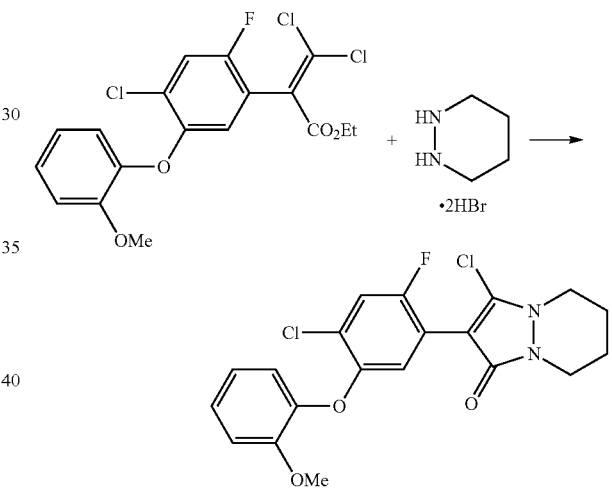

Hexahydropyridazine dihydrobromide (1.70 g, 6.86 mmol) and triethylamine (2.60 mL, 18.7 mmol) were added to a solution of ethyl 3,3-dichloro-2-[4-chloro-2-fluoro-5-(2-methoxyphenoxy)phenyl]acrylate (2.61 g, 6.21 mmol) in 1,4-dioxane (35 mL) at room temperature, followed by stirring for 15 hours while heating to reflux. After the reaction was completed, water (100 mL) was added to the reaction solution, and the resultant product was extracted with ethyl acetate (100 mL×4). The organic layer was dried over anhydrous magnesium sulfate, and concentrated under reduced pressure. The obtained crude product was purified by silica gel column chromatography (ethyl acetate), whereby 5-chloro-4-[4-chloro-2-fluoro-5-(2-methoxyphenoxy)phenyl]-1,2-tetramethylene-4-pyrazolin-3-one (2.54 g, yield: 97%) was obtained as a white solid. $^1$H-NMR (400 MHz, CDCl$_3$) δ1.82-1.89 (m, 2H), 1.94-2.01 (m, 2H), 3.54-3.59 (m, 2H), 3.74-3.79 (m, 2H), 3.86 (s, 3H), 6.86-7.01 (m, 4H), 7.10 (m, 1H), 7.25 (m, 1H). $^{19}$F-NMR (376 MHz, CDCl$_3$) δ−116.6 (s, 1F).

Example-130

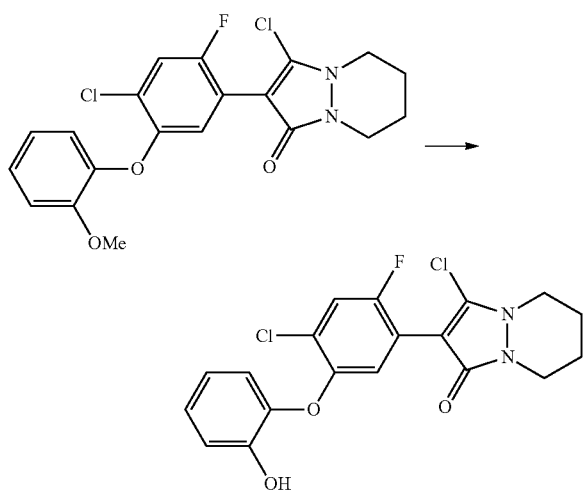

A solution (10.9 mL, 10.9 mmol) of 1M boron tribromide in dichloromethane was added dropwise to a solution of 5-chloro-4-[4-chloro-2-fluoro-5-(2-methoxyphenoxy)phenyl]-1,2-tetramethylene-4-pyrazolin-3-one (2.31 g, 5.46 mmol) in dichloromethane (20 mL) at 78° C., followed by stirring at room temperature for 2 hours. After the reaction was completed, the reaction solution was added to ice water, followed by stirring for 1 hour. The precipitated solid was filtered, whereby 5-chloro-4-[4-chloro-2-fluoro-5-(2-hydroxyphenoxy)phenyl]-1,2-tetramethylene-4-pyrazolin-3-one (2.20 g, yield: 98%) was obtained as a white solid. $^1$H-NMR (400 MHz, CDCl$_3$) δ1.85-1.92 (m, 2H), 1.97-2.04 (m, 2H), 3.59-3.64 (m, 2H), 3.78-3.82 (m, 2H), 6.78-6.84 (m, 2H), 6.97-7.06 (m, 2H), 7.24 (d, J=6.4 Hz, 1H), 7.28 (d, J=9.0 Hz, 1H). $^{19}$F-NMR (376 MHz, CDCl$_3$) δ−114.2 (s, 1F).

Example-131

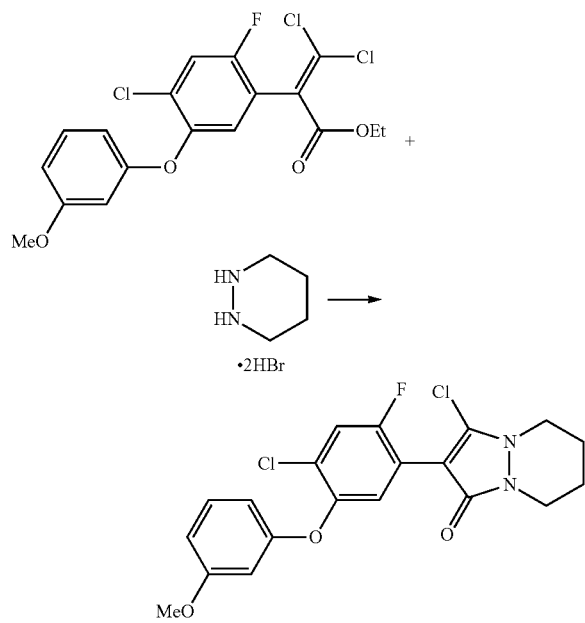

Hexahydropyridazine dihydrobromide (3.89 g, 15.7 mmol) and triethylamine (6.6 mL, 47.2 mmol) were added to a solution of ethyl 3,3-dichloro-2-[4-chloro-2-fluoro-5-(3-methoxyphenoxy)phenyl]acrylate (6.00 g, 14.3 mmol) in 1,4-dioxane (30 mL) at room temperature, followed by stirring for 22 hours while heating to reflux. After the reaction was completed, water (100 mL) was added to the reaction solution, and the resultant product was extracted with ethyl acetate (100 mL×3). The organic layer was dried over anhydrous magnesium sulfate, and concentrated under reduced pressure. The obtained crude product was purified by silica gel column chromatography (ethyl acetate), whereby 5-chloro-4-[4-chloro-2-fluoro-5-(3-methoxyphenoxy)phenyl]-1,2-tetramethylene-4-pyrazolin-3-one (5.03 g, yield: 83%) was obtained as a white solid. $^1$H-NMR (400 MHz, CDCl$_3$) δ1.84-1.91 (m, 2H), 1.96-2.03 (m, 2H), 3.57-3.62 (m, 2H), 3.78 (s, 3H), 3.76-3.82 (m, 2H), 6.53 (m, 1H), 6.56 (m, 1H), 6.63 (m, 1H), 7.24-7.16 (m, 2H), 7.27 (d, J=9.1 Hz, 1H).; $^{19}$F-NMR (376 MHz, CDCl$_3$) δ−114.7 (s, 1F).

Example-132

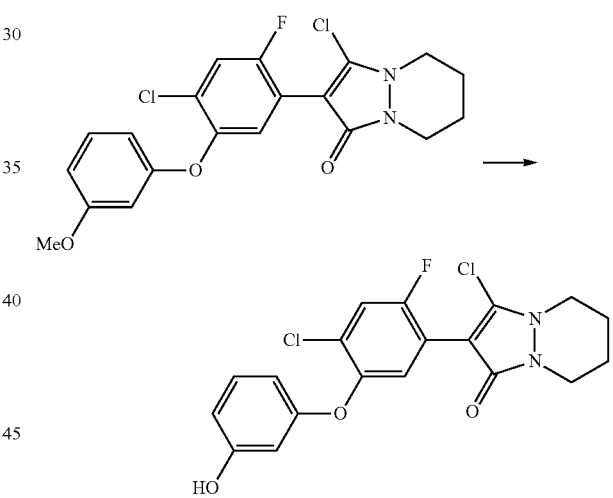

A solution (14.2 mL, 14.2 mmol) of 1M boron tribromide in dichloromethane was added dropwise to a solution of 5-chloro-4-[4-chloro-2-fluoro-5-(3-methoxyphenoxy)phenyl]-1,2-tetramethylene-4-pyrazolin-3-one (3.00 g, 7.09 mmol) in dichloromethane (28 mL) at −40° C., followed by stirring at room temperature for 2 hours. After the reaction was completed, the reaction solution was added to ice water, followed by stirring for 1 hour. The precipitated solid was filtered, whereby 5-chloro-4-[4-chloro-2-fluoro-5-(3-hydroxyphenoxy)phenyl]-1,2-tetramethylene-4-pyrazolin-3-one (2.70 g, yield: 93%) was obtained as a white solid. $^1$H-NMR (400 MHz, DMSO) δ1.82-1.74 (m, 2H), 1.95-1.86 (m, 2H), 3.70-3.60 (m, 4H), 6.31 (m, 1H), 6.39 (m, 1H), 6.53 (m, 1H), 7.16 (m, 1H), 7.19 (d, J=6.7 Hz, 1H), 7.71 (d, J=9.4 Hz, 1H), 9.66 (s, 1H). $^{19}$F-NMR (376 MHz, DMSO)) δ−114.4 (s, 1F).

Example-133

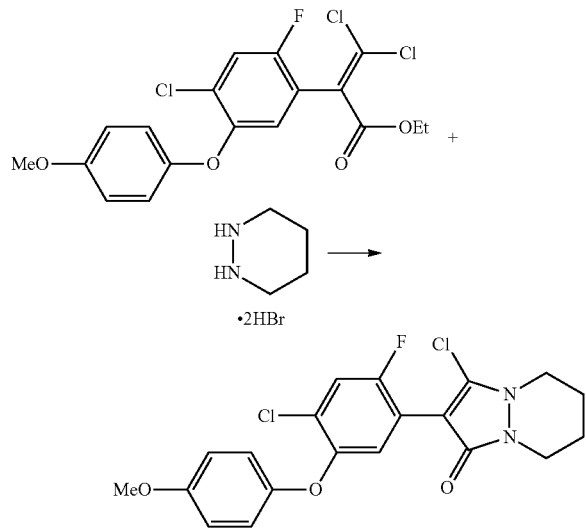

Hexahydropyridazine dihydrobromide (3.89 g, 15.7 mmol) and triethylamine (6.6 mL, 47.2 mmol) were added to a solution of ethyl 3,3-dichloro-2-[4-chloro-2-fluoro-5-(4-methoxyphenoxy)phenyl]acrylate (6.00 g, 14.3 mmol) in 1,4-dioxane (30 mL) at room temperature, followed by stirring for 23 hours while heating to reflux. After the reaction was completed, water (100 mL) was added to the reaction solution, and the resultant product was extracted with ethyl acetate (100 mL×4). The organic layer was dried over anhydrous magnesium sulfate, and concentrated under reduced pressure. The obtained crude product was recrystallized from a mixed solvent of chloroform and ether, whereby 5-chloro-4-[4-chloro-2-fluoro-5-(4-methoxyphenoxy)phenyl]-1,2-tetramethylene-4-pyrazolin-3-one (5.01 g, yield: 83%) was obtained as a white solid. $^1$H-NMR (400 MHz, CDCl$_3$) δ1.90-1.83 (m, 2H), 2.02-1.95 (m, 2H), 3.60-3.56 (m, 2H), 3.80-3.75 (m, 2H), 3.78 (s, 3H), 6.86 (d, J=9.2 Hz, 2H), 6.96 (d, J=9.2 Hz, 2H), 7.07 (d, J=6.5 Hz, 1H), 7.25 (d, J=8.2 Hz, 1H). $^{19}$F-NMR (376 MHz, CDCl$_3$) δ−116.3 (s, 1F).

Example-134

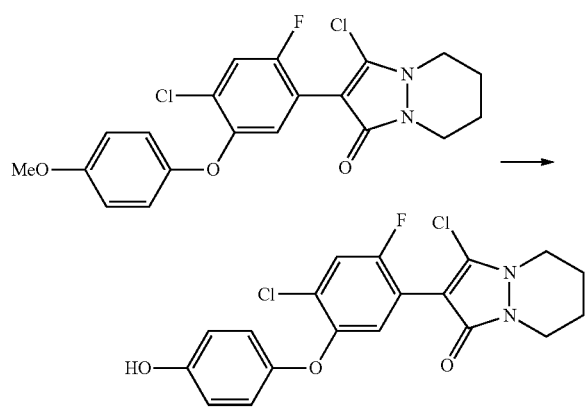

A solution (14.2 mL, 14.2 mmol) of 1M boron tribromide in dichloromethane was added dropwise to a solution of 5-chloro-4-[4-chloro-2-fluoro-5-(4-methoxyphenoxy)phenyl]-1,2-tetramethylene-4-pyrazolin-3-one (3.00 g, 7.09 mmol) in dichloromethane (30 mL) at −40° C., followed by stirring at room temperature for 2 hours. After the reaction was completed, the reaction solution was added to ice water, followed by stirring for 1 hour. The precipitated solid was filtered, whereby 5-chloro-4-[4-chloro-2-fluoro-5-(4-hydroxyphenoxy)phenyl]-1,2-tetramethylene-4-pyrazolin-3-one (3.07 g, yield: quantitative) was obtained as a white solid. $^1$H-NMR (400 MHz, DMSO) δ1.81-1.73 (m, 2H), 1.92-1.85 (m, 2H), 3.65-3.59 (m, 4H), 6.77 (d, J=9.0 Hz, 2H), 6.88 (d, J=9.0 Hz, 2H), 6.92 (d, J=6.6 Hz, 1H), 7.65 (d, J=6.6 Hz, 1H), 9.41 (s, 1H). $^{19}$F-NMR (376 MHz, DMSO)) δ−116.7 (s, 1F).

Example-135

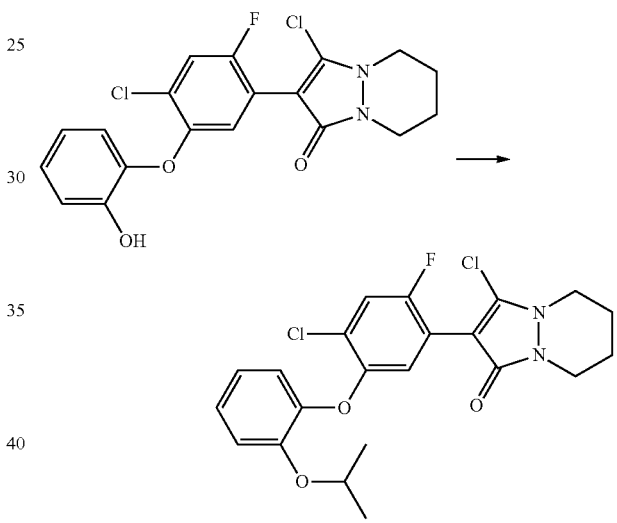

Potassium carbonate (0.14 g, 0.98 mmol) and 2-iodopropane (0.13 mL, 1.3 mmol) were added to a solution of 5-chloro-4-[4-chloro-2-fluoro-5-(2-hydroxyphenoxy)phenyl]-1,2-tetramethylene-4-pyrazolin-3-one (0.27 g, 0.65 mmol) in DMF (3 mL), followed by stirring at room temperature for 18 hours. After the reaction was completed, water (50 mL) was added to the reaction solution, and the resultant product was extracted with ethyl acetate (50 mL×3). The organic layer was washed with water (50 mL×3), dried over anhydrous magnesium sulfate, and concentrated under reduced pressure, and the obtained crude product was purified by silica gel column chromatography, whereby 5-chloro-4-[4-chloro-2-fluoro-5-(2-isopropoxyphenoxy)phenyl]-1,2-tetramethylene-4-pyrazolin-3-one (0.26 g, yield: 90%) was obtained as a white solid. $^1$H-NMR (400 MHz, CDCl$_3$) δ1.20 (d, J=6.1 Hz, 6H), 1.80-1.89 (m, 2H), 1.92-2.02 (m, 2H), 3.52-3.59 (m, 2H), 3.72-3.80 (m, 2H), 4.50 (sep, J=6.1 Hz, 1H), 6.87-6.93 (m, 1H), 6.93 (d, J=6.4 Hz, 1H), 6.95-7.02 (m, 2H), 7.03-7.10 (m, 1H), 7.24 (d, J=9.1 Hz, 1H). $^{19}$F-NMR (376 MHz, CDCl$_3$) δ−117.2 (s, 1F).

Example-136

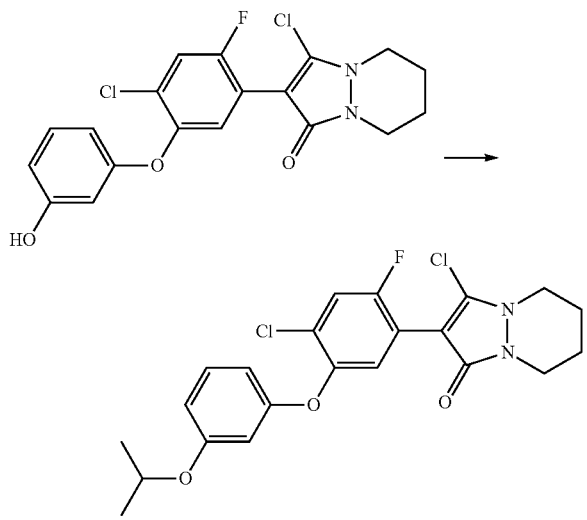

Potassium carbonate (0.13 g, 0.92 mmol) and 2-iodopropane (0.12 mL, 1.22 mmol) were added to a solution of 5-chloro-4-[4-chloro-2-fluoro-5-(3-hydroxyphenoxy)phenyl]-1,2-tetramethylene-4-pyrazolin-3-one (0.25 g, 0.61 mmol) in DMF (3 mL), followed by stirring at room temperature for 20 hours. After the reaction was completed, water (20 mL) was added to the reaction solution, and the resultant product was extracted with ethyl acetate (20 mL×3). The organic layer was washed sequentially with water (20 mL×3) and a saturated saline solution (20 mL), dried over magnesium sulfate, and concentrated under reduced pressure, and the obtained crude product was purified by silica gel column chromatography, whereby 5-chloro-4-[4-chloro-2-fluoro-5-(3-isopropoxyphenoxy)phenyl]-1,2-tetramethylene-4-pyrazolin-3-one (0.23 g, yield: 84%) was obtained as a white solid. $^1$H-NMR (400 MHz, CDCl$_3$) δ1.31 (d, J=6.0 Hz, 6H), 1.91-1.84 (m, 2H), 2.03-1.96 (m, 2H), 3.62-3.57 (m, 2H), 3.82-3.77 (m, 2H), 4.51 (sep, J=6.0 Hz, 1H), 6.53-6.47 (m, 2H), 6.60 (m, 1H), 7.17 (m, 1H), 7.21 (d, J=6.6 Hz, 1H), 7.26 (d, J=9.1 Hz, 1H). $^{19}$F-NMR (376 MHz, CDCl$_3$) δ−114.8 (s, 1F).

Example-137

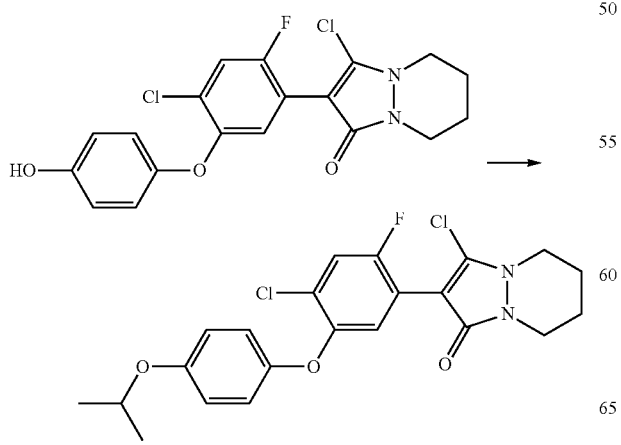

2-Iodopropane (0.12 mL, 1.22 mmol) was added to a suspension of 5-chloro-4-[4-chloro-2-fluoro-5-(4-hydroxyphenoxy)phenyl]-1,2-tetramethylene-4-pyrazolin-3-one (0.25 g, 0.61 mmol) and potassium carbonate (0.13 g, 0.92 mmol) in DMF (3 mL), followed by stirring at room temperature for 18 hours. After the reaction was completed, water (20 mL) was added to the reaction solution, and the resultant product was extracted with ethyl acetate (20 mL×3). The organic layer was dried over magnesium sulfate, and concentrated under reduced pressure, and the obtained crude product was purified by silica gel column chromatography (hexane:ethyl acetate), whereby 5-chloro-4-[4-chloro-2-fluoro-5-(4-isopropoxyphenoxy)phenyl]-1,2-tetramethylene-4-pyrazolin-3-one (0.12 g, yield: 42%) was obtained as a white solid. $^1$H-NMR (400 MHz, CDCl$_3$) δ1.32 (d, J=6.0 Hz, 6H), 1.90-1.84 (m, 2H), 2.02-1.95 (m, 2H), 3.61-3.56 (m, 2H), 3.80-3.76 (m, 2H), 4.46 (sep, J=6.0 Hz, 1H), 6.84 (d, J=9.1 Hz, 2H), 6.93 (d, J=9.2 Hz, 2H), 7.08 (d, J=6.6 Hz, 1H), 7.25 (m, 1H). $^{19}$F-NMR (376 MHz, CDCl$_3$) δ−116.2 (s, 1F).

Example-138

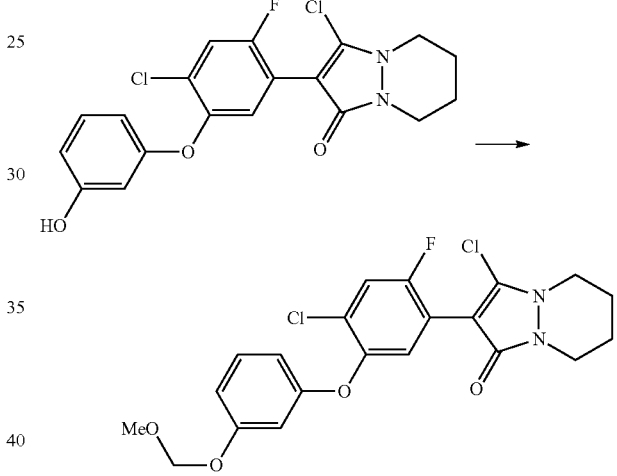

In the same manner as in Example-136, 5-chloro-4-[4-chloro-2-fluoro-5-(3-hydroxyphenoxy)phenyl]-1,2-tetramethylene-4-pyrazolin-3-one was reacted with chloromethyl methyl ether, whereby 5-chloro-4-[4-chloro-2-fluoro-5-[3-(methoxymethoxy)phenoxy]phenyl]-1,2-tetramethylene-4-pyrazolin-3-one was obtained with a yield of 65%. $^1$H-NMR (400 MHz, CDCl$_3$) δ1.84-1.92 (m, 2H), 1.96-2.04 (m, 2H), 3.47 (s, 3H), 3.57-3.63 (m, 2H), 3.76-3.82 (m, 2H), 5.15 (s, 2H), 6.58 (ddd, J=0.8, 2.4 and 8.0 Hz, 1H), 6.70 (t, J=2.4 z, 1H), 6.76 (ddd, J=0.8, 2.4 and 8.0 Hz, 1H), 7.20 (t, J=8.0 Hz, 1H), 7.23 (d, J=6.6 Hz, 1H), 7.27 (d, J=9.0 Hz, 1H). $^{19}$F-NMR (376 MHz, CDCl$_3$) δ−114.6 (s, 1F).

Example-139

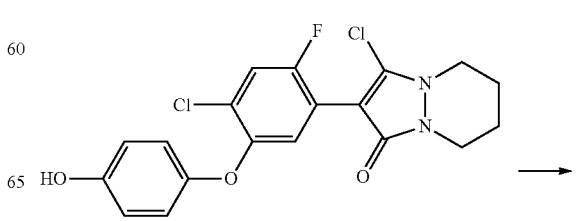

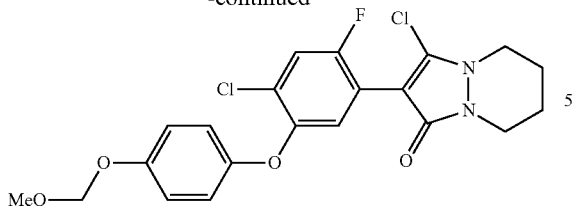

In the same manner as in Example-137, 5-chloro-4-[4-chloro-2-fluoro-5-(4-hydroxyphenoxy)phenyl]-1,2-tetramethylene-4-pyrazolin-3-one was reacted with chloromethyl methyl ether, whereby 5-chloro-4-[4-chloro-2-fluoro-5-[4-(methoxymethoxy)phenoxy]phenyl]-1,2-tetramethylene-4-pyrazolin-3-one was obtained with a yield of 53%. $^1$H-NMR (400 MHz, CDCl$_3$) δ1.83-1.91 (m, 2H), 1.95-2.03 (m, 2H), 3.48 (s, 3H), 3.56-3.51 (m, 2H), 3.76-3.81 (m, 2H), 5.13 (s, 2H), 6.94 (d, J=9.2 Hz, 2H), 7.00 (d, J=9.2 Hz, 2H), 7.11 (d, J=6.5 Hz, 1H), 7.25 (d, J=9.1 Hz, 1H). $^{19}$F-NMR (376 MHz, CDCl$_3$) δ−115.9 (s, 1F).

Example-140

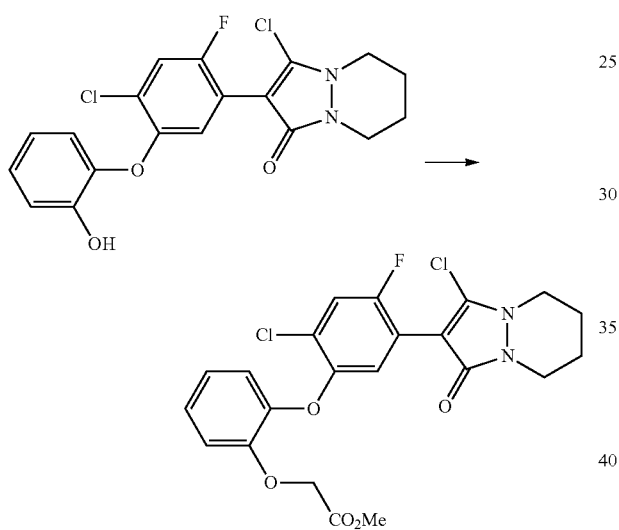

In the same manner as in Example-135, 5-chloro-4-[4-chloro-2-fluoro-5-(2-hydroxyphenoxy)phenyl]-1,2-tetramethylene-4-pyrazolin-3-one was reacted with methyl chloroacetate, whereby methyl 2-[2-{2-chloro-5-(5-chloro-3-oxo-1,2-tetramethylene-4-pyrazolin-4-yl)-4-fluorophenyloxy}phenyloxy]acetate was obtained with a yield of 74%. $^1$H-NMR (400 MHz, CDCl$_3$): δ1.82-1.90 (m, 2H), 1.94-2.02 (m, 2H), 3.55-3.60 (m, 2H), 3.75 (s, 3H), 3.75-3.79 (m, 2H), 4.71 (s, 2H), 6.91-7.09 (m, 5H), 7.26 (d, J=9.0 Hz, 1H). $^{19}$F-NMR (376 MHz, CDCl$_3$) δ−116.0 (s, 1F).

Example-141

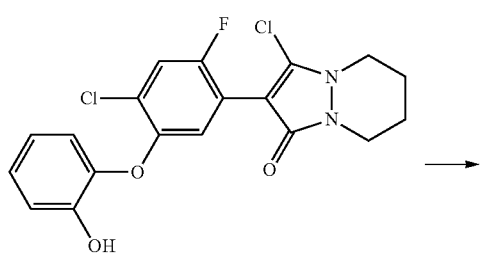

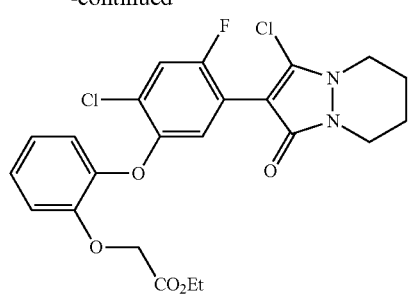

In the same manner as in Example-135, 5-chloro-4-[4-chloro-2-fluoro-5-(2-hydroxyphenoxy)phenyl]-1,2-tetramethylene-4-pyrazolin-3-one was reacted with ethyl chloroacetate, whereby ethyl 2-[2-{2-chloro-5-(5-chloro-3-oxo-1,2-tetramethylene-4-pyrazolin-4-yl)-4-fluorophenyloxy}phenyloxy]acetate was obtained with a yield of 69%. $^1$H-NMR (400 MHz, CDCl$_3$): δ1.25 (t, J=7.1 Hz, 3H), 1.82-1.90 (m, 2H), 1.95-2.02 (m, 2H), 3.55-3.60 (m, 2H), 3.74-3.80 (m, 2H), 4.22 (q, J=7.1 Hz, 2H), 4.69 (s, 2H), 6.91-7.09 (m, 5H), 7.26 (d, J=8.9 Hz, 1H). $^{19}$F-NMR (376 MHz, CDCl$_3$) δ−116.1 (s, 1F).

Example-142

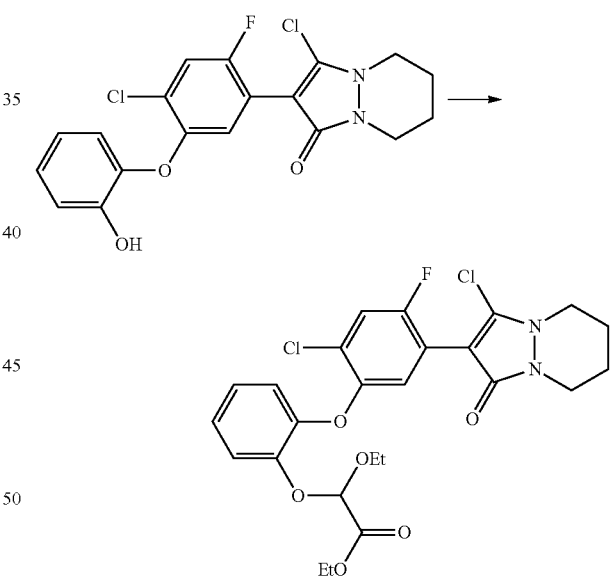

In the same manner as in Example-135, 5-chloro-4-[4-chloro-2-fluoro-5-(2-hydroxyphenoxy)phenyl]-1,2-tetramethylene-4-pyrazolin-3-one was reacted with ethyl 2-chloro-2-ethoxyacetate, whereby ethyl 2-[2-{2-chloro-5-(5-chloro-3-oxo-1,2-tetramethylene-4-pyrazolin-4-yl)-4-fluorophenyloxy}phenyloxy]-2-ethoxyacetate was obtained with a yield of 49%. $^1$H-NMR (400 MHz, CDCl$_3$) δ1.22 (t, J=7.1 Hz, 3H), 1.25 (t, J=7.1 Hz, 3H), 1.83-1.90 (m, 2H), 1.95-2.02 (m, 2H), 3.55-3.61 (m, 2H), 3.68-3.91 (m, 4H), 4.23 (q, J=7.1 Hz, 2H), 5.55 (s, 1H), 6.90 (m, 1H), 7.00-7.08 (m, 3H), 7.21 (m, 1H), 7.26 (d, J=9.1 Hz, 1H). $^{19}$F-NMR (376 MHz, CDCl$_3$) δ−115.6 (s, 1F).

Example-143

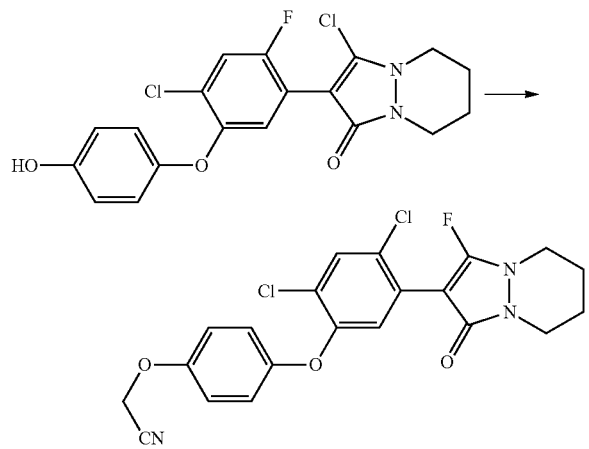

In the same manner as in Example-137, 5-chloro-4-[4-chloro-2-fluoro-5-(4-hydroxyphenoxy)phenyl]-1,2-tetramethylene-4-pyrazolin-3-one was reacted with bromoacetonitrile, whereby 5-chloro-4-[4-chloro-2-fluoro-5-[4-(cyanomethyloxy)phenoxy]phenyl]-1,2-tetramethylene-4-pyrazolin-3-one was obtained with a yield of 90%. $^1$H-NMR (400 MHz, CDCl$_3$) δ1.83-1.92 (m, 2H), 1.95-2.04 (m, 2H), 3.57-3.64 (m, 2H), 3.76-3.82 (m, 2H), 4.73 (s, 2H), 6.93-7.01 (m, 4H), 7.15 (d, J=6.4 Hz, 1H), 7.27 (d, J=9.2 Hz, 1H). $^{19}$F-NMR (376 MHz, CDCl$_3$) δ–115.0 (s, 1F).

Example-144

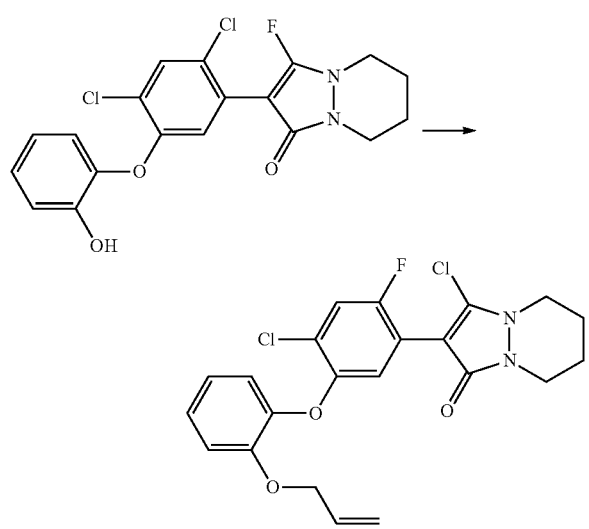

In the same manner as in Example-135, 5-chloro-4-[4-chloro-2-fluoro-5-(2-hydroxyphenoxy)phenyl]-1,2-tetramethylene-4-pyrazolin-3-one was reacted with allyl bromide, whereby 4-[5-{2-(allyloxy)phenoxy}-4-chloro-2-fluorophenyl]-5-chloro-1,2-tetramethylene-4-pyrazolin-3-one was obtained with a yield of 82%. $^1$H-NMR (400 MHz, CDCl$_3$): δ1.82-1.89 (m, 2H), 1.94-2.01 (m, 2H), 3.54-3.59 (m, 2H), 3.74-3.79 (m, 2H), 4.59 (td, J=1.2 and 5.4 Hz, 2H), 5.18 (qd, J=1.5 and 10.5 Hz, 1H), 5.28 (qd, J=1.5 and 17.1 Hz, 1H), 5.94 (ddt, J=5.4, 10.5 and 17.3 Hz, 1H), 6.88-7.01 (m, 4H), 7.08 (m, 1H), 7.25 (d, J=9.2 Hz, 1H). $^{19}$F-NMR (376 MHz, CDCl$_3$) δ–116.9 (s, 1F).

Example-145

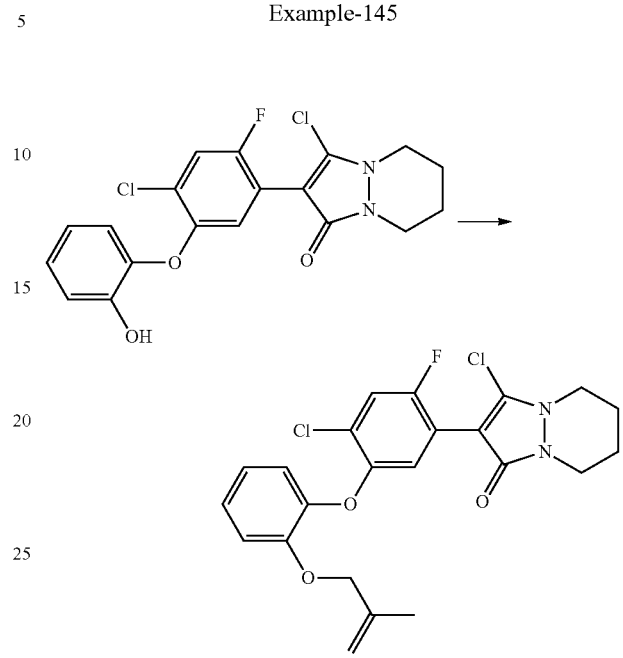

In the same manner as in Example-135, 5-chloro-4-[4-chloro-2-fluoro-5-(2-hydroxyphenoxy)phenyl]-1,2-tetramethylene-4-pyrazolin-3-one was reacted with methallyl bromide, whereby 5-chloro-4-[4-chloro-2-fluoro-5-[2-(methallyloxy)phenoxy]phenyl]-1,2-tetramethylene-4-pyrazolin-3-one was obtained with a yield of 78%. $^1$H-NMR (400 MHz, CDCl$_3$): δ1.67 (s, 3H), 1.82-1.89 (m, 2H), 1.94-2.01 (m, 2H), 3.54-3.59 (m, 2H), 3.73-3.78 (m, 2H), 4.44 (s, 2H), 4.88 (m, 1H), 4.95 (m, 1H), 6.89-7.11 (m, 5H), 7.24 (d, J=9.1 Hz, 1H). $^{19}$F-NMR (376 MHz, CDCl$_3$) δ–117.2 (s, 1F).

Example-146

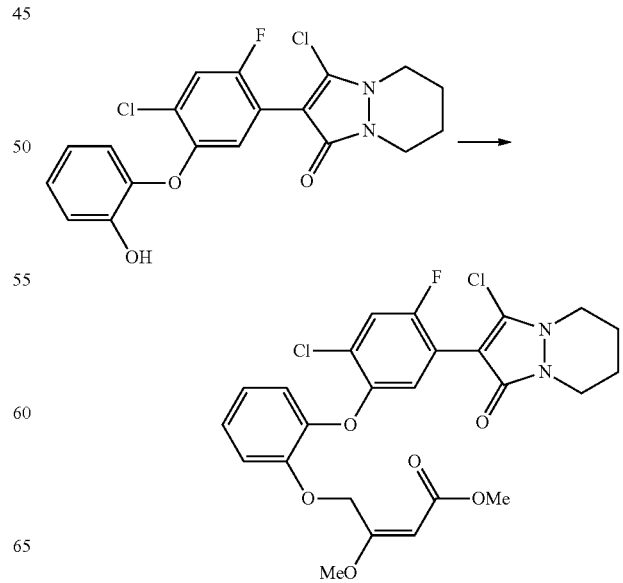

In the same manner as in Example-135, 5-chloro-4-[4-chloro-2-fluoro-5-(2-hydroxyphenoxy)phenyl]-1,2-tetramethylene-4-pyrazolin-3-one was reacted with methyl (E)-4-chloro-3-methoxy-2-butenoate, whereby methyl (E)-4-[2-[2-chloro-5-(5-chloro-3-oxo-1,2-tetramethylene-4-pyrazolin-4-yl)-4-fluorophenyloxy]phenyloxy]-3-methoxy-2-butenoate was obtained with a yield of 78%. $^1$H-NMR (400 MHz, CDCl$_3$): δ1.82-1.90 (m, 2H), 1.94-2.01 (m, 2H), 3.54-3.59 (m, 2H), 3.61 (s, 3H), 3.68 (s, 3H), 3.74-3.79 (m, 2H), 5.12 (s, 1H), 5.26 (s, 2H), 6.89-6.94 (m, 2H), 6.99 (d, J=6.6 Hz, 1H), 7.03-7.06 (m, 2H), 7.24 (d, J=9.1 Hz, 1H). $^{19}$F-NMR (376 MHz, CDCl$_3$) δ−116.6 (s, 1F).

Example-147

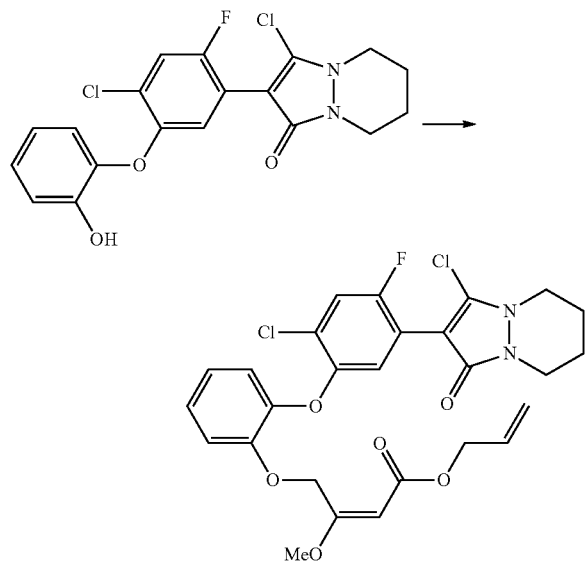

In the same manner as in Example-135, 5-chloro-4-[4-chloro-2-fluoro-5-(2-hydroxyphenoxy)phenyl]-1,2-tetramethylene-4-pyrazolin-3-one was reacted with allyl (E)-4-chloro-3-methoxy-2-butenoate, whereby allyl (E)-4-[2-[2-chloro-5-(5-chloro-3-oxo-1,2-tetramethylene-4-pyrazolin-4-yl)-4-fluorophenyloxy]phenyloxy]-3-methoxy-2-butenoate was obtained with a yield of 71%. $^1$H-NMR (400 MHz, CDCl$_3$): δ1.82-1.90 (m, 2H), 1.94-2.02 (m, 2H), 3.54-3.59 (m, 2H), 3.62 (s, 3H), 3.74-3.79 (m, 2H), 4.60 (td, J=1.4 and 5.8 Hz, 2H), 5.15 (s, 1H), 5.23 (qd, J=1.5 and 10.5 Hz, 1H), 5.26 (s, 2H), 5.32 (qd, J=1.5 and 17.1 Hz, 1H), 5.94 (ddt, J=5.8, 10.5 and 17.1 Hz, 1H), 6.89-6.95 (m, 2H), 6.99 (d, J=6.4 Hz, 1H), 7.02-7.06 (m, 2H), 7.24 (d, J=9.1 Hz, 1H). $^{19}$F-NMR (376 MHz, CDCl$_3$) δ−116.6 (s, 1F).

Example-148

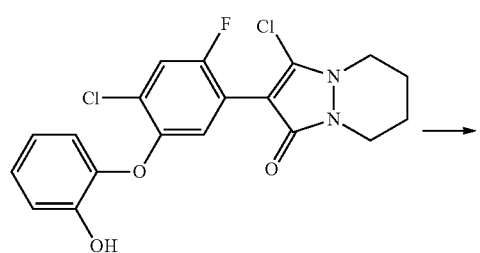

-continued

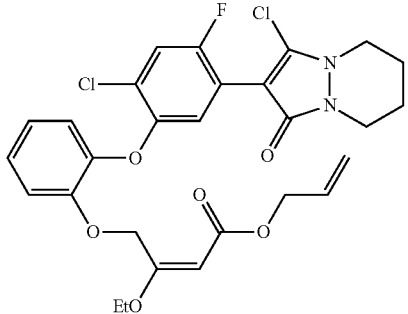

In the same manner as in Example-135, 5-chloro-4-[4-chloro-2-fluoro-5-(2-hydroxyphenoxy)phenyl]-1,2-tetramethylene-4-pyrazolin-3-one was reacted with allyl (E)-4-chloro-3-ethoxy-2-butenoate, whereby allyl (E)-4-[2-[2-chloro-5-(5-chloro-3-oxo-1,2-tetramethylene-4-pyrazolin-4-yl)-4-fluorophenyloxy]phenyloxy]-3-ethoxy-2-butenoate was obtained with a yield of 60%. $^1$H-NMR (400 MHz, CDCl$_3$): δ1.25 (t, J=7.0 Hz, 3H), 1.82-1.90 (m, 2H), 1.94-2.01 (m, 2H), 3.53-3.59 (m, 2H), 3.74-3.79 (m, 2H), 3.81 (q, J=7.0 Hz, 2H), 4.59 (td, J=1.5 and 5.8 Hz, 2H), 5.13 (s, 1H), 5.23 (qd, J=1.5 and 10.5 Hz, 1H), 5.25 (s, 2H), 5.32 (qd, J=1.5 and 17.1 Hz, 1H), 5.93 (ddt, J=5.8, 10.5 and 17.1 Hz, 1H), 6.88-6.95 (m, 2H), 6.97 (d, J=6.6 Hz, 1H), 7.03-7.07 (m, 2H), 7.23 (d, J=9.0 Hz, 1H). $^{19}$F-NMR (376 MHz, CDCl$_3$) δ−116.7 (s, 1F).

Example-149

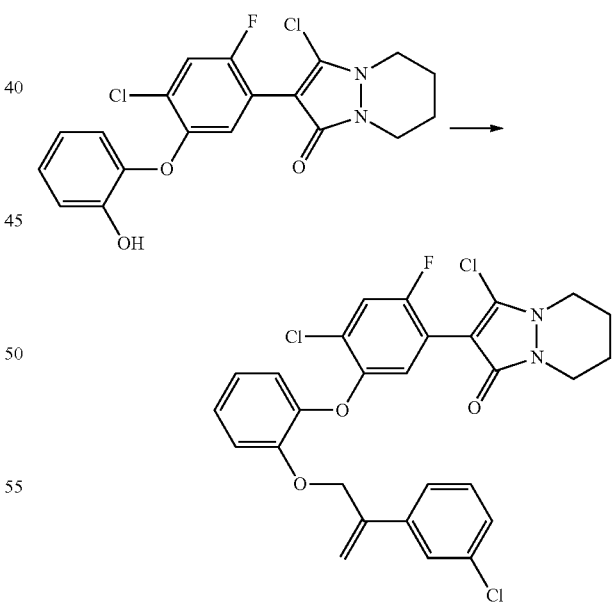

In the same manner as in Example-135, 5-chloro-4-[4-chloro-2-fluoro-5-(2-hydroxyphenoxy)phenyl]-1,2-tetramethylene-4-pyrazolin-3-one was reacted with 2-(3-chlorophenyl)allyl chloride, whereby 5-chloro-4-[4-chloro-5-[2-{2-(3-chlorophenyl)allyloxy}phenoxy]-2-fluorophenyl]-1,2-tetramethylene-4-pyrazolin-3-one was obtained with a yield of 79%. $^1$H-NMR (400 MHz, CDCl$_3$): δ1.82-1.89 (m, 2H), 1.94-2.01 (m, 2H), 3.54-3.59 (m, 2H), 3.74-3.79 (m, 2H), 4.88 (s, 2H), 5.36 (m, 1H), 5.49 (m, 1H), 6.92 (d, J=6.6 Hz, 1H), 6.94-7.12 (m, 4H), 7.18 (d, J=9.2 Hz, 1H), 7.20-7.30 (m, 3H), 7.40 (m, 1H). $^{19}$F-NMR (376 MHz, CDCl$_3$) δ–116.8 (s, 1F).

Example-150

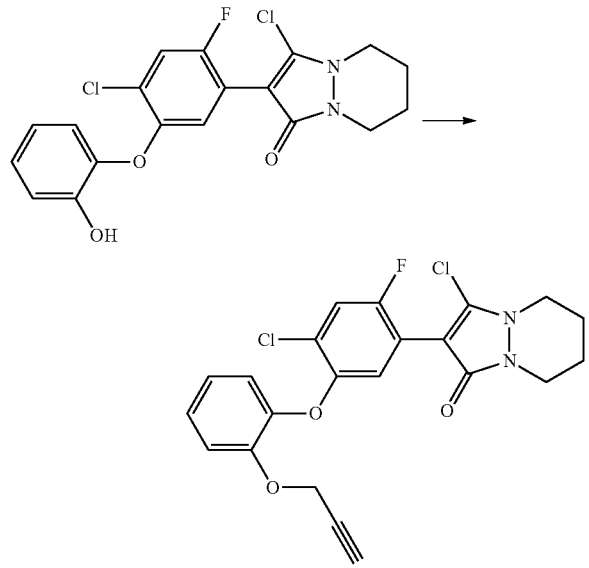 [SMILES: O=c1c(-c2cc(Oc3ccccc3O)c(Cl)cc2F)c(Cl)n2n1CCCC2 ; C=C(C)COc1ccccc1Oc1cc(-c2c(Cl)n3n(c2=O)CCCC3)c(F)cc1Cl]

In the same manner as in Example-135, 5-chloro-4-[4-chloro-2-fluoro-5-(2-hydroxyphenoxy)phenyl]-1,2-tetramethylene-4-pyrazolin-3-one was reacted with propargyl bromide, whereby 5-chloro-4-[4-chloro-2-fluoro-5-[2-(propargyloxy)phenoxy]phenyl]-1,2-tetramethylene-4-pyrazolin-3-one was obtained with a yield of 84%. $^1$H-NMR (400 MHz, CDCl$_3$) δ1.82-1.90 (m, 2H), 1.94-2.02 (m, 2H), 2.50 (t, J=2.4 Hz, 1H), 3.54-3.60 (m, 2H), 3.75-3.80 (m, 2H), 4.76 (d, J=2.4 Hz, 2H), 6.92 (dd, J=1.6 and 8.0 Hz, 1H), 6.97 (ddd, J=1.6, 7.1 and 8.0 Hz, 1H), 7.02 (d, J=6.4 Hz, 1H), 7.09 (ddd, J=1.6, 7.1 and 8.0 Hz, 1H), 7.17 (dd, J=1.6 and 8.0 Hz, 1H), 7.26 (d, J=9.0 Hz, 1H). $^{19}$F-NMR (376 MHz, CDCl$_3$) δ–116.1 (s, 1F).

Example-151

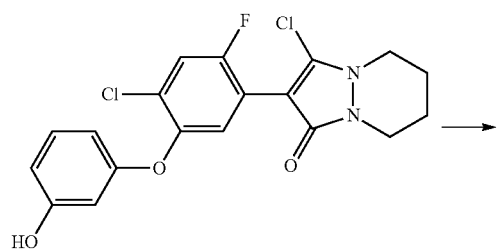

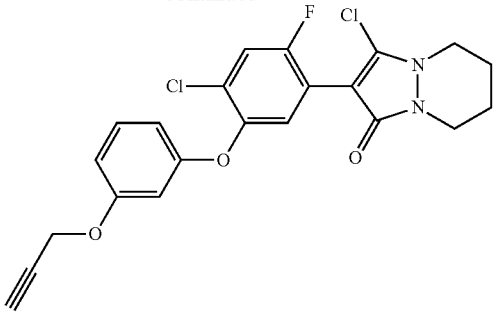

Potassium carbonate (0.13 g, 0.92 mmol) and propargyl bromide (0.097 mL, 1.22 mmol) were added to a solution of 5-chloro-4-[4-chloro-2-fluoro-5-(3-hydroxyphenoxy)phenyl]-1,2-tetramethylene-4-pyrazolin-3-one (0.25 g, 0.61 mmol) in DMF (3 mL), followed by stirring at room temperature for 20 hours. After the reaction was completed, water (20 mL) was added to the reaction solution, and the resultant product was extracted with ethyl acetate (20 mL×3). The organic layer was washed sequentially with water (20 mL×3) and a saturated saline solution (20 mL), dried over magnesium sulfate, and concentrated under reduced pressure, and the obtained crude product was purified by silica gel column chromatography, whereby 5-chloro-4-[4-chloro-2-fluoro-5-[3-(propargyloxy)phenoxy]phenyl]-1,2-tetramethylene-4-pyrazolin-3-one (0.20 g, yield: 74%) was obtained as a white solid. $^1$H-NMR (400 MHz, CDCl$_3$) δ1.91-1.89 (m, 2H), 2.03-1.96 (m, 2H), 2.54 (t, J=2.4 Hz, 1H), 3.62-3.57 (m, 2H), 3.81-3.76 (m, 2H), 4.66 (d, J=2.4 Hz, 2H), 6.59 (m, 1H), 6.61 (m, 1H), 6.69 (m, 1H), 7.21 (m, 1H), 7.23 (d, J=6.6 Hz, 1H), 7.27 (d, J=9.1 Hz, 1H). $^{19}$F-NMR (376 MHz, CDCl$_3$) δ–114.5 (s, 1F).

Example-152

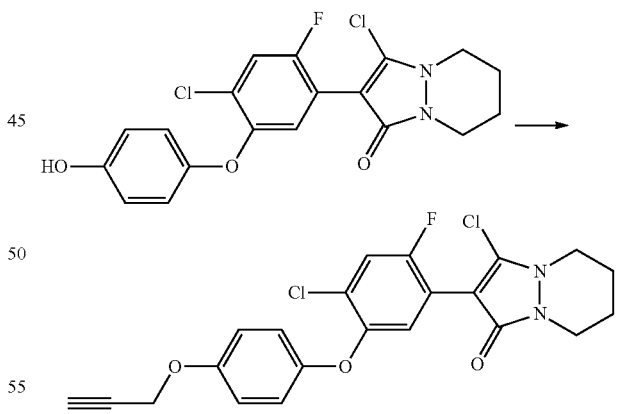

A suspension of a 55% oil dispersion (0.053 g, 1.22 mmol) of sodium hydride in DMF (3 mL) was cooled in an ice bath, and 5-chloro-4-[4-chloro-2-fluoro-5-(4-hydroxyphenoxy)phenyl]-1,2-tetramethylene-4-pyrazolin-3-one (0.25 g, 0.61 mmol) and propargyl bromide (0.097 mL, 1.22 mmol) were added thereto, followed by stirring at room temperature for 15 hours. After the reaction was completed, water (20 mL) was added to the reaction solution, and the resultant product was extracted with ethyl acetate (20 mL×3). The organic layer was dried over magnesium sulfate, and concentrated under reduced pressure, and the obtained crude product was purified by silica gel column chromatography, whereby 5-chloro-4-[4-chloro-2-fluoro-5-[4-(propargyloxy)phenoxy]phenyl]-1,2-tetramethylene-4-pyrazolin-3-one (0.21 g, yield: 78%) was obtained as a pale yellow solid. $^1$H-NMR (400 MHz, CDCl$_3$) δ1.91-1.88 (m, 2H), 2.02-1.95 (m, 2H), 2.52 (t, J=2.4 Hz, 1H), 3.59 (m, 2H), 3.78 (m, 2H), 4.65 (d, J=2.4 Hz, 2H), 6.98-6.91 (m, 4H), 7.10 (d, J=6.5 Hz, 1H), 7.25 (d, J=2.1 Hz, 1H). $^{19}$F-NMR (376 MHz, CDCl$_3$) δ−115.8 (s, 1F).

Example-153

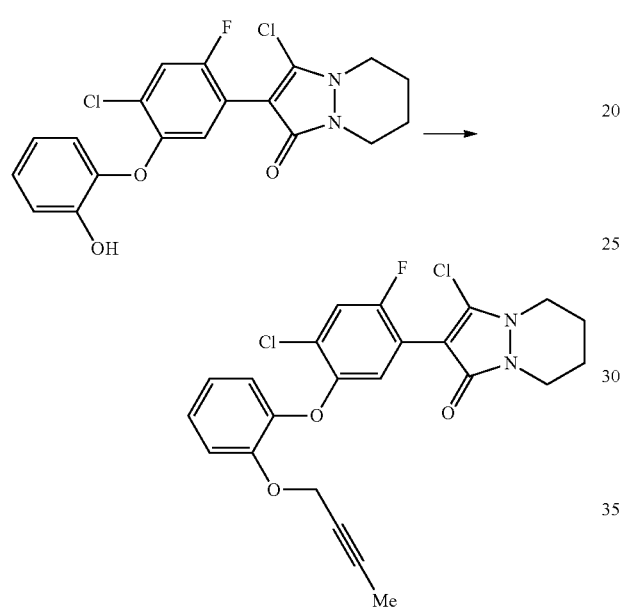

In the same manner as in Example-135, 5-chloro-4-[4-chloro-2-fluoro-5-(2-hydroxyphenoxy)phenyl]-1,2-tetramethylene-4-pyrazolin-3-one was reacted with 4-bromo-2-butyne, whereby 5-chloro-4-[4-chloro-2-fluoro-5-[2-(2-butynyloxy)phenoxy]phenyl]-1,2-tetramethylene-4-pyrazolin-3-one was obtained with a yield of 41%. $^1$H-NMR (400 MHz, CDCl$_3$): δ1.83 (t, J=2.4 Hz, 3H), 1.84-1.90 (m, 2H), 1.94-2.02 (m, 2H), 3.54-3.59 (m, 2H), 3.75-3.79 (m, 2H), 4.71 (q, J=2.4 Hz, 2H), 6.87-6.97 (m, 2H), 7.01 (d, J=6.4 Hz, 1H), 7.06-7.18 (m, 2H), 7.25 (d, J=9.0 Hz, 1H). $^{19}$F-NMR (376 MHz, CDCl$_3$) δ−116.2 (s, 1F).

Example-154

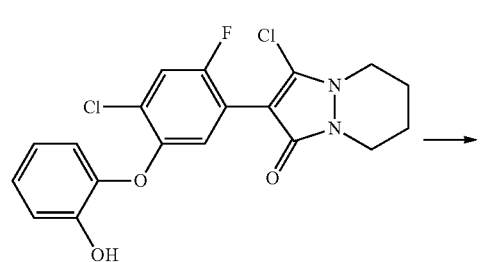

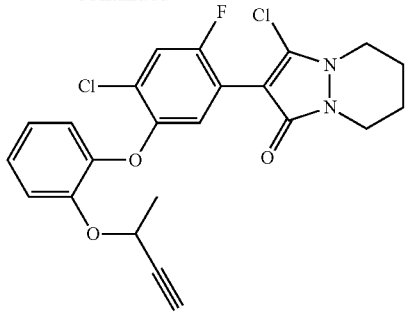

In the same manner as in Example-135, 5-chloro-4-[4-chloro-2-fluoro-5-(2-hydroxyphenoxy)phenyl]-1,2-tetramethylene-4-pyrazolin-3-one was reacted with 3-bromo-1-butyne, whereby 5-chloro-4-[4-chloro-2-fluoro-5-[2-(1-butyn-3-yloxy)phenoxy]phenyl]-1,2-tetramethylene-4-pyrazolin-3-one was obtained with a yield of 48%. $^1$H-NMR (400 MHz, CDCl$_3$): δ1.60 (s, 3H), 1.85-1.92 (m, 2H), 1.96-2.04 (m, 2H), 3.58-3.63 (m, 2H), 3.77-3.82 (m, 2H), 5.83 (s, 2H), 6.78-6.85 (m, 2H), 6.97-7.06 (m, 2H), 7.24 (d, J=6.6 Hz, 1H), 7.28 (d, J=9.0 Hz, 1H). $^{19}$F-NMR (376 MHz, CDCl$_3$) δ−114.2 (s, 1F).

Example-155

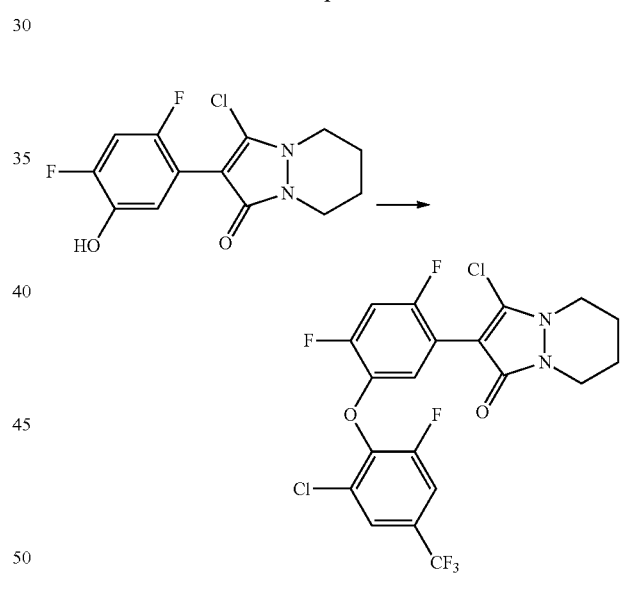

5-Chloro-4-(2,4-difluoro-5-hydroxyphenyl)-1,2-tetramethylene-4-pyrazolin-3-one (0.20 g, 0.67 mmol) and 3-chloro-4,5-difluorobenzotrifluoride (0.22 g, 1.00 mmol) were added to a solution of a 55% oil dispersion (44 mg, 1.01 mmol) of sodium hydride in DMF (3 mL) under ice-cooling, followed by stirring at room temperature for 24 hours. After the reaction was completed, water (20 mL) was added to the reaction solution, and the resultant product was extracted with ethyl acetate (20 mL×3). The organic layer was dried over magnesium sulfate, and concentrated under reduced pressure, and the obtained crude product was purified by silica gel column chromatography, whereby 5-chloro-4-[2,4-difluoro-5-(2-chloro-4-trifluoromethyl-6-fluorophenoxy)phenyl]-1,2-tetramethylene-4-pyrazolin-3- one (0.28 g, yield: 85%) was obtained. $^1$H-NMR (400 MHz, CDCl$_3$) δ7.55 (brs, 1H), 7.38-7.34 (m, 1H), 7.05-6.96 (m, 2H), 3.81-3.75 (m, 2H), 3.62-3.57 (m, 2H), 2.04-1.95 (m, 2H), 1.91-1.83 (m, 2H). $^{19}$F-NMR (376 MHz, CDCl$_3$) δ−62.6 (s, 3F), −112.8 (d, J=5.5 Hz, 1F), −122.2 (s, 1F), −128.5 (d, J=5.5H, 1F).

Example-156

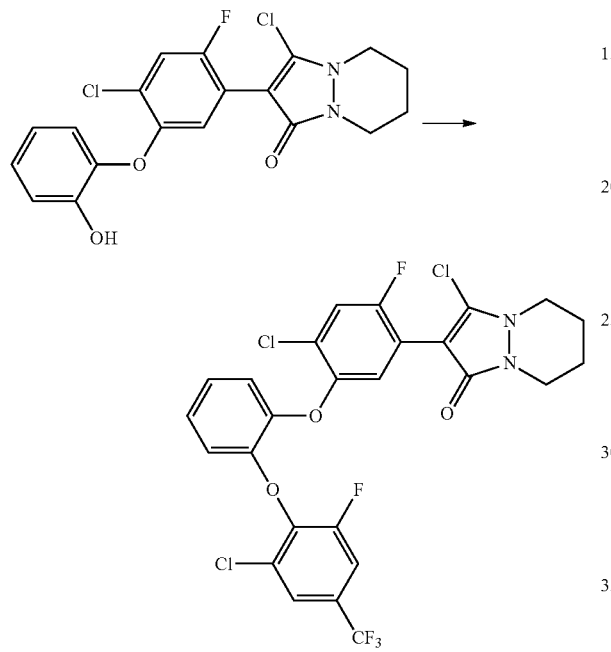

In the same manner as in Example-155, 5-chloro-4-[4-chloro-2-fluoro-5-(2-hydroxyphenoxy)phenyl]-1,2-tetramethylene-4-pyrazolin-3-one was reacted with 1-chloro-2,3-difluoro-5-(trifluoromethyl)benzene, whereby 5-chloro-4-[4-chloro-5-[2-{2-chloro-6-fluoro-4-(trifluoromethyl)phenoxy}phenoxy]-2-fluorophenyl]-1,2-tetramethylene-4-pyrazolin-3-one was obtained with a yield of 70%. $^1$H-NMR (400 MHz, CDCl$_3$): δ1.84-1.91 (m, 2H), 1.96-2.04 (m, 2H), 3.57-3.62 (m, 2H), 3.76-3.81 (m, 2H), 6.84 (m, 1H), 6.97-7.09 (m, 3H), 7.11 (d, J=6.4 Hz, 1H), 7.22 (d, J=9.0 Hz, 1H), 7.32 (m, 1H), 7.50 (m, 1H). $^{19}$F-NMR (376 MHz, CDCl$_3$) δ−122.1 (s, 1F), −115.4 (s, 1F), −62.5 (s, 3F).

Example-157

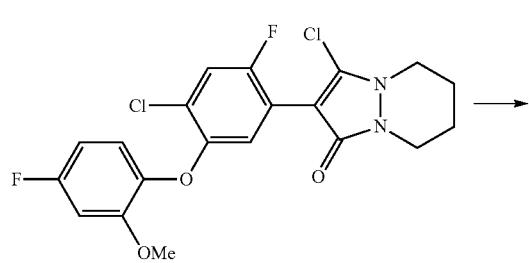

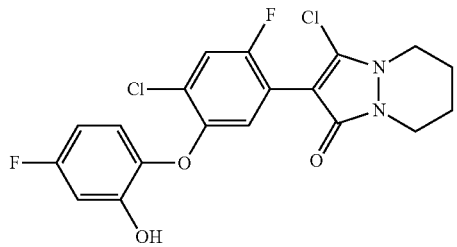

In the same manner as in Example-130, from 5-chloro-4-[4-chloro-2-fluoro-5-(4-fluoro-2-methoxyphenoxy)phenyl]-1,2-tetramethylene-4-pyrazolin-3-on, 5-chloro-4-[4-chloro-2-fluoro-5-(4-fluoro-2-hydroxyphenoxy)phenyl]-1,2-tetramethylene-4-pyrazolin-3-one was obtained with a yield of 87%. $^1$H-NMR (400 MHz, CDCl$_3$) δ1.85-1.92 (m, 2H), 1.97-2.04 (m, 2H), 3.59-3.64 (m, 2H), 3.77-3.82 (m, 2H), 6.53 (ddd, J=2.9, 8.9 and 11.1 Hz, 1H), 6.76 (dd, J=2.9 and 9.6 Hz, 1H), 6.80 (dd, J=5.4 and 8.9 Hz, 1H), 7.13 (d, J=6.4 Hz, 1H), 7.26 (d, J=9.1 Hz, 1H). $^{19}$F-NMR (376 MHz, CDCl$_3$) δ−116.6 (s, 1F), −114.9 (s, 1F).

Example-158

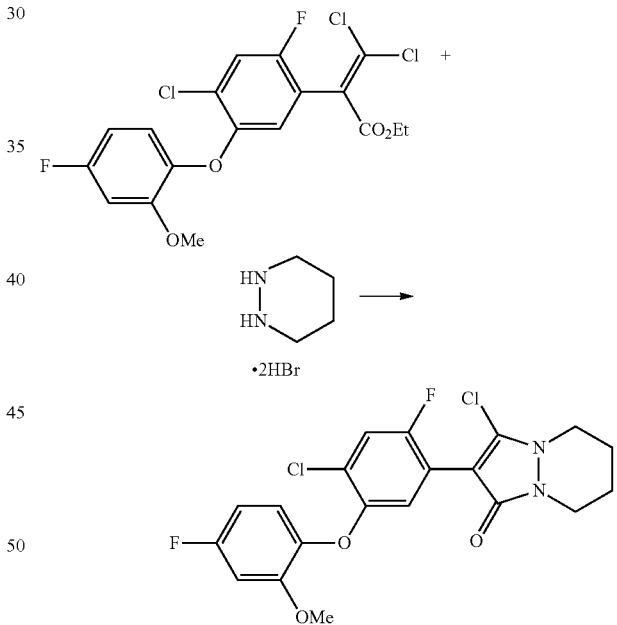

In the same manner as in Example-129, ethyl 3,3-dichloro-2-[4-chloro-2-fluoro-5-(4-fluoro-2-methoxyphenoxy)phenyl]acrylate was reacted with hexahydropyridazine dihydrobromide, whereby 5-chloro-4-[4-chloro-2-fluoro-5-(4-fluoro-2-methoxyphenoxy)phenyl]-1,2-tetramethylene-4-pyrazolin-3-one was obtained with a yield of 98%. $^1$H-NMR (400 MHz, CDCl$_3$) δ1.83-1.90 (m, 2H), 1.95-2.02 (m, 2H), 3.55-3.60 (m, 2H), 3.75-3.79 (m, 2H), 3.82 (s, 3H), 6.61 (ddd, J=2.9, 8.8 and 10.8 Hz, 1H), 6.72 (dd, J=2.9 and 10.1 Hz, 1H), 6.88 (d, J=6.4 Hz, 1H), 6.93 (dd, J=5.7 and 8.8 Hz, 1H), 7.24 (d, J=9.1 Hz, 1H). $^{19}$F-NMR (376 MHz, CDCl$_3$) δ−116.9 (s, 1F), −115.3 (s, 1F).

Example-159

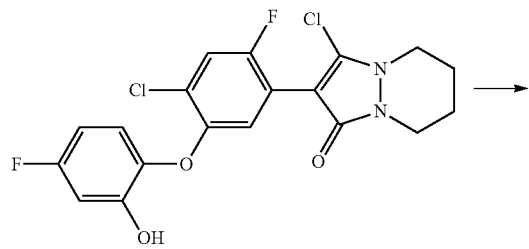

In the same manner as in Example-135, 5-chloro-4-[4-chloro-2-fluoro-5-(4-fluoro-2-hydroxyphenoxy)phenyl]-1,2-tetramethylene-4-pyrazolin-3-one was reacted with allyl bromide, whereby 4-[5-[2-(allyloxy)-4-fluorophenoxy]-4-chloro-2-fluorophenyl]-5-chloro-1,2-tetramethylene-4-pyrazolin-3-one was obtained with a yield of 91%. $^1$H-NMR (400 MHz, CDCl$_3$) δ1.82-1.90 (m, 2H), 1.94-2.02 (m, 2H), 3.54-3.59 (m, 2H), 3.74-3.79 (m, 2H), 4.53 (td, J=1.4 and 5.0 Hz, 2H), 5.20 (qd, J=1.4 and 10.5 Hz, 1H), 5.27 (qd, J=1.4 and 17.3 Hz, 1H), 5.90 (ddt, J=5.0, 10.5 and 17.1 Hz, 1H), 6.62 (ddd, J=2.9, 8.9 and 10.9 Hz, 1H), 6.72 (dd, J=2.9 and 10.0 Hz, 1H), 6.88 (d, J=6.4 Hz, 1H), 6.98 (dd, J=5.7 and 8.9 Hz, 1H), 7.24 (d, J=9.0 Hz, 1H). $^{19}$F-NMR (376 MHz, CDCl$_3$) δ–117.1 (s, 1F), –115.4 (s, 1F).

Example-160

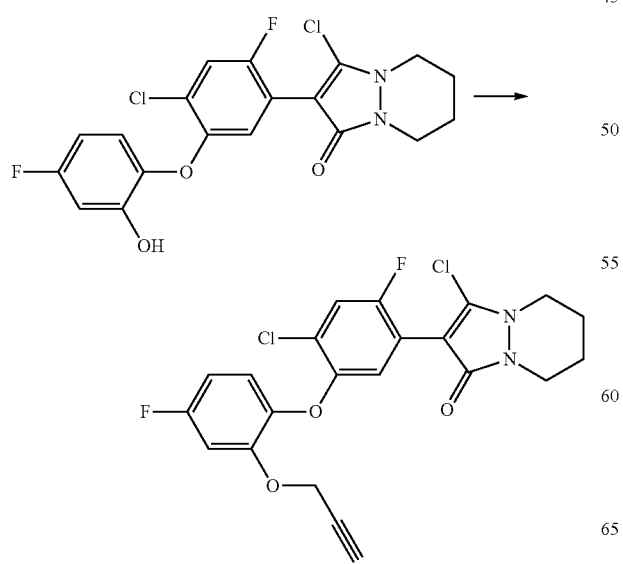

In the same manner as in Example-135, 5-chloro-4-[4-chloro-2-fluoro-5-(4-fluoro-2-hydroxyphenoxy)phenyl]-1,2-tetramethylene-4-pyrazolin-3-one was reacted with propargyl bromide, whereby 5-chloro-4-[4-chloro-2-fluoro-5-[4-fluoro-2-(propargyloxy)phenoxy]phenyl]-1,2-tetramethylene-4-pyrazolin-3-one was obtained with a yield of 92%. $^1$H-NMR (400 MHz, CDCl$_3$) δ1.83-1.90 (m, 2H), 1.95-2.02 (m, 2H), 2.52 (t, J=2.4 Hz, 1H), 3.55-3.60 (m, 2H), 3.75-3.79 (m, 2H), 4.73 (d, J=2.4 Hz, 2H), 6.68 (m, 1H), 6.88-6.97 (m, 3H), 7.25 (d, J=9.2 Hz, 1H). $^{19}$F-NMR (376 MHz, CDCl$_3$) δ–116.6 (s, 1F), –114.9 (s, 1F).

Example-161

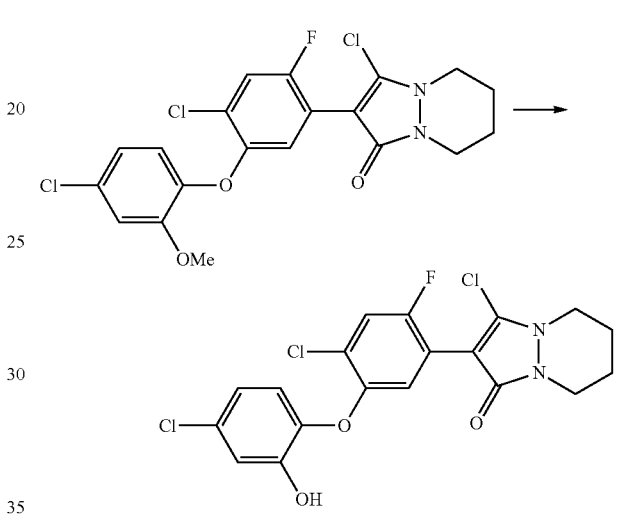

In the same manner as in Example-130, from 5-chloro-4-[4-chloro-2-fluoro-5-(4-chloro-2-methoxyphenoxy)phenyl]-1,2-tetramethylene-4-pyrazolin-3-on, 5-chloro-4-[4-chloro-2-fluoro-5-(4-chloro-2-hydroxyphenoxy)phenyl]-1,2-tetramethylene-4-pyrazolin-3-one was obtained with a yield of 86%. $^1$H-NMR (400 MHz, CDCl$_3$) δ1.86-1.93 (m, 2H), 1.98-2.04 (m, 2H), 3.60-3.65 (m, 2H), 3.78-3.82 (m, 2H), 6.74 (d, J=8.7 Hz, 1H), 6.78 (dd, J=2.4 and 8.7 Hz, 1H), 7.03 (d, J=2.4 Hz, 1H), 7.17 (d, J=6.5 Hz, 1H), 7.27 (d, J=8.7 Hz, 1H). $^{19}$F-NMR (376 MHz, CDCl$_3$) δ–114.3 (s, 1F).

Example-162

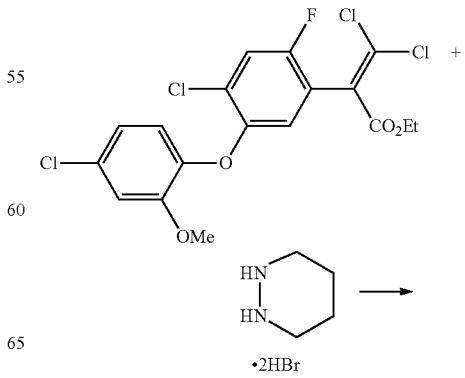

-continued

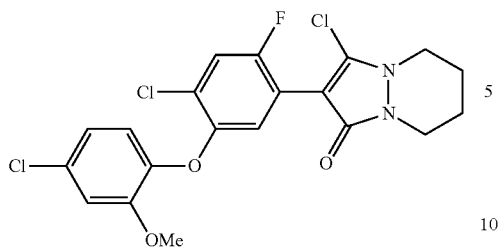

In the same manner as in Example-129, ethyl 3,3-dichloro-2-[4-chloro-5-(4-chloro-2-methoxyphenoxy)-2-fluorophenyl]acrylate was reacted with hexahydropyridazine dihydrobromide, whereby 5-chloro-4-[4-chloro-5-(4-chloro-2-methoxyphenoxy)-2-fluorophenyl]-1,2-tetramethylene-4-pyrazolin-3-one was obtained with a yield of 95%. $^1$H-NMR (400 MHz, CDCl$_3$) δ1.83-1.91 (m, 2H), 1.95-2.02 (m, 2H), 3.56-3.61 (m, 2H), 3.75-3.80 (m, 2H), 3.84 (s, 3H), 6.82-6.90 (m, 2H), 6.94-6.98 (m, 2H), 7.25 (d, J=9.1 Hz, 1H). $^{19}$F-NMR (376 MHz, CDCl$_3$) δ−116.0 (s, 1F).

Example-163

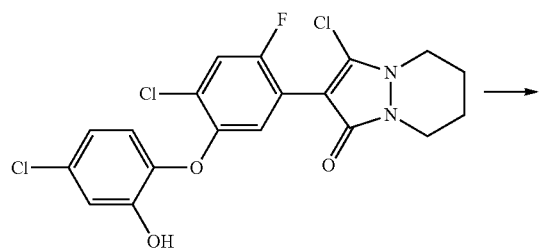

In the same manner as in Example-135, 5-chloro-4-[4-chloro-2-fluoro-5-(4-chloro-2-hydroxyphenoxy)phenyl]-1,2-tetramethylene-4-pyrazolin-3-one was reacted with allyl bromide, whereby 4-[5-(2-allyloxy-4-chlorophenoxy)-4-chloro-2-fluorophenyl]-5-chloro-1,2-tetramethylene-4-pyrazolin-3-one was obtained with a yield of 92%. $^1$H-NMR (400 MHz, CDCl$_3$) δ1.83-1.90 (m, 2H), 1.95-2.03 (m, 2H), 3.56-3.60 (m, 2H), 3.75-3.80 (m, 2H), 4.55 (td, J=1.6 and 5.1 Hz, 2H), 5.21 (qd, J=1.5 and 10.6 Hz, 1H), 5.28 (qd, J=1.5 and 17.3 Hz, 1H), 5.92 (ddt, J=5.1, 10.4 and 17.3 Hz, 1H), 6.88-6.90 (m, 2H), 6.94-6.98 (m, 2H), 7.23 (d, J=9.0 Hz, 1H). $^{19}$F-NMR (376 MHz, CDCl$_3$) δ−116.3 (s, 1F).

Example-164

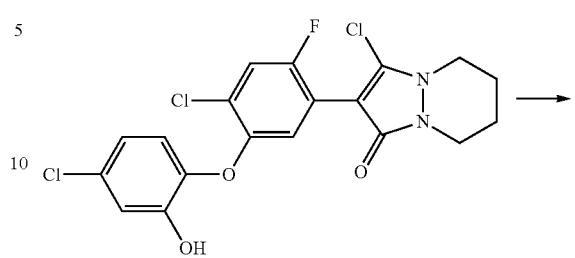

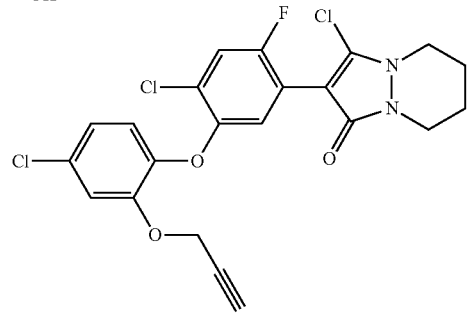

In the same manner as in Example-135, 5-chloro-4-[4-chloro-5-(4-chloro-2-hydroxyphenoxy)-2-fluorophenyl]-1,2-tetramethylene-4-pyrazolin-3-one was reacted with propargyl bromide, whereby 5-chloro-4-[4-chloro-5-[4-chloro-2-(propargyloxy)phenoxy]-2-fluorophenyl]-1,2-tetramethylene-4-pyrazolin-3-one was obtained with a yield of 90%. $^1$H-NMR (400 MHz, CDCl$_3$) δ1.84-1.91 (m, 2H), 1.95-2.03 (m, 2H), 2.54 (t, J=2.4 Hz, 1H), 3.56-3.61 (m, 2H), 3.76-3.80 (m, 2H), 4.75 (d, J=2.4 Hz, 2H), 6.85 (d, J=8.6 Hz, 1H), 6.94 (dd, J=2.4 and 8.6 Hz, 1H), 7.01 (d, J=6.4 Hz, 1H), 7.15 (d, J=2.4 Hz, 1H), 7.25 (d, J=9.0 Hz, 1H). $^{19}$F-NMR (376 MHz, CDCl$_3$) δ−115.6 (s, 1F).

Example-165

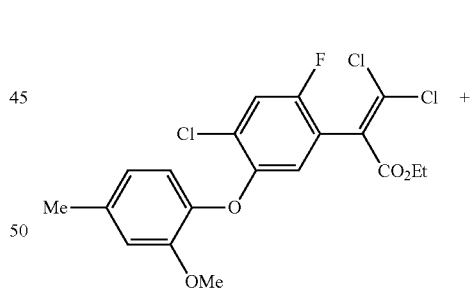

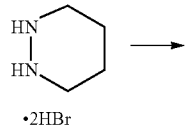

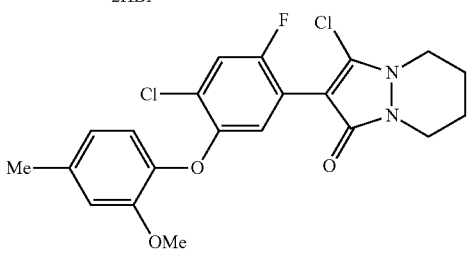

In the same manner as in Example-129, ethyl 3,3-dichloro-2-[4-chloro-2-fluoro-5-(2-methoxy-4-methylphenoxy)phenyl]acrylate was reacted with hexahydropyridazine dihydrobromide, whereby 5-chloro-4-[4-chloro-2-fluoro-5-(2-methoxy-4-methylphenoxy)phenyl]-1,2-tetramethylene-4-pyrazolin-3-one was obtained with a yield of 92%. $^1$H-NMR (400 MHz, CDCl$_3$) δ1.82-1.89 (m, 2H), 1.94-2.02 (m, 2H), 2.33 (s, 3H), 3.54-3.58 (m, 2H), 3.74-3.79 (m, 2H), 3.82 (s, 3H), 6.70 (dd, J=1.6 and 8.0 Hz, 1H), 6.79 (d, J=1.6 Hz, 1H), 6.83 (d, J=8.0 Hz, 1H), 6.90 (d, J=6.5 Hz, 1H), 7.24 (d, J=9.1 Hz, 1H). $^{19}$F-NMR (376 MHz, CDCl$_3$) δ−117.3 (s, 1F).

Example-166

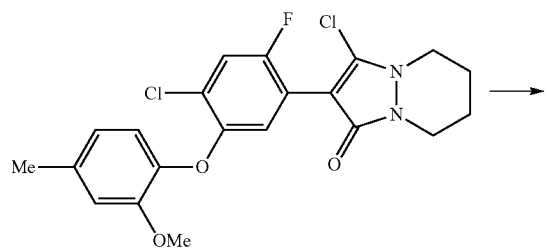

In the same manner as in Example-130, from 5-chloro-4-[4-chloro-2-fluoro-5-(2-methoxy-4-methylphenoxy)phenyl]-1,2-tetramethylene-4-pyrazolin-3-on, 5-chloro-4-[4-chloro-2-fluoro-5-(2-hydroxy-4-methylphenoxy)phenyl]-1,2-tetramethylene-4-pyrazolin-3-one was obtained with a yield of 89%. $^1$H-NMR (400 MHz, CDCl$_3$) δ1.84-1.91 (m, 2H), 1.96-2.03 (m, 2H), 2.27 (s, 3H), 3.58-3.62 (m, 2H), 3.77-3.81 (m, 2H), 6.61 (dd, J=1.7 and 8.0 Hz, 1H), 6.72 (d, J=8.2 Hz, 1H), 6.84 (d, J=1.7 Hz, 1H), 7.16 (d, J=6.5 Hz, 1H), 7.26 (d, J=9.1 Hz, 1H). $^{19}$F-NMR (376 MHz, CDCl$_3$) δ−115.1 (s, 1F).

Example-167

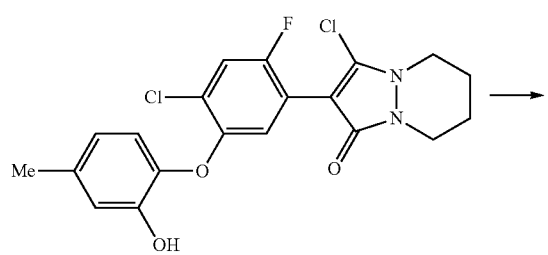

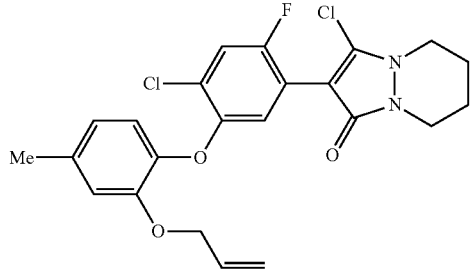

In the same manner as in Example-135, 5-chloro-4-[4-chloro-2-fluoro-5-(2-hydroxy-4-methylphenoxy)phenyl]-1,2-tetramethylene-4-pyrazolin-3-one was reacted with allyl bromide, whereby 4-[5-(2-allyloxy-4-methylphenoxy)-4-chloro-2-fluorophenyl]-5-chloro-1,2-tetramethylene-4-pyrazolin-3-one was obtained with a yield of 91%. $^1$H-NMR (400 MHz, CDCl$_3$) δ1.81-1.89 (m, 2H), 1.94-2.01 (m, 2H), 2.31 (s, 3H), 3.53-3.58 (m, 2H), 3.74-3.79 (m, 2H), 4.54 (td, J=1.6 and 5.1 Hz, 2H), 5.16 (qd, J=1.5 and 10.6 Hz, 1H), 5.26 (qd, J=1.5 and 17.2 Hz, 1H), 5.92 (ddt, J=5.1, 10.4 and 17.2 Hz, 1H), 6.72 (dd, J=1.7 and 8.1 Hz, 1H), 6.79 (d, J=1.7 Hz, 1H), 6.89 (d, J=8.0 Hz, 1H), 6.90 (d, J=6.5 Hz, 1H), 7.23 (d, J=9.1 Hz, 1H). $^{19}$F-NMR (376 MHz, CDCl$_3$) δ−117.6 (s, 1F).

Example-168

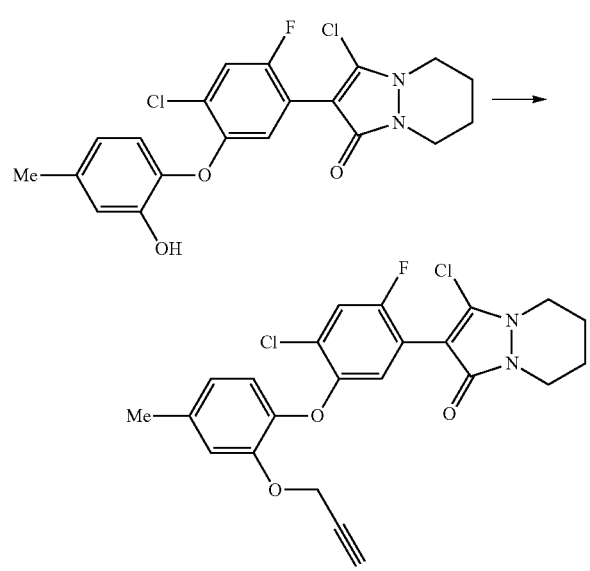

In the same manner as in Example-135, 5-chloro-4-[4-chloro-2-fluoro-5-(2-hydroxy-4-methylphenoxy)phenyl]-1,2-tetramethylene-4-pyrazolin-3-one was reacted with propargyl bromide, whereby 5-chloro-4-[4-chloro-2-fluoro-5-[4-methyl-2-(propargyloxy)phenoxy]phenyl]-1,2-tetramethylene-4-pyrazolin-3-one was obtained with a yield of 91%. $^1$H-NMR (400 MHz, CDCl$_3$) δ1.82-1.90 (m, 2H), 1.94-2.01 (m, 2H), 2.33 (s, 3H), 2.49 (t, J=2.4 Hz, 1H), 3.55-3.59 (m, 2H), 3.74-3.79 (m, 2H), 4.73 (d, J=2.4 Hz, 2H), 6.77 (dd, J=1.7 and 8.0 Hz, 1H), 6.84 (d, J=8.0 Hz, 1H), 6.94-6.97 (m, 2H), 7.24 (d, J=8.9 Hz, 1H). $^{19}$F-NMR (376 MHz, CDCl$_3$) δ−116.8 (s, 1F).

Reference Example-62

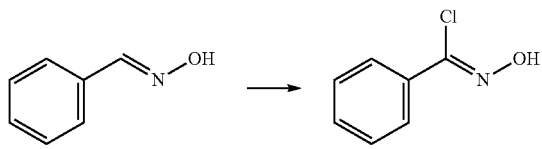 [SMILES: O/N=C/c1ccccc1 ; O/N=C(\Cl)c1ccccc1]

Benzaldoxime (1.0 g, 8.25 mmol) was dissolved in acetonitrile (15 mL), and N-chlorosuccinimide (1.1 g, 8.25 mmol) was added thereto, followed by stirring at room temperature for 5 hours. After the reaction was completed, the resultant product was concentrated under reduced pressure, whereby benzohydroxymoyl chloride (1.97 g) was obtained as a white solid. $^1$H-NMR (400 MHz, CDCl$_3$): δ7.39-7.86 (m, 5H), 8.34 (brs, 1H).

Reference Example-63

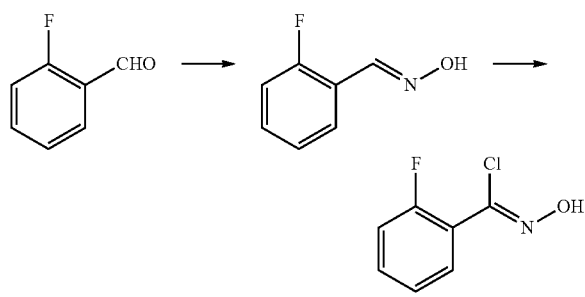

Hydroxylamine hydrochloride (748 mg, 10.4 mmol) was added to a solution of 2-fluorobezaldehyde (1.18 g, 9.49 mmol) in ethanol (10 mL) and water (10 mL), and a sodium hydroxide aqueous solution (37%, 1.8 mL) was added dropwise thereto under ice-cooling, followed by stirring at room temperature for 1 hour. After the reaction was completed, 2N hydrochloric acid was added to the reaction solution to acidify, and the resultant product was extracted with dichloromethane (10 mL×3). The organic layer was dried over anhydrous magnesium sulfate, and concentrated under reduced pressure, and the obtained crude product was purified by silica gel column chromatography (hexane:ethyl acetate=9:1), whereby 2-fluorobenzaldoxime (1.08 g, yield: 82%) was obtained as a white solid. $^1$H-NMR (400 MHz, CDCl$_3$): δ7.06-7.19 (m, 2H), 7.34 (m, 1H), 7.75 (m, 1H), 7.96 (brs, 1H), 8.38 (s, 1H). $^{19}$F-NMR (376 MHz, CDCl$_3$): δ-118.7 (s, 1F).

N-chlorosuccinimide (1.06 g, 7.94 mmol) was added to a solution of 2-fluorobenzaldoxime (1.00 g, 7.2 mmol) in DMF (5 mL), followed by stirring at room temperature for 2 hours. After the reaction was completed, the reaction solution was concentrated under reduced pressure, and the obtained crude product was purified by silica gel column chromatography (hexane:ethyl acetate=4:1), whereby 2-fluorobenzohydroxymoyl chloride (974 mg, yield: 78%) was obtained as a white solid. $^1$H-NMR (400 MHz, CDCl$_3$): δ7.12-7.25 (m, 2H), 7.45 (m, 1H), 7.67 (m, 1H), 8.65 (m, 1H). $^{19}$F-NMR (376 MHz, CDCl$_3$): δ-111.9 (s, 1F).

Reference Example-64

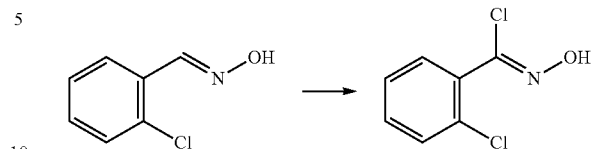

N-chlorosuccinimide (858 mg, 6.43 mmol) was added to a solution of 2-chlorobenzaldoxime (1.0 g, 6.43 mmol) in acetonitrile (15 mL), followed by stirring at room temperature for 25 hours. After the reaction was completed, the resultant product was concentrated under reduced pressure, whereby 2-chlorobenzohydroxymoyl chloride (1.77 g) was obtained as a pale yellow oily material. $^1$H-NMR (400 MHz, CDCl$_3$): δ7.31-7.49 (m, 4H), 8.25 (brs, 1H).

Reference Example-65

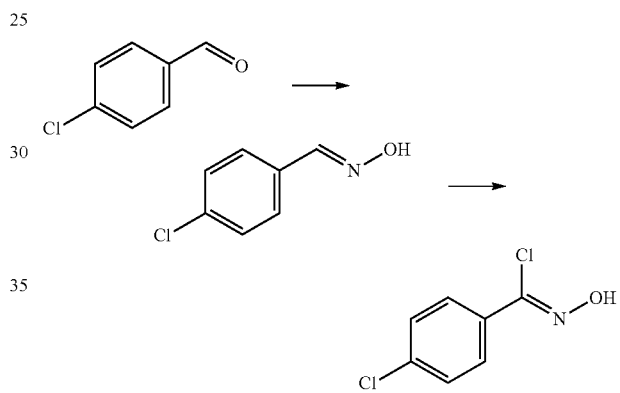

Hydroxylamine hydrochloride (748 mg, 10.4 mmol) was added to a solution of 4-chlorobezaldehyde (1.44 g, 9.49 mmol) in ethanol (10 mL) and water (10 mL), and a sodium hydroxide aqueous solution (37%, 1.8 mL) was added dropwise thereto under ice-cooling, followed by stirring at room temperature for 2 hours. After the reaction was completed, 2N hydrochloric acid was added to the reaction solution to acidify, and the resultant product was extracted with dichloromethane (10 mL×3). The organic layer was dried over anhydrous magnesium sulfate, and concentrated under reduced pressure, and the obtained crude product was purified by silica gel column chromatography (hexane:ethyl acetate=9:1), whereby 4-chlorobenzaldoxime (1.20 g, yield: 81%) was obtained as a white solid. $^1$H-NMR (400 MHz, CDCl$_3$): δ7.35-7.38 (m, 2H), 7.50-7.53 (m, 2H), 7.60 (brs, 1H), 8.10 (s, 1H).

N-chlorosuccinimide (1.13 g, 8.48 mmol) was added to a solution of 4-chlorobenzaldoxime in acetonitrile (15 mL), followed by stirring at room temperature for 19 hours. After the reaction was completed, the reaction solution was concentrated under reduced pressure, and the obtained crude product was purified by silica gel column chromatography (hexane:ethyl acetate=9:1), whereby 4-chlorobenzohydroxymoyl chloride (450 mg, yield: 28%) was obtained as a milky-white solid. $^1$H-NMR (400 MHz, CDCl$_3$): δ7.37-7.41 (m, 2H), 7.77-7.81 (m, 3H).

Reference Example-66

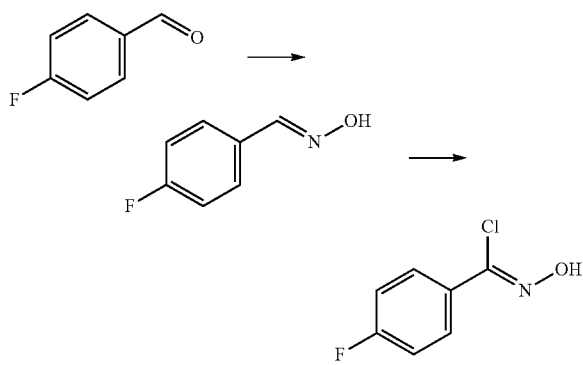

Hydroxylamine hydrochloride (748 mg, 10.4 mmol) was added to a solution of 4-fluorobezaldehyde (1.18 g, 9.49 mmol) in ethanol (10 mL) and water (10 mL), and a sodium hydroxide aqueous solution (37%, 1.8 mL) was added dropwise thereto under ice-cooling, followed by stirring at room temperature for 2 hours. After the reaction was completed, 2N hydrochloric acid was added to the reaction solution to acidify, and the resultant product was extracted with dichloromethane (10 mL×3). The organic layer was dried over anhydrous magnesium sulfate, and concentrated under reduced pressure, and the obtained crude product was purified by silica gel column chromatography (hexane:ethyl acetate=9:1), whereby 4-fluorobenzaldoxime (1.23 g, yield: 93%) was obtained as a white solid. $^1$H-NMR (400 MHz, CDCl$_3$): δ7.05-7.11 (m, 2H), 7.55-7.59 (m, 2H), 8.05 (brs, 1H), 8.12 (s, 1H). $^{19}$F-NMR (376 MHz, CDCl$_3$): δ−110 (s, 1F).

N-chlorosuccinimide (1.30 g, 9.72 mmol) was added to a solution of 4-fluorobenzaldoxime in acetonitrile (15 mL), followed by stirring at room temperature for 19 hours. After the reaction was completed, the reaction solution was concentrated under reduced pressure, and the obtained crude product was purified by silica gel column chromatography (hexane:ethyl acetate=9:1), whereby 4-fluorobenzohydroxymoyl chloride (649 mg, yield: 42%) was obtained as a white solid. $^1$H-NMR (400 MHz, CDCl$_3$): δ7.08-7.13 (m, 2H), 7.83-7.87 (m, 3H). $^{19}$F-NMR (376 MHz, CDCl$_3$): δ−109 (s, 1F).

Reference Example-67

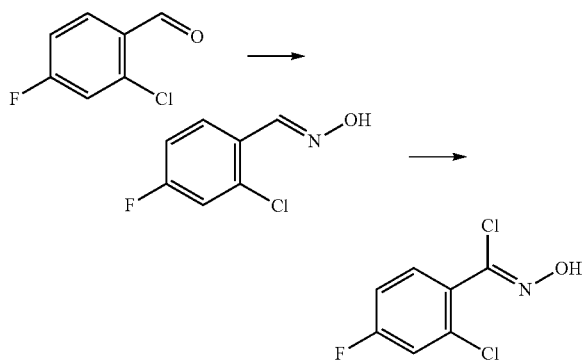

Hydroxylamine hydrochloride (455 mg, 6.35 mmol) was added to a solution of 2-chloro-4-fluorobezaldehyde (943 mg, 5.76 mmol) in ethanol (6 mL) and water (6 mL), and a sodium hydroxide aqueous solution (37%, 1.1 mL) was added dropwise thereto under ice-cooling, followed by stirring at room temperature for 2 hours. After the reaction was completed, 2N hydrochloric acid was added to the reaction solution to acidify, and the resultant product was extracted with dichloromethane (20 mL×2.10 mL×1). The organic layer was dried over anhydrous magnesium sulfate, and concentrated under reduced pressure, whereby 2-chloro-4-fluorobenzaldoxime (794 mg, yield: 79%) was obtained as a light yellow solid. $^1$H-NMR (400 MHz, CDCl$_3$): δ6.99 (m, 1H), 7.15 (dd, J=2.5 and 8.5 Hz, 1H), 7.60 (brs, 1H), 7.85 (dq, J=6.3 and 8.5 Hz, 1H), 8.50 (s, 1H). $^{19}$F-NMR (376 MHz, CDCl$_3$): δ−108 (s, 1F).

N-chlorosuccinimide (685 mg, 5.03 mmol) and DMF (5 mL) were added to a solution of 2-chloro-4-fluorobenzaldoxime in acetonitrile (10 mL), followed by stirring at room temperature for 18 hours. After the reaction was completed, the reaction solution was concentrated under reduced pressure, and the obtained crude product was purified by silica gel column chromatography (hexane:ethyl acetate=9:1), whereby 2-chloro-4-fluorobenzohydroxymoyl chloride (192 mg, yield: 20%) was obtained as a pale yellow solid. $^1$H-NMR (400 MHz, CDCl$_3$): δ7.06 (ddd, J=2.61, 7.84 and 8.63 Hz, 1H), 7.21 (dd, J=2.61 and 8.63 Hz, 1H), 7.48 (dd, J=6.00 and 8.63 Hz, 1H), 8.01 (brs, 1H). $^{19}$F-NMR (376 MHz, CDCl$_3$): δ−107 (s, 1F).

Reference Example-68

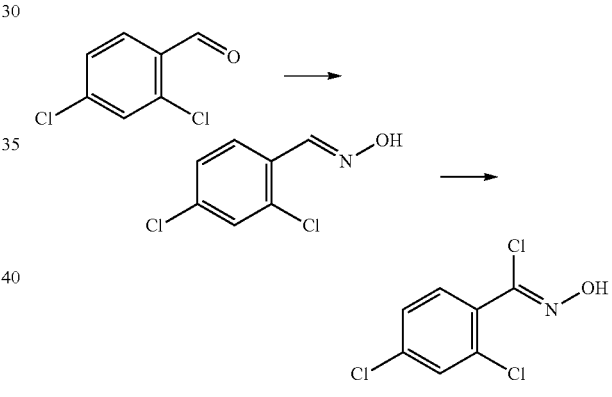

Hydroxylamine hydrochloride (748 mg, 10.4 mmol) was added to a solution of 2,4-dichlorobezaldehyde (1.75 g, 9.49 mmol) in ethanol (10 mL) and water (10 mL), and a sodium hydroxide aqueous solution (37%, 1.8 mL) was added dropwise thereto under ice-cooling, followed by stirring at room temperature for 2 hours. After the reaction was completed, 2N hydrochloric acid was added to the reaction solution to acidify, and the resultant product was extracted with dichloromethane (20 mL×2.10 mL×1). The organic layer was dried over anhydrous magnesium sulfate, and concentrated under reduced pressure, whereby 2,4-dichlorobenzaldoxime (1.76 g, yield: 98%) was obtained as a white solid. $^1$H-NMR (400 MHz, CDCl$_3$): δ7.26 (ddd, J=0.6, 2.2 and 8.7 Hz, 1H), 7.42 (d, J=2.2 Hz, 1H), 7.56 (s, 1H), 7.79 (d, J=8.7 Hz, 1H), 8.49 (s, 1H).

N-chlorosuccinimide (1.39 g, 10.2 mmol) and DMF (10 mL) were added to a solution of 2,4-dichlorobenzaldoxime in acetonitrile (20 mL), followed by stirring at room temperature for 17 hours. After the reaction was completed, the reaction solution was concentrated under reduced pressure, and the obtained crude product was purified by silica gel column chromatography (hexane:ethyl acetate=9:1), whereby 2,4-dichlorobenzohydroxymoyl chloride (1.64 g, yield: 79%) was obtained as an orange solid. ¹H-NMR (400 MHz, CDCl₃): δ7.32 (dd, J=2.0 and 8.3 Hz, 1H), 7.42 (d, J=8.3 Hz, 1H), 7.49 (d, J=2.0 Hz, 1H), 8.15 (s, 1H).

Example-169

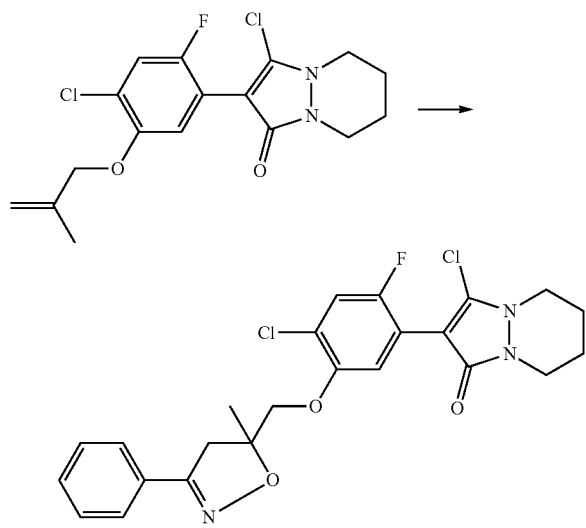

Benzohydroxymoyl chloride (101 mg, 0.65 mmol) and triethylamine (65.8 mg, 0.65 mmol) were added to a solution of 5-chloro-4-[4-chloro-2-fluoro-5-(methallyloxy)phenyl]-1,2-tetramethylene-4-pyrazolin-3-one (200 mg, 0.54 mmol) in dichloromethane (3 mL), followed by stirring at room temperature for 88 hours. After the reaction was completed, water (30 mL) was added to the reaction mixture, and the resultant product was extracted with chloroform (30 mL×2, 20 mL×1). The organic layer was washed with a saturated saline solution, dried over anhydrous magnesium sulfate, and concentrated under reduced pressure, whereby a crude product (326 mg) was obtained as a white yellow solid. This was purified by silica gel column chromatography (ethyl acetate:methanol=10:1), whereby 5-chloro-4-[4-chloro-2-fluoro-5-(5-methyl-3-phenyl-2-isoxazolin-5-ylmethyloxy)phenyl]-1,2-tetramethylene-4-pyrazolin-3-one (108 mg, yield: 41%) was obtained as a white yellow solid. ¹H-NMR (400 MHz, CDCl₃): δ1.63 (s, 3H), 1.88-1.97 (m, 2H), 1.99-2.04 (m, 2H), 3.15 (d, J=16.8 Hz, 1H), 3.59-3.62 (m, 2H), 3.63 (d, J=16.8 Hz, 1H), 3.80-3.84 (m, 2H), 4.01 (d, J=9.3 Hz, 1H), 4.10 (d, J=9.3 Hz, 1H), 7.11 (d, J=6.2 Hz, 1H), 7.16 (d, J=9.1 Hz, 1H), 7.39-7.69 (m, 5H). ¹⁹F-NMR (376 MHz, CDCl₃): δ−119 (s, 1F).

Example-170

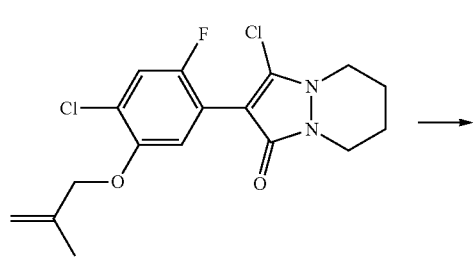

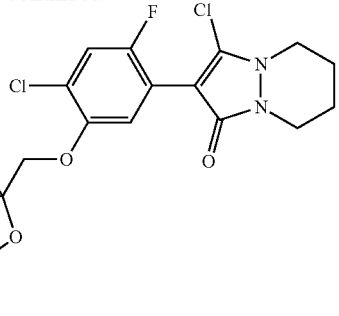

2-Fluorobenzohydroxymoyl chloride (140 mg, 0.81 mmol) and triethylamine (96 mg, 0.81 mmol) were added to a solution of 5-chloro-4-[4-chloro-2-fluoro-5-(methallyloxy)phenyl]-1,2-tetramethylene-4-pyrazolin-3-one (200 mg, 0.54 mmol) in dichloromethane (3 mL), followed by stirring at room temperature for 48 hours. After the reaction was completed, water (20 mL) was added to the reaction mixture, and the resultant product was extracted with chloroform (20 mL×3). The organic layer was washed with a saturated saline solution, dried over anhydrous magnesium sulfate, and concentrated under reduced pressure, whereby a crude product was obtained. This was purified by silica gel column chromatography (ethyl acetate:methanol=10:1), whereby 5-chloro-4-[4-chloro-2-fluoro-5-[[3-(2-fluorophenyl)-5-methyl-2-isoxazolin-5-yl]methyloxy]phenyl]-1,2-tetramethylene-4-pyrazolin-3-one (229 mg, yield: 84%) was obtained as a white solid. ¹H-NMR (400 MHz, CDCl₃): δ1.63 (s, 3H), 1.86-1.94 (m, 2H), 1.98-2.05 (m, 2H), 3.26 (dd, J=2.6 and 17.5 Hz, 1H), 3.59-3.65 (m, 2H), 3.69 (dd, J=2.6 and 17.5 Hz, 1H), 3.80-3.86 (m, 2H), 4.01 (d, J=9.4 Hz, 1H), 4.10 (d, J=9.4 Hz, 1H), 7.06-7.20 (m, 4H), 7.38 (m, 1H), 7.86 (dt, J=1.7 and 7.7 Hz, 1H). ¹⁹F-NMR (376 MHz, CDCl₃): δ−119 (s, 1F), −109 (s, 1F).

Example-171

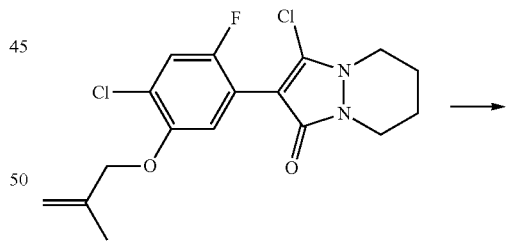

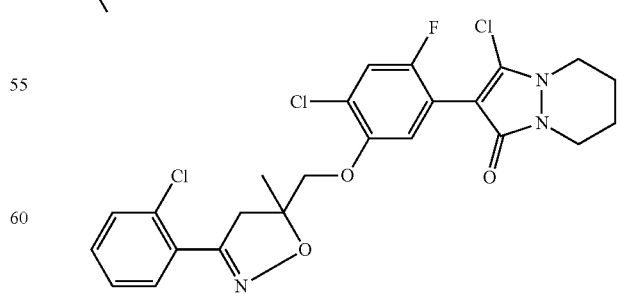

2-Chlorobenzohydroxymoyl chloride (154 mg, 0.81 mmol) and triethylamine (82 mg, 0.81 mmol) were added to a solution of 5-chloro-4-[4-chloro-2-fluoro-5-(methallyloxy)phenyl]-1,2-tetramethylene-4-pyrazolin-3-one (200 mg, 0.54 mmol) in dichloromethane (3 mL), followed by stirring at room temperature for 88 hours. After the reaction was completed, water (20 mL) was added to the reaction mixture, and the resultant product was extracted with chloroform (20 mL×1, 10 mL×2). The organic layer was washed with a saturated saline solution, dried over anhydrous magnesium sulfate, and was concentrated under reduced pressure, whereby an ocherous oily crude product (310 mg) was obtained. This was purified by silica gel column chromatography (ethyl acetate:methanol=10:1), whereby 5-chloro-4-[4-chloro-2-fluoro-5-[[3-(2-chlorophenyl)-5-methyl-2-isoxazolin-5-yl]methyloxy]phenyl]-1,2-tetramethylene-4-pyrazolin-3-one (198 mg, yield: 70%) was obtained as a white solid. $^1$H-NMR (400 MHz, CDCl$_3$): δ1.63 (s, 3H), 1.88-1.93 (m, 2H), 1.99-2.04 (m, 2H), 3.34 (d, J=17.2 Hz, 1H), 3.60-3.64 (m, 2H), 3.74 (d, J=17.2 Hz, 1H), 3.81-3.85 (m, 2H), 4.02 (d, J=9.4 Hz, 1H), 4.14 (d, J=9.4 Hz, 1H), 7.13 (d, J=6.2 Hz, 1H), 7.17 (d, J=9.1 Hz, 1H), 7.27-7.67 (m, 4H). $^{19}$F-NMR (376 MHz, CDCl$_3$): δ−119 (s, 1F).

Example-172

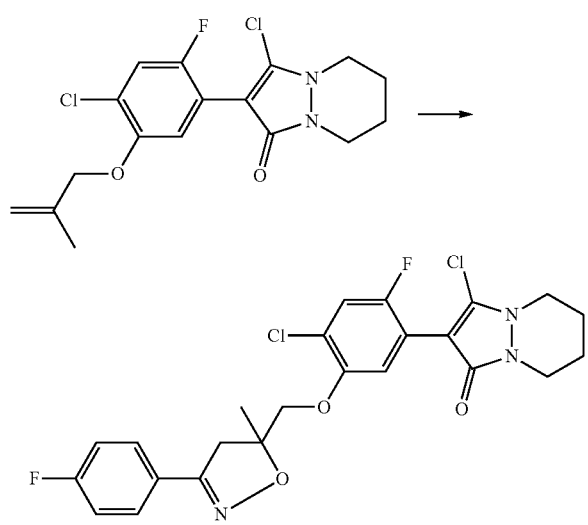

4-Fluorobenzohydroxymoyl chloride (141 mg, 0.81 mmol) and triethylamine (82 mg, 0.81 mmol) were added to a solution of 5-chloro-4-[4-chloro-2-fluoro-5-(methallyloxy)phenyl]-1,2-tetramethylene-4-pyrazolin-3-one (200 mg, 0.54 mmol) in dichloromethane (3 mL), followed by stirring at room temperature for 18 hours. After the reaction was completed, the reaction solution was loaded on the upper portion of a silica gel column, and purified by eluting with a 10:1 mixed solvent of ethyl acetate and methanol, whereby 5-chloro-4-[4-chloro-2-fluoro-5-[[3-(4-fluorophenyl)-5-methyl-2-isoxazolin-5-yl]methyloxy]phenyl]-1,2-tetramethylene-4-pyrazolin-3-one (238 mg, yield: 87%) was obtained as a white solid. $^1$H-NMR (400 MHz, CDCl$_3$): δ1.63 (s, 3H), 1.87-1.93 (m, 2H), 1.99-2.05 (m, 2H), 3.13 (d, J=17.1 Hz, 1H), 3.59-3.63 (m, 2H), 3.61 (d, J=17.1 Hz, 1H), 3.78-3.88 (m, 2H), 4.01 (d, J=9.6 Hz, 1H), 4.10 (d, J=9.6 Hz, 1H), 7.07-7.12 (m, 2H), 7.11 (d, J=6.2 Hz, 1H), 7.16 (d, J=9.1 Hz, 1H), 7.64-7.69 (s, 2H). $^{19}$F-NMR (376 MHz, CDCl$_3$): δ−118 (s, 1F), −110 (s, 1F).

Example-173

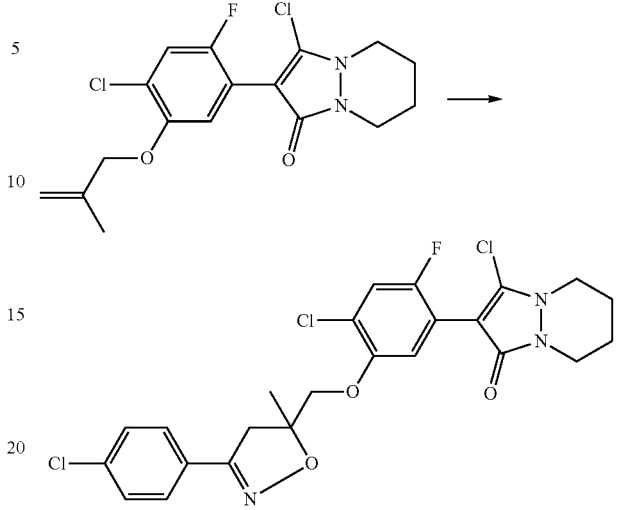

4-Chlorobenzohydroxymoyl chloride (154 mg, 0.81 mmol) and triethylamine (82 mg, 0.81 mmol) were added to a solution of 5-chloro-4-[4-chloro-2-fluoro-5-(methallyloxy)phenyl]-1,2-tetramethylene-4-pyrazolin-3-one (200 mg, 0.54 mmol) in dichloromethane (3 mL), followed by stirring at room temperature for 18 hours. After the reaction was completed, the reaction solution was loaded on the upper portion of a silica gel column, and purified by eluting with a 10:1 mixed solvent of ethyl acetate and methanol, whereby 5-chloro-4-[4-chloro-2-fluoro-5-[[3-(4-chlorophenyl)-5-methyl-2-isoxazolin-5-yl]methyloxy]phenyl]-1,2-tetramethylene-4-pyrazolin-3-one (198 mg, yield: 70%) was obtained as a white yellow solid. $^1$H-NMR (400 MHz, CDCl$_3$): δ1.63 (s, 3H), 1.87-1.93 (m, 2H), 1.99-2.05 (m, 2H), 3.12 (d, J=17.2 Hz, 1H), 3.57-3.67 (m, 2H), 3.61 (d, J=17.2 Hz, 2H), 3.78-3.88 (m, 2H), 4.01 (d, J=9.5 Hz, 1H), 4.11 (d, J=9.5 Hz, 1H), 7.11 (d, J=6.0 Hz, 1H), 7.16 (d, J=9.1 Hz, 1H), 7.38 (d, J=8.7 Hz, 2H), 7.61 (d, J=8.7 Hz, 2H). $^{19}$F-NMR (376 MHz, CDCl$_3$): δ−119 (s, 1F).

Example-174

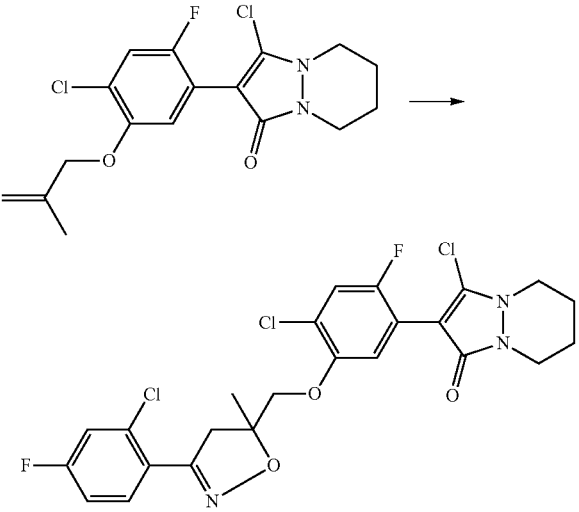

2-Chloro-4-fluorobenzohydroxymoyl chloride (169 mg, 0.81 mmol) and triethylamine (82 mg, 0.81 mmol) were added to a solution of 5-chloro-4-[4-chloro-2-fluoro-5-(methallyloxy)phenyl]-1,2-tetramethylene-4-pyrazolin-3-one (200 mg, 0.54 mmol) in dichloromethane (3 mL), followed by stirring at room temperature for 41 hours. After the reaction was completed, the reaction solution was loaded on the upper portion of a silica gel column, and purified by eluting with a 10:1 mixed solvent of ethyl acetate and methanol, whereby 5-chloro-4-[4-chloro-2-fluoro-5-[[3-(2-chloro-4-fluorophenyl)-5-methyl-2-isoxazolin-5-yl]methyloxy]phenyl]-1,2-tetramethylene-4-pyrazolin-3-one (155 mg, yield: 53%) was obtained as a white solid. $^1$H-NMR (400 MHz, CDCl$_3$): δ1.63 (s, 3H), 1.88-1.93 (m, 2H), 2.00-2.05 (m, 2H), 3.34 (d, J=17.1 Hz, 1H), 3.60-3.64 (m, 2H), 3.72 (d, J=17.1 Hz, 1H), 3.81-3.85 (m, 2H), 4.01 (d, J=9.5 Hz, 1H), 4.13 (d, J=9.5 Hz, 1H), 7.04 (ddd, J=2.5, 7.8 and 9.8 Hz, 1H), 7.13 (d, J=6.3 Hz, 1H), 7.17 (d, J=9.5 Hz, 1H), 7.18 (dd, J=2.9 and 8.6 Hz, 1H), 7.68 (dd, J=6.1 and 8.6 Hz, 1H). $^{19}$F-NMR (376 MHz, CDCl$_3$): δ−119 (s, 1F), −109 (s, 1F).

Example-175

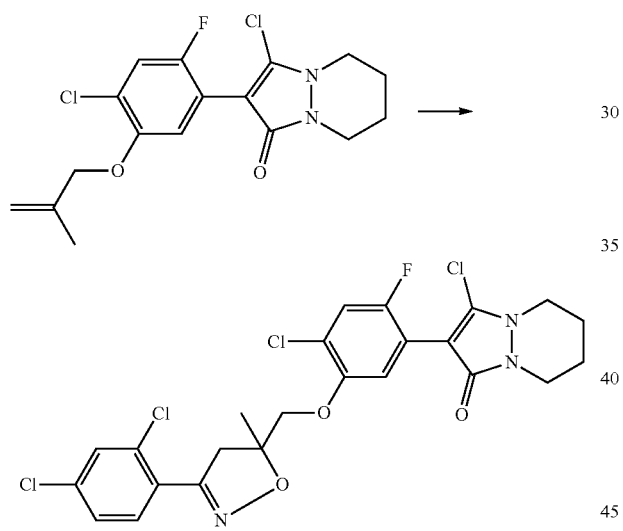

2,4-Dichlorobenzohydroxymoyl chloride (182 mg, 0.81 mmol) and triethylamine (82 mg, 0.81 mmol) were added to a solution of 5-chloro-4-[4-chloro-2-fluoro-5-(methallyloxy)phenyl]-1,2-tetramethylene-4-pyrazolin-3-one (200 mg, 0.54 mmol) in dichloromethane (3 mL), followed by stirring at room temperature for 46 hours. After the reaction was completed, the reaction solution was loaded on the upper portion of a silica gel column, and purified by eluting with a 10:1 mixed solvent of ethyl acetate and methanol, whereby 5-chloro-4-[4-chloro-2-fluoro-5-[[3-(2,4-dichlorophenyl)-5-methyl-2-isoxazolin-5-yl]methyloxy]phenyl]-1,2-tetramethylene-4-pyrazolin-3-one (144 mg, yield: 48%) was obtained as a white solid. $^1$H-NMR (400 MHz, CDCl$_3$): δ1.91 (s, 3H), 1.88-1.93 (m, 2H), 2.00-2.05 (m, 2H), 3.34 (d, J=17.3 Hz, 1H), 3.59-3.66 (m, 2H), 3.73 (d, J=17.3 Hz, 1H), 3.79-3.87 (m, 2H), 4.01 (d, J=9.5 Hz, 1H), 4.13 (d, J=9.5 Hz, 1H), 7.13 (d, J=6.2 Hz, 1H), 7.17 (d, J=9.2 Hz, 1H), 7.28 (dd, J=2.0 and 8.1 Hz, 1H), 7.44 (d, J=2.0 Hz, 1H), 7.64 (d, J=8.1 Hz, 1H). $^{19}$F-NMR (376 MHz, CDCl$_3$): δ−119 (s, 1F).

Example-176

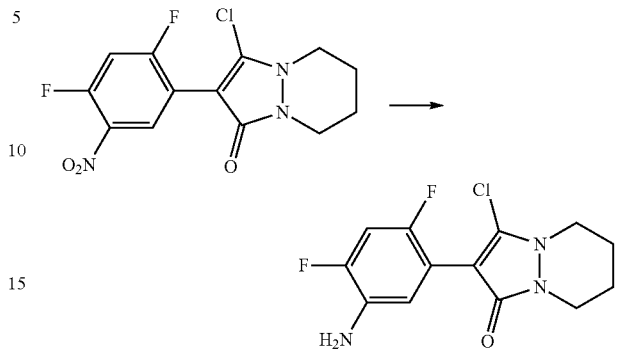

Concentrated hydrochloric acid (1.5 mL) was added to a solution of 5-chloro-4-(2,4-difluoro-5-nitrophenyl)-1,2-tetramethylene-4-pyrazolin-3-one (299 mg, 0.907 mmol) in ethanol (2 mL), and tin(II) chloride dihydrate (0.819 g, 3.63 mmol) was added thereto, followed by heating to reflux for 15 hours. After the reaction was completed, the reaction solution was poured into ice water, then, a sodium hydroxide aqueous solution was added thereto to basify the resultant product, and the resultant product was extracted with ethyl acetate (30 mL×3). The organic layer was dried over anhydrous magnesium sulfate, and concentrated under reduced pressure, whereby 4-(5-amino-2,4-difluorophenyl)-5-chloro-1,2-tetramethylene-4-pyrazolin-3-one (216 mg, yield: 79%) was obtained as a white solid. $^1$H-NMR (400 MHz, CDCl$_3$): δ1.84-1.92 (m, 2H), 1.97-2.05 (m, 2H), 3.44-3.75 (m, 4H), 3.79-3.86 (m, 2H), 6.83 (dd, J=9.5 and 10.8 Hz, 1H), 6.91 (dd, J=6.9 and 9.8 Hz, 1H). $^{19}$F-NMR (376 MHz, CDCl$_3$): δ−130.7 (s, 1F), −121.4 (s, 1F).

Example-177

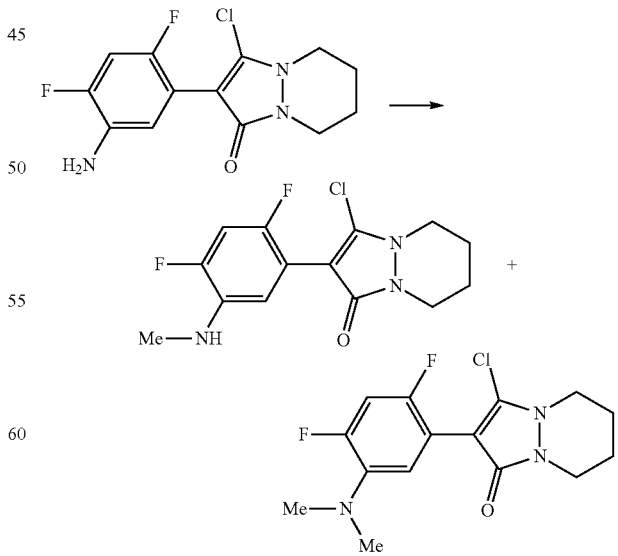

A 55% oil dispersion (100 mg, 2.29 mmol) of sodium hydride and methyl iodide (197 μL, 3.00 mmol) were added to a solution of 4-(5-amino-2,4-difluorophenyl)-5-chloro-1,2-tetramethylene-4-pyrazolin-3-one (300 mg, 1.00 mmol) in THF (10 mL) under ice-cooling, followed by stirring at room temperature for 24 hours. After the reaction was completed, water (20 mL) was added to the reaction solution, and the resultant product was extracted with ethyl acetate (20 mL×3). The organic layer was washed with a saturated saline solution, dried over anhydrous magnesium sulfate, and concentrated under reduced pressure, whereby a crude product was obtained. This was purified by silica gel column chromatography (ethyl acetate:methanol=20:1), whereby 4-[2,4-difluoro-5-(methyl amino)phenyl]-5-chloro-1,2-tetramethylene-4-pyrazolin-3-one (21 mg, yield: 7%) was obtained as a white solid, and 4-[2,4-difluoro-5-(dimethyl amino)phenyl]-5-chloro-1,2-tetramethylene-4-pyrazolin-3-one (114 mg, yield: 35%) was obtained as a white solid. 4-[2,4-Difluoro-5-(methyl amino)phenyl]-5-chloro-1,2-tetramethylene-4-pyrazolin-3-one: $^1$H-NMR (400 MHz, CDCl$_3$): δ1.85-1.93 (m, 2H), 1.97-2.04 (m, 2H), 2.86 (s, 3H), 3.56-3.61 (m, 4H), 3.80-3.86 (m, 2H), 6.76 (dd, J=6.9 and 9.7 Hz, 1H), 6.83 (dd, J=9.3 and 11.3 Hz, 1H). $^{19}$F-NMR (376 MHz, CDCl$_3$): δ−132.7 (d, J=2.4 Hz, 1F), −124.0 (d, J=2.4 Hz, 1F). 4-[2,4-Difluoro-5-(dimethyl amino)phenyl]-5-chloro-1,2-tetramethylene-4-pyrazolin-3-one: $^1$H-NMR (400 MHz, CDCl$_3$): δ1.86-1.93 (m, 2H), 1.98-2.04 (m, 2H), 2.81 (s, 6H), 3.57-3.62 (m, 4H), 3.81-3.86 (m, 2H), 6.85 (dd, J=9.3 and 12.1 Hz, 1H), 7.05 (dd, J=7.4 and 9.7 Hz, 1H). $^{19}$F-NMR (376 MHz, CDCl$_3$): δ−118.5 (d, J=5.2 Hz, 1F), −118.2 (d, J=5.2 Hz, 1F).

Example-178

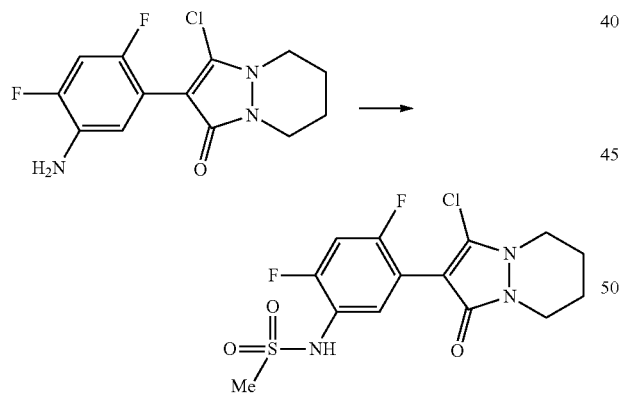

In the same manner as in Example-177, 5-chloro-4-(5-amino-2,4-difluorophenyl)-1,2-tetramethylene-4-pyrazolin-3-one was reacted with methyl sulfonyl chloride, whereby 5-chloro-4-[2,4-difluoro-5-(methyl sulfonyl amino)phenyl]-1,2-tetramethylene-4-pyrazolin-3-one was obtained with a yield of 98%. $^1$H-NMR (400 MHz, CDCl$_3$): δ1.88-1.95 (m, 2H), 1.99-2.06 (m, 2H), 3.07 (s, 3H), 3.61-3.66 (m, 2H), 3.81-3.86 (m, 2H), 6.85 (brs, 1H), 6.96 (dd, J=9.2 and 10.0 Hz, 1H), 7.64 (dd, J=7.5 and 8.9 Hz, 1H). $^{19}$F-NMR (376 MHz, CDCl$_3$): δ−123.1 (d, J=6.8 Hz, 1F), −109.6 (d, J=6.8 Hz, 1F).

Example-179

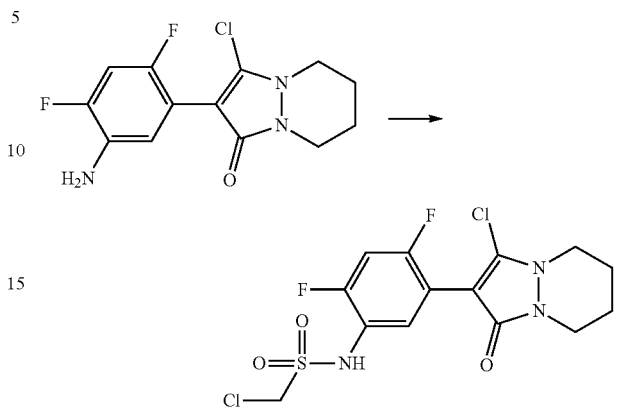

In the same manner as in Example-177, 5-chloro-4-(5-amino-2,4-difluorophenyl)-1,2-tetramethylene-4-pyrazolin-3-one was reacted with chloromethyl sulfonyl chloride, whereby 5-chloro-4-[5-(chloromethylsulfonylamino)-2,4-difluorophenyl]-1,2-tetramethylene-4-pyrazolin-3-one was obtained with a yield of 76%. $^1$H-NMR (400 MHz, CDCl$_3$): δ1.89-1.96 (m, 2H), 2.00-2.07 (m, 2H), 3.62-3.67 (m, 2H), 3.83-3.88 (m, 2H), 4.58 (s, 2H), 6.94 (t, J=9.5 Hz, 1H), 7.63 (t, J=8.0 Hz, 1H). $^{19}$F-NMR (376 MHz, CDCl$_3$): δ−120.7 (s, 1F), −108.4 (s, 1F).

Example-180

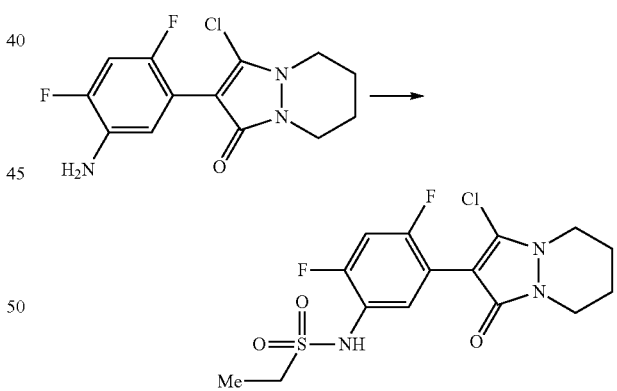

In the same manner as in Example-177, 5-chloro-4-(5-amino-2,4-difluorophenyl)-1,2-tetramethylene-4-pyrazolin-3-one was reacted with ethyl sulfonyl chloride, whereby 5-chloro-4-[5-(ethylsulfonylamino)-2,4-difluorophenyl]-1,2-tetramethylene-4-pyrazolin-3-one was obtained with a yield of 98%. $^1$H-NMR (400 MHz, CDCl$_3$): δ1.40 (t, J=7.4 Hz, 3H), 1.87-1.94 (m, 2H), 1.98-2.06 (m, 2H), 3.16 (q, J=7.4 Hz, 2H), 3.60-3.66 (m, 2H), 3.81-3.87 (m, 2H), 6.92 (brs, 1H), 6.93 (dd, J=9.2 and 10.0 Hz, 1H), 7.63 (dd, J=7.3 and 8.9 Hz, 1H). $^{19}$F-NMR (376 MHz, CDCl$_3$): δ−123.2 (d, J=6.7 Hz, 1F), −110.2 (d, J=6.7 Hz, 1F).

Example-181

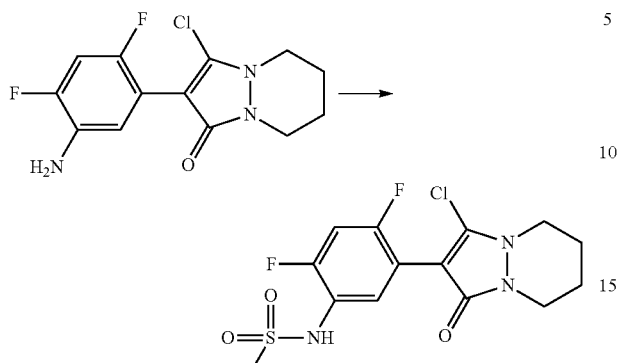

In the same manner as in Example-177, 5-chloro-4-(5-amino-2,4-difluorophenyl)-1,2-tetramethylene-4-pyrazolin-3-one was reacted with 2,2,2-trifluoroethyl sulfonyl chloride, whereby 5-chloro-4-[2,4-difluoro-5-(2,2,2-trifluoroethyl sulfonyl amino)phenyl]-1,2-tetramethylene-4-pyrazolin-3-one was obtained with a yield of 95%. $^1$H-NMR (400 MHz, CDCl$_3$): δ1.89-1.97 (m, 2H), 2.00-2.07 (m, 2H), 3.63-3.68 (m, 2H), 3.83-3.94 (m, 4H), 6.94 (t, J=9.7 Hz, 1H), 7.58 (m, 1H), 7.96 (brs, 1H). $^{19}$F-NMR (376 MHz, CDCl$_3$): δ−121.0 (m, 1F), −108.0 (m, 1F), −62.1 (s, 1F).

Example-182

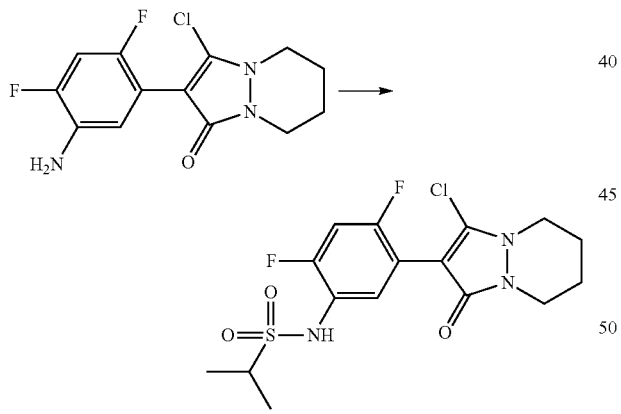

In the same manner as in Example-177, 5-chloro-4-(5-amino-2,4-difluorophenyl)-1,2-tetramethylene-4-pyrazolin-3-one was reacted with isopropyl sulfonyl chloride, whereby 5-chloro-4-[2,4-difluoro-5-(isopropylsulfonylamino)phenyl]-1,2-tetramethylene-4-pyrazolin-3-one was obtained with a yield of 12%. $^1$H-NMR (400 MHz, CDCl$_3$): δ1.42 (d, J=6.8 Hz, 6H), 1.86-1.94 (m, 2H), 1.98-2.06 (m, 2H), 3.33 (sep, J=6.8 Hz, 1H), 3.60-3.65 (m, 2H), 3.80-3.85 (m, 2H), 6.33 (brs, 1H), 6.96 (dd, J=9.1 and 10.2 Hz, 1H), 7.70 (dd, J=7.2 and 9.0 Hz, 1H). $^{19}$F-NMR (376 MHz, CDCl$_3$): δ−124.4 (m, 1F), −110.7 (m, 1F).

Example-183

In the same manner as in Example-177, 5-chloro-4-(5-amino-2,4-difluorophenyl)-1,2-tetramethylene-4-pyrazolin-3-one was reacted with cyclopropyl sulfonyl chloride, whereby 5-chloro-4-[5-(cyclopropylsulfonylamino)-2,4-difluorophenyl]-1,2-tetramethylene-4-pyrazolin-3-one was obtained with a yield of 41%. $^1$H-NMR (400 MHz, CDCl$_3$): δ0.97-1.03 (m, 2H), 1.18-1.23 (m, 2H), 1.87-1.94 (m, 2H), 1.99-2.06 (m, 2H), 2.54 (m, 1H), 3.60-3.65 (m, 2H), 3.80-3.86 (m, 2H), 6.44 (brs, 1H), 6.97 (dd, J=9.3 and 9.8 Hz, 1H), 7.70 (dd, J=7.3 and 8.9 Hz, 1H). $^{19}$F-NMR (376 MHz, CDCl$_3$): δ−123.7 (m, 1F), −109.8 (m, 1F).

Example-184

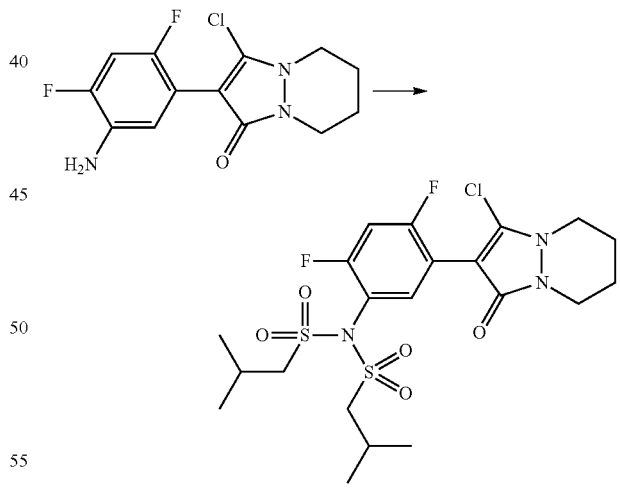

In the same manner as in Example-177, 5-chloro-4-(5-amino-2,4-difluorophenyl)-1,2-tetramethylene-4-pyrazolin-3-one was reacted with isobutyl sulfonyl chloride, whereby 5-chloro-4-[5-{bis(isobutylsulfonyl)amino}-2,4-difluorophenyl]-1,2-tetramethylene-4-pyrazolin-3-one was obtained with a yield of 38%. $^1$H-NMR (400 MHz, CDCl$_3$): δ1.12 (d, J=6.7 Hz, 6H), 1.13 (d, J=6.7 Hz, 6H), 1.87-1.94 (m, 2H), 1.99-2.06 (m, 2H), 2.42 (h, J=6.7 Hz, 2H), 3.44 (dd, J=6.7 and 13.6 Hz, 2H), 3.57 (dd, J=6.7 and 13.7 Hz, 2H), 3.61-3.66 (m, 2H), 3.80-3.85 (m, 2H), 7.03 (t, J=9.4 Hz, 1H), 7.64 (dd, J=7.3 and 8.3 Hz, 1H). $^{19}$F-NMR (376 MHz, CDCl$_3$): δ−112.1 (d, J=10.8 Hz, 1F), −101.5 (d, J=10.8 Hz, 1F).

Example-185

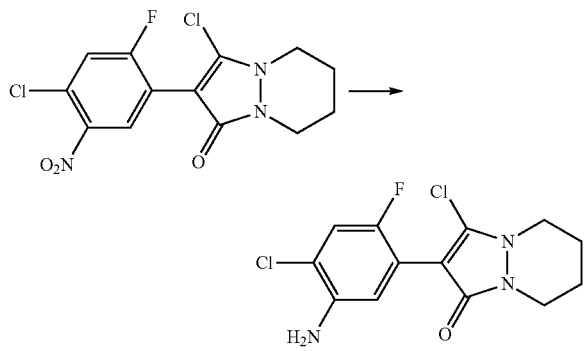

Concentrated hydrochloric acid (10 mL) was added to a solution of 5-chloro-4-(4-chloro-2-fluoro-5-nitrophenyl)-1,2-tetramethylene-4-pyrazolin-3-one (799 mg, 2.31 mmol) in ethanol (6 mL), and tin(II) chloride dihydrate (2.08 g, 9.24 mmol) was added thereto, followed by refluxing for 42 hours. After the reaction was completed, the reaction solution was poured into ice water, then, a sodium hydroxide aqueous solution was added thereto to basify the resultant product, and the resultant product was extracted with ethyl acetate (30 mL×3). The organic layer was dried over anhydrous magnesium sulfate, and concentrated under reduced pressure, whereby 4-(5-amino-4-chloro-2-fluorophenyl)-5-chloro-1,2-tetramethylene-4-pyrazolin-3-one (680 mg, yield: 93%) was obtained as an ocherous solid. $^1$H-NMR (400 MHz, CDCl$_3$): δ1.86-1.92 (m, 2H), 1.98-2.04 (m, 2H), 3.58-3.61 (m, 2H), 3.81-3.83 (m, 2H), 3.91 (brs, 2H), 6.92 (d, J=6.6 Hz, 1H), 8.22 (d, J=9.8 Hz, 1H). $^{19}$F-NMR (376 MHz, CDCl$_3$): δ−123 (s, 1F).

Example-186

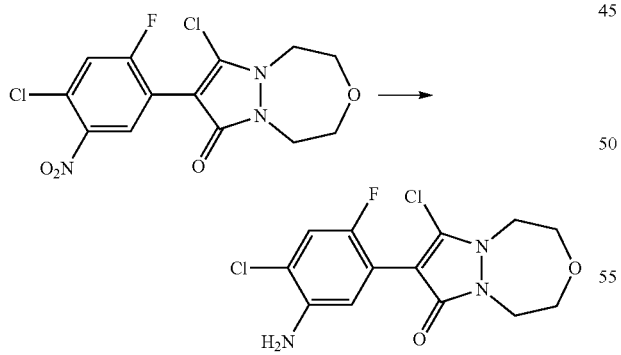

In the same manner as in Example-185, from 5-chloro-4-(4-chloro-2-fluoro-5-nitrophenyl)-1,2-oxadiethylene-4-pyrazolin-3-on, 4-(5-amino-4-chloro-2-fluorophenyl)-5-chloro-1,2-oxadiethylene-4-pyrazolin-3-one was obtained with a yield of 86%. $^1$H-NMR (400 MHz, CDCl$_3$): δ3.85-4.02 (m, 6H), 4.18-4.23 (m, 2H), 4.24-4.29 (m, 2H), 6.92 (d, J=6.5 Hz, 1H), 7.08 (d, J=9.3 Hz, 1H). $^{19}$F-NMR (376 MHz, CDCl$_3$): δ−123.5 (s, 1F).

Example-187

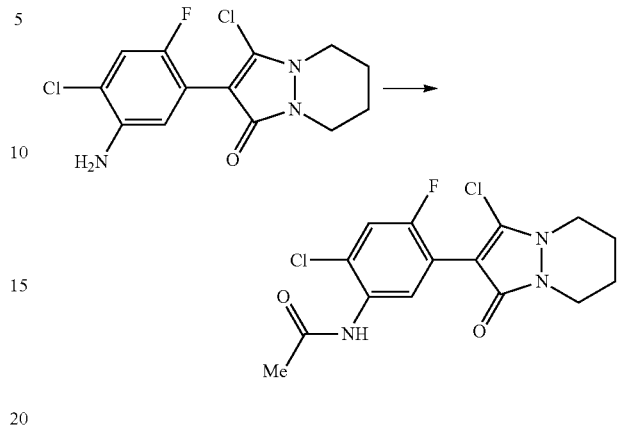

N,N-diisopropylethylamine (135 μL, 0.78 mmol) and acetic anhydride (72 μL, 0.77 mmol) were added to a solution of 4-(5-amino-4-chloro-2-fluorophenyl)-5-chloro-1,2-tetramethylene-4-pyrazolin-3-one (222 mg, 0.70 mmol) in dichloromethane (2 mL) under ice-cooling, followed by stirring at room temperature for 24 hours. After the reaction was completed, the reaction solution was loaded on the upper portion of a silica gel column, and purified by eluting with a 9:1 mixed solvent of ethyl acetate and methanol, whereby 4-[4-chloro-2-fluoro-5-(acetyl amino)phenyl]-5-chloro-1,2-tetramethylene-4-pyrazolin-3-one (151 mg, yield: 60%) was obtained as a white solid. $^1$H-NMR (400 MHz, CDCl$_3$): δ1.86-1.94 (m, 2H), 1.98-2.06 (m, 2H), 2.22 (s, 3H), 3.59-3.65 (m, 2H), 3.80-3.86 (m, 2H), 7.16 (d, J=9.0 Hz, 1H), 7.72 (brs, 1H), 8.28 (d, J=5.4 Hz, 1H). $^{19}$F-NMR (376 MHz, CDCl$_3$): δ−114.3 (s, 1F).

Example-188

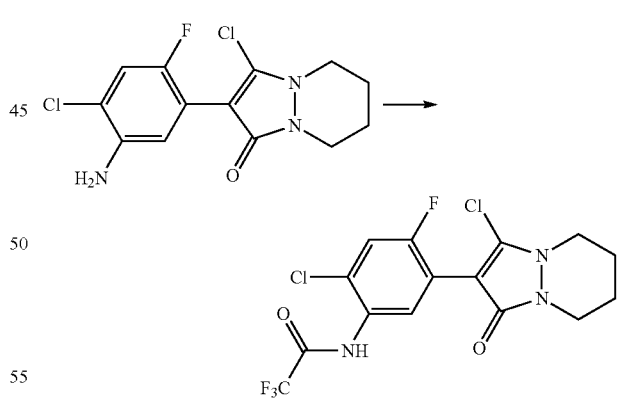

N,N-diisopropylethylamine (135 μL, 0.78 mmol) and trifluoroacetic anhydride (110 μL, 0.77 mmol) were added to a solution of 4-(5-amino-4-chloro-2-fluorophenyl)-5-chloro-1,2-tetramethylene-4-pyrazolin-3-one (222 mg, 0.70 mmol) in dichloromethane (2 mL) under ice-cooling, followed by stirring at room temperature for 24 hours. After the reaction was completed, the reaction solution was loaded on the upper portion of a silica gel column, and purified by eluting with a 9:1 mixed solvent of ethyl acetate and methanol, whereby 4-[4-chloro-2-fluoro-5-(trifluoroacetylamino)phenyl]-5-chloro-1,2-tetramethylene-4-pyrazolin-3-one (289 mg, yield: quantitative) was obtained as a white solid. ¹H-NMR (400 MHz, CDCl₃): δ1.86-1.96 (m, 2H), 1.99-2.09 (m, 2H), 3.61-3.70 (m, 2H), 3.80-3.89 (m, 2H), 7.25 (d, J=9.0 Hz, 1H), 8.24 (d, J=8.4 Hz, 1H), 8.51 (brs, 1H). ¹⁹F-NMR (376 MHz, CDCl₃): δ−110.4 (s, 1F), −75.6 (s, 3F).

Example-189

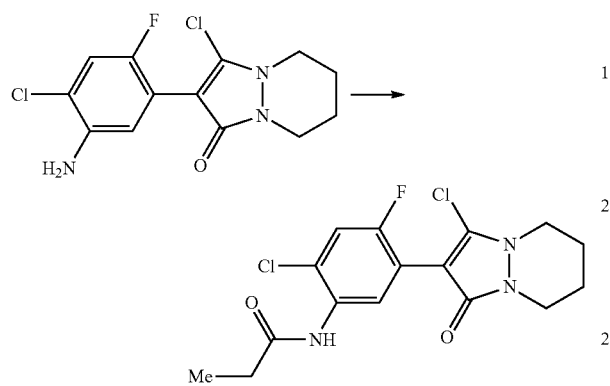

N,N-diisopropylethylamine (135 μL, 0.78 mmol) and propionyl chloride (69 μL, 0.77 mmol) were added to a solution of 4-(5-amino-4-chloro-2-fluorophenyl)-5-chloro-1,2-tetramethylene-4-pyrazolin-3-one (222 mg, 0.70 mmol) in dichloromethane (2 mL) under ice-cooling, followed by stirring at room temperature for 24 hours. After the reaction was completed, the reaction solution was loaded on the upper portion of a silica gel column, and purified by eluting with a 9:1 mixed solvent of ethyl acetate and methanol, whereby 4-[4-chloro-2-fluoro-5-(propionylamino)phenyl]-5-chloro-1,2-tetramethylene-4-pyrazolin-3-one (249 mg, yield: 95%) was obtained as a white solid. ¹H-NMR (400 MHz, CDCl₃): δ1.24 (t, J=7.5 Hz, 3H), 1.86-1.93 (m, 2H), 1.97-2.04 (m, 2H), 2.47 (q, J=7.5 Hz, 2H), 3.58-3.63 (m, 2H), 3.80-3.84 (m, 2H), 7.14 (d, J=9.0 Hz, 1H), 7.85 (brs, 1H), 8.29 (d, J=7.0 Hz, 1H). ¹⁹F-NMR (376 MHz, CDCl₃): δ−114.7 (s, 1F).

Example-190

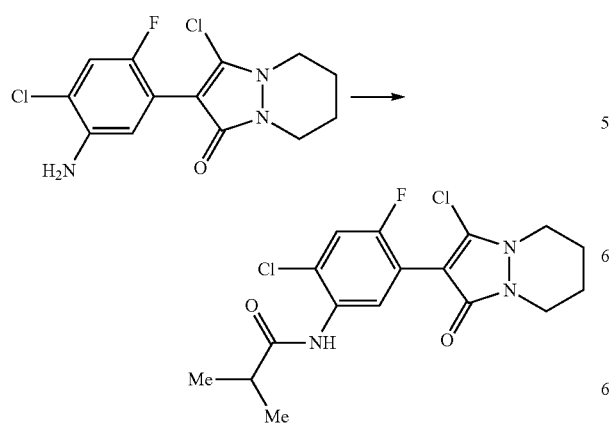

In the same manner as in Example-189, 4-(5-amino-4-chloro-2-fluorophenyl)-5-chloro-1,2-tetramethylene-4-pyrazolin-3-one was reacted with isobutyryl chloride, whereby 4-[4-chloro-2-fluoro-5-(isobutyryl amino)phenyl]-5-chloro-1,2-tetramethylene-4-pyrazolin-3-one was obtained quantitatively. ¹H-NMR (400 MHz, CDCl₃): δ1.27 (d, J=6.8 Hz, 6H), 1.84-1.93 (m, 2H), 1.96-2.05 (m, 2H), 2.59 (sept, J=6.8 Hz, 1H), 3.57-3.61 (m, 2H), 3.79-3.85 (m, 2H), 7.19 (d, J=9.0 Hz, 1H), 7.57 (brs, 1H), 8.37 (d, J=7.3 Hz, 1H). ¹⁹F-NMR (376 MHz, CDCl₃): δ−114.5 (s, 1F).

Example-191

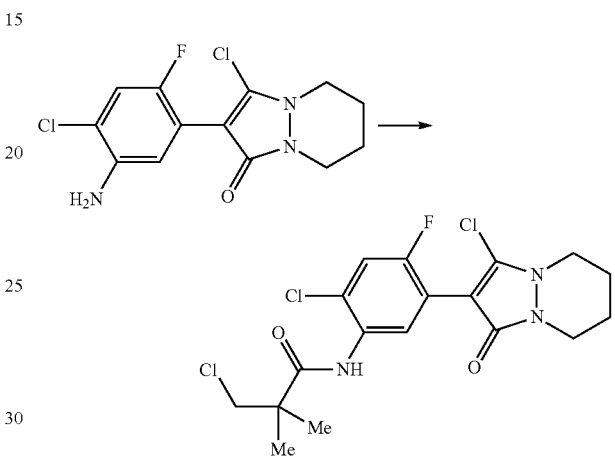

In the same manner as in Example-189, 4-(5-amino-4-chloro-2-fluorophenyl)-5-chloro-1,2-tetramethylene-4-pyrazolin-3-one was reacted with 3-chloro-2,2-dimethylpropionyl chloride, whereby 4-[4-chloro-5-(3-chloro-2,2-dimethylpropionylamino)-2-fluorophenyl]-5-chloro-1,2-tetramethylene-4-pyrazolin-3-one was obtained with a yield of 96%. ¹H-NMR (400 MHz, CDCl₃): δ1.43 (s, 6H), 1.85-1.92 (m, 2H), 1.97-2.05 (m, 2H), 3.57-3.62 (m, 2H), 3.69 (s, 2H), 3.79-3.84 (m, 2H), 7.21 (d, J=9.0 Hz, 1H), 7.90 (brs, 1H), 8.39 (d, J=7.7 Hz, 1H). ¹⁹F-NMR (376 MHz, CDCl₃): δ−113.9 (s, 1F).

Example-192

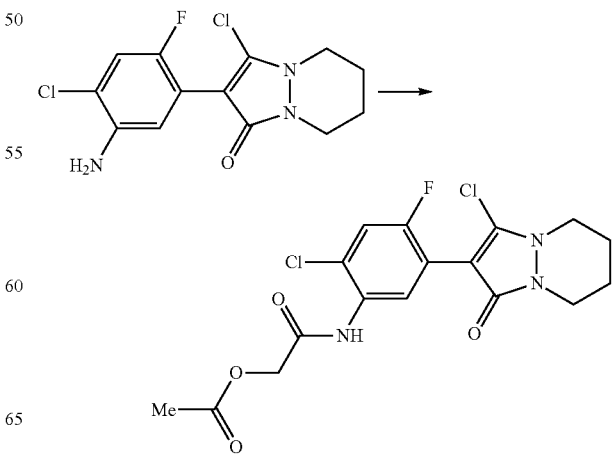

In the same manner as in Example-189, 4-(5-amino-4-chloro-2-fluorophenyl)-5-chloro-1,2-tetramethylene-4-pyrazolin-3-one was reacted with 2-(acetoxy)acetyl chloride, whereby 4-[5-[2-(acetoxy)acetyl amino]-4-chloro-2-fluorophenyl]-5-chloro-1,2-tetramethylene-4-pyrazolin-3-one was obtained quantitatively. ¹H-NMR (400 MHz, CDCl₃): δ1.86-1.93 (m, 2H), 1.98-2.04 (m, 2H), 2.25 (s, 3H), 3.59-3.64 (m, 2H), 3.80-3.85 (m, 2H), 4.73 (s, 2H), 7.23 (d, J=8.9 Hz, 1H), 8.32 (brs, 1H), 8.42 (d, J=7.2 Hz, 1H). ¹⁹F-NMR (376 MHz, CDCl₃): δ−113.2 (s, 1F).

Example-193

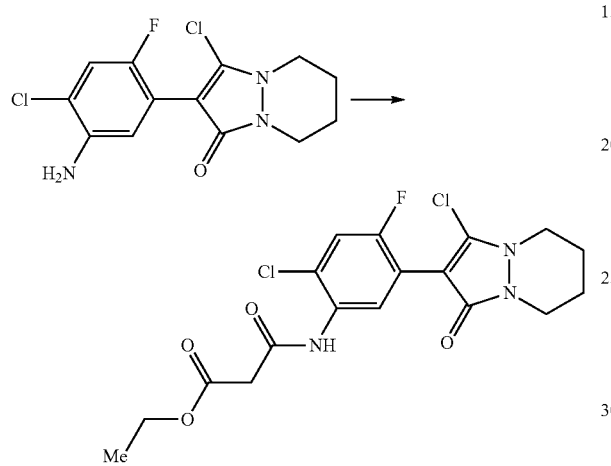

In the same manner as in Example-189, 4-(5-amino-4-chloro-2-fluorophenyl)-5-chloro-1,2-tetramethylene-4-pyrazolin-3-one was reacted with ethyl malonylchloride, whereby 4-[4-chloro-5-[2-(ethoxycarbonyl)acetyl amino]-2-fluorophenyl]-5-chloro-1,2-tetramethylene-4-pyrazolin-3-one was obtained with a yield of 99%. ¹H-NMR (400 MHz, CDCl₃): δ1.33 (t, J=7.2 Hz, 3H), 1.85-1.93 (m, 2H), 1.97-2.05 (m, 2H), 3.51 (s, 2H), 3.58-3.63 (m, 2H), 3.79-3.85 (m, 2H), 4.28 (q, J=7.2 Hz, 2H), 7.21 (d, J=8.9 Hz, 1H), 8.39 (d, J=7.2 Hz, 1H), 9.66 (brs, 1H). ¹⁹F-NMR (376 MHz, CDCl₃): δ−114.0 (s, 1F).

Example-194

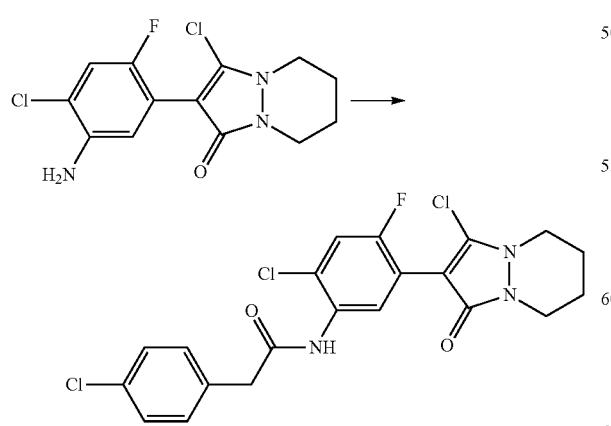

In the same manner as in Example-189, 4-(5-amino-4-chloro-2-fluorophenyl)-5-chloro-1,2-tetramethylene-4-pyrazolin-3-one was reacted with 2-(4-chlorophenyl)acetyl chloride, whereby 4-[4-chloro-5-[2-(4-chlorophenyl)acetyl amino]-2-fluorophenyl]-5-chloro-1,2-tetramethylene-4-pyrazolin-3-one was obtained quantitatively. ¹H-NMR (400 MHz, CDCl₃): δ1.84-1.94 (m, 2H), 1.97-2.06 (m, 2H), 3.56-3.66 (m, 2H), 3.74 (s, 2H), 3.78-3.85 (m, 2H), 7.12 (d, J=8.9 Hz, 1H), 7.30 (d, J=8.4 Hz, 2H), 7.37 (d, J=8.4 Hz, 2H), 7.67 (brs, 1H), 8.29 (d, J=7.1 Hz, 1H). ¹⁹F-NMR (376 MHz, CDCl₃): δ−113.8 (s, 1F).

Example-195

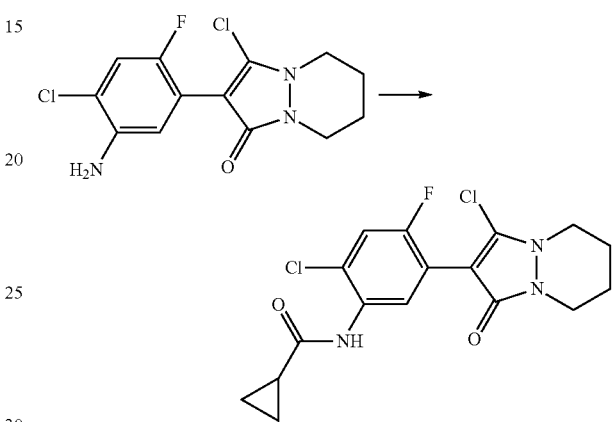

In the same manner as in Example-189, 4-(5-amino-4-chloro-2-fluorophenyl)-5-chloro-1,2-tetramethylene-4-pyrazolin-3-one was reacted with cyclopropanecarbonyl chloride, whereby 4-[4-chloro-5-(cyclopropylcarbonylamino)-2-fluorophenyl]-5-chloro-1,2-tetramethylene-4-pyrazolin-3-one was obtained with a yield of 87%. ¹H-NMR (400 MHz, CDCl₃): δ0.83-0.93 (m, 2H), 1.04-1.12 (m, 2H), 1.64 (m, 1H), 1.84-1.92 (m, 2H), 1.96-2.05 (m, 2H), 3.55-3.62 (m, 2H), 3.78-3.84 (m, 2H), 7.16 (m, 1H), 7.92 (brs, 1H), 8.33 (m, 1H). ¹⁹F-NMR (376 MHz, CDCl₃): δ−114.9 (s, 1F).

Example-196

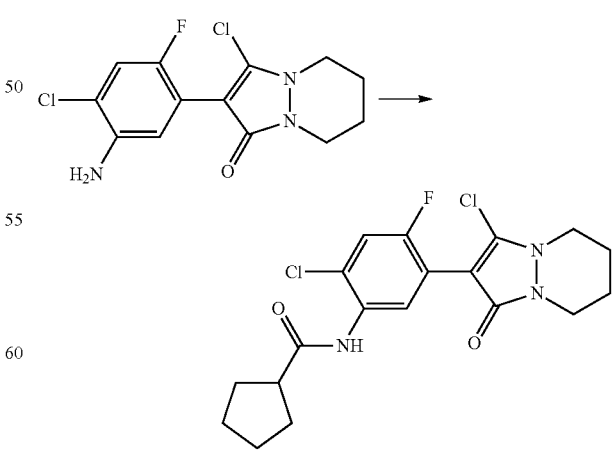

In the same manner as in Example-189, 4-(5-amino-4-chloro-2-fluorophenyl)-5-chloro-1,2-tetramethylene-4-pyrazolin-3-one was reacted with cyclopentanecarbonyl chloride, whereby 4-[4-chloro-5-(cyclopentylcarbonyl amino)-2-fluorophenyl]-5-chloro-1,2-tetramethylene-4-pyrazolin-3-one was obtained with a yield of 84%. ¹H-NMR (400 MHz, CDCl₃): δ1.60-1.69 (m, 2H), 1.73-1.83 (m, 2H), 1.84-2.04 (m, 8H), 2.76 (sept, J=8.0 Hz, 1H), 3.56-3.61 (m, 2H), 3.79-3.84 (m, 2H), 7.19 (d, J=9.1 Hz, 1H), 7.50 (brs, 1H), 8.39 (d, J=7.0 Hz, 1H). ¹⁹F-NMR (376 MHz, CDCl₃): δ−114.7 (s, 1F).

Example-197

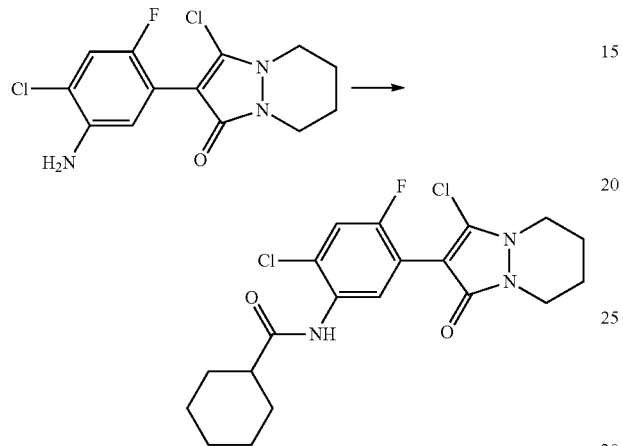

In the same manner as in Example-189, 4-(5-amino-4-chloro-2-fluorophenyl)-5-chloro-1,2-tetramethylene-4-pyrazolin-3-one was reacted with cyclohexanecarbonyl chloride, whereby 4-[4-chloro-5-(cyclohexylcarbonyl amino)-2-fluorophenyl]-5-chloro-1,2-tetramethylene-4-pyrazolin-3-one was obtained with a yield of 98%. ¹H-NMR (400 MHz, CDCl₃): δ1.19-1.40 (m, 4H), 1.46-1.59 (m, 2H), 1.80-1.92 (m, 4H), 1.95-2.06 (m, 4H), 2.30 (m, 1H), 3.57-3.62 (m, 2H), 3.79-3.85 (m, 2H), 7.19 (d, J=9.0 Hz, 1H), 7.53 (brs, 1H), 8.38 (d, J=7.3 Hz, 1H). ¹⁹F-NMR (376 MHz, CDCl₃): δ−114.6 (s, 1F).

Example-198

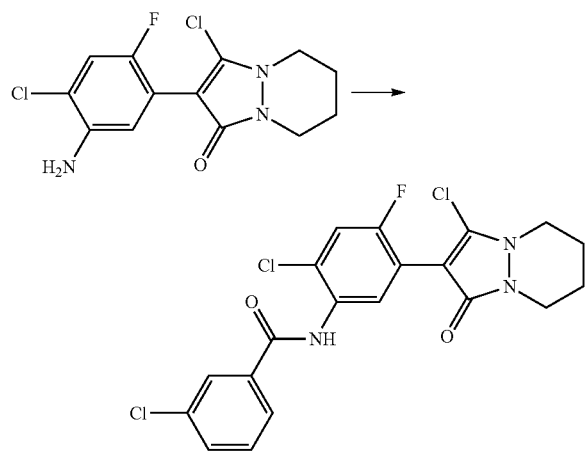

Triethylamine (155 μL, 1.10 mmol) and 3-chlorobenzoyl chloride (144 μL, 1.10 mmol) were added to a solution of 4-(5-amino-4-chloro-2-fluorophenyl)-5-chloro-1,2-tetramethylene-4-pyrazolin-3-one (316 mg, 1.00 mmol) in dichloromethane (2 mL) under ice-cooling, followed by stirring at room temperature for 24 hours. After the reaction was completed, a sodium hydrogencarbonate aqueous solution (3 mL) was added to the reaction solution, and the resultant product was extracted with chloroform (10 mL×3). The combined organic layer was washed with a saturated saline solution, dried over anhydrous magnesium sulfate, and concentrated under reduced pressure. The obtained crude product was purified by silica gel column chromatography (ethyl acetate), whereby 4-[4-chloro-5-(3-chlorobenzoyl amino)-2-fluorophenyl]-5-chloro-1,2-tetramethylene-4-pyrazolin-3-one (445 mg, yield: 98%) was obtained as a white solid. ¹H-NMR (400 MHz, CDCl₃): δ1.86-1.95 (m, 2H), 1.98-2.07 (m, 2H), 3.60-3.66 (m, 2H), 3.81-3.87 (m, 2H), 7.26 (d, J=8.8 Hz, 1H), 7.45 (t, J=7.9 Hz, 1H), 7.55 (ddd, J=1.0, 1.6 and 7.9 Hz, 1H), 7.76 (ddd, J=1.0, 1.6 and 7.9 Hz, 1H), 7.89 (t, J=1.6 Hz, 1H), 8.19 (brs, 1H), 8.52 (d, J=7.2 Hz, 1H). ¹⁹F-NMR (376 MHz, CDCl₃): δ−113.3 (s, 1F).

Example-199

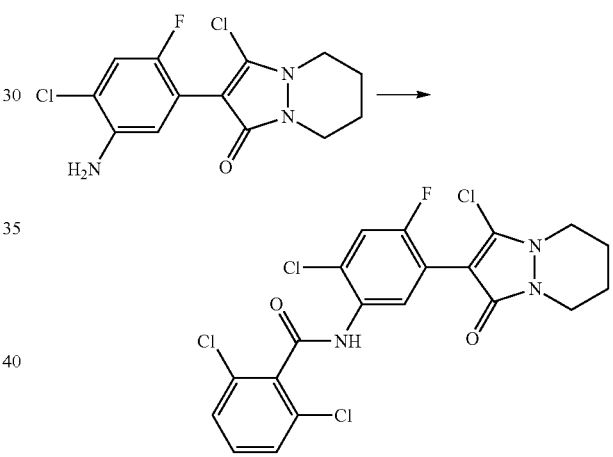

In the same manner as in Example-198, 4-(5-amino-4-chloro-2-fluorophenyl)-5-chloro-1,2-tetramethylene-4-pyrazolin-3-one was reacted with 2,6-dichlorobenzoyl chloride, whereby 4-[4-chloro-5-(2,6-dichlorobenzoylamino)-2-fluorophenyl]-5-chloro-1,2-tetramethylene-4-pyrazolin-3-one was obtained quantitatively. ¹H-NMR (400 MHz, CDCl₃): δ1.86-1.95 (m, 2H), 1.98-2.07 (m, 2H), 3.59-3.67 (m, 2H), 3.79-3.86 (m, 2H), 7.24 (d, J=9.0 Hz, 1H), 7.30-7.40 (m, 3H), 7.76 (brs, 1H), 8.44 (d, J=7.1 Hz, 1H). ¹⁹F-NMR (376 MHz, CDCl₃): δ−112.8 (s, 1F).

Example-200

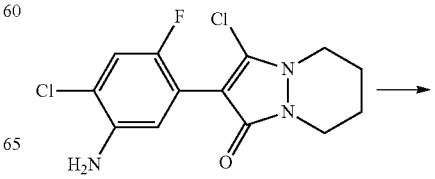

-continued

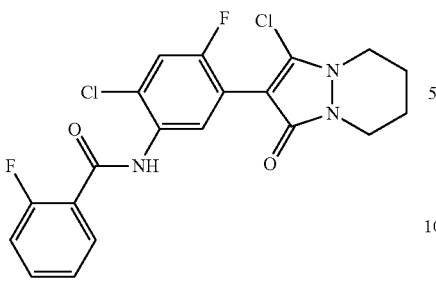

In the same manner as in Example-198, 4-(5-amino-4-chloro-2-fluorophenyl)-5-chloro-1,2-tetramethylene-4-pyrazolin-3-one was reacted with 2-fluorobenzoyl chloride, whereby 4-[4-chloro-2-fluoro-5-(2-fluorobenzoyl amino)phenyl]-5-chloro-1,2-tetramethylene-4-pyrazolin-3-one was obtained quantitatively. $^1$H-NMR (400 MHz, CDCl$_3$): δ1.86-1.95 (m, 2H), 1.98-2.07 (m, 2H), 3.59-3.66 (m, 2H), 3.81-3.88 (m, 2H), 7.21 (ddd, J=0.7, 8.3 and 12.4 Hz, 1H), 7.26 (d, J=9.0 Hz, 1H), 7.32 (ddd, J=0.7, 7.9 and 8.3 Hz, 1H), 7.54 (dddd, J=1.8, 5.2, 7.9 and 8.3 Hz, 1H), 8.18 (dt, J=1.8 and 7.9 Hz, 1H), 8.64 (d, J=7.3 Hz, 1H), 8.98 (d, J=16.2 Hz, 1H). $^{19}$F-NMR (376 MHz, CDCl$_3$): δ−113.8 (s, 1F), −112.5 (s, 1F).

Example-201

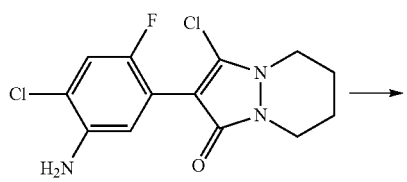

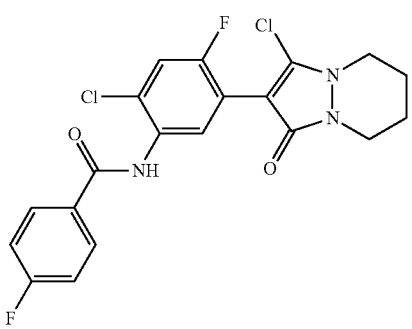

In the same manner as in Example-198, 4-(5-amino-4-chloro-2-fluorophenyl)-5-chloro-1,2-tetramethylene-4-pyrazolin-3-one was reacted with 4-fluorobenzoyl chloride, whereby 4-[4-chloro-2-fluoro-5-(4-fluorobenzoyl amino)phenyl]-5-chloro-1,2-tetramethylene-4-pyrazolin-3-one was obtained with a yield of 98%. $^1$H-NMR (400 MHz, CDCl$_3$): δ1.86-1.95 (m, 2H), 1.98-2.08 (m, 2H), 3.60-3.66 (m, 2H), 3.80-3.88 (m, 2H), 7.19 (t, J=8.7 Hz, 2H), 7.25 (d, J=9.1 Hz, 1H), 7.92 (dd, J=5.2 and 8.7 Hz, 2H), 8.19 (brs, 1H), 8.52 (d, J=7.2 Hz, 1H). $^{19}$F-NMR (376 MHz, CDCl$_3$): δ−113.8 (s, 1F).

Example-202

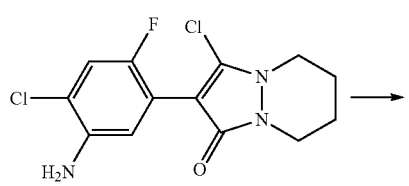

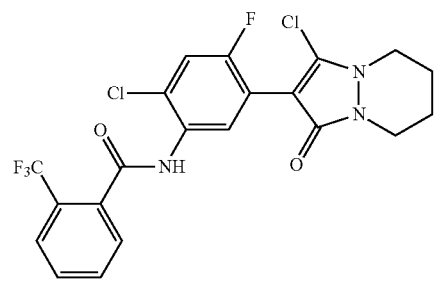

In the same manner as in Example-198, 4-(5-amino-4-chloro-2-fluorophenyl)-5-chloro-1,2-tetramethylene-4-pyrazolin-3-one was reacted with 2-(trifluoromethyl)benzoyl chloride, whereby 4-[4-chloro-2-fluoro-5-{2-(trifluoromethyl)benzoylamino}phenyl]-5-chloro-1,2-tetramethylene-4-pyrazolin-3-one was obtained quantitatively. $^1$H-NMR (400 MHz, CDCl$_3$): δ1.87-1.94 (m, 2H), 1.98-2.06 (m, 2H), 3.60-3.66 (m, 2H), 3.80-3.86 (m, 2H), 7.24 (d, J=9.0 Hz, 1H), 7.59-7.82 (m, 5H), 8.50 (d, J=7.1 Hz, 1H). $^{19}$F-NMR (376 MHz, CDCl$_3$): δ−113.1 (s, 1F), −58.7 (s, 3F).

Example-203

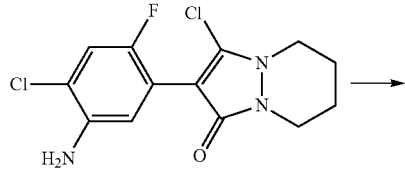

In the same manner as in Example-198, 4-(5-amino-4-chloro-2-fluorophenyl)-5-chloro-1,2-tetramethylene-4-pyrazolin-3-one was reacted with 3-(trifluoromethyl)benzoyl chloride, whereby 4-[4-chloro-2-fluoro-5-{3-(trifluoromethyl)benzoyl amino}phenyl]-5-chloro-1,2-tetramethylene-4-pyrazolin-3-one was obtained with a yield of 88%. $^1$H-NMR (400 MHz, CDCl$_3$): δ1.87-1.95 (m, 2H), 1.99-2.07 (m, 2H), 3.60-3.68 (m, 2H), 3.80-3.87 (m, 2H), 7.26 (d, J=8.9 Hz, 1H), 7.66 (t, J=7.8 Hz, 1H), 7.84 (d, J=7.8 Hz, 1H), 8.07 (d, J=7.8 Hz, 1H), 8.19 (s, 1H), 8.29 (brs, 1H), 8.50 (d, J=7.2 Hz, 1H). $^{19}$F-NMR (376 MHz, CDCl$_3$): δ−113.0 (s, 1F), −62.8 (s, 3F).

Example-204

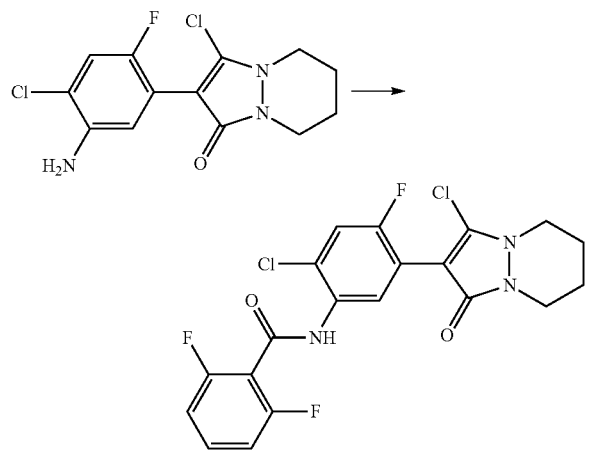

In the same manner as in Example-198, 4-(5-amino-4-chloro-2-fluorophenyl)-5-chloro-1,2-tetramethylene-4-pyrazolin-3-one was reacted with 2,6-difluorobenzoyl chloride, whereby 4-[4-chloro-2-fluoro-5-(2,6-difluorobenzoyl amino)phenyl]-5-chloro-1,2-tetramethylene-4-pyrazolin-3-one was obtained quantitatively. $^1$H-NMR (400 MHz, CDCl$_3$): δ1.86-1.94 (m, 2H), 1.98-2.06 (m, 2H), 3.59-3.65 (m, 2H), 3.80-3.85 (m, 2H), 7.02 (t, J=8.4 Hz, 2H), 7.25 (d, J=9.1 Hz, 1H), 7.44 (m, 1H), 8.07 (brs, 1H), 8.53 (d, J=7.1 Hz, 1H). $^{19}$F-NMR (376 MHz, CDCl$_3$): δ−113.2 (s, 1F), −110.9 (s, 2F).

Example-205

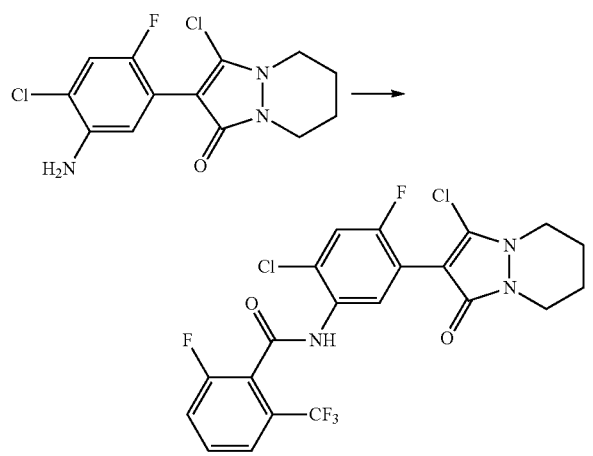

In the same manner as in Example-198, 4-(5-amino-4-chloro-2-fluorophenyl)-5-chloro-1,2-tetramethylene-4-pyrazolin-3-one was reacted with 2-fluoro-6-(trifluoromethyl)benzoyl chloride, whereby 4-[4-chloro-2-fluoro-5-{2-fluoro-6-(trifluoromethyl)benzoyl amino}phenyl]-5-chloro-1,2-tetramethylene-4-pyrazolin-3-one was obtained quantitatively. $^1$H-NMR (400 MHz, CDCl$_3$): δ1.84-1.94 (m, 2H), 1.97-2.07 (m, 2H), 3.59-3.66 (m, 2H), 3.73-3.80 (m, 2H), 7.21 (d, J=9.0 Hz, 1H), 7.39 (m, 1H), 7.53-7.62 (m, 2H), 8.11 (brs, 1H), 8.35 (d, J=6.9 Hz, 1H). $^{19}$F-NMR (376 MHz, CDCl$_3$): δ−112.7 (s, 1F), −112.6 (s, 1F), −59.1 (s, 3F).

Example-206

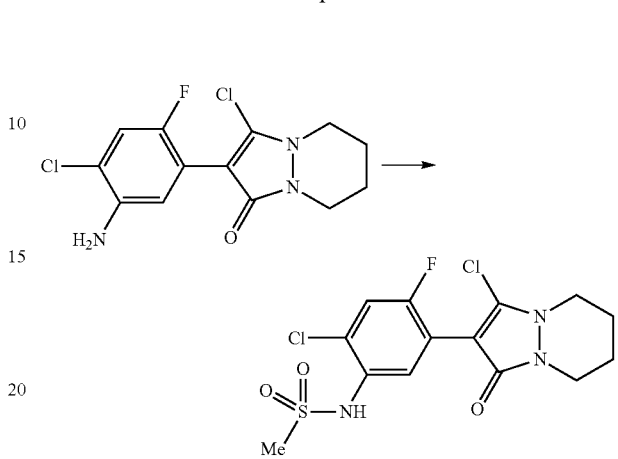

Pyridine (60.1 mg, 0.76 mmol) and methyl sulfonyl chloride (79.0 mg, 0.76 mmol) were added to a solution of 4-(5-amino-4-chloro-2-fluorophenyl)-5-chloro-1,2-tetramethylene-4-pyrazolin-3-one (219 mg, 0.69 mmol) in dichloromethane (2 mL) under ice-cooling, followed by stirring at room temperature for 41 hours. After the reaction was completed, a saturated sodium hydrogencarbonate aqueous solution (50 mL) was added to the reaction solution, and the resultant product was extracted with chloroform (30 mL×1, 20 mL×2). The organic layer was washed with 2N hydrochloric acid (30 mL), washed with a saturated saline solution, dried over anhydrous magnesium sulfate, and concentrated under reduced pressure, whereby a pale yellow oily crude product (245 mg) was obtained. This was purified by silica gel column chromatography (ethyl acetate), whereby 5-chloro-4-[4-chloro-2-fluoro-5-(methyl sulfonyl amino)phenyl]-1,2-tetramethylene-4-pyrazolin-3-one (132 mg, yield: 48%) was obtained as a white solid. $^1$H-NMR (400 MHz, CDCl$_3$): δ1.88-1.94 (m, 2H), 2.00-2.05 (m, 2H), 3.08 (s, 3H), 3.64 (t, J=5.6 Hz, 2H), 3.83 (t, J=5.6 Hz, 2H), 6.81 (brs, 1H), 7.24 (d, J=8.5 Hz, 1H), 7.75 (d, J=6.7 Hz, 1H). $^{19}$F-NMR (376 MHz, CDCl$_3$): δ−112 (s, 1F).

Example-207

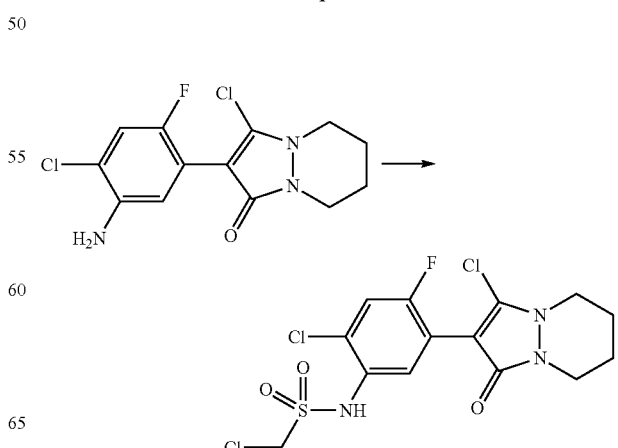

Pyridine (56 μL, 0.69 mmol) and chloromethyl sulfonyl chloride (62 μL, 0.69 mmol) were added to a solution of 4-(5-amino-4-chloro-2-fluorophenyl)-5-chloro-1,2-tetramethylene-4-pyrazolin-3-one (200 mg, 0.63 mmol) in dichloromethane (2 mL) under ice-cooling, followed by stirring at room temperature for 48 hours. After the reaction was completed, a sodium hydrogencarbonate aqueous solution (20 mL) was added to the reaction solution, and the resultant product was extracted with chloroform (20 mL×3). The combined organic layer was washed sequentially with 2N hydrochloric acid and a saturated saline solution, dried over anhydrous magnesium sulfate, and concentrated under reduced pressure. The obtained crude product was purified by silica gel column chromatography (ethyl acetate), whereby 5-chloro-4-[4-chloro-2-fluoro-5-(chloromethyl sulfonyl amino)phenyl]-1,2-tetramethylene-4-pyrazolin-3-one (148 mg, yield: 55%) was obtained as a white solid. $^1$H-NMR (400 MHz, CDCl$_3$): δ1.87-1.96 (m, 2H), 1.99-2.07 (m, 2H), 3.61-3.69 (m, 2H), 3.79-3.88 (m, 2H), 4.62 (s, 2H), 7.22 (d, J=9.2 Hz, 1H), 7.39 (brs, 1H), 7.77 (d, J=6.8 Hz, 1H). $^{19}$F-NMR (376 MHz, CDCl$_3$): δ−111.5 (s, 1F).

Example-208

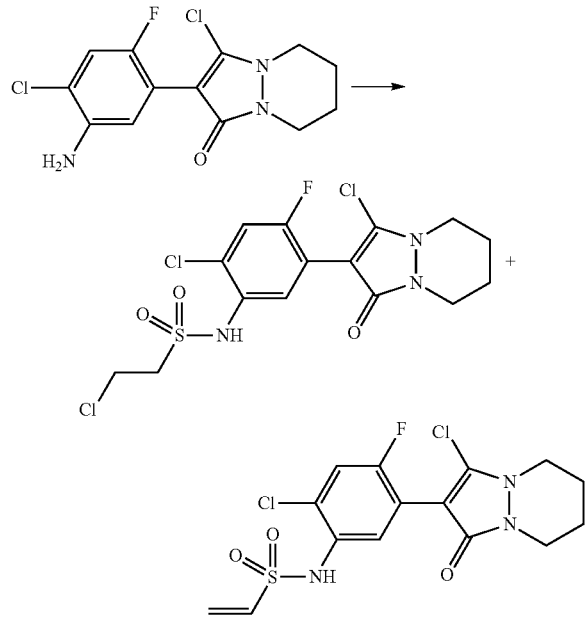

Pyridine (56 μL, 0.69 mmol) and 2-chloroethyl sulfonyl chloride (73 μL, 0.69 mmol) were added to a solution of 4-(5-amino-4-chloro-2-fluorophenyl)-5-chloro-1,2-tetramethylene-4-pyrazolin-3-one (200 mg, 0.63 mmol) in dichloromethane (2 mL) under ice-cooling, followed by stirring at room temperature for 48 hours. After the reaction was completed, a sodium hydrogencarbonate aqueous solution (20 mL) was added to the reaction solution, and the resultant product was extracted with chloroform (20 mL×3). The combined organic layer was washed sequentially with 2N hydrochloric acid and a saturated saline solution, dried over anhydrous magnesium sulfate, and concentrated under reduced pressure. The obtained crude product was purified by silica gel column chromatography (ethyl acetate), whereby 5-chloro-4-[4-chloro-2-fluoro-5-(2-chloroethylsulfonylamino)phenyl]-1,2-tetramethylene-4-pyrazolin-3-one (79 mg, yield: 31%) was obtained as a white solid, and 5-chloro-4-[4-chloro-2-fluoro-5-(vinylsulfonylamino)phenyl]-1,2-tetramethylene-4-pyrazolin-3-one (30 mg, yield: 5%) was obtained as a white solid. 5-Chloro-4-[4-chloro-2-fluoro-5-(2-chloroethyl sulfonyl amino)phenyl]-1,2-tetramethylene-4-pyrazolin-3-one: 5-chloro-4-[4-chloro-2-fluoro-5-(vinylsulfonylamino)phenyl]-1,2-tetramethylene-4-pyrazolin-3-one $^1$H-NMR (400 MHz, CDCl$_3$): δ1.88-1.97 (m, 2H), 1.99-2.08 (m, 2H), 3.52-3.58 (m, 2H), 3.64-3.70 (m, 2H), 3.83-3.93 (m, 4H), 7.16 (d, J=9.2 Hz, 1H), 7.64 (d, J=7.1 Hz, 1H), 7.93 (brs, 1H). $^{19}$F-NMR (376 MHz, CDCl$_3$): δ−111.7 (s, 1F). 5-Chloro-4-[4-chloro-2-fluoro-5-(vinylsulfonylamino)phenyl]-1,2-tetramethylene-4-pyrazolin-3-one: $^1$H-NMR (400 MHz, CDCl$_3$): δ1.87-1.96 (m, 2H), 1.99-2.06 (m, 2H), 3.60-3.68 (m, 2H), 3.80-3.88 (m, 2H), 6.02 (d, J=9.9 Hz, 1H), 6.35 (d, J=16.5 Hz, 1H), 6.59 (dd, J=9.9 and 16.5 Hz, 1H), 6.72 (brs, 1H), 7.21 (d, J=8.9 Hz, 1H), 7.72 (d, J=6.8 Hz, 1H). $^{19}$F-NMR (376 MHz, CDCl$_3$): δ−112.4 (s, 1F).

Example-209

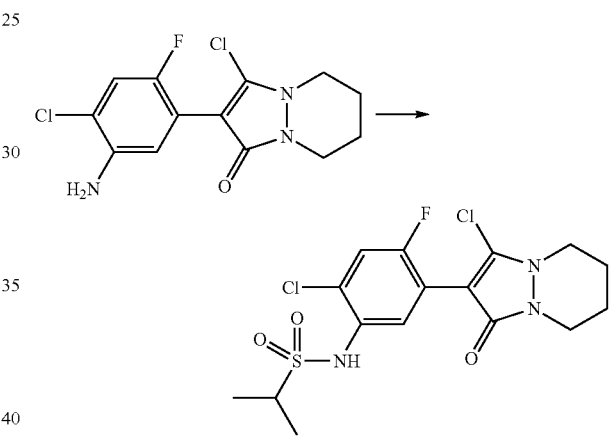

Pyridine (56 μL, 0.69 mmol) and isopropyl sulfonyl chloride (78 μL, 0.69 mmol) were added to a solution of 4-(5-amino-4-chloro-2-fluorophenyl)-5-chloro-1,2-tetramethylene-4-pyrazolin-3-one (200 mg, 0.63 mmol) in dichloromethane (2 mL) under ice-cooling, followed by stirring at room temperature for 48 hours. After the reaction was completed, a sodium hydrogencarbonate aqueous solution (20 mL) was added to the reaction solution, and the resultant product was extracted with chloroform (20 mL×3). The combined organic layer was washed sequentially with 2N hydrochloric acid and a saturated saline solution, dried over anhydrous magnesium sulfate, and concentrated under reduced pressure. The obtained crude product was purified by silica gel column chromatography (ethyl acetate), whereby 5-chloro-4-[4-chloro-2-fluoro-5-(isopropylsulfonylamino)phenyl]-1,2-tetramethylene-4-pyrazolin-3-one (162 mg, yield: 61%) was obtained as a white solid. $^1$H-NMR (400 MHz, CDCl$_3$): δ1.41 (d, J=6.9 Hz, 6H), 1.87-1.95 (m, 2H), 1.98-2.05 (m, 2H), 3.38 (sept, J=6.9 Hz, 1H), 3.61-3.66 (m, 2H), 3.80-3.85 (m, 2H), 7.62 (brs, 1H), 7.22 (d, J=8.9 Hz, 1H), 7.80 (d, J=6.8 Hz, 1H). $^{19}$F-NMR (376 MHz, CDCl$_3$): δ−113.8 (s, 1F).

Example-210

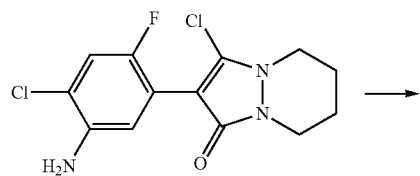

Pyridine (56 µL, 0.69 mmol) and N,N-dimethyl sulfamoyl chloride (74 µL, 0.69 mmol) were added to a solution of 4-(5-amino-4-chloro-2-fluorophenyl)-5-chloro-1,2-tetramethylene-4-pyrazolin-3-one (200 mg, 0.63 mmol) in dichloromethane (2 mL) under ice-cooling, followed by stirring at room temperature for 48 hours. After the reaction was completed, a sodium hydrogencarbonate aqueous solution (20 mL) was added to the reaction solution, and the resultant product was extracted with chloroform (20 mL×3). The combined organic layer was washed sequentially with 2N hydrochloric acid and a saturated saline solution, dried over anhydrous magnesium sulfate, and concentrated under reduced pressure. The obtained crude product was purified by silica gel column chromatography (ethyl acetate), whereby 5-chloro-4-[4-chloro-2-fluoro-5-(N,N-dimethyl sulfamoyl amino)phenyl]-1,2-tetramethylene-4-pyrazolin-3-one (218 mg, yield: 82%) was obtained as a white solid. $^1$H-NMR (400 MHz, CDCl$_3$): δ1.87-1.95 (m, 2H), 1.98-2.06 (m, 2H), 2.88 (s, 6H), 3.62-3.66 (m, 2H), 3.81-3.85 (m, 2H), 6.64 (brs, 1H), 7.21 (d, J=9.1 Hz, 1H), 7.75 (d, J=7.1 Hz, 1H). $^{19}$F-NMR (376 MHz, CDCl$_3$): δ−113.9 (s, 1F).

Example-211

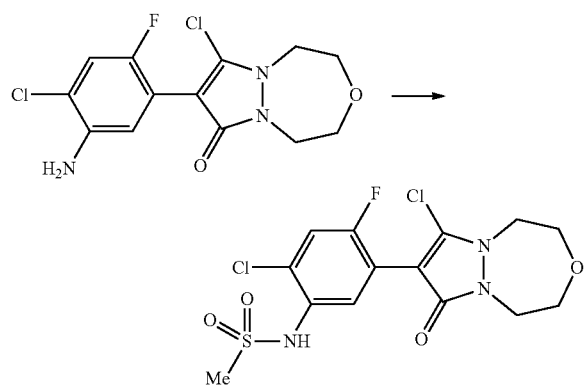

In the same manner as in Example-206, 4-(5-amino-4-chloro-2-fluorophenyl)-5-chloro-1,2-oxadiethylene-4-pyrazolin-3-one was reacted with methyl sulfonyl chloride, whereby 5-chloro-4-[4-chloro-2-fluoro-5-(methylsulfonylamino)phenyl]-1,2-oxadiethylene-4-pyrazolin-3-one was obtained with a yield of 97%. $^1$H-NMR (400 MHz, CDCl$_3$): δ3.07 (s, 3H), 3.92-3.97 (m, 4H), 4.23-4.31 (m, 4H), 6.95 (brs, 1H), 7.23 (d, J=8.5 Hz, 1H), 7.74 (d, J=6.9 Hz, 1H). $^{19}$F-NMR (376 MHz, CDCl$_3$): δ−112.4 (s, 1F).

Example-212

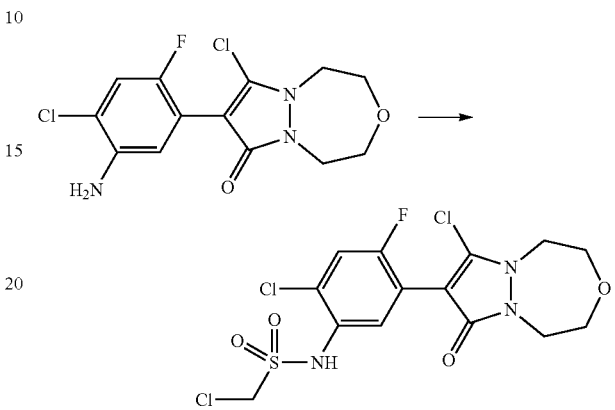

In the same manner as in Example-206, 4-(5-amino-4-chloro-2-fluorophenyl)-5-chloro-1,2-oxadiethylene-4-pyrazolin-3-one was reacted with chloromethyl sulfonyl chloride, whereby 5-chloro-4-[4-chloro-2-fluoro-5-(chloromethylsulfonylamino)phenyl]-1,2-oxadiethylene-4-pyrazolin-3-one was obtained with a yield of 63%. $^1$H-NMR (400 MHz, CDCl$_3$): δ3.92-3.97 (m, 4H), 4.23-4.31 (m, 4H), 4.60 (s, 2H), 7.20 (m, 1H), 7.62-7.98 (m, 2H). $^{19}$F-NMR (376 MHz, CDCl$_3$): δ−111.5 (s, 1F).

Example-213

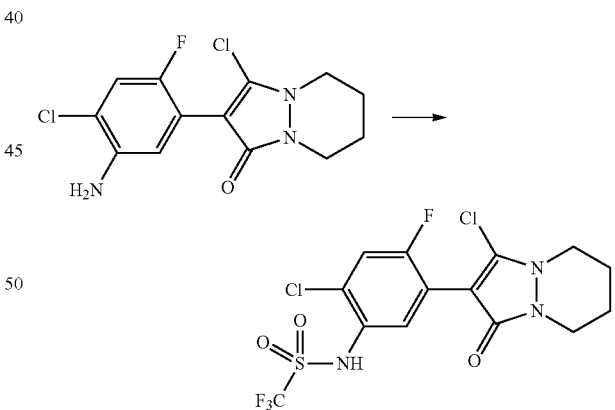

Triethylamine (0.13 mL, 1.25 mmol) and trifluoromethyl sulfonyl chloride (26.5 mg, 1.25 mmol) were added to a solution of 4-(5-amino-4-chloro-2-fluorophenyl)-5-chloro-1,2-tetramethylene-4-pyrazolin-3-one (305 mg, 0.96 mmol) in THF (3 mL) under ice-cooling, followed by stirring at room temperature for 21 hours. After the reaction was completed, water (20 mL) was added to the reaction solution, and the resultant product was extracted with ethyl acetate (30 mL×2, 20 mL×1). The organic layer was washed with a saturated saline solution, dried over anhydrous magnesium sulfate, and concentrated under reduced pressure, whereby a crude product (292 mg) was obtained as a brown solid. This was purified by silica gel column chromatography (ethyl acetate:methanol=30:1), whereby 5-chloro-4-[4-chloro-2-fluoro-5-(trifluoromethylsulfonylamino)phenyl]-1,2-tetramethylene-4-pyrazolin-3-one (64 mg, yield: 15%) was obtained as a white yellow solid. $^1$H-NMR (400 MHz, CDCl$_3$): δ1.89-1.94 (m, 2H), 2.00-2.06 (m, 2H), 3.63-3.66 (m, 2H), 3.82-3.85 (m, 2H), 7.26 (d, J=9.0 Hz, 1H), 7.50 (d, J=6.5 Hz, 1H). $^{19}$F-NMR (376 MHz, CDCl$_3$): δ−112 (s, 1F), −77.6 (d, J=17.6 Hz, 1F).

Example-214

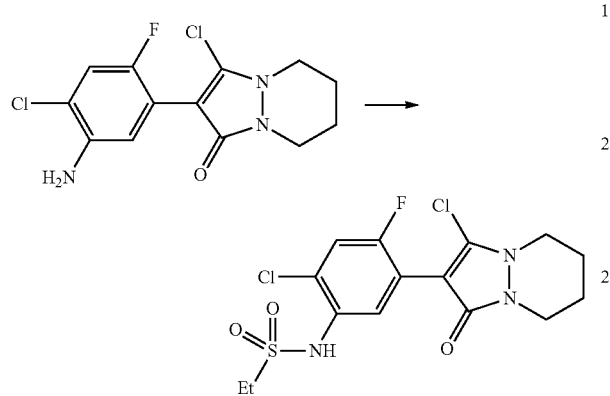

Pyridine (43.5 mg, 0.55 mmol) and ethyl sulfonyl chloride (70.7 mg, 0.55 mmol) were added to a solution of 4-(5-amino-4-chloro-2-fluorophenyl)-5-chloro-1,2-tetramethylene-4-pyrazolin-3-one (174 mg, 0.55 mmol) in dichloromethane (2 mL) under ice-cooling, followed by stirring at room temperature for 65 hours. After the reaction was completed, a saturated sodium hydrogencarbonate aqueous solution (50 mL) was added to the reaction solution, and the resultant product was extracted with chloroform (20 mL×2, 10 mL×1). The organic layer was washed with 2N hydrochloric acid (30 mL), washed with a saturated saline solution, dried over anhydrous magnesium sulfate, and concentrated under reduced pressure, and the resultant product was washed with ether, whereby a crude product (140 mg) was obtained as an ocherous solid. This was purified by silica gel column chromatography (ethyl acetate:methanol=30:1), whereby 5-chloro-4-(4-chloro-5-ethylsulfonylamino-2-fluorophenyl)-1,2-tetramethylene-4-pyrazolin-3-one (123 mg, yield: 55%) was obtained as a white solid. $^1$H-NMR (400 MHz, CDCl$_3$): δ1.39 (t, J=7.4 Hz, 3H), 1.88-1.94 (m, 2H), 1.99-2.05 (m, 2H), 3.21 (q, J=7.4 Hz, 2H), 3.62-3.65 (m, 2H), 3.81-3.84 (m, 2H), 6.70 (brs, 1H), 7.23 (d, J=8.8 Hz, 1H), 7.77 (d, J=6.8 Hz, 1H). $^{19}$F-NMR (376 MHz, CDCl$_3$): δ−113 (s, 1F).

Example-215

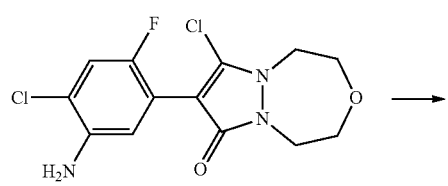

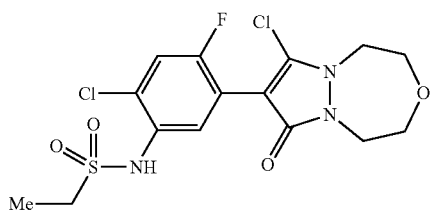

In the same manner as in Example-206, 4-(5-amino-4-chloro-2-fluorophenyl)-5-chloro-1,2-oxadiethylene-4-pyrazolin-3-one was reacted with ethyl sulfonyl chloride, whereby 5-chloro-4-[4-chloro-2-fluoro-5-(ethylsulfonylamino)phenyl]-1,2-oxadiethylene-4-pyrazolin-3-one was obtained with a yield of 29%. $^1$H-NMR (400 MHz, CDCl$_3$): δ1.39 (t, J=7.4 Hz, 3H), 3.20 (q, J=7.4 Hz, 2H), 3.92-3.96 (m, 4H), 4.21-4.29 (m, 4H), 6.71 (brs, 1H), 7.23 (d, J=8.8 Hz, 1H), 7.78 (d, J=6.5 Hz, 1H). $^{19}$F-NMR (376 MHz, CDCl$_3$): δ−113.3 (s, 1F).

Example-216

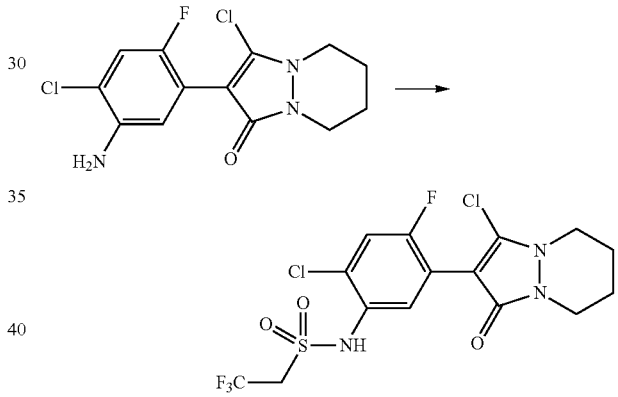

Pyridine (60 μL, 0.74 mmol) and 2,2,2-trifluoroethyl sulfonyl chloride (84 μL, 0.75 mmol) were added to a solution of 4-(5-amino-4-chloro-2-fluorophenyl)-5-chloro-1,2-tetramethylene-4-pyrazolin-3-one (215 mg, 0.68 mmol) in dichloromethane (2 mL) under ice-cooling, followed by stirring at room temperature for 48 hours. After the reaction was completed, a sodium hydrogencarbonate aqueous solution (20 mL) was added to the reaction solution, and the resultant product was extracted with chloroform (20 mL×3). The combined organic layer was washed sequentially with 2N hydrochloric acid and a saturated saline solution, dried over anhydrous magnesium sulfate, and concentrated under reduced pressure. The obtained crude product was purified by silica gel column chromatography (ethyl acetate), whereby 5-chloro-4-[4-chloro-2-fluoro-5-(2,2,2-trifluoroethylsulfonylamino)phenyl]-1,2-tetramethylene-4-pyrazolin-3-one (288 mg, yield: 92%) was obtained as a white solid. $^1$H-NMR (400 MHz, CDCl$_3$): δ1.89-1.97 (m, 2H), 2.00-2.08 (m, 2H), 3.64-3.71 (m, 2H), 3.83-3.89 (m, 2H), 3.93 (q, J=8.9 Hz, 2H), 7.18 (d, J=8.9 Hz, 1H), 7.67 (d, J=6.8 Hz, 1H), 8.12 (brs, 1H). $^{19}$F-NMR (376 MHz, CDCl$_3$): δ−110.9 (s, 1F), −61.8 (s, 3F).

Example-217

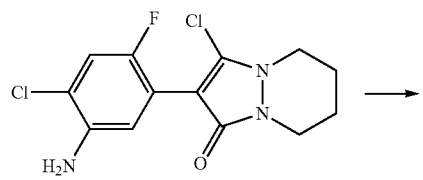

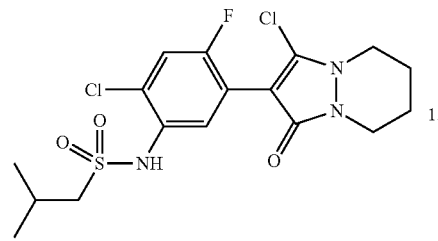

Pyridine (60 μL, 0.74 mmol) and isobutyl sulfonyl chloride (101 μL, 0.75 mmol) were added to a solution of 4-(5-amino-4-chloro-2-fluorophenyl)-5-chloro-1,2-tetramethylene-4-pyrazolin-3-one (215 mg, 0.68 mmol) in dichloromethane (2 mL) under ice-cooling, followed by stirring at room temperature for 48 hours. After the reaction was completed, a sodium hydrogencarbonate aqueous solution (20 mL) was added to the reaction solution, and the resultant product was extracted with chloroform (20 mL×3). The combined organic layer was washed sequentially with 2N hydrochloric acid and a saturated saline solution, dried over anhydrous magnesium sulfate, and concentrated under reduced pressure. The obtained crude product was purified by silica gel column chromatography (ethyl acetate), whereby 5-chloro-4-[4-chloro-2-fluoro-5-(isobutylsulfonylamino)phenyl]-1,2-tetramethylene-4-pyrazolin-3-one (215 mg, yield: 72%) was obtained as a white solid. $^1$H-NMR (400 MHz, CDCl$_3$): δ1.09 (d, J=6.7 Hz, 6H), 1.87-1.94 (m, 2H), 1.98-2.06 (m, 2H), 2.30 (h, J=6.7 Hz, 1H), 3.40 (d, J=6.7 Hz, 2H), 3.60-3.66 (m, 2H), 3.80-3.85 (m, 2H), 6.72 (brs, 1H), 7.23 (d, J=8.8 Hz, 1H), 7.75 (d, J=6.4 Hz, 1H). $^{19}$F-NMR (376 MHz, CDCl$_3$): δ−112.9 (s, 1F).

Example-218

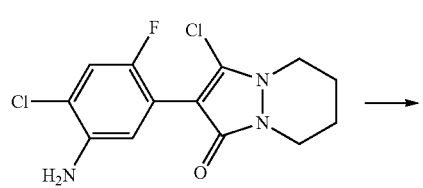

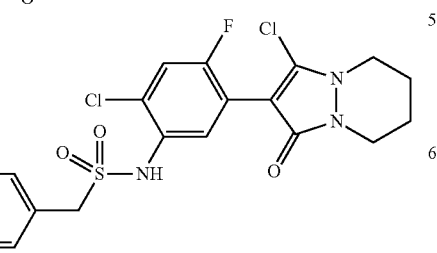

In the same manner as in Example-206, 4-(5-amino-4-chloro-2-fluorophenyl)-5-chloro-1,2-tetramethylene-4-pyrazolin-3-one was reacted with benzyl sulfonyl chloride, whereby 5-chloro-4-[5-(benzylsulfonylamino)-4-chloro-2-fluorophenyl]-1,2-tetramethylene-4-pyrazolin-3-one was obtained with a yield of 87%. $^1$H-NMR (400 MHz, CDCl$_3$): δ1.89-1.96 (m, 2H), 2.00-2.08 (m, 2H), 3.63-3.68 (m, 2H), 3.82-3.87 (m, 2H), 4.48 (s, 2H), 6.55 (brs, 1H), 7.21 (d, J=8.9 Hz, 1H), 7.24-7.35 (m, 6H). $^{19}$F-NMR (376 MHz, CDCl$_3$): δ−113.9 (s, 1F).

Example-219

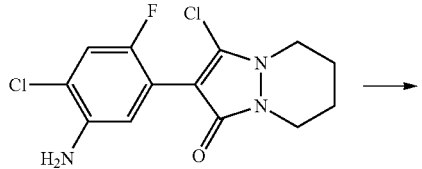

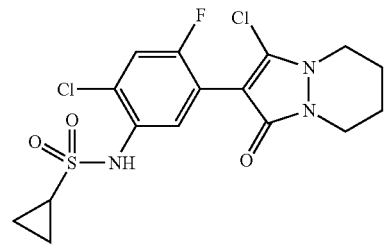

Pyridine (48.3 mg, 0.61 mmol) and cyclopropyl sulfonyl chloride (85.8 mg, 0.55 mmol) were added to a solution of 4-(5-amino-4-chloro-2-fluorophenyl)-5-chloro-1,2-tetramethylene-4-pyrazolin-3-one (192 mg, 0.61 mmol) in dichloromethane (2 mL) under ice-cooling, followed by stirring at room temperature for 65 hours. After the reaction was completed, a saturated sodium hydrogencarbonate aqueous solution (30 mL) was added to the reaction solution, and the resultant product was extracted with chloroform (20 mL×2, 10 mL×1). The organic layer was washed with 2N hydrochloric acid (30 mL), washed with a saturated saline solution, dried over anhydrous magnesium sulfate, and concentrated under reduced pressure. The obtained crude product was recrystallized from ethyl acetate. The obtained crystal was separated by filtration, and washed with ether, whereby 5-chloro-4-(4-chloro-5-cyclopropylsulfonylamino-2-fluorophenyl)-1,2-tetramethylene-4-pyrazolin-3-one (118 mg, yield: 46%) was obtained as a pale brown solid. $^1$H-NMR (400 MHz, CDCl$_3$): δ0.97-1.02 (m, 2H), 1.20-1.28 (m, 2H), 1.88-1.94 (m, 2H), 2.00-2.05 (m, 2H), 2.55 (m, 1H), 3.62-3.65 (m, 2H), 3.82-3.85 (m, 2H), 6.92 (brs, 1H), 7.21 (d, J=8.8 Hz, 1H), 7.77 (d, J=6.7 Hz, 1H). $^{19}$F-NMR (376 MHz, CDCl$_3$): δ−113 (s, 1F).

Example-220

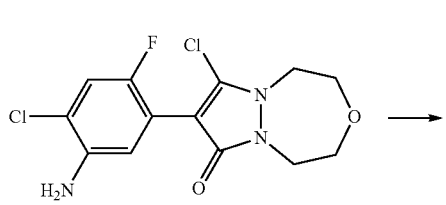

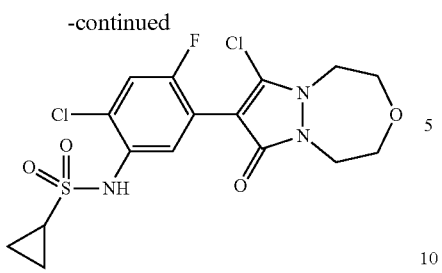

In the same manner as in Example-206, 4-(5-amino-4-chloro-2-fluorophenyl)-5-chloro-1,2-oxadiethylene-4-pyrazolin-3-one was reacted with cyclopropyl sulfonyl chloride, whereby 5-chloro-4-[4-chloro-2-fluoro-5-(cyclopropylsulfonylamino)phenyl]-1,2-oxadiethylene-4-pyrazolin-3-one was obtained with a yield of 17%. $^1$H-NMR (400 MHz, CDCl$_3$): δ0.96-1.04 (m, 2H), 1.19-1.24 (m, 2H), 2.54 (m, 1H), 3.91-3.98 (m, 4H), 4.21-4.31 (m, 4H), 6.72 (brs, 1H), 7.24 (d, J=9.0 Hz, 1H), 7.79 (d, J=6.8 Hz, 1H). $^{19}$F-NMR (376 MHz, CDCl$_3$): δ−112.7 (s, 1F).

Example-221

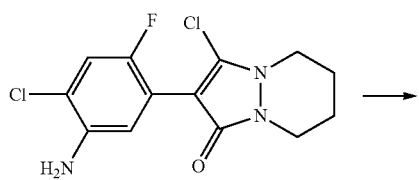

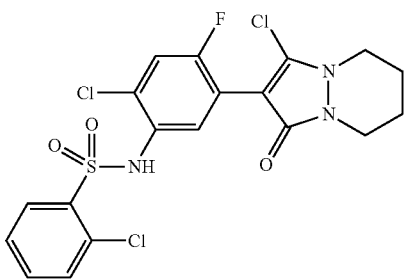

In the same manner as in Example-206, 4-(5-amino-4-chloro-2-fluorophenyl)-5-chloro-1,2-tetramethylene-4-pyrazolin-3-one was reacted with 2-chlorophenyl sulfonyl chloride, whereby 5-chloro-4-[4-chloro-2-fluoro-5-(2-chlorophenylsulfonylamino)phenyl]-1,2-tetramethylene-4-pyrazolin-3-one was obtained with a yield of 99%. $^1$H-NMR (400 MHz, CDCl$_3$): δ1.87-1.94 (m, 2H), 1.98-2.04 (m, 2H), 3.59-3.64 (m, 2H), 3.79-3.84 (m, 2H), 7.09 (d, J=8.8 Hz, 1H), 7.35-7.41 (m, 2H), 7.46-7.52 (m, 2H), 7.74 (d, J=6.8 Hz, 1H), 8.09 (m, 1H). $^{19}$F-NMR (376 MHz, CDCl$_3$): δ−112.8 (s, 1F).

Example-222

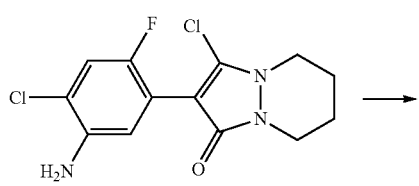

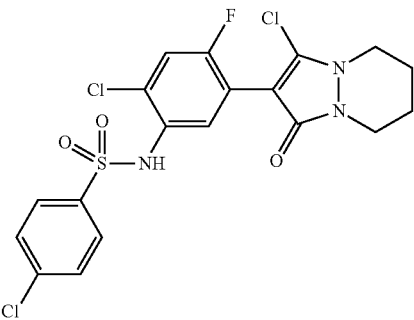

In the same manner as in Example-206, 4-(5-amino-4-chloro-2-fluorophenyl)-5-chloro-1,2-tetramethylene-4-pyrazolin-3-one was reacted with 4-chlorophenyl sulfonyl chloride, whereby 5-chloro-4-[5-(4-chlorophenylsulfonylamino)-4-chloro-2-fluorophenyl]-1,2-tetramethylene-4-pyrazolin-3-one was obtained with a yield of 81%. $^1$H-NMR (400 MHz, CDCl$_3$): δ1.89-1.96 (m, 2H), 2.00-2.07 (m, 2H), 3.62-3.68 (m, 2H), 3.83-3.88 (m, 2H), 7.02 (brs, 1H), 7.06 (d, J=8.7 Hz, 1H), 7.42 (d, J=8.8 Hz, 2H), 7.76 (d, J=8.8 Hz, 2H), 7.81 (d, J=7.0 Hz, 1H). $^{19}$F-NMR (376 MHz, CDCl$_3$): δ−111.5 (s, 1F).

Example-223

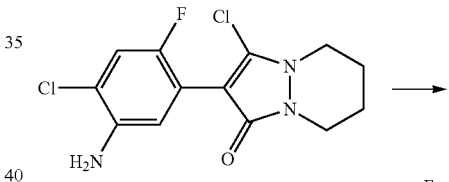

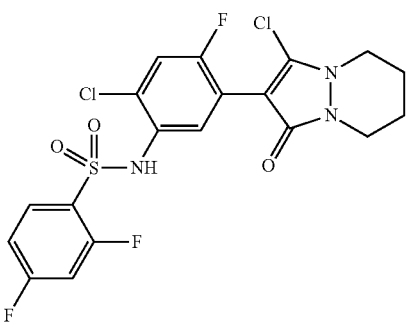

In the same manner as in Example-206, 4-(5-amino-4-chloro-2-fluorophenyl)-5-chloro-1,2-tetramethylene-4-pyrazolin-3-one was reacted with 2,4-difluorophenyl sulfonyl chloride, whereby 5-chloro-4-[4-chloro-2-fluoro-5-(2,4-difluorophenylsulfonylamino)phenyl]-1,2-tetramethylene-4-pyrazolin-3-one was obtained with a yield of 44%. $^1$H-NMR (400 MHz, CDCl$_3$): δ1.87-1.96 (m, 2H), 1.99-2.07 (m, 2H), 3.60-3.67 (m, 2H), 3.80-3.86 (m, 2H), 6.88-6.97 (m, 2H), 7.10 (d, J=8.9 Hz, 1H), 7.20 (brs, 1H), 7.76 (d, J=6.7 Hz, 1H), 7.89 (ddd, J=6.1, 8.5 and 9.5 Hz, 1H). $^{19}$F-NMR (376 MHz, CDCl$_3$): δ−111.8 (s, 1F), −103.2 (d, J=12.7 Hz, 1F), −99.0 (d, J=12.7 Hz, 1F).

Example-224

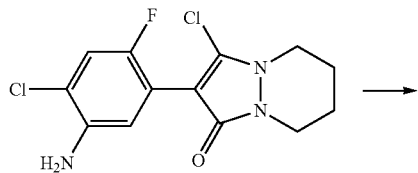

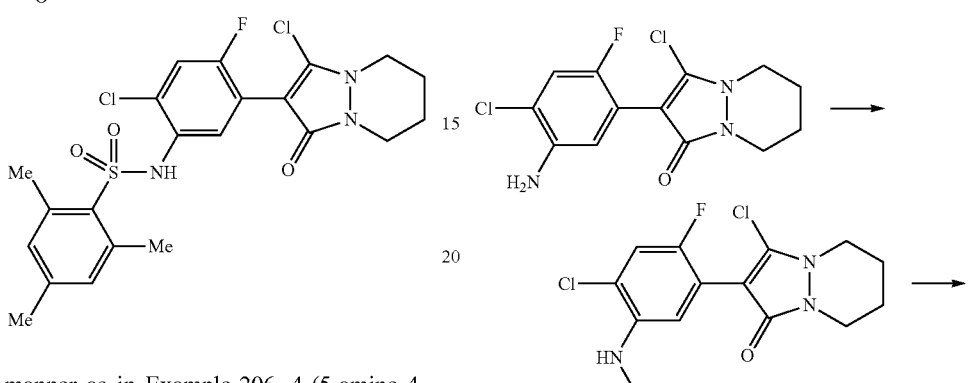

In the same manner as in Example-206, 4-(5-amino-4-chloro-2-fluorophenyl)-5-chloro-1,2-tetramethylene-4-pyrazolin-3-one was reacted with mesityl sulfonyl chloride, whereby 5-chloro-4-[4-chloro-2-fluoro-5-(mesitylsulfonylamino)phenyl]-1,2-tetramethylene-4-pyrazolin-3-one was obtained with a yield of 68%. $^1$H-NMR (400 MHz, CDCl$_3$): δ1.86-1.94 (m, 2H), 1.98-2.04 (m, 2H), 2.27 (s, 3H), 2.59 (s, 6H), 3.59-3.63 (m, 2H), 3.79-3.83 (m, 2H), 6.90 (s, 2H), 6.96 (brs, 1H), 7.09 (d, J=8.7 Hz, 1H), 7.58 (d, J=6.5 Hz, 1H). $^{19}$F-NMR (376 MHz, CDCl$_3$): δ−112.6 (s, 1F).

Example-225

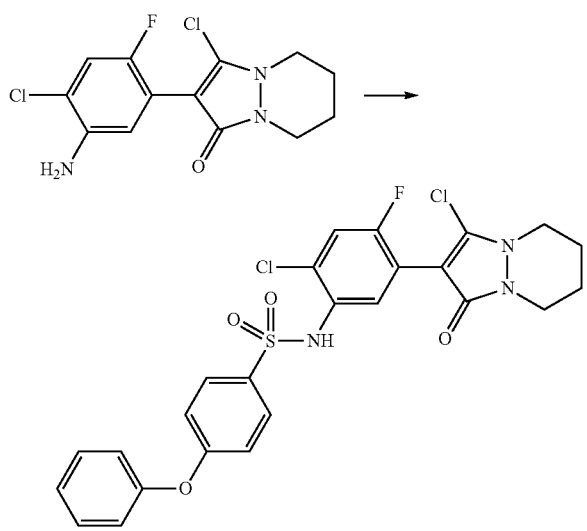

In the same manner as in Example-206, 4-(5-amino-4-chloro-2-fluorophenyl)-5-chloro-1,2-tetramethylene-4-pyrazolin-3-one was reacted with 4-phenoxyphenyl sulfonyl chloride, whereby 5-chloro-4-[5-(4-phenoxyphenylsulfonylamino)-4-chloro-2-fluorophenyl]-1,2-tetramethylene-4-pyrazolin-3-one was obtained with a yield of 14%. $^1$H-NMR (400 MHz, CDCl$_3$): δ1.87-1.95 (m, 2H), 1.989-2.07 (m, 2H), 3.61-3.66 (m, 2H), 3.81-3.86 (m, 2H), 6.82 (s, 1H), 6.96 (d, J=8.8 Hz, 2H), 7.02-7.10 (m, 2H), 7.20 (m, 1H), 7.36-7.42 (m, 2H), 7.75 (d, J=8.8 Hz, 2H), 7.83 (d, J=6.9 Hz, 1H). $^{19}$F-NMR (376 MHz, CDCl$_3$): δ−112.1 (s, 1F).

Example-226

Di-tert-butyl dicarbonate (381 μL, 1.7 mmol) and 4-(dimethylamino)pyridine (19 mg, 0.16 mmol) were added to a solution of 5-chloro-4-(5-amino-4-chloro-2-fluorophenyl)-1,2-tetramethylene-4-pyrazolin-3-one (500 mg, 1.60 mmol) in THF (5.0 mL), followed by stirring at 70° C. for 1.5 hours. After the reaction was completed, the reaction solution was concentrated under reduced pressure, and DMF (6.0 mL) was added to the obtained residue, and sodium hydride (138 mg, 3.2 mmol) and methyl iodide (197 μL, 1.7 mmol) were added thereto, followed by stirring for 24 hours. The reaction solution was neutralized with a saturated ammonium chloride aqueous solution, and diluted with water (20 mL), and the resultant product was extracted with ethyl acetate (20 mL×2). The organic layer was dried over magnesium sulfate, and concentrated under reduced pressure. A 6N-hydrochloric acid aqueous solution (3.0 mL) and THF (3.0 mL) were added to the obtained residue, followed by stirring for 6 hours. Water (20 mL) was added to the reaction solution, and the resultant product was extracted with ethyl acetate (20 mL×2). The organic layer was dried over magnesium sulfate, and concentrated under reduced pressure. The obtained crude product was purified by silica gel column chromatography (ethyl acetate:methanol=10:1), whereby 5-chloro-4-[4-chloro-2-fluoro-5-(methylamino)phenyl]-1,2-tetramethylene-4-pyrazolin-3-one (106 mg, yield: 22%) was obtained as a white solid. $^1$H-NMR (400 MHz, CDCl$_3$): δ1.86-1.91 (m, 2H), 1.98-2.04 (m, 2H), 2.89 (s, 3H), 3.58-3.63 (m, 2H), 3.80-3.85 (m, 2H), 4.14 (brs, 1H), 6.74 (d, J=6.5 Hz, 1H), 7.09 (d, J=9.2 Hz, 1H). $^{19}$F-NMR (376 MHz, CDCl$_3$): δ−126 (s, 1F).

Potassium carbonate (131 mg, 0.95 mmol) and propargyl bromide (71 μL, 0.95 mmol) were added to a solution of 5-chloro-4-[4-chloro-2-fluoro-5-(methylamino)phenyl]-1,2-tetramethylene-4-pyrazolin-3-one (113 mg, 0.32 mmol) in DMF, followed by stirring at 80° C. for 16 hours. Water (10 mL) was added to the reaction mixture, and the resultant product was extracted with ethyl acetate (10 mL×2). The organic layer was dried over anhydrous magnesium sulfate, and concentrated under reduced pressure. The obtained crude product was purified by silica gel column chromatography (ethyl acetate:methanol=10:1), whereby 5-chloro-4-[4-chloro-2-fluoro-5-(N-methyl-N-(propargyl) amino)phenyl]-1,2-tetramethylene-4-pyrazolin-3-one (73 mg, yield: 63%) was obtained as a yellow solid. $^1$H-NMR (400 MHz, CDCl$_3$): δ1.89-1.93 (m, 2H), 1.99-2.08 (m, 2H), 2.26 (t, J=2.4 Hz, 1H), 2.87 (s, 3H), 3.59-3.65 (m, 2H), 3.80-3.86 (m, 2H), 3.89 (d, J=2.4 Hz, 2H), 7.20 (d, J=9.3 Hz, 1H), 7.35 (d, J=7.0 Hz, 1H).

Example-227

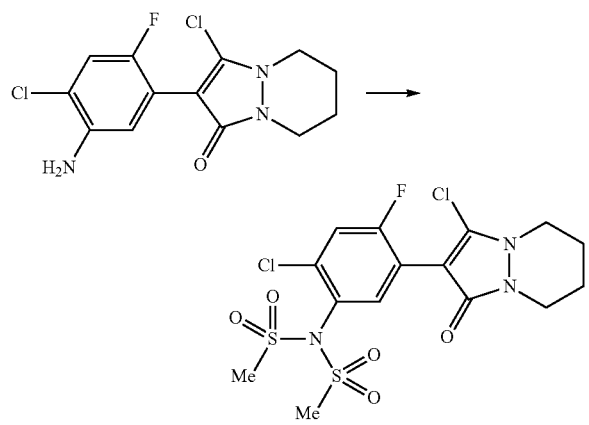

Triethylamine (76.9 mg, 1.25 mmol) and methyl sulfonyl chloride (79.3 mg, 0.69 mmol) were added to a solution of 4-(5-amino-4-chloro-2-fluorophenyl)-5-chloro-1,2-tetramethylene-4-pyrazolin-3-one (219 mg, 0.69 mmol) in THF (2 mL) under ice-cooling, followed by stirring at room temperature for 21 hours. After the reaction was completed, a saturated sodium hydrogencarbonate aqueous solution (50 mL) was added to the reaction solution, and the resultant product was extracted with ethyl acetate (20 mL×3). The organic layer was washed with a saturated saline solution, dried over anhydrous magnesium sulfate, and concentrated under reduced pressure, whereby a crude product (219 mg) was obtained as an ocherous solid. This was purified by silica gel column chromatography (ethyl acetate:methanol=10:1), whereby 5-chloro-4-[5-bis(methylsulfonyl) amino-4-chloro-2-fluorophenyl]-1,2-tetramethylene-4-pyrazolin-3-one (116 mg, yield: 36%) was obtained as a white yellow solid. $^1$H-NMR (400 MHz, CDCl$_3$): δ1.89-1.95 (m, 2H), 2.01-2.06 (m, 2H), 3.52 (s, 6H), 3.65-3.68 (m, 2H), 3.81-3.84 (m, 2H), 7.34 (d, J=9.3 Hz, 1H), 7.80 (d, J=6.8 Hz, 1H). $^{19}$F-NMR (376 MHz, CDCl$_3$): δ−104 (s, 1F).

Example-228

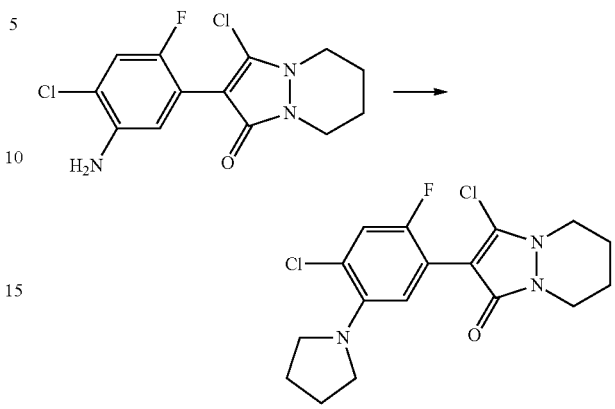

Potassium carbonate (192 mg, 1.39 mmol) and 1,4-dibromobutane (152 mg, 0.69 mmol) were added to a solution of 4-(5-amino-4-chloro-2-fluorophenyl)-5-chloro-1,2-tetramethylene-4-pyrazolin-3-one (200 mg, 0.63 mmol) in toluene (2 mL), followed by stirring at 80° C. to 100° C. for 41 hours. After the reaction was completed, the reaction solution was loaded on the upper portion of a silica gel column, and purified by eluting with a 20:1 mixed solution of ethyl acetate and methanol, whereby 5-chloro-4-(4-chloro-2-fluoro-5-pyrrolidinophenyl)-1,2-tetramethylene-4-pyrazolin-3-one (82 mg, yield: 35%) was obtained as a pink solid. $^1$H-NMR (400 MHz, CDCl$_3$): δ1.87-1.94 (m, 6H), 1.98-2.04 (m, 2H), 3.30-3.34 (m, 4H), 3.58-3.61 (m, 2H), 3.81-3.84 (m, 2H), 7.06 (d, J=6.87 Hz, 1H), 7.13 (d, J=9.27 Hz, 1H). $^{19}$F-NMR (376 MHz, CDCl$_3$): δ−121 (s, 1F).

Example-229

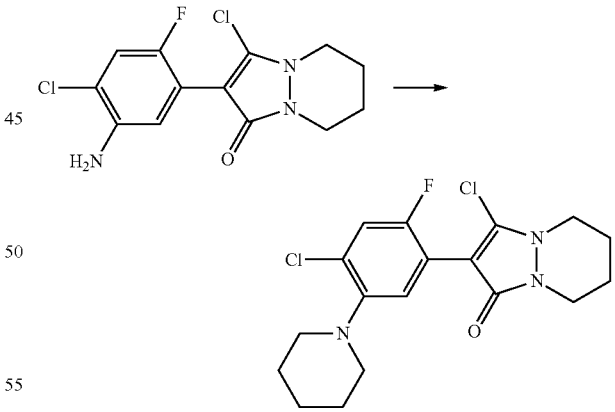

Potassium carbonate (338 mg, 2.44 mmol) and 1,5-diiodopentane (403 mg, 1.22 mmol) were added to a solution of 4-(5-amino-4-chloro-2-fluorophenyl)-5-chloro-1,2-tetramethylene-4-pyrazolin-3-one (350 mg, 1.11 mmol) in toluene (3 mL), followed by stirring at 100° C. for 42 hours. After the reaction was completed, the reaction solution was loaded on the upper portion of a silica gel column, and purified by eluting with a 10:1 mixed solution of ethyl acetate and methanol, whereby 5-chloro-4-(4-chloro-2-fluoro-5-piperidinophenyl)-1,2-tetramethylene-4-pyrazolin- 3-one (128 mg, yield: 30%) was obtained as a yellow solid. $^1$H-NMR (400 MHz, CDCl$_3$): δ1.52-1.58 (m, 2H), 1.70-2.75 (m, 4H), 1.87-1.93 (m, 2H), 1.99-2.04 (m, 2H), 3.93-3.96 (m, 2H), 3.59-3.62 (m, 2H), 3.81-3.84 (m, 2H), 7.16 (d, J=9.9 Hz, 1H), 7.18 (d, J=7.8 Hz, 1H). $^{19}$F-NMR (376 MHz, CDCl$_3$): δ−118 (s, 1F).

Example-230

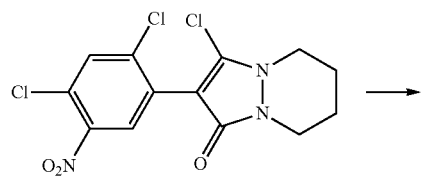

Concentrated hydrochloric acid (4 mL) was added to a solution of 5-chloro-4-(2,4-dichloro-5-nitrophenyl)-1,2-tetramethylene-4-pyrazolin-3-one (791 mg, 2.18 mmol) in ethanol (5 mL), and tin(II) chloride dihydrate (1.65 g, 8.72 mmol) was added thereto, followed by refluxing for 18 hours. After the reaction was completed, the temperature of the reaction solution was returned to room temperature, and after the reaction solution was poured into ice water, a sodium hydroxide aqueous solution was added thereto to basify, and the resultant product was extracted with ethyl acetate (50 mL×1, 20 mL×2). The organic layer was washed with a saturated saline solution (10 mL), dried over anhydrous magnesium sulfate, and concentrated under reduced pressure, whereby 4-(5-amino-2,4-dichlorophenyl)-5-chloro-1,2-tetramethylene-4-pyrazolin-3-one (632 mg, yield: 87%) was obtained as a white solid. $^1$H-NMR (400 MHz, CDCl$_3$): δ1.86-1.92 (m, 2H), 1.98-2.25 (m, 2H), 3.57-3.60 (m, 2H), 3.81-3.84 (m, 2H), 4.05 (brs, 2H), 6.76 (s, 1H), 7.35 (s, 1H).

Example-231

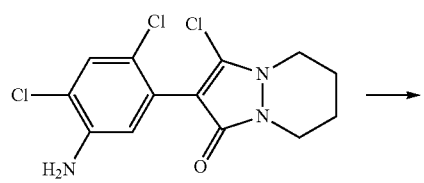

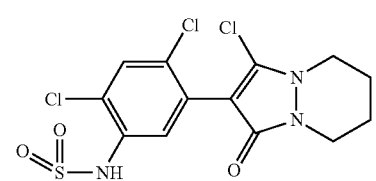

Pyridine (71 mg, 0.90 mmol) and methyl sulfonyl chloride (103 mg, 0.90 mmol) were added to a solution of 5-chloro-4-(2,4-dichloro-5-aminophenyl)-1,2-tetramethylene-4-pyrazolin-3-one (300 mg, 0.90 mmol) in dichloromethane (3 mL) under ice-cooling, followed by stirring at room temperature for 18 hours. After the reaction was completed, the reaction solution was loaded on the upper portion of a silica gel column, and purified by eluting with a 10:1 mixed solution of ethyl acetate and methanol, whereby 5-chloro-4-[2,4-dichloro-5-(methylsulfonylamino)phenyl]-1,2-tetramethylene-4-pyrazolin-3-one (204 mg, yield: 55%) was obtained as a white solid. $^1$H-NMR (400 MHz, CDCl$_3$): δ1.89-1.95 (m, 2H), 2.00-2.06 (m, 2H), 3.08 (s, 3H), 3.63-3.66 (m, 2H), 3.83-3.86 (m, 2H), 7.22 (brs, 1H), 7.51 (s, 1H), 7.60 (s, 1H).

Example-232

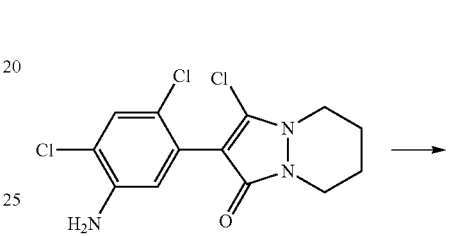

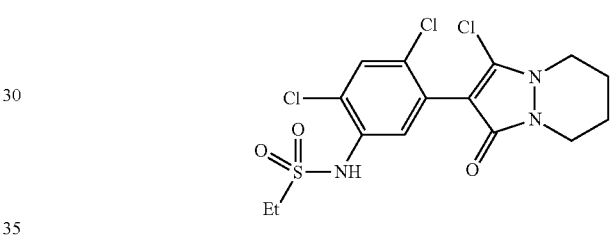

Pyridine (71 mg, 0.90 mmol) was added to a solution of 5-chloro-4-(2,4-dichloro-5-aminophenyl)-1,2-tetramethylene-4-pyrazolin-3-one (300 mg, 0.90 mmol) in dichloromethane (3 mL), and ethyl sulfonyl chloride (116 mg, 0.90 mmol) was added thereto under ice-cooling, followed by stirring at room temperature for 19 hours. After the reaction was completed, the reaction solution was loaded on the upper portion of a silica gel column, and purified by eluting with a 10:1 mixed solution of ethyl acetate and methanol, whereby 5-chloro-4-[2,4-dichloro-5-(ethylsulfonylamino)phenyl]-1,2-tetramethylene-4-pyrazolin-3-one (214 mg, yield: 56%) was obtained as a white solid. $^1$H-NMR (400 MHz, CDCl$_3$): δ1.37 (t, J=8.0 Hz, 3H), 1.89-1.94 (m, 2H), 2.00-2.05 (m, 2H), 3.20 (q, J=8.0 Hz, 2H), 3.62-3.65 (m, 2H), 3.82-3.85 (m, 2H), 6.78 (brs, 1H), 7.52 (s, 1H), 7.66 (s, 1H).

Example-233

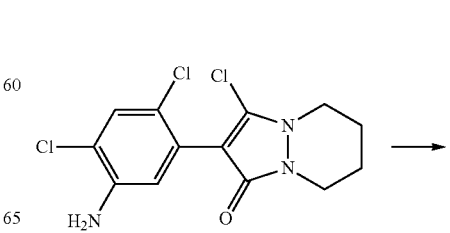

-continued

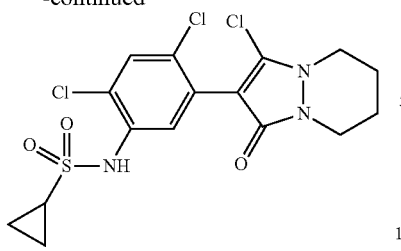

Pyridine (71 mg, 0.90 mmol) and cyclopropyl sulfonyl chloride (127 mg, 0.90 mmol) were added to a solution of 5-chloro-4-(2,4-dichloro-5-aminophenyl)-1,2-tetramethylene-4-pyrazolin-3-one (300 mg, 0.90 mmol) in dichloromethane (3 mL) under ice-cooling, followed by stirring at room temperature for 20 hours. After the reaction was completed, the reaction solution was loaded on the upper portion of a silica gel column, and purified by eluting with a 10:1 mixed solution of ethyl acetate and methanol, whereby 5-chloro-4-[5-(cyclopropylsulfonylamino)-2,4-dichlorophenyl]-1,2-tetramethylene-4-pyrazolin-3-one (62 mg, yield: 16%) was obtained as a white solid. $^1$H-NMR (400 MHz, CDCl$_3$): δ0.99-1.01 (m, 2H), 1.19-1.31 (m, 2H), 1.89-1.94 (m, 2H), 2.00-2.10 (m, 2H), 2.55 (m, 1H), 3.62-3.65 (m, 2H), 3.82-3.85 (m, 2H), 6.94 (brs, 1H), 7.53 (s, 1H), 7.67 (s, 1H).

Example-234

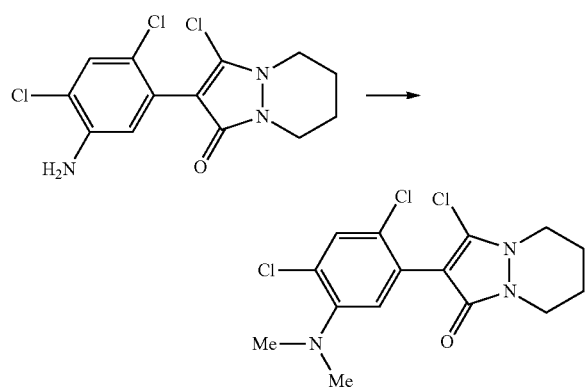

Cesium carbonate (336 mg, 1.03 mmol) and methyl iodide were added to a solution of 4-(5-amino-2,4-dichlorophenyl)-5-chloro-1,2-tetramethylene-4-pyrazolin-3-one (155 mg, 0.47 mmol) in acetonitrile (1 mL), followed by stirring at room temperature for 24 hours. After the reaction was completed, water (20 mL) was added to the reaction solution, and the resultant product was extracted with ethyl acetate (20 mL×3). The organic layer was washed with a saturated saline solution, dried over anhydrous magnesium sulfate, and concentrated under reduced pressure, whereby a yellow oily crude product (132 mg) was obtained. This was purified by silica gel column chromatography (ethyl acetate:methanol=10:1), whereby 5-chloro-4-[2,4-dichloro-5-(dimethyl amino)phenyl]-1,2-tetramethylene-4-pyrazolin-3-one (106 mg, yield: 63%) was obtained as a yellow oily material. $^1$H-NMR (400 MHz, CDCl$_3$): δ1.88-1.93 (m, 2H), 2.00-2.05 (m, 2H), 2.80 (s, 6H), 3.59-3.62 (m, 2H), 3.82-3.85 (m, 2H), 7.02 (s, 1H), 7.45 (s, 1H).

Example-235

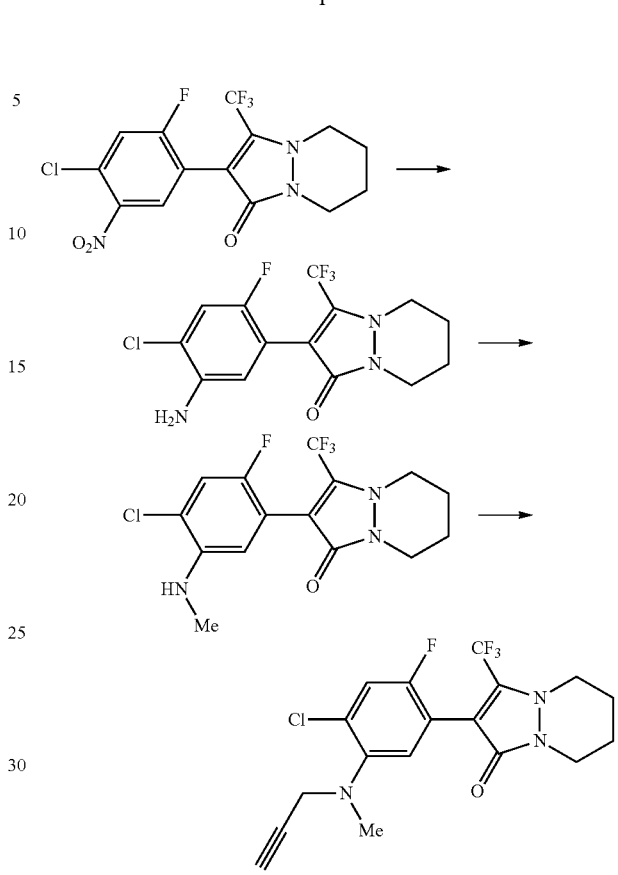

Concentrated hydrochloric acid (1 mL) was added to a solution of 4-(4-chloro-2-fluoro-5-nitrophenyl)-1,2-tetramethylene-5-trifluoromethyl-4-pyrazolin-3-one (300 mg, 0.79 mmol) in ethanol (2 mL), and tin(II) chloride dihydrate (446 mg, 1.98 mmol) was added thereto, followed by refluxing for 4.5 hours. After the reaction was completed, the temperature of the reaction solution was returned to room temperature, and after the reaction solution was poured into ice water, a sodium hydroxide aqueous solution was added thereto to basify, and the resultant product was extracted with ethyl acetate (20 mL×3). The organic layer was washed with a saturated saline solution (10 mL), dried over anhydrous magnesium sulfate, and concentrated under reduced pressure, whereby 4-(5-amino-4-chloro-2-fluorophenyl)-1,2-tetramethylene-5-trifluoromethyl-4-pyrazolin-3-one (279 mg, yield: quantitative) was obtained as a yellow solid. $^1$H-NMR (400 MHz, CDCl$_3$): δ1.88-1.96 (m, 2H), 2.01-2.10 (m, 2H), 3.64-3.70 (m, 2H), 3.88-3.93 (m, 2H), 3.93 (brs, 2H), 6.83 (d, J=6.6 Hz, 1H), 7.06 (d, J=9.0 Hz, 1H). $^{19}$F-NMR (376 MHz, CDCl$_3$): δ−126.2 (m, 1F), −61.6 (m, 3F).

Di-tert-butyl dicarbonate (206 mg, 0.944 mmol) and 4-(dimethylamino)pyridine (5 mg, 0.04 mmol) were added to a solution of 4-(5-amino-4-chloro-2-fluorophenyl)-1,2-tetramethylene-5-trifluoromethyl-4-pyrazolin-3-one (300 mg, 0.858 mmol) in THF (4.0 mL), followed by stirring at 70° C. for 1.5 hours. After the reaction was completed, the reaction solution was concentrated under reduced pressure, and DMF (4.0 mL) was added to the obtained residue, and sodium hydride (113 mg, 2.60 mmol) and methyl iodide (159 μL, 2.60 mmol) were added thereto, followed by stirring for 12 hours. The reaction solution was neutralized with a saturated ammonium chloride aqueous solution, and diluted with water (20 mL), and the resultant product was extracted with ethyl acetate (20 mL×2). The organic layer was dried over magnesium sulfate, and concentrated under reduced pressure. A 6N-hydrochloric acid (2.0 mL) and THF (2.0 mL) were added to the obtained residue, followed by stirring for 1 hour. Water (20 mL) was added to the reaction solution, and the resultant product was extracted with ethyl acetate (20 mL×2). The organic layer was dried over magnesium sulfate, and concentrated under reduced pressure. The obtained crude product was purified by silica gel column chromatography (ethyl acetate:methanol=10:1), and recrystallized, whereby 4-(4-chloro-2-fluoro-5-(methylamino)phenyl)-1,2-tetramethylene-5-trifluoromethyl-4-pyrazolin-3-one (81 mg, yield: 26%) was obtained as a white solid. $^1$H-NMR (400 MHz, CDCl$_3$): δ1.88-1.96 (m, 2H), 2.01-2.09 (m, 2H), 2.87 (s, 3H), 3.64-3.70 (m, 2H), 3.89-3.95 (m, 2H), 4.16 (brs. 1H), 6.65 (d, J=6.4 Hz, 1H), 7.08 (d, J=9.1 Hz, 1H). $^{19}$F-NMR (376 MHz, CDCl$_3$): δ−128.5 (m, 1F), −61.5 (m, 3F).

Potassium carbonate (91.2 mg, 0.66 mmol) and propargyl bromide (72 μL, 0.66 mmol) were added to a solution of 4-(4-chloro-2-fluoro-5-(methylamino)phenyl)-1,2-tetramethylene-5-trifluoromethyl-4-pyrazolin-3-one (80 mg, 0.22 mmol) in DMF (2 mL), followed by stirring at 80° C. for 16 hours. Water (10 mL) was added to the reaction mixture, and the resultant product was extracted with ethyl acetate (10 mL×2). The organic layer was dried over anhydrous magnesium sulfate, and concentrated under reduced pressure. The obtained crude product was purified by silica gel column chromatography (ethyl acetate:methanol=10:1), whereby 4-[4-chloro-2-fluoro-5-(N-methyl-N-(propargyl)amino)phenyl]-1,2-tetramethylene-5-(trifluoromethyl)-4-pyrazolin-3-one (28 mg, yield: 31%) was obtained as a yellow oily material. $^1$H-NMR (400 MHz, CDCl$_3$): δ1.89-1.97 (m, 2H), 2.02-2.10 (m, 2H), 2.25 (t, J=2.4 Hz, 1H), 2.86 (s, 3H), 3.66-3.71 (m, 2H), 3.88 (d, J=2.4 Hz, 2H), 3.80-3.95 (m, 2H), 7.17 (d, J=9.1 Hz, 1H), 7.24 (d, J=7.0 Hz, 1H). $^{19}$F-NMR (376 MHz, CDCl$_3$): δ−118.6 (m, 1F), −61.2 (m, 3F).

Reference Example-69

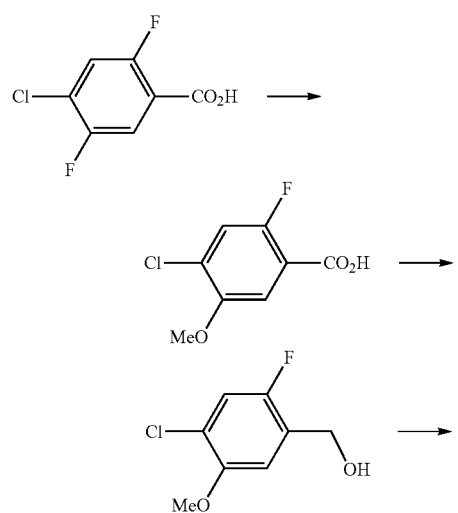

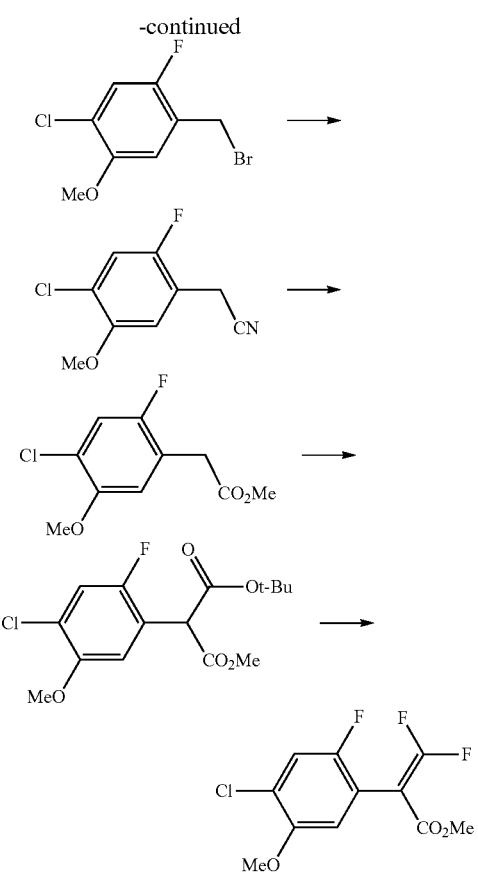

4-Chloro-2,5-difluorobenzoic acid (25.0 g, 126 mmol) and methanol (5.6 mL, 139 mmol) were added to a suspension of a 55% oil dispersion (10.99 g, 252 mmol) of sodium hydride in DMF (250 mL) under ice-cooling, followed by stirring at 120° C. for 12 hours. After the reaction was completed, the reaction solution was cooled to room temperature, and concentrated hydrochloric acid was added until the reaction solution became acidic, and the resultant product was extracted with diethyl ether (100 mL×3). The combined organic layer was washed with water, dried over magnesium sulfate, concentrated under reduced pressure, and dried under reduced pressure, whereby 4-chloro-2-fluoro-5-methoxybenzoic acid (23.97 g, yield: 93%) was obtained as a white solid. $^1$H-NMR (400 MHz, CDCl$_3$): δ4.07 (s, 3H), 7.11 (d, J=5.6 Hz, 1H), 7.93 (d, J=9.0 Hz, 1H). $^{19}$F-NMR (376 MHz, CDCl$_3$): δ−122.8 (s, 1F).

A borane-tetrahydrofuran complex (160 mL, 0.95M tetrahydrofuran solution) was added dropwise to a solution of 4-chloro-2-fluoro-5-methoxybenzoic acid (23.97 g, 117 mmol) in tetrahydrofuran (25 mL) under ice-cooling. After the resultant product was stirred at room temperature for 1 hour, water was added thereto, and the resultant product was extracted with diethyl ether (100 mL×3). The combined organic layer was dried over magnesium sulfate, and dried under reduced pressure, whereby (4-chloro-2-fluoro-5-methoxyphenyl)methanol (quantitative) was obtained as a white solid. $^1$H-NMR (400 MHz, CDCl$_3$): δ3.83 (s, 3H), 4.63 (s, 2H), 6.86 (d, J=5.9 Hz, 1H), 7.14 (d, J=9.1 Hz, 1H). $^{19}$F-NMR (376 MHz, CDCl$_3$): δ−126.2 (s, 1F).

Pyridine (0.48 mL, 5.9 mmol) and phosphorous tribromide (5.67 mL, 53.7 mmol) were added to a solution of (4-chloro-2-fluoro-5-methoxyphenyl)methanol (22.77 g, 119 mmol) in tetrahydrofuran (120 mL) under ice-cooling. The temperature of the mixed solution was slowly raised to room temperature, followed by stirring at room temperature for 1 hour. After the reaction was completed, the resultant product was diluted with ethyl acetate, and washed sequentially with water and a saturated saline solution. The organic layer was dried over magnesium sulfate, and concentrated under reduced pressure. The obtained crude product was purified by silica gel column chromatography (hexane), whereby 1-(bromomethyl)-4-chloro-2-fluoro-5-methoxy benzene (26.40 g, yield: 87%) was obtained. $^1$H-NMR (400 MHz, CDCl$_3$): δ3.87 (s, 3H), 4.46 (s, 2H), 6.68 (d, J=6.0 Hz, 1H), 7.13 (d, J=8.9 Hz, 1H). $^{19}$F-NMR (376 MHz, CDCl$_3$): δ−125.8 (s, 1F).

Water (250 g), potassium cyanide (10.38 g, 156 mmol), and tetrabutylammonium bromide (2.95 g, 10.4 mmol) were added to a solution of 1-(bromomethyl)-4-chloro-2-fluoro-5-methoxy benzene (26.40 g, 104 mmol) in dichloromethane (250 mL), followed by stirring at room temperature for 4 hours. After the reaction was completed, the resultant product was extracted with chloroform (100 mL×3). The combined organic layer was washed with water (100 mL), dried over magnesium sulfate, and concentrated under reduced pressure. The obtained crude product was purified by silica gel column chromatography (hexane:ethyl acetate=9:1), whereby 2-(4-chloro-2-fluoro-5-methoxyphenyl)acetonitrile (quantitative) was obtained as a white solid. $^1$H-NMR (400 MHz, CDCl$_3$): δ3.65 (s, 2H), 3.85 (s, 3H), 6.90 (d, J=6.0 Hz, 1H), 7.20 (d, J=8.8 Hz, 1H). $^{19}$F-NMR (376 MHz, CDCl$_3$): δ−125.1 (s, 1F).

Concentrated sulfuric acid (14.5 mL) was added to a solution of 2-(4-chloro-2-fluoro-5-methoxyphenyl)acetonitrile (9.98 g, 50.0 mmol) in methanol (25 mL), followed by heating to reflux for 15 hours. After the reaction was completed, the reaction solution was cooled to room temperature, and slowly poured into ice water, and the resultant product was extracted with chloroform (80 mL×3). The combined organic layer was washed with water (100 mL), dried over magnesium sulfate, and dried under reduced pressure, whereby methyl 2-(4-chloro-2-fluoro-5-methoxyphenyl) acetate (10.58 g, yield: 91%) was obtained as a white solid. $^1$H-NMR (400 MHz, CDCl$_3$): δ3.58 (s, 2H), 3.70 (s, 3H), 3.79 (s, 3H), 6.86 (d, J=6.1 Hz, 1H), 7.01 (d, J=9.1 Hz, 1H). $^{19}$F-NMR (376 MHz, CDCl$_3$): δ−126.5 (s, 1F).

A 55% oil dispersion (6.54 g, 150 mmol) of sodium hydride was added to a solution of methyl 2-(4-chloro-2-fluoro-5-methoxyphenyl)acetate (11.63 g, 50.0 mmol) in tetrahydrofuran (100 mL) under ice-cooling, followed by stirring at room temperature for 30 minutes. To this, tert-butyl dicarbonate (13.78 g, 60.0 mmol) and tetrabutylammonium chloride (4.17 g, 30 mol %) were added. The mixed solution was heated to reflux for 17 hours. After the reaction was completed, the reaction solution was cooled to room temperature, poured into a saturated ammonium chloride aqueous solution, and the resultant product was extracted with ethyl acetate. The organic layer was dried over magnesium sulfate, and concentrated under reduced pressure. The obtained crude product was purified by silica gel column chromatography (hexane:ethyl acetate=9:1), whereby tert-butyl 2-(4-chloro-2-fluoro-5-methoxyphenyl) malonate (10.17 g, yield: 61%) was obtained as a colorless oily material. $^1$H-NMR (400 MHz, CDCl$_3$): δ1.46 (s, 9H), 3.76 (s, 3H), 3.80 (s, 3H), 4.98 (s, 1H), 6.89 (d, J=6.1 Hz, 1H), 7.21 (d, J=9.5 Hz, 1H). $^{19}$F-NMR (376 MHz, CDCl$_3$): δ−125.5 (s, 1F).

A 55% oil dispersion (1.21 g, 27.7 mmol) of sodium hydride was added to a solution of tert-butyl 2-(4-chloro-2-fluoro-5-methoxyphenyl)malonate (9.21 g, 27.7 mmol) in tetrahydrofuran (40 mL) under ice-cooling, followed by stirring at room temperature for 30 minutes. To this, dibromodifluoromethane (7.99 mL, 83.1 mmol) was added, followed by stirring at room temperature for 3 days. After the reaction was completed, a saturated ammonium chloride aqueous solution was added thereto, and the resultant product was extracted with ethyl acetate. The organic layer was dried over magnesium sulfate, and concentrated under reduced pressure. The obtained crude product was purified by silica gel column chromatography (hexane:ethyl acetate=9:1), and distilled under reduced pressure, whereby methyl 2-(4-chloro-2-fluoro-5-methoxyphenyl)-3,3-difluoroacrylate (0.84 g, yield: 11%) was obtained as a colorless oily material. $^1$H-NMR (400 MHz, CDCl$_3$): δ3.76 (s, 3H), 3.79 (s, 3H), 6.93 (d, J=6.1 Hz, 1H), 7.02 (d, J=8.9 Hz, 1H). $^{19}$F-NMR (376 MHz, CDCl$_3$): δ−125.8 (s, 1F), −69.1 (d, J=15.5 Hz, 1F), −68.2 (d, J=15.5 Hz, 1F).

Example-236

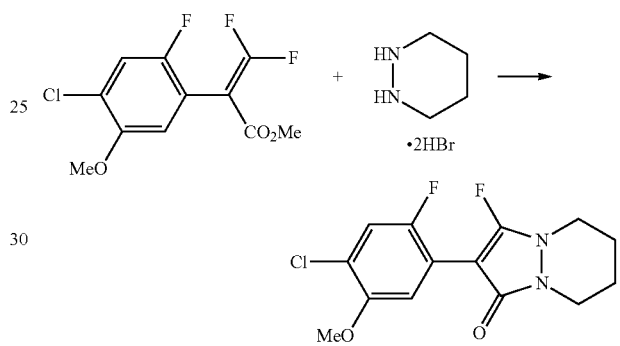

A solution of methyl 2-(4-chloro-2-fluoro-5-methoxyphenyl)-3,3-difluoroacrylate (817 mg, 2.91 mmol) in tetrahydrofuran (12 mL) was cooled to −78° C., and hexahydropyridazine dihydrobromide (758 mg, 3.06 mmol) and triethylamine (1.22 mL, 8.75 mmol) were added thereto, followed by raising the temperature to room temperature. The resultant product was stirred at 80° C. for 6 hours. After the reaction was completed, water (20 mL) was added to the reaction solution, and the resultant product was extracted with ethyl acetate (30 mL×2). The organic layer was dried over magnesium sulfate, and concentrated under reduced pressure, whereby a crude product was obtained. This was purified by silica gel column chromatography (ethyl acetate), whereby 4-(4-chloro-2-fluoro-5-methoxyphenyl)-5-fluoro-1,2-tetramethylene-4-pyrazolin-3-one (144 mg, yield: 16%) was obtained as a white solid. $^1$H-NMR (400 MHz, DMSO-d$_6$): δ1.82-1.91 (m, 2H), 1.92-2.01 (m, 2H), 3.47-3.55 (m, 2H), 3.74-3.80 (m, 2H), 3.81 (s, 3H), 6.90 (d, J=6.2 Hz, 1H), 7.48 (d, J=9.8 Hz, 1H). $^{19}$F-NMR (376 MHz, CDCl$_3$): δ−126.2 (s, 1F), −112.2 (s, 1F).

Example-237

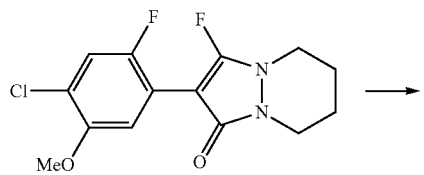

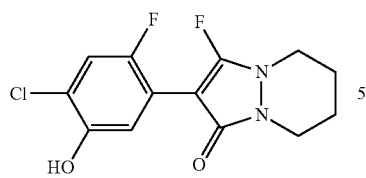

A solution (1.0 mL) of 1M boron tribromide in dichloromethane was added to a solution of 4-(4-chloro-2-fluoro-5-methoxyphenyl)-5-fluoro-1,2-tetramethylene-4-pyrazolin-3-one (144 mg, 0.46 mmol) in dichloromethane (1.0 mL) at −78° C. The resultant product was stirred at room temperature for 4 hours while slowly raising the reaction temperature to room temperature. After the reaction solution was poured into ice water, a 1N—HCl aqueous solution (5 mL) was added thereto. The precipitated solid was filtered, and dried under reduced pressure, whereby 4-(4-chloro-2-fluoro-5-hydroxyphenyl)-5-fluoro-1,2-tetramethylene-4-pyrazolin-3-one (125 mg, yield: 91%) was obtained as a pale yellow solid. $^1$H-NMR (400 MHz, CDCl$_3$): δ1.90-1.98 (m, 2H), 1.99-2.07 (m, 2H), 3.63-3.70 (m, 2H), 3.80-3.87 (m, 2H), 6.98 (d, J=6.8 Hz, 1H), 7.08 (d, J=9.5 Hz, 1H), 11.21 (brs, 1H). $^{19}$F-NMR (376 MHz, CDCl$_3$): δ−128.5 (s, 1F), −119.4 (s, 1F).

Reference Example-70

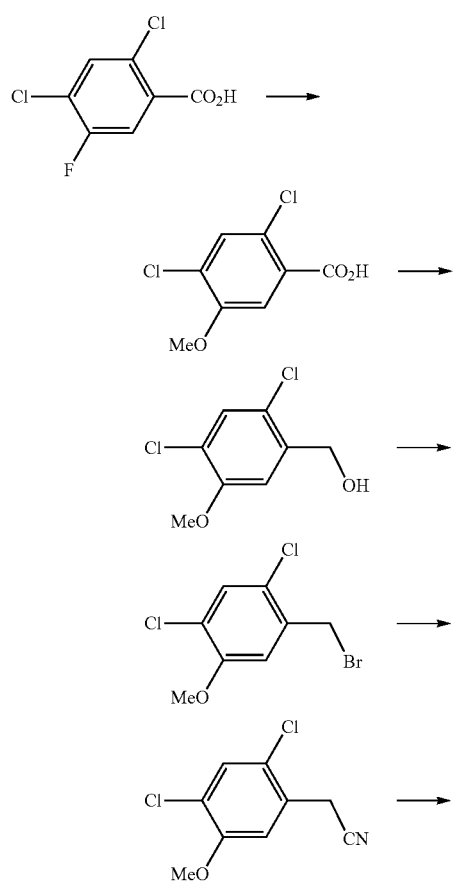

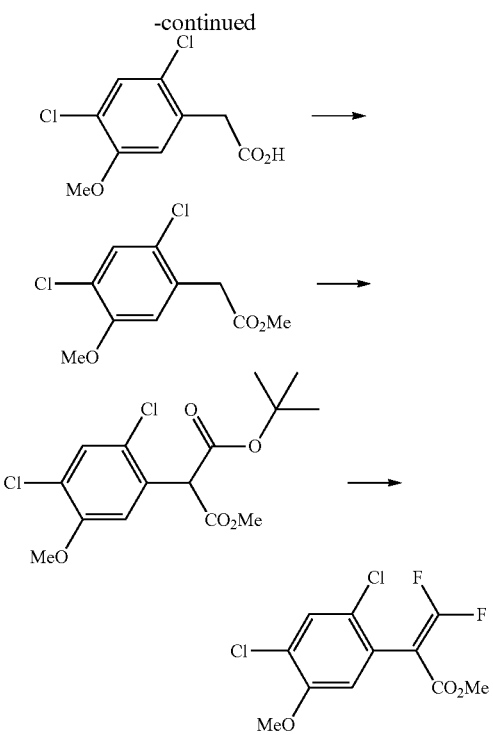

2,4-Dichloro-5-fluorobenzoic acid (25.0 g, 118 mmol), and methanol (5.4 mL, 134 mmol) were added to a suspension of a 55% oil dispersion (10.33 g, 237 mmol) of sodium hydride in DMF (250 mL) under ice-cooling, followed by stirring at 120° C. for 12 hours. After the reaction was completed, the reaction solution was cooled to room temperature, and concentrated hydrochloric acid was added until the reaction solution became acidic, and the resultant product was extracted with diethyl ether (100 mL×3). The combined organic layer was washed with water, dried over magnesium sulfate, concentrated under reduced pressure, and dried under reduced pressure, whereby 2,4-dichloro-5-methoxybenzoic acid (quantitative) was obtained as a pale gray solid. $^1$H-NMR (400 MHz, CDCl$_3$): δ3.96 (s, 3H), 7.52 (s, 1H), 7.58 (s, 1H).

A borane-tetrahydrofuran complex (162 mL, 0.95M tetrahydrofuran solution) was added dropwise to a solution of 2,4-dichloro-5-methoxybenzoic acid (26.08 g, 118 mmol) in tetrahydrofuran (25 mL) under ice-cooling. After the resultant product was stirred at room temperature for 1 hour, water was added thereto, and the resultant product was extracted with diethyl ether (100 mL×3). The combined organic layer was dried over magnesium sulfate, and concentrated under reduced pressure. The obtained crude product was purified by silica gel column chromatography (hexane:ethyl acetate=1:1), whereby (2,4-dichloro-5-methoxyphenyl)methanol (quantitative) was obtained as a white solid. $^1$H-NMR (400 MHz, CDCl$_3$): δ1.98 (t, J=6.0 Hz, 1H), 3.92 (s, 3H), 4.75 (d, J=6.0 Hz, 2H), 7.11 (s, 1H), 7.37 (s, 1H).

Pyridine (0.98 mL, 5.9 mmol) and phosphorous tribromide (5.6 mL, 53 mmol) were added to a solution of (2,4-dichloro-5-methoxyphenyl)methanol (24.43 g, 118 mmol) in tetrahydrofuran (250 mL) under ice-cooling. The temperature of the mixed solution was slowly raised to room temperature, followed by stirring at room temperature for 1 hour. After the reaction was completed, the resultant product was diluted with ethyl acetate, and washed sequentially with water and a saturated saline solution. The organic layer was dried over magnesium sulfate, and concentrated under reduced pressure. The obtained crude product was purified by silica gel column chromatography (hexane), whereby 1-(bromomethyl)-2,4-dichloro-5-methoxy benzene (25.09 g, yield: 79%) was obtained. $^1$H-NMR (400 MHz, CDCl$_3$): δ3.91 (s, 3H), 4.54 (s, 2H), 6.97 (s, 1H), 7.40 (s, 1H).

Water (200 g), potassium cyanide (9.26 g, 139 mmol), and tetrabutylammonium bromide (2.63 g, 10 mmol %) were added to a solution of 1-(bromomethyl)-2,4-dichloro-5-methoxy benzene (25.09 g, 92.9 mmol) in dichloromethane (200 mL), followed by stirring at room temperature for 24 hours. After the reaction was completed, the resultant product was extracted with chloroform (80 mL×3). The combined organic layer was washed with water (100 mL), dried over magnesium sulfate, and concentrated under reduced pressure. The obtained crude product was purified by silica gel column chromatography (hexane:ethyl acetate=9:1), whereby 2-(2,4-dichloro-5-methoxyphenyl)acetonitrile (18.92 g, yield: 94%) was obtained as a white solid. $^1$H-NMR (400 MHz, CDCl$_3$): δ3.82 (s, 2H), 3.94 (s, 3H), 7.06 (s, 1H), 7.43 (s, 1H).

A solution of sodium hydroxide (22.6 g, 525 mmol) in water (90 mL) was added to 2-(2,4-dichloro-5-methoxyphenyl)acetonitrile (18.92 g, 87.6 mmol), followed by refluxing for 4 hours. After the reaction was completed, the resultant product was cooled to room temperature, and concentrated hydrochloric acid was added until the resultant product became acidic. The produced precipitate was collected by filtration, and dissolved in diethyl ether, and washed with water. The organic layer was dried over magnesium sulfate, concentrated under reduced pressure, and dried under reduced pressure, whereby 2-(2,4-dichloro-5-methoxyphenyl) acetic acid (19.66 g, yield: 96%) was obtained as a pale yellow solid. $^1$H-NMR (400 MHz, CDCl$_3$): δ3.78 (s, 2H), 3.89 (s, 3H), 6.84 (s, 1H), 7.41 (s, 1H).

Concentrated sulfuric acid (5 mL) was added to a solution of 2-(2,4-dichloro-5-methoxyphenyl) acetic acid (19.66 g, 83.6 mmol) in methanol (30 mL), followed by heating to reflux for 15 hours. After the reaction was completed, the resultant product was cooled to room temperature, and diluted with diethyl ether. This was washed with water and a saturated sodium hydrogencarbonate aqueous solution. The organic layer was dried over magnesium sulfate, concentrated under reduced pressure, and dried under reduced pressure, whereby methyl 2-(2,4-dichloro-5-methoxyphenyl)acetate (18.97 g, yield: 91%) was obtained as a white solid. $^1$H-NMR (400 MHz, CDCl$_3$): δ3.73 (s, 3H), 3.74 (s, 2H), 3.89 (s, 3H), 6.86 (s, 1H), 7.40 (s, 1H).

A 55% oil dispersion (6.11 g, 140 mmol) of sodium hydride was added to a solution of methyl 2-(2,4-dichloro-5-methoxyphenyl)acetate (17.44 g, 70.0 mmol) in tetrahydrofuran (140 mL) under ice-cooling, followed by stirring at room temperature for 30 minutes. To this, tert-butyl dicarbonate (16.89 g, 73.5 mmol) and tetrabutylammonium chloride (5.84 g, 30 mol %) were added. The mixed solution was heated to reflux for 17 hours. After the reaction was completed, the reaction solution was cooled to room temperature, poured into a saturated ammonium chloride aqueous solution, and the resultant product was extracted with ethyl acetate. The organic layer was dried over magnesium sulfate, and concentrated under reduced pressure. The obtained crude product was purified by silica gel column chromatography (hexane:ethyl acetate=9:1), whereby tert-butyl 2-(2,4-dichloro-5-methoxyphenyl)malonate (16.09 g, yield: 66%) was obtained as a colorless oily material. $^1$H-NMR (400 MHz, CDCl$_3$): δ1.47 (s, 9H), 3.78 (s, 3H), 3.89 (s, 3H), 5.08 (s, 1H), 7.10 (s, 1H), 7.42 (s, 1H).

A 55% oil dispersion (1.75 g, 40 mmol) of sodium hydride was added to a solution of tert-butyl 2-(2,4-dichloro-5-methoxyphenyl)malonate (13.97 g, 40.0 mmol) in tetrahydrofuran (60 mL) under ice-cooling, followed by stirring at room temperature for 30 minutes. To this, dibromodifluoromethane (11.54 mL, 120 mmol) was added, followed by stirring at room temperature for 3 days. After the reaction was completed, a saturated ammonium chloride aqueous solution was added thereto, and the resultant product was extracted with ethyl acetate. The organic layer was dried over magnesium sulfate, and concentrated under reduced pressure. The obtained crude product was purified by silica gel column chromatography (hexane:ethyl acetate=9:1), and distilled under reduced pressure, whereby methyl 2-(2,4-dichloro-5-methoxyphenyl)-3,3-difluoroacrylate (7.33 g, yield: 62%) was obtained as a colorless oily material. $^1$H-NMR (400 MHz, CDCl$_3$): δ3.78 (s, 3H), 3.90 (s, 3H), 6.82 (s, 1H), 7.46 (s, 1H). $^{19}$F-NMR (376 MHz, CDCl$_3$): δ−67.4 (d, J=19.6 Hz, 1F), −66.8 (d, J=19.6 Hz, 1F).

Example-238

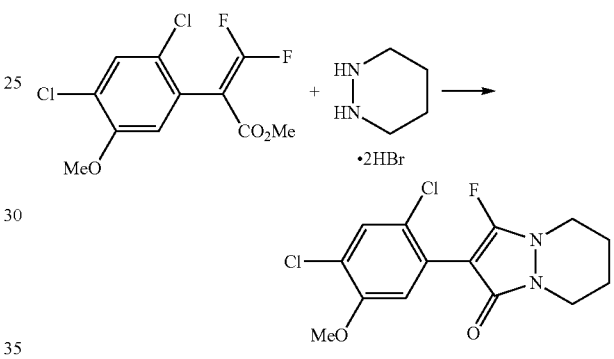

A solution of methyl 2-(2,4-dichloro-5-methoxyphenyl)-3,3-difluoroacrylate (2.97 g, 10.0 mmol) in tetrahydrofuran (40 mL) was cooled to −78° C., and hexahydropyridazine dihydrobromide (2.60 g, 10.5 mmol) and triethylamine (2.93 mL, 21.0 mmol) were added thereto, followed by raising the temperature to room temperature. The resultant product was stirred at 80° C. for 6 hours. After the reaction was completed, water (50 mL) was added to the reaction solution, and the resultant product was extracted with ethyl acetate (30 mL×2). The organic layer was dried over magnesium sulfate, and concentrated under reduced pressure, whereby a crude product was obtained. This was purified by silica gel column chromatography (ethyl acetate), whereby 4-(2,4-dichloro-5-methoxyphenyl)-5-fluoro-1,2-tetramethylene-4-pyrazolin-3-one (1.20 g, yield: 36%) was obtained as a white solid. $^1$H-NMR (400 MHz, CDCl$_3$): δ1.85-1.94 (m, 2H), 1.95-2.04 (m, 2H), 3.51-3.59 (m, 2H), 3.78-3.85 (m, 2H), 3.90 (s, 3H), 7.13 (s, 1H), 7.44 (s, 1H). $^{19}$F-NMR (376 MHz, CDCl$_3$): δ−112.2 (s, 1F).

Example-239

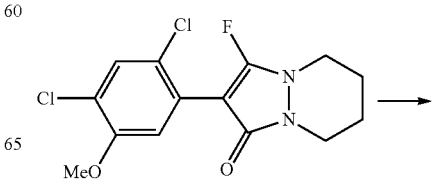

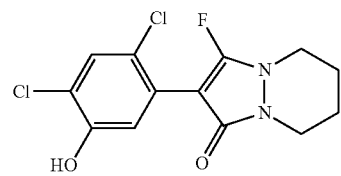

A solution (3.0 mL) of 1M boron tribromide in dichloromethane was added to a solution of 4-(2,4-dichloro-5-methoxyphenyl)-5-fluoro-1,2-tetramethylene-4-pyrazolin-3-one (497 mg, 1.5 mmol) in dichloromethane (3.0 mL) at −78° C. The resultant product was stirred at room temperature for 4 hours while slowly raising the reaction temperature to room temperature. After the reaction solution was poured into ice water, a 1N—HCl aqueous solution (20 mL) was added thereto. The precipitated solid was filtered, and dried under reduced pressure, whereby 4-(2,4-dichloro-5-hydroxyphenyl)-5-fluoro-1,2-tetramethylene-4-pyrazolin-3-one (quantitative) was obtained as a white solid. $^1$H-NMR (400 MHz, DMSO-$d_6$): δ1.72-1.82 (m, 2H), 1.84-1.93 (m, 2H), 3.54-3.69 (m, 4H), 7.09 (s, 1H), 7.54 (s, 1H), 10.62 (brs, 1H). $^{19}$F-NMR (376 MHz, DMSO-$d_6$): δ−114.2 (s, 1F).

Example-240

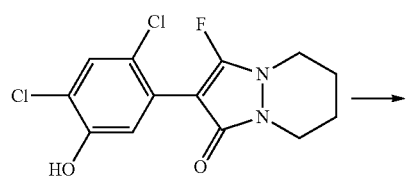

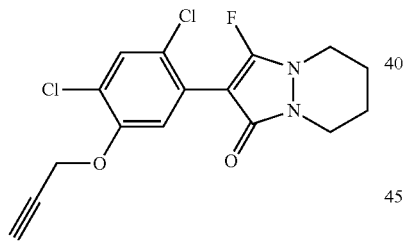

Potassium carbonate (415 mg, 3.0 mmol) and propargyl bromide (188 mg, 1.5 mmol) were added to a solution of 4-(2,4-dichloro-5-hydroxyphenyl)-5-fluoro-1,2-tetramethylene-4-pyrazolin-3-one (317 mg, 1.0 mmol) in acetone (10 mL), followed by stirring at room temperature for 2 days. After the reaction was completed, water (10 mL) was added to the reaction mixture, and the resultant product was extracted with chloroform (15 mL×3). The mixed organic layer was dried over magnesium sulfate, and concentrated under reduced pressure. The obtained residue was reprecipitated with chloroform/hexane, and dried under reduced pressure, whereby 4-[2,4-dichloro-5-(propargyloxy)phenyl]-5-fluoro-1,2-tetramethylene-4-pyrazolin-3-one (250 mg, yield: 70%) was obtained as a white solid. $^1$H-NMR (400 MHz, CDCl$_3$): δ1.85-1.94 (m, 2H), 1.95-2.04 (m, 2H), 2.56 (t, J=2.5 Hz, 1H), 3.53-3.59 (m, 2H), 3.77-3.84 (m, 2H), 4.79 (d, J=2.5 Hz, 2H), 7.25 (s, 1H), 7.46 (s, 1H). $^{19}$F-NMR (376 MHz, CDCl$_3$): δ−112.3 (s, 1F).

Example-241

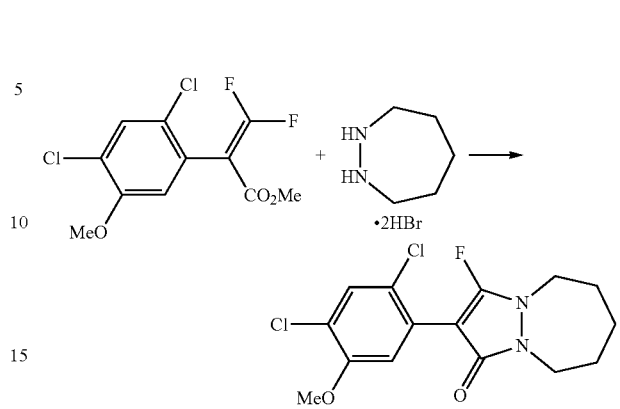

A solution of methyl 2-(2,4-dichloro-5-methoxyphenyl)-3,3-difluoroacrylate (2.08 g, 7.0 mmol) in tetrahydrofuran (28 mL) was cooled to −78° C., and 1,2-diazepane dihydrobromide (1.93 g, 7.4 mmol) and triethylamine (2.05 mL, 14.7 mmol) were added thereto, followed by raising the temperature to room temperature. The resultant product was stirred at 80° C. for 6 hours. After the reaction was completed, water (50 mL) was added to the reaction solution, and the resultant product was extracted with ethyl acetate (30 mL×2). The organic layer was dried over magnesium sulfate, and concentrated under reduced pressure, whereby a crude product was obtained. This was purified by silica gel column chromatography (ethyl acetate), whereby 4-(2,4-dichloro-5-methoxyphenyl)-5-fluoro-1,2-pentamethylene-4-pyrazolin-3-one (1.42 g, yield: 59%) was obtained as a white solid. $^1$H-NMR (400 MHz, CDCl$_3$): δ1.84 (brs, 6H), 3.86-3.94 (m, 2H), 3.91 (s, 3H), 4.01-4.10 (m, 2H), 7.18 (s, 1H), 7.42 (s, 1H). $^{19}$F-NMR (376 MHz, CDCl$_3$): δ−114.5 (s, 1F).

Example-242

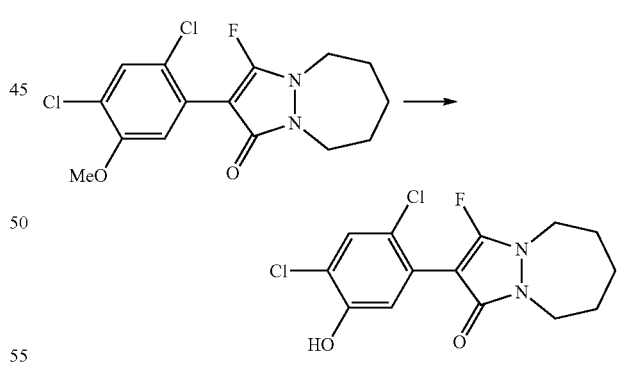

A solution (6.0 mL) of 1M boron tribromide in dichloromethane was added to a solution of 4-(2,4-dichloro-5-methoxyphenyl)-5-fluoro-1,2-pentamethylene-4-pyrazolin-3-one (1.04 g, 3.0 mmol) in dichloromethane (6.0 mL) at −78° C. The resultant product was stirred at room temperature for 4 hours while slowly raising the reaction temperature to room temperature. After the reaction solution was poured into ice water, a 1N—HCl aqueous solution (20 mL) was added thereto. The precipitated solid was filtered, and dried under reduced pressure, whereby 4-(2,4-dichloro-5-hydroxyphenyl)-5-fluoro-1,2-pentamethylene-4-pyrazolin- 3-one (0.986 g, yield: 99%) was obtained as a white solid. $^1$H-NMR (400 MHz, DMSO-d$_6$): δ1.71 (brs, 6H), 3.89-4.08 (m, 4H), 7.13 (s, 1H), 7.52 (s, 1H), 10.56 (brs, 1H). $^{19}$F-NMR (376 MHz, DMSO-d$_6$): δ−116.8 (s, 1F).

Example-243

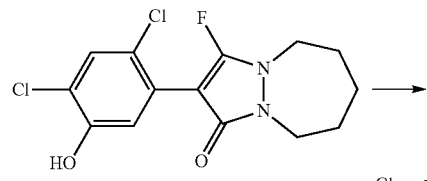

Potassium carbonate (622 mg, 4.5 mmol) and propargyl bromide (282 mg, 2.25 mmol) were added to a solution of 4-(2,4-dichloro-5-hydroxyphenyl)-5-fluoro-1,2-pentamethylene-4-pyrazolin-3-one (497 mg, 1.5 mmol) in acetone (15 mL), followed by stirring at room temperature for 2 days. After the reaction was completed, water (10 mL) was added to the reaction mixture, and the resultant product was extracted with chloroform (15 mL×3). The mixed organic layer was dried over magnesium sulfate, and concentrated under reduced pressure. The obtained residue was reprecipitated with chloroform/hexane, and dried under reduced pressure, whereby 4-[2,4-dichloro-5-(propargyloxy)phenyl]-5-fluoro-1,2-pentamethylene-4-pyrazolin-3-one (430 mg, yield: 78%) was obtained as a white solid. $^1$H-NMR (400 MHz, CDCl$_3$): δ1.85 (brs, 6H), 2.56 (t, J=2.2 Hz, 1H), 3.85-3.94 (m, 2H), 4.01-4.10 (m, 2H), 4.79 (d, J=2.2 Hz, 2H), 7.28 (s, 1H), 7.45 (s, 1H). $^{19}$F-NMR (376 MHz, CDCl$_3$): δ−114.6 (s, 1F).

Example-244

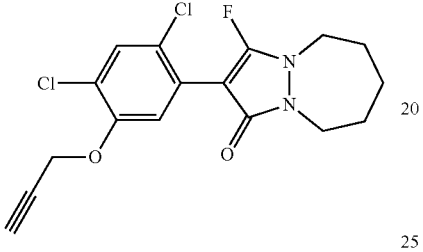

A solution of methyl 2-(2,4-dichloro-5-methoxyphenyl)-3,3-difluoroacrylate (2.08 g, 7.0 mmol) in tetrahydrofuran (28 mL) was cooled to −78° C., and 1,4,5-oxadiazepane dihydrobromide (1.94 g, 7.5 mmol) and triethylamine (2.05 mL, 14.7 mmol) were added thereto, followed by raising the temperature to room temperature. The resultant product was stirred at 80° C. for 15 hours. After the reaction was completed, water (50 mL) was added to the reaction solution, and the resultant product was extracted with ethyl acetate (30 mL×2). The organic layer was dried over magnesium sulfate, and concentrated under reduced pressure, whereby a crude product was obtained. This was purified by silica gel column chromatography (ethyl acetate:methanol=95:5), whereby 4-(2,4-dichloro-5-methoxyphenyl)-5-fluoro-1,2-oxadiethylene-4-pyrazolin-3-one (1.00 g, yield: 41%) was obtained as a white solid. $^1$H-NMR (400 MHz, CDCl$_3$): δ3.91 (s, 3H), 3.93-3.98 (m, 4H), 4.00-4.04 (m, 2H), 4.17-4.22 (m, 2H), 7.14 (s, 1H), 7.44 (s, 1H). $^{19}$F-NMR (376 MHz, CDCl$_3$): δ−112.4 (s, 1F).

Example-245

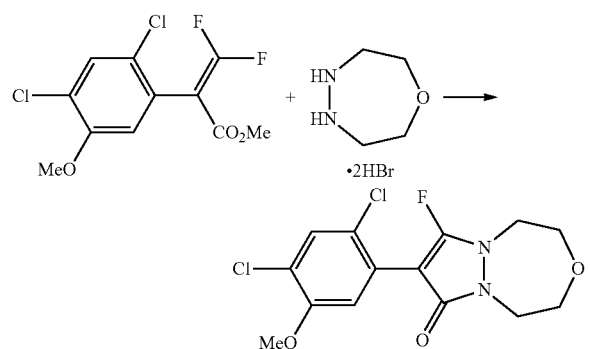

A solution (4.0 mL) of 1M boron tribromide in dichloromethane was added to a solution of 4-(2,4-dichloro-5-methoxyphenyl)-5-fluoro-1,2-oxadiethylene-4-pyrazolin-3-one (694 mg, 2.0 mmol) in dichloromethane (10.0 mL) at −78° C. The resultant product was stirred at room temperature for 4 hours while slowly raising the reaction temperature to room temperature. After the reaction solution was poured into ice water, a 1N—HCl aqueous solution (20 mL) was added thereto. The precipitated solid was filtered, and dried under reduced pressure, whereby 4-(2,4-dichloro-5-hydroxyphenyl)-5-fluoro-1,2-oxadiethylene-4-pyrazolin-3-one (646 mg, yield: 97%) was obtained as a white solid. $^1$H-NMR (400 MHz, DMSO-d$_6$): δ3.76-3.91 (m, 4H), 4.02-4.18 (m, 4H), 7.13 (s, 1H), 7.53 (s, 1H), 10.59 (brs, 1H). $^{19}$F-NMR (376 MHz, DMSO-d$_6$): δ−115.1 (s, 1F).

Example-246

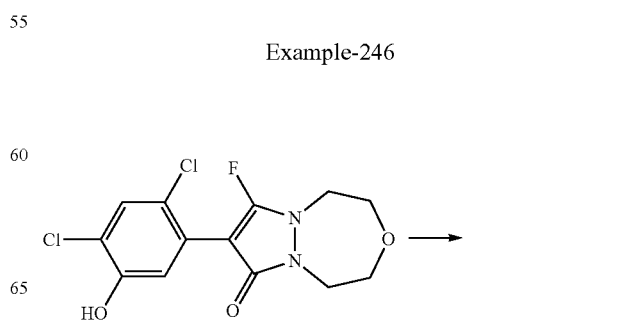

-continued

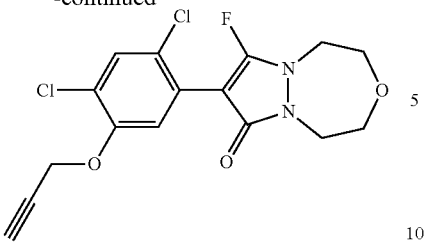

Potassium carbonate (498 mg, 3.6 mmol) and propargyl bromide (225 mg, 1.8 mmol) were added to a solution of 4-(2,4-dichloro-5-hydroxyphenyl)-5-fluoro-1,2-oxadiethylene-4-pyrazolin-3-one (400 mg, 1.2 mmol) in acetone (12 mL), followed by stirring at room temperature for 2 days. After the reaction was completed, water (10 mL) was added to the reaction mixture, and the resultant product was extracted with chloroform (15 mL×3). The mixed organic layer was dried over magnesium sulfate, and concentrated under reduced pressure, whereby a crude product was obtained. This was purified by silica gel column chromatography (ethyl acetate), whereby 4-[2,4-dichloro-5-(propargyloxy)phenyl]-5-fluoro-1,2-oxadiethylene-4-pyrazolin-3-one (305 mg, yield: 68%) was obtained as a white solid. $^1$H-NMR (400 MHz, CDCl$_3$): δ2.56 (t, J=2.3 Hz, 1H), 3.89-3.99 (m, 4H), 4.00-4.06 (m, 2H), 4.16-4.23 (m, 2H), 4.79 (d, J=2.3 Hz, 2H), 7.26 (s, 1H), 7.46 (s, 1H). $^{19}$F-NMR (376 MHz, CDCl$_3$): δ−112.5 (s, 1F).

Example-247

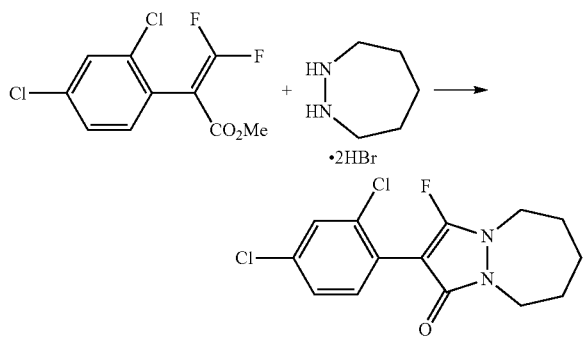

A solution of methyl 2-(2,4-dichlorophenyl)-3,3-difluoroacrylate (1.82 g, 6.81 mmol) in tetrahydrofuran (27 mL) was cooled to −78° C., and 1,2-diazepane dihydrobromide (1.78 g, 6.81 mmol) and triethylamine (2.85 mL, 20.4 mmol) were added thereto, followed by raising the temperature to room temperature. The resultant product was stirred at 80° C. for 15 hours. After the reaction was completed, water (50 mL) was added to the reaction solution, and the resultant product was extracted with ethyl acetate (60 mL×2). The organic layer was dried over magnesium sulfate, and concentrated under reduced pressure, whereby a crude product was obtained. This was purified by silica gel column chromatography (ethyl acetate), whereby 4-(2,4-dichlorophenyl)-5-fluoro-1,2-pentamethylene-4-pyrazolin-3-one (1.55 g, yield: 72%) was obtained as a white solid. $^1$H-NMR (400 MHz, CDCl$_3$): δ1.84 (m, 6H), 3.88 (m, 2H), 4.04 (m, 2H), 7.28 (d d, J=8.4 and 2.2 Hz, 1H), 7.44 (d, J=2.2 Hz, 1H), 7.50 (d, J=8.4 Hz, 1H). $^{19}$F-NMR (376 MHz, CDCl$_3$): δ−115.5 (s, 1F).

Example-248

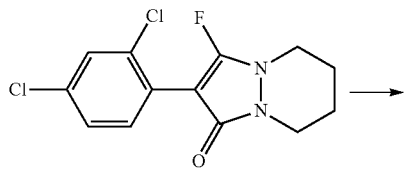

4-(2,4-Dichlorophenyl)-5-fluoro-1,2-tetramethylene-4-pyrazolin-3-one (1.0 g, 3.32 mmol) was susp was completed in concentrated sulfuric acid (3 mL), and a mixed acid prepared from concentrated nitric acid (334 mg, 3.66 mmol) and concentrated sulfuric acid (0.2 mL) was slowly added thereto under ice-cooling, followed by stirring for 2 hours. After the reaction was completed, the reaction solution was poured into ice water, and the resultant product was extracted with chloroform (50 mL×1, 20 mL×2). The organic layer was washed with a saturated saline solution (10 mL), dried over anhydrous magnesium sulfate, and concentrated under reduced pressure, whereby a crude product was obtained. This was purified by silica gel column chromatography (ethyl acetate), whereby 4-(2,4-dichloro-5-nitrophenyl)-5-fluoro-1,2-tetramethylene-4-pyrazolin-3-one (879 mg, yield: 76%) was obtained as a yellow solid. $^1$H-NMR (400 MHz, CDCl$_3$): δ1.86-1.96 (m, 2H), 1.97-2.07 (m, 2H), 3.57-3.64 (m, 2H), 3.77-3.85 (m, 2H), 7.64 (s, 1H), 8.17 (s, 1H). $^{19}$F-NMR (376 MHz, CDCl$_3$): δ−111.1 (s, 1F).

Example-249

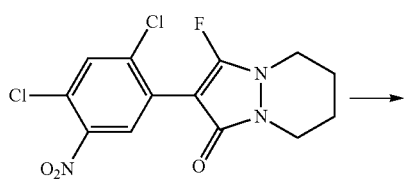

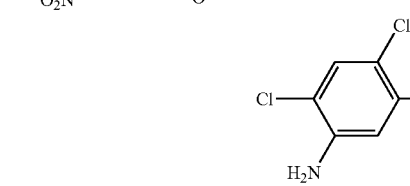

Water (0.45 g) and acetic acid (2.5 mL) were added to a solution of 4-(2,4-dichloro-5-nitrophenyl)-5-fluoro-1,2-tetramethylene-4-pyrazolin-3-one (872 mg, 2.52 mmol) in ethyl acetate (5 mL), and reduced iron (1.41 g, 25.2 mol) was added thereto, followed by stirring at 80° C. for 1 hour. After the reaction was completed, the reaction solution was cooled to room temperature, then, the insoluble matters were separated by filtration, and the solid was washed with a mixed solvent of ethyl acetate (50 mL) and acetic acid (10 mL). The combined organic layer was washed with water and a saturated sodium carbonate aqueous solution, dried over anhydrous magnesium sulfate, and concentrated under reduced pressure, whereby 4-(5-amino-2,4-dichlorophenyl)-5-fluoro-1,2-tetramethylene-4-pyrazolin-3-one (679 mg, yield: 85%) was obtained as a white solid. $^1$H-NMR (400 MHz, CDCl$_3$): δ1.82-1.91 (m, 2H), 1.94-2.02 (m, 2H), 3.47-3.55 (m, 2H), 3.75-3.82 (m, 2H), 4.06 (brs, 2H), 6.94 (s, 1H), 7.32 (s, 1H). $^{19}$F-NMR (376 MHz, CDCl$_3$): δ−113.3 (s, 1F).

Example-250

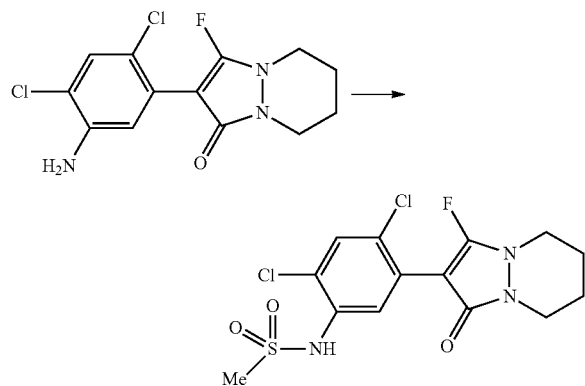

Pyridine (56 mg, 0.70 mmol) and methyl sulfonyl chloride (81.0 mg, 0.70 mmol) were added to a solution of 4-(5-amino-2,4-dichlorophenyl)-5-fluoro-1,2-tetramethylene-4-pyrazolin-3-one (200 mg, 0.63 mmol) in dichloromethane (5 mL) under ice-cooling, followed by stirring at room temperature for 48 hours. After the reaction was completed, a saturated sodium hydrogencarbonate aqueous solution (20 mL) was added to the reaction solution, and the resultant product was extracted with chloroform (20 mL×3). The organic layer was washed with 2N hydrochloric acid (30 mL), washed with a saturated saline solution, dried over anhydrous magnesium sulfate, and concentrated under reduced pressure, whereby a crude product was obtained. This was purified by silica gel column chromatography (ethyl acetate), whereby 4-[2,4-dichloro-5-(methylsulfonylamino)phenyl]-5-fluoro-1,2-tetramethylene-4-pyrazolin-3-one (157 mg, yield: 63%) was obtained as a white solid. $^1$H-NMR (400 MHz, CDCl$_3$): δ1.85-1.94 (m, 2H), 1.95-2.04 (m, 2H), 3.14 (s, 3H), 3.53-3.59 (m, 2H), 3.76-3.83 (m, 2H), 6.91 (brs, 1H), 7.56 (s, 1H), 7.76 (s, 1H). $^{19}$F-NMR (376 MHz, CDCl$_3$): δ−113.0 (s, 1F).

Example-251

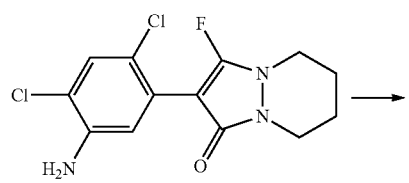

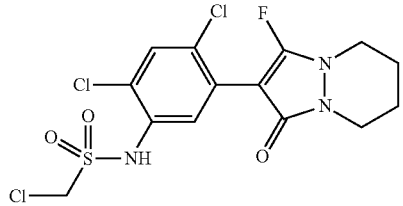

Pyridine (56 mg, 0.70 mmol) and chloromethyl sulfonyl chloride (115 mg, 0.70 mmol) were added to a solution of 4-(5-amino-2,4-dichlorophenyl)-5-fluoro-1,2-tetramethylene-4-pyrazolin-3-one (200 mg, 0.63 mmol) in dichloromethane (5 mL) under ice-cooling, followed by stirring at room temperature for 48 hours. After the reaction was completed, a saturated sodium hydrogencarbonate aqueous solution (20 mL) was added to the reaction solution, and the resultant product was extracted with chloroform (20 mL×3). The organic layer was washed with 2N hydrochloric acid (30 mL), washed with a saturated saline solution, dried over anhydrous magnesium sulfate, and concentrated under reduced pressure, whereby a crude product was obtained. This was purified by silica gel column chromatography (ethyl acetate), whereby 4-[5-(chloromethylsulfonylamino)-2,4-dichlorophenyl]-5-fluoro-1,2-tetramethylene-4-pyrazolin-3-one (54 mg, yield: 20%) was obtained as a white solid. $^1$H-NMR (400 MHz, CDCl$_3$): δ1.85-1.95 (m, 2H), 1.96-2.04 (m, 2H), 3.54-3.61 (m, 2H), 3.76-3.88 (m, 2H), 4.68 (s, 2H), 7.48 (s, 1H), 7.79 (s, 1H). $^{19}$F-NMR (376 MHz, CDCl$_3$): δ−112.4 (s, 1F).

Example-252

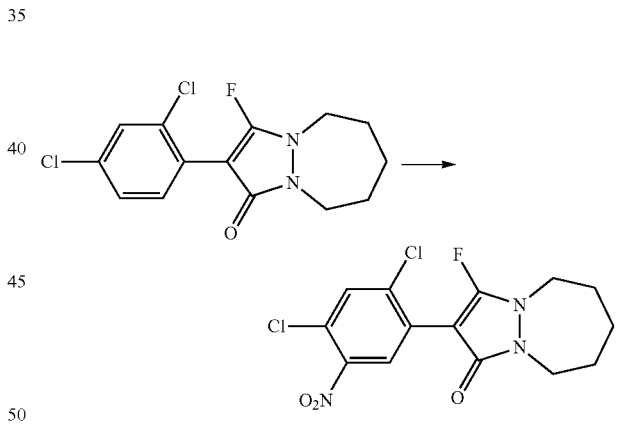

4-(2,4-Dichlorophenyl)-5-fluoro-1,2-pentamethylene-4-pyrazolin-3-one (1.0 g, 3.17 mmol) was susp was completed in concentrated sulfuric acid (5 mL), and a mixed acid prepared from concentrated nitric acid (319 mg, 3.49 mmol) and concentrated sulfuric acid (0.2 mL) was slowly added thereto under ice-cooling, followed by stirring for 2 hours. After the reaction was completed, the reaction solution was poured into ice water, and the resultant product was extracted with chloroform (50 mL×1, 20 mL×2). The organic layer was washed with a saturated saline solution (10 mL), dried over anhydrous magnesium sulfate, and concentrated under reduced pressure, whereby a crude product was obtained. This was purified by silica gel column chromatography (ethyl acetate), whereby 4-(2,4-dichloro-5-nitrophenyl)-5-fluoro-1,2-pentamethylene-4-pyrazolin-3-one (738 mg, yield: 64%) was obtained as a yellow solid.

¹H-NMR (400 MHz, CDCl₃): δ1.86 (m, 6H), 3.95 (m, 2H), 4.06 (m, 2H), 7.63 (s, 1H), 8.21 (s, 1H). ¹⁹F-NMR (376 MHz, CDCl₃): δ−114.1 (s, 1F).

Example-253

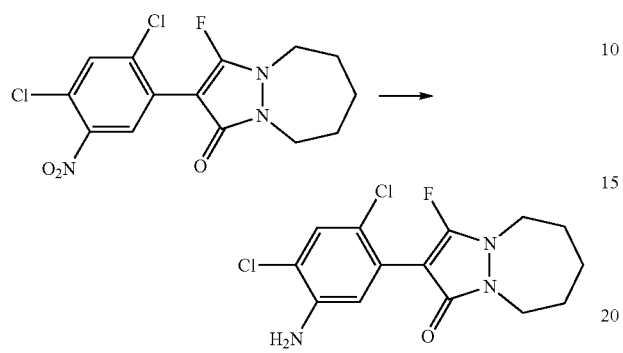

Water (0.3 g), and acetic acid (2.5 mL) were added to a solution of 4-(2,4-dichloro-5-nitrophenyl)-5-fluoro-1,2-pentamethylene-4-pyrazolin-3-one (540 mg, 1.64 mmol) in ethyl acetate (5 mL), and reduced iron (916 mg, 16.4 mol) was added thereto, followed by stirring at 80° C. for 1 hour. After the reaction was completed, the reaction solution was cooled to room temperature, then, the insoluble matters were separated by filtration, and the solid was washed with a mixed solvent of ethyl acetate (50 mL) and acetic acid (10 mL). The combined organic layer was washed with water and a saturated sodium carbonate aqueous solution, dried over anhydrous magnesium sulfate, and concentrated under reduced pressure, whereby 4-(5-amino-2,4-dichlorophenyl)-5-fluoro-1,2-pentamethylene-4-pyrazolin-3-one (443 mg, yield: 75%) was obtained as a white solid. ¹H-NMR (400 MHz, CDCl₃): δ1.83 (m, 6H), 3.87 (m, 2H), 3.82-3.94 (m, 2H), 3.95-4.21 (m, 4H), 6.98 (s, 1H), 7.31 (s, 1H). ¹⁹F-NMR (376 MHz, CDCl₃): δ−115.3 (s, 1F).

Example-254

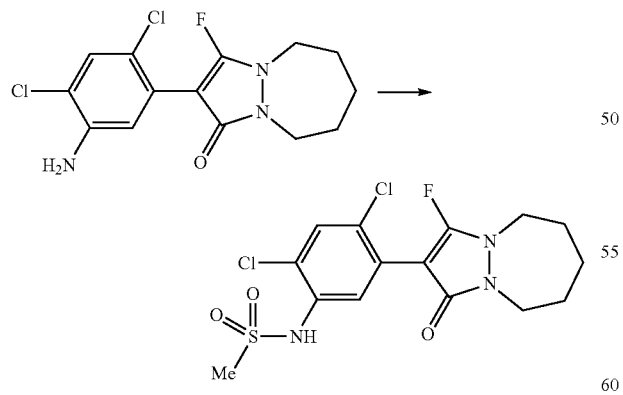

Pyridine (53 mg, 0.67 mmol) and methyl sulfonyl chloride (77.0 mg, 0.67 mmol) were added to a solution of 4-(5-amino-2,4-dichlorophenyl)-5-fluoro-1,2-pentamethylene-4-pyrazolin-3-one (200 mg, 0.61 mmol) in dichloromethane (5 mL) under ice-cooling, followed by stirring at room temperature for 48 hours. After the reaction was completed, a saturated sodium hydrogencarbonate aqueous solution (20 mL) was added to the reaction solution, and the resultant product was extracted with chloroform (20 mL×3). The organic layer was washed with 2N hydrochloric acid, washed with a saturated saline solution, dried over anhydrous magnesium sulfate, and concentrated under reduced pressure, whereby a crude product was obtained. This was purified by silica gel column chromatography (ethyl acetate), whereby 4-[2,4-dichloro-5-(methylsulfonylamino)phenyl]-5-fluoro-1,2-pentamethylene-4-pyrazolin-3-one (136 mg, yield: 55%) was obtained as a white solid. ¹H-NMR (400 MHz, CDCl₃): δ1.85 (m, 6H), 3.15 (s, 3H), 3.91 (m, 2H), 4.04 (m, 2H), 7.02 (brs, 1H), 7.48 (s, 1H), 7.77 (s, 1H). ¹⁹F-NMR (376 MHz, CDCl₃): δ−115.6 (s, 1F).

Example-255

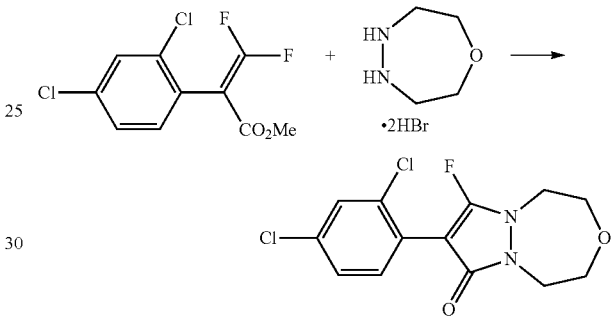

A solution of methyl 2-(2,4-dichlorophenyl)-3,3-difluoroacrylate (2.67 g, 10.0 mmol) in tetrahydrofuran (40 mL) was cooled to −78° C., and 1,4,5-oxadiazepane dihydrobromide (2.64 g, 10.0 mmol) and triethylamine (4.18 mL, 30.0 mmol) were added thereto, followed by raising the temperature to room temperature. The resultant product was stirred at 80° C. for 15 hours. After the reaction was completed, water (60 mL) was added to the reaction solution, and the resultant product was extracted with ethyl acetate (80 mL×2). The organic layer was dried over magnesium sulfate, and concentrated under reduced pressure, whereby a crude product was obtained. This was purified by silica gel column chromatography (ethyl acetate), whereby 4-(2,4-dichlorophenyl)-5-fluoro-1,2-oxadiethylene-4-pyrazolin-3-one (1.69 g, yield: 53%) was obtained as a white solid. ¹H-NMR (400 MHz, CDCl₃): δ3.92-3.97 (m, 4H), 3.98-4.03 (m, 2H), 4.16-4.22 (m, 2H), 7.29 (dd, J=8.4 and 2.2 Hz, 1H), 7.46 (d, J=2.2 Hz, 1H), 7.48 (d, J=8.4 Hz, 1H). ¹⁹F-NMR (376 MHz, CDCl₃): δ−113.4 (s, 1F).

Example-256

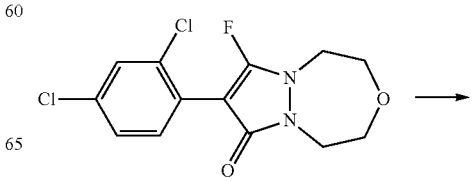

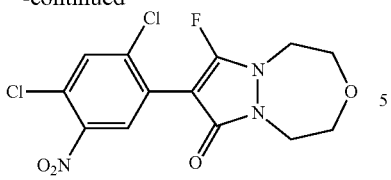

4-(2,4-Dichlorophenyl)-5-fluoro-1,2-oxadiethylene-4-pyrazolin-3-one (1.0 g, 3.15 mmol) was susp was completed in concentrated sulfuric acid (5 mL), and a mixed acid prepared from concentrated nitric acid (317 mg, 3.47 mmol) and concentrated sulfuric acid (0.2 mL) was slowly added thereto under ice-cooling, followed by stirring for 2 hours. After the reaction was completed, the reaction solution was poured into ice water, and the resultant product was extracted with chloroform (50 mL×1, 20 mL×2). The organic layer was washed with a saturated saline solution (10 mL), dried over anhydrous magnesium sulfate, and concentrated under reduced pressure, whereby a crude product was obtained. This was purified by silica gel column chromatography (ethyl acetate), whereby 4-(2,4-dichloro-5-nitrophenyl)-5-fluoro-1,2-oxadiethylene-4-pyrazolin-3-one (807 mg, yield: 71%) was obtained as a yellow solid. $^1$H-NMR (400 MHz, CDCl$_3$): δ3.92-4.00 (m, 4H), 4.06-4.11 (m, 2H), 4.18-4.24 (m, 2H), 7.65 (s, 1H), 8.18 (s, 1H). $^{19}$F-NMR (376 MHz, CDCl$_3$): δ−112.0 (s, 1F).

Example-257

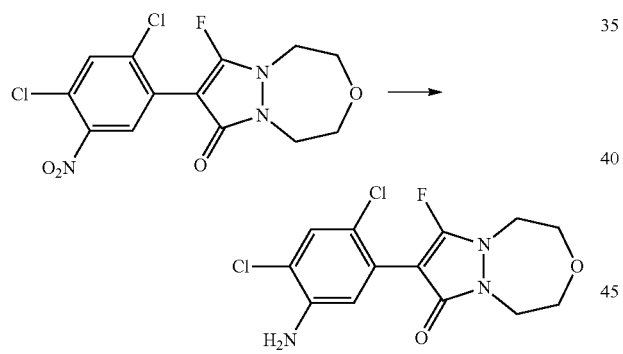

Water (0.3 g), and acetic acid (2.5 mL) were added to a solution of 4-(2,4-dichloro-5-nitrophenyl)-5-fluoro-1,2-oxadiethylene-4-pyrazolin-3-one (598 mg, 1.65 mmol) in ethyl acetate (5 mL), and reduced iron (921 mg, 16.5 mol) was added thereto, followed by stirring at 80° C. for 1 hour. After the reaction was completed, the reaction solution was cooled to room temperature, then, the insoluble matters were separated by filtration, and the solid was washed with a mixed solvent of ethyl acetate (50 mL) and acetic acid (10 mL). The combined organic layer was washed with water and a saturated sodium carbonate aqueous solution, dried over anhydrous magnesium sulfate, and concentrated under reduced pressure, whereby 4-(5-amino-2,4-dichlorophenyl)-5-fluoro-1,2-oxadiethylene-4-pyrazolin-3-one (440 mg, yield: 80%) was obtained as a white solid. $^1$H-NMR (400 MHz, CDCl$_3$): δ3.91-3.96 (m, 4H), 3.97-4.01 (m, 2H), 4.06 (brs, 2H), 4.15-4.20 (m, 2H), 6.95 (s, 1H), 7.32 (s, 1H). $^{19}$F-NMR (376 MHz, CDCl$_3$): δ−113.1 (s, 1F).

Example-258

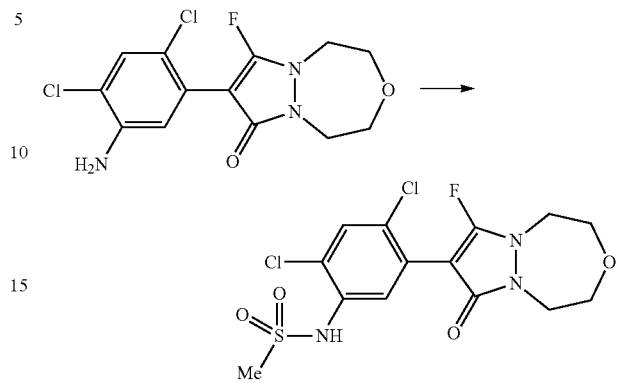

Pyridine (53 mg, 0.67 mmol) and methyl sulfonyl chloride (77.0 mg, 0.67 mmol) were added to a solution of 4-(5-amino-2,4-dichlorophenyl)-5-fluoro-1,2-oxadiethylene-4-pyrazolin-3-one (200 mg, 0.60 mmol) in dichloromethane (5 mL) under ice-cooling, followed by stirring at room temperature for 48 hours. After the reaction was completed, a saturated sodium hydrogencarbonate aqueous solution (20 mL) was added to the reaction solution, and the resultant product was extracted with chloroform (20 mL×3). The organic layer was washed with 2N hydrochloric acid (30 mL), washed with a saturated saline solution, dried over anhydrous magnesium sulfate, and concentrated under reduced pressure, whereby a crude product was obtained. This was purified by silica gel column chromatography (ethyl acetate), whereby 4-[2,4-dichloro-5-(methylsulfonylamino)phenyl]-5-fluoro-1,2-oxadiethylene-4-pyrazolin-3-one (133 mg, yield: 54%) was obtained as a white solid. $^1$H-NMR (400 MHz, CDCl$_3$): δ3.14 (s, 3H), 3.92-3.99 (m, 4H), 4.01-4.06 (m, 2H), 4.01-4.06 (m, 2H), 4.16-4.23 (m, 2H), 7.02 (brs, 1H), 7.49 (s, 1H), 7.76 (s, 1H). $^{19}$F-NMR (376 MHz, CDCl$_3$): δ−113.6 (s, 1F).

Example-259

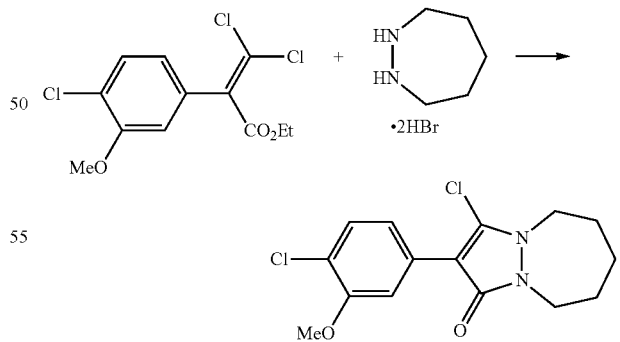

Triethylamine (3.7 mL, 26.7 mmol) and 1,2-diazepane dihydrobromide (2.33 g, 8.89 mmol) were added to a solution of ethyl 3,3-dichloro-2-(4-chloro-3-methoxyphenyl)acrylate (2.50 g, 8.08 mmol) in 1,4-dioxane (16 mL), followed by refluxing for 23 hours. After the reaction was completed, water (50 mL) was added to the reaction solution, and the resultant product was extracted with ethyl acetate (50 mL×3). The organic layer was washed with a saturated saline solution, dried over anhydrous magnesium sulfate, and concentrated under reduced pressure, whereby a crude product was obtained. This was purified by silica gel column chromatography (ethyl acetate:methanol=10:1), whereby 5-chloro-4-(4-chloro-3-methoxyphenyl)-1,2-pentamethylene-4-pyrazolin-3-one (1.59 g, yield: 60%) was obtained as a white solid. $^1$H-NMR (400 MHz, CDCl$_3$): δ1.79-1.86 (m, 6H), 3.94 (s, 3H), 4.07-4.11 (m, 2H), 4.11-4.16 (m, 2H), 7.32-7.36 (m, 2H), 7.69 (m, 1H).

Example-260

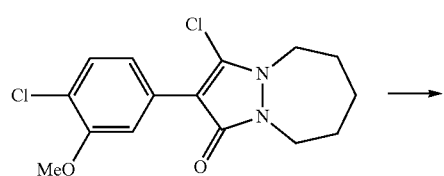

Boron tribromide (1 mol/L, 7.9 mL) was added dropwise to a solution of 5-chloro-4-(4-chloro-3-methoxyphenyl)-1,2-pentamethylene-4-pyrazolin-3-one (1.30 g, 3.97 mmol) in dichloromethane (16 mL) at −40° C. in an argon atmosphere, and the temperature was slowly raised to room temperature, followed by stirring for 5 hours. After the reaction was completed, the reaction solution was added little by little to ice water, and the resultant product was filtered, whereby a crude product was obtained as a white solid. This was washed with ether, whereby 5-chloro-4-(4-chloro-3-hydroxyphenyl)-1,2-pentamethylene-4-pyrazolin-3-one (1.11 g, yield: 90%) was obtained as a white solid. $^1$H-NMR (400 MHz, CDCl$_3$): δ1.77-1.90 (m, 6H), 4.07-4.12 (m, 2H), 4.13-4.17 (m, 2H), 7.27-7.32 (m, 2H), 7.36-7.70 (brs, 1H), 7.71 (m, 1H).

Example-261

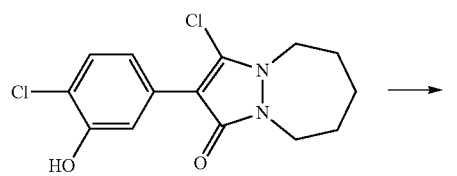

Potassium carbonate (590 mg, 4.31 mmol) and propargyl bromide (340 μL, 4.31 mmol) were added to a solution of 5-chloro-4-(4-chloro-3-hydroxyphenyl)-1,2-pentamethylene-4-pyrazolin-3-one (900 mg, 2.87 mmol) in DMF (14 mL), followed by stirring at room temperature for 14 hours. After the reaction was completed, water (50 mL) was added to the reaction solution, and the resultant product was extracted with ethyl acetate (50 mL×3). The organic layer was washed with water (50 mL×4), and a saturated saline solution (20 mL), dried over anhydrous magnesium sulfate, and concentrated under reduced pressure. The obtained crude product was dissolved in chloroform, then, hexane was added thereto, and the precipitated solid was collected by filtration, whereby 5-chloro-4-[4-chloro-3-(propargyloxy)phenyl]-1,2-pentamethylene-4-pyrazolin-3-one (691 mg, yield: 68%) was obtained as a white solid. $^1$H-NMR (400 MHz, CDCl$_3$): δ1.79-1.87 (m, 6H), 2.54 (t, J=2.4 Hz, 1H), 4.06-4.14 (m, 2H), 4.14-4.16 (m, 2H), 4.82 (d, J=2.4 Hz, 2H), 7.37 (d, J=8.3 Hz, 1H), 7.45 (dd, J=8.3 and 1.8 Hz, 1H), 7.75 (d, J=1.8 Hz, 1H).

Example-262

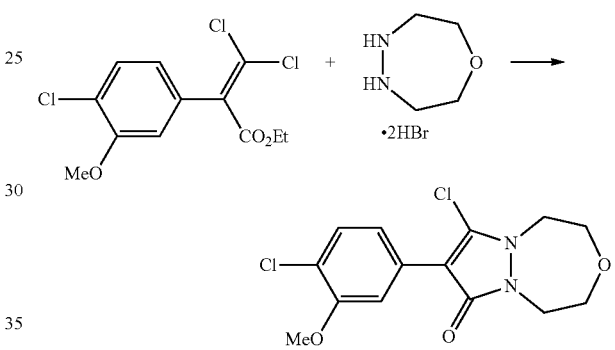

Triethylamine (3.7 mL, 26.7 mmol) and 1,4,5-oxadiazepane dihydrobromide (2.35 g, 8.89 mmol) were added to a solution of ethyl 3,3-dichloro-2-(4-chloro-3-methoxyphenyl)acrylate (2.50 g, 8.08 mmol) in 1,4-dioxane (16 mL), followed by refluxing for 8 hours. After the reaction was completed, water (50 mL) was added to the reaction solution, and the resultant product was extracted with ethyl acetate (50 mL×3). The organic layer was washed with a saturated saline solution, dried over anhydrous magnesium sulfate, and concentrated under reduced pressure, whereby a crude product was obtained. This was purified by silica gel column chromatography (chloroform:methanol=10:1), whereby 5-chloro-4-(4-chloro-3-methoxyphenyl)-1,2-oxadiethylene-4-pyrazolin-3-one (1.96 g, yield: 74%) was obtained as a yellow solid. $^1$H-NMR (400 MHz, CDCl$_3$): δ3.90-3.94 (m, 4H), 3.94 (s, 3H), 4.20-4.23 (m, 2H), 4.26-4.29 (m, 2H), 7.32 (dd, J=8.3 and 1.8 Hz, 1H), 7.37 (d, J=8.3 Hz, 1H), 7.62 (d, J=1.8 Hz, 1H).

Example-263

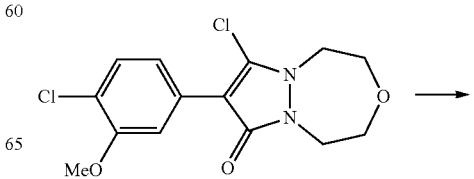

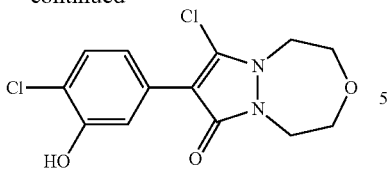

Boron tribromide (1 mol/L, 9.10 mL) was added dropwise to a solution of 5-chloro-4-(4-chloro-3-methoxyphenyl)-1,2-oxadiethylene-4-pyrazolin-3-one (1.50 g, 4.56 mmol) in dichloromethane (18 mL) at −40° C. in an argon atmosphere, and the temperature was slowly raised to room temperature, followed by stirring for 5 hours. After the reaction was completed, the reaction solution was added little by little to ice water, and the resultant product was filtered, whereby a crude product was obtained as a white solid. This was purified by silica gel column chromatography (chloroform:methanol=10:1), whereby 5-chloro-4-(4-chloro-3-hydroxyphenyl)-1,2-oxadiethylene-4-pyrazolin-3-one (960 mg, yield: 67%) was obtained as a white solid. $^1$H-NMR (400 MHz, CDCl$_3$): δ3.89-3.93 (m, 2H), 3.93-3.96 (m, 2H), 4.20-4.24 (m, 2H), 4.28-4.32 (m, 2H), 7.27 (dd, J=8.4 and 1.9 Hz, 1H), 7.31 (d, J=8.4 Hz, 1H), 7.37 (brs, 1H), 7.67 (d, J=1.9 Hz, 1 H).

Example-264

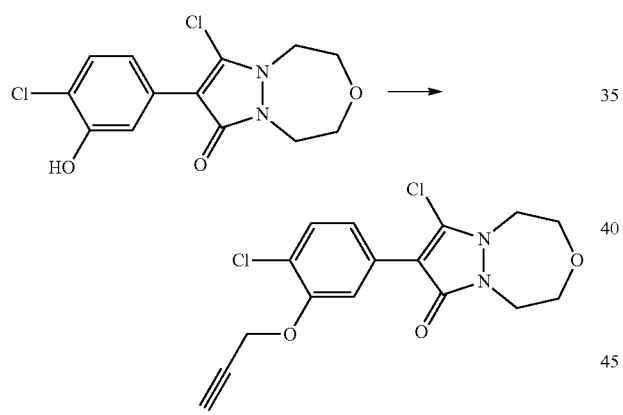

Potassium carbonate (460 mg, 3.33 mmol) and propargyl bromide (260 μL, 3.33 mmol) were added to a solution of 5-chloro-4-(4-chloro-3-hydroxyphenyl)-1,2-oxadiethylene-4-pyrazolin-3-one (700 mg, 2.22 mmol) in DMF (11 mL), followed by stirring at room temperature for 19 hours. After the reaction was completed, water (50 mL) was added to the reaction solution, and the resultant product was extracted with ethyl acetate (50 mL×3). The organic layer was washed with water (50 mL×4), and a saturated saline solution (20 mL), dried over anhydrous magnesium sulfate, and concentrated under reduced pressure, whereby a crude product was obtained. This was purified by silica gel column chromatography (chloroform:methanol=10:1), whereby 5-chloro-4-[4-chloro-3-(propargyloxy)phenyl]-1,2-oxadiethylene-4-pyrazolin-3-one (720 mg, yield: 92%) was obtained as a white solid. $^1$H-NMR (400 MHz, CDCl$_3$): δ2.55 (t, J=2.4 Hz, 1H), 3.90-3.95 (m, 4H), 4.19-4.23 (m, 2H), 4.21-4.29 (m, 2H), 4.82 (d, J=2.4 Hz, 2H), 7.38 (d, J=8.3 Hz, 1H), 7.43 (dd, J=8.3 and 1.8 Hz, 1H), 7.71 (d, J=1.8 Hz, 1H).

Example-265

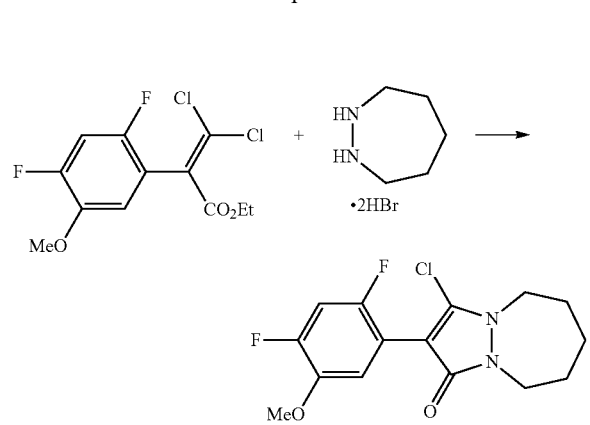

Triethylamine (3.4 mL, 24.4 mmol) and 1,2-diazepane dihydrobromide (2.13 g, 8.13 mmol) were added to a solution of ethyl 3,3-dichloro-2-(2,4-difluoro-5-methoxyphenyl)acrylate (2.30 g, 7.39 mmol) in 1,4-dioxane (15 mL), followed by refluxing for 7 hours. After the reaction was completed, water (50 mL) was added to the reaction solution, and the resultant product was extracted with ethyl acetate (50 mL×3). The organic layer was washed with a saturated saline solution, dried over anhydrous magnesium sulfate, and concentrated under reduced pressure, whereby a crude product was obtained. This was purified by silica gel column chromatography (ethyl acetate:methanol=9:1), whereby 5-chloro-4-(2,4-difluoro-5-methoxyphenyl)-1,2-pentamethylene-4-pyrazolin-3-one (1.43 g, yield: 59%) was obtained as a pale yellow solid. $^1$H-NMR (400 MHz, CDCl$_3$): δ1.81-1.87 (m, 6H), 3.88 (s, 3H), 4.06-4.11 (m, 2H), 4.11-4.15 (m, 2H), 6.90 (dd, J=11.0 and 9.4 Hz, 1H), 7.15 (dd, J=9.4 and 6.7 Hz, 1H). $^{19}$F-NMR (376 MHz, CDCl$_3$): δ−131.7 (d, J=3.8 Hz, 1F), −118.3 (d, J=3.8 Hz, 1F).

Example-266

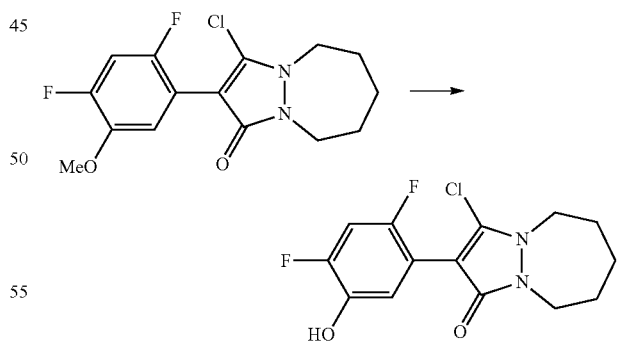

Boron tribromide (1 mol/L, 7.3 mL) was added dropwise to a solution of 5-chloro-4-(2,4-difluoro-5-methoxyphenyl)-1,2-pentamethylene-4-pyrazolin-3-one (1.20 g, 3.65 mmol) in dichloromethane (15 mL) at −40° C. in an argon atmosphere, and the temperature was slowly raised to room temperature, followed by stirring for 4 hours. After the reaction was completed, the reaction solution was added little by little to ice water, and the resultant product was filtered, whereby a crude product was obtained as a white solid. This was washed with ether, whereby 5-chloro-4-(2,4-difluoro-5-hydroxyphenyl)-1,2-pentamethylene-4-pyrazolin-3-one (1.13 g, yield: 99%) was obtained as a white solid. $^1$H-NMR (400 MHz, CDCl$_3$): δ1.77-1.93 (m, 6H), 4.09-4.14 (m, 2H), 4.14-4.20 (m, 2H), 6.81 (dd, J=10.7 and 9.6 Hz, 1H), 7.23 (dd, J=9.7 and 7.1 Hz, 1H). $^{19}$F-NMR (376 MHz, CDCl$_3$): δ−133.5 (s, 1F), −121.3 (s, 1F).

Example-267

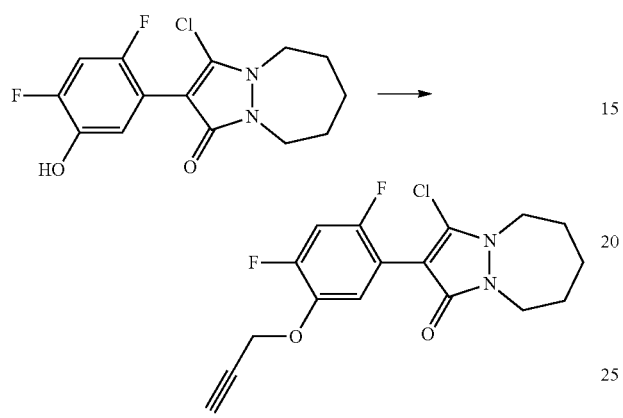

Potassium carbonate (590 mg, 4.29 mmol) and propargyl bromide (340 μL, 4.29 mmol) were added to a solution of 5-chloro-4-(2,4-difluoro-5-hydroxyphenyl)-1,2-pentamethylene-4-pyrazolin-3-one (900 mg, 2.86 mmol) in DMF (14 mL), followed by stirring at room temperature for 16 hours. After the reaction was completed, water (50 mL) was added to the reaction solution, and the resultant product was extracted with ethyl acetate (50 mL×3). The organic layer was washed with water (50 mL×4), and a saturated saline solution (20 mL), dried over anhydrous magnesium sulfate, and concentrated under reduced pressure. The obtained crude product was dissolved in chloroform, then, hexane was added thereto, and the precipitated solid was collected by filtration, whereby 5-chloro-4-[2,4-difluoro-5-(propargyloxy)phenyl]-1,2-pentamethylene-4-pyrazolin-3-one (886 mg, yield: 88%) was obtained as a white solid. $^1$H-NMR (400 MHz, CDCl$_3$): δ1.80-1.89 (m, 6H), 2.54 (t, J=2.4 Hz, 1H), 4.06-4.11 (m, 2H), 4.11-4.16 (m, 2H), 4.75 (d, J=2.4 Hz, 2H), 6.92 (dd, J=10.8 and 9.4 Hz, 1H), 7.26 (dd, J=9.2 and 6.9 Hz, 1H). $^{19}$F-NMR (376 MHz, CDCl$_3$): δ−129.7 (d, J=4.5 Hz, 1F), −116.0 (d, J=4.5 Hz, 1F).

Example-268

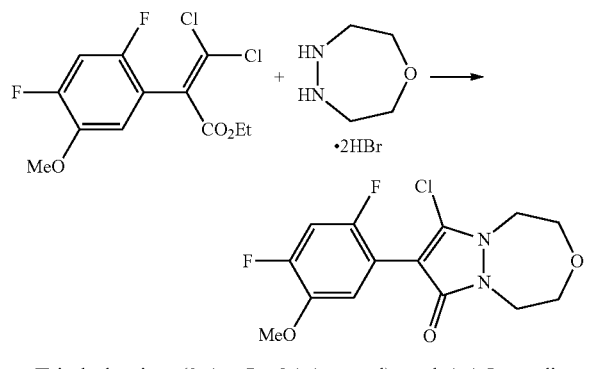

Triethylamine (3.4 mL, 24.4 mmol) and 1,4,5-oxadiazepane dihydrobromide (2.15 g, 8.13 mmol) were added to a solution of ethyl 3,3-dichloro-2-(2,4-difluoro-5-methoxyphenyl)acrylate (2.30 g, 7.39 mol) in 1,4-dioxane (15 mL), followed by refluxing for 6 hours. After the reaction was completed, water (50 mL) was added to the reaction solution, and the resultant product was extracted with ethyl acetate (50 mL×4). The organic layer was washed with a saturated saline solution, dried over anhydrous magnesium sulfate, and concentrated under reduced pressure, whereby a crude product was obtained. This was purified by silica gel column chromatography (ethyl acetate:methanol=9:1), whereby 5-chloro-4-(2,4-difluoro-5-methoxyphenyl)-1,2-oxadiethylene-4-pyrazolin-3-one (1.85 g, yield: 76%) was obtained as a white solid. $^1$H-NMR (400 MHz, CDCl$_3$): δ3.88 (s, 3H), 3.91-3.96 (m, 4H), 4.20-4.23 (m, 2H), 4.25-4.29 (m, 2H), 6.92 (dd, J=11.0 and 9.4 Hz, 1H), 7.12 (dd, J=9.4 and 6.7 Hz, 1H). $^{19}$F-NMR (376 MHz, CDCl$_3$): δ−130.9 (d, J=3.2 Hz, 1F), −118.2 (d, J=3.2 Hz, 1F).

Example-269

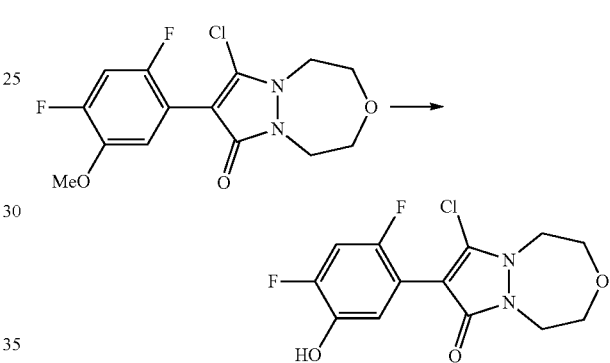

Boron tribromide (1 mol/L, 9.1 mL) was added dropwise to a solution of 5-chloro-4-(2,4-difluoro-5-methoxyphenyl)-1,2-oxadiethylene-4-pyrazolin-3-one (1.50 g, 4.59 mmol) in dichloromethane (18 mL) at −40° C. in an argon atmosphere, and the temperature was slowly raised to room temperature, followed by stirring for 5 hours. After the reaction was completed, the reaction solution was added little by little to ice water, and the resultant product was filtered, whereby a crude product was obtained as a white solid. This was washed with ether, whereby 5-chloro-4-(2,4-difluoro-5-hydroxyphenyl)-1,2-oxadiethylene-4-pyrazolin-3-one (880 mg, yield: 61%) was obtained as a white solid. $^1$H-NMR (400 MHz, CDCl$_3$): δ3.90-3.95 (m, 2H), 3.95-3.98 (m, 2H), 4.23-4.28 (m, 2H), 4.29-4.34 (m, 2H), 6.83 (dd, J=10.6 and 9.6 Hz, 1H), 7.19 (dd, J=9.6 and 7.0 Hz, 1H), 8.69 (brs, 1H). $^{19}$F-NMR (376 MHz, CDCl$_3$): δ−133.2 (s, 1F), −120.7 (s, 1F).

Example-270

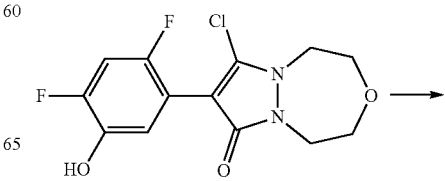

-continued

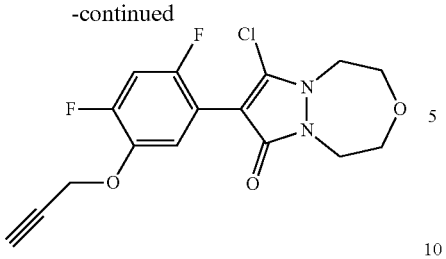

Potassium carbonate (390 mg, 2.84 mmol) and propargyl bromide (220 μL, 2.84 mmol) were added to a solution of 5-chloro-4-(2,4-difluoro-5-hydroxyphenyl)-1,2-oxadiethylene-4-pyrazolin-3-one (600 mg, 1.89 mmol) in DMF (9.5 mL), followed by stirring at room temperature for 27 hours. After the reaction was completed, water (50 mL) was added to the reaction solution, and the resultant product was extracted with ethyl acetate (50 mL×3). The organic layer was washed with water (50 mL×4), and a saturated saline solution (20 mL), dried over anhydrous magnesium sulfate, and concentrated under reduced pressure, whereby a crude product was obtained. This was recrystallized from chloroform, whereby 5-chloro-4-[2,4-difluoro-5-(propargyloxy)phenyl]-1,2-oxadiethylene-4-pyrazolin-3-one (525 mg, yield: 79%) was obtained as a white solid. $^1$H-NMR (400 MHz, CDCl$_3$): δ2.55 (t, J=2.4 Hz, 1H), 3.92-3.96 (m, 4H), 4.20-4.24 (m, 2H), 4.25-4.29 (m, 2H), 4.75 (d, J=2.4 Hz, 2H), 6.94 (dd, J=10.8 and 9.4 Hz, 1H), 7.25 (dd, J=9.2 and 6.8 Hz, 1H). $^{19}$F-NMR (376 MHz, CDCl$_3$): δ−129.0 (d, J=5.1 Hz, 1F), −115.9 (d, J=5.1 Hz, 1F).

Example-271

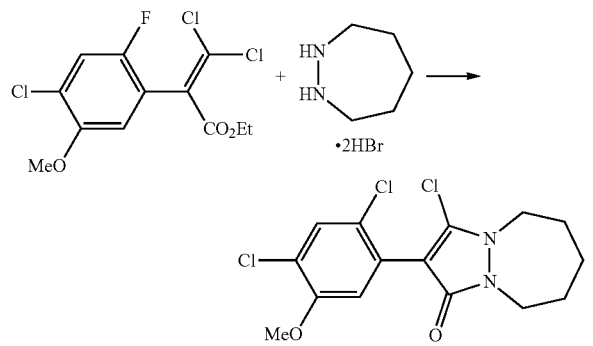

Triethylamine (4.0 mL, 28.8 mmol) and 1,2-diazepane dihydrobromide (2.51 g, 9.59 mmol) were added to a solution of ethyl 3,3-dichloro-2-(2,4-dichloro-5-methoxyphenyl)acrylate (3.00 g, 8.72 mmol) in 1,4-dioxane (17 mL), followed by refluxing for 16 hours. After the reaction was completed, water (50 mL) was added to the reaction solution, and the resultant product was extracted with ethyl acetate (50 mL×3). The organic layer was washed with a saturated saline solution, dried over anhydrous magnesium sulfate, and concentrated under reduced pressure, whereby a crude product was obtained. This was purified by silica gel column chromatography (ethyl acetate:methanol=9:1), whereby 5-chloro-4-(2,4-dichloro-5-methoxyphenyl)-1,2-pentamethylene-4-pyrazolin-3-one (1.21 g, yield: 38%) was obtained as a white solid. $^1$H-NMR (400 MHz, CDCl$_3$): δ1.81-1.89 (m, 6H), 3.89 (s, 3H), 4.05-4.16 (m, 4H), 6.95 (s, 1H), 7.45 (s, 1H).

Example-272

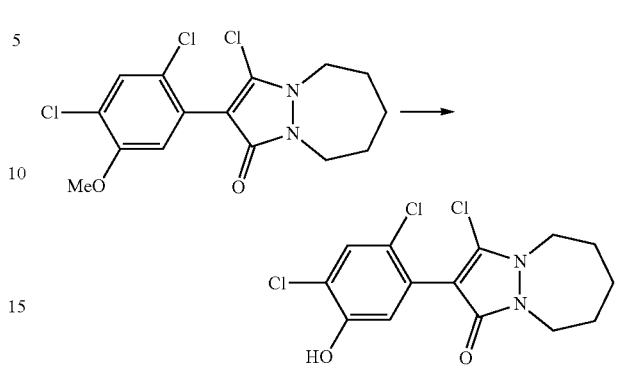

Boron tribromide (1 mol/L, 5.5 mL) was added dropwise to a solution of 5-chloro-4-(2,4-dichloro-5-methoxyphenyl)-1,2-pentamethylene-4-pyrazolin-3-one (1.00 g, 2.77 mmol) in dichloromethane (11 mL) at −40° C. in an argon atmosphere, and the temperature was slowly raised to room temperature, followed by stirring for 5 hours. After the reaction was completed, the reaction solution was added little by little to ice water, and the resultant product was filtered, whereby a crude product was obtained as a white solid. This was washed with ether, whereby 5-chloro-4-(2,4-dichloro-5-hydroxyphenyl)-1,2-pentamethylene-4-pyrazolin-3-one (962 mg, yield: quantitative) was obtained as a white solid. $^1$H-NMR (400 MHz, DMSO): δ1.63-1.75 (m, 6H), 3.99-4.05 (2H, m), 4.11-4.17 (m, 2H), 6.92 (s, 1H), 7.53 (s, 1H), 10.5 (brs, 1H).

Example-273

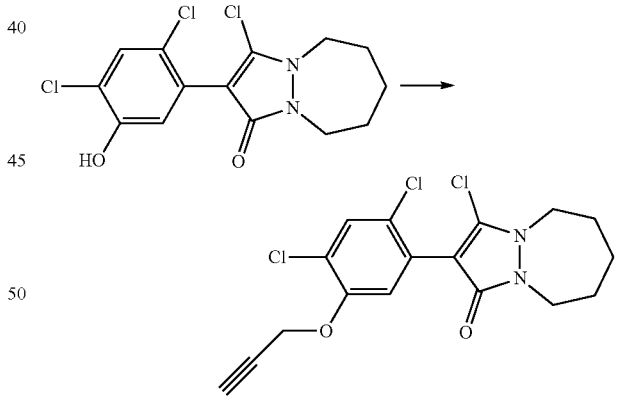

Potassium carbonate (420 mg, 3.02 mmol) and propargyl bromide (240 μL, 3.02 mmol) were added to a solution of 5-chloro-4-(2,4-dichloro-5-hydroxyphenyl)-1,2-pentamethylene-4-pyrazolin-3-one (700 mg, 2.01 mmol) in DMF (10 mL), followed by stirring at room temperature for 13 hours. After the reaction was completed, water (50 mL) was added to the reaction solution, and the resultant product was extracted with chloroform (100 mL×3). The organic layer was washed with water (50 mL×3), and a saturated saline solution (20 mL), dried over anhydrous magnesium sulfate, and concentrated under reduced pressure. The obtained crude product was dissolved in chloroform, then, hexane was added thereto, and the precipitated solid was collected by filtration, whereby 5-chloro-4-[2,4-dichloro-5-(propargyloxy)phenyl]-1,2-pentamethylene-4-pyrazolin-3-one (602 mg, yield: 77%) was obtained as a white solid. $^1$H-NMR (400 MHz, CDCl$_3$): δ1.82-1.88 (m, 6H), 2.55 (t, J=2.1 Hz, 1H), 4.06-4.11 (m, 2H), 4.11-4.16 (m, 2H), 4.76 (d, J=2.1 Hz, 2H), 7.06 (s, 1H), 7.46 (s, 1H).

Example-274

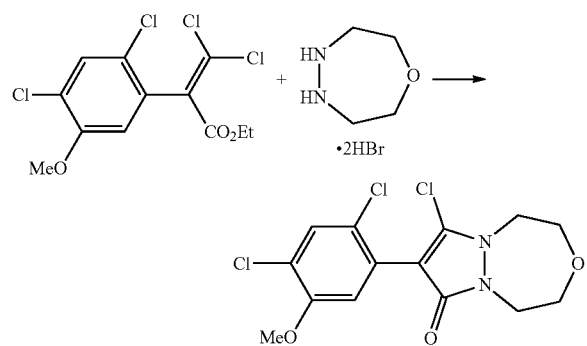

Triethylamine (3.3 mL, 24.0 mmol) and 1,4,5-oxadiazepane dihydrobromide (2.11 g, 8.00 mmol) were added to a solution of ethyl 3,3-dichloro-2-(2,4-dichloro-5-methoxyphenyl)acrylate (2.50 g, 7.27 mol) in 1,4-dioxane (14 mL), followed by refluxing for 7 hours. After the reaction was completed, water (50 mL) was added to the reaction solution, and the resultant product was extracted with ethyl acetate (50 mL×3). The organic layer was washed with a saturated saline solution, dried over anhydrous magnesium sulfate, and concentrated under reduced pressure, whereby a crude product was obtained. This was purified by silica gel column chromatography (ethyl acetate:methanol=9:1), whereby 5-chloro-4-(2,4-dichloro-5-methoxyphenyl)-1,2-oxadiethylene-4-pyrazolin-3-one (1.32 g, yield: 50%) was obtained as a white solid. $^1$H-NMR (400 MHz, CDCl$_3$): δ3.89 (s, 3H), 3.92-3.97 (m, 4H), 4.20-4.24 (m, 2H), 4.26-4.30 (m, 2H), 6.93 (s, 1H), 7.47 (s, 1H).

Example-275

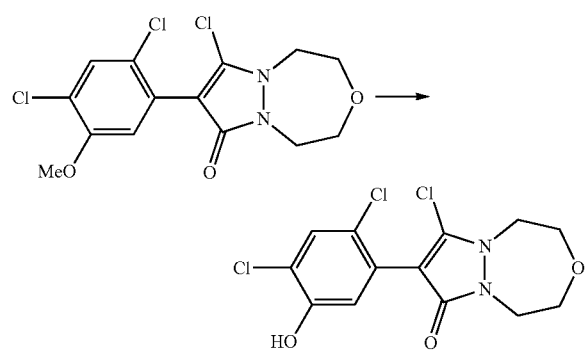

Boron tribromide (1 mol/L, 5.5 mL) was added dropwise to a solution of 5-chloro-4-(2,4-dichloro-5-methoxyphenyl)-1,2-oxadiethylene-4-pyrazolin-3-one (1.00 g, 2.75 mmol) in dichloromethane (11 mL) at −40° C. in an argon atmosphere, and the temperature was slowly raised to room temperature, followed by stirring for 4 hours. After the reaction was completed, the reaction solution was added little by little to ice water, and the resultant product was filtered, whereby a crude product was obtained as a white solid. This was washed with ether, whereby 5-chloro-4-(2,4-dichloro-5-hydroxyphenyl)-1,2-oxadiethylene-4-pyrazolin-3-one (730 mg, yield: 76%) was obtained as a white solid. $^1$H-NMR (400 MHz, CDCl$_3$): δ3.90-3.98 (m, 4H), 4.23-4.28 (m, 2H), 4.28-4.36 (m, 2H), 6.93 (s, 1H), 7.35 (s, 1H), 9.06 (s, 1H).

Example-276

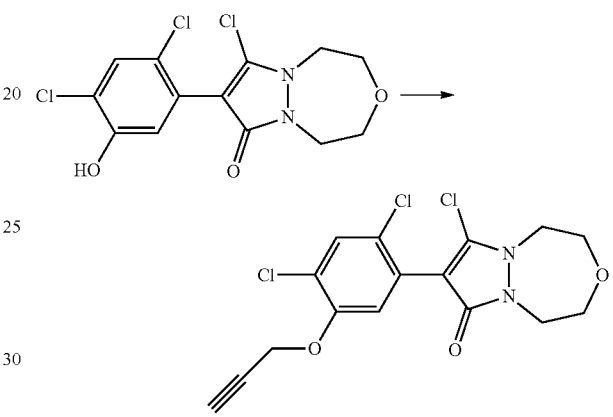

Potassium carbonate (300 mg, 2.15 mmol) and propargyl bromide (170 μL, 2.15 mmol) were added to a solution of 5-chloro-4-(2,4-dichloro-5-hydroxyphenyl)-1,2-oxadiethylene-4-pyrazolin-3-one (500 mg, 1.43 mmol) in DMF (7.2 mL), followed by stirring at room temperature for 30 hours. After the reaction was completed, water (50 mL) was added to the reaction solution, and the resultant product was extracted with ethyl acetate (50 mL×3). The organic layer was washed with water (50 mL×4), and a saturated saline solution (20 mL), dried over anhydrous magnesium sulfate, and concentrated under reduced pressure, whereby a crude product was obtained. This was purified by silica gel column chromatography (chloroform:methanol=9:1), whereby 5-chloro-4-[2,4-dichloro-5-(propargyloxy)phenyl]-1,2-oxadiethylene-4-pyrazolin-3-one (385 mg, yield: 71%) was obtained as a white solid. $^1$H-NMR (400 MHz, CDCl$_3$): δ2.55 (t, J=2.4 Hz, 1H), 3.93-3.97 (m, 4H), 4.20-4.25 (m, 2H), 4.24-4.30 (m, 2H), 4.77 (d, J=2.4 Hz, 2H), 7.06 (s, 1H), 7.49 (s, 1H).

Example-277

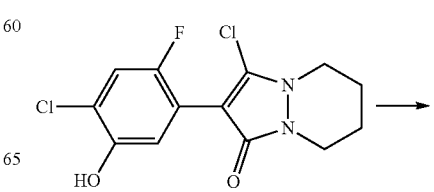

-continued

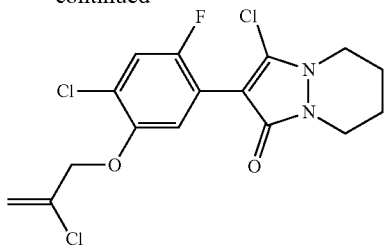

Potassium carbonate (343 mg, 2.48 mmol) and 2,3-dichloro-1-propene (169 mg, 1.48 mmol) were added to a solution of 5-chloro-4-(4-chloro-2-fluoro-5-hydroxyphenyl)-1,2-tetramethylene-4-pyrazolin-3-one (392 mg, 1.24 mmol) in dimethyl formamide (4 mL), followed by stirring at 50° C. for 18 hours. After the reaction was completed, water and hexane were added to the reaction solution, and the precipitated solid was filtered with suction, washed with water, and then, hexane, and dried, whereby 5-chloro-4-[4-chloro-2-fluoro-5-(2-chloroallyl)oxyphenyl]-1,2-tetramethylene-4-pyrazolin-3-one (387 mg, yield: 80%) was obtained as a white solid. $^1$H-NMR (400 MHz, CDCl$_3$): δ1.88-1.94 (m, 2H), 2.00-2.05 (m, 2H), 3.62-3.64 (m, 2H), 3.82-3.85 (m, 2H), 4.63 (dd, J=1.2 and 1.2 Hz, 2H), 5.47 (dt, J=1.2.0 and 1.2.0 Hz, 1H), 5.68 (dd, J=1.2.0 and 2.01.2 Hz, 2H), 7.11 (d, J=6.0 Hz, 1H), 7.20 (d, J=9.2 Hz, 1H). $^{19}$F-NMR (3776 MHz, CDCl$_3$): δ−118 (s, 1F).

Example-278

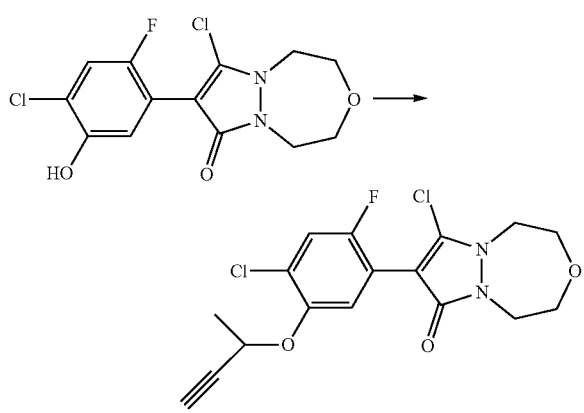

5-Chloro-4-(4-chloro-2-fluoro-5-hydroxyphenyl)-1,2-oxadiethylene-4-pyrazolin-3-one (0.25 g, 0.75 mmol) and 3-chloro-1-butyne (0.078 mL, 0.83 mmol) were added sequentially to a suspension of a 55% oil dispersion (0.036 g, 0.83 mmol) of sodium hydride in DMF (2 mL) under ice-cooling, followed by stirring at room temperature for 19 hours. After the reaction was completed, a saturated ammonium chloride aqueous solution (30 mL) was added to the reaction solution, and the resultant product was extracted with ethyl acetate (30 mL×3). The organic layer was washed with water (50 mL×4), and then, a saturated saline solution (20 mL×1), dried over anhydrous magnesium sulfate, and concentrated under reduced pressure. The obtained crude product was purified by silica gel column chromatography (hexane:ethyl acetate=1:5), whereby 5-chloro-4-[5-(1-butyn-3-yloxy)-4-chloro-2-fluorophenyl]-1,2-oxadiethylene-4-pyrazolin-3-one (0.077 g, yield: 27%) was obtained as a white solid. $^1$H-NMR (400 MHz, CDCl$_3$): δ1.70 (d, J=6.6 Hz, 3H), 2.51 (d, J=2.0 Hz, 1H), 3.92-3.96 (m, 4H), 4.20-4.24 (m, 2H), 4.25-4.29 (m, 2H), 4.88 (qd, J=6.6 and 2.0 Hz, 1H), 7.19 (d, J=9.2 Hz, 1H), 7.31 (d, J=6.4 Hz, 1H). $^{19}$F-NMR (376 MHz, CDCl$_3$): δ−117.9 (s, 1F).

Example-279

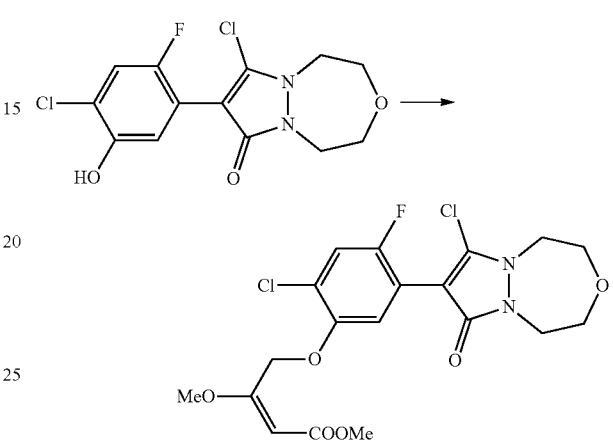

5-Chloro-4-(4-chloro-2-fluoro-5-hydroxyphenyl)-1,2-oxadiethylene-4-pyrazolin-3-one (0.25 g, 0.75 mmol) and methyl (E)-4-chloro-3-methoxy-2-butenoate (0.14 g, 0.83 mmol) were added sequentially to a suspension of a 55% oil dispersion (0.036 g, 0.83 mmol) of sodium hydride in DMF (2 mL) under ice-cooling, followed by stirring at room temperature for 21 hours. After the reaction was completed, a saturated ammonium chloride aqueous solution (30 mL) was added to the reaction solution, and the resultant product was extracted with ethyl acetate (30 mL×3). The organic layer was washed with water (50 mL×4), and then, a saturated saline solution (20 mL×1), dried over anhydrous magnesium sulfate, and concentrated under reduced pressure. The obtained crude product was purified by silica gel column chromatography (chloroform:methanol=10:1), whereby methyl (E)-4-[2-chloro-5-(5-chloro-3-oxo-1,2-oxadiethylene-4-pyrazolin-4-yl)-4-fluorophenyloxy]-3-methoxy-2-butenoate (0.22 g, yield: 63%) was obtained as a white solid. $^1$H-NMR (400 MHz, CDCl$_3$): δ3.69 (s, 3H), 3.72 (s, 3H), 3.92-3.96 (m, 4H), 4.19-4.23 (m, 2H), 4.42-4.27 (m, 2H), 5.21 (s, 1H), 5.26 (s, 2H), 7.14 (d, J=6.3 Hz, 1H), 7.17 (d, J=9.1 Hz, 1H). $^{19}$F-NMR (376 MHz, CDCl$_3$): δ−119.0 (s, 1F).

Example-280

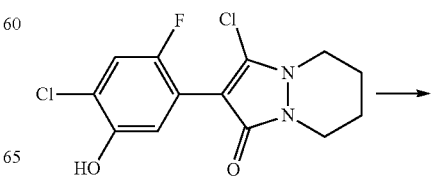

-continued

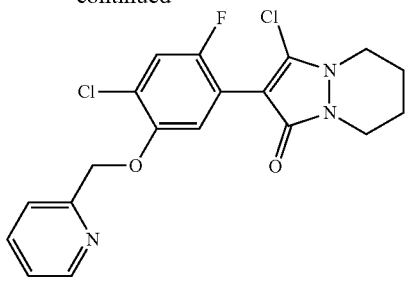

Potassium carbonate (289 mg, 2.09 mmol) and 2-(chloromethyl) pyridine hydrochloride (172 mg, 1.05 mmol) were added to a solution of 5-chloro-4-(4-chloro-2-fluoro-5-hydroxyphenyl)-1,2-tetramethylene-4-pyrazolin-3-one (300 mg, 0.95 mmol) in dimethyl formamide (3 mL), and the resultant product was stirred at room temperature for 18 hours, and stirred at 50° C. for 1 hour. After the reaction was completed, water and hexane were added to the reaction solution, and the precipitated solid was filtered with suction, washed with hexane, and dried, whereby 5-chloro-4-[4-chloro-2-fluoro-5-(pyridin-2-yl)methoxyphenyl]-1,2-tetramethylene-4-pyrazolin-3-one (311 mg, yield: 80%) was obtained as a white solid. $^1$H-NMR (400 MHz, CDCl$_3$): δ1.87-1.93 (m, 2H), 1.99-2.04 (m, 2H), 3.60-3.62 (m, 2H), 3.81-3.84 (m, 2H), 5.25 (s, 2H), 7.13 (d, J=6.0 Hz, 1H), 7.23 (d, J=9.2 Hz, 1H), 7.24 (m, 1H), 7.64 (m, 1H), 7.75 (m, 1H), 8.57 (m, 1H). $^{19}$F-NMR (376 MHz, CDCl$_3$): δ−118 (s, 1F).

Example-281

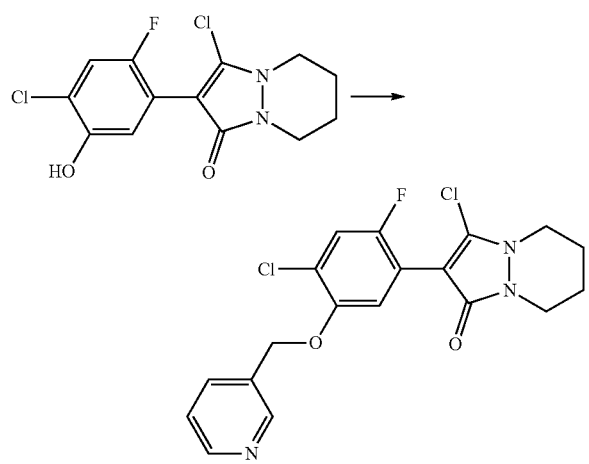

Potassium carbonate (289 mg, 2.09 mmol) and 3-(chloromethyl) pyridine hydrochloride (172 mg, 1.05 mmol) were added to a solution of 5-chloro-4-(4-chloro-2-fluoro-5-hydroxyphenyl)-1,2-tetramethylene-4-pyrazolin-3-one (300 mg, 0.95 mmol) in dimethyl formamide (3 mL), and the resultant product was stirred at room temperature for 18 hours, and stirred at 50° C. for 1 hour. After the reaction was completed, water and hexane were added to the reaction solution, and the precipitated solid was filtered with suction, washed with hexane, and dried, whereby 5-chloro-4-[4-chloro-2-fluoro-5-(pyridin-3-yl)methoxyphenyl]-1,2-tetramethylene-4-pyrazolin-3-one (291 mg, yield: 75%) was obtained as a white solid. $^1$H-NMR (400 MHz, CDCl$_3$): δ1.90-1.94 (m, 2H), 2.00-2.06 (m, 2H), 3.62-3.64 (m, 2H), 3.83-3.85 (m, 2H), 5.19 (s, 2H), 7.21 (d, J=9.0 Hz, 1H), 7.23 (d, J=6.2 Hz, 1H), 7.34 (ddd, J=8.0, 4.8 and 0.8 Hz, 1H), 7.83 (ddd, J=8.0, 2.0 and 1.6 Hz, 1H), 8.59 (ddd, J=4.8, 2.0 and 1.6 Hz, 1H), 8.59 (ddd, J=1.6, 1.6 and 0.8 Hz, 1H). $^{19}$F-NMR (376 MHz, CDCl$_3$): δ−118 (s, 1F).

Example-282

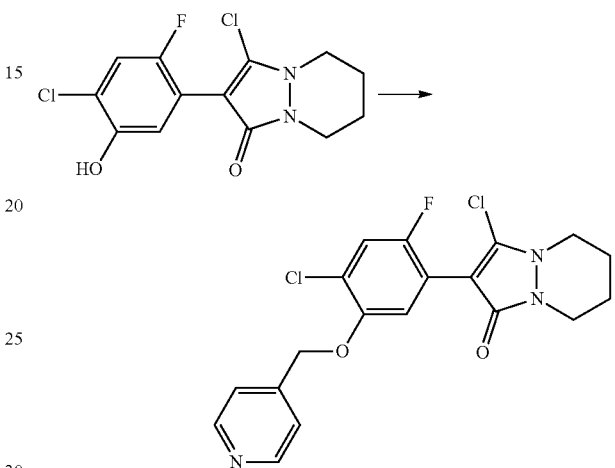

Potassium carbonate (289 mg, 2.09 mmol) and 4-(chloromethyl) pyridine hydrochloride (172 mg, 1.05 mmol) were added to a solution of 5-chloro-4-(4-chloro-2-fluoro-5-hydroxyphenyl)-1,2-tetramethylene-4-pyrazolin-3-one (300 mg, 0.95 mmol) in dimethyl formamide (3 mL), and the resultant product was stirred at room temperature for 21 hours, and stirred at 50° C. for 1 hour. After the reaction was completed, water was added to the reaction solution, and the resultant product was extracted with ethyl acetate. The organic layer was washed with water, and then, a saturated saline solution, dried over magnesium sulfate, and concentrated under reduced pressure. The obtained crude product was eluted and purified by silica gel column chromatography (ethyl acetate:methanol=8:1), whereby 5-chloro-4-[4-chloro-2-fluoro-5-(pyridin-4-yl)methoxyphenyl]-1,2-tetramethylene-4-pyrazolin-3-one (286 mg, yield: 74%) was obtained as a white solid. $^1$H-NMR (400 MHz, CDCl$_3$): δ1.88-1.93 (m, 2H), 2.00-2.05 (m, 2H), 3.61-3.64 (m, 2H), 3.82-3.85 (m, 2H), 5.15 (s, 2H), 7.16 (d, J=6.0 Hz, 1H), 7.23 (d, J=9.2 Hz, 1H), 7.39-7.41 (m, 2H), 8.62-8.63 (m, 1H). $^{19}$F-NMR (376 MHz, CDCl$_3$): δ−118 (s, 1F).

Example-283

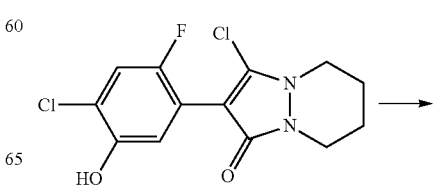

-continued

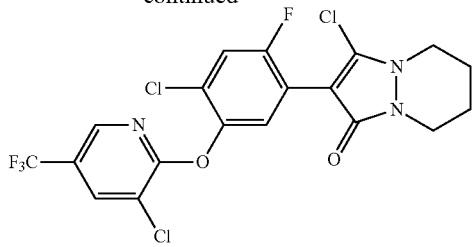

5-Chloro-4-(4-chloro-2-fluoro-5-hydroxyphenyl)-1,2-tetramethylene-4-pyrazolin-3-one (300 mg, 0.95 mmol) was added to a suspension of a 55% oil dispersion (45.6 mg, 1.05 mmol) of sodium hydride in dimethyl formamide (3 mL) under ice-cooling, followed by stirring at 50° C. for 15 minutes. 2,3-Dichloro-5-trifluoromethyl pyridine (238 mg, 1.05 mmol) was added thereto at the same temperature, followed by stirring for 23 hours. After the reaction was completed, ice water was poured into the reaction solution, and the resultant product was extracted with ethyl acetate. The organic layer was washed with water, and then, a saturated saline solution, dried over magnesium sulfate, and concentrated under reduced pressure. The obtained crude product was eluted and purified by silica gel column chromatography (ethyl acetate:methanol=10:1), whereby 5-chloro-4-[4-chloro-2-fluoro-5-(3-chloro-5-trifluoromethyl pyridin-2-yl)oxyphenyl]-1,2-tetramethylene-4-pyrazolin-3-one (344 mg, yield: 73%) was obtained as a white solid. $^1$H-NMR (400 MHz, CDCl$_3$): δ1.87-1.93 (m, 2H), 1.99-2.05 (m, 2H), 3.62-3.65 (m, 2H), 3.80-3.83 (m, 2H), 7.30 (d, J=9.2 Hz, 1H), 7.48 (d, J=6.8 Hz, 1H), 7.98 (d, J=2.0 Hz, 1H), 8.24 (dd, J=2.0 and 0.8 Hz, 1H). $^{19}$F-NMR (376 MHz, CDCl$_3$): δ−61.6 (s, 3F), −112 (s, 1F).

Example-284

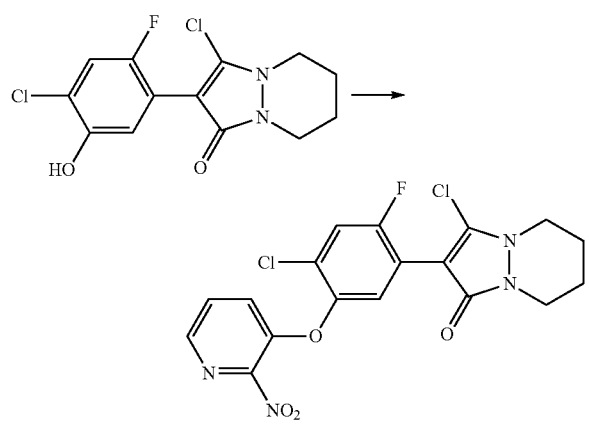

5-Chloro-4-(4-chloro-2-fluoro-5-hydroxyphenyl)-1,2-tetramethylene-4-pyrazolin-3-one (300 mg, 0.95 mmol) was added to a suspension of a 55% oil dispersion (62.2 mg, 1.43 mmol) of sodium hydride in dimethyl formamide (3 mL) under ice-cooling, followed by stirring at 50° C. for 15 minutes. 3-Chloro-2-nitropyridine (166 mg, 1.05 mmol) was added thereto at the same temperature, followed by stirring for 24 hours. After the reaction was completed, ice water was poured into the reaction solution, and the resultant product was extracted with ethyl acetate. The organic layer was washed with water, and then, a saturated saline solution, dried over magnesium sulfate, and concentrated under reduced pressure. The obtained crude product was eluted and purified by silica gel column chromatography (ethyl acetate:methanol=10:1), whereby 5-chloro-4-[4-chloro-2-fluoro-5-(2-nitropyridin-3-yl)oxyphenyl]-1,2-tetramethylene-4-pyrazolin-3-one (104 mg, yield: 25%) was obtained as a pale brown solid. $^1$H-NMR (400 MHz, CDCl$_3$): δ1.86-1.92 (m, 2H), 1.98-2.04 (m, 2H), 3.60-3.63 (m, 2H), 3.80-3.82 (m, 2H), 6.92 (dd, J=5.07.8 and 5.07.8 Hz, 1H), 7.28 (d, J=9.2 Hz, 1H), 7.45 (d, J=6.9 Hz, 1H), 7.75 (dd, J=7.8 and 1.8 Hz, 1H), 7.98 (dd, J=5.0 and 1.8 Hz, 1H). $^{19}$F-NMR (376 MHz, CDCl$_3$): δ−113 (s, 1F).

Example-285

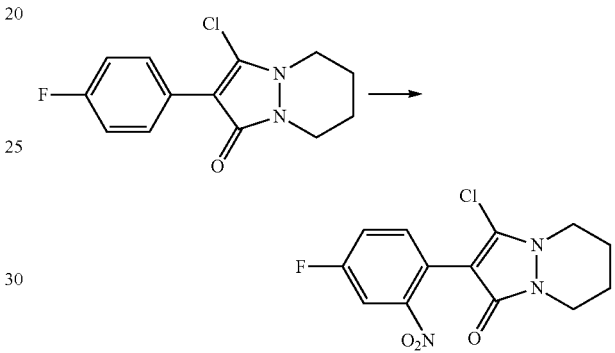

A mixed acid of nitric acid (1.46 g, 16.0 mmol) and sulfuric acid (4.6 mL) was added dropwise to a solution of 5-chloro-4-(4-fluorophenyl)-1,2-tetramethylene-4-pyrazolin-3-one (4.05 g, 15.2 mmol) in sulfuric acid (30 mL) under ice-cooling, followed by stirring for 4 hours under ice-cooling. After the reaction was completed, the reaction solution was poured into ice water (150 g), and the resultant product was extracted with chloroform (100 mL×3). The organic layer was washed with water (30 mL×1), and then, a saturated sodium hydrogencarbonate aqueous solution (30 mL×2), dried over anhydrous magnesium sulfate, and concentrated under reduced pressure, whereby 5-chloro-4-(4-fluoro-2-nitrophenyl)-1,2-tetramethylene-4-pyrazolin-3-one (3.11 g, yield: 66%) was obtained as a yellow solid. $^1$H-NMR (400 MHz, CDCl$_3$): δ1.87-1.94 (m, 2H), 1.99-2.06 (m, 2H), 3.60-3.65 (m, 2H), 3.79-3.84 (m, 2H), 7.36 (ddd, J=8.6, 7.5 and 2.7 Hz, 1H), 7.54 (dd, J=8.6 and 5.5 Hz, 1H), 7.76 (dd, J=8.3 and 2.7 Hz, 1H). $^{19}$F-NMR (376 MHz, CDCl$_3$): δ−109.9 (s, 1F).

Example-286

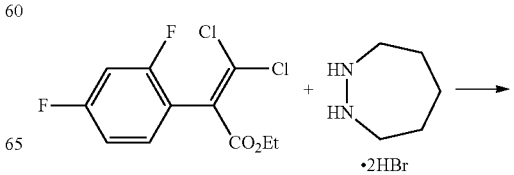

-continued

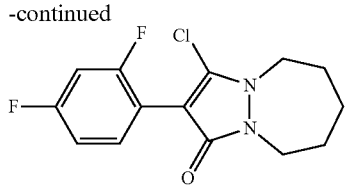

1,2-Diazepane dihydrobromide (20.5 g, 78.3 mmol) and triethylamine (32.7 mL, 235 mmol) were added to a solution of ethyl 3,3-dichloro-2-(2,4-difluorophenyl)acrylate (20.0 g, 71.2 mmol) in 1,4-dioxane (142 mL) at room temperature, followed by stirring for 4 hours while heating to reflux. After the reaction was completed, water (100 mL) was added to the reaction solution, and the resultant product was extracted with ethyl acetate (100 mL×3). The organic layer was dried over anhydrous magnesium sulfate, and concentrated under reduced pressure. The obtained crude product was dissolved in chloroform, then, hexane was added thereto, and the precipitated solid was collected by filtration, whereby 5-chloro-4-(2,4-difluorophenyl)-1,2-pentamethylene-4-pyrazolin-3-one (18.5 g, yield: 87%) was obtained as a white solid. $^1$H-NMR (400 MHz, CDCl$_3$): δ1.80-1.87 (m, 6H), 4.05-4.15 (m, 4H), 6.83-6.96 (m, 2H), 7.49 (m, 1H). $^{19}$F-NMR (376 MHz, CDCl$_3$): δ−110.9 (d, J=7.0 Hz, 1F), −107.6 (d, J=7.0 Hz, 1F).

Example-287

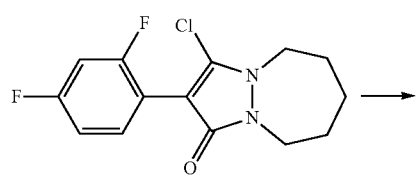

A mixed acid of nitric acid (0.96 g, 10.5 mmol) and sulfuric acid (3 mL) was added dropwise to a solution of 5-chloro-4-(2,4-difluorophenyl)-1,2-pentamethylene-4-pyrazolin-3-one (3.00 g, 10.0 mmol) in sulfuric acid (30 mL) under ice-cooling, followed by stirring for 3 hours under ice-cooling. After the reaction was completed, the reaction solution was poured into ice water (150 g), and the resultant product was extracted with ethyl acetate (100 mL×2). The organic layer was washed with a saturated sodium hydrogencarbonate aqueous solution (50 mL×3), and then, a saturated saline solution (30 mL×1), dried over anhydrous magnesium sulfate, and concentrated under reduced pressure, whereby 5-chloro-4-(2,4-difluoro-5-nitrophenyl)-1,2-pentamethylene-4-pyrazolin-3-one (3.26 g, yield: 95%) was obtained as a brown solid. $^1$H-NMR (400 MHz, CDCl$_3$): δ1.84-1.89 (m, 6H), 4.11-4.17 (m, 4H), 7.08 (dd, J=10.5 and 9.1 Hz, 1H), 8.36 (dd, J=8.4 and 7.3 Hz, 1H). $^{19}$F-NMR (376 MHz, CDCl$_3$): δ−113.3 (d, J=14.1 Hz, 1F), −95.8 (d, J=14.1 Hz, 1F).

Example-288

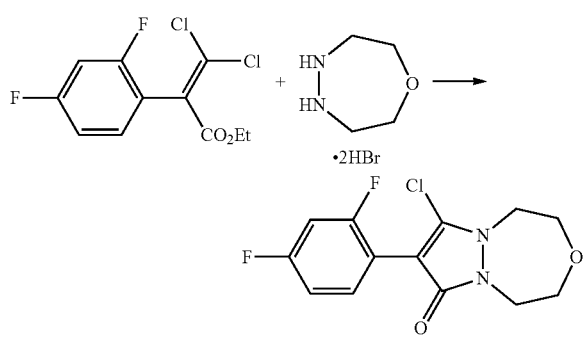

1,4,5-Oxadiazepane dihydrobromide (10.3 g, 39.2 mmol) and triethylamine (16.4 mL, 118 mmol) were added to a solution of ethyl 3,3-dichloro-2-(2,4-difluorophenyl)acrylate (10.0 g, 35.6 mmol) in 1,4-dioxane (71 mL) at room temperature, followed by stirring for 5 hours while heating to reflux. After the reaction was completed, water (100 mL) was added to the reaction solution, and the resultant product was extracted with ethyl acetate (100 mL×3). The organic layer was dried over anhydrous magnesium sulfate, and concentrated under reduced pressure. The obtained crude product was washed with ethyl acetate, whereby 5-chloro-4-(2,4-difluorophenyl)-1,2-oxadiethylene-4-pyrazolin-3-one (8.31 g, yield: 78%) was obtained as a white solid. $^1$H-NMR (400 MHz, CDCl$_3$): δ3.91-3.96 (m, 4H), 4.19-4.22 (m, 2H), 4.25-4.28 (m, 2H), 6.84-6.97 (m, 2H), 7.48 (m, 1H). $^{19}$F-NMR (376 MHz, CDCl$_3$): δ−110.2 (d, J=8.0 Hz, 1F), −107.5 (d, J=8.0 Hz, 1F).

Example-289

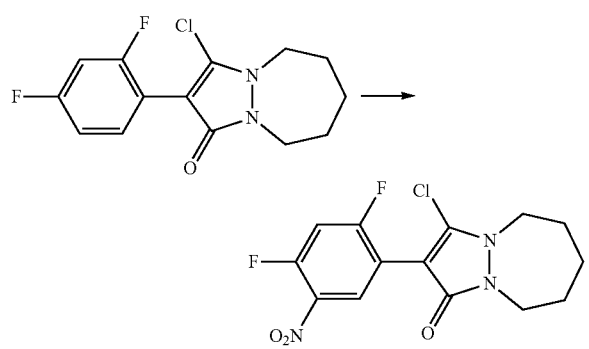

A mixed acid of nitric acid (0.92 g, 10.0 mmol) and sulfuric acid (3 mL) was added dropwise to a solution of 5-chloro-4-(2,4-difluorophenyl)-1,2-oxadiethylene-4-pyrazolin-3-one (2.87 g, 9.54 mmol) in sulfuric acid (30 mL) under ice-cooling, followed by stirring for 4 hours under ice-cooling. After the reaction was completed, the reaction solution was poured into ice water (150 g), and the resultant product was extracted with chloroform (100 mL×2). The organic layer was washed with a saturated sodium hydrogencarbonate aqueous solution (100 mL×2), dried over anhydrous magnesium sulfate, and concentrated under reduced pressure, whereby 5-chloro-4-(2,4-difluoro-5-nitrophenyl)-1,2-oxadiethylene-4-pyrazolin-3-one (3.12 g, yield:

95%) was obtained as a yellow solid. $^1$H-NMR (400 MHz, CDCl$_3$): δ3.93-3.97 (m, 4H), 4.26-4.32 (m, 4H), 7.10 (dd, J=10.5 and 9.2 Hz, 1H), 8.35 (dd, J=8.2 and 7.3 Hz, 1H). $^{19}$F-NMR (376 MHz, CDCl$_3$): δ−112.6 (d, J=14.2 Hz, 1F), −95.8 (d, J=14.2 Hz, 1F).

Example-290

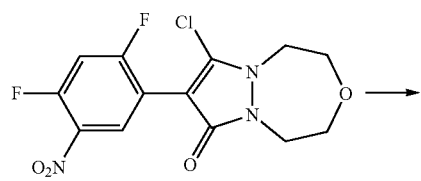

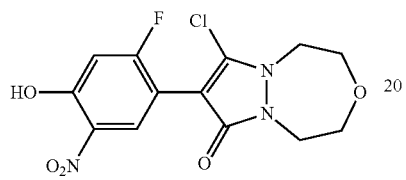

A 10N sodium hydroxide aqueous solution (29 mL) was added dropwise to a solution of 5-chloro-4-(2,4-difluoro-5-nitrophenyl)-1,2-oxadiethylene-4-pyrazolin-3-one (5.01 g, 14.5 mmol) in DMSO (48 mL), followed by stirring at room temperature for 5 hours. After the reaction was completed, the reaction solution was poured into ice water (400 g), and concentrated hydrochloric acid (25 mL) was added thereto, and the precipitated solid was collected by filtration. The obtained crude product was purified by silica gel column chromatography (chloroform:ethyl acetate=1:1), whereby 5-chloro-4-(2-fluoro-4-hydroxy-5-nitrophenyl)-1,2-oxadiethylene-4-pyrazolin-3-one (3.96 g, yield: 80%) was obtained as a yellow solid. $^1$H-NMR (400 MHz, CDCl$_3$): δ3.93-3.96 (m, 4H), 4.23-4.26 (m, 2H), 4.27-4.30 (m, 2H), 6.92 (d, J=10.4 Hz, 1H), 8.34 (d, J=7.3 Hz, 1H). $^{19}$F-NMR (376 MHz, CDCl$_3$): δ−95.0 (s, 1F).

Example-291

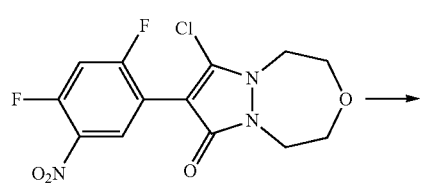

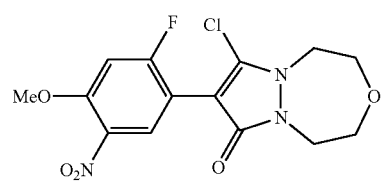

5-Chloro-4-(2,4-difluoro-5-nitrophenyl)-1,2-oxadiethylene-4-pyrazolin-3-one (3.30 g, 9.55 mmol) was added to a solution of a 55% oil dispersion (0.62 g, 14.3 mmol) of sodium hydride in 1,4-dioxane (48 mL), and methanol (0.96 mL, 23.9 mmol) was added dropwise thereto, followed by stirring at room temperature for 4 hours. After the reaction was completed, the reaction solution was poured into ice water (150 g), and the resultant product was extracted with chloroform (100 mL×3). The organic layer was dried over anhydrous magnesium sulfate, and concentrated under reduced pressure. The obtained crude product was dissolved in chloroform, then, hexane was added thereto, and the precipitated solid was collected by filtration, whereby 5-chloro-4-(2-fluoro-4-methoxy-5-nitrophenyl)-1,2-oxadiethylene-4-pyrazolin-3-one (2.75 g, yield: 80%) was obtained as a pale yellow solid. $^1$H-NMR (400 MHz, CDCl$_3$): δ3.92-3.95 (m, 4H), 3.98 (s, 3H), 4.22-4.26 (m, 2H), 4.26-4.30 (m, 2H), 6.86 (d, J=11.1 Hz, 1H), 8.14 (d, J=7.4 Hz, 1H). $^{19}$F-NMR (376 MHz, CDCl$_3$): δ−98.7 (s, 1F).

Example-292

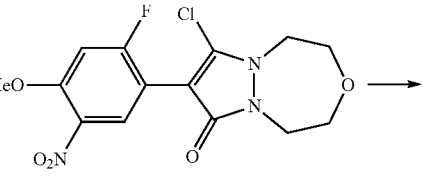

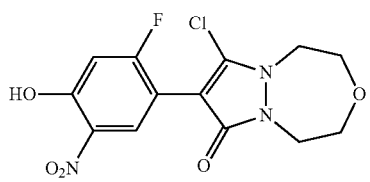

A 1M solution (7 mL) of boron tribromide in dichloromethane was added dropwise to a solution of 5-chloro-4-(2-fluoro-4-methoxy-5-nitrophenyl)-1,2-oxadiethylene-4-pyrazolin-3-one (1.00 g, 2.80 mmol) in dichloromethane (12 mL) at −40° C., followed by stirring for hours while slowly raising the temperature to room temperature. After the reaction was completed, the reaction solution was poured into ice water (100 g), and the resultant product was extracted with chloroform (100 mL×3). The organic layer was dried over anhydrous magnesium sulfate, and concentrated under reduced pressure. The obtained crude product was purified by silica gel column chromatography (chloroform:methanol=10:1), whereby 5-chloro-4-(2-fluoro-4-hydroxy-5-nitrophenyl)-1,2-oxadiethylene-4-pyrazolin-3-one (0.61 g, yield: 64%) was obtained as a yellow solid. $^1$H-NMR (400 MHz, CDCl$_3$): δ3.93-3.96 (m, 4H), 4.23-4.26 (m, 2H), 4.27-4.30 (m, 2H), 6.92 (d, J=10.4 Hz, 1H), 8.34 (d, J=7.3 Hz, 1H). $^{19}$F-NMR (376 MHz, CDCl$_3$): δ−95.0 (s, 1F).

Example-293

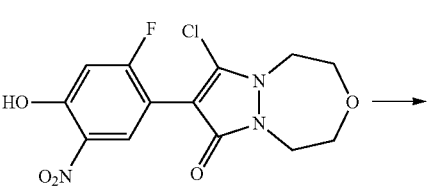

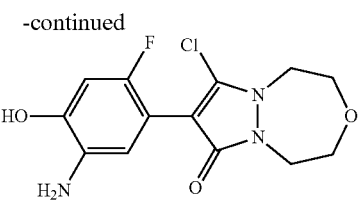

10% Palladium/carbon (0.062 g, 0.058 mmol) was added to a solution of 5-chloro-4-(2-fluoro-4-hydroxy-5-nitrophenyl)-1,2-oxadiethylene-4-pyrazolin-3-one (1.00 g, 2.91 mmol) in ethanol (12 mL), followed by stirring at room temperature for 15 hours in a hydrogen atmosphere. After the reaction was completed, a 10:1 mixed solvent of chloroform and methanol was added to the reaction solution, then, the catalyst was separated by filtration, and the filtrate was concentrated under reduced pressure. The obtained crude product was purified by silica gel column chromatography (chloroform:methanol=10:1), whereby 4-(5-amino-2-fluoro-4-hydroxyphenyl)-5-chloro-1,2-oxadiethylene-4-pyrazolin-3-one (0.83 g, yield: 91%) was obtained as a bluish green solid. $^1$H-NMR (400 MHz, CDCl$_3$): δ3.93-3.98 (m, 4H), 4.21-4.24 (m, 2H), 4.31-4.34 (m, 2H), 6.27 (d, J=10.8 Hz, 1H), 6.52 (d, J=7.3 Hz, 1H). $^{19}$F-NMR (376 MHz, CDCl$_3$): δ−124.2 (s, 1F). $^1$H-NMR (400 MHz, DMSO): δ3.77-3.83 (m, 4H), 4.09-4.13 (m, 2H), 4.17-4.21 (m, 2H), 6.51 (d, J=11.1 Hz, 1H), 6.56 (d, J=7.7 Hz, 1H). $^{19}$F-NMR (376 MHz, DMSO): δ−125.7 (s, 1F).

Example-294

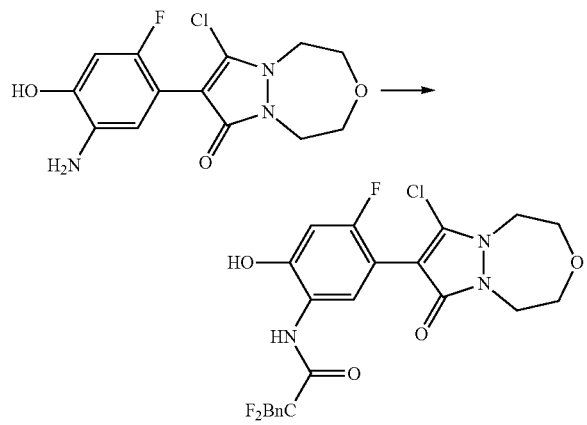

A 55% oil dispersion (0.28 g, 6.38 mmol) of sodium hydride was added to a mixed solution of 4-(5-amino-2-fluoro-4-hydroxyphenyl)-5-chloro-1,2-oxadiethylene-4-pyrazolin-3-one (2.00 g, 6.38 mmol) in THF (32 mL) and DMF (32 mL) at −15° C., followed by stirring at −15° C. for 1 hour, and ethyl bromodifluoroacetate (0.94 mL, 7.02 mmol) was added dropwise thereto, followed by stirring at 0° C. for 6 hours. After the reaction was completed, a saturated ammonium chloride aqueous solution (40 mL) was added to the reaction solution, and the resultant product was extracted with chloroform (100 mL×3). The organic layer was dried over anhydrous magnesium sulfate, and concentrated under reduced pressure. The obtained crude product was purified by silica gel column chromatography (chloroform:methanol=10:1), whereby 2-bromo-N-[5-(5-chloro-1,2-oxadiethylene-3-oxo-4-pyrazolin-4-yl)-4-fluoro-2-hydroxyphenyl]-2,2-difluoroacetamide (1.69 g, yield: 56%) was obtained as a white solid. $^1$H-NMR (400 MHz, DMSO): δ3.78-3.86 (m, 4H), 4.11-4.16 (m, 2H), 4.23-4.27 (m, 2H), 6.79 (d, J=11.2 Hz, 1H), 7.29 (d, J=7.9 Hz, 1H), 10.38 (s, 1H), 10.55 (s, 1H). $^{19}$F-NMR (376 MHz, DMSO): δ−59.9 (s, 2F), −111.5 (s, 1F).

Reference Example-71

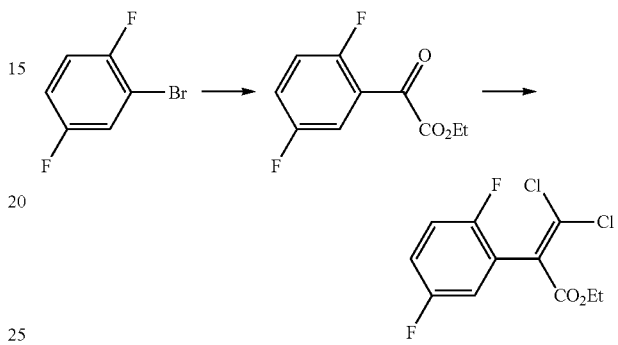

THF (25 mL) was added to metal magnesium (2.55 g, 105 mmol), and 2-bromo-1,4-difluoro benzene (19.70 g, 100 mmol) was slowly added thereto, whereby a Grignard reagent was prepared. The previously prepared Grignard reagent was added dropwise to the separately prepared solution of diethyl oxalate (15.34 g, 105 mmol) in THF (10 mL) at −40° C. or lower. After the dropping was completed, the reaction temperature was raised to 0° C., followed stirring for 1 hour. A saturated ammonium chloride aqueous solution and water (200 mL) were added to the reaction solution, and the resultant product was extracted with ethyl acetate (200 mL×2). After the organic layer was dried over magnesium sulfate and filtered, the solvent was distilled off under reduced pressure, and the resultant product was distilled under reduced pressure, whereby ethyl 2-(2,5-difluorophenyl)-2-oxoacetate (14.82 g, yield: 62%) was obtained as a colorless liquid. $^1$H-NMR (400 MHz, CDCl$_3$): δ1.40 (t, J=7.0 Hz, 3H), 4.44 (q, J=7.0 Hz, 2H), 7.16 (ddd, J=9.3, 9.3 and 4.0 Hz, 1H), 7.34 (dddd, J=9.3, 9.2, 7.3 and 3.3 Hz, 1H), 7.60 (ddd, J=8.2, 5.3 and 3.3 Hz, 1H). $^{19}$F-NMR (376 MHz, CDCl$_3$): δ−116.9 (d, J=7.8 Hz, 1F), −116.3 (d, J=7.8 Hz, 1F).

Carbon tetrachloride (41.7 g, 270 mmol) was added to a solution of triphenylphosphine (73.0 g, 270 mmol) in dichloromethane (60 mL) at 0° C., followed by stirring for 5 minutes. To the solution, ethyl 2-(2,5-difluorophenyl)-2-oxoacetate (28.9 g, 135 mmol) was added, followed by stirring at room temperature for 15 hours. The solvent was removed from the reaction mixture under reduced pressure, then, a mixed solvent of chloroform and ether was added to the residue, and the solid was separated by filtration. The filtrate was concentrated under reduced pressure, and the obtained crude product was distilled under reduced pressure, whereby ethyl 3,3-dichloro-2-(2,5-difluorophenyl)acrylate (32.2 g, yield: 85%) was obtained as a colorless liquid. $^1$H-NMR (400 MHz, CDCl$_3$): δ1.26 (t, J=7.2 Hz, 3H), 4.26 (q, J=7.2 Hz, 2H), 7.03-7.10 (m, 3H). $^{19}$F-NMR (376 MHz, CDCl$_3$): δ−118.8 (d, J=16.4 Hz, 1F) −118.3 (d, J=16.4 Hz, 1F).

Example-295

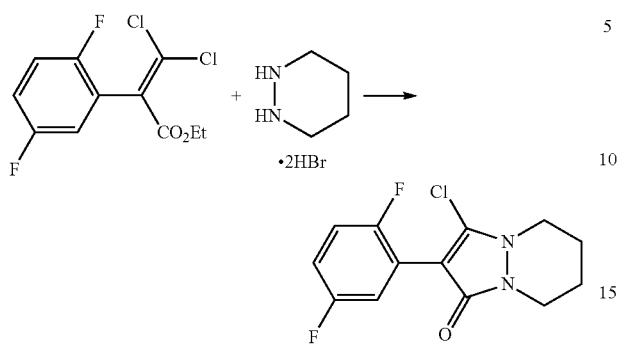

1,4-Dioxane (125 mL) and hexahydropyridazine dihydrobromide (13.64 g, 55.0 mmol) were added to ethyl 3,3-dichloro-2-(2,5-difluorophenyl)acrylate (14.05 g, 50.0 mmol), and triethylamine (23.0 mL, 165 mmol) was added thereto, followed by refluxing for 8 hours. After the reaction was completed, water (100 mL) was added to the reaction solution, and the resultant product was extracted with ethyl acetate (50 mL×3). The organic layer was dried over anhydrous magnesium sulfate, and concentrated under reduced pressure, whereby an orange oily crude product was obtained. This was purified by silica gel column chromatography (ethyl acetate:methanol=9:1), whereby 5-chloro-4-(2,5-difluorophenyl)-1,2-tetramethylene-4-pyrazolin-3-one (11.29 g, yield: 79%) was obtained as a white solid. $^{1}$H-NMR (400 MHz, CDCl$_{3}$): δ1.87-1.94 (m, 2H), 1.98-2.06 (m, 2H), 3.60-3.65 (m, 2H), 3.80-3.86 (m, 2H), 6.99 (dddd, J=10.8, 9.1, 7.3 and 3.2 Hz, 1H), 7.07 (ddd, J=9.1, 9.1 and 4.5 Hz, 1H), 7.24 (ddd, J=8.8, 5.5 and 3.2 Hz, 1H). $^{19}$F-NMR (376 MHz, CDCl$_{3}$): δ−119.2 (d, J=16.2 Hz, 1F), −117.6 (d, J=16.2 Hz, 1F).

Example-296

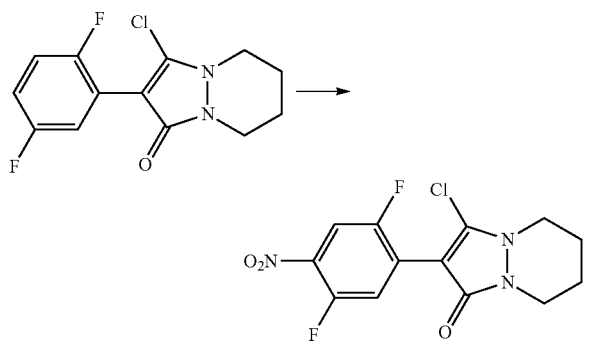

A mixed acid prepared from 69% nitric acid (548 mg, 6.0 mmol) and concentrated sulfuric acid (0.35 mL) was slowly added to a suspension of 5-chloro-4-(2,5-difluorophenyl)-1,2-tetramethylene-4-pyrazolin-3-one (1.42 g, 5.0 mmol) in concentrated sulfuric acid (5 mL) over 10 minutes under ice-cooling, followed by stirring at room temperature for 2 hours. After the reaction was completed, the reaction solution was poured into ice water (50 g), and the resultant product was extracted with chloroform (30 mL×3). The organic layer was washed with a saturated saline solution (30 mL), dried over magnesium sulfate, and concentrated under reduced pressure, whereby a crude product was obtained. This was purified by silica gel column chromatography (ethyl acetate), whereby 5-chloro-4-(2,5-difluoro-4-nitrophenyl)-1,2-tetramethylene-4-pyrazolin-3-one (858 mg, yield: 52%) was obtained as a yellow solid. $^{1}$H-NMR (400 MHz, CDCl$_{3}$): δ1.90-1.99 (m, 2H), 2.02-2.09 (m, 2H), 3.69-3.75 (m, 2H), 3.82-3.88 (m, 2H), 7.62 (dd, J=11.4 and 5.8 Hz, 1H), 7.87 (dd, J=9.1 and 6.3 Hz, 1H). $^{19}$F-NMR (376 MHz, CDCl$_{3}$): δ−122.1 (d, J=16.3 Hz, 1F), −112.0 (d, J=16.3 Hz, 1F).

Example-297

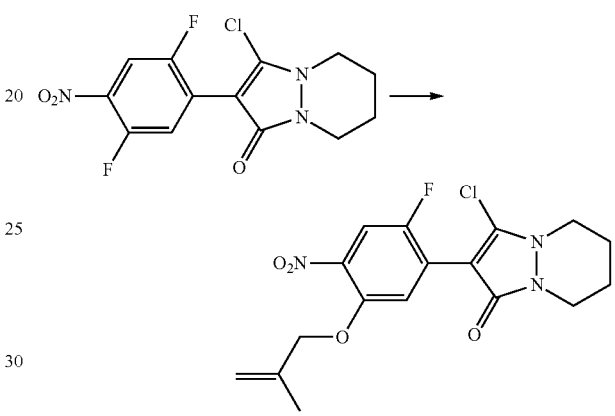

2-Methyl-2-propenol (0.10 mL, 1.2 mmol) and a 55% oil dispersion (53 mg, 1.2 mmol) of sodium hydride were added sequentially to a solution of 5-chloro-4-(2,5-difluoro-4-nitrophenyl)-1,2-tetramethylene-4-pyrazolin-3-one (330 mg, 1.0 mmol) in tetrahydrofuran (10 mL) under ice-cooling, followed by stirring at room temperature for 12 hours. After the reaction was completed, the reaction solution was poured into ice water (30 g), and the resultant product was extracted with chloroform (50 mL×3). The combined organic layer was washed with a saturated saline solution (50 mL), dried over magnesium sulfate, and concentrated under reduced pressure. The obtained crude product was purified by silica gel column chromatography (ethyl acetate), whereby 5-chloro-4-[2-fluoro-5-(methallyloxy)-4-nitrophenyl]-1,2-tetramethylene-4-pyrazolin-3-one (196 mg, yield: 51%) was obtained as a yellow solid. $^{1}$H-NMR (400 MHz, CDCl$_{3}$): δ1.84 (s, 3H), 1.89-1.98 (m, 2H), 2.00-2.09 (m, 2H), 3.66-3.73 (m, 2H), 3.82-3.88 (m, 2H), 4.57 (s, 2H), 5.03-5.18 (m, 2H), 7.37 (d, J=5.7 Hz, 1H), 7.72 (d, J=9.2 Hz, 1H). $^{19}$F-NMR (376 MHz, CDCl$_{3}$): δ−118.3 (s, 1F).

Example-298

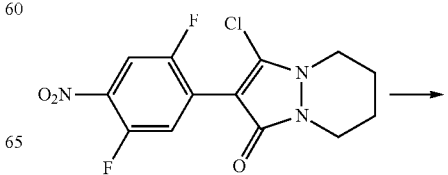

-continued

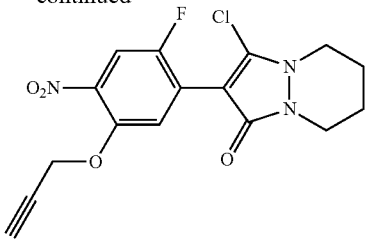

2-Propyn-1-ol (0.055 mL, 0.91 mmol) and a 55% oil dispersion (40 mg, 0.92 mmol) of sodium hydride were added sequentially to a solution of 5-chloro-4-(2,5-difluoro-4-nitrophenyl)-1,2-tetramethylene-4-pyrazolin-3-one (250 mg, 0.76 mmol) in tetrahydrofuran (4 mL) under ice-cooling, followed by stirring at room temperature for 30 minutes. After the reaction was completed, the reaction solution was poured into ice water (30 g), and the resultant product was extracted with chloroform (30 mL×3). The combined organic layer was washed with a saturated saline solution (50 mL), dried over magnesium sulfate, and concentrated under reduced pressure. The obtained crude product was purified by silica gel column chromatography (ethyl acetate), whereby 5-chloro-4-[2-fluoro-4-nitro-5-(propargyloxy)phenyl]-1,2-tetramethylene-4-pyrazolin-3-one (183 mg, yield: 66%) was obtained as a pale yellow solid. $^1$H-NMR (400 MHz, CDCl$_3$): δ1.90-1.98 (m, 2H), 2.01-2.09 (m, 2H), 2.60 (t, J=2.4 Hz, 1H), 3.68-3.73 (m, 2H), 3.82-3.89 (m, 2H), 4.86 (d, J=2.4 Hz, 2H), 7.51 (d, J=5.7 Hz, 1H), 7.73 (d, J=9.1 Hz, 1H). $^{19}$F-NMR (376 MHz, CDCl$_3$): δ−116.6 (s, 1F).

Example-299

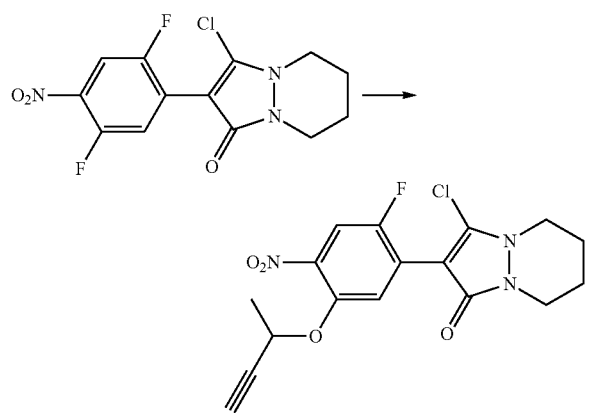

3-Butyn-2-ol (87 mg, 1.2 mmol) and a 55% oil dispersion (53 mg, 1.2 mmol) of sodium hydride were added sequentially to a solution of 5-chloro-4-(2,5-difluoro-4-nitrophenyl)-1,2-tetramethylene-4-pyrazolin-3-one (330 mg, 1.0 mmol) in tetrahydrofuran (10 mL) under ice-cooling, followed by stirring at room temperature for 12 hours. After the reaction was completed, the reaction solution was poured into ice water (30 g), and the resultant product was extracted with chloroform (30 mL×3). The combined organic layer was washed with a saturated saline solution (50 mL), dried over magnesium sulfate, and concentrated under reduced pressure. The obtained crude product was purified by silica gel column chromatography (ethyl acetate), whereby 5-chloro-4-[5-(1-butyn-3-yloxy)-2-fluoro-4-nitrophenyl]-1,2-tetramethylene-4-pyrazolin-3-one (295 mg, yield: 78%) was obtained as a pale yellow solid. $^1$H-NMR (400 MHz, CDCl$_3$): δ1.72 (d, J=6.6 Hz, 3H), 1.90-1.98 (m, 2H), 2.01-2.09 (m, 2H), 2.57 (t, J=2.1 Hz, 1H), 3.62-3.75 (m, 2H), 3.78-3.92 (m, 2H), 4.98 (qd, J=6.6 and 2.1 Hz, 1H), 7.56 (d, J=5.9 Hz, 1H), 7.69 (d, J=9.1 Hz, 1H). $^{19}$F-NMR (376 MHz, CDCl$_3$): δ−116.5 (s, 1F).

Example-300

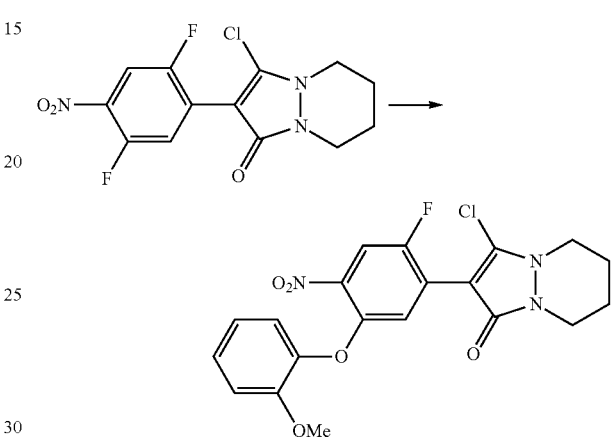

2-Methoxyphenol (150 mg, 1.2 mmol) and a 55% oil dispersion (53 mg, 1.2 mmol) of sodium hydride were added sequentially to a solution of 5-chloro-4-(2,5-difluoro-4-nitrophenyl)-1,2-tetramethylene-4-pyrazolin-3-one (330 mg, 1.0 mmol) in tetrahydrofuran (10 mL) under ice-cooling, followed by stirring at 50° C. for 18 hours. After the reaction was completed, the reaction solution was poured into ice water (30 g), and the resultant product was extracted with chloroform (30 mL×3). The combined organic layer was washed with a saturated saline solution (50 mL), dried over magnesium sulfate, and concentrated under reduced pressure. The obtained crude product was purified by silica gel column chromatography (ethyl acetate), whereby 5-chloro-4-[2-fluoro-5-(2-methoxyphenoxy)-4-nitrophenyl]-1,2-tetramethylene-4-pyrazolin-3-one (388 mg, yield: 89%) was obtained as a pale yellow solid. $^1$H-NMR (400 MHz, CDCl$_3$): δ1.84-1.91 (m, 2H), 1.95-2.03 (m, 2H), 3.60-3.64 (m, 2H), 3.74-3.79 (m, 2H), 3.80 (s, 3H), 6.92-7.02 (m, 1H), 7.07 (d, J=5.9 Hz, 1H), 7.08-7.11 (m, 2H), 7.14-7.20 (m, 1H), 7.79 (d, J=9.1 Hz, 1H). $^{19}$F-NMR (376 MHz, CDCl$_3$): δ−116.0 (s, 1F).

Example-301

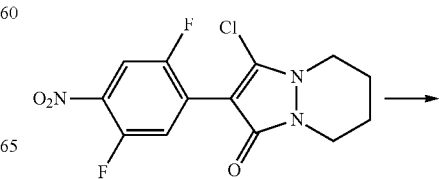

-continued

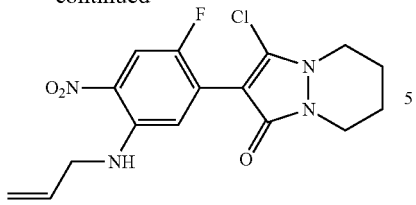

Allyl amine (1.05 g, 18.2 mmol) was added dropwise to a solution of 5-chloro-4-(2,5-difluoro-4-nitrophenyl)-1,2-tetramethylene-4-pyrazolin-3-one (2.00 g, 6.1 mmol) in tetrahydrofuran (30 mL) under ice-cooling. The mixed solution was stirred at room temperature for 24 hours. After the reaction was completed, the solvent was distilled off under reduced pressure. After water was added to the crude product, the produced precipitate was collected by filtration, washed with diethyl ether, and dried under reduced pressure, whereby 4-(5-allylamino-2-fluoro-4-nitrophenyl)-5-chloro-1,2-tetramethylene-4-pyrazolin-3-one (1.85 g, yield: 83%) was obtained as an orange solid. $^1$H-NMR (400 MHz, CDCl$_3$): δ1.88-1.98 (m, 2H), 2.00-2.09 (m, 2H), 3.64-3.74 (m, 2H), 3.80-3.89 (m, 2H), 3.94-4.04 (m, 2H), 5.21-5.38 (m, 2H), 5.89-6.03 (m, 1H), 7.08 (d, J=6.0 Hz, 1H), 7.96 (d, J=10.4 Hz, 1H), 8.06 (brs, 1H). $^{19}$F-NMR (376 MHz, CDCl$_3$): δ−125.6 (s, 1F).

Example-302

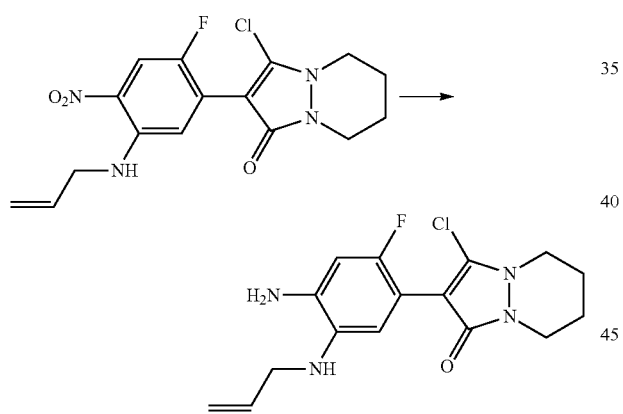

Water (0.72 g) and acetic acid (4.0 mL) were added to a solution of 4-(5-allylamino-2-fluoro-4-nitrophenyl)-5-chloro-1,2-tetramethylene-4-pyrazolin-3-one (1.47 g, 4.0 mmol) in ethyl acetate (20.0 mL), and reduced iron (2.23 g, 40.0 mmol) was added thereto, followed by stirring at 80° C. for 3 hours. After the reaction was completed, the reaction solution was cooled to room temperature, then, the insoluble matters were separated by filtration, and the solid was washed with ethyl acetate. The combined organic layer was washed with a saturated sodium hydrogencarbonate aqueous solution (20 mL×2), and a saturated saline solution (50 mL). The organic layer was dried over magnesium sulfate, concentrated under reduced pressure, and dried under reduced pressure, whereby 4-(5-allylamino-4-amino-2-fluorophenyl)-5-chloro-1,2-tetramethylene-4-pyrazolin-3-one (1.16 g, yield: 86%) was obtained as a pale yellow solid. $^1$H-NMR (400 MHz, CDCl$_3$): δ1.83-1.91 (m, 2H), 1.95-2.03 (m, 2H), 3.44-3.87 (m, 8H), 5.12-5.36 (m, 2H), 5.94-6.09 (m, 1H), 6.50 (d, J=10.7 Hz, 1H), 6.75 (d, J=6.7 Hz, 1H). $^{19}$F-NMR (376 MHz, CDCl$_3$): δ−122.6 (s, 1F).

Example-303

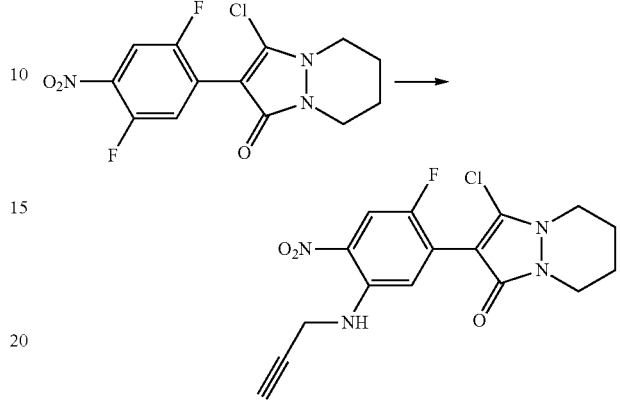

5-Chloro-4-(2,5-difluoro-4-nitrophenyl)-1,2-tetramethylene-4-pyrazolin-3-one (1.47 g, 4.45 mmol) was dissolved in anhydrous tetrahydrofuran (22 mL), and propargylamine (776 mg, 13.4 mmol) was added thereto under ice-cooling, followed by stirring at room temperature for 24 hours. During stirring, anhydrous tetrahydrofuran (22 mL), propargylamine (776 mg, 13.4 mmol), and N,N-diisopropylethylamine (575 mg, 0.76 mmol) were additionally added thereto, followed by stirring for 4 days and 22 hours in total. After the reaction was completed, the solvent was distilled off, and the resultant product was filtered with suction, washed with water and diethyl ether, and dried, whereby 5-chloro-4-[2-fluoro-4-nitro-5-(propargyl amino)phenyl]-1,2-tetramethylene-4-pyrazolin-3-one (1.51 g, yield: 93%) was obtained as a dark brown solid material. $^1$H-NMR (400 MHz, CDCl$_3$): δ1.91-1.96 (m, 2H), 2.02-2.07 (m, 2H), 2.30 (t, J=2.40 Hz, 1H), 3.68-3.71 (m, 2H), 3.84-3.87 (m, 2H), 4.14 (dd, J=2.40 and 5.60 Hz, 2H), 7.18 (d, J=6.0 Hz, 1H), 7.98 (d, J=10.0 Hz, 1H), 8.02 (brs, 1H). $^{19}$F-NMR (376 MHz, CDCl$_3$): δ−124 (s, 1F).

Example-304

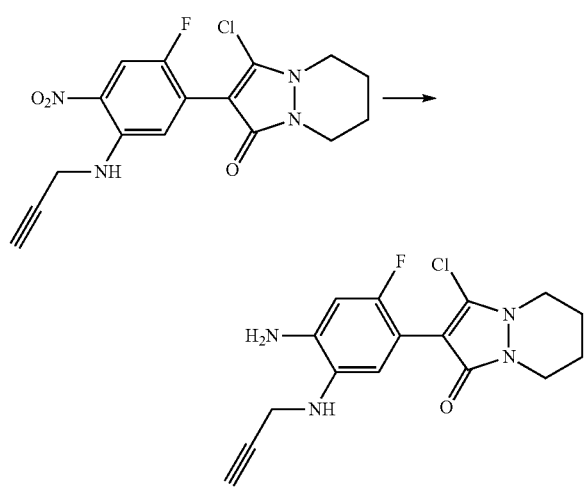 [SMILES: C#CCNc1cc(-c2c(Cl)n3n(c2=O)CCCC3)c(F)cc1[N+](=O)[O-] ; C#CCNc1cc(-c2c(Cl)n3n(c2=O)CCCC3)c(F)cc1N]

Ethyl acetate (20 mL), acetic acid (4.4 mL), and water (0.72 mL) were added to 5-chloro-4-[2-fluoro-4-nitro-5-(propargyl amino)phenyl]-1,2-tetramethylene-4-pyrazolin-3-one (1.46 g, 4.00 mmol), and reduced iron (2.23 g, 40.0 mmol) was added thereto, followed by stirring at 80° C. for 20 hours. After the reaction was completed, the resultant product was filtered using Celite, and washed with water and ethyl acetate, and the filtrate was extracted with ethyl acetate. The organic layer was washed with a saturated sodium hydrogencarbonate aqueous solution, dried over anhydrous magnesium sulfate, and concentrated under reduced pressure. The obtained crude product was eluted and purified by silica gel column chromatography (ethyl acetate:methanol=10:1), whereby 4-[4-amino-2-fluoro-5-(propargyl amino)phenyl]-5-chloro-1,2-tetramethylene-4-pyrazolin-3-one (803 mg, yield: 60%) was obtained as an orange solid material. $^{1}$H-NMR (400 MHz, CDCl$_3$): δ1.85-1.90 (m, 2H), 1.97-2.03 (m, 2H), 2.27 (t, J=2.40 Hz, 1H), 3.18 (brs, 1H), 3.54-3.57 (m, 2H), 3.72 (brs, 2H), 3.81-3.84 (m, 2H), 3.87 (brs, 2H), 6.51 (d, J=10.8 Hz, 1H), 6.86 (d, J=6.80H z, 1H). $^{19}$F-NMR (376 MHz, CDCl$_3$): δ−121 (s, 1F).

Specific examples of the bicyclic pyrazolinone derivative (1) of the present invention which can be prepared by a method according to the methods shown in Examples and Reference Examples described above are shown in Table-1; however, the present invention is not limited thereto.

TABLE 1

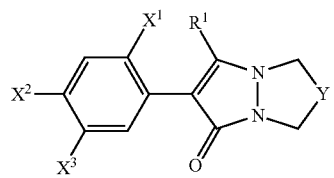

(1)

Bicyclic pyrazolinone derivative of the present invention

| Compound No. | Example No. | R$^1$ | X$^1$ | X$^2$ | X$^3$ | Y |
|---|---|---|---|---|---|---|
| 1-1 | 1 | F | H | F | H | (CH$_2$)$_2$ |
| 1-2 |   | F | H | F | H | (CH$_2$)$_2$ |
| 1-3 | 2 | F | H | F | H | CH$_2$OCH$_2$ |
| 1-4 |   | F | H | Cl | H | CH$_2$ |
| 1-5 |   | F | H | Cl | H | CHF |
| 1-6 | 3 | F | H | Cl | H | (CH$_2$)$_2$ |
| 1-7 |   | F | H | Cl | H | (CH$_2$)$_3$ |
| 1-8 |   | F | H | Cl | H | CH$_2$O |
| 1-9 |   | F | H | Cl | H | OCH$_2$ |
| 1-10 | 4 | F | H | Cl | H | CH$_2$OCH$_2$ |
| 1-11 |   | F | F | F | H | CH$_2$ |
| 1-12 |   | F | F | F | H | CHF |
| 1-13 | 5 | F | F | F | H | (CH$_2$)$_2$ |
| 1-14 |   | F | F | F | H | (CH$_2$)$_3$ |
| 1-15 |   | F | F | F | H | CH$_2$O |
| 1-16 |   | F | F | F | H | OCH$_2$ |
| 1-17 |   | F | F | F | H | CH$_2$OCH$_2$ |
| 1-18 |   | F | Cl | Cl | H | CH$_2$ |
| 1-19 |   | F | Cl | Cl | H | CHF |
| 1-20 | 6 | F | Cl | Cl | H | (CH$_2$)$_2$ |
| 1-21 |   | F | Cl | Cl | H | (CH$_2$)$_3$ |
| 1-22 |   | F | Cl | Cl | H | CH$_2$O |
| 1-23 |   | F | Cl | Cl | H | OCH$_2$ |
| 1-24 |   | F | Cl | Cl | H | CH$_2$OCH$_2$ |
| 1-25 |   | Cl | H | F | H | CH$_2$ |
| 1-26 |   | Cl | H | F | H | CHF |
| 1-27 | 7 | Cl | H | F | H | (CH$_2$)$_2$ |
| 1-28 |   | Cl | H | F | H | (CH$_2$)$_3$ |
| 1-29 |   | Cl | H | F | H | CH$_2$O |
| 1-30 |   | Cl | H | F | H | OCH$_2$ |
| 1-31 |   | Cl | H | F | H | CH$_2$OCH$_2$ |
| 1-32 |   | Cl | H | F | HO | CH$_2$ |
| 1-33 |   | Cl | H | F | HO | CHF |
| 1-34 | 8 | Cl | H | F | HO | (CH$_2$)$_2$ |
| 1-35 |   | Cl | H | F | HO | (CH$_2$)$_3$ |
| 1-36 |   | Cl | H | F | HO | CH$_2$O |
| 1-37 |   | Cl | H | F | HO | OCH$_2$ |
| 1-38 |   | Cl | H | F | HO | CH$_2$OCH$_2$ |
| 1-39 | 8 | Cl | H | F | CH$_3$O | (CH$_2$)$_2$ |
| 1-40 | 9 | Cl | H | F | (CH$_3$)$_2$CHO | (CH$_2$)$_2$ |
| 1-41 | 10 | Cl | H | F | HC≡CCH$_2$O | (CH$_2$)$_2$ |
| 1-42 |   | Cl | H | F | HC≡CCH$_2$O | (CH$_2$)$_3$ |
| 1-43 | 11 | Cl | H | Cl | HO | (CH$_2$)$_2$ |
| 1-44 | 11 | Cl | H | Cl | CH$_3$O | (CH$_2$)$_2$ |
| 1-45 | 259 | Cl | H | Cl | CH$_3$O | (CH$_2$)$_3$ |

TABLE 1-continued

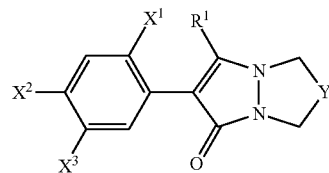

Bicyclic pyrazolinone derivative of the present invention

| Compound No. | Example No. | $R^1$ | $X^1$ | $X^2$ | $X^3$ | Y |
|---|---|---|---|---|---|---|
| 1-46 | 262 | Cl | H | Cl | $CH_3O$ | $CH_2OCH_2$ |
| 1-47 | 12 | Cl | H | Cl | $CH_3CH_2O$ | $(CH_2)_2$ |
| 1-48 | 13 | Cl | H | Cl | $CH_3CH_2CH_2O$ | $(CH_2)_2$ |
| 1-49 | 14 | Cl | H | Cl | $(CH_3)_2CHO$ | $(CH_2)_2$ |
| 1-50 | | Cl | H | Cl | $(CH_3)_2CHO$ | $(CH_2)_3$ |
| 1-51 | | Cl | H | Cl | $(CH_3)_2CHO$ | $CH_2OCH_2$ |
| 1-52 | 15 | Cl | H | Cl | cyclo-$C_5H_9O$ | $(CH_2)_2$ |
| 1-53 | | Cl | H | Cl | cyclo-$C_5H_9O$ | $(CH_2)_3$ |
| 1-54 | | Cl | H | Cl | cyclo-$C_5H_9O$ | $CH_2OCH_2$ |
| 1-55 | 16 | Cl | H | Cl | cyclo-$C_4H_7CH_2O$ | $(CH_2)_2$ |
| 1-56 | 17 | Cl | H | Cl | $CH_3OCOCH(CH_3)O$ | $(CH_2)_2$ |
| 1-57 | 18 | Cl | H | Cl | $N{\equiv}CCH_2O$ | $(CH_2)_2$ |
| 1-58 | 19 | Cl | H | Cl | $C_6H_5CH_2O$ | $(CH_2)_2$ |
| 1-59 | 20 | Cl | H | Cl | $H_2C{=}CHCH_2O$ | $(CH_2)_2$ |
| 1-60 | | Cl | H | Cl | $HC{\equiv}CCH_2O$ | $CH_2$ |
| 1-61 | | Cl | H | Cl | $HC{\equiv}CCH_2O$ | CHF |
| 1-62 | 21 | Cl | H | Cl | $HC{\equiv}CCH_2O$ | $(CH_2)_2$ |
| 1-63 | 261 | Cl | H | Cl | $HC{\equiv}CCH_2O$ | $(CH_2)_3$ |
| 1-64 | | Cl | H | Cl | $HC{\equiv}CCH_2O$ | $CH_2O$ |
| 1-65 | | Cl | H | Cl | $HC{\equiv}CCH_2O$ | $OCH_2$ |
| 1-66 | 264 | Cl | H | Cl | $HC{\equiv}CCH_2O$ | $CH_2OCH_2$ |
| 1-67 | 22 | Cl | H | Cl | $HC{\equiv}CCH(CH_3)O$ | $(CH_2)_2$ |
| 1-68 | | Cl | H | Cl | $HC{\equiv}CCH(CH_3)O$ | $(CH_2)_3$ |
| 1-69 | | Cl | H | Cl | $HC{\equiv}CCH(CH_3)O$ | $CH_2OCH_2$ |
| 1-70 | 23 | Cl | H | Cl | $(CH_3)_3COO$ | $(CH_2)_2$ |
| 1-71 | 24 | Cl | H | Cl | $ClCH_2SO_2O$ | $(CH_2)_2$ |
| 1-72 | 25 | Cl | H | Cl | $(CH_3)_2CHOCOO$ | $(CH_2)_2$ |
| 1-73 | | Cl | F | F | H | $CH_2$ |
| 1-74 | | Cl | F | F | H | CHF |
| 1-75 | 26, 27 | Cl | F | F | H | $(CH_2)_2$ |
| 1-76 | 286 | Cl | F | F | H | $(CH_2)_3$ |
| 1-77 | | Cl | F | F | H | $CH_2O$ |
| 1-78 | | Cl | F | F | H | $OCH_2$ |
| 1-79 | 288 | Cl | F | F | H | $CH_2OCH_2$ |
| 1-80 | | Cl | F | F | HO | $CH_2$ |
| 1-81 | | Cl | F | F | HO | CHF |
| 1-82 | 29 | Cl | F | F | HO | $(CH_2)_2$ |
| 1-83 | 266 | Cl | F | F | HO | $(CH_2)_3$ |
| 1-84 | | Cl | F | F | HO | $CH_2O$ |
| 1-85 | | Cl | F | F | HO | $OCH_2$ |
| 1-86 | 269 | Cl | F | F | HO | $CH_2OCH_2$ |
| 1-87 | 28 | Cl | F | F | $CH_3O$ | $(CH_2)_2$ |
| 1-88 | 265 | Cl | F | F | $CH_3O$ | $(CH_2)_3$ |
| 1-89 | 268 | Cl | F | F | $CH_3O$ | $CH_2OCH_2$ |
| 1-90 | 30 | Cl | F | F | $CH_3OCH_2O$ | $(CH_2)_2$ |
| 1-91 | | Cl | F | F | $CH_3OCH_2O$ | $(CH_2)_3$ |
| 1-92 | | Cl | F | F | $CH_3OCH_2O$ | $CH_2OCH_2$ |
| 1-93 | 31 | Cl | F | F | $(CH_3)_2CHCH_2CH_2O$ | $(CH_2)_2$ |
| 1-94 | | Cl | F | F | $(CH_3)_2CHCH_2CH_2O$ | $(CH_2)_3$ |
| 1-95 | | Cl | F | F | $(CH_3)_2CHCH_2CH_2O$ | $CH_2OCH_2$ |
| 1-96 | 32 | Cl | F | F | $(CH_3)_2CHCH_2O$ | $(CH_2)_2$ |
| 1-97 | 33 | Cl | F | F | $CH_3CH_2OCOCH(CH_3CH_2O)O$ | $(CH_2)_2$ |
| 1-98 | 34 | Cl | F | F | cyclo-$C_5H_9O$ | $(CH_2)_2$ |
| 1-99 | | Cl | F | F | $H_2C{=}CHCH_2O$ | $CH_2$ |
| 1-100 | | Cl | F | F | $H_2C{=}CHCH_2O$ | CHF |
| 1-101 | 35 | Cl | F | F | $H_2C{=}CHCH_2O$ | $(CH_2)_2$ |
| 1-102 | | Cl | F | F | $H_2C{=}CHCH_2O$ | $(CH_2)_3$ |
| 1-103 | | Cl | F | F | $H_2C{=}CHCH_2O$ | $CH_2O$ |
| 1-104 | | Cl | F | F | $H_2C{=}CHCH_2O$ | $OCH_2$ |
| 1-105 | | Cl | F | F | $H_2C{=}CHCH_2O$ | $CH_2OCH_2$ |

TABLE 1-continued

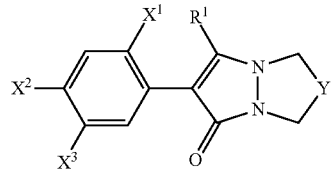

Bicyclic pyrazolinone derivative of the present invention

| Compound No. | Example No. | $R^1$ | $X^1$ | $X^2$ | $X^3$ | Y |
|---|---|---|---|---|---|---|
| 1-106 | 36 | Cl | F | F | $H_2C=C(CH_3)CH_2O$ | $(CH_2)_2$ |
| 1-107 | | Cl | F | F | $H_2C=C(CH_3)CH_2O$ | $(CH_2)_3$ |
| 1-108 | | Cl | F | F | $H_2C=C(CH_3)CH_2O$ | $CH_2OCH_2$ |
| 1-109 | 37 | Cl | F | F | $H_2C=C(CH_3)CH_2O$ | $(CH_2)_2$ |
| 1-110 | | Cl | F | F | $H_2C=C(CH_3)CH_2O$ | $(CH_2)_3$ |
| 1-111 | | Cl | F | F | $H_2C=C(CH_3)CH_2O$ | $CH_2OCH_2$ |
| 1-112 | 38 | Cl | F | F | 2-Cyclohexenyloxy | $(CH_2)_2$ |
| 1-113 | 39 | Cl | F | F | $HC\equiv CCH_2O$ | $(CH_2)_2$ |
| 1-114 | 40 | Cl | F | F | $HC\equiv CCH(CH_3)O$ | $(CH_2)_2$ |
| 1-115 | 41 | Cl | F | F | $H_3CC\equiv CCH_2O$ | $(CH_2)_2$ |
| 1-116 | | Cl | F | F | $NO_2$ | $CH_2$ |
| 1-117 | | Cl | F | F | $NO_2$ | $CHF$ |
| 1-118 | 42, 43 | Cl | F | F | $NO_2$ | $(CH_2)_2$ |
| 1-119 | 287 | Cl | F | F | $NO_2$ | $(CH_2)_3$ |
| 1-120 | | Cl | F | F | $NO_2$ | $CH_2O$ |
| 1-121 | | Cl | F | F | $NO_2$ | $OCH_2$ |
| 1-122 | 289 | Cl | F | F | $NO_2$ | $CH_2OCH_2$ |
| 1-123 | | Cl | F | Cl | H | $CH_2$ |
| 1-124 | | Cl | F | Cl | H | $CHF$ |
| 1-125 | 44 | Cl | F | Cl | H | $(CH_2)_2$ |
| 1-126 | | Cl | F | Cl | H | $(CH_2)_3$ |
| 1-127 | | Cl | F | Cl | H | $CH_2O$ |
| 1-128 | | Cl | F | Cl | H | $OCH_2$ |
| 1-129 | 45 | Cl | F | Cl | H | $CH_2OCH_2$ |
| 1-130 | 45 | Cl | F | Cl | $CH_3$ | $(CH_2)_2$ |
| 1-131 | | Cl | F | Cl | $CH_3$ | $(CH_2)_3$ |
| 1-132 | | Cl | F | Cl | $CH_3$ | $CH_2OCH_2$ |
| 1-133 | | Cl | F | Cl | HO | $CH_2$ |
| 1-134 | | Cl | F | Cl | HO | $CHF$ |
| 1-135 | 47 | Cl | F | Cl | HO | $(CH_2)_2$ |
| 1-136 | 48 | Cl | F | Cl | HO | $(CH_2)_3$ |
| 1-137 | | Cl | F | Cl | HO | $CH_2O$ |
| 1-138 | | Cl | F | Cl | HO | $OCH_2$ |
| 1-139 | 50 | Cl | F | Cl | HO | $CH_2OCH_2$ |
| 1-140 | 47 | Cl | F | Cl | $CH_3O$ | $(CH_2)_2$ |
| 1-141 | 48 | Cl | F | Cl | $CH_3O$ | $(CH_2)_3$ |
| 1-142 | 49 | Cl | F | Cl | $CH_3O$ | $CH_2OCH_2$ |
| 1-143 | 51 | Cl | F | Cl | $CHF_2O$ | $(CH_2)_2$ |
| 1-144 | | Cl | F | Cl | $CHF_2O$ | $(CH_2)_3$ |
| 1-145 | | Cl | F | Cl | $CHF_2O$ | $CH_2OCH_2$ |
| 1-146 | 52 | Cl | F | Cl | $CH_3CH_2O$ | $(CH_2)_2$ |
| 1-147 | | Cl | F | Cl | $CH_3CH_2O$ | $(CH_2)_3$ |
| 1-148 | | Cl | F | Cl | $CH_3CH_2O$ | $CH_2OCH_2$ |
| 1-149 | | Cl | F | Cl | $(CH_3)_2CHO$ | $CH_2$ |
| 1-150 | | Cl | F | Cl | $(CH_3)_2CHO$ | $CHF$ |
| 1-151 | 53 | Cl | F | Cl | $(CH_3)_2CHO$ | $(CH_2)_2$ |
| 1-152 | | Cl | F | Cl | $(CH_3)_2CHO$ | $(CH_2)_3$ |
| 1-153 | | Cl | F | Cl | $(CH_3)_2CHO$ | $CH_2O$ |
| 1-154 | | Cl | F | Cl | $(CH_3)_2CHO$ | $OCH_2$ |
| 1-155 | | Cl | F | Cl | $(CH_3)_2CHO$ | $CH_2OCH_2$ |
| 1-156 | 54 | Cl | F | Cl | $(CH_3)_2CHCH_2O$ | $(CH_2)_2$ |
| 1-157 | | Cl | F | Cl | $(CH_3)_2CHCH_2O$ | $(CH_2)_3$ |
| 1-158 | | Cl | F | Cl | $(CH_3)_2CHCH_2O$ | $CH_2OCH_2$ |
| 1-159 | 55 | Cl | F | Cl | $(CH_3)_2CHCH_2CH_2O$ | $(CH_2)_2$ |
| 1-160 | | Cl | F | Cl | $(CH_3)_2CHCH_2CH_2O$ | $(CH_2)_3$ |
| 1-161 | | Cl | F | Cl | $(CH_3)_2CHCH_2CH_2O$ | $CH_2OCH_2$ |
| 1-162 | 56 | Cl | F | Cl | $CH_3OCOCH_2O$ | $(CH_2)_2$ |
| 1-163 | 57 | Cl | F | Cl | $CH_3CH_2OCOCH_2O$ | $(CH_2)_2$ |
| 1-164 | 58 | Cl | F | Cl | $(CH_3)_2CHOCOCH_2O$ | $(CH_2)_2$ |
| 1-165 | 59 | Cl | F | Cl | $(CH_3)_3COCOCH_2O$ | $(CH_2)_2$ |
| 1-166 | 60 | Cl | F | Cl | $CH_3OCOCH(CH_3)O$ | $(CH_2)_2$ |
| 1-167 | 61 | Cl | F | Cl | $CH_3CH_2OCOCH(CH_3CH_2O)O$ | $(CH_2)_2$ |
| 1-168 | 62 | Cl | F | Cl | $H_2C=CHCH_2OCOCH_2O$ | $(CH_2)_2$ |
| 1-169 | | Cl | F | Cl | $N\equiv CCH_2O$ | $CH_2$ |
| 1-170 | | Cl | F | Cl | $N\equiv CCH_2O$ | $CHF$ |

TABLE 1-continued

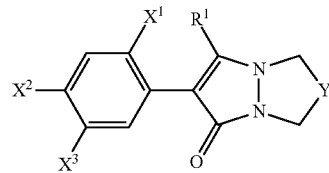

Bicyclic pyrazolinone derivative of the present invention

| Compound No. | Example No. | R¹ | X¹ | X² | X³ | Y |
|---|---|---|---|---|---|---|
| 1-171 | 63 | Cl | F | Cl | N≡CCH$_2$O | (CH$_2$)$_2$ |
| 1-172 | | Cl | F | Cl | N≡CCH$_2$O | (CH$_2$)$_3$ |
| 1-173 | | Cl | F | Cl | N≡CCH$_2$O | CH$_2$O |
| 1-174 | | Cl | F | Cl | N≡CCH$_2$O | OCH$_2$ |
| 1-175 | | Cl | F | Cl | N≡CCH$_2$O | CH$_2$OCH$_2$ |
| 1-176 | 64 | Cl | F | Cl | cyclo-C$_3$H$_5$CH$_2$O | (CH$_2$)$_2$ |
| 1-177 | | Cl | F | Cl | cyclo-C$_3$H$_5$CH$_2$O | (CH$_2$)$_3$ |
| 1-178 | | Cl | F | Cl | cyclo-C$_3$H$_5$CH$_2$O | CH$_2$OCH$_2$ |
| 1-179 | | Cl | F | Cl | cyclo-C$_5$H$_9$O | CH$_2$ |
| 1-180 | | Cl | F | Cl | cyclo-C$_5$H$_9$O | CHF |
| 1-181 | 65 | Cl | F | Cl | cyclo-C$_5$H$_9$O | (CH$_2$)$_2$ |
| 1-182 | 66 | Cl | F | Cl | cyclo-C$_5$H$_9$O | (CH$_2$)$_3$ |
| 1-183 | | Cl | F | Cl | cyclo-C$_5$H$_9$O | CH$_2$O |
| 1-184 | | Cl | F | Cl | cyclo-C$_5$H$_9$O | OCH$_2$ |
| 1-185 | | Cl | F | Cl | cyclo-C$_5$H$_9$O | CH$_2$OCH$_2$ |
| 1-186 | 67 | Cl | F | Cl | cyclo-C$_5$H$_9$CH$_2$O | (CH$_2$)$_2$ |
| 1-187 | | Cl | F | Cl | cyclo-C$_5$H$_9$CH$_2$O | (CH$_2$)$_3$ |
| 1-188 | 68 | Cl | F | Cl | cyclo-C$_6$H$_{11}$CH$_2$O | (CH$_2$)$_2$ |
| 1-189 | | Cl | F | Cl | cyclo-C$_6$H$_{11}$CH$_2$O | (CH$_2$)$_3$ |
| 1-190 | | Cl | F | Cl | 2-F—C$_6$H$_4$CH$_2$O | (CH$_2$)$_2$ |
| 1-191 | | Cl | F | Cl | 3-F—C$_6$H$_4$CH$_2$O | (CH$_2$)$_2$ |
| 1-192 | 69 | Cl | F | Cl | 4-F—C$_6$H$_4$CH$_2$O | (CH$_2$)$_2$ |
| 1-193 | | Cl | F | Cl | 2-Cl—C$_6$H$_4$CH$_2$O | (CH$_2$)$_2$ |
| 1-194 | | Cl | F | Cl | 3-Cl—C$_6$H$_4$CH$_2$O | (CH$_2$)$_2$ |
| 1-195 | | Cl | F | Cl | 4-Cl—C$_6$H$_4$CH$_2$O | (CH$_2$)$_2$ |
| 1-196 | | Cl | F | Cl | 2-CF$_3$—C$_6$H$_4$CH$_2$O | (CH$_2$)$_2$ |
| 1-197 | | Cl | F | Cl | 3-CF$_3$—C$_6$H$_4$CH$_2$O | (CH$_2$)$_2$ |
| 1-198 | | Cl | F | Cl | 4-CF$_3$—C$_6$H$_4$CH$_2$O | (CH$_2$)$_2$ |
| 1-199 | | Cl | F | Cl | H$_2$C=CHCH$_2$O | CH$_2$ |
| 1-200 | | Cl | F | Cl | H$_2$C=CHCH$_2$O | CHF |
| 1-201 | 70 | Cl | F | Cl | H$_2$C=CHCH$_2$O | (CH$_2$)$_2$ |
| 1-202 | | Cl | F | Cl | H$_2$C=CHCH$_2$O | (CH$_2$)$_3$ |
| 1-203 | | Cl | F | Cl | H$_2$C=CHCH$_2$O | CH$_2$O |
| 1-204 | | Cl | F | Cl | H$_2$C=CHCH$_2$O | OCH$_2$ |
| 1-205 | | Cl | F | Cl | H$_2$C=CHCH$_2$O | CH$_2$OCH$_2$ |
| 1-206 | 71 | Cl | F | Cl | H$_2$C=CHCF$_2$O | (CH$_2$)$_2$ |
| 1-207 | | Cl | F | Cl | H$_2$C=CHCF$_2$O | (CH$_2$)$_3$ |
| 1-208 | | Cl | F | Cl | H$_2$C=CHCF$_2$O | CH$_2$OCH$_2$ |
| 1-209 | 72 | Cl | F | Cl | CH$_3$CH=CHCH$_2$O | (CH$_2$)$_2$ |
| 1-210 | | Cl | F | Cl | CH$_3$CH=CHCH$_2$O | (CH$_2$)$_3$ |
| 1-211 | | Cl | F | Cl | CH$_3$CH=CHCH$_2$O | CH$_2$OCH$_2$ |
| 1-212 | | Cl | F | Cl | H$_2$C=C(CH$_3$)CH$_2$O | CH$_2$ |
| 1-213 | | Cl | F | Cl | H$_2$C=C(CH$_3$)CH$_2$O | CHF |
| 1-214 | 73 | Cl | F | Cl | H$_2$C=C(CH$_3$)CH$_2$O | (CH$_2$)$_2$ |
| 1-215 | | Cl | F | Cl | H$_2$C=C(CH$_3$)CH$_2$O | (CH$_2$)$_3$ |
| 1-216 | | Cl | F | Cl | H$_2$C=C(CH$_3$)CH$_2$O | CH$_2$O |
| 1-217 | | Cl | F | Cl | H$_2$C=C(CH$_3$)CH$_2$O | OCH$_2$ |
| 1-218 | | Cl | F | Cl | H$_2$C=C(CH$_3$)CH$_2$O | CH$_2$OCH$_2$ |
| 1-219 | 74 | Cl | F | Cl | (CH$_3$)$_2$C=CHCH$_2$O | (CH$_2$)$_2$ |
| 1-220 | | Cl | F | Cl | (CH$_3$)$_2$C=CHCH$_2$O | (CH$_2$)$_3$ |
| 1-221 | | Cl | F | Cl | (CH$_3$)$_2$C=CHCH$_2$O | CH$_2$OCH$_2$ |
| 1-222 | 75 | Cl | F | Cl | H$_2$C=CHCH$_2$CH$_2$O | (CH$_2$)$_2$ |
| 1-223 | | Cl | F | Cl | H$_2$C=CHCH$_2$CH$_2$O | (CH$_2$)$_3$ |
| 1-224 | | Cl | F | Cl | H$_2$C=CHCH$_2$CH$_2$O | CH$_2$OCH$_2$ |
| 1-225 | | Cl | F | Cl | 2-F—C$_6$H$_4$CH=CHCH$_2$O | (CH$_2$)$_3$ |
| 1-226 | 76 | Cl | F | Cl | 4-F—C$_6$H$_4$CH=CHCH$_2$O | (CH$_2$)$_2$ |
| 1-227 | | Cl | F | Cl | 4-F—C$_6$H$_4$CH=CHCH$_2$O | (CH$_2$)$_3$ |
| 1-228 | 77 | Cl | F | Cl | H$_2$C=C(3-Cl—C$_6$H$_4$)CCH$_2$O | (CH$_2$)$_2$ |
| 1-229 | | Cl | F | Cl | H$_2$C=C(4-Cl—C$_6$H$_4$)CCH$_2$O | (CH$_2$)$_3$ |
| 1-230 | 78 | Cl | F | Cl | H$_2$C=C(2,3-F$_2$-4-CH$_3$CH$_2$O—C$_6$H$_2$)CH$_2$O | (CH$_2$)$_2$ |
| 1-231 | | Cl | F | Cl | 2-Cyclopentenyloxy | (CH$_2$)$_2$ |
| 1-232 | 79 | Cl | F | Cl | 2-Cyclohexenyloxy | (CH$_2$)$_2$ |
| 1-233 | 80 | Cl | F | Cl | glycidyloxy | (CH$_2$)$_2$ |
| 1-234 | | Cl | F | Cl | glycidyloxy | (CH$_2$)$_3$ |
| 1-235 | | Cl | F | Cl | glycidyloxy | CH$_2$OCH$_2$ |

TABLE 1-continued

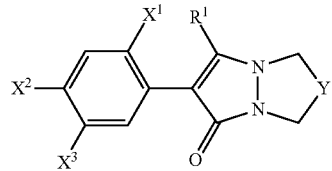

Bicyclic pyrazolinone derivative of the present invention

| Compound No. | Example No. | $R^1$ | $X^1$ | $X^2$ | $X^3$ | Y |
|---|---|---|---|---|---|---|
| 1-236 |  | Cl | F | Cl | HC≡CCH$_2$O | CH$_2$ |
| 1-237 |  | Cl | F | Cl | HC≡CCH$_2$O | CHF |
| 1-238 | 81 | Cl | F | Cl | HC≡CCH$_2$O | (CH$_2$)$_2$ |
| 1-239 | 82 | Cl | F | Cl | HC≡CCH$_2$O | (CH$_2$)$_3$ |
| 1-240 |  | Cl | F | Cl | HC≡CCH$_2$O | CH$_2$O |
| 1-241 |  | Cl | F | Cl | HC≡CCH$_2$O | OCH$_2$ |
| 1-242 | 83 | Cl | F | Cl | HC≡CCH$_2$O | CH$_2$OCH$_2$ |
| 1-243 | 84 | Cl | F | Cl | HC≡CCH(CH$_3$)O | (CH$_2$)$_2$ |
| 1-244 |  | Cl | F | Cl | HC≡CCH(CH$_3$)O | (CH$_2$)$_3$ |
| 1-245 | 278 | Cl | F | Cl | HC≡CCH(CH$_3$)O | CH$_2$OCH$_2$ |
| 1-246 | 85 | Cl | F | Cl | H$_3$CC≡CCH$_2$O | (CH$_2$)$_2$ |
| 1-247 |  | Cl | F | Cl | H$_3$CC≡CCH$_2$O | (CH$_2$)$_3$ |
| 1-248 |  | Cl | F | Cl | H$_3$CC≡CCH$_2$O | CH$_2$OCH$_2$ |
| 1-249 | 86 | Cl | F | Cl | CH$_3$CH$_2$OCOO | (CH$_2$)$_2$ |
| 1-250 | 87 | Cl | F | Cl | (CH$_3$)$_2$CHCH$_2$OCOO | (CH$_2$)$_2$ |
| 1-251 | 88 | Cl | F | Cl | 4-F—C$_6$H$_4$COO | (CH$_2$)$_2$ |
| 1-252 | 89 | Cl | F | Cl | 4-Cl—C$_6$H$_4$COO | (CH$_2$)$_2$ |
| 1-253 | 90 | Cl | F | Cl | CF$_3$SO$_2$O | (CH$_2$)$_2$ |
| 1-254 | 91 | Cl | F | Cl | 2-Cl-6-F-4-CF$_3$—C$_6$H$_2$O | (CH$_2$)$_2$ |
| 1-255 |  | Cl | F | Cl | 2,6-Cl$_2$-4-CF$_3$—C$_6$H$_2$O | (CH$_2$)$_2$ |
| 1-256 |  | Cl | F | Cl | 2,4-(CF$_3$)$_2$—C$_6$H$_2$O | (CH$_2$)$_2$ |
| 1-257 | 92 | Cl | F | Cl | CH$_3$OCOC(Cl)HCH$_2$ | (CH$_2$)$_2$ |
| 1-258 |  | Cl | F | Cl | CH$_3$OCOC(Cl)HCH$_2$ | (CH$_2$)$_3$ |
| 1-259 |  | Cl | F | Cl | CH$_3$OCOC(Cl)HCH$_2$ | CH$_2$OCH$_2$ |
| 1-260 | 93 | Cl | F | Cl | CH$_3$CH$_2$OCOC(Cl)HCH$_2$ | (CH$_2$)$_2$ |
| 1-261 | 94 | Cl | F | Cl | N≡C | (CH$_2$)$_2$ |
| 1-262 |  | Cl | F | Cl | N≡C | (CH$_2$)$_3$ |
| 1-263 |  | Cl | F | Cl | N≡C | CH$_2$OCH$_2$ |
| 1-264 | 95 | Cl | F | Cl | HOOC | (CH$_2$)$_2$ |
| 1-265 |  | Cl | F | Cl | CH$_3$CH$_2$OOC | (CH$_2$)$_2$ |
| 1-266 |  | Cl | F | Cl | NO$_2$ | CH$_2$ |
| 1-267 |  | Cl | F | Cl | NO$_2$ | CHF |
| 1-268 | 96 | Cl | F | Cl | NO$_2$ | (CH$_2$)$_2$ |
| 1-269 |  | Cl | F | Cl | NO$_2$ | (CH$_2$)$_3$ |
| 1-270 |  | Cl | F | Cl | NO$_2$ | CH$_2$O |
| 1-271 |  | Cl | F | Cl | NO$_2$ | OCH$_2$ |
| 1-272 | 97 | Cl | F | Cl | NO$_2$ | CH$_2$OCH$_2$ |
| 1-273 |  | Cl | F | CF$_3$ | H | CH$_2$ |
| 1-274 |  | Cl | F | CF$_3$ | H | CHF |
| 1-275 | 98 | Cl | F | CF$_3$ | H | (CH$_2$)$_2$ |
| 1-276 |  | Cl | F | CF$_3$ | H | (CH$_2$)$_3$ |
| 1-277 |  | Cl | F | CF$_3$ | H | CH$_2$O |
| 1-278 |  | Cl | F | CF$_3$ | H | OCH$_2$ |
| 1-279 |  | Cl | F | CF$_3$ | H | CH$_2$OCH$_2$ |
| 1-280 | 99 | Cl | Cl | Cl | H | (CH$_2$)$_2$ |
| 1-281 |  | Cl | Cl | Cl | H | (CH$_2$)$_3$ |
| 1-282 |  | Cl | Cl | Cl | H | CH$_2$OCH$_2$ |
| 1-283 |  | Cl | Cl | Cl | HO | CH$_2$ |
| 1-284 |  | Cl | Cl | Cl | HO | CHF |
| 1-285 | 100 | Cl | Cl | Cl | HO | (CH$_2$)$_2$ |
| 1-286 | 272 | Cl | Cl | Cl | HO | (CH$_2$)$_3$ |
| 1-287 |  | Cl | Cl | Cl | HO | CH$_2$O |
| 1-288 |  | Cl | Cl | Cl | HO | OCH$_2$ |
| 1-289 | 275 | Cl | Cl | Cl | HO | CH$_2$OCH$_2$ |
| 1-290 |  | Cl | Cl | Cl | CH$_3$O | CH$_2$ |
| 1-291 |  | Cl | Cl | Cl | CH$_3$O | CHF |
| 1-292 | 101 | Cl | Cl | Cl | CH$_3$O | (CH$_2$)$_2$ |
| 1-293 | 271 | Cl | Cl | Cl | CH$_3$O | (CH$_2$)$_3$ |
| 1-294 |  | Cl | Cl | Cl | CH$_3$O | CH$_2$O |
| 1-295 |  | Cl | Cl | Cl | CH$_3$O | OCH$_2$ |
| 1-296 | 274 | Cl | Cl | Cl | CH$_3$O | CH$_2$OCH$_2$ |
| 1-297 | 102 | Cl | Cl | Cl | NO$_2$ | (CH$_2$)$_2$ |
| 1-298 |  | Cl | Cl | Cl | NO$_2$ | (CH$_2$)$_3$ |
| 1-299 |  | Cl | Cl | Cl | NO$_2$ | CH$_2$OCH$_2$ |
| 1-300 |  | Cl | Cl | Cl | HC≡CCH$_2$O | CH$_2$ |

TABLE 1-continued

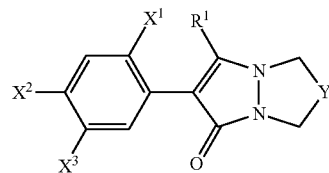

Bicyclic pyrazolinone derivative of the present invention

| Compound No. | Example No. | R¹ | X¹ | X² | X³ | Y |
|---|---|---|---|---|---|---|
| 1-301 | | Cl | Cl | Cl | HC≡CCH₂O | CHF |
| 1-302 | 103 | Cl | Cl | Cl | HC≡CCH₂O | (CH₂)₂ |
| 1-303 | 273 | Cl | Cl | Cl | HC≡CCH₂O | (CH₂)₃ |
| 1-304 | | Cl | Cl | Cl | HC≡CCH₂O | CH₂O |
| 1-305 | | Cl | Cl | Cl | HC≡CCH₂O | OCH₂ |
| 1-306 | 276 | Cl | Cl | Cl | HC≡CCH₂O | CH₂OCH₂ |
| 1-307 | 104 | Cl | Cl | Cl | cyclo-C₅H₉O | (CH₂)₂ |
| 1-308 | | Cl | Cl | Cl | cyclo-C₅H₉O | (CH₂)₃ |
| 1-309 | | Cl | Cl | Cl | cyclo-C₅H₉O | CH₂OCH₂ |
| 1-310 | | CF₃ | H | Cl | H | (CH₂)₂ |
| 1-311 | 105 | CF₃ | H | Cl | H | (CH₂)₃ |
| 1-312 | | CF₃ | H | Cl | H | (CH₂)₃ |
| 1-313 | | CF₃ | H | Cl | H | CH₂OCH₂ |
| 1-314 | 106 | CF₃ | H | Cl | CH₃O | (CH₂)₂ |
| 1-315 | | CF₃ | H | Cl | HC≡CCH₂O | (CH₂)₂ |
| 1-316 | | CF₃ | H | Cl | H₂C=CHCH₂O | (CH₂)₂ |
| 1-317 | | CH₃ | F | Cl | H | CH₂ |
| 1-318 | | CH₃ | F | Cl | H | CHF |
| 1-319 | 107 | CH₃ | F | Cl | H | (CH₂)₂ |
| 1-320 | | CH₃ | F | Cl | H | (CH₂)₃ |
| 1-321 | | CH₃ | F | Cl | H | CH₂O |
| 1-322 | | CH₃ | F | Cl | H | OCH₂ |
| 1-323 | | CH₃ | F | Cl | H | CH₂OCH₂ |
| 1-324 | | CH₃ | F | Cl | HO | (CH₂)₂ |
| 1-325 | | CH₃ | F | Cl | CH₃O | (CH₂)₂ |
| 1-326 | | CH₃ | F | Cl | HC≡CCH₂O | (CH₂)₂ |
| 1-327 | | CH₃ | F | Cl | H₂C=CHCH₂O | (CH₂)₂ |
| 1-328 | | CH₃ | F | Cl | NO₂ | (CH₂)₂ |
| 1-329 | 108 | CF₃ | F | Cl | H | (CH₂)₂ |
| 1-330 | 109 | CF₃ | F | Cl | H | (CH₂)₃ |
| 1-331 | | CF₃ | F | Cl | H | CH₂OCH₂ |
| 1-332 | | CF₃ | F | Cl | HO | (CH₂)₂ |
| 1-333 | | CF₃ | F | Cl | CH₃O | (CH₂)₂ |
| 1-334 | | CF₃ | F | Cl | HC≡CCH₂O | (CH₂)₂ |
| 1-335 | | CF₃ | F | Cl | H₂C=CHCH₂O | (CH₂)₂ |
| 1-336 | 110 | CF₃ | F | Cl | NO₂ | (CH₂)₂ |
| 1-337 | 111 | CF₃ | F | Cl | NO₂ | (CH₂)₃ |
| 1-338 | | CF₃ | F | Cl | NO₂ | CH₂OCH₂ |
| 1-339 | 112 | CF₃ | Cl | Cl | H | (CH₂)₂ |
| 1-340 | 155 | Cl | F | F | 2-Cl-6-F-4-CF₃—C₆H₂O | (CH₂)₂ |
| 1-341 | | Cl | F | F | 2,6-Cl₂-4-CF₃—C₆H₂O | (CH₂)₂ |
| 1-342 | | Cl | F | F | 2,4-(CF₃)₂—C₆H₂O | (CH₂)₂ |
| 1-343 | | Cl | F | F | 2-Cl-6-F-4-CF₃—C₆H₂O | (CH₂)₃ |
| 1-344 | | Cl | F | F | 2,6-Cl₂-4-CF₃—C₆H₂O | (CH₂)₃ |
| 1-345 | | Cl | F | F | 2,4-(CF₃)₂—C₆H₂O | (CH₂)₃ |
| 1-346 | 156 | Cl | F | Cl | 2-Cl-6-F-4-CF₃—C₆H₂O | (CH₂)₂ |
| 1-347 | | Cl | F | Cl | 2,6-Cl₂-4-CF₃—C₆H₂O | (CH₂)₂ |
| 1-348 | | Cl | F | Cl | 2,4-(CF₃)₂—C₆H₂O | (CH₂)₂ |
| 1-349 | | Cl | F | Cl | 2-Cl-6-F-4-CF₃—C₆H₂O | (CH₂)₃ |
| 1-350 | | Cl | F | Cl | 2,6-Cl₂-4-CF₃—C₆H₂O | (CH₂)₃ |
| 1-351 | 237 | F | F | Cl | HO | (CH₂)₂ |
| 1-352 | 236 | F | F | Cl | CH₃O | (CH₂)₂ |
| 1-353 | | F | F | Cl | HC≡CCH₂O | (CH₂)₂ |
| 1-354 | | F | F | Cl | HC≡CCH₂O | (CH₂)₃ |
| 1-355 | | F | F | Cl | HC≡CCH₂O | CH₂OCH₂ |
| 1-356 | 238 | F | Cl | Cl | CH₃O | (CH₂)₂ |
| 1-357 | 239 | F | Cl | Cl | HO | (CH₂)₂ |
| 1-358 | 240 | F | Cl | Cl | HC≡CCH₂O | (CH₂)₂ |
| 1-359 | 241 | F | Cl | Cl | CH₃O | (CH₂)₃ |
| 1-360 | 242 | F | Cl | Cl | HO | (CH₂)₃ |

TABLE 1-continued

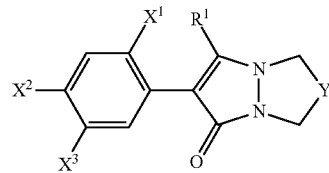

Bicyclic pyrazolinone derivative of the present invention

| Compound No. | Example No. | $R^1$ | $X^1$ | $X^2$ | $X^3$ | Y |
|---|---|---|---|---|---|---|
| 1-361 | 243 | F | Cl | Cl | HC≡CCH$_2$O | (CH$_2$)$_3$ |
| 1-362 | 244 | F | Cl | Cl | CH$_3$O | CH$_2$OCH$_2$ |
| 1-363 | 245 | F | Cl | Cl | HO | CH$_2$OCH$_2$ |
| 1-364 | 246 | F | Cl | Cl | HC≡CCH$_2$O | CH$_2$OCH$_2$ |
| 1-365 | 260 | Cl | H | Cl | HO | (CH$_2$)$_3$ |
| 1-366 | 263 | Cl | H | Cl | HO | CH$_2$OCH$_2$ |
| 1-367 | 267 | Cl | F | F | HC≡CCH$_2$O | (CH$_2$)$_3$ |
| 1-368 | 270 | Cl | F | F | HC≡CCH$_2$O | CH$_2$OCH$_2$ |
| 1-369 | 277 | Cl | F | Cl | H$_2$C=C(Cl)CH$_2$O | (CH$_2$)$_2$ |
| 1-370 | 280 | Cl | F | Cl | 2-pyridylmethyloxy | (CH$_2$)$_2$ |
| 1-371 | 281 | Cl | F | Cl | 3-pyridylmethyloxy | (CH$_2$)$_2$ |
| 1-372 | 282 | Cl | F | Cl | 4-pyridylmethyloxy | (CH$_2$)$_2$ |
| 1-373 |  | Cl | F | Cl | 2-pyridylmethyloxy | (CH$_2$)$_3$ |
| 1-374 |  | Cl | F | Cl | 3-pyridylmethyloxy | (CH$_2$)$_3$ |
| 1-375 |  | Cl | F | Cl | 4-pyridylmethyloxy | (CH$_2$)$_3$ |
| 1-376 |  | Cl | F | Cl | 2-pyridylmethyloxy | CH$_2$OCH$_2$ |
| 1-377 |  | Cl | F | Cl | 3-pyridylmethyloxy | CH$_2$OCH$_2$ |
| 1-378 |  | Cl | F | Cl | 4-pyridylmethyloxy | CH$_2$OCH$_2$ |
| 1-379 |  | Cl | F | Cl | (6-chloropyridin-3-yl)methoxy | CH$_2$OCH$_2$ |
| 1-380 |  | Cl | F | Cl | (3,4-dimethoxypyridin-2-yl)methyloxy | (CH$_2$)$_2$ |
| 1-381 |  | Cl | F | Cl | (3,5-dimethyl-4-methoxypyridin-2-yl)methyloxy | (CH$_2$)$_2$ |
| 1-382 |  | Cl | F | Cl | [3-methyl-4-(2,2,2-trifluoroethoxy)]pyridin-2-yl)methyloxy | (CH$_2$)$_2$ |
| 1-383 |  | Cl | F | Cl | (6-chloropyridin-3-yl)methoxy | (CH$_2$)$_2$ |
| 1-384 | 283 | Cl | F | Cl | 3-chloro-5-(trifluoromethyl)pyridin-2-yloxy | (CH$_2$)$_2$ |
| 1-385 |  | Cl | F | Cl | 2-methoxypyridin-3-yloxy | (CH$_2$)$_2$ |
| 1-386 | 284 | Cl | F | Cl | 2-nitropyridin-3-yloxy | (CH$_2$)$_2$ |
| 1-387 |  | Cl | F | Cl | 2-[(methyloxycarbonyl)methyloxy]pyridin-3-yloxy | (CH$_2$)$_2$ |
| 1-388 |  | Cl | F | Cl | 2-[(ethyloxycarbonyl)methyloxy]pyridin-3-yloxy | (CH$_2$)$_2$ |
| 1-389 |  | Cl | F | Cl | 2-methoxypyridin-3-yloxy | (CH$_2$)$_3$ |
| 1-390 |  | Cl | F | Cl | 2-[(methyloxycarbonyl)methyloxy]pyridin-3-yloxy | (CH$_2$)$_3$ |
| 1-391 |  | Cl | F | Cl | 2-[(ethyloxycarbonyl)methyloxy]pyridin-3-yloxy | (CH$_2$)$_3$ |
| 1-392 |  | Cl | F | Cl | (3,4-dimethoxypyridin-2-yl)methoxy | CH$_2$OCH$_2$ |
| 1-393 |  | Cl | F | Cl | (3,5-dimethyl-4-methoxypyridin-2-yl)methoxy | CH$_2$OCH$_2$ |
| 1-394 |  | Cl | F | Cl | [3-methyl-4-(2,2,2-trifluoroethoxy)]pyridin-2-yl)methoxy | CH$_2$OCH$_2$ |
| 1-395 |  | Cl | F | Cl | 5-fluoropyridin-2-yloxy | CH$_2$OCH$_2$ |
| 1-396 |  | Cl | F | Cl | 3-nitropyridin-2-yloxy | CH$_2$OCH$_2$ |
| 1-397 |  | Cl | F | Cl | 5-nitropyridin-2-yloxy | CH$_2$OCH$_2$ |
| 1-398 |  | Cl | F | Cl | 3-trifluoromethylpyridin-2-yloxy | CH$_2$OCH$_2$ |
| 1-399 |  | Cl | F | Cl | 4-trifluoromethylpyridin-2-yloxy | CH$_2$OCH$_2$ |
| 1-400 |  | Cl | F | Cl | 5-trifluoromethylpyridin-2-yloxy | CH$_2$OCH$_2$ |
| 1-401 |  | Cl | F | Cl | 6-trifluoromethylpyridin-2-yloxy | CH$_2$OCH$_2$ |
| 1-402 |  | Cl | F | Cl | 3,5-dichloropyridin-2-yloxy | CH$_2$OCH$_2$ |
| 1-403 |  | Cl | F | Cl | 6-chloro-3-nitropyridin-2-yloxy | CH$_2$OCH$_2$ |
| 1-404 |  | Cl | F | Cl | 2-methoxypyridin-3-yloxy | CH$_2$OCH$_2$ |
| 1-405 |  | Cl | F | Cl | 2-[(methyloxycarbonyl)methyloxy]pyridin-3-yloxy | CH$_2$OCH$_2$ |
| 1-406 |  | Cl | F | Cl | 2-[(ethyloxycarbonyl)methyloxy]pyridin-3-yloxy | CH$_2$OCH$_2$ |
| 1-407 | 247 | F | Cl | Cl | H | (CH$_2$)$_3$ |
| 1-408 | 255 | F | Cl | Cl | H | CH$_2$OCH$_2$ |
| 1-409 | 248 | F | Cl | Cl | NO$_2$ | (CH$_2$)$_2$ |
| 1-410 | 252 | F | Cl | Cl | NO$_2$ | (CH$_2$)$_3$ |
| 1-411 | 256 | F | Cl | Cl | NO$_2$ | CH$_2$OCH$_2$ |
| 1-412 | 285 | Cl | NO$_2$ | F | H | (CH$_2$)$_2$ |
| 1-413 | 290, 292 | Cl | F | HO | NO$_2$ | CH$_2$OCH$_2$ |
| 1-414 | 291 | Cl | F | CH$_3$O | NO$_2$ | CH$_2$OCH$_2$ |
| 1-415 | 295 | Cl | F | H | F | (CH$_2$)$_2$ |
| 1-416 | 296 | Cl | F | NO$_2$ | F | (CH$_2$)$_2$ |
| 1-417 | 297 | Cl | F | NO$_2$ | H$_2$C=C(CH$_3$)CH$_2$O | (CH$_2$)$_2$ |
| 1-418 | 298 | Cl | F | NO$_2$ | HC≡CCH$_2$O | (CH$_2$)$_2$ |
| 1-419 | 299 | Cl | F | NO$_2$ | HC≡CCH(CH$_3$)O | (CH$_2$)$_2$ |

Specific examples of the bicyclic pyrazolinone derivative of the present invention in which the substituent $X^3$ on the benzene ring in the bicyclic pyrazolinone derivative of the present invention represented by the following general formula (1) is a substituted alkenyloxy group represented by General Formula (1-1a) are shown in Table-2; however, the present invention is not limited thereto.

TABLE 2

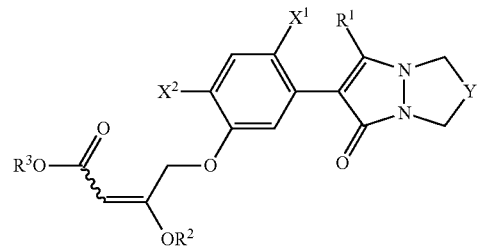

Bicyclic pyrazolinone derivative of the present invention

| Compound No. | Example No. | $R^1$ | $X^1$ | $X^2$ | $R^2$ | $R^3$ | Y |
|---|---|---|---|---|---|---|---|
| 2-1 | 113 | Cl | F | Cl | $CH_3$ | $CH_3$ | $(CH_2)_2$ |
| 2-2 | | Cl | F | Cl | $CH_3$ | $CH_3$ | $(CH_2)_3$ |
| 2-3 | 279 | Cl | F | Cl | $CH_3$ | $CH_3$ | $CH_2OCH_2$ |
| 2-4 | 114 | Cl | F | F | $CH_3$ | $CH_3$ | $(CH_2)_2$ |
| 2-5 | 115 | Cl | Cl | Cl | $CH_3$ | $CH_3$ | $(CH_2)_2$ |
| 2-6 | | Cl | Cl | Cl | $CH_3$ | $CH_3$ | $(CH_2)_3$ |
| 2-7 | | Cl | Cl | Cl | $CH_3$ | $CH_3$ | $CH_2OCH_2$ |
| 2-8 | 116 | Cl | F | Cl | $CH_3$ | $H_2C=CHCH_2$ | $(CH_2)_2$ |
| 2-9 | | Cl | F | Cl | $CH_3$ | $H_2C=CHCH_2$ | $(CH_2)_3$ |
| 2-10 | | Cl | F | Cl | $CH_3$ | $H_2C=CHCH_2$ | $CH_2OCH_2$ |
| 2-11 | 117 | Cl | F | Cl | $CH_3CH_2$ | $H_2C=CHCH_2$ | $(CH_2)_2$ |
| 2-12 | 118 | Cl | F | Cl | $CH_3CH_2$ | $CH_3$ | $(CH_2)_2$ |
| 2-13 | 119 | Cl | F | Cl | $CH_3CH_2CH_2$ | $CH_3$ | $(CH_2)_2$ |
| 2-14 | 120 | Cl | F | Cl | $CH_3$ | $CH_3CH_2$ | $(CH_2)_2$ |
| 2-15 | | Cl | F | Cl | $CH_3$ | $CH_3CH_2$ | $(CH_2)_3$ |
| 2-16 | | Cl | F | Cl | $CH_3$ | $CH_3CH_2$ | $CH_2O$ |
| 2-17 | | Cl | F | Cl | $CH_3$ | $CH_3CH_2$ | $OCH_2$ |
| 2-18 | | Cl | F | Cl | $CH_3$ | $CH_3CH_2$ | $CH_2OCH_2$ |
| 2-19 | 121 | Cl | F | Cl | $CH_3CH_2$ | $CH_3CH_2$ | $(CH_2)_2$ |
| 2-20 | 122 | Cl | F | Cl | $CH_3CH_2CH_2$ | $CH_3CH_2$ | $(CH_2)_2$ |
| 2-21 | | Cl | F | Cl | $CH_3CH_2CH_2$ | $CH_3CH_2$ | $(CH_2)_3$ |
| 2-22 | | Cl | F | Cl | $CH_3CH_2CH_2$ | $CH_3CH_2$ | $CH_2OCH_2$ |
| 2-23 | 123 | Cl | F | Cl | $CH_3CH_2$ | $CH_3CH_2CH_2$ | $(CH_2)_2$ |
| 2-24 | | Cl | F | Cl | $CH_3CH_2$ | $CH_3CH_2CH_2$ | $(CH_2)_3$ |
| 2-25 | | Cl | F | Cl | $CH_3CH_2$ | $CH_3CH_2CH_2$ | $CH_2OCH_2$ |
| 2-26 | 124 | Cl | F | Cl | $CH_3CH_2$ | $(CH_3)_2CH$ | $(CH_2)_2$ |
| 2-27 | 125 | Cl | F | Cl | $CH_3CH_2$ | $(CH_3)_2CHCH_2$ | $(CH_2)_2$ |
| 2-28 | | Cl | F | Cl | $CH_3CH_2$ | $(CH_3)_2CHCH_2$ | $(CH_2)_3$ |
| 2-29 | | Cl | F | Cl | $CH_3CH_2$ | $(CH_3)_2CHCH_2$ | $CH_2OCH_2$ |
| 2-30 | 126 | Cl | F | Cl | $CH_3CH_2$ | $H_2C=C(CH_3)CH_2$ | $(CH_2)_2$ |
| 2-31 | | Cl | F | Cl | $CH_3CH_2$ | $H_2C=C(CH_3)CH_2$ | $(CH_2)_3$ |
| 2-32 | | Cl | F | Cl | $CH_3CH_2$ | $H_2C=C(CH_3)CH_2$ | $CH_2OCH_2$ |
| 2-33 | 127 | Cl | F | Cl | $CH_3CH_2CH_2$ | $H_2C=C(CH_3)CH_2$ | $(CH_2)_2$ |
| 2-34 | 128 | Cl | F | Cl | $CH_3CH_2CH_2$ | $(CH_3)_2CHCH_2$ | $(CH_2)_2$ |

Specific examples of the bicyclic pyrazolinone derivative (1g) of the present invention which is the bicyclic pyrazolinone derivative of the present invention in which the substituent $X^3$ on the benzene ring in the bicyclic pyrazolinone derivative of the present invention represented by the following general formula (1) is a substituted phenyloxy group, and which can be prepared by the method shown in Preparation Method-3 are shown in Table-3; however, the present invention is not limited thereto.

TABLE 3

(1g)

Bicyclic pyrazolinone derivative (1g) of the present invention

| Compound No. | Example No. | $R^1$ | $X^1$ | $X^2$ | $(X^{4d})_n$ | Position of substituent | $X^{4e}$—O Type of substituent | Y |
|---|---|---|---|---|---|---|---|---|
| 3-1 | 130 | Cl | F | Cl | H | 2 | HO | $(CH_2)_2$ |
| 3-2 | 129 | Cl | F | Cl | H | 2 | $CH_3O$ | $(CH_2)_2$ |
| 3-3 |  | Cl | F | Cl | H | 2 | $CH_3O$ | $(CH_2)_3$ |
| 3-4 | 132 | Cl | F | Cl | H | 3 | HO | $(CH_2)_2$ |
| 3-5 | 131 | Cl | F | Cl | H | 3 | $CH_3O$ | $(CH_2)_2$ |
| 3-6 | 134 | Cl | F | Cl | H | 4 | HO | $(CH_2)_2$ |
| 3-7 | 133 | Cl | F | Cl | H | 4 | $CH_3O$ | $(CH_2)_2$ |
| 3-8 | 135 | Cl | F | Cl | H | 2 | $(CH_3)_2CHO$ | $(CH_2)_2$ |
| 3-9 |  | Cl | F | Cl | H | 2 | $(CH_3)_2CHO$ | $(CH_2)_3$ |
| 3-10 |  | Cl | F | Cl | H | 2 | $(CH_3)_2CHO$ | $CH_2OCH_2$ |
| 3-11 | 136 | Cl | F | Cl | H | 3 | $(CH_3)_2CHO$ | $(CH_2)_2$ |
| 3-12 |  | Cl | F | Cl | H | 3 | $(CH_3)_2CHO$ | $(CH_2)_3$ |
| 3-13 | 137 | Cl | F | Cl | H | 4 | $(CH_3)_2CHO$ | $(CH_2)_2$ |
| 3-14 | 138 | Cl | F | Cl | H | 3 | $CH_3OCH_2O$ | $(CH_2)_2$ |
| 3-15 | 139 | Cl | F | Cl | H | 4 | $CH_3OCH_2O$ | $(CH_2)_2$ |
| 3-16 | 140 | Cl | F | Cl | H | 2 | $CH_3OCOCH_2O$ | $(CH_2)_2$ |
| 3-17 | 141 | Cl | F | Cl | H | 2 | $CH_3CH_2OCOCH_2O$ | $(CH_2)_2$ |
| 3-18 | 142 | Cl | F | Cl | H | 2 | $CH_3CH_2OCOCH(CH_3CH_2O)O$ | $(CH_2)_2$ |
| 3-19 |  | Cl | F | Cl | H | 2 | $CH_3CH_2OCOCH(CH_3CH_2O)O$ | $(CH_2)_3$ |
| 3-20 | 143 | Cl | F | Cl | H | 4 | $N\equiv CCH_2O$ | $(CH_2)_2$ |
| 3-21 | 144 | Cl | F | Cl | H | 2 | $H_2C\!=\!CHCH_2O$ | $(CH_2)_2$ |
| 3-22 | 145 | Cl | F | Cl | H | 2 | $H_2C\!=\!C(CH_3)CH_2O$ | $(CH_2)_2$ |
| 3-23 | 146 | Cl | F | Cl | H | 2 | $CH_3OCOCH\!=\!C(CH_3O)CH_2O$ | $(CH_2)_2$ |
| 3-24 | 147 | Cl | F | Cl | H | 2 | $H_2C\!=\!CHCH_2OCOCH\!=\!C(CH_3O)CH_2O$ | $(CH_2)_2$ |
| 3-25 | 148 | Cl | F | Cl | H | 2 | $H_2C\!=\!CHCH_2OCOCH\!=\!C(CH_3CH_2O)CH_2O$ | $(CH_2)_2$ |
| 3-26 | 149 | Cl | F | Cl | H | 2 | 3-Cl—$C_6H_4C(\!=\!CH_2)CH_2O$ | $(CH_2)_2$ |
| 3-27 | 150 | Cl | F | Cl | H | 2 | $H_2C\!=\!CHCH_2O$ | $(CH_2)_2$ |
| 3-28 | 151 | Cl | F | Cl | H | 3 | $H_2C\!=\!CHCH_2O$ | $(CH_2)_2$ |
| 3-29 | 152 | Cl | F | Cl | H | 4 | $H_2C\!=\!CHCH_2O$ | $(CH_2)_2$ |
| 3-30 | 153 | Cl | F | Cl | H | 2 | $H_3CC\equiv CCH_2O$ | $(CH_2)_2$ |
| 3-31 | 154 | Cl | F | Cl | H | 2 | $HC\equiv CCH(CH_3)O$ | $(CH_2)_2$ |
| 3-32 | 157 | Cl | F | Cl | 4-F | 2 | HO | $(CH_2)_2$ |
| 3-33 | 158 | Cl | F | Cl | 4-F | 2 | $CH_3O$ | $(CH_2)_2$ |
| 3-34 | 159 | Cl | F | Cl | 4-F | 2 | $H_2C\!=\!CHCH_2O$ | $(CH_2)_2$ |
| 3-35 | 160 | Cl | F | Cl | 4-F | 2 | $HC\equiv CCH_2O$ | $(CH_2)_2$ |
| 3-36 | 161 | Cl | F | Cl | 4-Cl | 2 | HO | $(CH_2)_2$ |
| 3-37 | 162 | Cl | F | Cl | 4-Cl | 2 | $CH_3O$ | $(CH_2)_2$ |
| 3-38 | 163 | Cl | F | Cl | 4-Cl | 2 | $H_2C\!=\!CHCH_2O$ | $(CH_2)_2$ |
| 3-39 | 164 | Cl | F | Cl | 4-Cl | 2 | $HC\equiv CCH_2O$ | $(CH_2)_2$ |
| 3-40 | 166 | Cl | F | Cl | 4-$CH_3$ | 2 | HO | $(CH_2)_2$ |
| 3-41 | 165 | Cl | F | Cl | 4-$CH_3$ | 2 | $CH_3O$ | $(CH_2)_2$ |
| 3-42 | 167 | Cl | F | Cl | 4-$CH_3$ | 2 | $H_2C\!=\!CHCH_2O$ | $(CH_2)_2$ |
| 3-43 | 168 | Cl | F | Cl | 4-$CH_3$ | 2 | $HC\equiv CCH_2O$ | $(CH_2)_2$ |
| 3-44 | 300 | Cl | F | $NO_2$ | H | 2 | $CH_3O$ | $(CH_2)_2$ |

Specific examples of the bicyclic pyrazolinone derivative (1i) of the present invention which is the bicyclic pyrazolinone derivative of the present invention in which the substituent $X^3$ on the benzene ring in the bicyclic pyrazolinone derivative of the present invention represented by the following general formula (1) is a substituted isoxazolin-5-yl methyloxy group represented by General Formula (1-3), and which can be prepared by the method shown in Preparation Method-4 are shown in Table-4; however, the present invention is not limited thereto.

TABLE 4

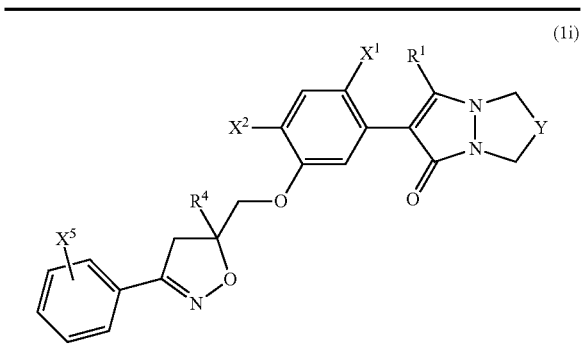

(1i)

Bicyclic pyrazolinone derivative (1i) of the present invention

| Compound No. | Example No. | R¹ | X¹ | X² | R⁴ | X⁵ | Y |
|---|---|---|---|---|---|---|---|
| 4-1 | 169 | Cl | F | Cl | CH₃ | H | (CH₂)₂ |
| 4-2 | | Cl | F | Cl | CH₃CH₂ | H | (CH₂)₂ |
| 4-3 | 170 | Cl | F | Cl | CH₃ | 2-F | (CH₂)₂ |
| 4-4 | | Cl | F | Cl | CH₃ | 3-F | (CH₂)₂ |
| 4-5 | 171 | Cl | F | Cl | CH₃ | 2-Cl | (CH₂)₂ |
| 4-6 | | Cl | F | Cl | CH₃ | 3-Cl | (CH₂)₂ |
| 4-7 | 172 | Cl | F | Cl | CH₃ | 4-F | (CH₂)₂ |
| 4-8 | 173 | Cl | F | Cl | CH₃ | 4-Cl | (CH₂)₂ |
| 4-9 | | Cl | F | Cl | CH₃ | 4-Cl | (CH₂)₃ |
| 4-10 | | Cl | F | Cl | CH₃ | 4-Cl | CH₂OCH₂ |

TABLE 4-continued

Bicyclic pyrazolinone derivative (1i) of the present invention

| Compound No. | Example No. | R¹ | X¹ | X² | R⁴ | X⁵ | Y |
|---|---|---|---|---|---|---|---|
| 4-11 | 174 | Cl | F | Cl | CH₃ | 2-Cl-4-F | (CH₂)₂ |
| 4-12 | 175 | Cl | F | Cl | CH₃ | 2,4-Cl₂ | (CH₂)₂ |
| 4-13 | | Cl | F | Cl | CH₃ | 2-CH₃ | (CH₂)₂ |
| 4-14 | | Cl | F | Cl | CH₃ | 4-CH₃ | (CH₂)₂ |
| 4-15 | | Cl | F | Cl | CH₃ | 4-(CH₃)₂CH | (CH₂)₂ |
| 4-16 | | Cl | F | Cl | CH₃ | 4-CF₃ | (CH₂)₂ |
| 4-17 | | Cl | F | Cl | CH₃ | 4-CF₃O | (CH₂)₂ |

Specific examples of the bicyclic pyrazolinone derivative (1m, 1n, or 1o) of the present invention which is the bicyclic pyrazolinone derivative of the present invention in which the substituent $X^3$ on the benzene ring in the bicyclic pyrazolinone derivative of the present invention represented by the following general formula (1) is an amino group which may be substituted, and which can be prepared by the method shown in Preparation Method-6 are shown in Table-5; however, the present invention is not limited thereto. In the table, the compound in which the two $X^{3f}$'s are hydrogen atoms is the bicyclic pyrazolinone derivative represented by General Formula (1m), and the compound in which one $X^{3f}$ is a hydrogen atom is the bicyclic pyrazolinone derivative represented by General Formula (1n).

TABLE 5

Bicyclic pyrazolinone derivatives (1m, 1n, and 1o) of the present invention

| Compound No. | Example No. | R¹ | X¹ | X² | X³ᶠ | X³ᶠ | Y |
|---|---|---|---|---|---|---|---|
| 5-1 | 176 | Cl | F | F | H | H | (CH₂)₂ |
| 5-2 | 177 | Cl | F | F | H | CH₃ | (CH₂)₂ |

TABLE 5-continued

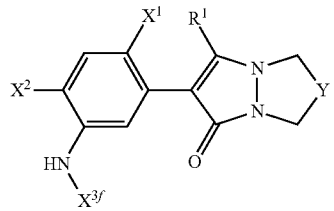

(1n)

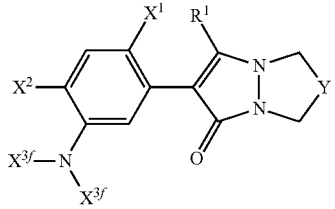

(1o)

Bicyclic pyrazolinone derivatives (1m, 1n, and 1o) of the present invention

| Compound No. | Example No. | $R^1$ | $X^1$ | $X^2$ | $X^{3f}$ | $X^{3f}$ | Y |
|---|---|---|---|---|---|---|---|
| 5-3 | 178 | Cl | F | F | H | $CH_3SO_2$ | $(CH_2)_2$ |
| 5-4 | 179 | Cl | F | F | H | $ClCH_2SO_2$ | $(CH_2)_2$ |
| 5-5 | 180 | Cl | F | F | H | $CH_3CH_2SO_2$ | $(CH_2)_2$ |
| 5-6 | | Cl | F | F | H | $CF_3CH_2SO_2$ | $(CH_2)_2$ |
| 5-7 | 182 | Cl | F | F | H | $(CH_3)_2CHSO_2$ | $(CH_2)_2$ |
| 5-8 | 183 | Cl | F | F | H | cyclo-$C_3H_5SO_2$ | $(CH_2)_2$ |
| 5-9 | 177 | Cl | F | F | $CH_3$ | $CH_3$ | $(CH_2)_2$ |
| 5-10 | 184 | Cl | F | F | $(CH_3)_2CHCH_2SO_2$ | $(CH_3)_2CHCH_2SO_2$ | $(CH_2)_2$ |
| 5-11 | 185 | Cl | F | Cl | H | H | $(CH_2)_2$ |
| 5-12 | | Cl | F | Cl | H | H | $(CH_2)_3$ |
| 5-13 | 186 | Cl | F | Cl | H | H | $CH_2OCH_2$ |
| 5-14 | 187 | Cl | F | Cl | H | $CH_3CO$ | $(CH_2)_2$ |
| 5-15 | 188 | Cl | F | Cl | H | $CF_3CO$ | $(CH_2)_2$ |
| 5-16 | 189 | Cl | F | Cl | H | $CH_3CH_2CO$ | $(CH_2)_2$ |
| 5-17 | 190 | Cl | F | Cl | H | $(CH_3)_2CHCO$ | $(CH_2)_2$ |
| 5-18 | 191 | Cl | F | Cl | H | $ClCH_2C(CH_3)_2CO$ | $(CH_2)_2$ |
| 5-19 | 192 | Cl | F | Cl | H | $CH_3COOCH_2CO$ | $(CH_2)_2$ |
| 5-20 | 193 | Cl | F | Cl | H | $CH_3CH_2OCOCH_2CO$ | $(CH_2)_2$ |
| 5-21 | 194 | Cl | F | Cl | H | 4-Cl—$C_6H_4CH_2CO$ | $(CH_2)_2$ |
| 5-22 | 195 | Cl | F | Cl | H | cyclo-$C_3H_5CO$ | $(CH_2)_2$ |
| 5-23 | 196 | Cl | F | Cl | H | cyclo-$C_5H_9CO$ | $(CH_2)_2$ |
| 5-24 | 197 | Cl | F | Cl | H | cyclo-$C_6H_{11}CO$ | $(CH_2)_2$ |
| 5-25 | 198 | Cl | F | Cl | H | 3-Cl—$C_6H_4CO$ | $(CH_2)_2$ |
| 5-26 | 199 | Cl | F | Cl | H | 2,6-$Cl_2$—$C_6H_3CO$ | $(CH_2)_2$ |
| 5-27 | 200 | Cl | F | Cl | H | 2-F—$C_6H_4CO$ | $(CH_2)_2$ |
| 5-28 | 201 | Cl | F | Cl | H | 4-F—$C_6H_4CO$ | $(CH_2)_2$ |
| 5-29 | 202 | Cl | F | Cl | H | 2-$CF_3$—$C_6H_4CO$ | $(CH_2)_2$ |
| 5-30 | 203 | Cl | F | Cl | H | 3-$CF_3$—$C_6H_4CO$ | $(CH_2)_2$ |
| 5-31 | 204 | Cl | F | Cl | H | 2,6-$F_2$—$C_6H_3CO$ | $(CH_2)_2$ |
| 5-32 | 205 | Cl | F | Cl | H | 2-F-6-$CF_3$—$C_6H_3CO$ | $(CH_2)_2$ |
| 5-33 | | Cl | F | Cl | H | $CH_3SO_2$ | $CH_2$ |
| 5-34 | | Cl | F | Cl | H | $CH_3SO_2$ | CHF |
| 5-35 | 206 | Cl | F | Cl | H | $CH_3SO_2$ | $(CH_2)_2$ |
| 5-36 | | Cl | F | Cl | H | $CH_3SO_2$ | $(CH_2)_3$ |
| 5-37 | | Cl | F | Cl | H | $CH_3SO_2$ | $CH_2O$ |
| 5-38 | | Cl | F | Cl | H | $CH_3SO_2$ | $OCH_2$ |
| 5-39 | | Cl | F | Cl | H | $CH_3SO_2$ | $CH_2OCH_2$ |
| 5-40 | 207 | Cl | F | Cl | H | $ClCH_2SO_2$ | $(CH_2)_2$ |
| 5-41 | | Cl | F | Cl | H | $ClCH_2SO_2$ | $(CH_2)_3$ |
| 5-42 | 208 | Cl | F | Cl | H | $ClCH_2CH_2SO_2$ | $(CH_2)_2$ |
| 5-43 | 208 | Cl | F | Cl | H | $H_2C=CHSO_2$ | $(CH_2)_2$ |
| 5-44 | 209 | Cl | F | Cl | H | $(CH_3)_2CHSO_2$ | $(CH_2)_2$ |
| 5-45 | 210 | Cl | F | Cl | H | $(CH_3)_2NSO_2$ | $(CH_2)_2$ |
| 5-46 | 211 | Cl | F | Cl | H | $CH_3SO_2$ | $CH_2OCH_2$ |
| 5-47 | | Cl | F | Cl | H | $ClCH_2SO_2$ | $CH_2O$ |
| 5-48 | | Cl | F | Cl | H | $ClCH_2SO_2$ | $OCH_2$ |
| 5-49 | 212 | Cl | F | Cl | H | $ClCH_2SO_2$ | $CH_2OCH_2$ |
| 5-50 | 213 | Cl | F | Cl | H | $CF_3SO_2$ | $(CH_2)_2$ |
| 5-51 | 214 | Cl | F | Cl | H | $CH_3CH_2SO_2$ | $(CH_2)_2$ |
| 5-52 | | Cl | F | Cl | H | $CH_3CH_2SO_2$ | $(CH_2)_3$ |
| 5-53 | | Cl | F | Cl | H | $CH_3CH_2SO_2$ | $CH_2OCH_2$ |

TABLE 5-continued

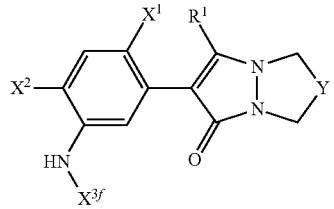

(1n)

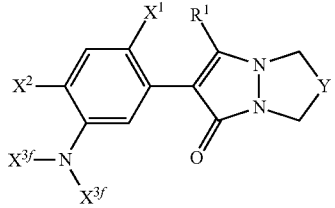

(1o)

Bicyclic pyrazolinone derivatives (1m, 1n, and 1o) of the present invention

| Compound No. | Example No. | $R^1$ | $X^1$ | $X^2$ | $X^{3f}$ | $X^{3f}$ | Y |
|---|---|---|---|---|---|---|---|
| 5-54 | 215 | Cl | F | Cl | H | $CH_3CH_2SO_2$ | $CH_2OCH_2$ |
| 5-55 | 216 | Cl | F | Cl | H | $CF_3CH_2SO_2$ | $(CH_2)_2$ |
| 5-56 | 217 | Cl | F | Cl | H | $(CH_3)_2CHCH_2SO_2$ | $(CH_2)_2$ |
| 5-57 | 218 | Cl | F | Cl | H | $C_6H_5CH_2SO_2$ | $(CH_2)_2$ |
| 5-58 | 219 | Cl | F | Cl | H | cyclo-$C_3H_5SO_2$ | $(CH_2)_2$ |
| 5-59 | | Cl | F | Cl | H | cyclo-$C_3H_5SO_2$ | $(CH_2)_3$ |
| 5-60 | 220 | Cl | F | Cl | H | cyclo-$C_3H_5SO_2$ | $CH_2OCH_2$ |
| 5-61 | | Cl | F | Cl | H | 2-F—$C_6H_4SO_2$ | $(CH_2)_2$ |
| 5-62 | | Cl | F | Cl | H | 4-F—$C_6H_4SO_2$ | $(CH_2)_2$ |
| 5-63 | 221 | Cl | F | Cl | H | 2-Cl—$C_6H_4SO_2$ | $(CH_2)_2$ |
| 5-64 | 222 | Cl | F | Cl | H | 4-Cl—$C_6H_4SO_2$ | $(CH_2)_2$ |
| 5-65 | 223 | Cl | F | Cl | H | 2,4-$F_2$—$C_6H_3SO_2$ | $(CH_2)_2$ |
| 5-66 | 224 | Cl | F | Cl | H | 2,4,6-$(CH_3)_3$—$C_6H_2SO_2$ | $(CH_2)_2$ |
| 5-67 | 225 | Cl | F | Cl | H | 4-$(C_6H_5O)$—$C_6H_4SO_2$ | $(CH_2)_2$ |
| 5-68 | 226 | Cl | F | Cl | $CH_3$ | HC≡$CCH_2$ | $(CH_2)_2$ |
| 5-69 | | Cl | F | Cl | $CH_3$ | HC≡$CCH_2$ | $(CH_2)_3$ |
| 5-70 | | Cl | F | Cl | $CH_3$ | HC≡$CCH_2$ | $CH_2OCH_2$ |
| 5-71 | 227 | Cl | F | Cl | $CH_3SO_2$ | $CH_3SO_2$ | $(CH_2)_2$ |
| 5-72 | | Cl | F | Cl | $CH_3SO_2$ | $CH_3SO_2$ | $(CH_2)_3$ |
| 5-73 | | Cl | F | Cl | $CH_3SO_2$ | $CH_3SO_2$ | $CH_2OCH_2$ |
| 5-74 | 228 | Cl | F | Cl | —$(CH_2)_4$— | | $(CH_2)_2$ |
| 5-75 | 229 | Cl | F | Cl | —$(CH_2)_5$— | | $(CH_2)_2$ |
| 5-76 | | Cl | F | Cl | —$(CH_2)_6$— | | $(CH_2)_2$ |
| 5-77 | 230 | Cl | Cl | Cl | H | H | $(CH_2)_2$ |
| 5-78 | 231 | Cl | Cl | Cl | H | $CH_3SO_2$ | $(CH_2)_2$ |
| 5-79 | 232 | Cl | Cl | Cl | H | $CH_3CH_2SO_2$ | $(CH_2)_2$ |
| 5-80 | 233 | Cl | Cl | Cl | H | cyclo-$C_3H_5SO_2$ | $(CH_2)_2$ |
| 5-81 | 234 | Cl | Cl | Cl | $CH_3$ | $CH_3$ | $(CH_2)_2$ |
| 5-82 | 235 | $CF_3$ | F | Cl | H | H | $(CH_2)_2$ |
| 5-83 | 235 | $CF_3$ | F | Cl | $CH_3$ | H | $(CH_2)_2$ |
| 5-84 | 235 | $CF_3$ | F | Cl | $CH_3$ | HC≡$CCH_2$ | $(CH_2)_2$ |
| 5-85 | | $CF_3$ | F | Cl | $CH_3$ | HC≡$CCH_2$ | $(CH_2)_3$ |
| 5-86 | | $CF_3$ | F | Cl | $CH_3$ | HC≡$CCH_2$ | $CH_2OCH_2$ |
| 5-87 | 293 | Cl | F | HO | H | H | $CH_2OCH_2$ |
| 5-88 | 294 | Cl | F | HO | H | $BrF_2CCO$ | $CH_2OCH_2$ |
| 5-89 | 301 | Cl | F | $NO_2$ | H | $H_2C$=$CHCH_2$ | $(CH_2)_2$ |
| 5-90 | 302 | Cl | F | $NH_2$ | H | $H_2C$=$CHCH_2$ | $(CH_2)_2$ |
| 5-91 | 303 | Cl | F | $NO_2$ | H | HC≡$CCH_2$ | $(CH_2)_2$ |
| 5-92 | 304 | Cl | F | $NH_2$ | H | HC≡$CCH_2$ | $(CH_2)_2$ |
| 5-93 | 249 | F | Cl | Cl | H | H | $(CH_2)_2$ |
| 5-94 | 253 | F | Cl | Cl | H | H | $(CH_2)_3$ |
| 5-95 | 257 | F | Cl | Cl | H | H | $CH_2OCH_2$ |
| 5-96 | 250 | F | Cl | Cl | H | $CH_3SO_2$ | $(CH_2)_2$ |
| 5-97 | 251 | F | Cl | Cl | H | $ClCH_2SO_2$ | $(CH_2)_2$ |
| 5-98 | 254 | F | Cl | Cl | H | $CH_3SO_2$ | $(CH_2)_3$ |
| 5-99 | 258 | F | Cl | Cl | H | $CH_3SO_2$ | $CH_2OCH_2$ |

Next, the present invention will be described in more detail with reference to Formulation Examples of herbicides containing the compound of the present invention as an effective component and Test Examples using the herbicide of the present invention; however, the herbicide of the present invention is not limited thereto. Moreover, "parts" in Formulation Examples represents "parts by weight".

Formulation Example-1

Emulsifiable Concentrate 10 parts of the compound of the present invention, 31 parts of xylene, 27 parts of dimethyl formamide, 22 parts of 1-methyl-2-pyrrolidone, 1 part of 1,3-dimethyl-2-imidazolidine, and 9 parts of NK. ST-30 (manufactured by TAKEMOTO OIL & FAT Co., Ltd.) were homogeneously mixed, whereby an emulsifiable concentrate was obtained.

Formulation Example-2

Wettable Powder

A mixture of 50 parts of the compound of the present invention, 25 parts of diatomaceous earth, 22 parts of clay, and 3 parts of Lunox 1000C (manufactured by TOHO Chemical Industry Co., Ltd.) was homogeneously mixed and pulverized, whereby a wettable powder was obtained.

Formulation Example-3

Granule

After a mixture of 5 parts of the compound of the present invention, 35 parts of bentonite, 55 parts of talc, and 5 parts of sodium lignosulfonate was homogeneously mixed and pulverized, water was added thereto, and the resultant product was kneaded, granulated using an extrusion granulator, dried, and graded, whereby granules were obtained.

Using the formulation prepared according to the methods described above, the herbicidal effect of the bicyclic pyrazolinone derivative of the invention according to the methods shown in Test Examples below was examined. The herbicidal effect with respect to the test weeds or the phytotoxicity with respect to the test crops was examined according to the following criteria, and evaluated in six stage scores of 0 to 5.

Evaluation Criteria of Herbicidal Effect and Phytotoxicity
5: Herbicidal effect/phytotoxicity was 90% or greater
4: Herbicidal effect/phytotoxicity was 70% to 90%
3: Herbicidal effect/phytotoxicity was 50% to 70%
2: Herbicidal effect/phytotoxicity was 30% to 50%
1: Herbicidal effect/phytotoxicity was 10% to 30%
0: Herbicidal effect/phytotoxicity was 0% to 10%

Test Example-1

Herbicidal Effect Test by a Treatment Before Weeds are Generated Under Submerged Conditions A plastic cup of 30 cm$^2$ was filled with paddy soil, soil puddling was performed, seeds of *Echinochloa oryzicola* (barnyard grass), *Cyperus difformis* (smallflower umbrella plant), *Monochoria vaginalis* (monochoria), *Scirpus juncoides* (bulrush), and *Eleocharis acicularis* (needle spikerush), and *Lindernia procumbens* (common false pimpernel), *Rotala indica* (indian toothcup), *Elatine triandra* (waterwort) as other annual broad leaf weeds were seeded therein, and kept in a submerged state. A wettable powder or an emulsifiable concentrate of the compound of the present invention prepared according to Formulation Example was diluted on the weed seeding day, and a submersing treatment was performed so as to be a predetermined dosage. The herbicidal effect with respect to the test weeds about 15 days after the treatment was evaluated according to the evaluation criteria in six stages of 0 to 5 described above. The results are shown in Table-6.

TABLE 6

Herbicidal effect by a treatment before weeds are generated under submerged conditions

| Compound No. | Application amount g a.i/ha | *Echinochloa oryzicola* | *Cyperus difformis* | Broadleaf weed | *Monochoria vaginalis* | *Scirpus juncoides* | *Eleocharis acicularis* |
|---|---|---|---|---|---|---|---|
| 1-52 | 500 | 5 | 5 | 5 | 5 | 5 | 5 |
| 1-62 | 500 | 5 | 5 | 5 | 5 | 5 | 5 |
| 1-63 | 500 | 5 | 5 | 5 | 5 | 5 | 5 |
| 1-75 | 500 | 5 | 5 | 5 | 5 | 5 | 5 |
| 1-87 | 500 | 5 | 5 | 5 | 5 | 5 | 5 |
| 1-89 | 500 | 5 | 5 | 5 | 5 | 5 | 5 |
| 1-90 | 500 | 5 | 5 | 5 | 5 | 5 | 5 |
| 1-93 | 500 | 5 | 5 | 5 | 5 | 5 | 5 |
| 1-98 | 500 | 5 | 5 | 5 | 5 | 5 | 5 |
| 1-101 | 500 | 5 | 5 | 5 | 5 | 5 | 5 |
| 1-106 | 500 | 5 | 5 | 5 | 5 | 5 | 5 |
| 1-109 | 500 | 5 | 5 | 5 | 5 | 5 | 5 |
| 1-112 | 500 | 5 | 5 | 5 | 5 | 5 | 5 |
| 1-113 | 500 | 5 | 5 | 5 | 5 | 5 | 5 |
| 1-114 | 500 | 5 | 5 | 5 | 5 | 5 | 5 |
| 1-115 | 500 | 5 | 5 | 5 | 5 | 5 | 5 |
| 1-125 | 500 | 5 | 5 | 5 | 5 | 5 | 5 |
| 1-129 | 500 | 5 | 5 | 5 | 5 | 5 | 5 |
| 1-130 | 500 | 5 | 5 | 5 | 5 | 5 | 5 |
| 1-140 | 500 | 5 | 5 | 5 | 5 | 5 | 5 |
| 1-143 | 500 | 5 | 5 | 5 | 5 | 5 | 5 |
| 1-146 | 500 | 5 | 5 | 5 | 5 | 5 | 5 |
| 1-151 | 500 | 5 | 5 | 5 | 5 | 5 | 5 |
| 1-156 | 500 | 5 | 5 | 5 | 5 | 5 | 5 |

TABLE 6-continued

Herbicidal effect by a treatment before weeds are generated under submerged conditions

| Compound No. | Application amount g a.i/ha | Echinochloa oryzicola | Cyperus difformis | Broadleaf weed | Monochoria vaginalis | Scirpus juncoides | Eleocharis acicularis |
|---|---|---|---|---|---|---|---|
| 1-159 | 500 | 5 | 5 | 5 | 5 | 5 | 5 |
| 1-165 | 500 | 5 | 5 | 5 | 5 | 5 | 5 |
| 1-166 | 500 | 5 | 5 | 5 | 5 | 5 | 5 |
| 1-171 | 500 | 5 | 5 | 5 | 5 | 5 | 5 |
| 1-176 | 500 | 5 | 5 | 5 | 5 | 5 | 5 |
| 1-181 | 500 | 5 | 5 | 5 | 5 | 5 | 5 |
| 1-186 | 500 | 5 | 5 | 5 | 5 | 5 | 5 |
| 1-188 | 500 | 5 | 5 | 5 | 5 | 5 | 5 |
| 1-192 | 500 | 5 | 5 | 5 | 5 | 5 | 5 |
| 1-201 | 500 | 5 | 5 | 5 | 5 | 5 | 5 |
| 1-206 | 500 | 5 | 5 | 5 | 5 | 5 | 5 |
| 1-209 | 500 | 5 | 5 | 5 | 5 | 5 | 5 |
| 1-214 | 500 | 5 | 5 | 5 | 5 | 5 | 5 |
| 1-219 | 500 | 5 | 5 | 5 | 5 | 5 | 5 |
| 1-222 | 500 | 5 | 5 | 5 | 5 | 5 | 5 |
| 1-226 | 500 | 5 | 5 | 5 | 5 | 5 | 5 |
| 1-232 | 500 | 5 | 5 | 5 | 5 | 5 | 5 |
| 1-238 | 500 | 5 | 5 | 5 | 5 | 5 | 5 |
| 1-243 | 500 | 5 | 5 | 5 | 5 | 5 | 5 |
| 1-245 | 500 | 5 | 5 | 5 | 5 | 5 | 5 |
| 1-246 | 500 | 5 | 5 | 5 | 5 | 5 | 5 |
| 1-254 | 500 | 5 | 5 | 5 | 5 | 5 | 5 |
| 1-257 | 500 | 5 | 5 | 5 | 5 | 5 | 5 |
| 1-260 | 500 | 5 | 5 | 5 | 5 | 5 | 5 |
| 1-280 | 500 | 5 | 5 | 5 | 5 | 5 | 5 |
| 1-292 | 500 | 5 | 5 | 5 | 5 | 5 | 5 |
| 1-293 | 500 | 5 | 5 | 5 | 5 | 5 | 5 |
| 1-296 | 500 | 5 | 5 | 5 | 5 | 5 | 5 |
| 1-302 | 500 | 5 | 5 | 5 | 5 | 5 | 5 |
| 1-303 | 500 | 5 | 5 | 5 | 5 | 5 | 5 |
| 1-306 | 500 | 5 | 5 | 5 | 5 | 5 | 5 |
| 1-307 | 500 | 5 | 5 | 5 | 5 | 5 | 5 |
| 1-340 | 500 | 5 | 5 | 5 | 5 | 5 | 5 |
| 1-356 | 500 | 5 | 5 | 5 | 5 | 5 | 5 |
| 1-358 | 500 | 5 | 5 | 5 | 5 | 5 | 5 |
| 1-361 | 500 | 5 | 5 | 5 | 5 | 5 | 5 |
| 1-364 | 500 | 5 | 5 | 5 | 5 | 5 | 5 |
| 1-367 | 500 | 5 | 5 | 5 | 5 | 5 | 5 |
| 1-368 | 500 | 5 | 5 | 5 | 5 | 5 | 5 |
| 1-369 | 500 | 5 | 5 | 5 | 5 | 5 | 5 |
| 1-386 | 500 | 5 | 5 | 5 | 5 | 5 | 5 |
| 2-1 | 500 | 5 | 5 | 5 | 5 | 5 | 5 |
| 2-3 | 500 | 5 | 5 | 5 | 5 | 5 | 5 |
| 2-5 | 500 | 5 | 5 | 5 | 5 | 5 | 5 |
| 2-8 | 500 | 5 | 5 | 5 | 5 | 5 | 5 |
| 2-11 | 500 | 5 | 5 | 5 | 5 | 5 | 5 |
| 2-12 | 500 | 5 | 5 | 5 | 5 | 5 | 5 |
| 2-13 | 500 | 5 | 5 | 5 | 5 | 5 | 5 |
| 2-14 | 500 | 5 | 5 | 5 | 5 | 5 | 5 |
| 2-19 | 500 | 5 | 5 | 5 | 5 | 5 | 5 |
| 2-20 | 500 | 5 | 5 | 5 | 5 | 5 | 5 |
| 2-23 | 500 | 5 | 5 | 5 | 5 | 5 | 5 |
| 2-26 | 500 | 5 | 5 | 5 | 5 | 5 | 5 |
| 2-27 | 500 | 5 | 5 | 5 | 5 | 5 | 5 |
| 2-30 | 500 | 5 | 5 | 5 | 5 | 5 | 5 |
| 2-33 | 500 | 5 | 5 | 5 | 5 | 5 | 5 |
| 2-34 | 500 | 5 | 5 | 5 | 5 | 5 | 5 |
| 3-1 | 500 | 5 | 5 | 5 | 5 | 5 | 5 |
| 3-2 | 500 | 5 | 5 | 5 | 5 | 5 | 5 |
| 3-4 | 500 | 5 | 5 | 5 | 5 | 5 | 5 |
| 3-5 | 500 | 5 | 5 | 5 | 5 | 5 | 5 |
| 3-7 | 500 | 5 | 5 | 5 | 5 | 5 | 5 |
| 3-8 | 500 | 5 | 5 | 5 | 5 | 5 | 5 |
| 3-11 | 500 | 5 | 5 | 5 | 5 | 5 | 5 |
| 3-13 | 500 | 5 | 5 | 5 | 5 | 5 | 5 |
| 3-14 | 500 | 5 | 5 | 5 | 5 | 5 | 5 |
| 3-15 | 500 | 5 | 5 | 5 | 5 | 5 | 5 |
| 3-16 | 500 | 5 | 5 | 5 | 5 | 5 | 5 |
| 3-17 | 500 | 5 | 5 | 5 | 5 | 5 | 5 |
| 3-18 | 500 | 5 | 5 | 5 | 5 | 5 | 5 |
| 3-20 | 500 | 5 | 5 | 5 | 5 | 5 | 5 |
| 3-21 | 500 | 5 | 5 | 5 | 5 | 5 | 5 |
| 3-22 | 500 | 5 | 5 | 5 | 5 | 5 | 5 |

TABLE 6-continued

Herbicidal effect by a treatment before weeds are generated under submerged conditions

| Compound No. | Application amount g a.i/ha | Echinochloa oryzicola | Cyperus difformis | Broadleaf weed | Monochoria vaginalis | Scirpus juncoides | Eleocharis acicularis |
|---|---|---|---|---|---|---|---|
| 3-23 | 500 | 5 | 5 | 5 | 5 | 5 | 5 |
| 3-24 | 500 | 5 | 5 | 5 | 5 | 5 | 5 |
| 3-25 | 500 | 5 | 5 | 5 | 5 | 5 | 5 |
| 3-26 | 500 | 5 | 5 | 5 | 5 | 5 | 5 |
| 3-27 | 500 | 5 | 5 | 5 | 5 | 5 | 5 |
| 3-29 | 500 | 5 | 5 | 5 | 5 | 5 | 5 |
| 3-30 | 500 | 5 | 5 | 5 | 5 | 5 | 5 |
| 3-31 | 500 | 5 | 5 | 5 | 5 | 5 | 5 |
| 3-33 | 500 | 5 | 5 | 5 | 5 | 5 | 5 |
| 3-34 | 500 | 5 | 5 | 5 | 5 | 5 | 5 |
| 3-35 | 500 | 5 | 5 | 5 | 5 | 5 | 5 |
| 3-37 | 500 | 5 | 5 | 5 | 5 | 5 | 5 |
| 3-38 | 500 | 5 | 5 | 5 | 5 | 5 | 5 |
| 3-39 | 500 | 5 | 5 | 5 | 5 | 5 | 5 |
| 3-41 | 500 | 5 | 5 | 5 | 5 | 5 | 5 |
| 3-42 | 500 | 5 | 5 | 5 | 5 | 5 | 5 |
| 3-43 | 500 | 5 | 5 | 5 | 5 | 5 | 5 |
| 4-1 | 500 | 5 | 5 | 5 | 5 | 5 | 5 |
| 4-3 | 500 | 5 | 5 | 5 | 5 | 5 | 5 |
| 4-5 | 500 | 5 | 5 | 5 | 5 | 5 | 5 |
| 4-7 | 500 | 5 | 5 | 5 | 5 | 5 | 5 |
| 4-8 | 500 | 5 | 5 | 5 | 5 | 5 | 5 |
| 4-11 | 500 | 5 | 5 | 5 | 5 | 5 | 5 |
| 4-12 | 500 | 5 | 5 | 5 | 5 | 5 | 5 |
| 5-68 | 500 | 5 | 5 | 5 | 5 | 5 | 5 |

Test Example-2

Herbicidal Effect and Phytotoxicity Test by a Soil Treatment Before Weeds are Generated Under Upland Field Conditions A vat having an area of 81 cm² and a depth of 3.5 cm was filled with upland soil, then, seeds of *Amaranthus viridis* (green *amaranthus*), *Chenopodium album* (common lambsquarters), and corn were seeded thereto, and the seeds were covered with soil of about 0.5 cm. Next day, a wettable powder or an emulsifiable concentrate of the compound of the present invention prepared according to Formulation Example was diluted, and a spray treatment was uniformly performed on the covered oil so as to be a predetermined dosage. The herbicidal effect with respect to the test weeds and the phytotoxicity with respect to corn about 21 days after the treatment were evaluated according to the evaluation criteria in six stages of 0 to 5 described above. The results are shown in Table-7.

TABLE 7

Herbicidal effect by a soil treatment before weeds are generated under upland field conditions

| Compound No. | Application amount g a.i/ha | Amaranthus viridis | Chenopodium album | Phytotoxicity Corn |
|---|---|---|---|---|
| 1-89 | 500 | 5 | 5 | 0 |
| 1-151 | 500 | 5 | 5 | 0 |
| 1-181 | 500 | 5 | 5 | 0 |
| 1-214 | 500 | 5 | 5 | 0 |
| 1-238 | 500 | 5 | 5 | 1 |
| 1-239 | 500 | 5 | 5 | 0 |
| 1-243 | 500 | 5 | 5 | 0 |
| 1-245 | 500 | 5 | 5 | 0 |
| 1-292 | 500 | 5 | 5 | 2 |
| 1-296 | 500 | 5 | 5 | 0 |
| 1-302 | 500 | 5 | 5 | 2 |
| 1-303 | 500 | 5 | 5 | 0 |
| 1-306 | 500 | 5 | 5 | 1 |
| 1-358 | 500 | 5 | 5 | 0 |
| 1-367 | 500 | 5 | 5 | 0 |
| 1-368 | 500 | 5 | 5 | 0 |
| 1-369 | 500 | 5 | 5 | 0 |
| 1-418 | 500 | 5 | 5 | 0 |
| 2-3 | 500 | 5 | 5 | 0 |
| 3-18 | 500 | 5 | 5 | 0 |
| 3-40 | 500 | 5 | 5 | 0 |
| 5-35 | 500 | 5 | 5 | 0 |
| 5-49 | 500 | 5 | 5 | 0 |
| 5-58 | 500 | 5 | 5 | 0 |
| 5-71 | 500 | 5 | 5 | 0 |

Test Example-3

Herbicidal Effect Test and Phytotoxicity Test by a Foliage Treatment Before Weeds are Generated Under Upland Field Conditions A vat having an area of 81 cm² and a depth of 3.5 cm was filled with upland soil, then, seeds of *Ipomoea purpurea* (tall morning glory), *Amaranthus viridis* (green *amaranthus*), *Abutilon theophrasti* (velvetleaf), *Chenopodium album*

(common lambsquarters), and corn were seeded thereto, and the seeds were covered with soil of about 0.5 cm. Next day, a wettable powder or an emulsifiable concentrate of the compound of the present invention prepared according to Formulation Example was diluted, and a spray treatment was uniformly performed on the covered oil so as to be a predetermined dosage. The herbicidal effect with respect to the test weeds and the phytotoxicity with respect to corn about 21 days after the treatment were evaluated according to the evaluation criteria in six stages of 0 to 5 described above. The results are shown in Table-8.

TABLE 8

Herbicidal effect by a soil treatment before weeds are generated under upland field conditions

| Compound No. | Application amount g a.i/ha | Herbicidal effect | | | | Phytotoxicity Corn |
|---|---|---|---|---|---|---|
| | | Ipomoea purpurea | Amaranthus viridis | Abutilon theophrast | Chenopodium album | |
| 1-238 | 100 | 5 | 5 | 5 | 5 | 0 |
| | 50 | 5 | 4 | 5 | 5 | 0 |
| 1-306 | 100 | 5 | 5 | 4 | 5 | 1 |
| | 50 | 4 | 5 | 3 | 5 | 0 |
| 2-3 | 100 | 5 | 5 | 5 | 5 | 0 |
| | 50 | 2 | 5 | 5 | 4 | 0 |

Test Example-4

Herbicidal Effect Test and Phytotoxicity Test by a Foliage Treatment after Weeds are Generated Under Upland Field Conditions A vat having an area of 65 cm² and a depth of 2 cm was filled with upland soil, then, seeds of *Amaranthus viridis* (green *amaranthus*), *Abutilon theophrasti* (velvetleaf), *Chenopodium album* (common lambsquarters), and the seeds were covered with soil of about 0.5 cm. While watering was suitably performed on there, the seeds were grown for 14 days. A wettable powder or an emulsifiable concentrate of the compound of the present invention prepared according to Formulation Example was diluted, and a spray treatment was uniformly performed on the foliage portion of the plant so as to be a predetermined dosage in the amount of water of 4000 L per hectare. The herbicidal effect with respect to the test weeds and the phytotoxicity with respect to corn about 14 days after the treatment were evaluated according to the evaluation criteria in six stages of 0 to 5 described above. The results are shown in Table-9.

TABLE 9

Herbicidal effect by a foliage treatment after weeds are generated under upland field conditions

| Compound No. | Application amount g a.i/ha | Herbicidal effect | | | Phytotoxicity Corn |
|---|---|---|---|---|---|
| | | Amaranthus viridis | Abutilon theophrast | Chenopodium album | |
| 1-44 | 500 | 5 | 5 | 5 | 0 |
| 1-49 | 500 | 5 | 5 | 5 | 0 |
| 1-52 | 500 | 5 | 5 | 5 | 0 |
| 1-59 | 500 | 5 | 5 | 5 | 0 |
| 1-62 | 500 | 5 | 5 | 5 | 0 |
| 1-63 | 500 | 5 | 5 | 5 | 1 |
| 1-66 | 500 | 5 | 5 | 5 | 1 |
| 1-67 | 500 | 5 | 5 | 5 | 0 |
| 1-70 | 500 | 5 | 5 | 5 | 0 |
| 1-87 | 500 | 5 | 5 | 5 | 2 |
| 1-90 | 500 | 5 | 5 | 5 | 3 |
| 1-101 | 500 | 5 | 5 | 5 | 3 |
| 1-113 | 500 | 5 | 5 | 5 | 3 |
| 1-114 | 500 | 5 | 5 | 5 | 3 |
| 1-115 | 500 | 5 | 5 | 5 | 3 |
| 1-125 | 500 | 5 | 5 | 5 | 1 |
| 1-130 | 500 | 5 | 5 | 5 | 1 |
| 1-140 | 500 | 5 | 5 | 5 | 2 |
| 1-141 | 500 | 5 | 5 | 5 | 0 |
| 1-146 | 500 | 5 | 5 | 5 | 0 |
| 1-151 | 500 | 5 | 5 | 5 | 1 |
| 1-156 | 500 | 5 | 5 | 5 | 2 |
| 1-163 | 500 | 5 | 5 | 5 | 0 |
| 1-171 | 500 | 5 | 5 | 5 | 3 |
| 1-176 | 500 | 5 | 5 | 5 | 2 |
| 1-181 | 500 | 5 | 5 | 5 | 1 |
| 1-182 | 500 | 5 | 5 | 5 | 1 |
| 1-188 | 500 | 5 | 5 | 5 | 0 |
| 1-192 | 500 | 5 | 5 | 5 | 1 |
| 1-201 | 500 | 5 | 5 | 5 | 2 |
| 1-209 | 500 | 5 | 5 | 5 | 2 |
| 1-214 | 500 | 5 | 5 | 5 | 2 |
| 1-219 | 500 | 5 | 5 | 5 | 2 |
| 1-222 | 500 | 5 | 5 | 5 | 2 |
| 1-226 | 500 | 5 | 5 | 5 | 3 |
| 1-228 | 500 | 5 | 5 | 5 | 1 |
| 1-230 | 500 | 5 | 5 | 5 | 0 |
| 1-238 | 500 | 5 | 5 | 5 | 3 |
| 1-239 | 500 | 5 | 5 | 5 | 2 |
| 1-243 | 500 | 5 | 5 | 5 | 1 |
| 1-245 | 500 | 5 | 5 | 5 | 1 |
| 1-246 | 500 | 5 | 5 | 5 | 1 |

TABLE 9-continued

Herbicidal effect by a foliage treatment after weeds are generated under upland field conditions

| Compound No. | Application amount g a.i/ha | Herbicidal effect Amaranthus viridis | Abutilon theophrast | Chenopodium album | Phytotoxicity Corn |
|---|---|---|---|---|---|
| 1-292 | 500 | 5 | 5 | 5 | 1 |
| 1-302 | 500 | 5 | 5 | 5 | 1 |
| 1-303 | 500 | 5 | 5 | 5 | 1 |
| 1-306 | 500 | 5 | 5 | 5 | 1 |
| 1-307 | 500 | 5 | 5 | 5 | 0 |
| 1-336 | 500 | 5 | 5 | 5 | 0 |
| 1-358 | 500 | 5 | 5 | 5 | 1 |
| 1-364 | 500 | 5 | 5 | 5 | 1 |
| 1-368 | 500 | 5 | 5 | 5 | 1 |
| 1-369 | 500 | 5 | 5 | 5 | 1 |
| 2-1 | 500 | 5 | 5 | 5 | 1 |
| 2-3 | 500 | 5 | 5 | 5 | 1 |
| 2-8 | 500 | 5 | 5 | 5 | 2 |
| 2-14 | 500 | 5 | 5 | 5 | 0 |
| 2-20 | 500 | 5 | 5 | 5 | 0 |
| 2-23 | 500 | 5 | 5 | 5 | 0 |
| 2-27 | 500 | 5 | 5 | 5 | 0 |
| 2-30 | 500 | 5 | 5 | 5 | 0 |
| 3-2 | 500 | 5 | 5 | 5 | 2 |
| 3-8 | 500 | 5 | 5 | 5 | 0 |
| 3-11 | 500 | 5 | 5 | 5 | 0 |
| 3-17 | 500 | 5 | 5 | 5 | 0 |
| 3-21 | 500 | 5 | 5 | 5 | 1 |
| 3-22 | 500 | 5 | 5 | 5 | 0 |
| 3-23 | 500 | 5 | 5 | 5 | 0 |
| 3-24 | 500 | 5 | 5 | 5 | 0 |
| 3-28 | 500 | 5 | 5 | 5 | 0 |
| 3-30 | 500 | 5 | 5 | 5 | 1 |
| 3-35 | 500 | 5 | 5 | 5 | 1 |
| 3-41 | 500 | 5 | 5 | 5 | 1 |
| 3-42 | 500 | 5 | 5 | 5 | 0 |
| 3-43 | 500 | 5 | 5 | 5 | 0 |
| 4-1 | 500 | 5 | 5 | 5 | 0 |
| 4-5 | 500 | 5 | 5 | 5 | 1 |
| 4-8 | 500 | 5 | 5 | 5 | 2 |
| 4-11 | 500 | 5 | 5 | 5 | 2 |
| 4-12 | 500 | 5 | 5 | 5 | 1 |
| 5-11 | 500 | 5 | 5 | 5 | 1 |
| 5-35 | 500 | 5 | 5 | 5 | 0 |
| 5-49 | 500 | 5 | 5 | 5 | 1 |
| 5-51 | 500 | 5 | 5 | 5 | 0 |
| 5-58 | 500 | 5 | 5 | 5 | 0 |
| 5-63 | 500 | 5 | 5 | 5 | 0 |
| 5-71 | 500 | 5 | 5 | 5 | 0 |

Test Example-5

Herbicidal Effect and Phytotoxicity Test by a Foliage Treatment after Weeds are Generated Under Upland Field Conditions A vat having an area of 81 cm$^2$ and a depth of 3.5 cm was filled with upland soil, then, seeds of *Ipomoea purpurea* (tall morning glory), *Amaranthus viridis* (green *amaranthus*), *Abutilon theophrasti* (velvetleaf), *Chenopodium album* (common lambsquarters), and corn were seeded thereto, and the seeds were covered with soil of about 0.5 cm. While watering was suitably performed on there, the seeds were grown for 14 days. A wettable powder or an emulsifiable concentrate of the compound of the present invention prepared according to Formulation Example was diluted, and a spray treatment was uniformly performed on the foliage portion of the plant so as to be a predetermined dosage in the amount of water of 4000 L per hectare. The herbicidal effect with respect to the test weeds and the phytotoxicity with respect to corn about 14 days after the treatment were evaluated according to the evaluation criteria in six stages of 0 to 5 described above. The results are shown in Table-10.

TABLE 10

Herbicidal effect by a foliage treatment after weeds are generated under upland field conditions

| Compound No. | Application amount g a.i/ha | Herbicidal effect Ipomoea purpurea | Amaranthus viridis | Abutilon theophrasti | Chenopodium album | Phytotoxicity Corn |
|---|---|---|---|---|---|---|
| 1-238 | 25 | 5 | 5 | 5 | 5 | 0 |
|  | 12.5 | 5 | 5 | 5 | 5 | 0 |
| 1-306 | 25 | 5 | 5 | 5 | 5 | 0 |
|  | 12.5 | 5 | 5 | 5 | 5 | 0 |
| 2-3 | 25 | 5 | 5 | 5 | 5 | 1 |
|  | 12.5 | 5 | 5 | 5 | 5 | 0 |

INDUSTRIAL APPLICABILITY

It is possible to effectively control harmful weeds by treating a paddy field or an upland field with an effective amount of the bicyclic pyrazolinone derivative of the present invention.

The invention claimed is:
1. A bicyclic pyrazolinone derivative represented by General Formula (1):

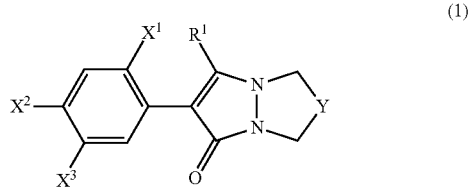

wherein,
$R^1$ represents a halogen atom or a $C_1$-$C_4$ haloalkyl group;
$X^1$ represents a hydrogen atom or a halogen atom;
$X^2$ represents a halogen atom, a cyano group, a thiocyano group, a trifluoromethyl group, a hydroxyl group, a $C_1$-$C_6$ alkyloxy group, a nitro group, or an amino group;
$X^3$ represents a hydrogen atom; a halogen atom; a hydroxyl group; a cyano group; a thiocyano group; a $C_1$-$C_6$ alkyl group which may be substituted with one or more substituents selected from the group consisting of a halogen atom, a ($C_1$-$C_4$ alkyl)oxycarbonyl group, and a cyano group; a $C_2$-$C_6$ alkenyl group which may be substituted with one or more substituents selected from the group consisting of a halogen atom, a ($C_1$-$C_4$ alkyl)oxycarbonyl group, and a cyano group; a $C_1$-$C_{12}$ alkyloxy group which may be substituted with one or more substituents selected from the group consisting of a $C_1$-$C_6$ alkyloxy group, a ($C_1$-$C_4$ alkyl)oxycarbonyl group, and a cyano group; a $C_1$-$C_{12}$ haloalkyloxy group; a $C_3$-$C_8$ cycloalkyloxy group; a glycidyloxy group; a $C_2$-$C_6$ alkenyloxy group which may be substituted with one or more substituents selected from the group consisting of a halogen atom and a ($C_1$-$C_4$ alkyl)oxycarbonyl group; an alkenyloxy group represented by General Formula (1-1a):

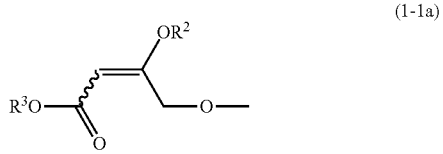

(wherein, $R^2$ represents a $C_1$-$C_6$ alkyl group, and $R^3$ represents a $C_1$-$C_6$ alkyl group or a $C_2$-$C_6$ alkenyl group); a $C_5$-$C_8$ cycloalkenyloxy group; a $C_2$-$C_6$ alkynyloxy group which may be substituted with a halogen atom; a $C_7$-$C_8$ aralkyloxy group which may be substituted with one or more substituents selected from the group consisting of a halogen atom and a trifluoromethyl group; a ($C_1$-$C_4$ alkyl)oxycarbonyloxy group; a ($C_2$-$C_6$ alkenyl)oxycarbonyloxy group; a phenyloxycarbonyloxy group which may be substituted with a halogen atom; a $C_1$-$C_4$ alkyl sulfonyloxy group; a $C_1$-$C_4$ haloalkyl sulfonyloxy group; a phenyl sulfonyloxy group which may be substituted with one or more substituents selected from the group consisting of a halogen atom and a $C_1$-$C_4$ alkyl group; a nitro group; an amino group which may be substituted with one or more substituents selected from the group consisting of a $C_1$-$C_4$ alkyl group, a $C_2$-$C_6$ alkenyl group, a $C_2$-$C_6$ alkynyl group, a $C_2$-$C_8$ acyl group which may be substituted with a halogen atom, a $C_1$-$C_4$ alkyl sulfonyl group which may be substituted with a halogen atom, a $C_3$-$C_8$ cycloalkyl sulfonyl group, a $C_2$-$C_6$ alkenyl sulfonyl group, a $C_7$-$C_8$ aralkyl sulfonyl group, a substituted or unsubstituted phenyl sulfonyl group, wherein the phenyl may be substituted with one or more substituents selected from the group consisting of a halogen atom, a $C_1$-$C_4$ alkyl group, a trifluoromethyl group, and phenyloxy group, and a di($C_1$-$C_4$ alkyl)amino sulfonyl group; a $C_4$-$C_7$ cyclic polymethylene imino group; a carboxyl group; a ($C_1$-$C_4$ alkyl)oxycarbonyl group; a ($C_2$-$C_6$ alkenyl)oxycarbonyl group; a phenyloxycarbonyl group which may be substituted with a halogen atom; a phenyloxy group which may be substituted, represented by General Formula (1-2a):

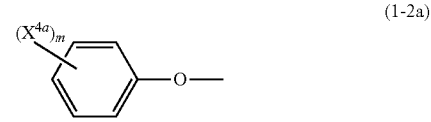

(wherein, $X^{4a}$ represents a hydrogen atom; a halogen atom; a $C_1$-$C_6$ alkyl group which may be substituted with one or more substituents selected from the group consisting of a ($C_1$-$C_4$ alkyl)oxycarbonyl group, and a cyano group; a $C_1$-$C_6$ haloalkyl group; a $C_1$-$C_6$ alkyloxy group which may be substituted with one or more substituents selected from the group consisting of a ($C_1$-$C_4$ alkyl)oxycarbonyl group and a cyano group; a $C_1$-$C_6$ haloalkyloxy group; a $C_2$-$C_6$ alkenyloxy group which may be substituted with one or more substituents selected from the group consisting of a halogen atom and a phenyl group which may be substituted with a halogen atom; a $C_2$-$C_6$ alkynyloxy group which may be substituted with a halogen atom; a phenyl group which may be substituted with one or more substituents selected from the group consisting of a halogen atom and a trifluoromethyl group; a ($C_1$-$C_4$ alkyl)oxycarbonyl group; a cyano group; a nitro group; an amino group; or an alkenyloxy group represented by General Formula (1-1a), and m represents an integer of 1 to 3, and when $X^{4a}$ is an alkenyloxy group represented by General Formula (1-1a), m is 1); a pyridyloxy group which may be substituted with one or more substituents selected from the group consisting of a halogen atom, a $C_1$-$C_4$ alkyl group, a $C_1$-$C_4$ haloalkyl group, a $C_1$-$C_4$ alkyloxy group, a ($C_1$-$C_4$ alkyloxy)carbonyl methyloxy group, a cyano group, and a nitro group; a pyridylmethyloxy group which may be substituted with one or more substituents selected from the group consisting of a halogen atom, a $C_1$-$C_4$ alkyl group, a $C_1$-$C_4$ haloalkyl group, a cyano group, and a nitro group; or an isoxazolin-5-yl methyloxy group represented by General Formula (1-3):

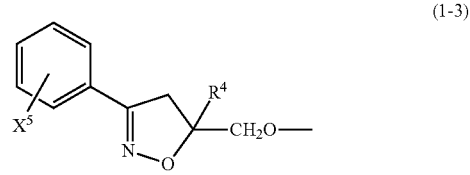

(wherein, $X^5$ represents a hydrogen atom, a halogen atom, a $C_1$-$C_6$ alkyl group, a $C_1$-$C_6$ haloalkyl group, a $C_1$-$C_6$ alkyloxy group, or a $C_1$-$C_6$ haloalkyloxy group, and $R^4$ represents a $C_1$-$C_4$ alkyl group); and Y represents a methylene group, a fluoromethylene group, a dimethylene group, a trimethylene group, a tetramethylene group, an oxamethylene group, or an oxadimethylene group.

2. The bicyclic pyrazolinone derivative according to claim 1,
wherein, in General Formula (1), each of $X^1$ and $X^2$ is independently the same as or different from each other, and is a halogen atom, $R^1$ is a halogen atom or a trifluoromethyl group, and Y is a methylene group, a dimethylene group, a trimethylene group, or an oxadimethylene group.

3. The bicyclic pyrazolinone derivative according to claim 1,
wherein, in General Formula (1), $X^1$ is a fluorine atom or a chlorine atom, $X^2$ is a chlorine atom, $R^1$ is a chlorine atom or a trifluoromethyl group, and Y is a dimethylene group.

4. The bicyclic pyrazolinone derivative according to claim 1,
wherein, in General Formula (1), $X^3$ represents a $C_1$-$C_{12}$ alkyloxy group which may be substituted with one or more substituents selected from the group consisting of a $C_1$-$C_6$ alkyloxy group, a ($C_1$-$C_4$ alkyl)oxycarbonyl group, and a cyano group; a $C_3$-$C_8$ cycloalkyloxy group; a $C_2$-$C_6$ alkenyloxy group which may be substituted with a halogen atom; an alkenyloxy group represented by General Formula (1-1a):

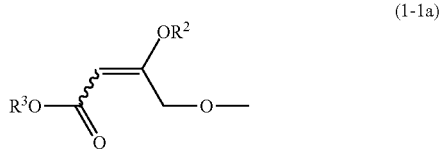

(wherein, $R^2$ represents a $C_1$-$C_6$ alkyl group, and $R^3$ represents a $C_1$-$C_6$ alkyl group or a $C_2$-$C_6$ alkenyl group); a $C_2$-$C_6$ alkynyloxy group which may be substituted with a halogen atom; a $C_7$-$C_8$ aralkyloxy group which may be substituted with one or more substituents selected from the group consisting of a halogen atom and a trifluoromethyl group; a ($C_1$-$C_4$ alkyl)oxycarbonyl group; a cyano group; a phenyloxy group, which may be substituted, represented by General Formula (1-2a):

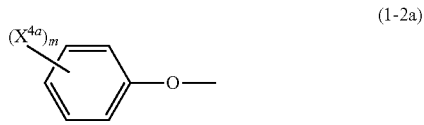

(wherein, $X^{4a}$ represents a hydrogen atom; a halogen atom; a $C_1$-$C_6$ alkyl group which may be substituted with one or more substituents selected from the group consisting of a ($C_1$-$C_4$ alkyl)oxycarbonyl group and a cyano group; a $C_1$-$C_6$ haloalkyl group; a $C_1$-$C_6$ alkyloxy group which may be substituted with one or more substituents selected from the group consisting of a ($C_1$-$C_4$ alkyl)oxycarbonyl group and a cyano group; a $C_1$-$C_6$ haloalkyloxy group; a $C_2$-$C_6$ alkenyloxy group which may be substituted with one or more substituents selected from the group consisting of a halogen atom and a phenyl group which may be substituted with a halogen atom; a $C_2$-$C_6$ alkynyloxy group which may be substituted with a halogen atom; a phenyl group which may be substituted with one or more substituents selected from the group consisting of a halogen atom and a trifluoromethyl group; a ($C_1$-$C_4$ alkyl)oxycarbonyl group; a cyano group; a nitro group; an amino group; or an alkenyloxy group represented by General Formula (1-1a), and m represents an integer of 1 to 3, and when $X^{4a}$ is an alkenyloxy group represented by General Formula (1-1a), m is 1); a pyridyloxy group which may be substituted with one or more substituents selected from the group consisting of a halogen atom, a $C_1$-$C_4$ alkyl group, a $C_1$-$C_4$ haloalkyl group, a $C_1$-$C_4$ alkyloxy group, a ($C_1$-$C_4$ alkyloxy)carbonyl methyloxy group, a cyano group, and a nitro group; or an isoxazolin-5-yl methyloxy group represented by General Formula (1-3):

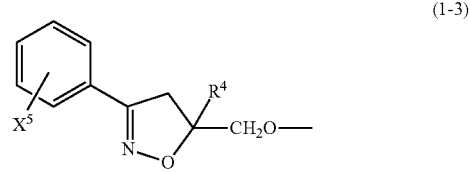

(wherein, $X^5$ represents a hydrogen atom, a halogen atom, a $C_1$-$C_6$ alkyl group, a $C_1$-$C_6$ haloalkyl group, a $C_1$-$C_6$ alkyloxy group, or a $C_1$-$C_6$ haloalkyloxy group, and $R^4$ represents a $C_1$-$C_4$ alkyl group).

5. The bicyclic pyrazolinone derivative according to claim 1,
wherein, in General Formula (1), $X^3$ is a $C_2$-$C_6$ alkenyloxy group or a $C_2$-$C_6$ alkynyloxy group.

6. The bicyclic pyrazolinone derivative according to claim 1,
wherein the compound represented by General Formula (1) is one compound selected from the group consisting of
4-(5-allyloxy-4-chloro-2-fluorophenyl)-5-chloro-1,2-tetramethylene-4-pyrazolin-3-one,
5-chloro-4-[4-chloro-2-fluoro-5-(propargyloxy)phenyl]-1,2-tetramethylene-4-pyrazolin-3-one,
5-chloro-4-[5-(2-butynyloxy)-4-chloro-2-fluorophenyl]-1,2-tetramethylene-4-pyrazolin-3-one,
5-chloro-4-[4-chloro-2-fluoro-5-(propargyloxy)phenyl]-1,2-pentamethylene-4-pyrazolin-3-one,
5-chloro-4-[4-chloro-2-fluoro-5-(2-methoxyphenoxy) phenyl]-1,2-tetramethylene-4-pyrazolin-3-one,
5-chloro-4-[2,4-dichloro-5-(propargyloxy)phenyl]-1,2-oxadiethylene-4-pyrazolin-3-one,
5-chloro-4-[2,4-dichloro-5-(propargyloxy)phenyl]-1,2-tetramethylene-4-pyrazolin-3-one, and
methyl (E)-4-[2-chloro-5-(5-chloro-3-oxo-1,2-oxadiethylene-4-pyrazolin-4-yl)-4-fluorophenyloxy]-3-methoxy-2-butenoate.

7. A herbicide, comprising:
the bicyclic pyrazolinone derivative according to claim 1 as an effective component.

8. A herbicide according to claim 7, which is for upland field weed control or for paddy field weed control.

9. The herbicide according to claim 8, which is for upland field weed control,
wherein a crop in the upland field is wheat, soybean, or corn.

10. The herbicide according to claim 7, which is a foliage and/or soil treatment agent.

11. A method of using the bicyclic pyrazolinone derivative according to claim 1 comprising controlling weeds with said bicyclic pyrazolinone derivative.

12. A method for controlling weeds, comprising:
    applying an effective amount of the bicyclic pyrazolinone derivative according to claim 1.

* * * * *